(12) United States Patent
Khosla et al.

(10) Patent No.: US 11,708,608 B2
(45) Date of Patent: Jul. 25, 2023

(54) THERAPEUTIC AND DIAGNOSTIC METHODS FOR IL-33-MEDIATED DISORDERS

(71) Applicant: Genentech, Inc., South San Francisco, CA (US)

(72) Inventors: Rajita Khosla, Foster City, CA (US); Vladimir Ramirez-Carrozzi, Millbrae, CA (US); Tracy Staton, Stanford, CA (US); Brian Yaspan, Pacifica, CA (US); Joseph Arron, San Mateo, CA (US); David Choy, Fairfield, CA (US); Amy Dressen, San Bruno, CA (US)

(73) Assignee: Genentech, Inc., South San Francisco, CA (US)

( * ) Notice: Subject to any disclaimer, the term of this patent is extended or adjusted under 35 U.S.C. 154(b) by 552 days.

(21) Appl. No.: 15/525,460

(22) PCT Filed: Nov. 10, 2015

(86) PCT No.: PCT/US2015/059982
§ 371 (c)(1),
(2) Date: May 9, 2017

(87) PCT Pub. No.: WO2016/077366
PCT Pub. Date: May 19, 2016

(65) Prior Publication Data
US 2018/0171405 A1 Jun. 21, 2018

Related U.S. Application Data

(60) Provisional application No. 62/165,703, filed on May 22, 2015, provisional application No. 62/077,854, filed on Nov. 10, 2014.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6869* (2013.01); *C12Q 2600/106* (2013.01); *C12Q 2600/156* (2013.01); *C12Q 2600/158* (2013.01); *C12Q 2600/172* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,084,083 A | 7/2000 | Levinson | |
| 6,156,887 A | 12/2000 | Levinson | |
| 6,204,371 B1 | 3/2001 | Levinson | |
| 6,288,218 B1 | 9/2001 | Levinson | |
| 6,414,117 B1 | 7/2002 | Levinson | |
| 6,562,343 B1 | 5/2003 | Levinson | |
| 7,172,750 B2 | 2/2007 | Levinson | |
| 7,560,530 B1 | 7/2009 | Chackerian et al. | |
| 8,187,596 B1 | 5/2012 | Chackerian et al. | |
| 9,090,694 B2 | 7/2015 | Duffy et al. | |
| 9,212,227 B2 | 12/2015 | Duffy et al. | |
| 9,309,319 B2 | 4/2016 | Fertig et al. | |
| 9,523,696 B2 | 12/2016 | Snider | |
| 2003/0158399 A1 | 8/2003 | Levinson | |
| 2007/0042978 A1 | 2/2007 | Girard et al. | |
| 2010/0260770 A1 | 10/2010 | Coyle | |
| 2011/0045501 A1 | 2/2011 | Bosch et al. | |
| 2011/0165063 A1 | 7/2011 | Hsieh et al. | |
| 2012/0207752 A1 | 8/2012 | Chackerian et al. | |
| 2013/0287777 A1 | 10/2013 | Duffy et al. | |
| 2013/0336980 A1 | 12/2013 | Duffy et al. | |
| 2014/0105887 A1 | 4/2014 | Chackerian et al. | |
| 2014/0271658 A1* | 9/2014 | Murphy .................. | A61P 37/08 536/23.53 |
| 2016/0145344 A1 | 5/2016 | Akbari | |
| 2016/0168640 A1 | 6/2016 | Khosla et al. | |
| 2016/0235838 A1 | 8/2016 | Weiner et al. | |

(Continued)

FOREIGN PATENT DOCUMENTS

| CN | 1917902 A | 2/2007 |
|---|---|---|
| EP | 1725261 B1 | 1/2011 |

(Continued)

OTHER PUBLICATIONS

Sotos et al.; Statistics Education Research Journal, 8(2) 33-55, 2009.*
Andiappan (BMC Genetics. 2010. 11: 36).*
Grotenboer et al; J Allergy Clin Immunol, 2013, vol. 131, pp. 856-865; Feb. 4, 2013.*
Corren et al; NEJM, vol. 365, pp. 1088-1098, 2011.*
Akhabir et al., "Lung expression quantitative trait loci data set identifies important functional polymorphisms in the asthma-associated IL1RL1 region," J Allergy Clin Immunol. 134(3):729-31 (2014).

(Continued)

*Primary Examiner* — Jehanne S Sitton
(74) *Attorney, Agent, or Firm* — Clark & Elbing LLP; Thomas J. Takara

(57) ABSTRACT

The invention relates to methods of treating a patient suffering from an IL-33-mediated disorder, such as asthma, comprising administering to the patient an IL-33 axis binding antagonist based on the genotype of the /L1RL1gene, the genotype of a polymorphism in genomic vicinity to the IL-33 gene, the expression level of periostin or the expression level of soluble ST2. The invention further relates to methods of determining whether a patient is at increased risk of an IL-33-mediated disorder, as well as methods of determining whether a patient suffering from such a disorder is likely to respond to a treatment comprising an IL-33 axis binding antagonist, based on the genotype of the /L1RL1gene the genotype of a polymorphism in genomic vicinity to the IL-33 gene, the expression level of periostin or the expression level of soluble ST2.

12 Claims, 15 Drawing Sheets
Specification includes a Sequence Listing.

(56) References Cited

U.S. PATENT DOCUMENTS

| | | | |
|---|---|---|---|
| 2017/0066831 A1 | 3/2017 | Duffy et al. | |
| 2017/0096483 A1 | 4/2017 | Orengo et al. | |

FOREIGN PATENT DOCUMENTS

| | | | |
|---|---|---|---|
| EP | 2271672 B1 | 11/2015 | |
| EP | 2734222 B1 | 10/2016 | |
| JP | 2014-506321 A | 3/2014 | |
| WO | WO-96/27603 A1 | 9/1996 | |
| WO | WO-01/21641 A1 | 3/2001 | |
| WO | WO-01/70817 A1 | 9/2001 | |
| WO | WO-2005/062967 A2 | 7/2005 | |
| WO | WO-2005/079844 A2 | 9/2005 | |
| WO | WO-2007/127749 A2 | 11/2007 | |
| WO | WO-2007/130627 A2 | 11/2007 | |
| WO | WO-2007/131031 A2 | 11/2007 | |
| WO | WO-2007/140205 A2 | 12/2007 | |
| WO | WO-2007/143295 A2 | 12/2007 | |
| WO | WO-2008/066443 A1 | 6/2008 | |
| WO | WO-2008/132709 A1 | 11/2008 | |
| WO | WO-2008/144610 A1 | 11/2008 | |
| WO | WO-2009/053098 A1 | 4/2009 | |
| WO | WO-2009/120899 A2 | 10/2009 | |
| WO | WO-2009/120903 A9 | 10/2009 | |
| WO | WO-2010/087972 A2 | 8/2010 | |
| WO | WO-2010/102251 A2 | 9/2010 | |
| WO | WO-2011/031600 A1 | 3/2011 | |
| WO | WO-2011/047266 A1 | 4/2011 | |
| WO | WO-2011/143562 A2 | 11/2011 | |
| WO | WO-2012/055891 A1 | 5/2012 | |
| WO | WO-2012/083132 A2 | 6/2012 | |
| WO | WO-2012/088094 A2 | 6/2012 | |
| WO | WO-2012/103240 A2 | 8/2012 | |
| WO | WO-2012/113927 A1 | 8/2012 | |
| WO | WO-2012/145209 A2 | 10/2012 | |
| WO | WO-2013/165894 A2 | 11/2013 | |
| WO | WO-2013/173761 A2 | 11/2013 | |
| WO | WO-2014/062621 A1 | 4/2014 | |
| WO | WO-2014/072446 A1 | 5/2014 | |
| WO | WO-2014/090800 A1 | 6/2014 | |
| WO | WO-2014/126277 A1 | 8/2014 | |
| WO | WO-2014/128254 A1 | 8/2014 | |
| WO | WO-2014/152195 A1 | 9/2014 | |
| WO | WO-2014/164959 A2 | 10/2014 | |
| WO | WO-2014/178392 A1 | 11/2014 | |
| WO | WO-2015/042521 A1 | 3/2015 | |
| WO | WO-2015/054012 A1 | 4/2015 | |
| WO | WO-2015/061441 A1 | 4/2015 | |
| WO | WO-2015/077888 A1 | 6/2015 | |
| WO | WO-2015/099175 A1 | 7/2015 | |
| WO | WO-2015/106080 A1 | 7/2015 | |
| WO | WO-2015/132602 A1 | 9/2015 | |
| WO | WO-2015/143343 A2 | 9/2015 | |
| WO | WO-2015/164354 A1 | 10/2015 | |
| WO | WO-2015/179918 A1 | 12/2015 | |
| WO | WO-2016/020502 A1 | 2/2016 | |
| WO | WO-2016/077366 A1 | 5/2016 | |
| WO | WO-2016/077381 A1 | 5/2016 | |
| WO | WO-2016/085832 A1 | 6/2016 | |
| WO | WO-2016/090250 A1 | 6/2016 | |
| WO | WO-2016/122865 A1 | 8/2016 | |
| WO | WO-2016/138590 A1 | 9/2016 | |
| WO | WO-2016/140921 A1 | 9/2016 | |
| WO | WO-2016/149276 A1 | 9/2016 | |
| WO | WO-2016/156440 A1 | 10/2016 | |
| WO | WO-2016/207304 A2 | 12/2016 | |
| WO | WO-2017/009750 A1 | 1/2017 | |
| WO | WO-2017/021814 A1 | 2/2017 | |
| WO | WO-2017/187307 A1 | 11/2017 | |

OTHER PUBLICATIONS

Ho et al., "Common genetic variation at the IL1RL1 locus regulates IL-33/ST2 signaling," J Clin Invest. 123(10):4208-18 (2013).

Ito et al., "ST2: the biomarker at the heart of GVHD severity," Blood. 125(1):10-1 (2015).
Jang et al., "Interleukin-33 and Mast Cells Bridge Innate and Adaptive Immunity: From the Allergologist's Perspective," Int Neurourol J. 19(3):142-50 (2015).
Kakkar et al., "The IL-33/ST2 pathway: therapeutic target and novel biomarker," Nat Rev Drug Discov. 7(10):827-40 (2008).
Qiu et al., "Anti-interleukin-33 inhibits cigarette smoke-induced lung inflammation in mice," Immunology. 138(1):76-82 (2013).
Ramirez-Carrozzi et al., "Functional analysis of protective IL1RL1 variants associated with asthma risk," J Allergy Clin Immunol. 135(4):1080-3.e3 (2015).
Sedhom et al., "Neutralisation of the interleukin-33/ST2 pathway ameliorates experimental colitis through enhancement of mucosal healing in mice," Gut. 62(12):1714-23 (2013).
International Search Report and Written Opinion for International Patent Application No. PCT/US2015/059982, dated May 4, 2016 (26 pages).
Invitation to Pay Additional Fees for International Patent Application No. PCT/US2015/059982, dated Feb. 22, 2016 (11 pages).
International Preliminary Report on Patentability for International Patent Application No. PCT/US2015/059982, dated May 16, 2017 (14 pages).
Nabe, "Interleukin (IL)-33: new therapeutic target for atopic diseases," J Pharmacol Sci. 126(2):85-91 (2014).
Kim et al., "Anti-IL-33 antibody has a therapeutic effect in a murine model of allergic rhinitis," Allergy. 67(2):183-90 (2012).
Li et al., "IL-33 neutralization suppresses lupus disease in lupus-prone mice," Inflammation. 37(3):824-32 (2014).
International Preliminary Report on Patentability for International Patent Application No. PCT/US2015/060008, dated May 16, 2017 (9 pages).
International Search Report and Written Opinion for International Application No. PCT/US2015/060008, dated Mar. 4, 2016 (15 pages).
Hamzaoui et al., "Induced sputum levels of IL-33 and soluble ST2 in young asthmatic children," J Asthma. 50(8):803-9 (2013).
Matsumoto, "Serum periostin: a novel biomarker for asthma management," Allergol Int. 63(2):153-60 (2014).
Cairns, "Inhibitors of mast cell tryptase beta as therapeutics for the treatment of asthma and inflammatory disorders," Pulm Pharmacol Ther. 18(1):55-66 (2005).
Brown et al., "Tolerance of single, but not multiple, amino acid replacements in antibody $V_H$ CDR2: a means of minimizing B cell wastage from somatic hypermutation?" J Immunol. 156(9):3285-91 (1996).
Liu et al., "Anti-IL-33 antibody treatment inhibits airway inflammation in a murine model of allergic asthma," Biochem Biophys Res Commun. 386(1):181-5 (2009).
Yuan et al., "Construction of human nonimmune library and selection of scFvs against IL-33," Appl Biochem Biotechnol. 167(3):498-509 (2012).
Communication pursuant to Article 94(3) EPC for European Patent Application No. 15802254.1, dated Oct. 18, 2019 (6 pages).
Gasset et al., "A peptide mimetic of an anti-CD4 monoclonal antibody by rational design," Biochem Biophys Res Commun. 307(1):198-205 (2003).
Paul, Chapter 9: Structure and Function of Immunoglobulins. *Fundamental Immunology, Third Edition*. Raven Press Ltd., 292-295 (1993).
Office Action for U.S. Appl. No. 14/937,778, dated Nov. 2, 2017 (13 pages).
Notice of Reasons for Rejection for Japanese Patent Application No. 2017-525088, dated Dec. 24, 2019 (12 pages).
Askmyr et al., "Selective killing of candidate AML stem cells by antibody targeting of IL1RAP," Blood. 121(18):3709-13 (2013).
Xi et al., "IL-33 amplifies an innate immune response in the degenerating retina," J Exp Med. 213(2):189-207 (2016).
Xia et al., "Increased IL-33 expression in chronic obstructive pulmonary disease," Am J Physiol Lung Cell Mol Physiol. 308(7):L619-L627 (2015).
Decision of Rejection for Japanese Patent Application No. 2017-525088, dated Nov. 4, 2020 (8 pages).

(56) References Cited

OTHER PUBLICATIONS

Alves-Filho et al., "Interleukin-33 attenuates sepsis by enhancing neutrophil influx to the site of infection," Nat Med. 16(6):708-12 (2010) (6 pages).
Bonilla et al., "The Alarmin Interleukin-33 Drives Protective Antiviral CD8+ T Cell Responses," Science. 335(6071):984-9 (2012) (7 pages).
Fournié et al., "The Pro-tumorigenic IL-33 Involved in Antitumor Immunity: A Yin and Yang Cytokine," Front Immunol. 9:2506 (2018) (9 pages).
Liew et al., "Interleukin-33 in health and disease," Nat Rev Immunol. 16(11):676-689 (2016).
Lu et al., "Interleukin-33 prevents the development of autoimmune diabetes in NOD mice," Int Immunopharmacol. 70:9-15 (2019).
O'Donnell et al., "An antitumorigenic role for the IL-33 receptor, ST2L, in colon cancer," Br J Cancer. 114(1):37-43 (2016).
Sakai et al., "Interleukin-33 is Hepatoprotective During Liver Ischemia/Reperfusion in Mice," Hepatology. 56(4):1468-78 (2012).
English translation of Chinese Office Action for Chinese Patent Application No. 201580072832.7, dated Nov. 30, 2021 (3 pages).

\* cited by examiner

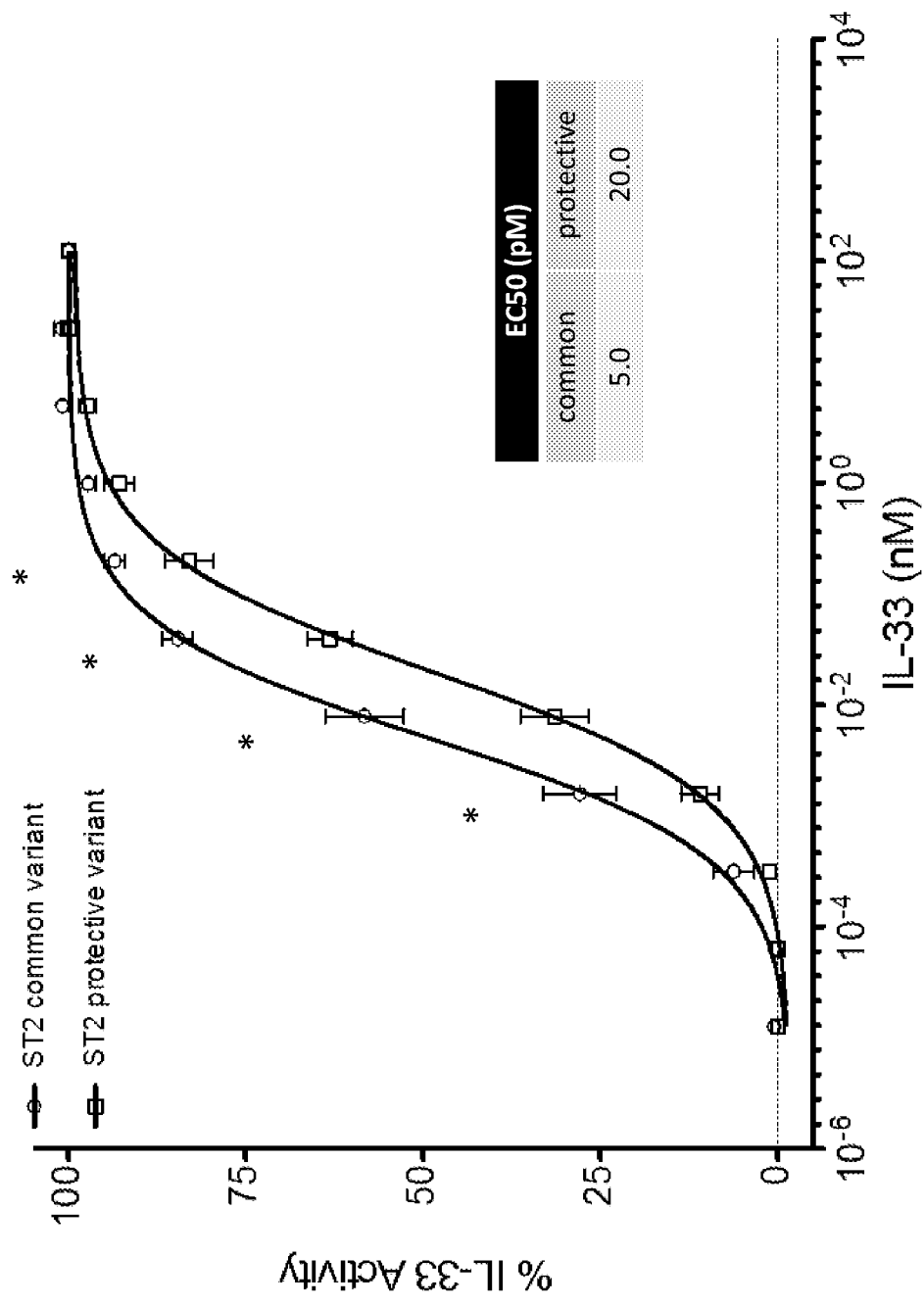

| EC50 (pM) | | | | | |
|---|---|---|---|---|---|
| common | TIR A433T | TIR Q501R | C-term T549I L551S | protective | Parental |
| 3.4 | 3.6 | 4.3 | 3.5 | 3.7 | 4.0 |

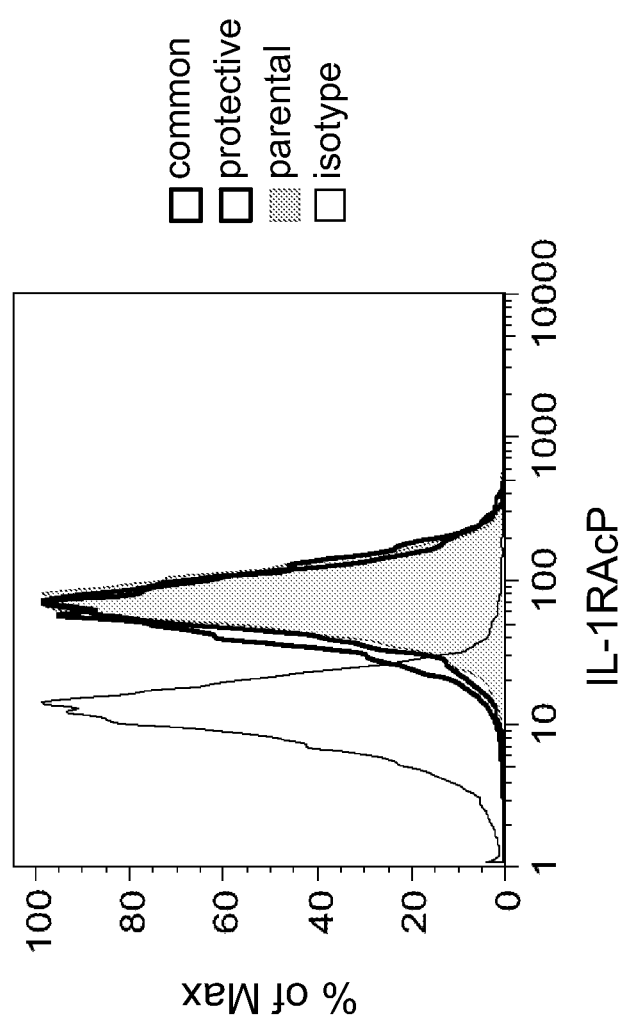

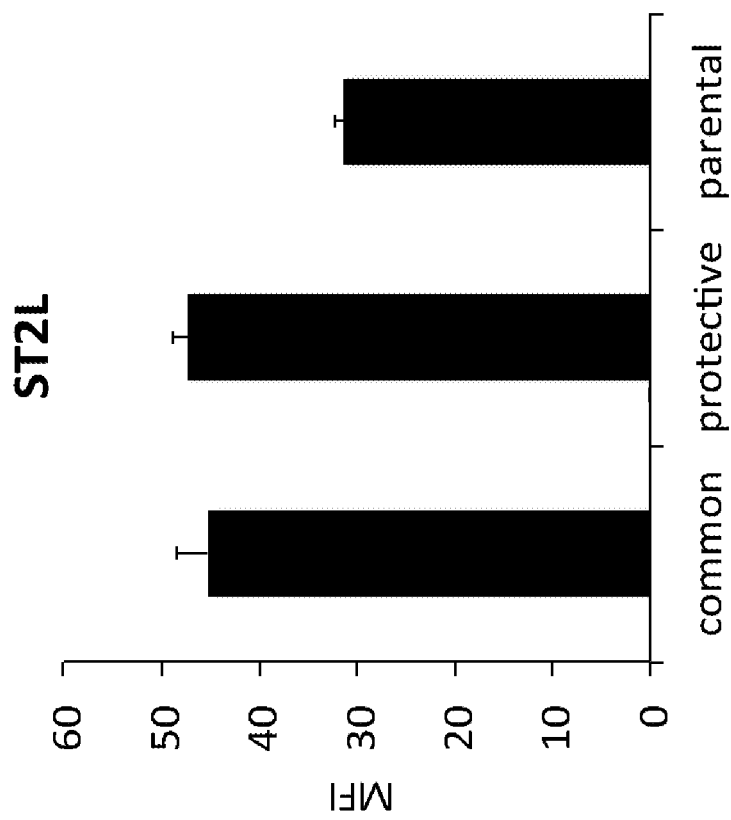

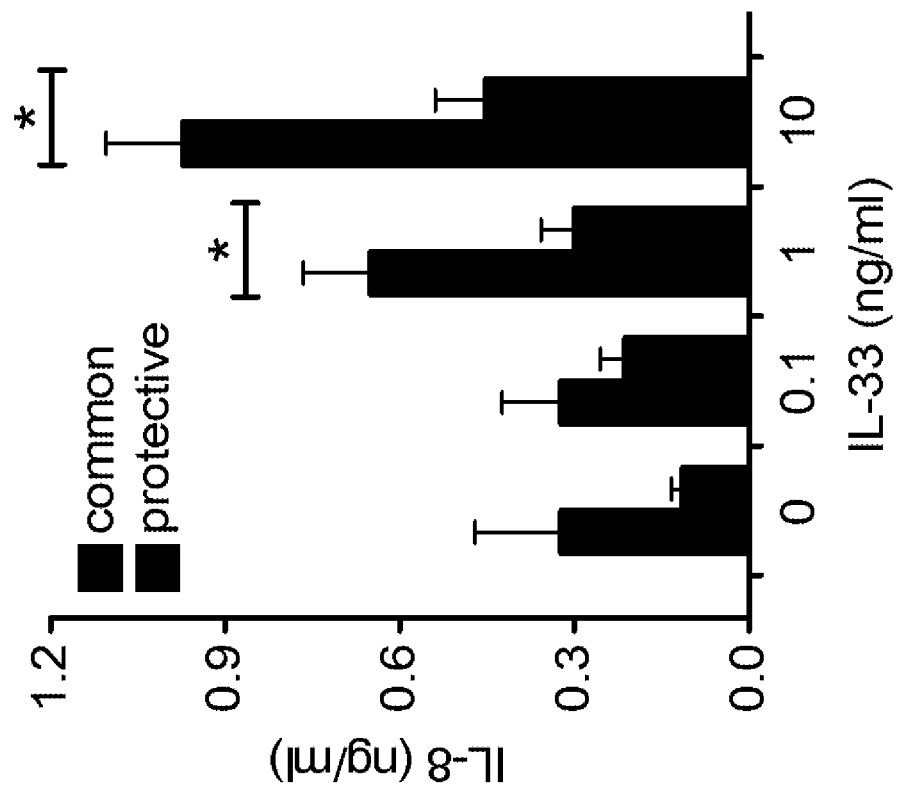

Figure 6

| | CHR | SNP | Location/function | All vs. control | | Periostin High vs. control | | Periostin Low vs. control | | MAF | | |
|---|---|---|---|---|---|---|---|---|---|---|---|---|
| | | | | P | OR | P | OR | P | OR | CTRL | HI | LO |
| ST2 | 2 | rs3771166# | intronic | 5.83E-05 | 0.70 | 0.009 | 0.73 | 4.17E-05 | 0.63 | 0.38 | 0.34 | 0.30 |
| ST2 | 2 | rs10204137 | Q>R | 2.97E-05 | 0.68 | 0.007 | 0.72 | 2.34E-05 | 0.62 | 0.38 | 0.34 | 0.30 |
| ST2 | 2 | rs10206753 | L>S | 5.77E-05 | 0.70 | 0.013 | 0.74 | 2.97E-05 | 0.63 | 0.38 | 0.34 | 0.31 |
| ST2 | 2 | rs10192157 | T>I | 7.41E-05 | 0.70 | 0.012 | 0.74 | 4.78E-05 | 0.64 | 0.38 | 0.34 | 0.31 |
| ST2 | 2 | rs4988956 | A>T | 7.70E-05 | 0.70 | 0.012 | 0.74 | 5.19E-05 | 0.64 | 0.38 | 0.34 | 0.31 |

THERAPEUTIC AND DIAGNOSTIC METHODS FOR IL-33-MEDIATED DISORDERS

FIELD OF THE INVENTION

The present invention is directed to methods of treating patients suffering from interleukin-33 (IL-33)-mediated disorders and methods of determining whether a patient is at increased risk for an IL-33-mediated disorder.

BACKGROUND

Interleukin-33 (IL-33) is a member of the interleukin-1 (IL-1) cytokine family that is encoded by the IL33 gene, and is constitutively expressed in structural cells, such as smooth muscle, epithelial, and endothelial cells. IL-33 can be induced by inflammatory factors in macrophages and dendritic cells. Cellular stress caused by environmental triggers, such as allergens, toxins, and pathogens, can lead to IL-33 release. Bioavailable IL-33 associates with a heterodimeric IL-33 receptor complex composed of suppression of tumorigenicity 2 (ST2) protein and interleukin-1 receptor accessory protein (IL-1RAcP) to activate the AP-1 and NF-κB pathways through the adaptor protein myeloid differentiation primary response 88 (MyD88) and possibly MyD88-adapter-like (Mal) protein. IL-33 stimulates a number of cell types, including innate type II (ILC2) cells, mast cells, basophils, eosinophils, and dendritic cells, to promote Type 2 immunity.

The IL-33 pathway has been suggested to be involved in various diseases, including allergy-related diseases, for which there remains a need to develop improved methods for identifying patient populations best suited to therapy options.

SUMMARY

The present invention is directed to methods of treating patients suffering from interleukin-33 (IL-33)-mediated disorders and methods of determining whether a patient is at increased risk for an IL-33-mediated disorder.

In one aspect, the invention features a method of treating a patient suffering from an interleukin-33 (IL-33)-mediated disorder, the method comprising administering to the patient a therapy comprising an IL-33 axis binding antagonist, wherein the genotype of the patient has been determined to comprise a G allele at polymorphism rs4988956 (SEQ ID NO: 1) or an equivalent allele at a polymorphism in linkage disequilibrium with polymorphism rs4988956 (SEQ ID NO: 1).

In another aspect, the invention features a method of determining whether a patient is at increased risk of an IL-33-mediated disorder, the method comprising determining the genotype at polymorphism rs4988956 (SEQ ID NO: 1) or at a polymorphism in linkage disequilibrium with polymorphism rs4988956 (SEQ ID NO: 1) in a sample derived from the patient, wherein the patient is at increased risk of an IL-33-mediated disorder if the genotype of the patient comprises a G allele at polymorphism rs4988956 (SEQ ID NO: 1) or an equivalent allele at the polymorphism in linkage disequilibrium with polymorphism rs4988956 (SEQ ID NO: 1). In some embodiments, the method further comprises administering an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining in a sample derived from a patient suffering from an IL-33-mediated disorder the genotype at polymorphism rs4988956 (SEQ ID NO: 1) or at a polymorphism in linkage disequilibrium with polymorphism rs4988956 (SEQ ID NO: 1); and (b) identifying the patient as likely to respond to treatment comprising an IL-33 axis binding antagonist based on the genotype, wherein the presence of each G allele at polymorphism rs4988956 (SEQ ID NO: 1) or each equivalent allele at the polymorphism in linkage disequilibrium with polymorphism rs4988956 (SEQ ID NO: 1) indicates that the patient has an increased likelihood of being responsive to treatment comprising an IL-33 axis binding antagonist. In some embodiments, the method further comprises administering an IL-33 axis binding antagonist to the patient.

In some embodiments of any one of the above aspects, the method further comprises determining the level of periostin in a sample derived from the patient. In some embodiments, the patient has an increased likelihood of being responsive to treatment with an IL-33 axis binding antagonist if the level of periostin in the sample is at or below a reference level of periostin. In other embodiments, the patient has an increased likelihood of being responsive to treatment with an IL-33 axis binding antagonist if the level of periostin in the sample is at or above a reference level of periostin.

In some embodiments of any one of the above aspects, the polymorphism in linkage disequilibrium with polymorphism rs4988956 (SEQ ID NO: 1) has a D' value greater than or equal to 0.6 to polymorphism rs4988956 (SEQ ID NO: 1). In some embodiments, the D' value is greater than or equal to 0.8. In some embodiments, the polymorphism in linkage disequilibrium with polymorphism rs4988956 (SEQ ID NO: 1) is a polymorphism in Table 3. In some embodiments, the equivalent allele is the minor allele of the polymorphism in linkage disequilibrium with polymorphism rs4988956 (SEQ ID NO: 1). In some embodiments, the equivalent allele is the major allele of the polymorphism in linkage disequilibrium with polymorphism rs4988956 (SEQ ID NO: 1).

In another aspect, the invention features a method of treating a patient suffering from an IL-33-mediated disorder, the method comprising administering to the patient a therapy comprising an IL-33 axis binding antagonist, wherein the genotype of the patient has been determined to comprise an A allele at polymorphism rs10204137 (SEQ ID NO: 2) or an equivalent allele at a polymorphism in linkage disequilibrium with polymorphism rs10204137 (SEQ ID NO: 2).

In another aspect, the invention features a method of determining whether a patient is at increased risk of an IL-33-mediated disorder, the method comprising determining the genotype at polymorphism rs10204137 (SEQ ID NO: 2) or at a polymorphism in linkage disequilibrium with polymorphism rs10204137 (SEQ ID NO: 2) in a sample derived from the patient, wherein the patient is at increased risk of an IL-33-mediated disorder if the genotype of the patient comprises an A allele at polymorphism rs10204137 (SEQ ID NO: 2) or an equivalent allele at the polymorphism in linkage disequilibrium with polymorphism rs10204137 (SEQ ID NO: 2). In some embodiments, the method further comprises administering an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining in a sample derived from a patient suffering from an IL-33-mediated disorder the genotype at polymorphism rs10204137 (SEQ ID NO: 2) or at a polymorphism in linkage disequilibrium with polymorphism rs10204137 (SEQ ID NO: 2); and (b) identifying the patient as likely to respond to treatment comprising an IL-33 axis binding antagonist based on the genotype, wherein the presence of each A allele at polymorphism rs10204137 (SEQ ID NO: 2) or each equivalent allele at the polymorphism in linkage disequilibrium with polymorphism rs10204137 (SEQ ID NO: 2) indicates that the patient has an increased likelihood of being responsive to treatment comprising an IL-33 axis binding antagonist. In some embodiments, the method further comprises administering an IL-33 axis binding antagonist to the patient.

In some embodiments of any one of the above aspects, the method further comprises determining the level of periostin in a sample derived from the patient. In some embodiments, the patient has an increased likelihood of being responsive to treatment with an IL-33 axis binding antagonist if the level of periostin in the sample is at or below a reference level of periostin. In other embodiments, the patient has an increased likelihood of being responsive to treatment with an IL-33 axis binding antagonist if the level of periostin in the sample is at or above a reference level of periostin.

In some embodiments of any one of the above aspects, the polymorphism in linkage disequilibrium with polymorphism rs10204137 (SEQ ID NO: 2) has a D' value greater than or equal to 0.6 to polymorphism rs10204137 (SEQ ID NO: 2). In some embodiments, the D' value is greater than or equal to 0.8. In some embodiments, the polymorphism in linkage disequilibrium with polymorphism rs10204137 (SEQ ID NO: 2) is a polymorphism in Table 3. In some embodiments, the equivalent allele is the minor allele of the polymorphism in linkage disequilibrium with polymorphism rs10204137 (SEQ ID NO: 2). In other embodiments, the equivalent allele is the major allele of the polymorphism in linkage disequilibrium with polymorphism rs10204137 (SEQ ID NO: 2).

In another aspect, the invention features a method of treating a patient suffering from an IL-33-mediated disorder, the method comprising administering to the patient a therapy comprising an IL-33 axis binding antagonist, wherein the genotype of the patient has been determined to comprise a C allele at polymorphism rs10192036 (SEQ ID NO: 3) or an equivalent allele at a polymorphism in linkage disequilibrium with polymorphism rs10192036 (SEQ ID NO: 3).

In another aspect, the invention features a method of determining whether a patient is at increased risk of an IL-33-mediated disorder, the method comprising determining the genotype at polymorphism rs10192036 (SEQ ID NO: 3) or at a polymorphism in linkage disequilibrium with polymorphism rs10192036 (SEQ ID NO: 3) in a sample derived from the patient, wherein the patient is at increased risk of an IL-33-mediated disorder if the genotype of the patient comprises a C allele at polymorphism rs10192036 (SEQ ID NO: 3) or an equivalent allele at the polymorphism in linkage disequilibrium with polymorphism rs10192036 (SEQ ID NO: 3). In some embodiments, the method further comprises administering an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining in a sample derived from a patient suffering from an IL-33-mediated disorder the genotype at polymorphism rs10192036 (SEQ ID NO: 3) or at a polymorphism in linkage disequilibrium with polymorphism rs10192036 (SEQ ID NO: 3); and (b) identifying the patient as likely to respond to treatment comprising an IL-33 axis binding antagonist based on the genotype, wherein the presence of each C allele at polymorphism rs10192036 (SEQ ID NO: 3) or each equivalent allele at the polymorphism in linkage disequilibrium with polymorphism rs10192036 (SEQ ID NO: 3) indicates that the patient has an increased likelihood of being responsive to treatment comprising an IL-33 axis binding antagonist. In some embodiments, the method further comprises administering an IL-33 axis binding antagonist to the patient.

In some embodiments of any one of the above aspects, the method further comprises determining the level of periostin in a sample derived from the patient. In some embodiments, the patient has an increased likelihood of being responsive to treatment with an IL-33 axis binding antagonist if the level of periostin in the sample is at or below a reference level of periostin. In other embodiments, the patient has an increased likelihood of being responsive to treatment with an IL-33 axis binding antagonist if the level of periostin in the sample is at or above a reference level of periostin.

In some embodiments of any one of the above aspects, the polymorphism in linkage disequilibrium with polymorphism rs10192036 (SEQ ID NO: 3) has a D' value greater than or equal to 0.6 to polymorphism rs10192036 (SEQ ID NO: 3). In some embodiments, the D' value is greater than or equal to 0.8. In some embodiments, the polymorphism in linkage disequilibrium with polymorphism rs10192036 (SEQ ID NO: 3) is a polymorphism in Table 3. In some embodiments, the equivalent allele is the minor allele of the polymorphism in linkage disequilibrium with polymorphism rs10192036 (SEQ ID NO: 3). In other embodiments, the equivalent allele is the major allele of the polymorphism in linkage disequilibrium with polymorphism rs10192036 (SEQ ID NO: 3).

In another aspect, the invention features a method of treating a patient suffering from an IL-33-mediated disorder, the method comprising administering to the patient a therapy comprising an IL-33 axis binding antagonist, wherein the genotype of the patient has been determined to comprise a C allele at polymorphism rs10192157 (SEQ ID NO: 4) or an equivalent allele at a polymorphism in linkage disequilibrium with polymorphism rs10192157 (SEQ ID NO: 4).

In another aspect, the invention features a method of determining whether a patient is at increased risk of an IL-33-mediated disorder, the method comprising determining the genotype at polymorphism rs10192157 (SEQ ID NO: 4) or at a polymorphism in linkage disequilibrium with polymorphism rs10192157 (SEQ ID NO: 4) in a sample derived from the patient, wherein the patient is at increased risk of an IL-33-mediated disorder if the genotype of the patient comprises a C allele at polymorphism rs10192157 (SEQ ID NO: 4) or an equivalent allele at the polymorphism in linkage disequilibrium with polymorphism rs10192157 (SEQ ID NO: 4). In some embodiments, the method further comprises administering an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining in a sample derived from a patient suffering from an IL-33-mediated disorder the genotype at polymorphism rs10192157 (SEQ ID NO: 4) or at a polymorphism in linkage disequilibrium with polymorphism rs10192157 (SEQ ID NO: 4); and (b) identifying the patient as likely to respond to treatment comprising an IL-33 axis binding antagonist based on the genotype, wherein the presence of each C allele at polymorphism rs10192157 (SEQ ID NO: 4) or each equivalent allele at the polymorphism in linkage disequilibrium with polymorphism rs10192157 (SEQ ID NO: 4) indicates that the patient has an increased likelihood of being responsive to treatment comprising an IL-33 axis binding antagonist. In some embodiments, the method further comprises administering an IL-33 axis binding antagonist to the patient.

In some embodiments of any one of the above aspects, the method further comprises determining the level of periostin in a sample derived from the patient. In some embodiments, the patient has an increased likelihood of being responsive to treatment with an IL-33 axis binding antagonist if the level of periostin in the sample is at or below a reference level of periostin. In other embodiments, the patient has an increased likelihood of being responsive to treatment with an IL-33 axis binding antagonist if the level of periostin in the sample is at or above a reference level of periostin.

In some embodiments of any one of the above aspects, the polymorphism in linkage disequilibrium with polymorphism rs10192157 (SEQ ID NO: 4) has a D' value greater than or equal to 0.6 to polymorphism rs10192157 (SEQ ID NO: 4). In some embodiments, the D' value is greater than or equal to 0.8. In some embodiments, the polymorphism in linkage disequilibrium with polymorphism rs10192157 (SEQ ID NO: 4) is a polymorphism in Table 3. In some embodiments, the equivalent allele is the minor allele of the polymorphism in linkage disequilibrium with polymorphism rs10192157 (SEQ ID NO: 4). In other embodiments, the equivalent allele is the major allele of the polymorphism in linkage disequilibrium with polymorphism rs10192157 (SEQ ID NO: 4).

In another aspect, the invention features a method of treating a patient suffering from an IL-33-mediated disorder, the method comprising administering to the patient a therapy comprising an IL-33 axis binding antagonist, wherein the genotype of the patient has been determined to comprise a T allele at polymorphism rs10206753 (SEQ ID NO: 5) or an equivalent allele at a polymorphism in linkage disequilibrium with polymorphism rs10206753 (SEQ ID NO: 5).

In another aspect, the invention features a method of determining whether a patient is at increased risk of an IL-33-mediated disorder, the method comprising determining the genotype at polymorphism rs10206753 (SEQ ID NO: 5) or at a polymorphism in linkage disequilibrium with polymorphism rs10206753 (SEQ ID NO: 5) in a sample derived from the patient, wherein the patient is at increased risk of an IL-33-mediated disorder if the genotype of the patient comprises a T allele at polymorphism rs10206753 (SEQ ID NO: 5) or an equivalent allele at the polymorphism in linkage disequilibrium with polymorphism rs10206753 (SEQ ID NO: 5). In some embodiments, the method further comprises administering an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining in a sample derived from a patient suffering from an IL-33-mediated disorder the genotype at polymorphism rs10206753 (SEQ ID NO: 5) or at a polymorphism in linkage disequilibrium with polymorphism rs10206753 (SEQ ID NO: 5); and (b) identifying the patient as likely to respond to treatment comprising an IL-33 axis binding antagonist based on the genotype, wherein the presence of each T allele at polymorphism rs10206753 (SEQ ID NO: 5) or each equivalent allele at the polymorphism in linkage disequilibrium with polymorphism rs10206753 (SEQ ID NO: 5) indicates that the patient has an increased likelihood of being responsive to treatment comprising an IL-33 axis binding antagonist. In some embodiments, the method further comprises administering an IL-33 axis binding antagonist to the patient.

In some embodiments of any one of the above aspects, the method further comprises determining the level of periostin in a sample derived from the patient. In some embodiments, the patient has an increased likelihood of being responsive to treatment with an IL-33 axis binding antagonist if the level of periostin in the sample is at or below a reference level of periostin. In other embodiments, the patient has an increased likelihood of being responsive to treatment with an IL-33 axis binding antagonist if the level of periostin in the sample is at or above a reference level of periostin.

In some embodiments of any one of the above aspects, the polymorphism in linkage disequilibrium with polymorphism rs10206753 (SEQ ID NO: 5) has a D' value greater than or equal to 0.6 to polymorphism rs10206753 (SEQ ID NO: 5). In some embodiments, the D' value is greater than or equal to 0.8. In some embodiments, the polymorphism in linkage disequilibrium with polymorphism rs10206753 (SEQ ID NO: 5) is a polymorphism in Table 3. In some embodiments, the equivalent allele is the minor allele of the polymorphism in linkage disequilibrium with polymorphism rs10206753 (SEQ ID NO: 5). In other embodiments, the equivalent allele is the major allele of the polymorphism in linkage disequilibrium with polymorphism rs10206753 (SEQ ID NO: 5).

In another aspect, the invention features a method of treating a patient suffering from an IL-33-mediated disorder, the method comprising administering to the patient a therapy comprising an IL-33 axis binding antagonist, wherein the genotype of the patient has been determined to comprise a T allele at polymorphism rs4742165 (SEQ ID NO: 6) or an equivalent allele at a polymorphism in linkage disequilibrium with polymorphism rs4742165 (SEQ ID NO: 6).

In another aspect, the invention features a method of determining whether a patient is at increased risk of an IL-33-mediated disorder, the method comprising determining the genotype at polymorphism rs4742165 (SEQ ID NO: 6) or at a polymorphism in linkage disequilibrium with polymorphism rs4742165 (SEQ ID NO: 6) in a sample derived from the patient, wherein the patient is at increased risk of an IL-33-mediated disorder if the genotype of the patient comprises a T allele at polymorphism rs4742165 (SEQ ID NO: 6) or an equivalent allele at the polymorphism in linkage disequilibrium with polymorphism rs4742165 (SEQ ID NO: 6). In some embodiments, the method further comprises administering an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining in a sample derived from a patient suffering from an IL-33-mediated disorder the genotype at polymorphism rs4742165 (SEQ ID NO: 6) or at a polymorphism in linkage disequilibrium with polymorphism rs4742165 (SEQ ID NO: 6); and (b) identifying the patient as likely to respond to treatment comprising an IL-33 axis binding antagonist based on the genotype, wherein the presence of each T allele at polymorphism rs4742165 (SEQ ID NO: 6) or each equivalent allele at the polymorphism in linkage disequilibrium with polymorphism rs4742165 (SEQ ID NO: 6) indicates that the patient has an increased likelihood of being responsive to treatment comprising an IL-33 axis binding antagonist. In some embodiments, the method further comprises administering an IL-33 axis binding antagonist to the patient.

In some embodiments of any one of the above aspects, the polymorphism in linkage disequilibrium with polymorphism rs4742165 (SEQ ID NO: 6) has a D' value greater than or equal to 0.6 to polymorphism rs4742165 (SEQ ID NO: 6). In some embodiments, the D' value is greater than or equal to 0.8. In some embodiments, the polymorphism in linkage disequilibrium with polymorphism rs4742165 (SEQ ID NO: 6) is a polymorphism in Table 4. In some embodiments, the equivalent allele is the minor allele of the polymorphism in linkage disequilibrium with polymorphism rs4742165 (SEQ ID NO: 6). In other embodiments, the equivalent allele is the major allele of the polymorphism in linkage disequilibrium with polymorphism rs4742165 (SEQ ID NO: 6).

In another aspect, the invention features a method of treating a patient suffering from an IL-33-mediated disorder, the method comprising administering to the patient a therapy comprising an IL-33 axis binding antagonist, wherein the genotype of the patient has been determined to comprise two or more of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In another aspect, the invention features a method of determining whether a patient is at increased risk of an IL-33-mediated disorder, the method comprising determining the genotype at two or more polymorphisms selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), rs4742165 (SEQ ID NO: 6), and a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6) in a sample derived from the patient, wherein the patient is at increased risk of an IL-33-mediated disorder if: (a) the genotype of the patient comprises a G allele at polymorphism rs4988956 (SEQ ID NO: 1); (b) the genotype of the patient comprises an A allele at polymorphism rs10204137 (SEQ ID NO: 2); (c) the genotype of the patient comprises a C allele at polymorphism rs10192036 (SEQ ID NO: 3); (d) the genotype of the patient comprises a C allele at polymorphism rs10192157 (SEQ ID NO: 4); (e) the genotype of the patient comprises a T allele at polymorphism rs10206753 (SEQ ID NO: 5) (f) the genotype of the patient comprises a T allele at polymorphism rs4742165 (SEQ ID NO: 6); and/or (g) the genotype of the patient comprises an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6). In some embodiments, the method further comprises administering an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining in a sample derived from a patient suffering from an IL-33-mediated disorder the genotype at two or more polymorphisms selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), rs4742165 (SEQ ID NO: 6), and a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); and (b) identifying the patient as likely to respond to treatment comprising an IL-33 axis binding antagonist based on the genotype, wherein the presence of: (i) each G allele at polymorphism rs4988956 (SEQ ID NO: 1); (ii) each A allele at polymorphism rs10204137 (SEQ ID NO: 2); (iii) each C allele at polymorphism rs10192036 (SEQ ID NO: 3); (iv) each C allele at polymorphism rs10192157 (SEQ ID NO: 4); (v) each T allele at polymorphism rs10206753 (SEQ ID NO: 5); (vi) each T allele at polymorphism rs4742165 (SEQ ID NO: 6); and/or (vii) each equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6) indicates that the patient has an increased likelihood of being responsive to treatment comprising an IL-33 axis binding antagonist. In some embodiments of this aspect, the patient has been determined to comprise a G allele at polymorphism rs4988956 (SEQ ID NO: 1) and an A allele at polymorphism rs10204137 (SEQ ID NO: 2). In some embodiments of this aspect, the genotype of the patient has been determined to comprise a G allele at polymorphism rs4988956 (SEQ ID NO: 1) and a C allele at polymorphism rs10192036 (SEQ ID NO: 3). In some embodiments of this aspect, the genotype of the patient has been determined to further comprise a C allele at polymorphism rs10192157 (SEQ ID NO: 4) or a T allele at polymorphism rs10206753 (SEQ ID NO: 5). In some embodiments of this aspect, the genotype of the patient has been determined to further comprise a C allele at polymorphism rs10192157 (SEQ ID NO: 4) and a T allele at polymorphism rs10206753 (SEQ ID NO: 5). In some embodiments of this aspect, the genotype of the patient has been determined to comprise: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); and a T allele at polymorphism rs4742165 (SEQ ID NO: 6). In some embodiments, the method further comprises administering an IL-33 axis binding antagonist to the patient.

In some embodiments of any one of the above aspects, the method further comprises determining the level of periostin in a sample derived from the patient. In some embodiments, the patient has an increased likelihood of being responsive to treatment with an IL-33 axis binding antagonist if the level of periostin in the sample is at or below a reference level of periostin. In other embodiments, the patient has an increased likelihood of being responsive to treatment with an IL-33 axis binding antagonist if the level of periostin in the sample is at or above a reference level of periostin.

In some embodiments of any one of the above aspects, the polymorphism in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6) has a D' value greater than or equal to 0.6 to the selected polymorphism. In some embodiments, the D' value is greater than or equal to 0.8. In some embodiments, the polymorphism in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6) is a polymorphism in Table 3 or Table 4. In some embodiments, the equivalent allele is the minor allele of the polymorphism in linkage disequilibrium with polymorphism rs4742165 (SEQ ID NO: 6). In other embodiments, the equivalent allele is the major allele of the polymorphism in linkage disequilibrium with polymorphism rs10206753 (SEQ ID NO: 5).

In another aspect, the invention features a method of selecting a therapy for a patient having an IL-33-mediated disorder, the method comprising: (a) determining the level of periostin in a sample derived from the patient; (b) comparing the level of periostin in the sample derived from the patient to a reference level of periostin; and (c) selecting a therapy comprising an IL-33 axis binding antagonist if the level of periostin in the sample is at or below the reference level. In some embodiments, the method further comprises administering a therapy comprising an IL-33 axis binding antagonist to the patient.

In another aspect, the invention features a method of treating a patient suffering from an IL-33-mediated disorder, the method comprising administering to the patient a therapy comprising an IL-33 axis binding antagonist, wherein the level of soluble ST2 (sST2) in a sample derived from the patient has been determined to be at or above a reference level of sST2.

In another aspect, the invention features a method of determining whether a patient is at increased risk of an IL-33-mediated disorder, the method comprising: (a) determining the level of sST2 in a sample derived from the patient; and (b) comparing the level of sST2 in the sample derived from the patient to a reference level of sST2, wherein the patient is at an increased risk of an IL-33-mediated disorder if the level of sST2 in the sample derived from the patient is at or above the reference level. In some embodiments, the method further comprises administering a therapy comprising an IL-33 axis binding antagonist to the patient.

In another aspect, the invention features a method of selecting a therapy for a patient having an IL-33-mediated disorder, the method comprising: (a) determining the level of sST2 in a sample derived from the patient; (b) comparing the level of sST2 in the sample derived from the patient to a reference level of sST2; and (c) selecting a therapy comprising an IL-33 axis binding antagonist if the level of sST2 in the sample is at or above the reference level. In some embodiments, the method further comprises administering a therapy comprising an IL-33 axis binding antagonist to the patient.

In another aspect, the invention features a method of determining whether a patient suffering from an IL-33-mediated disorder is likely to respond to treatment comprising an IL-33 axis binding antagonist, the method comprising: (a) determining the level of sST2 in a sample derived from the patient; (b) comparing the level of sST2 in the sample derived from the patient to a reference level of sST2; and (c) identifying the patient as likely to respond to treatment comprising an IL-33 axis binding antagonist based on the level of sST2 in the sample derived from the patient, wherein the patient has an increased likelihood of being responsive to treatment comprising an IL-33 axis binding antagonist if the level of sST2 in the sample is at or above the reference level. In some embodiments, the method further comprises administering a therapy comprising an IL-33 axis binding antagonist to the patient.

In another aspect, the invention features a method for assessing a treatment response of a patient treated with an IL-33 axis binding antagonist, the method comprising: (a) determining the level of sST2 in a sample derived from the patient at a time point during or after administration of the IL-33 axis binding antagonist; and (b) maintaining, adjusting, or stopping the treatment of the patient based on a comparison of the level of sST2 in the sample derived from the patient with a reference level of sST2, wherein a change in the level of sST2 in the sample derived from the patient compared to the reference level is indicative of a response to treatment with the IL-33 axis binding antagonist. In some embodiments of this aspect, the change is an increase in the level of sST2 and treatment is maintained. In other embodiments of this aspect, the change is a decrease in the level of sST2 and treatment is stopped.

In another aspect, the invention features a method for monitoring the response of a patient treated with a IL-33 axis binding antagonist, the method comprising: (a) determining the level of sST2 in a sample derived from the patient at a time point during or after administration of the IL-33 axis binding antagonist; and (b) comparing the level of sST2 in the sample derived from the patient with a reference level of sST2, thereby monitoring the response in the patient undergoing treatment with the IL-33 axis binding antagonist.

In some embodiments of any one of the above aspects, the method further comprises determining the level of periostin in a sample derived from the patient. In some embodiments, the patient has an increased likelihood of being responsive to treatment with an IL-33 axis binding antagonist if the level of periostin in the sample is at or below a reference level of periostin. In other embodiments, the patient has an increased likelihood of being responsive to treatment with an IL-33 axis binding antagonist if the level of periostin in the sample is at or above a reference level of periostin.

In some embodiments of any one of the above aspects, the level of sST2 is a level of sST2 protein. In some embodiments, the sample derived from the patient is a whole blood sample, a serum sample, a plasma sample, or a combination thereof. In some embodiments, the sample derived from the patient is a serum sample. In some embodiments, the reference level of sST2 is a level of sST2 determined from a group of individuals, wherein each member of the group has a genotype comprising two G alleles at polymorphism rs4742165 (SEQ ID NO: 6). In some embodiments, the reference level of sST2 is a level of sST2 determined from a group of individuals, wherein each member of the group has a genotype comprising two G alleles at polymorphism rs3771166 (SEQ ID NO: 8). In some embodiments, the group of individuals is suffering from asthma. In some embodiments, the reference level of sST2 is a median level. In some embodiments, the group of individuals is a group of female individuals and the patient is female. In some embodiments, the group of individuals is a group of male individuals and the patient is male. In some embodiments, the reference level is determined in an individual at an earlier timepoint, e.g., before treatment with an IL-33 axis binding antagonist or at an earlier timepoint during treatment with an IL-33 axis binding antagonist.

In some embodiments of any one of the above aspects, the IL-33 axis binding antagonist is administered in combination with a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some embodiments, the IL-33 axis binding antagonist is an IL-33 binding antagonist, an ST2 binding antagonist, or an IL-1RAcP binding antagonist. In some embodiments, (a) the IL-33 binding antagonist is an anti-IL33 antibody or antigen-binding fragment thereof; (b) the ST2 binding antagonist is an ST2-Fc protein, an anti-ST2 antibody, or antigen-binding fragment thereof; or (c) the IL-1RAcP binding antagonist is an anti-IL-1RAcP antibody.

In some embodiments of any one of the above aspects, the IL-33-mediated disorder is selected from the group consisting of an inflammatory condition, an immune disorder, a fibrotic disorder, an eosinophilic disorder, an infection, pain, a central nervous system disorder, a solid tumor, and an ophthalmologic disorder. In some embodiments, the inflammatory condition is selected from the group consisting of asthma, sepsis, septic shock, atopic dermatitis, allergic rhinitis, rheumatoid arthritis, and chronic obstructive pulmonary disease (COPD). In some embodiments, the immune disorder is selected from the group consisting of asthma, rheumatoid arthritis, allergy, anaphylaxis, anaphylactic shock, allergic rhinitis, psoriasis, inflammatory bowel disease (IBD), Crohn's disease, diabetes, and liver disease. In some embodiments, the fibrotic disease is idiopathic pulmonary fibrosis (IPF). In some embodiments, the eosinophilic disorder is an eosinophil-associated gastrointestinal disorder (EGID). In some embodiments, the EGID is eosinophilic esophagitis. In some embodiments, the infection is a helminth infection, a protozoan infection, or a viral infection. In some embodiments, the protozoan infection is a *Leishmania major* infection. In some embodiments, the viral infection is a respiratory syncytial virus (RSV) infection or an influenza infection. In some embodiments, the pain is inflammatory pain. In some embodiments, the central nervous system disorder is Alzheimer's disease. In some embodiments, the solid tumor is selected from the group consisting of breast tumor, colon tumor, prostate tumor, lung tumor, kidney tumor, liver tumor, pancreas tumor, stomach tumor, intestinal tumor, brain tumor, bone tumor, and skin tumor. In some embodiments, the ophthalmologic disorder is age-related macular degeneration (AMD) or retinopathy of the eye.

In some embodiments of any one of the above aspects, the reference level of periostin is between about 23 ng/ml and about 50 ng/ml.

In some embodiments of any one of the above aspects, the sample derived from the patient is a whole blood sample, a serum sample, a plasma sample, or a combination thereof.

In another aspect, the invention features an IL-33 axis binding antagonist for use in treating a patient suffering from an IL-33-mediated disorder, wherein the patient, prior to any administration of an IL-33 axis binding antagonist, has been determined to comprise a G allele at polymorphism rs4988956 (SEQ ID NO: 1) or an equivalent allele at a polymorphism in linkage disequilibrium with polymorphism rs4988956 (SEQ ID NO: 1).

In another aspect, the invention features a use of an effective amount of an IL-33 axis binding antagonist in the manufacture of a medicament for use in treating a patient suffering from an IL-33-mediated disorder, wherein the patient has been determined to comprise a G allele at polymorphism rs4988956 (SEQ ID NO: 1) or an equivalent allele at a polymorphism in linkage disequilibrium with polymorphism rs4988956 (SEQ ID NO: 1).

In another aspect, the invention features a composition comprising an effective amount of an IL-33 axis binding antagonist for use in a method of treating a patient suffering from an IL-33-mediated disorder, wherein the patient has been determined to comprise a G allele at polymorphism rs4988956 (SEQ ID NO: 1) or an equivalent allele at a polymorphism in linkage disequilibrium with polymorphism rs4988956 (SEQ ID NO: 1).

In another aspect, the invention features an IL-33 axis binding antagonist for use in treating a patient suffering from an IL-33-mediated disorder, wherein the patient, prior to any administration of an IL-33 axis binding antagonist, has been determined to comprise an A allele at polymorphism rs10204137 (SEQ ID NO: 2) or an equivalent allele at a polymorphism in linkage disequilibrium with polymorphism rs10204137 (SEQ ID NO: 2).

In another aspect, the invention features a use of an effective amount of an IL-33 axis binding antagonist in the manufacture of a medicament for use in treating a patient suffering from an IL-33-mediated disorder, wherein the patient has been determined to comprise an A allele at polymorphism rs10204137 (SEQ ID NO: 2) or an equivalent allele at a polymorphism in linkage disequilibrium with polymorphism rs10204137 (SEQ ID NO: 2).

In another aspect, the invention features a composition comprising an effective amount of an IL-33 axis binding antagonist for use in a method of treating a patient suffering from an IL-33-mediated disorder, wherein the patient has been determined to comprise an A allele at polymorphism rs10204137 (SEQ ID NO: 2) or an equivalent allele at a polymorphism in linkage disequilibrium with polymorphism rs10204137 (SEQ ID NO: 2).

In another aspect, the invention features an IL-33 axis binding antagonist for use in treating a patient suffering from an IL-33-mediated disorder, wherein the patient, prior to any administration of an IL-33 axis binding antagonist, has been determined to comprise a C allele at polymorphism rs10192036 (SEQ ID NO: 3) or an equivalent allele at a polymorphism in linkage disequilibrium with polymorphism rs10192036 (SEQ ID NO: 3).

In another aspect, the invention features a use of an effective amount of an IL-33 axis binding antagonist in the manufacture of a medicament for use in treating a patient suffering from an IL-33-mediated disorder, wherein the patient has been determined to comprise a C allele at polymorphism rs10192036 (SEQ ID NO: 3) or an equivalent allele at a polymorphism in linkage disequilibrium with polymorphism rs10192036 (SEQ ID NO: 3).

In another aspect, the invention features a composition comprising an effective amount of an IL-33 axis binding antagonist for use in a method of treating a patient suffering from an IL-33-mediated disorder, wherein the patient has been determined to comprise a C allele at polymorphism rs10192036 (SEQ ID NO: 3) or an equivalent allele at a polymorphism in linkage disequilibrium with polymorphism rs10192036 (SEQ ID NO: 3).

In another aspect, the invention features an IL-33 axis binding antagonist for use in treating a patient suffering from an IL-33-mediated disorder, wherein the patient, prior to any administration of an IL-33 axis binding antagonist, has been determined to comprise a C allele at polymorphism rs10192157 (SEQ ID NO: 4) or an equivalent allele at a polymorphism in linkage disequilibrium with polymorphism rs10192157 (SEQ ID NO: 4).

In another aspect, the invention features a use of an effective amount of an IL-33 axis binding antagonist in the manufacture of a medicament for use in treating a patient suffering from an IL-33-mediated disorder, wherein the patient has been determined to comprise a C allele at polymorphism rs10192157 (SEQ ID NO: 4) or an equivalent allele at a polymorphism in linkage disequilibrium with polymorphism rs10192157 (SEQ ID NO: 4).

In another aspect, the invention features a composition comprising an effective amount of an IL-33 axis binding antagonist for use in a method of treating a patient suffering from an IL-33-mediated disorder, wherein the patient has been determined to comprise a C allele at polymorphism rs10192157 (SEQ ID NO: 4) or an equivalent allele at a polymorphism in linkage disequilibrium with polymorphism rs10192157 (SEQ ID NO: 4).

In another aspect, the invention features an IL-33 axis binding antagonist for use in treating a patient suffering from an IL-33-mediated disorder, wherein the patient, prior to any administration of an IL-33 axis binding antagonist, has been determined to comprise a T allele at polymorphism rs10206753 (SEQ ID NO: 5) or an equivalent allele at a polymorphism in linkage disequilibrium with polymorphism rs10206753 (SEQ ID NO: 5).

In another aspect, the invention features a use of an effective amount of an IL-33 axis binding antagonist in the manufacture of a medicament for use in treating a patient suffering from an IL-33-mediated disorder, wherein the patient has been determined to comprise a T allele at polymorphism rs10206753 (SEQ ID NO: 5) or an equivalent allele at a polymorphism in linkage disequilibrium with polymorphism rs10206753 (SEQ ID NO: 5).

In another aspect, the invention features a composition comprising an effective amount of an IL-33 axis binding antagonist for use in a method of treating a patient suffering from an IL-33-mediated disorder, wherein the patient has been determined to comprise a T allele at polymorphism rs10206753 (SEQ ID NO: 5) or an equivalent allele at a polymorphism in linkage disequilibrium with polymorphism rs10206753 (SEQ ID NO: 5).

In another aspect, the invention features an IL-33 axis binding antagonist for use in treating a patient suffering from an IL-33-mediated disorder, wherein the patient, prior to any administration of an IL-33 axis binding antagonist, has been determined to comprise a T allele at polymorphism rs4742165 (SEQ ID NO: 6) or an equivalent allele at a polymorphism in linkage disequilibrium with polymorphism rs4742165 (SEQ ID NO: 6).

In another aspect, the invention features a use of an effective amount of an IL-33 axis binding antagonist in the manufacture of a medicament for use in treating a patient suffering from an IL-33-mediated disorder, wherein the patient has been determined to comprise a T allele at polymorphism rs4742165 (SEQ ID NO: 6) or an equivalent allele at a polymorphism in linkage disequilibrium with polymorphism rs4742165 (SEQ ID NO: 6).

In another aspect, the invention features a composition comprising an effective amount of an IL-33 axis binding antagonist for use in a method of treating a patient suffering from an IL-33-mediated disorder, wherein the patient has been determined to comprise a T allele at polymorphism rs4742165 (SEQ ID NO: 6) or an equivalent allele at a polymorphism in linkage disequilibrium with polymorphism rs4742165 (SEQ ID NO: 6).

In another aspect, the invention features an IL-33 axis binding antagonist for use in treating a patient suffering from an IL-33-mediated disorder, wherein the patient, prior to any administration of an IL-33 axis binding antagonist, has been determined to comprise two or more of the following alleles: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In another aspect, the invention features a use of an effective amount of an IL-33 axis binding antagonist in the manufacture of a medicament for use in treating a patient suffering from an IL-33-mediated disorder, wherein the patient has been determined to comprise two or more of the following alleles: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In another aspect, the invention features a composition comprising an effective amount of an IL-33 axis binding antagonist for use in a method of treating a patient suffering from an IL-33-mediated disorder, wherein the patient has been determined to comprise two or more of the following alleles: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In another aspect, the invention features an IL-33 axis binding antagonist for use in treating a patient suffering from an IL-33-mediated disorder, wherein the patient, prior to any administration of an IL-33 axis binding antagonist, has been determined to have a level of sST2 in a sample derived from the patient at or above a reference level.

In another aspect, the invention features a use of an effective amount of an IL-33 axis binding antagonist in the manufacture of a medicament for use in treating a patient suffering from an IL-33-mediated disorder, wherein the patient has been determined to have a level of sST2 in a sample derived from the patient at or above a reference level.

In another aspect, the invention features a composition comprising an effective amount of an IL-33 axis binding antagonist for use in a method of treating a patient suffering from an IL-33-mediated disorder, wherein the patient has been determined to have a level of sST2 in a sample derived from the patient at or above a reference level.

BRIEF DESCRIPTION OF THE DRAWINGS

FIGS. 1C and 1D are graphs showing the results of reporter assay experiments to determine the IL-33 response of the common ST2 variant or protective ST2 variant (A433T Q501R T549I L551S), HEK-BLUE™ cells expressing the indicated variant were stimulated with increasing concentrations of recombinant human IL-33 (FIG. 1C) or IL-1β (FIG. 1D) for 20 h. Cytokine activity was measured by induction of the NF-κB/AP-1 secreted alkaline phosphatase (SEAP) reporter gene. Graphs show mean±SEM of 3 single clone cell lines. * indicates p<0.05. Data are representative of three independent experiments. The half-maximal effective concentration (EC50) of IL-33 (FIG. 1C) or IL-1β (FIG. 1D) for the indicated variant is shown in the table.

FIG. 3B is a histogram showing the results of flow cytometry experiments comparing IL-1RAcP surface expression levels in HEK-BLUE™ cells expressing the indicated IL1RL1 variants.

FIG. 3C is a graph showing the mean fluorescence intensity (MFI) of ST2 surface expression from the graphs shown in FIG. 3A.

FIG. 4 is a graph showing interleukin-8 (IL-8) secretion levels of purified blood eosinophils obtained from human donors carrying either the protective or common IL1RL1 variants treated with the indicated concentration of purified IL-33, as assessed by an enzyme-linked immunosorbent assay (ELISA).

FIG. 6 is a table showing the association of protective IL1RL1 variants with periostin levels. CHR, chromosome; P, p value; OR, odds ratio; and MAF, minor allele frequency.

DETAILED DESCRIPTION OF EMBODIMENTS OF THE INVENTION

I. Definitions

Figures 1A, 1B:
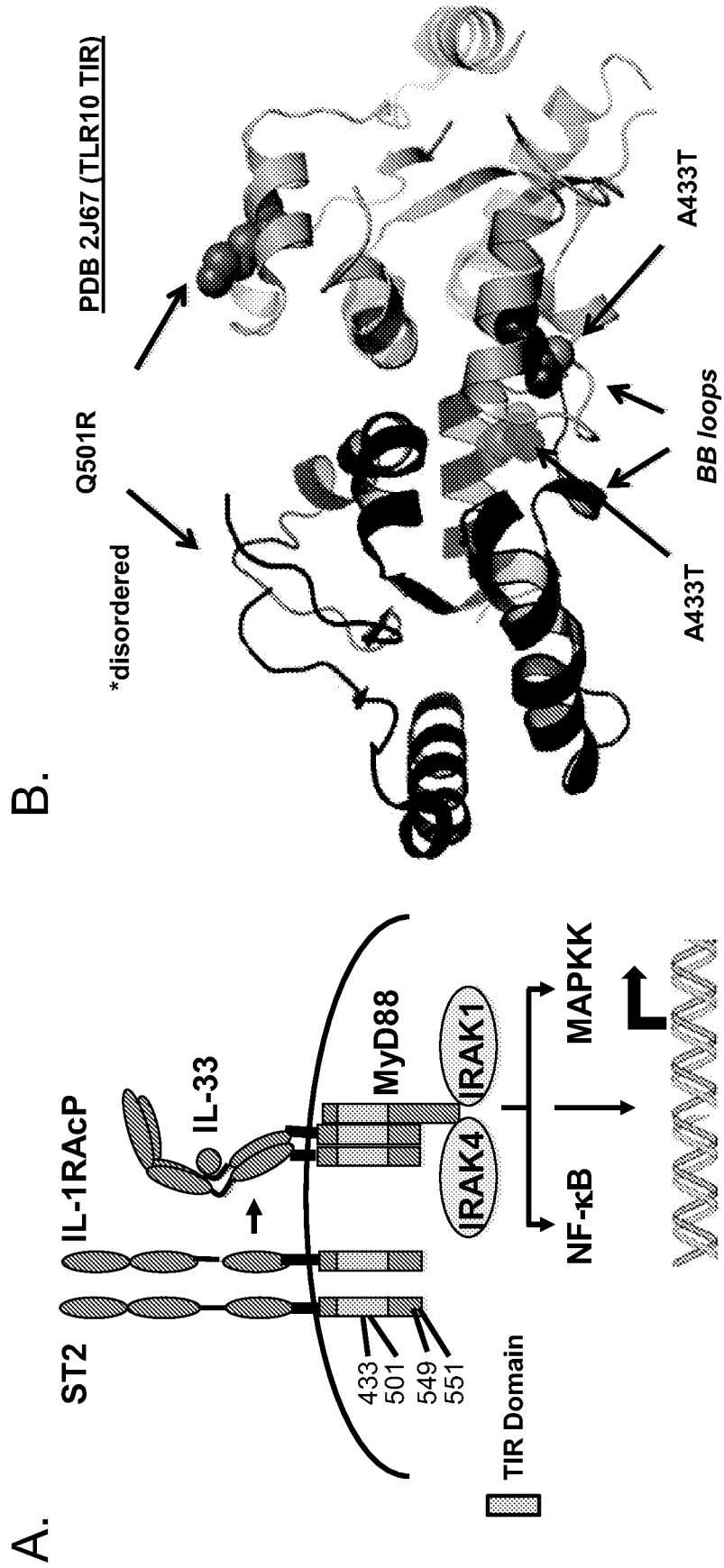
FIG. 1A shows a schematic representation of the interleukin-33 (IL-33) receptor complex. Red lines indicate the location of the indicated protective ST2 variants. MAPKK, Mitogen activated protein kinase kinase.
FIG. 1B is a rendering of the crystal structure of the TLR10 Toll/Interleukin-1 receptor (TIR) domain showing the mapped locations of the A433T and Q501R variants of ST2.
Figure 1D:
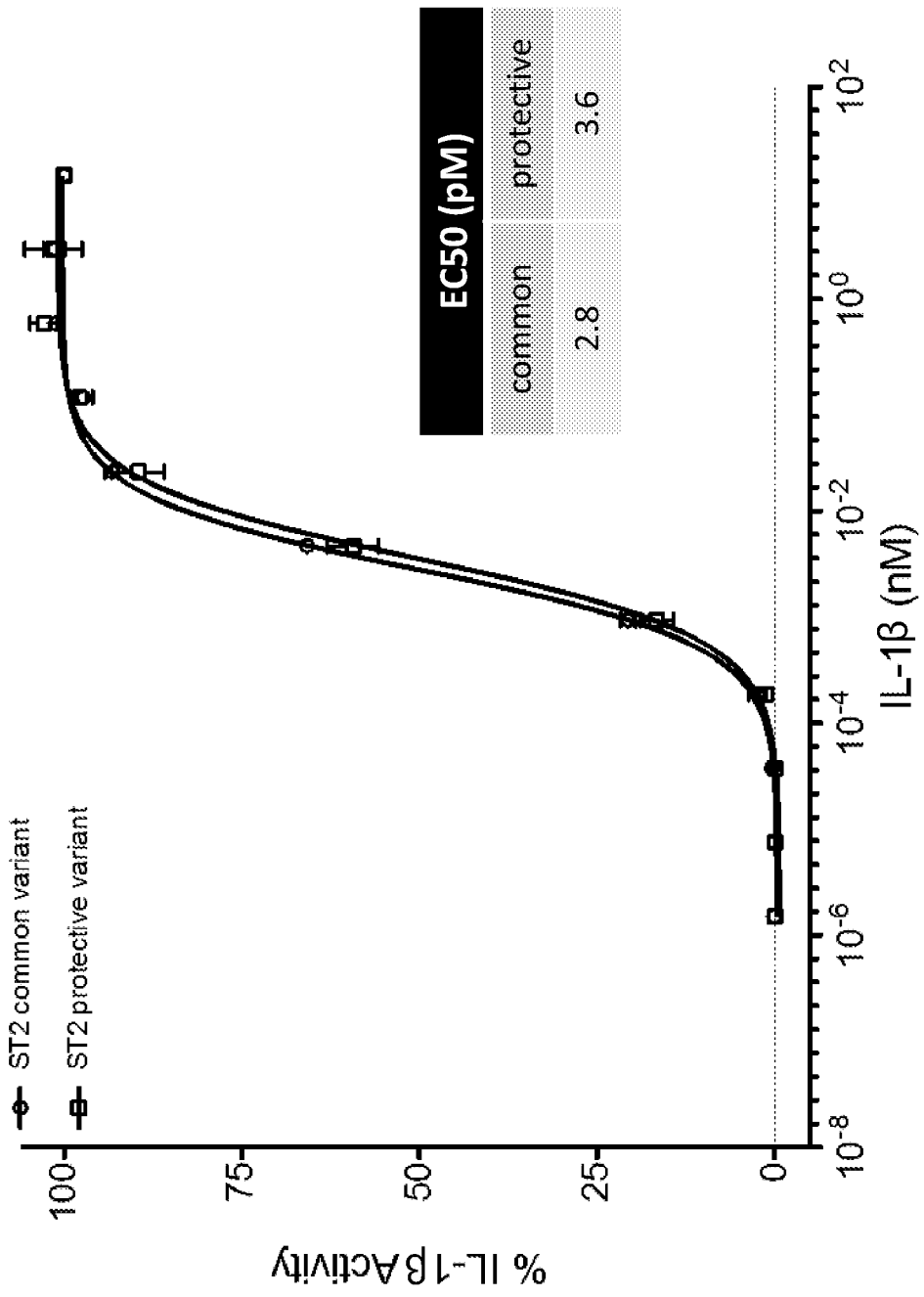
Figure 2A:
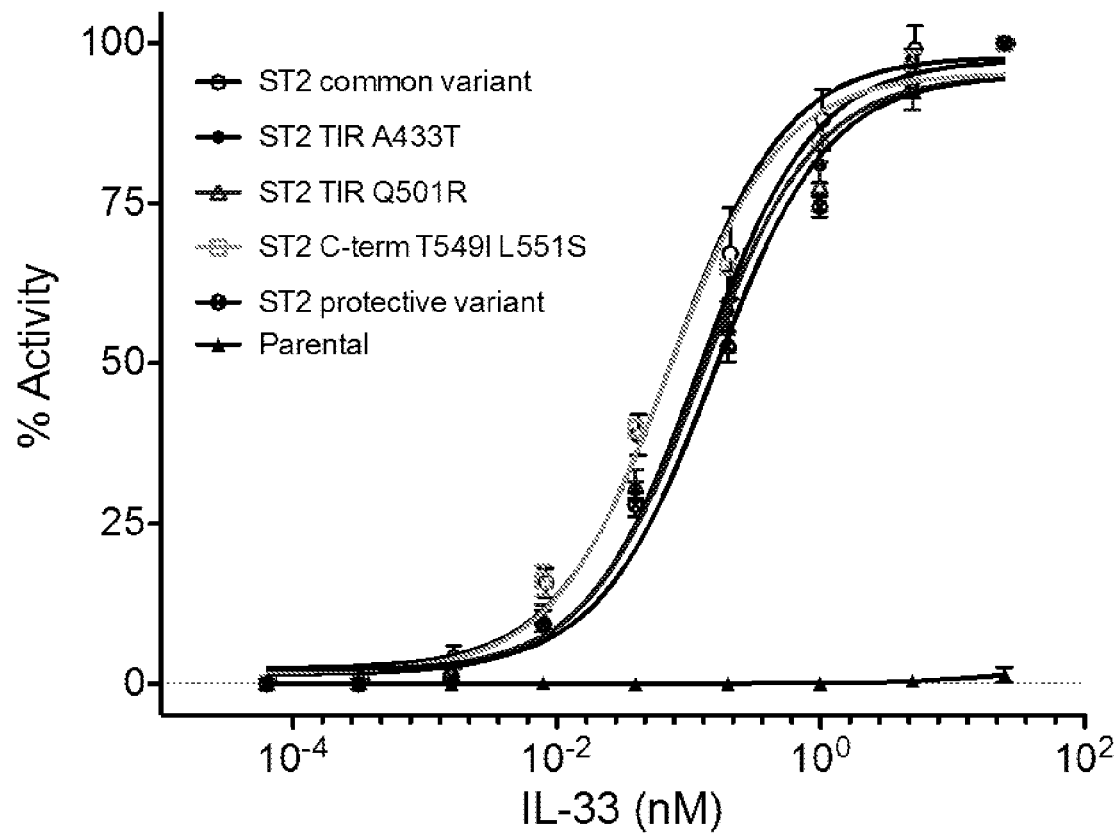
FIGS. 2A and 2B are graphs showing the results of reporter assay experiments to determine the IL-33 response of the common variant or protective ST2 variants. Batch clones of HEK-BLUE™ cells expressing the indicated ST2 variant were stimulated with increasing concentrations of human recombinant IL-33 (FIG. 2A) or IL-1β (FIG. 2B) for 20 h. Cytokine activity was measured by induction of the NF-κB/AP-1 SEAP reporter gene. Graphs show mean±SD of triplicates. Data are representative of three independent experiments. The table shows the EC50 of IL-33 (FIG. 2A) or IL-1β (FIG. 2B) for the indicated variant.
Figure 2B:
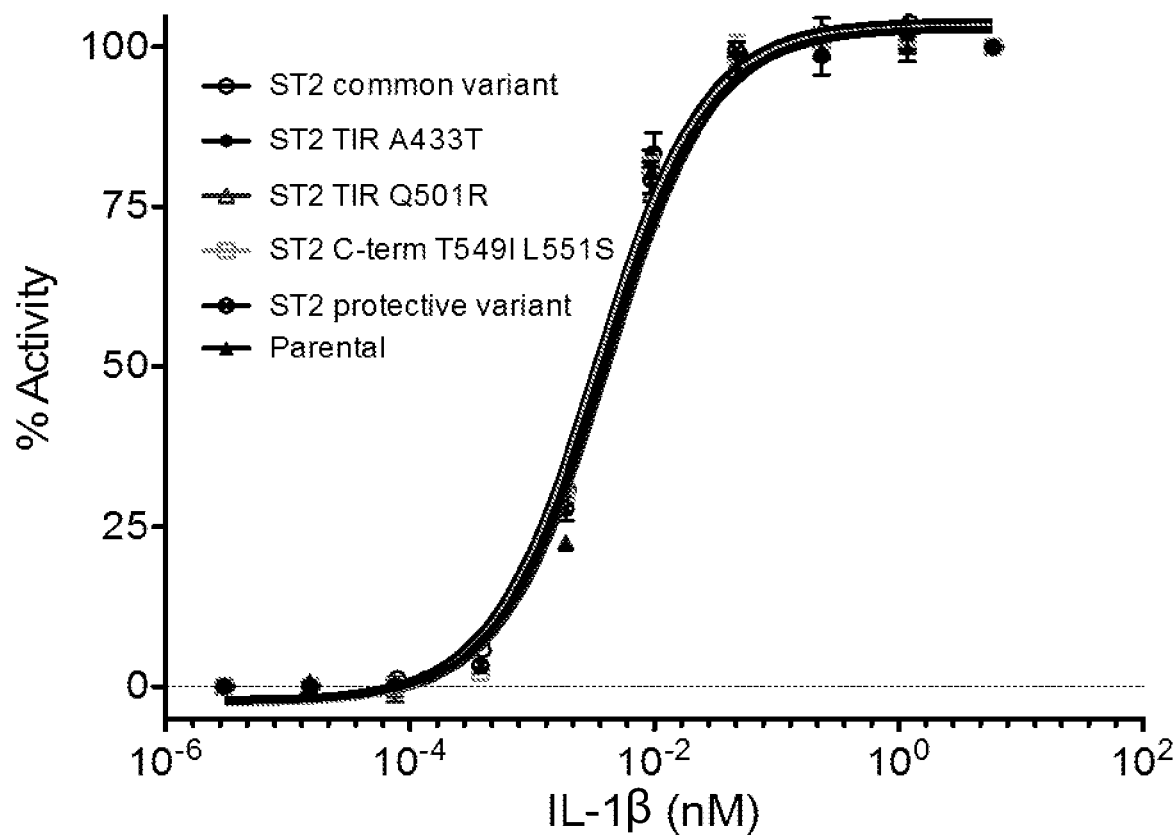

The term "administering" means the administration of a pharmaceutical composition (e.g., comprising an interleukin-33 (IL-33) axis binding antagonist) to a patient (e.g., a patient suffering from asthma or pulmonary fibrosis (e.g., idiopathic pulmonary fibrosis)).

"Antagonists" as used herein refer to compounds or agents which inhibit or reduce the biological activity of the molecule to which they bind. Antagonists include antibodies, synthetic or native-sequence peptides, immunoadhesins, and small-molecule antagonists that bind to, for example, an IL-33 axis protein, optionally conjugated with or fused to another molecule. A "blocking" antibody or an "antagonist" antibody is one which inhibits or reduces biological activity of the antigen it binds.

The term "asthma" refers herein to a disorder characterized by variable and recurring symptoms, reversible airflow obstruction (e.g., by bronchodilator), and bronchial hyperresponsiveness, which may or may not be associated with underlying inflammation. Asthma may therefore be inflammatory/inflamed asthma or non-inflammatory/non-inflamed asthma. Examples of asthma include allergic asthma, exercise-induced asthma, aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, and other asthmas as mentioned in Bousquet et al. (*J. Allergy Clin. Immunol.* 126(5): 926-938, 2010).

The terms "biomarker" and "marker" are used interchangeably herein to refer to a DNA, RNA, protein, carbohydrate, or glycolipid-based molecular marker, the expression or presence of which in a subject's or patient's sample can be detected by standard methods (or methods disclosed herein) and is useful, for example, for identifying the risk profile of a subject for a disease or disorder and/or the likelihood of responsiveness or sensitivity of a mammalian subject to a treatment (e.g., a treatment comprising an IL-33 axis binding antagonist (e.g., an ST2 binding antagonist)). Expression of such a biomarker may be determined to be higher or lower in a sample obtained from a patient that has an increased or decreased likelihood of being responsive to an IL-33 axis binding antagonist (e.g., an ST2 binding antagonist) than a reference level (including, e.g., the median expression level of the biomarker in samples from a group/population of patients (e.g., asthma patients); the level of the biomarker in samples from a group/population of control individuals (e.g., healthy individuals); or the level in a sample previously obtained from the individual at a prior time). In some embodiments, individuals having an expression level that is greater than or less than the reference expression level of at least one gene, such as periostin or ST2 (e.g., sST2), can also be identified as likely to respond to treatment comprising an IL-33 axis binding antagonist (e.g., an ST2 binding antagonist).

A "disorder" or "disease" is any condition that would benefit from treatment or diagnosis (e.g., determination of risk for an IL-33-mediated disorder) with a method of the invention. This includes chronic and acute disorders or diseases including those pathological conditions which predispose the mammal to the disorder in question. Examples of disorders to be treated herein include IL-33-mediated disorders (e.g., asthma, allergic rhinitis, atopic dermatitis, and fibrosis (e.g., pulmonary fibrosis, e.g., idiopathic pulmonary fibrosis)).

The term "effective amount" refers to an amount of a drug effective to treat a disease or disorder in a subject or patient, such as a mammal, e.g., a human.

The term "genotype" refers to a description of the alleles of a gene contained in an individual or a sample. In the context of this invention, no distinction is made between the genotype of an individual and the genotype of a sample originating from the individual. Although typically a genotype is determined from samples of diploid cells, a genotype can be determined from a sample of haploid cells, such as a sperm cell.

The terms "interleukin 1 receptor-like 1 (IL1RL1)" and "ST2," used interchangeably herein, refer to any native ST2 from any vertebrate source, including mammals such as primates (e.g., humans) and rodents (e.g., mice and rats), unless otherwise indicated. ST2 is also referred to in the art as DER4, T1, and FIT-1. The term encompasses "full-length," unprocessed ST2, as well as any form of ST2 that results from processing in the cell. At least four isoforms of ST2 are known in the art, including soluble (sST2, also known as IL1RL1-a) and transmembrane (ST2L, also known as IL1RL1-b), which arise from differential mRNA expression from a dual promoter system, and ST2V and ST2LV, which arise from alternative splicing, as described below. The domain structure of ST2L includes three extracellular immunoglobulin-like C2 domains, a transmembrane domain, and a cytoplasmic Toll/Interleukin-1 receptor (TIR) domain. sST2 lacks the transmembrane and cytoplasmic domains contained within ST2L and includes a unique 9 amino acid (a.a.) C-terminal sequence (see, e.g., Kakkar et al. *Nat. Rev. Drug Disc.* 7: 827-840, 2008). sST2 can function as a decoy receptor to inhibit soluble IL-33. The term also encompasses naturally occurring variants of ST2, e.g., splice variants (e.g., ST2V, which lacks the third immunoglobulin motif and has a unique hydrophobic tail, and ST2LV, which lacks the transmembrane domain of ST2L) or allelic variants (e.g., variants that are protective against asthma risk or that confer asthma risk as described herein). The amino acid sequence of an exemplary human ST2 can be found, for example, under UniProtKB accession number Q01638. ST2 is a part of the IL-33 receptor along with the co-receptor protein IL-1RAcP. Binding of IL-33 to ST2 and the co-receptor interleukin-1 receptor accessory protein (IL-1RAcP) forms a 1:1:1 ternary signaling complex to promote downstream signal transduction, as depicted in FIG. 1A (see, e.g., Lingel et al. *Structure* 17(10): 1398-1410, 2009, and Liu et al. *Proc. Natl. Acad. Sci.* 110(37): 14918-14924, 2013).

The term "interleukin-33 (IL-33)," as used herein, refers to any native IL-33 from any vertebrate source, including mammals such as primates (e.g., humans) and rodents (e.g., mice and rats), unless otherwise indicated. IL-33 is also referred to in the art as nuclear factor of high endothelial venules (NF-HEV; see, e.g., Baekkevold et al. *Am. J. Pathol.* 163(1): 69-79, 2003), DVS27, C9orf26, and interleukin-1 family member 11 (IL-1F11). The term encompasses "full-length," unprocessed IL-33, as well as any form of IL-33 that results from processing in the cell. Human full-length, unprocessed IL-33 contains 270 a.a. and may also be referred to as IL-33$_{1-270}$. Processed forms of human IL-33 include, for example, IL-33$_{95-270}$, IL-33$_{99-270}$, IL-33$_{109-270}$, IL-33$_{112-270}$, IL-33$_{1-178}$, and IL-33$_{179-270}$ (Lefrangais et al. *Proc. Natl. Acad. Sci.* 109(5): 1673-1678, 2012 and Martin, *Semin. Immunol.* 25: 449-457, 2013). In some embodiments, processed forms of human IL-33, e.g., IL-33$_{95-270}$, IL-33$_{99-270}$, IL-33$_{109-270}$, or other forms processed by proteases such as calpain, proteinase 3, neutrophil elastase, and cathepsin G may have increased biological activity compared to full-length IL-33. The term also encompasses naturally occurring variants of IL-33, for example, splice variants (e.g., the constitutively active splice variant spIL-33 which lacks exon 3, Hong et al. *J. Biol. Chem.* 286(22): 20078-20086, 2011) or allelic variants. IL-33 may be present within a cell (e.g., within the nucleus) or as a secreted cytokine form. Full-length IL-33 protein contains a helix-turn-helix DNA-binding motif including nuclear localization sequence (a.a. 1-75 of human IL-33), which includes a chromatin binding motif (a.a. 40-58 of human IL-33). Forms of IL-33 that are processed and secreted lack these N-terminal motifs. The amino acid sequence of an exemplary human IL-33 can be found, for example, under UniProtKB accession number O95760.

By "IL-33 axis" is meant a nucleic acid (e.g., a gene or mRNA transcribed from the gene) or polypeptide that is involved in IL-33 signal transduction. For example, the IL-33 axis may include the ligand IL-33, a receptor (e.g., ST2 and/or IL-1RAcP), adaptor molecules (e.g., MyD88), or proteins that associate with receptor molecules and/or adaptor molecules (e.g., kinases, such as interleukin-1 receptor-associated kinase 1 (IRAK1) and interleukin-1 receptor-associated kinase 4 (IRAK4), or E3 ubiquitin ligases, such as TNF receptor associated factor 6 (TRAF6)).

An "IL-33 axis binding antagonist" refers to a molecule that inhibits the interaction of an IL-33 axis binding partner with one or more of its binding partners. As used herein, an IL-33 axis binding antagonist includes IL-33 binding antagonists, ST2 binding antagonists, and IL1RAcP binding antagonists. Exemplary IL-33 axis binding antagonists include anti-IL-33 antibodies and antigen-binding fragments thereof (e.g., anti-IL-33 antibodies such as ANB-020 (AnaptysBio Inc.) or any of the antibodies described in EP1725261, U.S. Pat. No. 8,187,596, WO2011031600, WO2014164959, WO2015099175 or WO2015106080, which are each incorporated herein by reference in their entirety); polypeptides that bind IL-33 and/or its receptor (ST2 and/or IL-1RAcP) and block ligand-receptor interaction (e.g., ST2-Fc proteins; immunoadhesins, peptibodies, and soluble ST2, or derivatives thereof); anti-IL-33 receptor antibodies (e.g., anti-ST2 antibodies, for example, AMG-282 (Amgen) or STLM15 (Janssen) or any of the anti-ST2 antibodies described in WO 2013/173761 or WO 2013/165894, which are each incorporated herein by reference in their entirety; or ST2-Fc proteins, such as those described in WO 2013/173761; WO 2013/165894; or WO 2014/152195, which are each incorporated herein by reference in their entirety); and IL-33 receptor antagonists, such as small molecule inhibitors, aptamers that bind IL-33, and nucleic acids that hybridize under stringent conditions to IL-33 axis nucleic acid sequences (e.g., short interfering RNAs (siRNA) or clustered regularly interspaced short palindromic repeat RNAs (CRISPR-RNA or crRNA)).

The term "ST2 binding antagonist" refers to a molecule that inhibits the interaction of an ST2 with IL-33, IL1RAcP, and/or a second ST2 molecule. The ST2 binding antagonist may be a protein, such as an "ST2-Fc protein" that includes an IL-33-binding domain (e.g., all or a portion of an ST2 or IL1RAcP protein) and a multimerizing domain (e.g., an Fc portion of an immunoglobulin, e.g., an Fc domain of an IgG selected from the isotypes IgG1, IgG2, IgG3, and IgG4, as well as any allotype within each isotype group), which are attached to one another either directly or indirectly through a linker (e.g., a serine-glycine (SG) linker, glycine-glycine (GG) linker, or variant thereof (e.g., a SGG, a GGS, an SGS, or a GSG linker)), and includes, but is not limited to, ST2-Fc proteins and variants thereof described in WO 2013/173761, WO 2013/165894, and WO 2014/152195, which are each incorporated herein by reference in their entirety.

The term "IL-33-mediated disorder," as used herein, refers to any disorder or condition mediated by, or associated with, the IL-33 axis. In some embodiments, IL-33-mediated disorders are associated with excess IL-33 levels or activity in which atypical symptoms may manifest due to the levels or activity of IL-33 locally and/or systemically in the body. Exemplary IL-33-mediated disorders include inflammatory conditions, immune disorders, fibrotic disorders, eosinophilic disorders, infections, pain, central nervous system disorders, solid tumors, and ophthalmologic disorders. IL-33-mediated disorders are described, for example, in Liew et al. *Nature Reviews Immunology* 10: 103-110, 2010, which is incorporated herein by reference in its entirety.

Exemplary inflammatory conditions include asthma (e.g., allergic asthma, exercise-induced asthma, aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, etc.), airway inflammation, airway hyperreactivity, airway hyperresponsiveness, rhinosinusitis, rhinosinusitis with polyps, nasal polyposis, arthritis (e.g., osteoarthritis, rheumatoid arthritis, collagen-induced arthritis, arthritic joints as a result of injury, etc.), eosinophilic inflammation, mast cell-mediated inflammatory diseases, sepsis, septic shock, seronegative enthesopathy and arthropathy (SEA) syndrome, osteoporosis, eosinophilic esophagitis, scleroderma, dermatitis, atopic dermatitis, allergic rhinitis, bullous pemphigoid, chronic urticaria, cartilage inflammation, polymyalgia rheumatic, polyarteritis nodossa, Wegener's granulomatosis, Behcet's disease, myolitis, polymyolitis, dermatomyolitis, dermatomyositis, vasculitis, arteritis, diabetic nephropathy, interstitial cystitis, graft versus host disease (GVHD), gastrointestinal inflammatory conditions (e.g., inflammatory bowel disease (IBD), ulcerative colitis (UC), Crohn's disease (CD), colitis (e.g., colitis caused by environmental insults (e.g., caused by or associated with a therapeutic regimen, such as chemotherapy, radiation therapy, etc.), infectious colitis, ischemic colitis, collagenous or lymphocytic colitis, necrotizing enterocolitis, colitis in conditions such as chronic granulomatous disease or celiac disease, food allergies, gastritis, infectious gastritis or enterocolitis (e.g., *Helicobacter pylori*-infected chronic active gastritis), and other forms of gastrointestinal inflammation caused by an infectious agent), and inflammatory pulmonary conditions (e.g., chronic obstructive pulmonary disease (COPD), eosinophilic pulmonary inflammation, infection-induced pulmonary conditions (including those associated with viral (e.g., influenza, parainfluenza, rotavirus, human metapneumovirus, and respiratory syncytial virus), bacterial, fungal (e.g., *Aspergillus*), parasitic, or prion infection, allergen-induced pulmonary conditions, pollutant-induced pulmonary conditions (e.g., asbestosis, silicosis, or berylliosis), gastric aspiration-induced pulmonary conditions, immune dysregulation, inflammatory conditions with genetic predisposition such as cystic fibrosis, physical trauma-induced pulmonary conditions (e.g., ventilator injury), emphysema, bronchitis, sarcoidosis, histiocytosis, lymphangiomyomatosis, acute lung injury, acute respiratory distress syndrome, chronic lung disease, bronchopulmonary dysplasia, pneumonia (e.g., community-acquired pneumonia, nosocomial pneumonia, ventilator-associated pneumonia, viral pneumonia, bacterial pneumonia, and severe pneumonia), airway exacerbations, and acute respiratory distress syndrome (ARDS)).

Exemplary immune disorders include those mediated at least in part by mast cells, such as asthma (e.g., allergic asthma), eczema, itch, allergy, atopic allergy, anaphylaxis, anaphylactic shock, allergic bronchopulmonary aspergillosis, allergic rhinitis, allergic conjunctivitis, as well as autoimmune disorders including rheumatoid arthritis, juvenile rheumatoid arthritis, psoriatic arthritis, pancreatitis, psoriasis, plaque psoriasis, guttate psoriasis, inverse psoriasis, pustular psoriasis, erythrodermic psoriasis, paraneoplastic autoimmune diseases, autoimmune hepatitis, bullous pemphigoid, myasthenia gravis, inflammatory bowel disease, Crohn's disease, ulcerative colitis, celiac disease, thyroiditis (e.g., Graves' disease), Sjogren's syndrome, Guillain-Barre disease, Raynaud's phenomenon, Addison's disease, liver diseases (e.g., primary biliary cirrhosis, primary sclerosing cholangitis, non-alcoholic fatty liver disease, and non-alcoholic steatohepatitis), and diabetes (e.g., type I diabetes).

As used herein, the terms "fibrotic disorder" or "fibrosis" refer to conditions involving formation of excess fibrous connective tissue in an organ or tissue. Exemplary fibrotic disorders include lung fibrosis, liver fibrosis (e.g., fibrosis associated with cirrhosis (e.g., alcohol-induced cirrhosis, viral-induced cirrhosis, post-hepatitis C cirrhosis, and primary biliary cirrhosis), schistosomiasis, cholangitis (e.g., sclerosing cholangitis), and autoimmune-induced hepatitis), kidney fibrosis (e.g., tubulointerstitial fibrosis, scleroderma, diabetic nephritis, and glomerular nephritis), dermal fibrosis (e.g., scleroderma, hypertrophic and keloid scarring, nephrogenic fibrosing dermatopathy, and burns), myelofibrosis, neurofibromatosis, fibroma, intestinal fibrosis, and fibrotic adhesions resulting from surgical procedures), heart fibrosis (e.g., fibrosis associated with myocardial infarction), vascular fibrosis (e.g., fibrosis associated with postangioplasty arterial restenosis and atherosclerosis), eye fibrosis (e.g., fibrosis associated with post-cataract surgery, proliferative vitreoretinopathy, and retro-orbital fibrosis), and bone marrow fibrosis (e.g., idiopathic myelofibrosis and drug-induced myelofibrosis). The fibrosis can be organ-specific or systemic (e.g., systemic sclerosis and fibrosis associated with GVHD).

Examples of lung fibrosis include, for example, lung or pulmonary fibrosis associated with idiopathic pulmonary fibrosis, fibrosis with collagen vascular disease, Hermansky-Pudlak syndrome, adult respiratory distress syndrome, non-specific interstitial pneumonia, respiratory bronciolitis, sarcoidosis, histiocytosis X, bronchiolitis obliterans, and cryptogenic organizing pneumonia. In one embodiment, the lung fibrosis is idiopathic pulmonary fibrosis.

As used herein, an "eosinophilic disorder" is a disorder associated with excess eosinophil numbers in which atypical symptoms may manifest due to the levels or activity of eosinophils locally or systemically in the body. Eosinophilic disorders include but are not limited to, asthma (including aspirin sensitive asthma, atopic asthma, and severe asthma), eosinophilic inflammation, atopic dermatitis, allergic rhinitis (including seasonal allergic rhinitis), non-allergic rhinitis, chronic eosinophilic pneumonia, allergic bronchopulmonary aspergillosis, celiac disease, Churg-Strauss syndrome (periarteritis nodosa plus atopy), eosinophilic myalgia syndrome, hypereosinophilic syndrome, edematous reactions including episodic angiodema, helminth infections, where eosinophils may have a protective role, onchocercal dermatitis, eosinophil-associated gastrointestinal disorders (EGIDs), including but not limited to, eosinophilic esophagitis, eosinophilic gastritis, eosinophilic gastroenteritis, eosinophilic enteritis and eosinophilic colitis, nasal micropolyposis and polyposis, aspirin intolerance, and obstructive sleep apnea. Eosinophil-derived secretory products have also been associated with the promotion of angiogenesis and connective tissue formation in tumors and the fibrotic responses seen in conditions such as chronic asthma, Crohn's disease, scleroderma and endomyocardial fibrosis (Munitz et al. *Allergy* 59: 268-275, 2004; Adamko et al. *Allergy* 60: 13-22, 2005; Oldhoff et al. *Allergy* 60: 693-696, 2005). Other examples include cancer (e.g., glioblastoma (such as glioblastoma multiforme) and non-Hodgkin's lymphoma (NHL)), atopic dermatitis, allergic rhinitis, inflammatory bowel disease, fibrosis (e.g., pulmonary fibrosis (e.g., idiopathic pulmonary fibrosis (IPF) and pulmonary fibrosis secondary to sclerosis) and hepatic fibrosis), and COPD.

Examples of infection include helminth infection (e.g., nematode infection, such as *Trichuris muris* infection of mice, which is a model for infection by the human parasite *Trichuris trichiura*), protozoan infection (e.g., *Leishmania major* infection), and viral infection (e.g., respiratory syncytial virus infection and influenza virus infection).

Examples of pain include inflammatory pain, hyperalgesia (e.g., mechanical hyperalgesia), allodynia, and hypernociception (e.g., cutaneous and articular hypernociception, which may or may not be antigen-induced).

Examples of central nervous system disorders include subarachnoid hemorrhage, inflammatory diseases of the central nervous system, neurodegenerative diseases (e.g., Alzheimer's disease, multiple sclerosis, Parkinson's disease, Huntington's disease), bipolar disorder, and infection of the central nervous system (e.g., viral infection).

Examples of solid tumors include tumors of the colon, breast, prostate, lung, kidney, liver, pancreas, ovary, head and neck, oral cavity, stomach, duodenum, small intestine, large intestine, gastrointestinal tract, anus, gall bladder, labium, nasopharynx, skin, uterus, male genital organ, urinary organs, bladder, and skin. Solid tumors of non-epithelial origin include sarcomas, brain tumors, and bone tumors.

Examples of ophthalmologic disorders include age-related macular degeneration (AMD), including wet or dry AMD, geographic atrophy (GA), retinopathy (e.g., diabetic retinopathy (DR) and retinopathy of prematurity (ROP)), polypoidal choroidal vasculopathy (PCV), diabetic macular edema, dry eye disease, Bechet's disease, and retina detachment.

The above list is not all-inclusive, and it will be understood by the skilled artisan that a disease or disorder may fall within various categories. For example, asthma can be categorized in some instances as both an inflammatory disorder and immune disorder and considered by some clinicians to be an autoimmune disorder.

As used herein, "chemoattractant receptor-homologous molecule expressed on Th2 cells (CRTH2)" refers to any native CRTH2 from any vertebrate source, including mammals such as primates (e.g., humans) and rodents (e.g., mice and rats), unless otherwise indicated. CRTH2 is also referred to as G protein coupled receptor 44 (GPR44), cluster of differentiation 294 (CD294), DL1R, and DP2. The term encompasses "full-length," unprocessed CRTH2, as well as any form of CRTH2 that results from processing in the cell. The amino acid sequence of an exemplary human CRTH2 can be found, for example, under UniProtKB accession number Q9Y5Y4.

The term "CRTH2 binding antagonist" refers to a molecule that decreases, blocks, inhibits, abrogates or interferes with signal transduction resulting from the interaction of CRTH2 with one or more of its binding partners, such as prostaglandin $D_2$. Exemplary CRTH2 binding antagonists known in the art include AMG-853, AP768, AP-761, MLN6095, and ACT129968.

The term "interleukin-5 (IL-5)," as used herein, refers to any native IL-5 from any vertebrate source, including mammals such as primates (e.g. humans) and rodents (e.g., mice and rats), unless otherwise indicated. The term encompasses "full-length," unprocessed IL-5, as well as any form of IL-5 that results from processing in the cell. The term also encompasses naturally occurring variants of IL-5, such as splice variants or allelic variants. The amino acid sequence of an exemplary IL-5 can be found, for example, under UniProtKB accession number P05113.

The term "IL-5 binding antagonist" refers to a molecule that decreases, blocks, inhibits, abrogates or interferes with signal transduction resulting from the interaction of IL-5 with one or more of its binding partners, such as IL-5 receptor, alpha (IL5RA). Exemplary IL-5 binding antagonists that can be used in the methods of the invention include, for example, anti-IL-5 antibodies (e.g., mepolizumab and reslizumab) and anti-IL-5R antibodies.

As used herein, "interleukin-13 (IL-13)" refers to any native IL-13 from any vertebrate source, including mammals such as primates (e.g., humans) and rodents (e.g., mice and rats), unless otherwise indicated. IL-13 is a cytokine secreted by many cell types, including T helper type 2 (Th2) cells. The term encompasses "full-length," unprocessed IL-13, as well as any form of IL-13 that results from processing in the cell. The amino acid sequence of an exemplary human IL-13 can be found, for example, under UniProtKB accession number P35225.

The term "IL-13 binding antagonist" refers to a molecule that decreases, blocks, inhibits, abrogates or interferes with signal transduction resulting from the interaction of IL-13 with one or more of its binding partners, such as IL-4 receptor alpha (IL4Ra), IL-13 receptor alpha1 (IL13RA1) and IL-13 receptor alpha2 (IL13RA2). IL-13 binding antagonists include anti-IL-13 antibodies, for example, lebrikizumab, 228B/C-1, 228A-4, 227-26, and 227-43 (see, for example, U.S. Pat. Nos. 7,674,459; 8,067,199; 8,088,618; 8,318,160; and 8,734,797).

As used herein, "interleukin-17 (IL-17)" refers to any native IL-17 from any vertebrate source, including mammals such as primates (e.g., humans) and rodents (e.g., mice and rats), unless otherwise indicated, and includes family members IL-17A, IL-17B, IL-17C, IL-17D, IL-17E, and IL-17F. The term encompasses "full-length," unprocessed IL-17, as well as any form of IL-17 that results from processing in the cell. The amino acid sequence of an exemplary human IL-17A can be found, for example, under UniProtKB accession number Q16552. The amino acid sequence of an exemplary human IL-17B can be found, for example, under UniProtKB accession number Q9UHF5. The amino acid sequence of an exemplary human IL-17C can be found, for example, under UniProtKB accession number Q9P0M4. The amino acid sequence of an exemplary human IL-17D can be found, for example, under UniProtKB accession number Q8TAD2. The amino acid sequence of an exemplary human IL-17E can be found, for example, under UniProtKB accession number Q9H293. The amino acid sequence of an exemplary human IL-17F can be found, for example, under UniProtKB accession number Q96PD4.

The term "IL-17 binding antagonist" refers to a molecule that decreases, blocks, inhibits, abrogates or interferes with signal transduction resulting from the interaction of IL-17 with one or more of its binding partners, such as interleukin-17 receptor (IL-17R) family member proteins interleukin 17 receptor A (IL17RA), interleukin 17 receptor B (IL17RB), interleukin 17 receptor C (IL17RC), interleukin 17 receptor D (IL17RD), interleukin 17 receptor E (IL17RE), and interleukin 17 receptor E-like (IL17REL). Exemplary IL-17 binding antagonists include, for example, anti-IL-17 antibodies (e.g., ixekizumab (LY2439821) and anti-IL-17R antibodies (e.g., brodalumab (AMG-827)).

The term "Janus kinase 1 (JAK1)," as used herein, refers to any native JAK1 from any vertebrate source, including mammals such as primates (e.g. humans) and rodents (e.g., mice and rats), unless otherwise indicated. The term encompasses "full-length," unprocessed JAK1 as well as any form of JAK1 that results from processing in the cell. The term also encompasses naturally occurring variants of JAK1, e.g., splice variants or allelic variants. The amino acid sequence of an exemplary JAK1 can be found, for example, under UniProtKB accession number P23458.

The term "JAK1 antagonist," as used herein, refers to compounds or agents which inhibit or reduce the biological activity of JAK1. Exemplary JAK1 antagonists include small molecule inhibitors (e.g., ruxolitinib, GLPG0634, and GSK2586184).

As used herein, "tryptase-beta" refers to any native tryptase-beta from any vertebrate source, including mammals such as primates (e.g., humans) and rodents (e.g., mice and rats), unless otherwise indicated. As used herein, the term encompasses tryptase beta-1 (encoded by the TPSAB1 gene, which also encodes tryptase alpha-1) and tryptase beta-2 (encoded by the TPSB2 gene). The term encompasses "full-length," unprocessed tryptase-beta as well as any form of tryptase-beta that results from processing in the cell. The amino acid sequence of an exemplary human tryptase beta-2 can be found, for example, under UniProtKB accession number P20231.

The term "tryptase-beta antagonist," as used herein, refers to compounds or agents which inhibit or reduce the biological activity of tryptase beta.

The phrase "informing the patient" with respect to a treatment, as used herein, refers to using the information or data generated relating to the genotype of a polymorphism as described herein and/or the level or presence of at least one marker, for example, periostin, in a sample of a patient to identify the patient as suitably treated or not suitably treated with a therapy (e.g., a therapy comprising an IL-33 axis binding antagonist (e.g., an ST2 binding antagonist)). In some embodiments the recommendation may include the identification of a patient who requires adaptation of an effective amount of a therapy (e.g., an IL-33 axis binding antagonist (e.g., an ST2 binding antagonist)) being administered. In some embodiments, recommending a treatment includes recommending that the amount of a therapy (e.g., an IL-33 axis binding antagonist (e.g., an ST2 binding antagonist)) being administered is adapted. The phrase "informing the patient" or "providing a recommendation," with respect to a treatment, as used herein also may refer to using the information or data generated for proposing or selecting a therapy (e.g., therapy comprising an IL-33 axis binding antagonist (e.g., an ST2 binding antagonist)) for a patient identified or selected as more or less likely to respond to the therapy. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of a marker, for example, periostin, to a reference level. In some embodiments, the information or data includes an indication that a marker, for example, periostin, is present or absent in the sample. In some embodiments, the information or data includes an indication that the patient is suitably treated or not suitably treated with a therapy (e.g., therapy comprising an IL-33 axis binding antagonist (e.g., an ST2 binding antagonist)).

A "kit" is any manufacture (e.g., a package or container) comprising at least one reagent, for example, a probe for determining the genotype of a polymorphism as described herein and/or a medicament for treatment of an IL-33-mediated disorder (e.g., an IL-33 axis binding antagonist (e.g., an ST2 binding antagonist)). The manufacture is preferably promoted, distributed, or sold as a unit for performing the methods of the present invention.

The terms "level," "level of expression," or "expression level" are used interchangeably and generally refer to the amount of a polynucleotide or an amino acid product or protein in a biological sample. "Expression" generally refers to the process by which gene-encoded information is converted into the structures present and operating in the cell. Therefore, according to the invention, "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. "Expressed genes" include those that are transcribed into a polynucleotide as mRNA and then translated into a protein, and also those that are transcribed into RNA but not translated into a protein (e.g., transfer and ribosomal RNAs).

The terms "oligonucleotide" and "polynucleotide" are used interchangeably and refer to a molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning. Chimeras of deoxyribonucleotides and ribonucleotides may also be in the scope of the present invention.

The term "patient" refers to any single animal, more specifically a mammal (including such non-human animals as, for example, dogs, cats, horses, rabbits, zoo animals, cows, pigs, sheep, and non-human primates) for which diagnosis or treatment is desired. Even more specifically, the patient herein is a human. In the context of the present invention, the patient may be a subject of any suitable population group, for example, any population group described in Example 4. In some embodiments, the patient may belong to a population group of African ancestry, Asian ancestry, and/or European ancestry, for example, a patient of Northern European ancestry. The patient may be a clinical patient, a clinical trial volunteer, an experimental animal, etc. The patient may be suspected of having, at risk for having, or diagnosed with an IL-33-mediated disorder (e.g., asthma or pulmonary fibrosis (e.g., idiopathic pulmonary fibrosis)).

The term "a patient suffering from" refers to a patient showing clinical signs in respect to a certain disease, such as, for example, an IL-33-mediated disorder (e.g., asthma or pulmonary fibrosis (e.g., idiopathic pulmonary fibrosis)).

The term "periostin," as used herein, refers to a protein that, in humans, is encoded by the POSTN gene, including any known isoform or variant thereof. Periostin is also referred to in the art as osteoblast specific factor or OSF-2. Human periostin isoforms 1, 2, 3 and 4 are known in the art as comprising the following amino acid sequences: NP_006466.2; NP_001129406.1, NP_001129407.1, and NP_001129408.1, respectively, according to the NCBI database. An additional form of periostin is described in U.S. Patent Publication 2012/0156194. This isoform is referred to herein as "isoform 5" and has been partially sequenced. Isoform 5 comprises the amino acid sequence of SEQ ID NO: 23 of U.S. Patent Publication 2012/0156194, the entirety of which is incorporated herein by reference. In some embodiments, periostin is serum periostin or plasma periostin (i.e., periostin from a serum sample obtained from whole blood or a plasma sample obtained from whole blood, respectively, the whole blood obtained from a patient).

The term "pharmaceutical composition" refers to a sterile preparation that is in such form as to permit the biological activity of the medicament to be effective, and which contains no additional components that are unacceptably toxic to a subject to which the formulation would be administered.

A nucleotide position in a genome at which more than one sequence is possible in a population is referred to herein as a "polymorphism" or "polymorphic site." A polymorphic site may be a nucleotide sequence of two or more nucleotides, an inserted nucleotide or nucleotide sequence, a deleted nucleotide or nucleotide sequence, or a microsatellite, for example. A polymorphic site that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic site which is a single nucleotide in length is referred to herein as a single nucleotide polymorphism (SNP), as described below. When there are two, three or four alternative nucleotide sequences at a polymorphic site, each nucleotide sequence is referred to as a "polymorphic variant" or "nucleic acid variant." Each possible variant in the DNA sequence is referred to as an "allele." Typically, the first identified allelic form is arbitrarily designated as the reference form and other allelic forms are designated as alternative or variant alleles. A "common" allele is an allele that is prevalent in a given population, e.g., the allele is present in multiple members of a population at a generally accepted frequency of greater than about 2%. Where two polymorphic variants exist, the polymorphic variant represented in a majority of samples from a population is referred to as a "prevalent allele," or "major allele," and the polymorphic variant that is less prevalent in the population is referred to as an "uncommon allele" or "minor allele." An individual who carries two prevalent alleles or two uncommon alleles is "homozygous" with respect to the polymorphism. An individual who carries one prevalent allele and one uncommon allele is "heterozygous" with respect to the polymorphism. With C/G or NT SNPs, the alleles are ambiguous and dependent on the strand used to extract the data from the genotyping platform. With these C/G or NT SNPs, the C or G nucleotide or the A or T nucleotide, respectively, may be the risk allele and is determined by correlation of allele frequencies.

The allele that correlates with an increased risk for a disease or disorder (e.g., an IL-33-mediated disorder, such an asthma) or is associated with an odds ratio or relative risk of >1 is referred to as the "risk allele" or "effect allele." The "risk allele" or "effect allele" may be the minor allele or major allele.

"Equivalent allele" or "surrogate allele," as used herein, refers to an allele that is expected to behave similarly to a risk allele and is selected based on allele frequencies and/or high $r^2$ value (greater than or equal to ($\geq$) 0.6) and/or high D' value ($\geq$0.6) with the risk alleles and/or selected SNP as defined herein. In one embodiment, the high $r^2$ value is $\geq$0.6, $\geq$0.7, $\geq$0.8, $\geq$0.9, or 1.0. In one embodiment, the high D' value is $\geq$0.6, $\geq$0.7, $\geq$0.8, $\geq$0.9, or 1.0.

"Linkage disequilibrium" or "LD" when used herein refers to alleles at different loci that are not associated at random, i.e., not associated in proportion to their frequencies. If the alleles are in positive linkage disequilibrium, then the alleles occur together more often than expected assuming statistical independence. Conversely, if the alleles are in negative linkage disequilibrium, then the alleles occur together less often than expected assuming statistical independence.

"Odds ratio" or "OR" when used herein refers to the ratio of the odds of the disease for individuals with the marker (allele or polymorphism) relative to the odds of the disease in individuals without the marker (allele or polymorphism).

"Haplotype" when used herein refers to a group of alleles on a single chromosome that are closely enough linked to be inherited usually as a unit.

In certain embodiments, the term "reference level" herein refers to a predetermined value. As the skilled artisan will appreciate, the reference level is predetermined and set to meet the requirements in terms of, for example, specificity and/or sensitivity. These requirements can vary, e.g., from regulatory body to regulatory body. It may be, for example, that assay sensitivity or specificity, respectively, has to be set to certain limits, e.g., 80%, 90% or 95%. These requirements may also be defined in terms of positive or negative predictive values. Nonetheless, based on the teaching given in the present invention it will always be possible to arrive at the reference level meeting those requirements. In one embodiment, the reference level is determined in healthy individuals. The reference value in one embodiment has been predetermined in the disease entity to which the patient belongs (e.g., an IL-33-mediated disorder, such as asthma). In certain embodiments, the reference level can be set to any percentage between, e.g., 25% and 75% of the overall distribution of the values in a disease entity investigated. In other embodiments, the reference level can be set to, for example, the median, tertiles, quartiles, or quintiles as determined from the overall distribution of the values in a disease entity investigated or in a given population. In one embodiment, the reference level is set to the median value as determined from the overall distribution of the values in a disease entity investigated. In one embodiments, the reference level may depend on the gender of the patient, e.g., males may have a different reference level than females.

In certain embodiments, the term "increase" or "above" refers to a level at the reference level or to an overall increase of 5%, 10%, 20%, 25%, 30%, 40%, 50%, 60%, 70%, 80%, 85%, 90%, 95%, 100% or greater, in the level of a marker (e.g., periostin or sST2) detected by the methods described herein, as compared to the level from a reference sample.

In certain embodiments, the term "decrease" or "below" herein refers to a level below the reference level or to an overall reduction of 5%, 10%, 20%, 25%, 30%, 40%, 50%, 60%, 70%, 80%, 85%, 90%, 95%, 96%, 97%, 98%, 99% or greater, in the level of a marker (e.g., periostin or sST2) detected by the methods described herein, as compared to the level from a reference sample.

In certain embodiments, the term "at a reference level" refers to a level of a marker (e.g., periostin or sST2) that is the same as the level, detected by the methods described herein, from a reference sample.

A "response" of a patient or a patient's "responsiveness" to treatment or therapy, for example treatment comprising an IL-33 axis binding antagonist (e.g., an ST2 binding antagonist), refers to the clinical or therapeutic benefit imparted to a patient at risk for or having an IL-33-mediated disorder (e.g., asthma or pulmonary fibrosis, e.g., idiopathic pulmonary fibrosis) from or as a result of the treatment. Such benefit may include cellular or biological responses, a complete response, a partial response, a stable disease (without progression or relapse), or a response with a later relapse of the patient from or as a result of the treatment with the antagonist. A skilled person will readily be in position to determine whether a patient is responsive. For example, a patient suffering from asthma who is responsive to treatment comprising an IL-33 axis binding antagonist (e.g., an ST2 binding antagonist) may show observable and/or measurable reduction in or absence of one or more of the following exemplary symptoms: recurrent wheezing, coughing, trouble breathing, chest tightness, symptoms that occur or worsen at night, symptoms that are triggered by cold air, exercise or exposure to allergens.

The term "single nucleotide polymorphism" or "SNP" refers to a single base substitution within a DNA sequence that leads to genetic variability. Single nucleotide polymorphisms may occur at any region of a gene. In some instances the polymorphism can result in a change in protein sequence. The change in protein sequence may affect protein function or not.

The term "selected SNP" when used herein refers to a SNP selected from the group consisting of polymorphism rs4988956 (SEQ ID NO: 1); polymorphism rs10204137 (SEQ ID NO: 2); polymorphism rs10192036 (SEQ ID NO: 3); polymorphism rs10192157 (SEQ ID NO: 4); polymorphism rs10206753 (SEQ ID NO: 5); and polymorphism rs4742165 (SEQ ID NO: 6).

The term "alternate SNP" when used herein refers to a SNP that is expected to behave similarly to a selected SNP and is selected based on similar allele frequencies and/or has linkage disequilibrium with a selected SNP as measured by an $r^2 \geq 0.6$ and/or $D' \geq 0.6$. Alternate SNPs include SNPs listed in Tables 3 and 4 that are in linkage disequilibrium with the SNPs described herein including polymorphism rs4988956 (SEQ ID NO: 1); polymorphism rs10204137 (SEQ ID NO: 2); polymorphism rs10192036 (SEQ ID NO: 3); polymorphism rs10192157 (SEQ ID NO: 4); polymorphism rs10206753 (SEQ ID NO: 5); and polymorphism rs4742165 (SEQ ID NO: 6). In some embodiments, the alternate SNP is in Table 3. In other embodiments, the alternate SNP is in Table 4.

The terms "sample" and "biological sample" are used interchangeably to refer to any biological sample obtained from an individual including body fluids, body tissue (e.g., lung samples), nasal samples (including nasal swabs or nasal polyps), sputum, cells, or other sources. Body fluids include, e.g., lymph, sera, whole fresh blood, frozen whole blood, plasma (including fresh or frozen), peripheral blood mononuclear cells, urine, saliva, semen, synovial fluid and spinal fluid. Methods for obtaining tissue biopsies and body fluids from mammals are well known in the art.

As used herein, "therapy" or "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Those in need of treatment include can include those already with the disorder as well as those at risk to have the disorder or those in whom the disorder is to be prevented. A patient may be successfully "treated" for asthma if, for example, after receiving an asthma therapy, the patient shows observable and/or measurable reduction in or absence of one or more of the following: recurrent wheezing, coughing, trouble breathing, chest tightness, symptoms that occur or worsen at night, symptoms that are triggered by cold air, exercise or exposure to allergens.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

II. Therapeutic Methods

The present invention provides methods of treating a patient suffering from an IL-33-mediated disorder (e.g., asthma or pulmonary fibrosis, e.g., idiopathic pulmonary fibrosis). In some embodiments, the methods of the invention include administering a therapy to a patient based on the presence and/or expression level of a biomarker of the invention, for example, a polymorphism (e.g., a polymorphism selected from the group consisting of rs4988956 (SEQ ID NO: 1); rs10204137 (SEQ ID NO: 2); rs10192036 (SEQ ID NO: 3); rs10192157 (SEQ ID NO: 4); rs10206753 (SEQ ID NO: 5); rs4742165 (SEQ ID NO: 6); and a SNP that is in linkage disequilibrium to rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and/or rs4742165 (SEQ ID NO: 6)), periostin, and/or sST2. In some instances, the polymorphism that is in linkage disequilibrium to rs4988956 (SEQ ID NO: 1), rs10204137 (SEQ ID NO: 2), rs10192036 (SEQ ID NO: 3), rs10192157 (SEQ ID NO: 4), and/or rs10206753 (SEQ ID NO: 5) is listed in Table 3. In some instances, the polymorphism that is in linkage disequilibrium to rs4742165 (SEQ ID NO: 6) is listed in Table 4.

In some embodiments, the methods of the invention include administering to the patient a therapy comprising one or more (e.g., 1, 2, 3, 4, 5, 6, or 7) of an IL-33 axis binding antagonist (e.g., an ST2 binding antagonist), a tryptase-beta binding antagonist, a CRTH2 binding antagonist, an interleukin-13 (IL-13) binding antagonist, an interleukin-17 (IL-17) binding antagonist, a Janus kinase 1 (JAK1) antagonist, and/or an interleukin-5 (IL-5) binding antagonist, wherein the genotype of the patient has been determined to comprise at least one (e.g., 1, 2, 3, 4, 5, 6, 7, or more than 7) allele(s) selected from the group consisting of a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6). In some embodiments, the SNP that is in linkage disequilibrium with polymorphism rs4988956 (SEQ ID NO: 1), polymorphism rs10204137 (SEQ ID NO: 2), polymorphism rs10192036 (SEQ ID NO: 3), polymorphism rs10192157 (SEQ ID NO: 4), and/or polymorphism rs10206753 (SEQ ID NO: 5) is listed in Table 3. In some embodiments, the SNP that is in linkage disequilibrium with polymorphism rs4742165 (SEQ ID NO: 6) is listed in Table 4.

In some embodiments, the methods of the invention include administering to the patient a therapy comprising one or more (e.g., 1, 2, 3, 4, 5, 6, or 7) of an IL-33 axis binding antagonist (e.g., an ST2 binding antagonist), a tryptase-beta binding antagonist, a CRTH2 binding antagonist, an interleukin-13 (IL-13) binding antagonist, an interleukin-17 (IL-17) binding antagonist, a Janus kinase 1 (JAK1) antagonist, and/or an interleukin-5 (IL-5) binding antagonist, wherein the genotype of the patient has been determined to comprise at least one allele (e.g., 1, 2, 3, 4, or 5 alleles) listed in Table 2 (e.g., the genotype of the patient may comprise a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); and/or a T allele at polymorphism rs10206753 (SEQ ID NO: 5)).

In some embodiments, the methods of the invention include administering to the patient a therapy comprising one or more (e.g., 1, 2, 3, 4, 5, 6, or 7) of an IL-33 axis binding antagonist (e.g., an ST2 binding antagonist), a tryptase-beta binding antagonist, a CRTH2 binding antagonist, an interleukin-13 (IL-13) binding antagonist, an interleukin-17 (IL-17) binding antagonist, a Janus kinase 1 (JAK1) antagonist, and/or an interleukin-5 (IL-5) binding antagonist, wherein the genotype of the patient has been determined to comprise a T allele at polymorphism rs4742165 (SEQ ID NO: 6).

In any of the preceding methods, the equivalent allele may be at an alternate SNP that is in linkage disequilibrium with one or more of the selected SNPs described herein. In some embodiments, the linkage disequilibrium is a D' value or an $r^2$ value. In some embodiments, the D' measure between the selected SNP and the alternate SNP is ≥0.60 (e.g., ≥0.60, ≥0.65, ≥0.7, ≥0.75, ≥0.8, ≥0.85, ≥0.9, ≥0.95, or higher). In some embodiments, the D' value between the selected SNP and the alternate SNP is ≥0.70, ≥0.80, or ≥0.90. In some embodiments, the D' value between the selected SNP and the alternate SNP is 1.0. In some embodiments, the $r^2$ value between the selected SNP and the alternate SNP is ≥0.60 (e.g., ≥0.60, ≥0.65, ≥0.7, ≥0.75, ≥0.8, ≥0.85, ≥0.9, ≥0.95, or higher). In some embodiments the $r^2$ value between the selected SNP and the alternate SNP is ≥0.70, ≥0.80, or ≥0.90. In some embodiments, the $r^2$ value between the selected SNP and the alternate SNP is 1.0. In some embodiments, the alternate SNP is a SNP designated in Table 3 or 4. In any of the preceding methods, the equivalent allele may be the minor allele or the major allele. In some instances, the equivalent allele is the minor allele. In other instances, the equivalent allele is the major allele.

The genotype of a patient can be determined using any of the methods or assays described herein (e.g., in Section IV of the Detailed Description of the Invention or in Example 1) or that are known in the art. In some embodiments, the methods are directed to, or further include, determining the level of a biomarker (e.g., periostin or sST2) in a sample derived from the patient. The level of a biomarker (e.g., periostin or sST2) can be determined using any of the assays or methods described herein or known in the art. For example, the level of periostin can be determined, for example, using the periostin assays described in WO 2012/083132, the entirety of which is incorporated herein by reference. In another example, the level of sST2 can be determined using any of the assays or methods described herein or known in the art, for example, in Example 3.

In other embodiments, the methods of the invention include administering to the patient a therapy comprising one or more (e.g., 1, 2, 3, 4, 5, 6, or 7) of an IL-33 axis binding antagonist (e.g., an ST2 binding antagonist), a tryptase-beta binding antagonist, a CRTH2 binding antagonist, an interleukin-13 (IL-13) binding antagonist, an interleukin-17 (IL-17) binding antagonist, a Janus kinase 1 (JAK1) antagonist, and/or an interleukin-5 (IL-5) binding antagonist, wherein the patient, prior to any administration of an IL-33 axis binding antagonist, has been determined to have a level of sST2 in a sample derived from the patient at or above a reference level. In some instances, the level of sST2 is a level of sST2 protein. In some instances, the sample derived from a patient is a whole blood sample, a serum sample, a plasma sample, or a combination thereof. In some instances, the sample derived from a patient a serum sample. In some instances, the reference level of sST2 is a level of sST2 determined from a group of individuals, wherein each member of the group has a genotype comprising two G alleles at polymorphism rs4742165 (SEQ ID NO: 6). In some instances, the reference level of sST2 is a level of sST2 determined from a group of individuals, wherein each member of the group has a genotype comprising two G alleles at polymorphism rs3771166 (SEQ ID NO: 8). In some instances, the group of individuals is suffering from asthma. In some instances, the reference level of sST2 is a median level. In some instances, the group of individuals is a group of female individuals and the patient is female. In some instances, the group of individuals is a group of male individuals and the patient is male.

In some embodiments, the IL-33 mediated disorder may be an inflammatory condition, an immune disorder, a fibrotic disorder, an eosinophilic disorder, an infection, pain, a central nervous system disorder, a solid tumor, or an ophthalmologic disorder. For example, in some instances, an inflammatory condition may be asthma, airway hyperresponsiveness, airway inflammation, sepsis, septic shock, atopic dermatitis, allergic rhinitis, rheumatoid arthritis, or chronic obstructive pulmonary disease (COPD). In some instances, an immune disorder may be asthma, rheumatoid arthritis, allergy, atopic allergy, anaphylaxis, anaphylactic shock, allergic rhinitis, psoriasis, inflammatory bowel disease (IBD), Crohn's disease, diabetes, or liver disease. In some instances, the fibrotic disease may be idiopathic pulmonary fibrosis (IPF). In some instances, the eosinophilic disorder may be an eosinophil-associated gastrointestinal disorder (EGID). In some instances, the EGID may be eosinophilic esophagitis. In some instances, the infection may be a helminth infection, a protozoan infection, or a viral infection. In some instances, the protozoan infection may be *Leishmania major* infection. In some instances, the viral infection may be respiratory syncytial virus (RSV) infection or influenza infection. In some instances, the pain may be inflammatory pain. In some instances, the central nervous system disorder may be Alzheimer's disease. In some instances, the solid tumor may be a breast tumor, colon tumor, prostate tumor, lung tumor, kidney tumor, liver tumor, pancreas tumor, stomach tumor, intestinal tumor, brain tumor, bone tumor, or skin tumor. In some embodiments, the ophthalmologic disorder may be age-related macular degeneration (AMD) or retinopathy of the eye. In particular instances, the IL-33-mediated disorder may be asthma, allergic rhinitis, atopic dermatitis, COPD, eosinophilic esophagitis, or pulmonary fibrosis (e.g., IPF). For example, in some instances, the IL-33-mediated disorder is asthma. In other instances, the IL-33-mediated disorder is pulmonary fibrosis (e.g., IPF).

In some instances, the methods of the invention include administering to the patient a therapy comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist. For example, the method may include administering a therapy comprising an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, or an IL-5 binding antagonist. In other instances, the method may include administering a therapy comprising at least two agents, for example, an IL-33 axis binding antagonist (e.g., an ST2 binding antagonist) and a tryptase-beta binding antagonist, an IL-33 axis binding antagonist (e.g., an ST2 binding antagonist) and a CRTH2 binding antagonist, an IL-33 axis binding antagonist (e.g., an ST2 binding antagonist) and an IL-13 binding antagonist, an IL-33 axis binding antagonist (e.g., an ST2 binding antagonist) and an IL-17 binding antagonist, an IL-33 axis binding antagonist (e.g., an ST2 binding antagonist) and a JAK1 antagonist, an IL-33 axis binding antagonist (e.g., an ST2 binding antagonist) and an IL-5 binding antagonist, a tryptase-beta binding antagonist and a CRTH2 binding antagonist, a tryptase-beta binding antagonist and an IL-13 binding antagonist, a tryptase-beta binding antagonist and an IL-17 binding antagonist, a tryptase-beta binding antagonist and a JAK1 antagonist, a tryptase-beta binding antagonist and an IL-5 binding antagonist, a CRTH2 binding antagonist and an IL-13 binding antagonist, a CRTH2 binding antagonist and an IL-17 binding antagonist, a CRTH2 binding antagonist and a JAK1 antagonist, a CRTH2 binding antagonist and an IL-5 binding antagonist, an IL-13 binding antagonist and an IL-17 binding antagonist, an IL-13 binding antagonist and a JAK1 antagonist, an IL-13 binding antagonist and an IL-5 binding antagonist, an IL-17 binding antagonist and a JAK1 antagonist, an IL-17 binding antagonist and an IL-5 binding antagonist, or a JAK1 antagonist and an IL-5 binding antagonist. In other instances, the method may include administering a therapy comprising at least three agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In other instances, the method may include administering a therapy comprising at least four agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In other instances, the method may include administering a therapy comprising at least five agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In yet other instances, the method may include administering a therapy comprising at least six agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In yet other instances, the method may include administering a therapy comprising an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist.

In some instances, the invention includes an IL-33 axis binding antagonist (e.g., an ST2 binding antagonist) for use in treating a patient suffering from an IL-33-mediated disorder, wherein the patient, prior to any administration of an IL-33 axis binding antagonist (e.g., an ST2 binding antagonist), has been determined to comprise one, two, three, four, five, six, seven, or more than seven of the following alleles: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In some instances, the invention includes the use of an effective amount of an IL-33 axis binding antagonist (e.g., an ST2 binding antagonist) in the manufacture of a medicament for use in treating a patient suffering from an IL-33-mediated disorder, wherein the patient has been determined to comprise one, two, three, four, five, six, seven, or more than seven of the following alleles: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In some instances, the invention includes a composition including an effective amount of an IL-33 axis binding antagonist (e.g., an ST2 binding antagonist) for use in a method of treating a patient suffering from an IL-33-mediated disorder, wherein the patient has been determined to comprise one, two, three, four, five, six, or seven, or more than seven of the following alleles: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6);

and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6). The composition may be a pharmaceutical composition.

In some instances, the invention includes an IL-33 axis binding antagonist (e.g., an ST2 binding antagonist) for use in treating a patient suffering from an IL-33-mediated disorder, wherein the patient, prior to any administration of an IL-33 axis binding antagonist (e.g., an ST2 binding antagonist), has been determined to have a level of sST2 in a sample derived from the patient at or above a reference level. In some instances, the level of sST2 is a level of sST2 protein. In some instances, the sample derived from a patient is a whole blood sample, a serum sample, a plasma sample, or a combination thereof. In some instances, the sample derived from a patient a serum sample. In some instances, the reference level of sST2 is a level of sST2 determined from a group of individuals, wherein each member of the group has a genotype comprising two G alleles at polymorphism rs4742165 (SEQ ID NO: 6). In some instances, the reference level of sST2 is a level of sST2 determined from a group of individuals, wherein each member of the group has a genotype comprising two G alleles at polymorphism rs3771166 (SEQ ID NO: 8). In some instances, the group of individuals is suffering from asthma. In some instances, the reference level of sST2 is a median level. In some instances, the group of individuals is a group of female individuals and the patient is female. In some instances, the group of individuals is a group of male individuals and the patient is male.

In other instances, the invention includes the use of an effective amount of an IL-33 axis binding antagonist (e.g., an ST2 binding antagonist) in the manufacture of a medicament for use in treating a patient suffering from an IL-33-mediated disorder, wherein the patient has been determined to have a level of sST2 in a sample derived from the patient at or above a reference level. In some instances, the level of sST2 is a level of sST2 protein. In some instances, the sample derived from a patient is a whole blood sample, a serum sample, a plasma sample, or a combination thereof. In some instances, the sample derived from a patient a serum sample. In some instances, the reference level of sST2 is a level of sST2 determined from a group of individuals, wherein each member of the group has a genotype comprising two G alleles at polymorphism rs4742165 (SEQ ID NO: 6). In some instances, the reference level of sST2 is a level of sST2 determined from a group of individuals, wherein each member of the group has a genotype comprising two G alleles at polymorphism rs3771166 (SEQ ID NO: 8). In some instances, the group of individuals is suffering from asthma. In some instances, the reference level of sST2 is a median level. In some instances, the group of individuals is a group of female individuals and the patient is female. In some instances, the group of individuals is a group of male individuals and the patient is male.

In some instances, the invention includes a composition including an effective amount of an IL-33 axis binding antagonist (e.g., an ST2 binding antagonist) for use in a method of treating a patient suffering from an IL-33-mediated disorder, wherein the patient has been determined to have a level of sST2 in a sample derived from the patient at or above a reference level. In some instances, the level of sST2 is a level of sST2 protein. In some instances, the sample derived from a patient is a whole blood sample, a serum sample, a plasma sample, or a combination thereof. In some instances, the sample derived from a patient a serum sample. In some instances, the reference level of sST2 is a level of sST2 determined from a group of individuals, wherein each member of the group has a genotype comprising two G alleles at polymorphism rs4742165 (SEQ ID NO: 6). In some instances, the reference level of sST2 is a level of sST2 determined from a group of individuals, wherein each member of the group has a genotype comprising two G alleles at polymorphism rs3771166 (SEQ ID NO: 8). In some instances, the group of individuals is suffering from asthma. In some instances, the reference level of sST2 is a median level. In some instances, the group of individuals is a group of female individuals and the patient is female. In some instances, the group of individuals is a group of male individuals and the patient is male.

Exemplary IL-33 axis binding antagonists include anti-IL-33 antibodies such as ANB-020 (AnaptyxBio Inc.) or any of the antibodies described in WO2014164959, EP1725261, U.S. Pat. No. 8,187,569, WO2011031600, WO2015099175 or WO2015106080, which are each incorporated herein by reference in their entirety; or anti-ST2 antibodies such as AMG-282 (Amgen) or STLM15 (Janssen), or any of the antibodies described in WO2013173761 or WO2013165894, which are each incorporated herein by reference in their entirety.

Exemplary ST2 binding antagonists include ST2-Fc proteins and variants thereof described in WO 2013/173761, WO 2013/165894, and WO 2014/152195, which are each incorporated herein by reference in their entirety.

Exemplary CRTH2 binding antagonists that can be used in the methods of the invention include, for example, AMG-853, AP768, AP-761, MLN6095, and ACT129968.

Exemplary IL-13 binding antagonists that can be used in the methods of the invention include, for example, anti-IL-13 antibodies, including lebrikizumab, 228B/C-1, 228A-4, 227-26, and 227-43. Additional anti-IL-13 antibodies are described, for example, in U.S. Pat. Nos. 7,674,459; 8,067,199; 8,088,618; 8,318,160; and 8,734,797.

Exemplary IL-17 binding antagonists that can be used in the methods of the invention include, for example, anti-IL-17 antibodies (e.g., ixekizumab (LY2439821) and anti-IL-17R antibodies (e.g., brodalumab (AMG-827)).

Exemplary JAK1 antagonists that can be used in the methods of the invention include, for example, small molecule inhibitors (e.g., ruxolitinib, GLPG0634, and GSK2586184).

Exemplary IL-5 binding antagonists that can be used in the methods of the invention include, for example, anti-IL-5 antibodies (e.g., mepolizumab and reslizumab) and anti-IL-5R antibodies.

In some embodiments, the genotype of the patient includes one or more (e.g., 1, 2, 3, 4, 5, 6, 7, or more than 7) of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In other embodiments, the genotype of the patient includes at least two of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

For example, in some instances the genotype of the patient includes a G allele at polymorphism rs4988956 (SEQ ID NO: 1) and an A allele at polymorphism rs10204137 (SEQ ID NO: 2); a G allele at polymorphism rs4988956 (SEQ ID NO: 1) and a C allele at polymorphism rs10192036 (SEQ ID NO: 3); a G allele at polymorphism rs4988956 (SEQ ID NO: 1) and a C allele at polymorphism rs10192157 (SEQ ID NO: 4); a G allele at polymorphism rs4988956 (SEQ ID NO: 1) and a T allele at polymorphism rs10206753 (SEQ ID NO: 5); a G allele at polymorphism rs4988956 (SEQ ID NO: 1) and a T allele at polymorphism rs4742165 (SEQ ID NO: 6); a G allele at polymorphism rs4988956 (SEQ ID NO: 1) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); an A allele at polymorphism rs10204137 (SEQ ID NO: 2) and a C allele at polymorphism rs10192036 (SEQ ID NO: 3); an A allele at polymorphism rs10204137 (SEQ ID NO: 2) and a C allele at polymorphism rs10192157 (SEQ ID NO: 4); an A allele at polymorphism rs10204137 (SEQ ID NO: 2) and a T allele at polymorphism rs10206753 (SEQ ID NO: 5); an A allele at polymorphism rs10204137 (SEQ ID NO: 2) and a T allele at polymorphism rs4742165 (SEQ ID NO: 6); an A allele at polymorphism rs10204137 (SEQ ID NO: 2) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); a C allele at polymorphism rs10192036 (SEQ ID NO: 3) and a C allele at polymorphism rs10192157 (SEQ ID NO: 4); a C allele at polymorphism rs10192036 (SEQ ID NO: 3) and a T allele at polymorphism rs10206753 (SEQ ID NO: 5); a C allele at polymorphism rs10192036 (SEQ ID NO: 3) and a T allele at polymorphism rs4742165 (SEQ ID NO: 6); a C allele at polymorphism rs10192036 (SEQ ID NO: 3) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); a C allele at polymorphism rs10192157 (SEQ ID NO: 4) and a T allele at polymorphism rs10206753 (SEQ ID NO: 5); a C allele at polymorphism rs10192157 (SEQ ID NO: 4) and a T allele at polymorphism rs4742165 (SEQ ID NO: 6); a C allele at polymorphism rs10192157 (SEQ ID NO: 4) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); a T allele at polymorphism rs10206753 (SEQ ID NO: 5) and a T allele at polymorphism rs4742165 (SEQ ID NO: 6); a T allele at polymorphism rs10206753 (SEQ ID NO: 5) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); or a T allele at polymorphism rs4742165 (SEQ ID NO: 6) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In other embodiments, the genotype of the patient includes at least three of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In other embodiments, the genotype of the patient includes at least four of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In some embodiments, the genotype of the patient includes a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); and a T allele at polymorphism rs10206753 (SEQ ID NO: 5). In some embodiments, the genotype of the patient includes a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); and a T allele at polymorphism rs4742165 (SEQ ID NO: 6). In some embodiments, the genotype of the patient includes a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In any of the preceding embodiments, the equivalent allele may be in an alternate SNP that is in linkage disequilibrium with one or more of the selected SNPs described herein. In some embodiments, the linkage disequilibrium is a D' value or an $r^2$ value. In some embodiments, the D' measure between the selected SNP and the alternate SNP is ≥0.60 (e.g., ≥0.60, ≥0.65, ≥0.7, ≥0.75, ≥0.8, ≥0.85, ≥0.9, ≥0.95, or higher). In some embodiments, the D' value between the selected SNP and the alternate SNP is ≥0.70, ≥0.80, or ≥0.90. In some embodiments, the D' value between the selected SNP and the alternate SNP is 1.0. In some embodiments, the $r^2$ value between the selected SNP and the alternate SNP is ≥0.60 (e.g., ≥0.60, ≥0.65, ≥0.7, ≥0.75, ≥0.8, ≥0.85, ≥0.9, ≥0.95, or higher). In some embodiments the $r^2$ value between the selected SNP and the alternate SNP is ≥0.70, ≥0.80, or ≥0.90. In some embodiments, the $r^2$ value between the selected SNP and the alternate SNP is 1.0. In some embodiments, the alternate SNP is a SNP designated in Table 3 or 4. In any of the preceding methods, the equivalent allele may be the minor allele or the major allele. In some instances, the equivalent allele is the minor allele. In other instances, the equivalent allele is the major allele.

The therapy (e.g., a therapy comprising one or more (e.g., 1, 2, 3, 4, 5, 6, or 7) of an IL-33 axis binding antagonist (e.g., an ST2 binding antagonist), a tryptase-beta binding antagonist, a CRTH2 binding antagonist, an interleukin-13 (IL-13) binding antagonist, an interleukin-17 (IL-17) binding antagonist, a Janus kinase 1 (JAK1) antagonist, and/or an interleukin-5 (IL-5) binding antagonist) is administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the antagonist may suitably be administered by pulse infusion, e.g., with declining doses of the antagonist.

As a general proposition, the effective amount of the antagonist administered parenterally per dose will be in the range of about 20 mg to about 5000 mg, by one or more dosages. Exemplary dosage regimens for antibodies such as anti-IL-33 antibodies include 100 or 400 mg every 1, 2, 3, or 4 weeks or is administered a dose of about 1, 3, 5, 10, 15, or 20 mg/kg every 1, 2, 3, or 4 weeks. The dose may be administered as a single dose or as multiple doses (e.g., 2 or 3 doses), such as infusions. As noted above, however, these suggested amounts of antagonist are subject to a great deal of therapeutic discretion. The key factor in selecting an appropriate dose and scheduling is the result obtained, as indicated above. In some embodiments, the antagonist is administered as close to the first sign, diagnosis, appearance, or occurrence of the IL-33-mediated disorder as possible. The pharmaceutical composition comprising an antagonist will be formulated, dosed, and administered in a fashion consistent with good medical practice. Factors for consideration in this context include the particular type of IL-33-mediated disorder being treated, the particular mammal being treated, the clinical condition of the individual patient, the cause of the IL-33-mediated disorder, the site of delivery of the agent, possible side-effects, the type of antagonist, the method of administration, the scheduling of administration, and other factors known to medical practitioners. The effective amount of the antagonist to be administered will be governed by such considerations.

An antagonist, for example, an IL-33 axis binding antagonist (e.g., an ST2 binding antagonist), a tryptase-beta binding antagonist, a CRTH2 binding antagonist, an interleukin-13 (IL-13) binding antagonist, an interleukin-17 (IL-17) binding antagonist, a JAK1 antagonist, or an interleukin-5 (IL-5) binding antagonist, may be combined in a pharmaceutical combination formulation, or dosing regimen as combination therapy, with at least one additional compound having anti-asthma, anti-inflammatory, anti-autoimmune, anti-fibrotic, and/or anti-cancer properties. The at least one additional compound of the pharmaceutical combination formulation or dosing regimen preferably has complementary activities to the antagonist composition such that they do not adversely affect each other.

Suitable dosages for any of the above co-administered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. The combined administration includes co-administration, using separate formulations or a single pharmaceutical formulation, and consecutive administration in either order, wherein preferably there is a time period while both (or all) active agents simultaneously exert their biological activities. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e. serially, whereas in combination therapy, effective dosages of two or more active ingredients are administered together. When administered sequentially, the combination may be administered in two or more administrations.

In the context of the invention, a therapy (e.g., a therapy comprising one or more (e.g., 1, 2, 3, 4, 5, 6, or 7) of an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and/or an IL-5 binding antagonist) may be administered in addition to or as a co-therapy or a co-treatment with a further asthma therapy, as described below or known in the art. Moderate asthma is currently treated with a daily inhaled anti-inflammatory-corticosteroid or mast cell inhibitor such as cromolyn sodium or nedocromil plus an inhaled beta2-agonist as needed (3-4 times per day) to relieve breakthrough symptoms or allergen- or exercise-induced asthma. Exemplary inhaled corticosteroids include QVAR®, PULMICORT®, SYMBICORT®, AEROBID®, FLOVENT®, FLONASE®, ADVAIR®, and AZMACORT®. Additional asthma therapies include long acting bronchial dilators (LABD). In certain embodiments, the LABD is a long-acting beta-2 agonist (LABA), leukotriene receptor antagonist (LTRA), long-acting muscarinic antagonist (LAMA), theophylline, or oral corticosteroids (OCS). Exemplary LABDs include SYMBICORT®, ADVAIR®, BROVANA®, FORADIL®, PERFOROMIST™ and SEREVENT®.

In the context of the present invention, the therapy (e.g., a therapy comprising one or more (e.g., 1, 2, 3, 4, 5, 6, or 7) of an IL-33 axis binding antagonist (e.g., an ST2 binding antagonist, e.g., an ST2-Fc protein), a tryptase-beta binding antagonist, a CRTH2 binding antagonist, an IL-13 binding antagonist, an IL-17 binding antagonist, a JAK1 antagonist, and/or an IL-5 binding antagonist) may be administered in addition to or as a co-therapy or a co-treatment with one or more chemotherapeutic agents administered as part of standard chemotherapy regimen for a solid tumor as known in the art. Examples of agents included in such standard chemotherapy regimens include 5-fluorouracil, leucovorin, irinotecan, gemcitabine, erlotinib, capecitabine, taxanes, such as docetaxel and paclitaxel, interferon alpha, vinorelbine, and platinum-based chemotherapeutic agents, such as paclitaxel, carboplatin, cisplatin and oxaliplatin. Examples of co-treatments for metastatic pancreatic cancer include gemcitabine-erlotinib plus bevacizumab at a dosage of 5 mg/kg or 10 mg/kg of body weight given once every two weeks or 7.5 mg/kg or 15 mg/kg of body weight given once every three weeks. Examples of co-treatments for renal cell cancer include interferon alpha plus bevacizumab at a dosage of or 10 mg/kg of body weight given once every two weeks. Further, a patient may be co-treated with a combination of irinotecan, 5-fluorouracil, leucovorin, also referred to as IFL, as, for example, a bolus-IFL, with a combination of oxaliplatin, leucovorin, and 5-fluorouracil, also referred to a FOLFOX4 regimen, or with a combination of capecitabine and oxaliplatin, also referred to as XELOX. Accordingly, in a further embodiment of the invention, the patient suffering from an IL-33-mediated disorder is being treated with one or more chemotherapeutic agents such as 5-fluorouracil, leucovorin, irinotecan, gemcitabine-erlotinib, capecitabine and/or platinum-based chemotherapeutic agents, such as paclitaxel, carboplatin and oxaliplatin. Further, the therapy to be administered may be administered as a co-therapy or a co-treatment with radiotherapy.

The at least one additional compound may be a chemotherapeutic agent, a cytotoxic agent, a cytokine, a growth inhibitory agent, an anti-hormonal agent, and combinations thereof. Such molecules are suitably present in combination in amounts that are effective for the purpose intended. A pharmaceutical composition containing an IL-33 axis binding antagonist (e.g., an anti-IL-33 antibody or an ST2 binding antagonist, e.g., an ST2-Fc protein) may also comprise a therapeutically effective amount of an anti-neoplastic agent, a chemotherapeutic agent a growth inhibitory agent, a cytotoxic agent, or combinations thereof.

III. Diagnostic Methods

The present invention provides methods for identifying and/or monitoring patients at increased risk (i.e., increased susceptibility) of having or developing one or more IL-33-mediated disorders (e.g., asthma or pulmonary fibrosis (e.g., idiopathic pulmonary fibrosis)). The methods are useful, inter alia, for increasing the likelihood that administration of a therapy (e.g., a therapy comprising one or more (e.g., 1, 2, 3, 4, 5, 6, or 7) of an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist) to a patient having an IL-33-mediated disorder will be efficacious. In several embodiments, the methods include determining the genotype at one or more polymorphisms (e.g., IL1RL1 and/or IL33 polymorphisms) in a biological sample from a patient (e.g., the polymorphisms listed in Table 1, Table 2, Table 3, and Table 4). In some embodiments, the invention provides methods for identifying and/or monitoring patients at increased risk (i.e., increased susceptibility) of having or developing one or more IL-33-mediated disorder (e.g., asthma or pulmonary fibrosis (e.g., idiopathic pulmonary fibrosis)) based on the presence and/or expression level of a biomarker of the invention, for example, a polymorphism (e.g., a polymorphism selected from the group consisting of rs4988956 (SEQ ID NO: 1); rs10204137 (SEQ ID NO: 2); rs10192036 (SEQ ID NO: 3); rs10192157 (SEQ ID NO: 4); rs10206753 (SEQ ID NO: 5); rs4742165 (SEQ ID NO: 6); a polymorphism that is in linkage disequilibrium to rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and/or rs4742165 (SEQ ID NO: 6)); periostin; and/or sST2. In some instances, the polymorphism that is in linkage disequilibrium to rs4988956 (SEQ ID NO: 1); rs10204137 (SEQ ID NO: 2); rs10192036 (SEQ ID NO: 3); rs10192157 (SEQ ID NO: 4); and/or rs10206753 (SEQ ID NO: 5) is listed in Table 3. In some instances, the polymorphism that is in linkage disequilibrium to rs4742165 (SEQ ID NO: 6) is listed in Table 4. In some embodiments, the methods include determining the level of one or more biomarkers (e.g., periostin and/or sST2) in a sample derived from the patient.

The methods and assays of the invention provide for convenient, efficient, and potentially cost-effective means to obtain data and information useful in assessing appropriate or effective therapies for treating patients (e.g., patients suffering from an IL-33-mediated disorder). For example, a patient could provide a biological sample (e.g., a blood sample, nasal samples, lung samples, sputum, etc.) before treatment (e.g., administration of a therapy comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist) and the sample could be examined by way of various in vitro assays to determine whether the patient's cells are likely to be responsive to the treatment.

The methods may be conducted in a variety of assay formats, including assays detecting genetic information (e.g., DNA or RNA sequencing), genetic or protein expression (such as polymerase chain reaction (PCR) and enzyme immunoassays), and biochemical assays detecting appropriate activity, for example, as described below. The presence of one or more of the alleles for the polymorphisms listed in Table 2 in a sample from a patient correlates with the likelihood that the patient is at risk for an IL-33-mediated disorder (e.g., asthma or pulmonary fibrosis (e.g., idiopathic pulmonary fibrosis)). Example 1 shows that the presence of one or more of the alleles for the polymorphisms listed in Table 2 indicates such risk, and thus in various embodiments determination of the genotype at one or more of these polymorphisms in the methods described herein are included in the invention.

In one instance, this invention provides a method of determining whether a patient is at increased risk of an IL-33-mediated disorder (e.g., asthma or pulmonary fibrosis (e.g., idiopathic pulmonary fibrosis)), the method including determining the genotype of at least one allele (e.g., 1, 2, 3, 4, 5, 6, 7, or more than 7 alleles) listed in Table 1, Table 2, Table 3, or Table 4 in a sample derived from the patient, wherein the patient is at increased risk of an IL-33-mediated disorder if the genotype of the patient comprises an allele listed in Table 2; a T allele at polymorphism rs4742165 (SEQ ID NO: 6); and/or an equivalent allele in a SNP that is in linkage disequilibrium to rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and/or rs4742165 (SEQ ID NO: 6).

For example, in some embodiments, the method includes determining the genotype at one or more polymorphisms (e.g., 1, 2, 3, 4, 5, 6, 7, or more than 7 polymorphisms) selected from the group consisting of rs4988956 (SEQ ID NO: 1); rs10204137 (SEQ ID NO: 2); rs10192036 (SEQ ID NO: 3); rs10192157 (SEQ ID NO: 4); rs10206753 (SEQ ID NO: 5); rs4742165 (SEQ ID NO: 6); and a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6) in a sample derived from the patient, wherein the patient is at increased risk of asthma if the genotype of the patient comprises (a) a G allele at polymorphism rs4988956 (SEQ ID NO: 1); (b) an A allele at polymorphism rs10204137 (SEQ ID NO: 2); (c) a C allele at polymorphism rs10192036 (SEQ ID NO: 3); (d) a C allele at polymorphism rs10192157 (SEQ ID NO: 4); (e) a T allele at polymorphism rs10206753 (SEQ ID NO: 5); (f) a T allele at polymorphism rs4742165 (SEQ ID NO: 6); and/or (g) an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In some instances, the patient is at an increased risk of an IL-33-mediated disorder if the genotype of the patient includes one or more (e.g., 1, 2, 3, 4, 5, 6, 7, or more than 7) of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6). In some instances, the genotype of the patient at increased risk of an IL-33-mediated disorder includes a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5) a T allele at polymorphism rs4742165 (SEQ ID NO: 6); or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In other embodiments, the genotype of a patient at increased risk for an IL-33-mediated disorder includes at least two of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

For example, in some instances the genotype of the patient includes a G allele at polymorphism rs4988956 (SEQ ID NO: 1) and an A allele at polymorphism rs10204137 (SEQ ID NO: 2); a G allele at polymorphism rs4988956 (SEQ ID NO: 1) and a C allele at polymorphism rs10192036 (SEQ ID NO: 3); a G allele at polymorphism rs4988956 (SEQ ID NO: 1) and a C allele at polymorphism rs10192157 (SEQ ID NO: 4); a G allele at polymorphism rs4988956 (SEQ ID NO: 1) and a T allele at polymorphism rs10206753 (SEQ ID NO: 5); a G allele at polymorphism rs4988956 (SEQ ID NO: 1) and a T allele at polymorphism rs4742165 (SEQ ID NO: 6); a G allele at polymorphism rs4988956 (SEQ ID NO: 1) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); an A allele at polymorphism rs10204137 (SEQ ID NO: 2) and a C allele at polymorphism rs10192036 (SEQ ID NO: 3); an A allele at polymorphism rs10204137 (SEQ ID NO: 2) and a C allele at polymorphism rs10192157 (SEQ ID NO: 4); an A allele at polymorphism rs10204137 (SEQ ID NO: 2) and a T allele at polymorphism rs10206753 (SEQ ID NO: 5); an A allele at polymorphism rs10204137 (SEQ ID NO: 2) and a T allele at polymorphism rs4742165 (SEQ ID NO: 6); an A allele at polymorphism rs10204137 (SEQ ID NO: 2) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); a C allele at polymorphism rs10192036 (SEQ ID NO: 3) and a C allele at polymorphism rs10192157 (SEQ ID NO: 4); a C allele at polymorphism rs10192036 (SEQ ID NO: 3) and a T allele at polymorphism rs10206753 (SEQ ID NO: 5); a C allele at polymorphism rs10192036 (SEQ ID NO: 3) and a T allele at polymorphism rs4742165 (SEQ ID NO: 6); a C allele at polymorphism rs10192036 (SEQ ID NO: 3) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); a C allele at polymorphism rs10192157 (SEQ ID NO: 4) and a T allele at polymorphism rs10206753 (SEQ ID NO: 5); a C allele at polymorphism rs10192157 (SEQ ID NO: 4) and a T allele at polymorphism rs4742165 (SEQ ID NO: 6); a C allele at polymorphism rs10192157 (SEQ ID NO: 4) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); a T allele at polymorphism rs10206753 (SEQ ID NO: 5) and a T allele at polymorphism rs4742165 (SEQ ID NO: 6); a T allele at polymorphism rs10206753 (SEQ ID NO: 5) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); or a T allele at polymorphism rs4742165 (SEQ ID NO: 6) and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In other embodiments, the genotype of a patient at risk for an IL-33-mediated disorder includes at least three of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In other embodiments, the genotype of the patient includes at least four of the following: a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and/or an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In other embodiments, the genotype of the patient at risk for an IL-33-mediated disorder includes a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); and a T allele at polymorphism rs10206753 (SEQ ID NO: 5). In some embodiments, the genotype of the patient includes a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); and a T allele at polymorphism rs4742165 (SEQ ID NO: 6). In some embodiments, the genotype of the patient includes a G allele at polymorphism rs4988956 (SEQ ID NO: 1); an A allele at polymorphism rs10204137 (SEQ ID NO: 2); a C allele at polymorphism rs10192036 (SEQ ID NO: 3); a C allele at polymorphism rs10192157 (SEQ ID NO: 4); a T allele at polymorphism rs10206753 (SEQ ID NO: 5); a T allele at polymorphism rs4742165 (SEQ ID NO: 6); and an equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6).

In another embodiment, the present invention provides a method of determining whether a patient suffering from an IL-33-mediated disorder (e.g., asthma or pulmonary fibrosis (e.g., idiopathic pulmonary fibrosis)) is likely to respond to treatment comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist, the method comprising: (a) determining in a sample derived from a patient suffering from an IL-33-mediated disorder the genotype at one or more polymorphisms (e.g., 1, 2, 3, 4, 5, 6, 7, or more than 7 polymorphisms) selected from the group consisting of rs4988956 (SEQ ID NO: 1); rs10204137 (SEQ ID NO: 2); rs10192036 (SEQ ID NO: 3); rs10192157 (SEQ ID NO: 4); rs10206753 (SEQ ID NO: 5); rs4742165 (SEQ ID NO: 6); and a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); and (b) identifying the patient as likely to respond to the treatment based on the genotype, wherein the presence of: (i) each G allele at polymorphism rs4988956 (SEQ ID NO: 1); (ii) each A allele at polymorphism rs10204137 (SEQ ID NO: 2); (iii) each C allele at polymorphism rs10192036 (SEQ ID NO: 3); (iv) each C allele at polymorphism rs10192157 (SEQ ID NO: 4); (v) each T allele at polymorphism rs10206753 (SEQ ID NO: 5); (vi) each T allele at polymorphism rs4742165 (SEQ ID NO: 6); and/or (vii) each equivalent allele at a polymorphism that is in linkage disequilibrium with a polymorphism selected from the group consisting of rs4988956 (SEQ ID NO: 1), rs10204137 (SEQ ID NO: 2), rs10192036

(SEQ ID NO: 3), rs10192157 (SEQ ID NO: 4), rs10206753 (SEQ ID NO: 5), and rs4742165 (SEQ ID NO: 6) indicates that the patient has an increased likelihood of being responsive to the treatment. In some instances, the method further includes determining the level of periostin in a sample derived from the patient. In these instances, the method may further include informing the patient that they have an increased likelihood of being responsive to treatment comprising one or more (e.g., 1, 2, 3, 4, 5, 6, or 7) of an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist if the level of periostin in the sample is at, below, or above a reference level of periostin.

In another embodiment, the present invention provides a method of improving the therapeutic efficacy of an IL-33-mediated disorder therapy for a patient suffering from an IL-33-mediated disorder, the method including: (a) determining in a sample derived from a patient suffering from asthma the genotype at one or more (e.g., 1, 2, 3, 4, 5, 6, 7, or more than 7) polymorphisms selected from the group consisting of rs4988956 (SEQ ID NO: 1); rs10204137 (SEQ ID NO: 2); rs10192036 (SEQ ID NO: 3); rs10192157 (SEQ ID NO: 4); rs10206753 (SEQ ID NO: 5); rs4742165 (SEQ ID NO: 6); and a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6); and (b) identifying the patient as more suitably treated by the addition of one or more (e.g., 1, 2, 3, 4, 5, 6, or 7) of an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist to the IL-33-mediated disorder therapy based on the genotype, wherein the presence of: (i) each G allele at polymorphism rs4988956 (SEQ ID NO: 1); (ii) each A allele at polymorphism rs10204137 (SEQ ID NO: 2); (iii) each C allele at polymorphism rs10192036 (SEQ ID NO: 3); (iv) each C allele at polymorphism rs10192157 (SEQ ID NO: 4); (v) each T allele at polymorphism rs10206753 (SEQ ID NO: 5); (vi) each T allele at polymorphism rs4742165 (SEQ ID NO: 6); and/or (vii) each equivalent allele at a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6) indicates an increased likelihood of improving the therapeutic efficacy of an IL-33-mediated disorder therapy by the addition of an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist. In some instances, the method further includes determining the level of periostin in a sample derived from the patient. In these instances, the method may further include informing the patient that they have an increased likelihood of being responsive to treatment with an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist if the level of periostin in the sample is at, below, or above a reference level of periostin.

In any of the preceding embodiments, the equivalent allele may be in an alternate SNP that is in linkage disequilibrium with one or more of the selected SNPs described herein. In some embodiments, the linkage disequilibrium is a D' value or an $r^2$ value. In some embodiments, the D' measure between the selected SNP and the alternate SNP is ≥0.60 (e.g., ≥0.60, ≥0.65, ≥0.7, ≥0.75, ≥0.8, ≥0.85, ≥0.9, ≥0.95, or higher). In some embodiments, the D' value between the selected SNP and the alternate SNP is ≥0.70, ≥0.80, or ≥0.90. In some embodiments, the D' value between the selected SNP and the alternate SNP is 1.0. In some embodiments, the $r^2$ value between the selected SNP and the alternate SNP is ≥0.60 (e.g., ≥0.60, ≥0.65, ≥0.7, ≥0.75, ≥0.8, ≥0.85, ≥0.9, ≥0.95, or higher). In some embodiments the $r^2$ value between the selected SNP and the alternate SNP is ≥0.70, ≥0.80, or ≥0.90. In some embodiments, the $r^2$ value between the selected SNP and the alternate SNP is 1.0. In some embodiments, the alternate SNP is a SNP designated in Table 3 or 4. In any of the preceding methods, the equivalent allele may be the minor allele or the major allele. In some instances, the equivalent allele is the minor allele. In other instances, the equivalent allele is the major allele.

In any of the above diagnostic methods, the method may further include administering to the patient a therapy comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist. For example, the method may further include administering a therapy comprising an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, or an IL-5 binding antagonist. In other instances, the method may further include administering a therapy comprising at least two agents, for example, an IL-33 axis binding antagonist (e.g., an ST2 binding antagonist) and a tryptase-beta binding antagonist, an IL-33 axis binding antagonist (e.g., an ST2 binding antagonist) and a CRTH2 binding antagonist, an IL-33 axis binding antagonist (e.g., an ST2 binding antagonist) and an IL-13 binding antagonist, an IL-33 axis binding antagonist (e.g., an ST2 binding antagonist) and an IL-17 binding antagonist, an IL-33 axis binding antagonist (e.g., an ST2 binding antagonist) and a JAK1 antagonist, an IL-33 axis binding antagonist (e.g., an ST2 binding antagonist) and an IL-5 binding antagonist, a tryptase-beta binding antagonist and a CRTH2 binding antagonist, a tryptase-beta binding antagonist and an IL-13 binding antagonist, a tryptase-beta binding antagonist and an IL-17 binding antagonist, a tryptase-beta binding antagonist and a JAK1 antagonist, a tryptase-beta binding antagonist and an IL-5 binding antagonist, a CRTH2 binding antagonist and an IL-13 binding antagonist, a CRTH2 binding antagonist and an IL-17 binding antagonist, a CRTH2 binding antagonist and a JAK1 antagonist, a CRTH2 binding antagonist and an IL-5 binding antagonist, an IL-13 binding antagonist and an IL-17 binding antagonist, an IL-13 binding antagonist and a JAK1 antagonist, an IL-13 binding antagonist and an IL-5 binding antagonist, an IL-17 binding antagonist and a JAK1 antagonist, an IL-17 binding antagonist and an IL-5 binding antagonist, or a JAK1 antagonist and an IL-5 binding antagonist. In other instances, the method may further include administering a therapy comprising at least three agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In other instances, the method may further include administering a therapy comprising at least four agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In other instances, the method may further include administering a therapy comprising at least five agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In yet other instances, the method may further include administering a therapy comprising at least six agents selected from an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist. In yet other instances, the method may include administering a therapy comprising an IL-33 axis binding antagonist (e.g., an ST2 binding antagonist), a tryptase-beta binding antagonist, a CRTH2 binding antagonist, an IL-13 binding antagonist, an IL-17 binding antagonist, a JAK1 antagonist, and an IL-5 binding antagonist.

In yet other instances, the present invention provides a method of selecting a therapy for a patient having an IL-33-mediated disorder, the method comprising: (a) determining the level of periostin in a sample derived from the patient; (b) comparing the level of periostin in the sample derived from the patient to a reference level of periostin, wherein a level of periostin in the sample at or below the reference level of periostin identifies a patient who is likely to respond to treatment comprising an IL-33 axis binding antagonist (e.g., an ST2 binding antagonist); and (c) selecting a therapy comprising an IL-33 axis binding antagonist (e.g., an ST2 binding antagonist) if the patient is identified as likely to respond to treatment comprising an IL-33 axis binding antagonist (e.g., an ST2 binding antagonist) and recommending to the patient the selected therapy comprising an IL-33 axis binding antagonist (e.g., an ST2 binding antagonist). In some embodiments, the method further includes administering an asthma therapy including an antagonist selected from one or more of an IL-33 binding antagonist (e.g., an anti-IL-33 antibody or antigen-binding fragment thereof), a ST2 binding antagonist (e.g., an ST2-Fc protein, an anti-ST2 antibody, or antigen-binding fragment thereof), and/or an IL-1RAcP binding antagonist (e.g., an anti-IL1RAcP antibody). For example, in some embodiments, the method further includes administering an IL-33 binding antagonist, a ST2 binding antagonist, or an IL1RAcP binding antagonist. In some embodiments, the method further includes administering at least two of the following: an IL-33 binding antagonist, a ST2 binding antagonist, and an IL1RAcP binding antagonist (e.g., an IL-33 binding antagonist and an ST2 binding antagonist (e.g., an ST2-Fc protein); an IL-33 binding antagonist and an IL1RAcP binding antagonist; or an ST2 binding antagonist (e.g., an ST2-Fc protein) and an IL1RAcP binding antagonist). In some embodiments, the method further includes administering an IL-33 binding antagonist, a ST2 binding antagonist (e.g., an ST2-Fc protein), and an IL1RAcP binding antagonist.

In other instances, the present invention provides a method of determining whether a patient is at increased risk of an IL-33-mediated disorder (e.g., asthma or pulmonary fibrosis (e.g., idiopathic pulmonary fibrosis)), the method comprising: (a) determining the level of sST2 in a sample derived from the patient; and (b) comparing the level of sST2 in the sample derived from the patient to a reference level of sST2, wherein the patient is at an increased risk of an IL-33-mediated disorder if the level of sST2 in the sample derived from the patient is at or above the reference level. In some instances, the method further includes administering a therapy comprising a therapy comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist. In some instances, the method further includes determining the level of periostin in a sample derived from the patient. In these instances, the method may further include informing the patient that they have an increased likelihood of being responsive to treatment with an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist if the level of periostin in the sample is at, below, or above a reference level of periostin.

In yet another instance, the present invention provides a method of selecting a therapy for a patient having an IL-33 mediated disorder (e.g., asthma or pulmonary fibrosis (e.g., idiopathic pulmonary fibrosis)), the method comprising: (a) determining the level of sST2 in a sample derived from the patient; (b) comparing the level of sST2 in the sample derived from the patient to a reference level of sST2; and (c) selecting a therapy comprising an IL-33 axis binding antagonist if the level of sST2 in the sample is at or above the reference level. In some instances, the method further includes administering a therapy comprising a therapy comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist. In some instances, the method further includes determining the level of periostin in a sample derived from the patient. In these instances, the method may further include informing the patient that they have an increased likelihood of being responsive to treatment with an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist if the level of periostin in the sample is at, below, or above a reference level of periostin.

In another instance, the present invention provides a method of determining whether a patient suffering from an IL-33-mediated disorder is likely to respond to treatment comprising an IL-33 axis binding antagonist, the method comprising: (a) determining the level of sST2 in a sample derived from the patient; (b) comparing the level of sST2 in the sample derived from the patient to a reference level of sST2; and (c) identifying the patient as likely to respond to treatment comprising an IL-33 axis binding antagonist based on the level of sST2 in the sample derived from the patient, wherein the patient has an increased likelihood of being responsive to treatment comprising an IL-33 axis binding antagonist if the level of sST2 in the sample is at or above the reference level. In some instances, the method further includes administering a therapy comprising a therapy comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist. In some instances, the method further includes determining the level of periostin in a sample derived from the patient. In these instances, the method may further include informing the patient that they have an increased likelihood of being responsive to treatment with an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist if the level of periostin in the sample is at, below, or above a reference level of periostin.

In another instance, the present invention provides a method for assessing a treatment response of a patient treated with an IL-33 axis binding antagonist, the method comprising: (a) determining the level of sST2 in a sample derived from the patient at a time point during or after administration of the IL-33 axis binding antagonist; and (b) maintaining, adjusting, or stopping the treatment of the patient based on a comparison of the level of sST2 in the sample derived from the patient with a reference level of sST2, wherein a change in the level of sST2 in the sample derived from the patient compared to the reference level is indicative of a response to treatment with the IL-33 axis binding antagonist. In some embodiments, the change is an increase in the level of sST2 and treatment is maintained. In some embodiments, the change is an increase in the level of sST2 and treatment is changed to a different therapeutic agent (e.g., a different IL-33 axis binding antagonist). In some embodiments, the change is an increase in the level of sST2 and treatment is changed by increasing the dose of the IL-33 binding antagonist or increasing the frequency of dosing the IL-33 binding antagonist. In other embodiments, the change is a decrease in the level of sST2 and treatment is maintained. In other embodiments, the change is a decrease in the level of sST2 and treatment is decreased. In other embodiments, the change is a decrease in the level of sST2 and treatment is changed by decreasing the dose of the IL-33 binding antagonist or decreasing the frequency of dosing the IL-33 binding antagonist. In other embodiments, the change is a decrease in the level of sST2 and treatment is stopped. In some instances, the method further includes determining the level of periostin in a sample derived from the patient. In these instances, the method may further include informing the patient that they have an increased likelihood of being responsive to treatment with an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist if the level of periostin in the sample is at, below, or above a reference level of periostin.

In yet another instance, the present invention provides a method for monitoring the response of a patient treated with an IL-33 axis binding antagonist, the method comprising: (a) determining the level of sST2 in a sample derived from the patient at a time point during or after administration of the IL-33 axis binding antagonist; and (b) comparing the level of sST2 in the sample derived from the patient with a reference level of sST2, thereby monitoring the response in the patient undergoing treatment with the IL-33 axis binding antagonist. In some instances, the method further includes determining the level of periostin in a sample derived from the patient. In these instances, the method may further include informing the patient that they have an increased likelihood of being responsive to treatment with an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist if the level of periostin in the sample is at, below, or above a reference level of periostin.

In any of the preceding methods, the level of sST2 may be, for example, a level of sST2 protein or a level of sST2 nucleic acid (e.g., mRNA). In some embodiments, the level is a level of sST2 protein. In any of the preceding methods, the sample derived from the patient may be a whole blood sample, a serum sample, a plasma sample, or a combination thereof. In some embodiments, the sample derived from the patient may be a serum sample.

In any of the preceding methods, in some embodiments, the level of sST2 in the sample derived from the patient may be at least 1.1-fold, 1.2-fold, 1.3-fold, 1.4-fold, 1.5-fold, 1.6-fold, 1.7-fold, 1.8-fold, 1.9-fold, 2-fold, 2.2-fold, 2.4-fold, 2.6-fold, 2.8-fold, 3-fold, 3.5-fold, 4-fold, 4.5-fold, 5-fold, 5.5-fold, 6-fold, 6.5-fold, 7-fold, 7.5-fold, 8-fold, 9-fold, 10-fold, 15-fold, or 20-fold above the reference level. In any of the preceding methods, in some embodiments, the level of sST2 in the sample derived from the patient may be at least 1.1-fold, 1.2-fold, 1.3-fold, 1.4-fold, 1.5-fold, 1.6-fold, 1.7-fold, 1.8-fold, 1.9-fold, 2-fold, 2.2-fold, 2.4-fold, 2.6-fold, 2.8-fold, 3-fold, 3.5-fold, 4-fold, 4.5-fold, 5-fold, 5.5-fold, 6-fold, 6.5-fold, 7-fold, 7.5-fold, 8-fold, 9-fold, 10-fold, 15-fold, or 20-fold below the reference level.

Any suitable reference level of sST2 may be used in any of the preceding methods. In any of the preceding methods, the reference level may be is a level of sST2 determined from a group of individuals, wherein each member of the group has a genotype comprising two G alleles at polymorphism rs4742165 (SEQ ID NO: 6). In any of the preceding methods, the reference level of sST2 may be a level of sST2 determined from a group of individuals, wherein each member of the group has a genotype comprising two G alleles at polymorphism rs3771166 (SEQ ID NO: 8). In some instances, the group of individuals is suffering from asthma. In some embodiments, the reference level of sST2 may be an average, a median, or any suitable value. In some instances, reference level is a median level. In some instances, the group of individuals is a group of female individuals and the patient is female. In other instances, the group of individuals is a group of male individuals and the patient is male. In any of the preceding methods, the reference level of sST2 may be determined in an individual at an earlier timepoint, e.g., before administration of an IL-33 binding antagonist or at an earlier timepoint during treatment with an IL-33 binding antagonist.

In some instances, any of the preceding methods further includes administering a therapy comprising a therapy comprising one or more (e.g., 1, 2, 3, 4, 5, 6, or 7) of the following: an IL-33 axis binding antagonist (e.g., an ST2 binding antagonist), a tryptase-beta binding antagonist, a CRTH2 antagonist, an IL-13 binding antagonist, an IL-17 binding antagonist, a JAK1 antagonist, and/or an IL-5 binding antagonist. In some embodiments, the IL-33 axis binding antagonist is an IL-33 binding antagonist, an ST2 binding antagonist, or an IL-1RAcP binding antagonist.

In some instances, any of the preceding methods further includes administering an antagonist selected from one or more of an IL-33 binding antagonist (e.g., an anti-IL-33 antibody or antigen-binding fragment thereof), a ST2 binding antagonist (e.g., an ST2-Fc protein, an anti-ST2 antibody, or antigen-binding fragment thereof), and/or an IL-1RAcP binding antagonist (e.g., an anti-IL1RAcP antibody) based on the level of sST2 in a sample derived from the patient being at or above a reference level. For example, in some embodiments, the method further includes administering an IL-33 binding antagonist, a ST2 binding antagonist, or an IL1RAcP binding antagonist. In some embodiments, the method further includes administering at least two of the following: an IL-33 binding antagonist, a ST2 binding antagonist, and an IL1RAcP binding antagonist (e.g., an IL-33 binding antagonist and an ST2 binding antagonist (e.g., an ST2-Fc protein); an IL-33 binding antagonist and an IL1RAcP binding antagonist; or an ST2 binding antagonist (e.g., an ST2-Fc protein) and an IL1RAcP binding antagonist). In some embodiments, the method further includes administering an IL-33 binding antagonist, a ST2 binding antagonist (e.g., an ST2-Fc protein), and an IL1RAcP binding antagonist.

One of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgment of the attending physician to determine the most appropriate course of treatment for an individual patient, based upon test results, patient condition and history, and his or her own experience. There may even be occasions, for example, when a physician will choose to treat a patient with an IL-33 axis binding antagonist (e.g., an ST2 binding antagonist) even when a patient is not determined to be at increased risk of an IL-33-mediated disorder (e.g., asthma and/or pulmonary fibrosis (e.g., idiopathic pulmonary fibrosis)), based on data from diagnostic tests or from other criteria, particularly if all or most of the other obvious treatment options have failed, or if some synergy is anticipated when given with another treatment.

The present invention also provides a method of identifying a biomarker that is useful for monitoring sensitivity or responsiveness to an IL-33 axis binding antagonist, such as an anti-IL-33 antibody or an ST2 binding antagonist, the method comprising: (a) measuring the level of a candidate biomarker in samples from patients with IL-33-mediated disorders obtained before any dose of an IL-33 axis binding antagonist (e.g., an ST2 binding antagonist) is administered to the patients, wherein an change (i.e., an increase or decrease) in the expression of the candidate biomarker relative to a control indicates that the biomarker is diagnostic for more effective treatment of the IL-33-mediated disorder with an IL-33 axis binding antagonist (e.g., an ST2 binding antagonist). In some embodiments, the biomarker is genetic and its expression is analyzed.

IV. Detection of Nucleic Acid Polymorphisms

In several embodiments, the methods of treatment and diagnosis provided by the invention involve determination of the genotype of a patient at one or more polymorphisms (e.g., polymorphisms in IL1RL1 described in Tables 1 and 2). Detection techniques for evaluating nucleic acids for the presence of a SNP involve procedures well known in the field of molecular genetics. Many, but not all, of the methods involve amplification of nucleic acids. Ample guidance for performing amplification is provided in the art. Exemplary references include manuals such as Erlich, ed., *PCR Technology: Principles and Applications for DNA Amplification*, Freeman Press, 1992; Innis et al. eds., *PCR Protocols: A Guide to Methods and Applications*, Academic Press, 1990; Ausubel, ed., *Current Protocols in Molecular Biology*, 1994-1999, including supplemental updates through April 2004; and Sambrook et al. eds., *Molecular Cloning, A Laboratory Manual*, 2001. General methods for detection of single nucleotide polymorphisms are disclosed in Kwok, ed., *Single Nucleotide Polymorphisms: Methods and Protocols*, Humana Press, 2003.

Although the methods typically employ PCR steps, other amplification protocols may also be used. Suitable amplification methods include ligase chain reaction (see, e.g., Wu et al. *Genomics* 4:560-569, 1988); strand displacement assay (see, e.g., Walker et al. *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al. *Proc. Natl. Acad. Sci. USA* 86:1173-1177, 1989); and self-sustained sequence replication (3SR) (Guatelli et al. *Proc. Natl. Acad. Sci. USA* 87:1874-1878, 1990; WO 1992/08800). Alternatively, methods that amplify the probe to detectable levels can be used, such as Qβ-replicase amplification (Kramer et al. *Nature* 339:401-402, 1989; Lomeli et al. *Clin. Chem.* 35:1826-1831, 1989). A review of known amplification methods is provided, for example, by Abramson et al. *Curr. Opin. Biotech.* 4:41-47, 1993.

Detection of the genotype, haplotype, SNP, microsatellite, or other polymorphism of an individual can be performed using oligonucleotide primers and/or probes. Oligonucleotides can be prepared by any suitable method, usually chemical synthesis. Oligonucleotides can be synthesized using commercially available reagents and instruments. Alternatively, they can be purchased through commercial sources. Methods of synthesizing oligonucleotides are well known in the art (see, e.g., Narang et al. *Meth. Enzymol.* 68:90-99, 1979; Brown et al. *Meth. Enzymol.* 68:109-151, 1979; Beaucage et al. *Tetra. Lett.* 22:1859-1862, 1981; and the solid support method of U.S. Pat. No. 4,458,066). In addition, modifications to the above-described methods of synthesis may be used to desirably impact enzyme behavior with respect to the synthesized oligonucleotides. For example, incorporation of modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

The genotype of an individual (e.g., a patient suffering from or at risk for an IL-33-mediated disorder, for example, asthma or pulmonary fibrosis (e.g., idiopathic pulmonary fibrosis)) can be determined using many detection methods that are well known in the art. Most assays entail one of several general protocols: hybridization using allele-specific oligonucleotides, primer extension, allele-specific ligation, sequencing, or electrophoretic separation techniques, e.g., single-stranded conformational polymorphism (SSCP) and heteroduplex analysis. Exemplary assays include 5'-nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and MALDI-TOF (matrix assisted laser desorption ionization-time of flight) mass spectrometry. Two methods that can also be used are assays based on invasive cleavage with Flap nucleases and methodologies employing padlock probes.

Determination of the presence or absence of a particular allele is generally performed by analyzing a nucleic acid sample that is obtained from the individual to be analyzed. Often, the nucleic acid sample comprises genomic DNA. The genomic DNA is typically obtained from blood samples, but may also be obtained from other cells or tissues.

It is also possible to analyze RNA samples for the presence of polymorphic alleles. For example, mRNA can be used to determine the genotype of an individual at one or more polymorphic sites. In this case, the nucleic acid sample is obtained from cells in which the target nucleic acid is expressed, e.g., T helper-2 (Th2) cells and mast cells. Such an analysis can be performed by first reverse-transcribing the target RNA using, for example, a viral reverse transcriptase, and then amplifying the resulting cDNA; or using a combined high-temperature reverse-transcription-polymerase chain reaction (RT-PCR), as described in U.S. Pat. Nos. 5,310,652; 5,322,770; 5,561,058; 5,641,864; and 5,693,517.

The sample may be taken from a patient who is suspected of having, or is diagnosed as having an IL-33-mediated disorder, and hence is likely in need of treatment, or from a normal individual who is not suspected of having any disorder. For determination of genotypes, patient samples, such as those containing cells, or nucleic acids produced by these cells, may be used in the methods of the present invention. Bodily fluids or secretions useful as samples in the present invention include, e.g., blood, urine, saliva, stool, pleural fluid, lymphatic fluid, sputum, ascites, prostatic fluid, cerebrospinal fluid (CSF), or any other bodily secretion or derivative thereof. The word blood is meant to include whole blood, plasma, serum, or any derivative of blood. Sample nucleic acid for use in the methods described herein can be obtained from any cell type or tissue of a subject. For example, a subject's bodily fluid (e.g. blood) can be obtained by known techniques. Alternatively, nucleic acid tests can be performed on dry samples (e.g., hair or skin).

The sample may be frozen, fresh, fixed (e.g., formalin fixed), centrifuged, and/or embedded (e.g., paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the genotype in the sample. Likewise, biopsies may also be subjected to post-collection preparative and storage techniques, e.g., fixation.

Frequently used methodologies for analysis of nucleic acid samples to detect SNPs which are useful in the present invention are briefly described below. However, any method known in the art can be used in the invention to detect the presence of single nucleotide substitutions.

a. Allele-Specific Hybridization

This technique, also commonly referred to as allele-specific oligonucleotide hybridization (ASO) (e.g., Stoneking et al. *Am. J. Hum. Genet.* 48:70-382, 1991; Saiki et al. *Nature* 324, 163-166, 1986; EP 235,726; and WO 1989/11548), relies on distinguishing between two DNA molecules differing by one base by hybridizing an oligonucleotide probe that is specific for one of the variants to an amplified product obtained from amplifying the nucleic acid sample. This method typically employs short oligonucleotides, e.g., 15-20 bases in length. The probes are designed to differentially hybridize to one variant versus another. Principles and guidance for designing such probe is available in the art, for example, in the references cited herein. Hybridization conditions should be sufficiently stringent that there is a significant difference in hybridization intensity between alleles, and producing an essentially binary response, whereby a probe hybridizes to only one of the alleles. Some probes are designed to hybridize to a segment of target DNA such that the polymorphic site aligns with a central position (e.g., in a 15-base oligonucleotide at the 7 position; in a 16-based oligonucleotide at either the 8 or 9 position) of the probe, but this design is not required.

The amount and/or presence of an allele can be determined by measuring the amount of allele-specific oligonucleotide that is hybridized to the sample. Typically, the oligonucleotide is labeled with a label such as a fluorescent label. For example, an allele-specific oligonucleotide is applied to immobilized oligonucleotides representing SNP sequences. After stringent hybridization and washing conditions, fluorescence intensity is measured for each SNP oligonucleotide.

In one embodiment, the nucleotide present at the polymorphic site is identified by hybridization under sequence-specific hybridization conditions with an oligonucleotide probe or primer exactly complementary to one of the polymorphic alleles in a region encompassing the polymorphic site. The probe or primer hybridizing sequence and sequence-specific hybridization conditions are selected such that a single mismatch at the polymorphic site destabilizes the hybridization duplex sufficiently so that it is effectively not formed. Thus, under sequence-specific hybridization conditions, stable duplexes will form only between the probe or primer and the exactly complementary allelic sequence. Thus, oligonucleotides from about 10 to about 35 nucleotides in length, usually from about 15 to about 35 nucleotides in length, which are exactly complementary to an allele sequence in a region which encompasses the polymorphic site are within the scope of the invention.

In an alternative embodiment, the nucleotide present at the polymorphic site is identified by hybridization under sufficiently stringent hybridization conditions with an oligonucleotide substantially complementary to one of the SNP alleles in a region encompassing the polymorphic site, and exactly complementary to the allele at the polymorphic site. Because mismatches which occur at non-polymorphic sites are mismatches with both allele sequences, the difference in the number of mismatches in a duplex formed with the target allele sequence and in a duplex formed with the corresponding non-target allele sequence is the same as when an oligonucleotide exactly complementary to the target allele sequence is used. In this embodiment, the hybridization conditions are relaxed sufficiently to allow the formation of stable duplexes with the target sequence, while maintaining sufficient stringency to preclude the formation of stable duplexes with non-target sequences. Under such sufficiently stringent hybridization conditions, stable duplexes will form only between the probe or primer and the target allele. Thus, oligonucleotides from about 10 to about 35 nucleotides in length, usually from about 15 to about 35 nucleotides in length, which are substantially complementary to an allele sequence in a region which encompasses the polymorphic site, and are exactly complementary to the allele sequence at the polymorphic site, are within the scope of the invention.

The use of substantially, rather than exactly, complementary oligonucleotides may be desirable in assay formats in which optimization of hybridization conditions is limited.

For example, in a typical multi-target immobilized-oligonucleotide assay format, probes or primers for each target are immobilized on a single solid support. Hybridizations are carried out simultaneously by contacting the solid support with a solution containing target DNA. As all hybridizations are carried out under identical conditions, the hybridization conditions cannot be separately optimized for each probe or primer. The incorporation of mismatches into a probe or primer can be used to adjust duplex stability when the assay format precludes adjusting the hybridization conditions. The effect of a particular introduced mismatch on duplex stability is well known, and the duplex stability can be routinely both estimated and empirically determined, as described above. Suitable hybridization conditions, which depend on the exact size and sequence of the probe or primer, can be selected empirically using the guidance provided herein and well known in the art. The use of oligonucleotide probes or primers to detect single base pair differences in sequence is described in, for example, Conner et al. *Proc. Natl. Acad. Sci. USA* 80:278-282, 1983, and U.S. Pat. Nos. 5,468,613 and 5,604,099.

The proportional change in stability between a perfectly matched and a single-base mismatched hybridization duplex depends on the length of the hybridized oligonucleotides. Duplexes formed with shorter probe sequences are destabilized proportionally more by the presence of a mismatch. Oligonucleotides between about 15 and about 35 nucleotides in length are often used for sequence-specific detection. Furthermore, because the ends of a hybridized oligonucleotide undergo continuous random dissociation and re-annealing due to thermal energy, a mismatch at either end destabilizes the hybridization duplex less than a mismatch occurring internally. For discrimination of a single base pair change in target sequence, the probe sequence is selected which hybridizes to the target sequence such that the polymorphic site occurs in the interior region of the probe.

The above criteria for selecting a probe sequence that hybridizes to a specific allele apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A reverse line-blot detection assay is described in the example.

An allele-specific probe that is specific for one of the polymorphism variants is often used in conjunction with the allele-specific probe for the other polymorphism variant. In some embodiments, the probes are immobilized on a solid support and the target sequence in an individual is analyzed using both probes simultaneously. Examples of nucleic acid arrays are described by WO 95/11995. The same array or a different array can be used for analysis of characterized polymorphisms. WO 95/11995 also describes subarrays that are optimized for detection of variant forms of a pre-characterized polymorphism. Such a subarray can be used in detecting the presence of the polymorphisms described herein.

b. Allele-Specific Primers

Polymorphisms are also commonly detected using allele-specific amplification or primer extension methods. These reactions typically involve use of primers that are designed to specifically target a polymorphism via a mismatch at the 3'-end of a primer. The presence of a mismatch affects the ability of a polymerase to extend a primer when the polymerase lacks error-correcting activity. For example, to detect an allele sequence using an allele-specific amplification- or extension-based method, a primer complementary to one allele of a polymorphism is designed such that the 3'-terminal nucleotide hybridizes at the polymorphic position. The presence of the particular allele can be determined by the ability of the primer to initiate extension. If the 3'-terminus is mismatched, the extension is impeded.

In some embodiments, the primer is used in conjunction with a second primer in an amplification reaction. The second primer hybridizes at a site unrelated to the polymorphic position. Amplification proceeds from the two primers leading to a detectable product signifying the particular allelic form is present. Allele-specific amplification- or extension-based methods are described in, for example, WO 93/22456; U.S. Pat. Nos. 5,137,806; 5,595,890; 5,639,611; and 4,851,331.

Using allele-specific amplification-based genotyping, identification of the alleles requires only detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g. in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, allele-specific amplification methods can be performed in reactions that employ multiple allele-specific primers to target particular alleles. Primers for such multiplex applications are generally labeled with distinguishable labels or are selected such that the amplification products produced from the alleles are distinguishable by size. Thus, for example, both alleles in a single sample can be identified using a single amplification by gel analysis of the amplification product.

As in the case of allele-specific probes, an allele-specific oligonucleotide primer may be exactly complementary to one of the polymorphic alleles in the hybridizing region or may have some mismatches at positions other than the 3'-terminus of the oligonucleotide, which mismatches occur at non-polymorphic sites in both allele sequences.

c. Detectable Probes i) 5'-Nuclease Assay Probes

Genotyping can also be performed using a "TAQMAN®" or "5'-nuclease assay," as described in U.S. Pat. Nos. 5,210, 015; 5,487,972; and 5,804,375; and Holland et al. *Proc. Natl. Acad. Sci. USA* 88:7276-7280, 1988. In the TAQMAN® assay, labeled detection probes that hybridize within the amplified region are added during the amplification reaction. The probes are modified so as to prevent the probes from acting as primers for DNA synthesis. The amplification is performed using a DNA polymerase having 5'- to 3'-exonuclease activity. During each synthesis step of the amplification, any probe which hybridizes to the target nucleic acid downstream from the primer being extended is degraded by the 5'- to 3'-exonuclease activity of the DNA polymerase. Thus, the synthesis of a new target strand also results in the degradation of a probe, and the accumulation of degradation product provides a measure of the synthesis of target sequences.

The hybridization probe can be an allele-specific probe that discriminates between the SNP alleles. Alternatively, the method can be performed using an allele-specific primer and a labeled probe that binds to amplified product.

Any method suitable for detecting degradation product can be used in a 5'-nuclease assay. Often, the detection probe is labeled with two fluorescent dyes, one of which is capable of quenching the fluorescence of the other dye. The dyes are attached to the probe, usually one attached to the 5'-terminus and the other is attached to an internal site, such that quenching occurs when the probe is in an unhybridized state and such that cleavage of the probe by the 5'- to 3'-exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673 describe alternative methods for detecting the degradation of probe which occurs concomitant with amplification.

ii) Secondary Structure Probes

Probes detectable upon a secondary structural change are also suitable for detection of a polymorphism, including SNPs. Exemplified secondary structure or stem-loop structure probes include molecular beacons or SCORPION® primer/probes. Molecular beacon probes are single-stranded oligonucleic acid probes that can form a hairpin structure in which a fluorophore and a quencher are usually placed on the opposite ends of the oligonucleotide. At either end of the probe short complementary sequences allow for the formation of an intramolecular stem, which enables the fluorophore and the quencher to come into close proximity. The loop portion of the molecular beacon is complementary to a target nucleic acid of interest. Binding of this probe to its target nucleic acid of interest forms a hybrid that forces the stem apart. This causes a conformation change that moves the fluorophore and the quencher away from each other and leads to a more intense fluorescent signal. Molecular beacon probes are, however, highly sensitive to small sequence variation in the probe target (see, e.g., Tyagi et al. *Nature Biotech.* 14:303-308, 1996; Tyagi et al. *Nature Biotech.* 16:49-53, 1998; Piatek et al. *Nature Biotech.* 16: 359-363, 1998; Marras et al. *Genetic Analysis: Biomolecular Engineering* 14:151-156, 1999; Tapp et al, *BioTechniques* 28: 732-738, 2000). A SCORPION® primer/probe comprises a stem-loop structure probe covalently linked to a primer.

d. DNA Sequencing and Single Base Extensions

SNPs can also be detected by direct sequencing. Methods include e.g. dideoxy sequencing-based methods and other methods such as Maxam and Gilbert sequence (see, e.g. Sambrook and Russell, supra).

Other detection methods include PYROSEQUENCING™ of oligonucleotide-length products. Such methods often employ amplification techniques such as PCR. For example, in pyrosequencing, a sequencing primer is hybridized to a single stranded, PCR-amplified, DNA template and incubated with the enzymes DNA polymerase, ATP sulfurylase, luciferase, and apyrase, and the substrates adenosine 5' phosphosulfate (APS) and luciferin. The first of four deoxynucleotide triphosphates (dNTP) is added to the reaction. DNA polymerase catalyzes the incorporation of the deoxynucleotide triphosphate into the DNA strand if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of APS. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated. Apyrase, a nucleotide degrading enzyme, continuously degrades unincorporated dNTPs and excess ATP. When degradation is complete, another dNTP is added.

Another similar method for characterizing SNPs does not require use of a complete PCR, but typically uses only the extension of a primer by a single, fluorescence-labeled dideoxyribonucleic acid molecule (ddNTP) that is complementary to the nucleotide to be investigated. The nucleotide at the polymorphic site can be identified via detection of a primer that has been extended by one base and is fluorescently labeled (e.g., Kobayashi et al, *Mol. Cell. Probes,* 9:175-182, 1995).

e. Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (see, e.g. Erlich, ed., *PCR Technology, Principles and Applications for DNA Amplification,* W. H. Freeman and Co., 1992).

Distinguishing of microsatellite polymorphisms can be done using capillary electrophoresis. Capillary electrophoresis conveniently allows identification of the number of repeats in a particular microsatellite allele. The application of capillary electrophoresis to the analysis of DNA polymorphisms is well known to those in the art (see, for example, Szantai et al. *J Chromatogr A.* 1079(1-2):41-9, 2005; Bjorheim et al. *Electrophoresis* 26(13):2520-30, 2005 and Mitchelson, *Mol. Biotechnol.* 24(1):41-68, 2003).

The identity of the allelic variant may also be obtained by analyzing the movement of a nucleic acid comprising the polymorphic region in polyacrylamide gels containing a gradient of denaturant, which is assayed using denaturing gradient gel electrophoresis (DGGE) (see, e.g. Myers et al.

*Nature* 313:495-498, 1985). When DGGE is used as the method of analysis, DNA will be modified to insure that it does not completely denature, for example, by adding a GC clamp of approximately 40 bp of high-melting GC-rich DNA by PCR. In a further embodiment, a temperature gradient is used in place of a denaturing agent gradient to identify differences in the mobility of control and sample DNA (see, e.g., Rosenbaum et al. *Biophys. Chem.* 265:1275, 1987).

f. Single-Strand Conformation Polymorphism Analysis

Alleles of target sequences can be differentiated using single-strand conformation polymorphism analysis, which identifies base differences by alteration in electrophoretic migration of single stranded PCR products, as described, e.g., in Orita et al. *Proc. Nat. Acad. Sci.* 86, 2766-2770, 1989; Cotton *Mutat. Res.* 285:125-144, 1993; and Hayashi *Genet. Anal. Tech. Appl.* 9:73-79, 1992. Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (see, e.g., Keen et al. *Trends Genet.* 7:5-10, 1991).

SNP detection methods often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g. $^{32}$P, electron-dense reagents, enzyme, such as peroxidase or alkaline phosphatase, biotin, or haptens and proteins for which antisera or monoclonal antibodies are available. Labeling techniques are well known in the art (see, e.g. *Current Protocols in Molecular Biology*, supra; Sambrook et al., supra).

g. Additional Methods to Determine the Genotype of an Individual at Polymorphisms DNA microarray technology, e.g., DNA chip devices, high-density microarrays for high-throughput screening applications, and lower-density microarrays may be used. Methods for microarray fabrication are known in the art and include various inkjet and microjet deposition or spotting technologies and processes, in situ or on-chip photolithographic oligonucleotide synthesis processes, and electronic DNA probe addressing processes. DNA microarray hybridization applications have been successfully applied in the areas of gene expression analysis and genotyping for point mutations, single nucleotide polymorphisms (SNPs), and short tandem repeats (STRs). Additional methods include interference RNA microarrays and combinations of microarrays and other methods such as laser capture microdissection (LCM), comparative genomic hybridization (CGH), array CGH, and chromatin immunoprecipitation (ChIP). See, e.g., He et al. *Adv. Exp. Med. Biol.* 593:117-133, 2007 and Heller *Annu. Rev. Biomed. Eng.* 4:129-153, 2002.

In some embodiments, protection from cleavage agents (such as a nuclease, hydroxylamine or osmium tetroxide and with piperidine) can be used to detect mismatched bases in RNA/RNA, DNA/DNA, or RNA/DNA heteroduplexes (see, e.g., Myers et al. *Science* 230:1242, 1985). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene with a sample nucleic acid, e.g., RNA or DNA, obtained from a tissue sample. The double-stranded duplexes are treated with an agent that cleaves single-stranded regions of the duplex, such as duplexes formed based on base pair mismatches between the control and sample strands. For instance, RNA/DNA duplexes can be treated with RNase and DNA/DNA hybrids can be treated with 51 nuclease to enzymatically digest the mismatched regions. Alternatively, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. *Proc. Natl. Acad. Sci. USA* 85:4397-4401, 1988; Saleeba et al. *Meth. Enzymol.* 217:286-295, 1992.

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In another embodiment, identification of the allelic variant is carried out using an oligonucleotide ligation assay (OLA), as described, for example, in U.S. Pat. No. 4,998,617 and Laridegren et al. *Science* 241:1077-1080, 1988. The OLA protocol uses two oligonucleotides which are designed to be capable of hybridizing to abutting sequences of a single strand of a target. One of the oligonucleotides is linked to a separation marker, e.g., by biotinylation, and the other is detectably labeled. If the precise complementary sequence is found in a target molecule, the oligonucleotides will hybridize such that their termini abut, and create a ligation substrate. Ligation then permits the labeled oligonucleotide to be recovered using avidin or another biotin ligand. Also known in the art is a nucleic acid detection assay that combines attributes of PCR and OLA (see, e.g., Nickerson et al. *Proc. Natl. Acad. Sci. USA* 87:8923-8927, 1990). In this method, PCR is used to achieve the exponential amplification of target DNA, which is then detected using OLA.

A single base polymorphism can be detected by using a specialized exonuclease-resistant nucleotide, as described, for example, in U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

A solution-based method may also be used for determining the identity of the nucleotide of the polymorphic site (see, e.g., WO 1991/02087). As above, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method that may be used is described in WO 92/15712. This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. The method is usually a heterogeneous phase assay, in which the primer or the target molecule is immobilized to a solid phase.

Many other primer-guided nucleotide incorporation procedures for assaying polymorphic sites in DNA have been described (Komher et al. *Nucl. Acids. Res.* 17:7779-7784, 1989; Sokolov *Nucl. Acids Res.* 18:3671, 1990; Syvanen et al. *Genomics* 8:684-692, 1990; Kuppuswamy et al. *Proc. Natl. Acad. Sci. USA* 88:1143-1147, 1991; Prezant et al. *Hum. Mutat.* 1:159-164, 1992; Ugozzoli et al. *GATA* 9:107-112, 1992; Nyren et al. *Anal. Biochem.* 208:171-175, 1993). These methods all rely on the incorporation of labeled deoxynucleotides to discriminate between bases at a polymorphic site.

V. Biomarkers

The therapeutic and diagnostic methods of the invention can involve determination of the level of one or more biomarkers (e.g., periostin and/or sST2). The determination of the level of biomarkers can be performed by any of the methods known in the art or described below.

A. Detection of Gene Expression

The genetic biomarkers described herein (e.g., periostin) can be detected using any method known in the art. For example, tissue or cell samples from mammals can be conveniently assayed for, e.g., mRNAs or DNAs from a genetic biomarker of interest using Northern, dot-blot, or PCR analysis, array hybridization, RNase protection assay, or using DNA SNP chip microarrays, which are commercially available, including DNA microarray snapshots. For example, real-time PCR (RT-PCR) assays such as quantitative PCR assays are well known in the art. In an illustrative embodiment of the invention, a method for detecting mRNA from a genetic biomarker of interest (e.g., periostin and/or sST2) in a biological sample comprises producing cDNA from the sample by reverse transcription using at least one primer; amplifying the cDNA so produced; and detecting the presence of the amplified cDNA. In addition, such methods can include one or more steps that allow one to determine the levels of mRNA in a biological sample (e.g., by simultaneously examining the levels a comparative control mRNA sequence of a "housekeeping" gene such as an actin family member). Optionally, the sequence of the amplified cDNA can be determined.

i. Detection of Nucleic Acids

In one specific embodiment, expression of a biomarker (e.g., periostin and/or sST2) can be performed by RT-PCR technology. Probes used for PCR may be labeled with a detectable marker, such as, for example, a radioisotope, fluorescent compound, bioluminescent compound, a chemiluminescent compound, metal chelator, or enzyme. Such probes and primers can be used to detect the presence of an expressed biomarker (e.g., periostin) in a sample. As will be understood by the skilled artisan, a great many different primers and probes may be prepared based on the sequences provided in herein and used effectively to amplify, clone and/or determine the presence and/or levels of a biomarker (e.g., periostin).

Other methods include protocols that examine or detect mRNAs from a biomarker (e.g., periostin and/or sST2 mRNAs), in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment (see, e.g., WO 2001/75166). See, for example, U.S. Pat. Nos. 5,700,637, 5,445,934, and 5,807,522, Lockart, *Nat. Biotech.* 14:1675-1680, 1996; and Cheung et al. *Nat. Genet.* 21(Suppl):15-19, 1999 fora discussion of array fabrication.

In addition, the DNA profiling and detection method utilizing microarrays described in European Patent EP 1753878 may be employed. This method rapidly identifies and distinguishes between different DNA sequences utilizing short tandem repeat (STR) analysis and DNA microarrays. In an embodiment, a labeled STR target sequence is hybridized to a DNA microarray carrying complementary probes. These probes vary in length to cover the range of possible STRs. The labeled single-stranded regions of the DNA hybrids are selectively removed from the microarray surface utilizing a post-hybridization enzymatic digestion. The number of repeats in the unknown target is deduced based on the pattern of target DNA that remains hybridized to the microarray.

One example of a microarray processor is the Affymetrix GENECHIP® system, which is commercially available and comprises arrays fabricated by direct synthesis of oligonucleotides on a glass surface. Other systems may be used as known to one skilled in the art.

The specialized microarrays herein, e.g., oligonucleotide microarrays or cDNA microarrays, may comprise one or more biomarkers having expression profiles that correlate with either sensitivity or resistance to one or more IL-33 axis binding antagonists (e.g., an ST2 binding antagonist, e.g., an ST2-Fc protein). Other methods that can be used to detect nucleic acids, for use in the invention, involve high-throughput RNA sequence expression analysis, including RNA-based genomic analysis, such as, for example, RNASeq.

Many references are available to provide guidance in applying the above techniques (Kohler et al. *Hybridoma Techniques*, Cold Spring Harbor Laboratory, 1980; Tijssen, *Practice and Theory of Enzyme Immunoassays*, Elsevier, 1985; Campbell, *Monoclonal Antibody Technology*, Elsevier, 1984; Hurrell, *Monoclonal Hybridoma Antibodies:*

*Techniques and Applications*, CRC Press, 1982; and Zola, *Monoclonal Antibodies: A Manual of Techniques*, pp. 147-158, CRC Press, Inc., 1987). Northern blot analysis is a conventional technique well known in the art and is described, for example, in Sambrook et al, supra. Typical protocols for evaluating the status of genes and gene products are found, for example in Ausubel et al., supra.

ii. Detection of Proteins

As to detection of protein biomarkers, such as periostin and/or sST2, various protein assays are available including, for example, antibody-based methods as well as mass spectroscopy and other similar means known in the art. In the case of antibody-based methods, for example, the sample may be contacted with an antibody specific for the biomarker (e.g., periostin protein or sST2 protein) under conditions sufficient for an antibody-biomarker complex to form, and then detecting the complex. Detection of the presence of the protein biomarker may be accomplished in a number of ways, such as by Western blotting (with or without immunoprecipitation), 2-dimensional sodium dodecyl sulfate polyacrylamide gel electrophoresis (SDS-PAGE), immunoprecipitation, fluorescence activated cell sorting (FACS™), flow cytometry, and enzyme-linked immunosorbent assay (ELISA) procedures for assaying a wide variety of tissues and samples, including plasma or serum. A wide range of immunoassay techniques using such an assay format are available, see, e.g., U.S. Pat. Nos. 4,016,043; 4,424,279; and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested is brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g., 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed, dried, and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e., radioisotopes) and chemiluminescent molecules.

In the case of an enzyme immunoassay (EIA), an enzyme is conjugated to the second antibody, generally by means of glutaraldehyde or periodate. As will be readily recognized, however, a wide variety of different conjugation techniques exist, which are readily available to the skilled artisan. Examples of commonly used enzymes suitable for methods of the present invention include horseradish peroxidase, glucose oxidase, beta-galactosidase, and alkaline phosphatase. The substrates to be used with the specific enzymes are generally chosen for the production, upon hydrolysis by the corresponding enzyme, of a detectable color change. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker (e.g., periostin and/or sST2) which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

In some embodiments of the present invention, a Total Periostin Assay, as described in WO 2012/083132, is used to determine the level of periostin in a sample derived from the patient.

For example, a periostin capture ELISA assay that is very sensitive (sensitivity of approximately 1.88 ng/ml) referred to as the E4 assay is described below. The antibodies recognize periostin isoforms 1-4 (SEQ ID NOs:5-8 of WO 2012/083132) at nanomolar affinity.

The steps of the method are as follows. Dilute 80 µL of purified monoclonal antibody, 25D4 (Coat Antibody, SEQ ID NOs: 1 and 2 of WO 2012/083132 expressed from a hybridoma or a CHO cell line) with phosphate buffered saline (PBS) to a final concentration of 2 µg/mL. Coat a microtiter plate overnight, covered, at 2-8° C. with Coat Antibody, 100 µL per well. Wash the plate three times with 400 µL wash buffer (PBS/0.05% Tween (polysorbate 20) per well per cycle of wash buffer at room temperature. Add 200 µL per well of blocking buffer to the plate. Incubate covered plate at room temp with shaking for 1.5 hours.

Prepare a recombinant human periostin (rhuPeriostin) standard curve (Standard Stock of rhuPeriostin=rhuPeriostin isoform 1, R&D systems #3548-F2, 5.25 ng/ml, in Assay Diluent (PBS/0.5% bovine serum albumin (BSA)/0.05% polysorbate 20/0.05% ProClin300, pH7.4). Standard curve diluent=PBS/0.5% BSA/0.05% polysorbate 20, 0.05% ProClin300, pH 7.4.

Prepare controls and samples. Three controls: Spike Source Control (rhuPeriostin full length, isoform 1, R&D Systems #3548-F2), Normal Matrix Control (normal human serum pool, Bioreclamation, Inc.), High Matrix Control (normal human serum pool, plus 100 ng/ml rhuPeriostin spike).

For example:

10 µL Control(or sample)serum+1.99 mL sample/control diluent=1:200

300 µL 1:200 dilution+300 µL sample/control diluent=1:400

300 µL 1:400 dilution+300 µL sample/control diluent=1:800

300 µL 1:800 dilution+300 µL sample/control diluent=1:1600

Each dilution is run in singlicate.

Construct Matrix Controls using a normal human serum pool. Use unspiked pooled human serum as the Normal Control. Generate the High Control by spiking 100 ng/mL rhuPeriostin into the pooled serum as described above. Compute mean, standard deviation (SD), and % coefficient of variance (CV, expressed in percent) for the four dilutions for each control on every plate. CV quantifies magnitude of variance in replicate measurements with respect to mean of replicates (e.g., % CV=100*(SD/mean)). Evaluate these mean concentrations across all plates to determine inter-plate precision. This control table is then used to define the Normal and High Control pass/fail criteria, setting allowable variance to ±20% of the mean concentration for each control.

Wash the plate three times with 400 µL per well per cycle of wash buffer (PBS/0.05% polysorbate 20). Add diluted standards (duplicate wells), controls (all four dilutions), and samples (all four dilutions) to the plate, 100 µL per well. Incubate the plate covered, at room temperature with shaking for 2 hours at room temp. Dilute 80 µL detection MAb stock I (biotinylated murine anti-human periostin, MAb 23B9, 7.5 µg/ml in Assay Diluent) to 12 mL with Assay Diluent=50 ng/mL. Wash plate four times with 400 µL per well per cycle of wash buffer. Add diluted detection MAb to plate, 100 µL per well. Incubate covered plate at room temp for one hour with shaking. Dilute 80 µL streptavidin-HRP stock I (AMDEX streptavidin-HRP, GE Healthcare #RPN4401, approximately 1 mg/ml) diluted 1:80 in Assay Diluent to 12 mL with Assay Diluent=1:12 k. Wash the plate four times with 400 µL per well per cycle of wash buffer. Add diluted streptavidin-HRP to the plate, 100 µL per well. Incubate covered plate at room temperature for 45 min with shaking. Bring Kirkegaard and Perry (KPL) two-step TMB reagents to room temperature; do not combine. Wash the plate four times with 400 µL per well per cycle of wash buffer. Mix equal volumes of KPL TMB substrate components and add to the plate, 100 µL per well. Incubate the plate for 20 minutes at room temperature with shaking. Add 1 M phosphoric acid to plate, 100 µL per well. Read the plate using 450 nm read wavelength and 650 nm reference wavelength.

In other embodiments, the ELECSYS® periostin assay described in WO 2012/083132 is used to determine the level of periostin in a sample derived from the patient, as described below.

The quantitative detection of periostin is assessed in an automated Roche cobas e601 ELECSYS® analyzer (Roche Diagnostics GmbH). The test is carried out in the sandwich format wherein the analyte periostin is sandwiched between two monoclonal antibodies binding to two different epitopes on periostin. One antibody is biotinylated and enables the capture of the immunocomplex to streptavidin-coated magnetic beads. The second antibody bears a complexed ruthenium cation as the signaling moiety that allows a voltage dependent electrochemi-luminescent detection of the bound immunocomplex.

In detail, the reagents used are as follows:

Beads (M): Streptavidin-coated magnetic microparticles 0.72 mg/mL; preservative.

Reagent 1 (R1): Anti-periostin-antibody~biotin:
This purified mouse monoclonal-antibody corresponds to the coating antibody 25D4 described above in relation to the E4 assay and is used in biotinylated form>1.0 mg/L; TRIS buffer>100 mmol/L, pH 7.0; preservative.

Reagent 2 (R2): Anti-periostin-antibody~Ru(bpy):
This purified mouse monoclonal anti-periostin antibody corresponds to the detection antibody 23B9 described above in relation to the E4 assay and is used in labeled form (labeled with a (Tris(2,2'-bipyridyl)ruthenium(II)-complex (Ru(bpy)) complex)>1.0 mg/L; TRIS buffer>100 mmol/L, pH 7.0; preservative.

The immunoassay is carried out using two incubations. In the first incubation of about 9 minutes, periostin in 20 µL of sample and the biotinylated monoclonal anti-periostin antibody (R1) form a complex. In the second incubation step of an additional 9 minutes, ruthenylated monoclonal anti-periostin antibody (R2) and streptavidin-coated microparticles (M) are added to the vial of the first incubation so that a 3-membered sandwich complex is formed and becomes bound to the solid phase (microparticles) via the interaction of biotin and streptavidin.

The reaction mixture is aspirated into the measuring cell where the microparticles are magnetically captured onto the surface of a platinum electrode. Unbound substances are washed away and the cell flushed with ProCell, a reagent containing tripropylamine. Application of a voltage to the electrode then induces a chemi-luminescent emission which is measured by a photomultiplier. Results are determined via an instrument-specific calibration curve which is generated by 2-point calibration and a master curve provided via the reagent barcode. Calibrator 1 is analyte free, whereas calibrator 2 contains 50 ng/mL rhuPeriostin in a buffered matrix. To verify calibration, two controls with approximately 30 and 80 ng/mL periostin are employed.

In some embodiments, an exemplary reference level for periostin levels is 23 ng/ml, for example, when using the E4 assay described above. For instance, when using the E4 assay, a patient may have a periostin level at or greater than a reference level if the patient's periostin level is 23 ng/ml or higher, 24 ng/ml or higher, 25 ng/ml or higher, 26 ng/ml or higher, 27 ng/ml or higher, 28 ng/ml or higher, 29 ng/ml or higher, 30 ng/ml or higher, 31 ng/ml or higher, 32 ng/ml or higher, 33 ng/ml or higher, 34 ng/ml or higher, 35 ng/ml or higher, 36 ng/ml or higher, 37 ng/ml or higher, 38 ng/ml or higher, 39 ng/ml or higher, 40 ng/ml or higher, 41 ng/ml or higher, 42 ng/ml or higher, 43 ng/ml or higher, 44 ng/ml or higher, 45 ng/ml or higher, 46 ng/ml or higher, 47 ng/ml or higher, 48 ng/ml or higher, 49 ng/ml or higher, 50 ng/ml or higher, 51 ng/ml or higher, 52 ng/ml or higher, 53 ng/ml or higher, 54 ng/ml or higher, 55 ng/ml or higher, 56 ng/ml or higher, 57 ng/ml or higher, 58 ng/ml or higher, 59 ng/ml or higher, 60 ng/ml or higher, 61 ng/ml or higher, 62 ng/ml or higher, 63 ng/ml or higher, 64 ng/ml or higher, 65 ng/ml or higher, 66 ng/ml or higher, 67 ng/ml or higher, 68 ng/ml or higher, 69 ng/ml or higher or 70 ng/ml or higher in the serum or plasma.

When using the E4 assay, a patient may have a periostin level at or below a reference level if the patient's periostin level is 23 ng/ml or lower, 22 ng/ml or lower, 21 ng/ml or lower, 20 ng/ml or lower, 19 ng/ml or lower, 18 ng/ml or lower, 17 ng/ml or lower, 16 ng/ml or lower, 15 ng/ml or lower, 14 ng/ml or lower, 13 ng/ml or lower, 12 ng/ml or lower, 11 ng/ml or lower, 10 ng/ml or lower, 9 ng/ml or lower, 8 ng/ml or lower, 7 ng/ml or lower, 6 ng/ml or lower, 5 ng/ml or lower, 4 ng/ml or lower, 3 ng/ml or lower, 2 ng/ml or lower, or 1 ng/ml or lower.

In other embodiments, an exemplary reference level for periostin levels is 50 ng/ml, for example, when using the ELECSYS® periostin assay described above. For instance, when using the ELECSYS® periostin assay, a patient may have a periostin level at or greater than a reference level if the patient's periostin level is 50 ng/ml or higher, 51 ng/ml or higher, 52 ng/ml or higher, 53 ng/ml or higher, 54 ng/ml or higher, 55 ng/ml or higher, 56 ng/ml or higher, 57 ng/ml or higher, 58 ng/ml or higher, 59 ng/ml or higher, 60 ng/ml or higher, 61 ng/ml or higher, 62 ng/ml or higher, 63 ng/ml or higher, 64 ng/ml or higher, 65 ng/ml or higher, 66 ng/ml or higher, 67 ng/ml or higher, 68 ng/ml or higher, 69 ng/ml or higher, 70 ng/ml or higher, 71 ng/ml or higher, 72 ng/ml or higher, 73 ng/ml or higher, 74 ng/ml or higher, 75 ng/ml or higher, 76 ng/ml or higher, 77 ng/ml or higher, 78 ng/ml or higher, 79 ng/ml or higher, 80 ng/ml or higher, 81 ng/ml or higher, 82 ng/ml or higher, 83 ng/ml or higher, 84 ng/ml or higher, 85 ng/ml or higher, 86 ng/ml or higher, 87 ng/ml or higher, 88 ng/ml or higher, 89 ng/ml or higher, 90 ng/ml or higher, 91 ng/ml or higher, 92 ng/ml or higher, 93 ng/ml or higher, 94 ng/ml or higher, 95 ng/ml or higher, 96 ng/ml or higher, 97 ng/ml or higher, 98 ng/ml or higher, or 99 ng/ml or higher.

When using the ELECSYS® periostin assay, a patient may have a periostin level at or below a reference level if the patient's periostin level is 50 ng/ml or lower, 49 ng/ml or lower, 48 ng/ml or lower, 47 ng/ml or lower, 46 ng/ml or lower, 45 ng/ml or lower, 44 ng/ml or lower, 43 ng/ml or lower, 42 ng/ml or lower, 41 ng/ml or lower, 40 ng/ml or lower, 39 ng/ml or lower, 38 ng/ml or lower, 37 ng/ml or lower, 36 ng/ml or lower, 35 ng/ml or lower, 34 ng/ml or lower, 33 ng/ml or lower, 32 ng/ml or lower, 31 ng/ml or lower, 30 ng/ml or lower, 29 ng/ml or lower, 28 ng/ml or lower, 27 ng/ml or lower, 26 ng/ml or lower, 25 ng/ml or lower, 24 ng/ml or lower, 23 ng/ml or lower, 22 ng/ml or lower, 21 ng/ml or lower, 20 ng/ml or lower, 19 ng/ml or lower, 18 ng/ml or lower, 17 ng/ml or lower, 16 ng/ml or lower, 15 ng/ml or lower, 14 ng/ml or lower, 13 ng/ml or lower, 12 ng/ml or lower, 11 ng/ml or lower, 10 ng/ml or lower, 9 ng/ml or lower, 8 ng/ml or lower, 7 ng/ml or lower, 6 ng/ml or lower, 5 ng/ml or lower, 4 ng/ml or lower, 3 ng/ml or lower, 2 ng/ml or lower, or 1 ng/ml or lower.

In some embodiments, the level of sST2 in a patient sample may be determined using any suitable method known in the art and/or described herein, for example, in Example 3. In some embodiments, a patient may have a sST2 level at or above a reference level if the patient's sST2 level is 0.1 ng/ml or higher, 0.5 ng/ml or higher, 1 ng/ml or higher, 2 ng/ml or higher, 3 ng/ml or higher, 4 ng/ml or higher, 5 ng/ml or higher, 6 ng/ml or higher, 7 ng/ml or higher, 8 ng/ml or higher, 9 ng/ml or higher, 10 ng/ml or higher, 11 ng/ml or higher, 12 ng/ml or higher, 13 ng/ml or higher, 14 ng/ml or higher, 15 ng/ml or higher, 16 ng/ml or higher, 17 ng/ml or higher, 18 ng/ml or higher, 19 ng/ml or higher, 20 ng/ml or higher, 21 ng/ml or higher, 22 ng/ml or higher, 23 ng/ml or higher, 24 ng/ml or higher, 25 ng/ml or higher, 26 ng/ml or higher, 27 ng/ml or higher, 28 ng/ml or higher, 29 ng/ml or higher, 30 ng/ml or higher, 31 ng/ml or higher, 32 ng/ml or higher, 33 ng/ml or higher, 34 ng/ml or higher, 35 ng/ml or higher, 36 ng/ml or higher, 37 ng/ml or higher, 38 ng/ml or higher, 39 ng/ml or higher, 40 ng/ml or higher, 41 ng/ml or higher, 42 ng/ml or higher, 43 ng/ml or higher, 44 ng/ml or higher, 45 ng/ml or higher, 46 ng/ml or higher, 47 ng/ml or higher, 48 ng/ml or higher, 49 ng/ml or higher, 50 ng/ml or higher, or higher than 50 ng/ml.

VI. Kits

In some embodiments, the invention provides a kit for carrying out the methods of the invention, for example, for determining the genotype of a patient at a polymorphism as described herein. In some embodiments, the invention provides a kit for determining whether a patient is at risk of an IL-33-mediated disorder (e.g., asthma or pulmonary fibrosis (e.g., idiopathic pulmonary fibrosis)). Such kits typically contain one of more of the compositions described above and instructions for use. As an example only, the invention also provides kits for determining whether a patient is at risk of an IL-33-mediated disorder (e.g., asthma) containing a first and second oligonucleotide specific for a polymorphic region of 11RL1, for example, specific for polymorphism rs4988956 (SEQ ID NO: 1); polymorphism rs10204137 (SEQ ID NO: 2); polymorphism rs10192036 (SEQ ID NO: 3); polymorphism rs10192157 (SEQ ID NO: 4); or polymorphism rs10206753 (SEQ ID NO: 5). In another example, the invention also provides kits for determining whether a patient is at risk of an IL-33-mediated disorder (e.g., asthma) containing a first and second oligonucleotide specific for a polymorphic region of 133, for example, polymorphism rs4742165 (SEQ ID NO: 6). In yet another example, the invention provides kits for determining whether a patient is at risk of an IL-33-mediated disorder (e.g., asthma) containing a first and second oligonucleotide specific for a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6), for example, any polymorphism listed in Table 3 or Table 4. As another example, the invention also provides kits for determining whether a patient is likely to respond to treatment comprising an IL-33 axis binding antagonist (e.g., an ST2 binding antagonist) containing a first and second oligonucleotide specific for a polymorphic region of 11RL1, for example, specific for polymorphism rs4988956 (SEQ ID NO: 1); polymorphism rs10204137 (SEQ ID NO: 2); polymorphism rs10192036 (SEQ ID NO: 3); polymorphism rs10192157 (SEQ ID NO: 4); or polymorphism rs10206753 (SEQ ID NO: 5). As yet another example, the invention also provides kits for determining whether a patient is likely to respond to treatment comprising an IL-33 axis binding antagonist (e.g., an ST2 binding antagonist) containing a first and second oligonucleotide specific for a polymorphic region of 133, for example, polymorphism rs4742165 (SEQ ID NO: 6). In a further example, the invention provides kits for determining whether a patient is likely to respond to treatment comprising an IL-33 axis binding antagonist (e.g., an ST2 binding antagonist) containing a first and second oligonucleotide specific for a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6), for example, any polymorphism listed in Table 3 or Table 4.

Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, e.g., less than 1 kb from the polymorphism. Specific oligonucleotides are capable of hybridizing to a sequence, and under suitable conditions will not bind to a sequence differing by a single nucleotide.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In some embodiments, the surface is silica or glass. In some embodiments, the surface is a metal electrode.

Yet other kits of the invention comprise at least one reagent necessary to perform the assay. For example, the kit can comprise an enzyme. Alternatively the kit can comprise a buffer or any other necessary reagent.

The kits can include all or some of the positive controls, negative controls, reagents, primers, sequencing markers, probes and antibodies described herein for determining the subject's genotype at one or more polymorphisms in the IL1RL1 gene (e.g., polymorphism rs4988956 (SEQ ID NO: 1); polymorphism rs10204137 (SEQ ID NO: 2); polymorphism rs10192036 (SEQ ID NO: 3); polymorphism rs10192157 (SEQ ID NO: 4); or polymorphism rs10206753 (SEQ ID NO: 5), one or more polymorphisms in the IL33 gene (e.g., polymorphism rs4742165 (SEQ ID NO: 6)), or one or more polymorphisms that is in linkage disequilibrium with a polymorphism in the IL1RL1 gene or IL33 gene (e.g., a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6), for example, any polymorphism listed in Table 3 or Table 4).

For use in detection of the biomarkers (e.g., periostin), kits or articles of manufacture are also provided by the invention. Such kits can be used to determine if a subject with an IL-33-mediated disorder is likely to respond to treatment comprising an IL-33 axis binding antagonist (e.g., an ST2 binding antagonist). These kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a protein or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein (e.g., avidin or streptavidin) bound to a reporter molecule, such as an enzymatic, florescent, or radioisotope label.

Such kits will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above.

The kits of the invention have a number of embodiments. A typical embodiment is a kit comprising a container, a label on said container, and a composition contained within said container, wherein the composition includes a primary antibody that binds to a protein or autoantibody biomarker (e.g., periostin), and the label on said container indicates that the composition can be used to evaluate the presence of such proteins or antibodies in a sample, and wherein the kit includes instructions for using the antibody for evaluating the presence of biomarker proteins in a particular sample type. The kit can further comprise a set of instructions and materials for preparing a sample and applying antibody to the sample. The kit may include both a primary and secondary antibody, wherein the secondary antibody is conjugated to a label, e.g., an enzymatic label.

Another embodiment is a kit comprising a container, a label on said container, and a composition contained within said container, wherein the composition includes one or more polynucleotides that hybridize to a complement of a biomarker (e.g., periostin) under stringent conditions, and the label on said container indicates that the composition can be used to evaluate the presence of a biomarker (e.g., periostin) in a sample, and wherein the kit includes instructions for using the polynucleotide(s) for evaluating the presence of the biomarker RNA or DNA in a particular sample type.

Other optional components of the kit include one or more buffers (e.g., block buffer, wash buffer, substrate buffer, etc.), other reagents such as substrate (e.g., chromogen) that is chemically altered by an enzymatic label, epitope retrieval solution, control samples (positive and/or negative controls), control slide(s), etc. Kits can also include instructions for interpreting the results obtained using the kit. In further specific embodiments, for antibody-based kits, the kit can comprise, for example: (1) a first antibody (e.g., attached to a solid support) that binds to a biomarker protein (e.g., periostin); and, optionally, (2) a second, different antibody that binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a polymorphic region of the IL1RL1 gene (e.g., polymorphism rs4988956 (SEQ ID NO: 1); polymorphism rs10204137 (SEQ ID NO: 2); polymorphism rs10192036 (SEQ ID NO: 3); polymorphism rs10192157 (SEQ ID NO: 4); or polymorphism rs10206753 (SEQ ID NO: 5); a polymorphic region of the IL33 gene (e.g., polymorphism rs4742165 (SEQ ID NO: 6)), or a polymorphism that is in linkage disequilibrium with a polymorphism in the IL1RL1 gene or IL33 gene (e.g., a polymorphism that is in linkage disequilibrium with a polymorphism selected from the group consisting of rs4988956 (SEQ ID NO: 1), rs10204137 (SEQ ID NO: 2), rs10192036 (SEQ ID NO: 3), rs10192157 (SEQ ID NO: 4), rs10206753 (SEQ ID NO: 5), and rs4742165 (SEQ ID NO: 6), for example, any polymorphism listed in Table 3 or Table 4), as described above, and/or a nucleic acid sequence encoding a biomarker protein (e.g., periostin or sST2) or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples that can be assayed and compared to the test sample. Each component of the kit can be enclosed within an individual container and all of the various containers can be within a single package, along with instructions for interpreting the results of the assays performed using the kit.

VII. Pharmaceutical Formulations

Therapeutic formulations of the antagonists used in accordance with the present invention (e.g., an IL-33 axis binding antagonist (e.g., an ST2 binding antagonist, e.g., an ST2-Fc protein), a tryptase-beta binding antagonist, a CRTH2 antagonist, an IL-13 binding antagonist, an IL-17 binding antagonist, a JAK1 antagonist, and/or an IL-5 binding antagonist) are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics*, 8th Ed., Pergamon Press, 1990; A. Gennaro (ed.), *Remington's Pharmaceutical Sciences*, 18th Edition, Mack Publishing Co., Pennsylvania, 1990; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) Dermatological and Transdermal Formulations (Drugs and the Pharmaceutical Sciences), Vol 119, Marcel Dekker, 2002.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethyl-benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of antagonist present in the formulation, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

EXAMPLES

The following examples are provided to illustrate, but not to limit the presently claimed invention.

Example 1. Identification of Causative SNPs that Confer Protection from Asthma Risk In this analysis, we have identified amino acid changing variants in IL1RL1 associated with asthma risk (see Table 1 and 2) that are tightly linked ($r^2=1.0$) to the intronic SNP rs3771166. These amino acid changing SNPs were identified in the 1000 Genomes European samples and tested for association with asthma risk in our case-control dataset.

Asthma cases included 522 samples from patients of European ancestry from Genentech clinical trials BOBCAT, EXTRA, MILLY, and MOLLY, which were compared to control samples from 4465 individuals of European ancestry from the Cancer Genetic Markers of Susceptibility (CGEMS) genome-wide association study (GWAS) (Jia et al. *J. Allergy Clin. Immunol.* 130: 647-654, 2012; Hanania et al. *Am. J. Respir. Crit. Care Med.* 187: 804-811, 2013; Corren et al. *N. Engl. J. Med.* 365: 1088-1098, 2011; Noonen et al. *J. Allergy Clin. Immunol.* 132: 567-574, 2013). These same polymorphisms have also been reported to be associated with risk to cardiovascular disease and elevated soluble ST2 (sST2) and IL-33 levels (Ho et al. *J. Clin. Invest.* 123: 4208-4218, 2013).

This analysis revealed that these SNPs are each protective from asthma risk in the study population (see Table 1). Two SNPs, rs10192036 and rs10204137, are located in the same codon, resulting only in Q501R due to tight linkage disequilibrium (LD) between the two SNPS ($r^2$=1.0).

TABLE 1

Multiple amino acid changing SNPs within IL1RL1 are protective for asthma risk

| SNP | Amino acid change | Chr | Position | MAF Cases (n = 522) | MAF Controls (n = 4465) | P value | OR |
| --- | --- | --- | --- | --- | --- | --- | --- |
| rs4988956 | A433T | 2 | 102968007 | 0.32 | 0.38 | 5.38E−04 | 0.78 |
| rs10192036 | Q501K | 2 | 102968211 | 0.32 | 0.38 | 5.32E−04 | 0.78 |
| rs10204137 | Q501R | 2 | 102968212 | 0.32 | 0.38 | 5.32E−04 | 0.78 |
| rs10192157 | T549I | 2 | 102968356 | 0.32 | 0.38 | 5.32E−04 | 0.78 |
| rs10206753 | L551S | 2 | 102968362 | 0.32 | 0.38 | 5.32E−04 | 0.78 |
| rs3771166 | intronic | 2 | 102986222 | 0.32 | 0.37 | 3.55E−04 | 0.77 |

Chr, chromosome;
MAF, minor allele frequency;
OR, odds ratio

The locus containing IL1RL1 on chromosome 2 is complex, containing multiple linkage disequilibrium (LD) blocks, each of which contain SNPs predisposing to asthma susceptibility. Furthermore, the SNPs in IL1RL1 are in LD with SNPs in IL18R1, making it difficult to assign causality to either gene. To address this issue, a conditional analysis of rs3771166 on SNPs in the locus within 500 kb in either direction was performed. Conditioning on the rs3771166 genotype eliminated the majority of the signal in the region, with only one SNP retaining its unconditioned p-value (rs17766515; p=0.01). From this same window, we selected SNPs not in LD with rs3771166 (D'<0.6) and performed a conditional analysis of these SNPs on rs3771166. For these analyses, rs3771166 retained its statistical significance (max p=0.01). These conditional analyses and the functional analysis presented below indicate that the amino acid changing SNPs in IL1RL1 captured by the tagSNP rs3771166 are the causal SNPs in this region. In view of these results, individuals whose genotype includes the common IL1RL1 variants are at an increased risk of asthma compared to the individuals whose genotype includes the protective IL1RL1 variants. The genotypes for each causative SNP of patients at an increased risk of asthma are shown in Table 2.

TABLE 2

SNP genotypes associated with increased risk of asthma

| SNP | Genotype |
| --- | --- |
| rs4988956 | G |
| rs10204137 | A |

TABLE 2-continued

SNP genotypes associated with increased risk of asthma

| SNP | Genotype |
| --- | --- |
| rs10192036 | C |
| rs10192157 | C |
| rs10206753 | T |

The functional significance of these amino acid mutations in vivo was investigated to determine how these protective variants influence the IL-33 response. These variants result in coding changes to the intracellular region of ST2, which contains the signal-modulating Toll/IL-1R (TIR) domain of the receptor. The TIR domain is critical for downstream signal transduction by IL-1 cytokine family and Toll-like receptors (TLR), and mutations or deletions in this domain can result in diminished or abrogated responses to ligand. IL-33-induced dimerization of ST2 and IL-1RAcP is thought to promote TIR-TIR domain interaction, followed by recruitment of the adaptor molecule MyD88 and Myddosome assembly (see FIG. 1A). Two of the variants in IL1RL1, A443T and Q501R, are located within the TIR domain, while the T549I and L551S variants map to a poorly-characterized region of the C-terminus that has not been implicated in signal propagation (see FIG. 1A). To further define how the polymorphisms within the TIR domain may affect IL-33 signaling, the location of each variant was mapped to the known structure of the TLR10 TIR dimer (FIG. 1B). The Q501R variant mapped to the αD helix of the TIR domain, which is partially disordered in the TLR10 TIR dimer, while the A433T variant mapped to the αB helix in close proximity to the B-B loop (FIG. 1B). The conserved B-B loop of the TIR is thought to mediate dimerization of TLR10-linked TIR domains (Nyman et al. *J. Biol. Chem.* 283: 11861-11865, 2008).

Figure 3A:
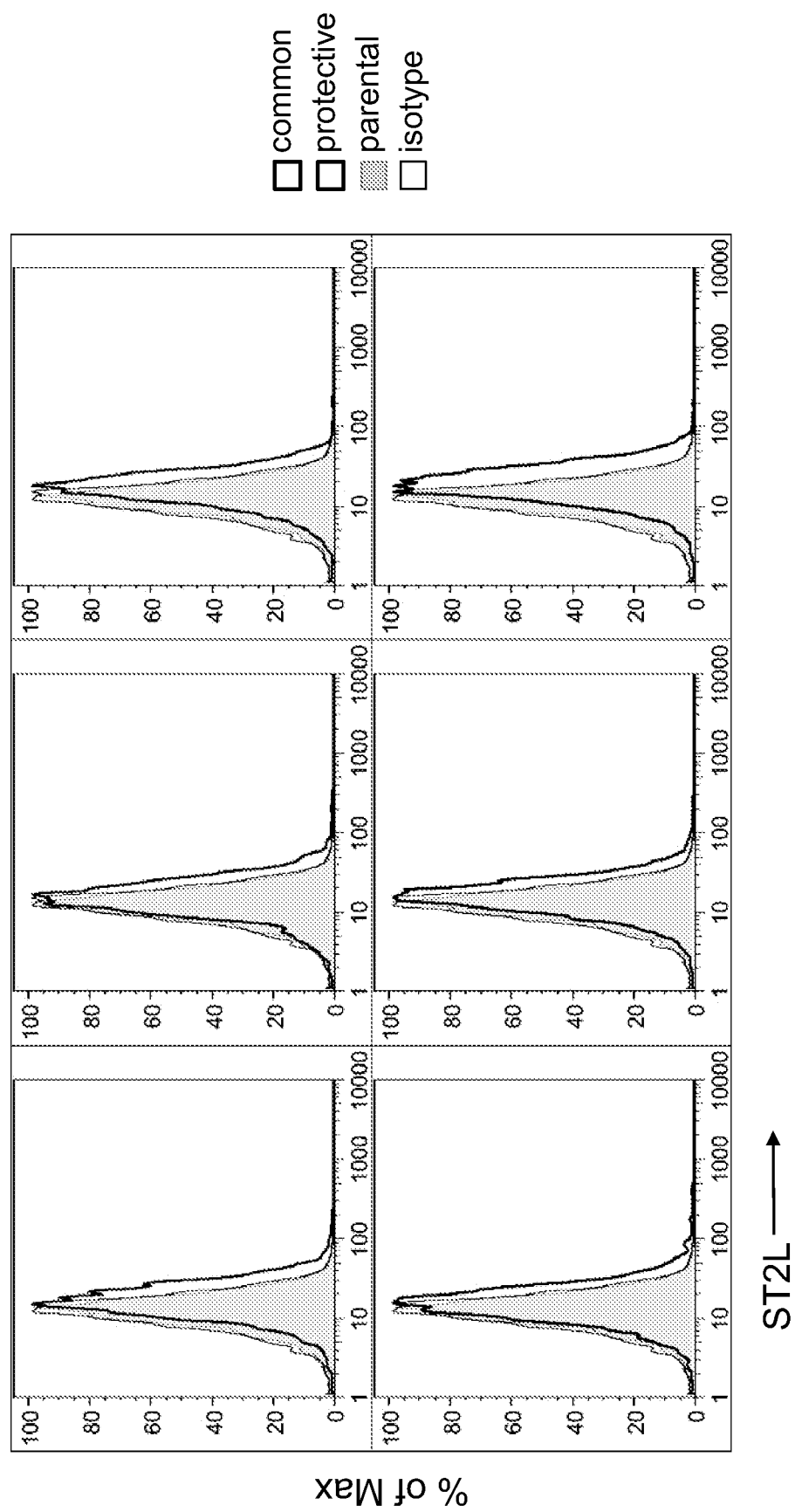
FIG. 3A are histograms showing the results of flow cytometry experiments comparing the surface expression levels of the indicated IL1RL1 variants in HEK-BLUE™ cells.
Figure 3D:
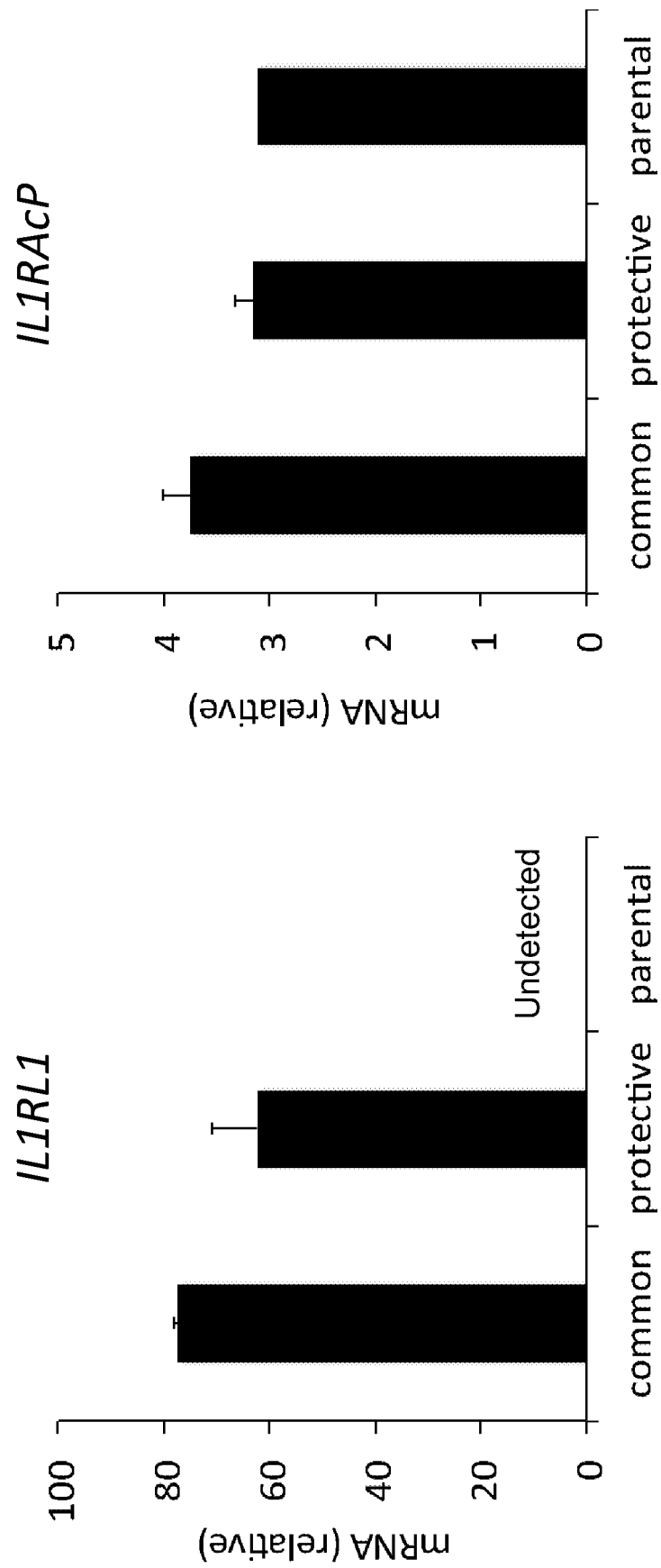
FIG. 3D are graphs showing the results of quantitative reverse transcription polymerase chain reaction (RT-PCR) measurements of IL1RL1 (left panel) and IL1RAcP (right panel) expression. mRNA levels are presented relative to expression of the housekeeping gene RPL19 (encoding the ribosomal protein L19).

To test the effects of these missense variants on IL-33-mediated signaling, cell lines expressing various permutations of the protective IL1RL1 variants were generated. Single TIR mutants, double C-terminal mutants, or mutants containing all four polymorphisms were generated and incorporated into expression vectors. To avoid endogenous IL-33 activity, HEK-BLUE™ (Invivogen) IL-1β cells that are responsive to IL-1β but are devoid of IL-33 activity were used. Stimulation of HEK-BLUE™ IL-1β cells with IL-1β results in robust NF-κB and AP-1 activation, which can be measured by NF-κB/AP-1-driven secreted alkaline phosphatase (SEAP) reporter activity. Stable transfection of ST2 expression vectors to HEK-BLUE™ IL-1β cells resulted in IL-33-dependent reporter activity, thus enabling the evaluation of both IL-1β and IL-33 responses using the same reporter system. While activation with IL-1β resulted in similar reporter gene induction between the different cell-lines, the response to IL-33 was diminished in cells expressing mutations in the TIR domains alone, or all 4 missense variants (see FIGS. 1C, 1D, 2A, and 2B). As a control, measurement of receptor expression revealed equivalent surface levels of all ST2 mutants (see FIGS. 3A-3C).

Figures 5A, 5B:
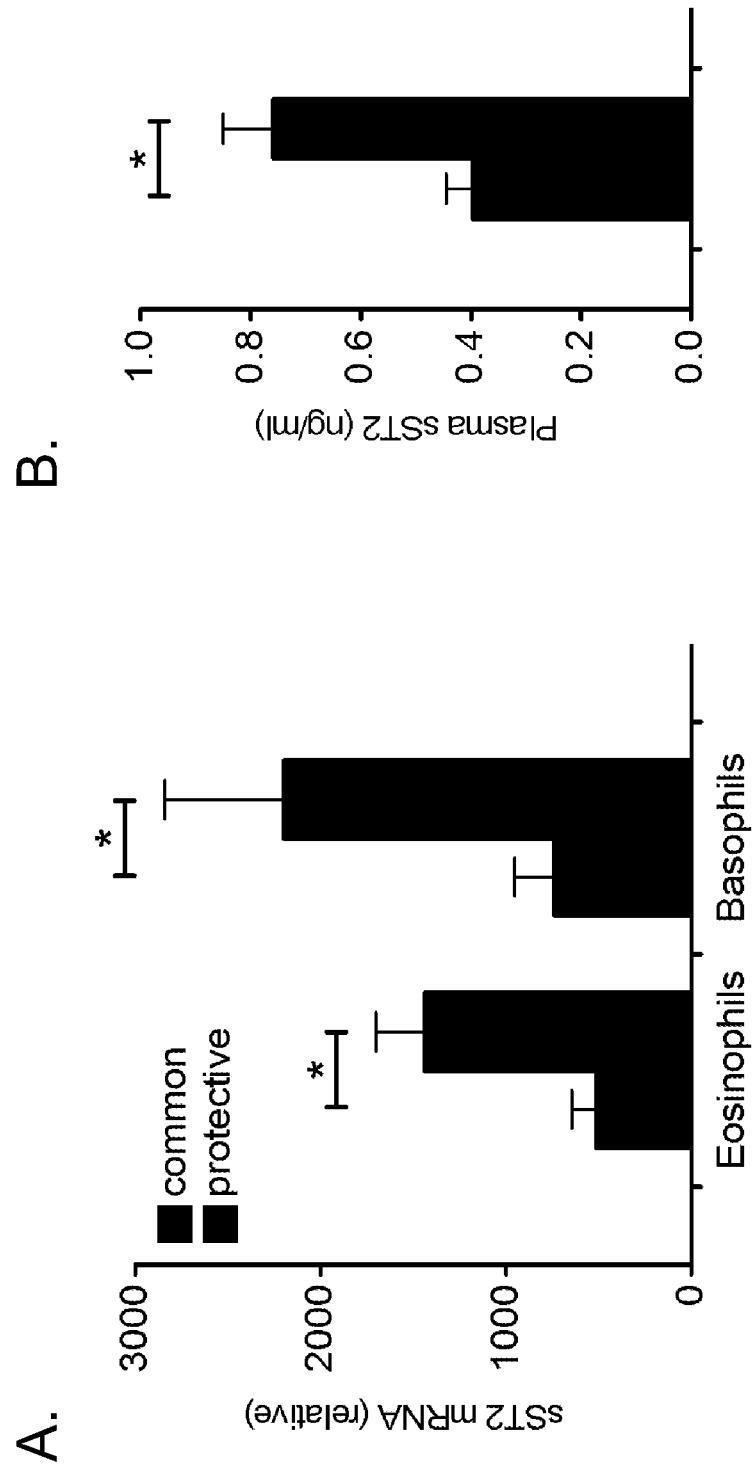
FIG. 5A is a graph showing quantitative RT-PCR of sST2 mRNA levels from purified blood eosinophils and basophils from human donors carrying either the protective or common IL1RL1 variants, as assessed by ELISA.
FIG. 5B is a graph showing plasma sST2 levels from human donors carrying either the protective or common IL1RL1 variants, as assessed by ELISA. Plots display mean±SEM of 3 single clones or 4 individual donors per group. * indicates p<0.05 as determined by paired t test.

To further elucidate how the protective ST2 variants could affect IL-33 activity in the context of asthma, we compared IL-33 activity and ST2 expression between human donors carrying either the protective IL1RL1 variants or the common IL1RL1 variants. In agreement with the reporter cell lines, we observed reduced IL-33-mediated interleukin-8 (IL-8) secretion from purified blood eosinophils derived from individuals carrying the protective IL1RL1 variants compared to individuals carrying the common IL1RL1 variants (FIG. 4). Further, we observed greater soluble ST2 expression in these individuals (FIGS. 5A and 5B).

These results provide a link between the genetic predisposition to asthma and IL-33 mediated responses. Given that IL-33 has a pro-inflammatory role in Th2-mediated immunity, perturbations to this pathway that diminish the IL-33 response can promote protection from asthma risk. The location of the variants within the TIR domain of ST2 predicts alterations to MyD88-mediated signaling. The subtle decrease in IL-33 responses conferred by these variants is consistent with the nature of the amino acid substitutions, the modest protective OR of the variants in IL1RL1 in the asthma genetics studies, and the chemical properties of their side chains. The fact that individuals bearing the common IL1RL1 variants are at increased risk of asthma compared to individuals bearing the protective IL1RL1 variants indicates that the genotype at these amino acid changing SNPs can be used in diagnostic methods to determine whether a patient is at increased risk of asthma. Further, these patients are likely to be responsive to therapies including an IL-33 axis binding antagonist, for example, an anti-IL-33 antibody or an ST2 binding antagonist, e.g., an ST2-Fc protein.

Methods
Stable Expression of ST2L and Protective Variants

ST2L cDNA was cloned into the pCMV Neo expression vector, and the protective variants were generated via PCR-based site-directed mutagenesis. Stable transfection of linearized plasmids into HEK-BLUE™ IL-1β reporter cells (Invivogen) was performed using LIPOFECTAMINE® (Life Technologies). HEK-BLUE™ IL-1β cells were maintained in DMEM, 2 mM L-glutamine, 10% heat-inactivated fetal bovine serum (FBS), NORMOCIN™ (100 μg/ml), hygromycin B (200 μg/ml), ZEOCIN™ (100 μg/ml), 50 U/ml penicillin and 50 μg/ml streptomycin. After 48 h, the transfected cells were selected in HEK-BLUE™ IL-1β growth media supplemented with 2 mg/ml G418 for 2 weeks. Stable expression of ST2L was confirmed via flow cytometry and mRNA analysis. Single clonal cultures were generated through limiting dilution of the batch cultures.

Cell Culture and Stimulation

IL-33 pathway activity in stably-transfected HEK-BLUE™ IL-1β reporter cells was measured via a colorimetric assay performed according to the manufacturer's instructions. Briefly, stably-transfected HEK-BLUE™ IL-1β reporter cells (50,000 cells/well in 96-well plates) were stimulated with increasing concentrations of IL-33 or IL-1β for 20 h at 37° C. in 5% $CO_2$. SEAP reporter activity was detected from supernatants with the QUANTI-BLUE™ assay (Invivogen) using a spectrophotometer at 620 nm.

RNA Isolation and Quantitative RT-PCR

RNA was isolated with an RNEASY® Mini Kit (Qiagen). An ABI 7500 Real-Time PCR system (Applied Biosystems) and TAQMAN® One-Step RT-PCR Master Mix (Applied Biosystems) were used for real-time RT-PCR (primers and probe sets from Applied Biosystems). Results were normalized to those of RPL19 and relative expression was calculated by change in threshold (ΔΔCT method).

Recombinant Proteins

Recombinant processed human IL-33 ($IL-33_{112-270}$) was prepared in-house. Recombinant IL-1β was purchased from R&D Systems.

Flow Cytometry Analysis

ST2L surface expression was detected using a biotinylated polyclonal antibody (BAF523, R&D Systems). Surface expression of IL-1RAcP was detected with an allophycocyanin (APC)-conjugated monoclonal antibody (FAB676A, R&D Systems). Mean fluorescence intensity (MFI) was calculated using FLOWJO™ software.

Human Eosinophil and Basophils Isolation

Primary human eosinophils and basophils were enriched from whole blood via negative selection using Miltenyi Biotec kits. Purity (>92%) was confirmed by flow cytometry analysis. Eosinophils were plated at $1 \times 10^6$ cells/ml in DMEM supplemented with 10% FBS, GLUTAMAX™, penicillin/streptomycin and containing 10 ng/ml recombinant human IL-3 (R&D Systems). Cell culture supernatants were collected after 24 h.

ELISA Analysis

IL-8 secretion from culture supernatants and plasma sST2 levels were measured using ELISA kits obtained from R&D Systems.

Genotyping

Asthma cases were genotyped on the ILLUMINA® 2.5M Omni array and variants were called using Illumina's GENOMESTUDIO™ software. Population controls were from the Cancer Genetic Markers of Susceptibility study (CGEMS) (cgems.cancer.gov). Population controls consisted of controls from the Cancer Genetic Markers of Susceptibility study (CGEMS) and were downloaded via database of Genotypes and Phenotypes (dbGAP) authorized access.

Sample Quality Control

Various quality control measures were performed on the asthma cases and controls. Samples missing more than 10% of the genotypes were removed (n=29). Samples with heterozygosity±3 standard deviations (SD) from the mean were removed (n=47). Identity by descent (IBD) analysis was performed to identify and remove related samples with a proportion of alleles shared IBD>0.4 (n=11). We assessed population substructure by filtering the GWAS data on minor allele frequency (MAF) and linkage disequilibrium. This subset of SNPs was merged with HapMap data and was then analyzed in EIGENSTRAT (Price et al. *Nat. Genet.* 38: 904-909, 2006) to use principle components to remove ancestry outliers that did not cluster near Caucasian samples (n=242). After applying quality control filters, we analyzed 4,987 Northern European Caucasian samples, including 522 asthma cases and 4465 controls.

SNP Quality Control

Quality control was performed to identify and remove low-quality SNPs. SNPs with a genotyping call rate <95% were excluded from analysis. SNPs showing evidence of deviation from Hardy Weinberg Equilibrium (HWE) were also removed (Purcell et al. *Am. J. Hum. Genet.* 81(3): 559-575, 2007). In addition, any SNP that failed liftover to human genome assembly hg19 or had a 1000 Genomes Project (kgp) identifier that did not map to a Reference SNP ID (rsid) were also removed from the dataset. After these quality control measures, 297,157 SNPs remained for imputation.

Genotype Imputation

Genotype imputation was performed for those samples using a workflow that included pre-phasing using Shapeit (Delaneau et al. *Nat. Methods* 9: 179-181, 2012) followed by imputation using IMPUTE2 (Marchini et al. *Nat. Genet.* 39: 906-913, 2007) and reference haplotypes from the 1000 Genomes Project (Durbin et al. *Nature* 467: 1061-1073, 2010).

Example 2. Periostin Levels are Predictive of Asthma Risk for Individuals Bearing the Protective ST2 Variants To examine whether asthma biomarkers can be used to refine diagnostic and prognostic methods for determining whether asthma patients are likely to respond to IL-33 axis binding antagonists, we tested whether the level of periostin was predictive of asthma susceptibility in individuals bearing the protective SNPs shown in FIG. 6. The individuals were classified as having high or low periostin levels, and the association of each group with asthma was determined. Individuals with low periostin levels compared to reference levels bearing the protective SNPs were less susceptible to asthma (i.e., lower odds ratio) compared to those with high periostin levels (FIG. 6). However, both groups were less susceptible to asthma compared to individuals bearing the common variants.

Example 3. Association of Serum sST2 Levels with IL-33 Axis Genetic Susceptibility Factors To examine whether peripheral blood sST2 levels were linked with IL-33 pathway activity via association of the IL-33 axis genetic susceptibility factors for asthma, we extended our previous findings of an association of serum sST2 levels with 11RL1 genetic variants in healthy donors (described in Example 1) and measured serum sST2 levels at baseline in 760 well-characterized, moderate-to-severe asthmatics from the BOBCAT (Jia et al. *J. Allergy Clin. Immunol.* 130:647-654, 2012), MILLY (Corren et al. *N. Engl. J. Med.* 365:1088-1098, 2011), and COSTA (Jeffrey et al. in: C101. Allergic airway inflammation and hyper-responsiveness: novel mechanisms and therapy American Thoracic Society; 2015. p. A5168-A) clinical studies.

Utilizing a previously described asthma discovery set (Ramirez-Carrozzi et al. *J. Allergy Clin. Immunol.* 135: 1080-1083, 2015), we scanned the IL33 locus, which was identified previously as an asthma risk locus (see, e.g., Moffatt et al. *N. Engl. J. Med.* 363:1211-1221, 2010), and identified rs4742165 (SEQ ID NO: 6) as the top SNP in that locus by P-value (OR=1.71; $P=5.26 \times 10^{-4}$). The SNP identified in Moffatt et al. supra (rs1342326; SEQ ID NO: 7) was not in our dataset, and the strongest proxy was not associated with risk of disease, however, the $r^2$ for this SNP with rs1342326 ($r^2=0.66$) was under a threshold that is commonly used to identify a strongly-linked SNP ($r^2 \geq 0.8$) (Moffatt et al. supra). Therefore, we performed an expression quantitative train linkage (eQTL) analysis of rs3771166 (SEQ ID NO: 8) and rs4742165 (SEQ ID NO: 6) with asthmatic serum sST2, to assess their combined genetic effect. IL1RL1 and 133 are located on chromosomes 2 and 9, respectively, so they are completely independent of each other.

Figure 7A:
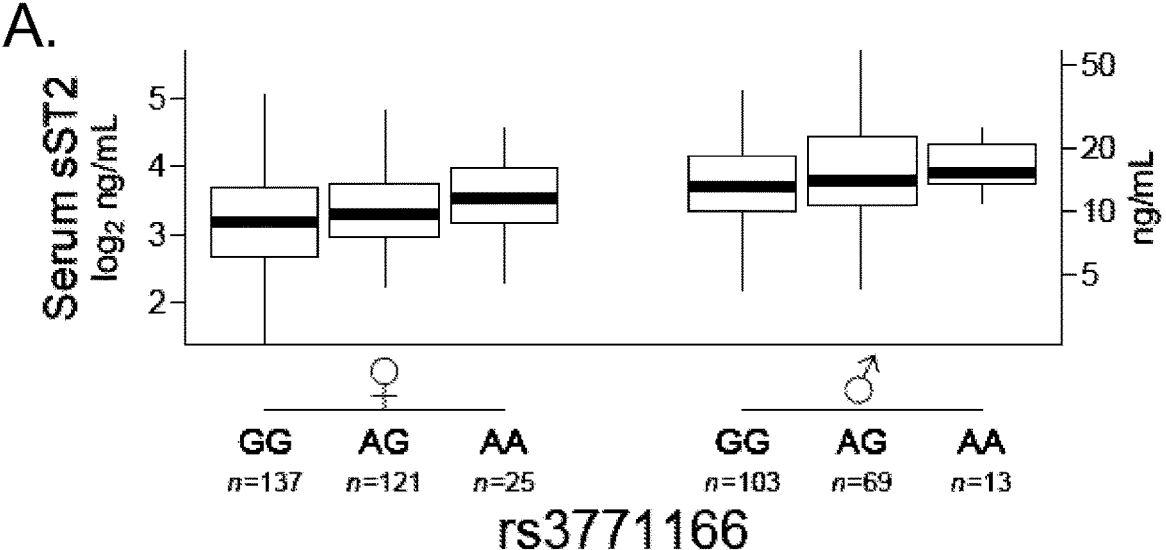
FIG. 7A is a box plot graph showing observed distributions of log 2-transformed asthmatic serum soluble ST2 (sST2) by genotype at rs3771166 and sex (female ♀, male ♂).
Figure 7B:
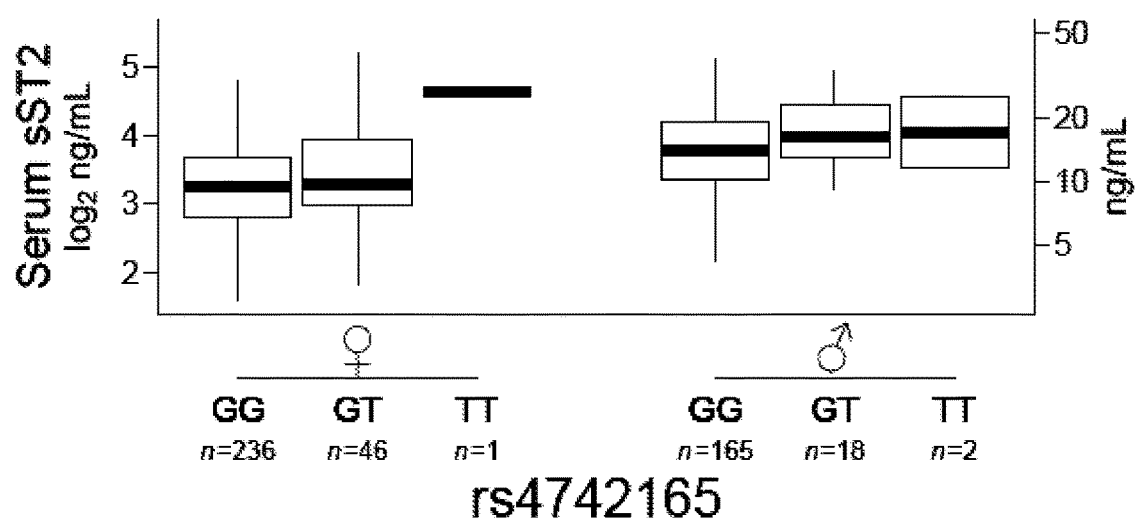
FIG. 7B is a box plot graph showing observed distributions of log 2-transformed asthmatic serum soluble ST2 (sST2) by genotype at rs4742165 and sex (female ♀, male ♂).
Figure 7C:
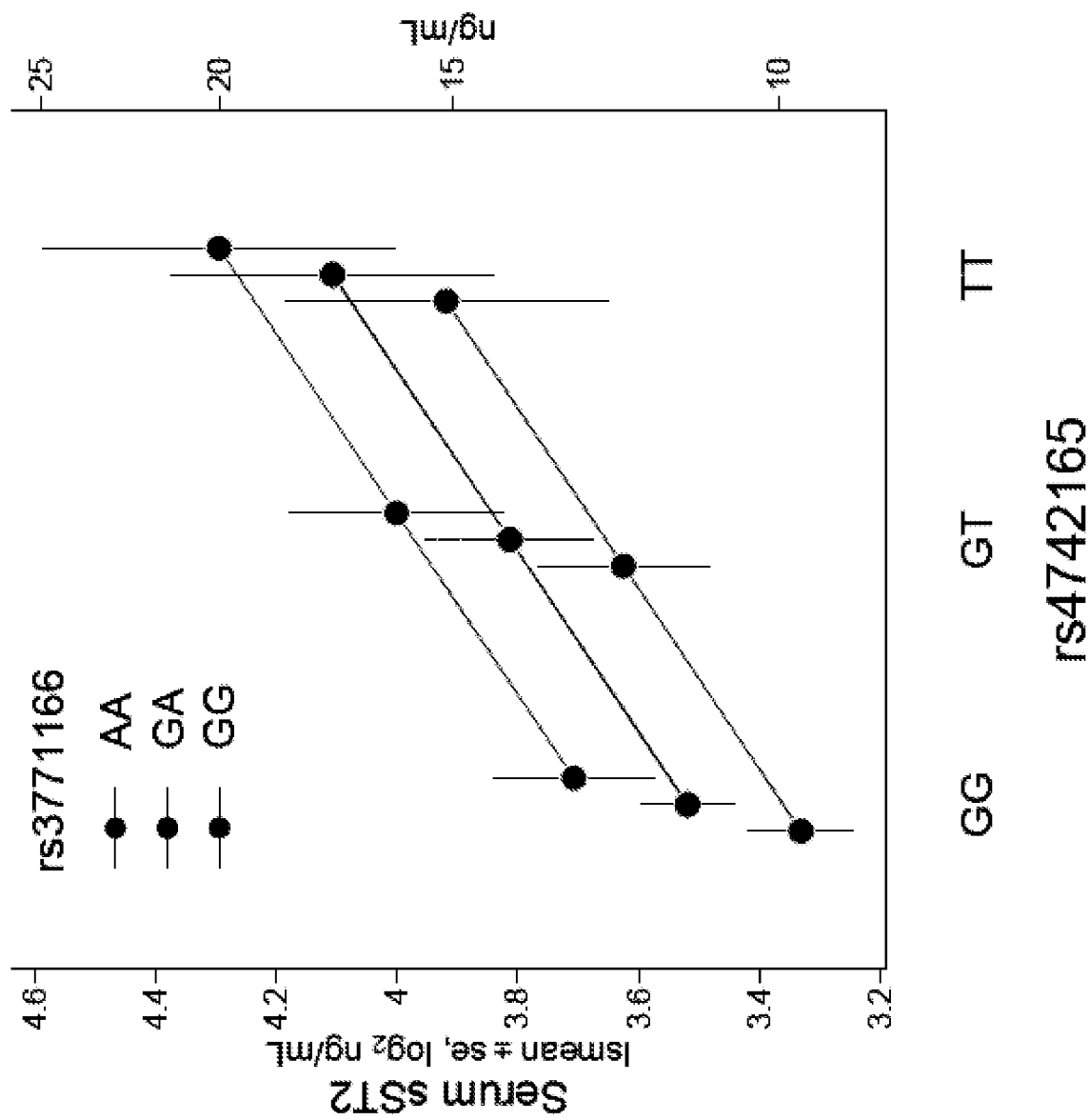
FIG. 7C is a graph showing the least squares mean (lsmean) and standard error of log 2-transformed asthmatic sST2 levels with rs4742165 (x-axis) and rs3771166 genotypes (series). Right axes correspond to untransformed values of sST2 levels (ng/mL).

The observed distribution and summary statistics of serum sST2 by the genotypes of rs3771166 and rs4742165 and sex are represented in FIGS. 7A and 7B, respectively. Median levels of serum sST2 were greater in males as was previously reported (Ramirez-Carrozzi et al. *J. Allergy Clin. Immunol.* 135:1080-1083, 2015 and Ho et al. *J. Clin. Invest.* 123: 4208-4218, 2013). In addition, median levels of serum sST2 increased with genotype of increasing minor allele count. Multiple regression of $\log_2$-transformed serum sST2 levels with rs3771166 and rs4742165 genotypes, adjusted for sex, was employed to assess the strength and significance of these SNPs to simultaneously predict serum sST2 levels. All terms were statistically significant (P<0.05, ANOVA F-test), indicating that rs4742165 predicted serum sST2 levels, even after accounting for rs3771166. The magnitude and variability of the predictivity of genotypes are represented by a plot of serum sST2 least squares means (lsmean) and standard errors (FIG. 7C). The magnitude of the genetic effect of rs4742165 was approximately 1.6 times greater than that of rs3771166. Soluble ST2 levels increased 23% and 14% for each minor allele count of rs4742165 and rs3771166, respectively. Serum sST2 levels were 43% higher in male as compared to female subjects.

Figure 8:
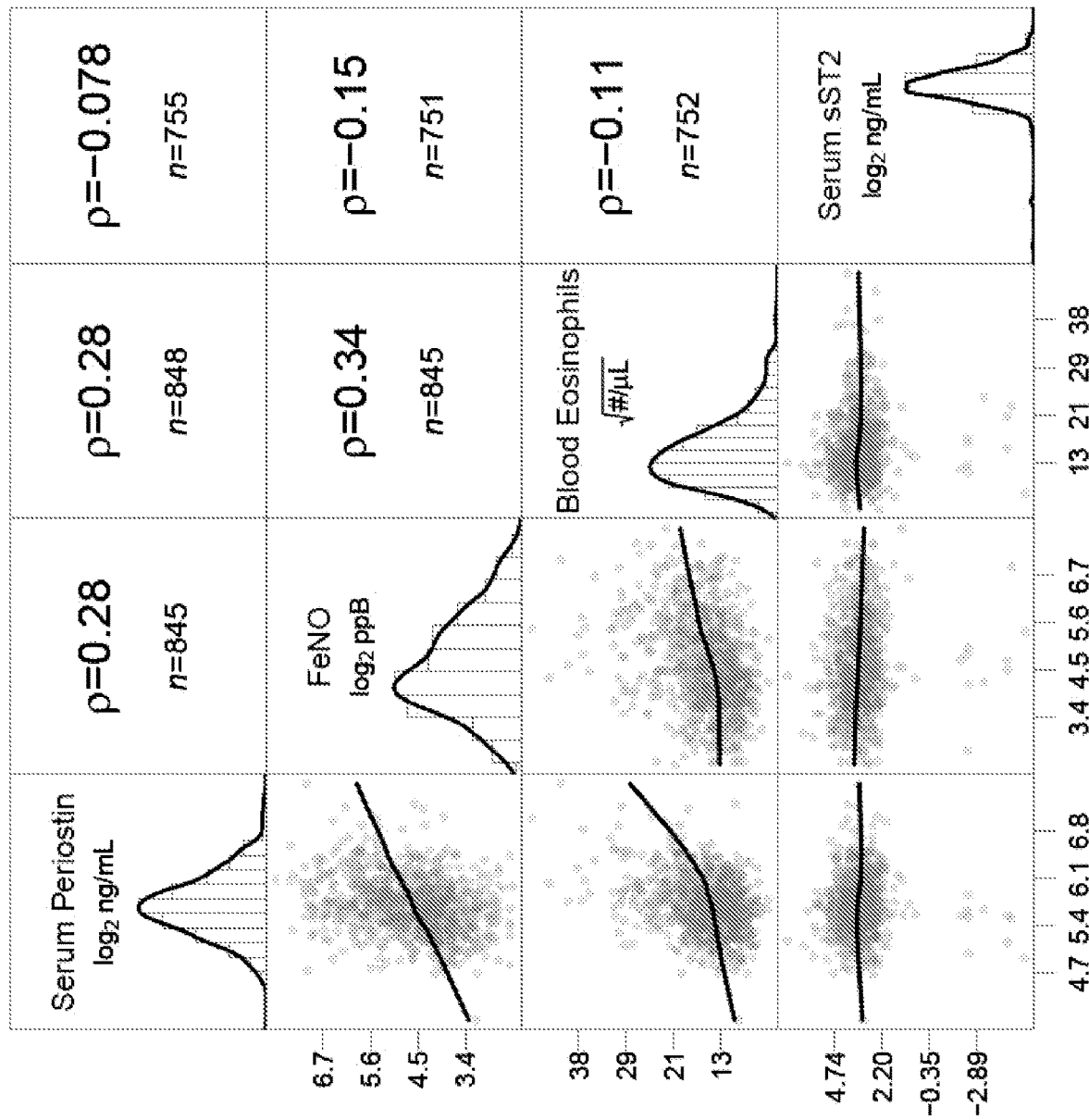
FIG. 8 is a series of graphs showing pairwise correlation of baseline biomarker levels. Pairwise analyses are represented for baseline biomarker levels. Lower panels are scatterplots and upper panels are Spearman's p estimates and counts of paired data. The x and y axes are defined by the row and column intersection with the diagonal (biomarker and units) and plot margins (scales). A line represents a LOWESS fit of the data.

IL-33 is a potent stimulator of Type 2 cytokine production, e.g., IL-13, in mast cells and group 2 innate lymphoid cells (ILC2) (Nagarkar et al. *J. Allergy Clin. Immunol.* 136:202-205, 2015). Therefore, we assessed the pair-wise relationship of serum periostin, fractional exhaled nitric oxide (FeNO), and blood eosinophil counts, which are each Type 2 biomarkers which predict response to IL-13 blockade in asthmatics (Arron et al. *Ann. Am. Thorac. Soc.* 10(Suppl): S206-213, 2013), with serum sST2 levels (FIG. 8). Interestingly, no correlation was observed between serum sST2 and each Type 2 biomarker (Spearman's p estimates −0.15 to −0.078). These data suggest that the biology associated with sST2 may play a role in both Type 2 high and Type 2 low asthma.

These data demonstrate a positive link between serum sST2 levels with/33-associated risk of asthma, indicating that sST2 may be a biomarker of IL-33 axis activity in asthma and may have utility in predicting clinical response and measuring pharmacodynamic effects of IL-33 axis targeted therapies, including IL-33 axis binding antagonists, such as anti-IL-33 antibodies.

Methods

Biomarkers sST2 was measured by ELISA (#DST200, R&D Systems, Quantikine). Serum periostin was measured by immunoassay using the ELECSYS® Periostin assay on the Cobas e601 analyzer (Roche Professional Diagnostics, Penzberg, Germany), as previously reported (Jia et al. *J. Allergy Clin. Immunol.* 130:647-654, 2012). FeNO was measured using the NIOX MING® device (Aerocrine, Solna, Sweden). Blood eosinophil count was assessed as part of a Complete Blood Cell Count (CBC) on automated hematology analyzers at central laboratories.

Statistics

R software (RCoreteam. R: A Language and Environment for Statistical Computing) was used for plotting and analysis. Spearman's rank correlation was utilized to assess correlation of baseline biomarker levels. Expression Quantitative Trail Linkage (eQTL) was performed as described previously (Stranger et al. *Nat. Genet.* 39:1217-1224, 2007). Multiple linear regression was utilized to model $\log_2$-transformed serum sST2 levels with respect to rs4742165 (SEQ ID NO: 6) and rs3771166 genotypes, adjusted for sex. Significance of model terms was determined by F-test.

Genotyping

Asthma cases were genotyped as described above in Example 1.

Example 4. SNPs in High Linkage Disequilibrium with IL-33 Axis Genetic Susceptibility Factors HapMap (International HapMap Consortium, *Nature* 437 (7063):1299-1320, 2005) linkage disequilibrium (LD) data and the 1000 Genomes dataset (McVean et al. *Nature.* 491: 56-65, 2012) were used to identify SNPs in high LD with the IL-33 axis genetic susceptibility factors (selected SNPs) described in Examples 1 and 3. SNPs in high LD with the selected SNPs rs4988956 (SEQ ID NO: 1); rs10204137 (SEQ ID NO: 2); rs10192036 (SEQ ID NO: 3); rs10192157 (SEQ ID NO: 4); rs10206753 (SEQ ID NO: 5); and/or rs4742165 (SEQ ID NO: 6), such as those presented in Tables 3 and 4, function as alternate SNPs that may be used as biomarkers for IL-33-mediated disorders, e.g., asthma. The genotype at these selected or alternate SNPs can be used in diagnostic methods to determine whether a patient is at increased risk of an IL-33-mediated disorder, e.g., asthma. Further, patients having the equivalent allele of the alternate SNP are likely to be responsive to therapies including an IL-33 axis binding antagonist, for example, an anti-IL-33 antibody or an ST2 binding antagonist, e.g., an ST2-Fc protein. With respect to the SNPs described in Tables 3 and 4, typically the minor allele in a population is the equivalent allele, although it is possible in some cases that the major allele in a population is the equivalent allele. Routine methods in the art can be used to confirm whether a given allele of the SNPs listed in Table 3 and 4 is an equivalent allele.

HapMap samples were separated based on ancestry in order to identify ancestry-specific LD SNPs. These populations were grouped into several categories: (1) ASW (African ancestry in Southwest USA), LWK (Luhya in Webuye, Kenya), MKK (Maasai in Kinyawa, Kenya), and YRI (Yoruba in lbadan, Nigeria; West Africa); (2) CEU (Utah residents with Northern and Western European ancestry from the CEPH collection) and TSI (Toscans in Italy); (3) CHB (Han Chinese in Beijing, China), CHD (Chinese in Metropolitan Denver, Colo.), and JPT (Japanese in Tokyo, Japan); and (4) GIH (Gujarati Indians in Houston, Tex.) and MEX (Mexican ancestry in Los Angeles, Calif.). Within the different ancestry groups, LD was assessed for SNPs in regions around rs4988956 (SEQ ID NO: 1) or rs4742165 (SEQ ID NO: 6), and were included if the D' values was greater than or equal to 0.6. There was a subset of SNPs where LD information was available in the HapMap data but allele frequency data were not available. For these SNPs, the information from the WOO Genomes Project (1000GP) was used. These SNPs are indicated in the column "Freq Source" in Tables 3 and 4 with the label "1000GP."

For the SNPs in Tables 3 and 4 that were missing HapMap allele frequencies, the following tags were used:

For CEU ancestry, this is indicated as "EUR_MAF" and comes from the minor allele and frequency of the SNP in 1000 Genomes Phase 1 combined European population. For Asian populations, this is indicated as "ASN_MAF" and comes from the minor allele and frequency of the SNP in the 1000 Genomes Phase 1 combined Asian population. For YRI ancestry, this is indicated as "AFR_MAF" and comes from the minor allele and frequency of the SNP in the 1000 Genomes Phase 1 combined African population.

Table 3 shows SNPs in linkage disequilibrium with rs4988956 (SEQ ID NO: 1). Because rs4988956 (SEQ ID NO: 1), rs10204137 (SEQ ID NO: 2), rs10192036 (SEQ ID NO: 3), rs10192157 (SEQ ID NO: 4), and rs10206753 (SEQ ID NO: 5) are all 100% linked, the SNPs in Table 3 are also in linkage disequilibrium with rs10204137 (SEQ ID NO: 2), rs10192036 (SEQ ID NO: 3), rs10192157 (SEQ ID NO: 4), and rs10206753 (SEQ ID NO: 5). Table 4 shows SNPs in linkage disequilibrium with rs4742165 (SEQ ID NO: 6).

Terms used in Tables 3 and 4 are defined as follows: (1) Ancestry or "ANC" refers to the ancestry of the population used to determine $r^2$ and D' values; (2) "LD_SNP" refers to the SNP in LD with the IL-33 axis genetic susceptibility SNPs rs4988956 (SEQ ID NO: 1) with respect to Table 3 and rs4742165 (SEQ ID NO: 6) with respect to Table 4 (rsID designation comes from NCBI dbSNP build 137 (Jun. 6, 2012)); (3) CHR refers to the chromosome location of the LD_SNP (genome build hg19; UCSC HG19 Genome Assembly; February 2009); (4) BP refers to the DNA base pair location of the LD_SNP (genome build hg19; UCSC HG19 Genome Assembly; February 2009); (5) "RSQ" refers to the r-squared ($r^2$) value of the IL-33 axis genetic susceptibility SNP and the LD_SNP; "DPRIME" refers to the D' value of the IL-33 axis genetic susceptibility SNP and the LD_SNP; (6) "LD SOURCE" refers to the database from which the LD data for a given LD_SNP was obtained; (7) "FREQ SOURCE" refers to the database (i.e., HapMap or 1000 gp) from which the allele frequency data for a given LD_SNP was obtained; (8) "A1" refers to allele 1 of the LD_SNP; (9) A1 FREQ refers to the allele frequency of allele 1 of the LD_SNP; (10) A2 refers to allele 2 of the LD_SNP; (11) "A2 FREQ" refers to the allele frequency of allele 2 of the LD_SNP; and (12) ALLELES refers to the alleles of the LD_SNP.

TABLE 3

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|-----|--------|-----|-----|-----|--------|-----------|-------------|-----|---------|-----|---------|---------|
| JPT | rs1005043 | 2 | 102511858 | 0.05 | 0.62 | HapMap | HapMap | A | 0.436 | G | 0.564 | A/G |
| CHB | rs1005043 | 2 | 102511858 | 0.17 | 1 | HapMap | HapMap | A | 0.53 | G | 0.47 | A/G |
| CHD | rs1005043 | 2 | 102511858 | 0.098 | 0.814 | HapMap | HapMap | A | 0.541 | G | 0.459 | A/G |
| CHB | rs1014286 | 2 | 102515532 | 0.162 | 1 | HapMap | HapMap | G | 0.524 | A | 0.476 | G/A |
| CHD | rs1014286 | 2 | 102515532 | 0.096 | 0.808 | HapMap | HapMap | G | 0.536 | A | 0.464 | G/A |
| JPT | rs1014286 | 2 | 102515532 | 0.047 | 0.623 | HapMap | HapMap | G | 0.429 | A | 0.571 | G/A |
| YRI | rs10168308 | 2 | 102430350 | 0.019 | 1 | HapMap | HapMap | G | 0.956 | A | 0.044 | G/A |
| MKK | rs10168308 | 2 | 102430350 | 0.018 | 1 | HapMap | HapMap | G | 0.975 | A | 0.025 | G/A |
| LWK | rs10172153 | 2 | 102313878 | 0.004 | 0.919 | HapMap | HapMap | T | 0.983 | C | 0.017 | T/C |
| MKK | rs10172153 | 2 | 102313878 | 0.018 | 1 | HapMap | HapMap | T | 0.976 | C | 0.024 | T/C |
| YRI | rs10172153 | 2 | 102313878 | 0.019 | 1 | HapMap | HapMap | T | 0.965 | C | 0.035 | T/C |
| CHB | rs10175045 | 2 | 102469664 | 0.132 | 0.677 | HapMap | HapMap | T | 0.643 | C | 0.357 | T/C |
| MKK | rs10175045 | 2 | 102469664 | 0.063 | 0.761 | HapMap | HapMap | T | 0.073 | C | 0.927 | T/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| YRI | rs10175045 | 2 | 102469664 | 0.071 | 1 | HapMap | HapMap | T | 0.027 | C | 0.973 | T/C |
| CEU | rs10175045 | 2 | 102469664 | 0.273 | 1 | HapMap | HapMap | T | 0.265 | C | 0.735 | T/C |
| LWK | rs10175045 | 2 | 102469664 | 0.129 | 1 | HapMap | HapMap | T | 0.039 | C | 0.961 | T/C |
| ASW | rs10175045 | 2 | 102469664 | 0.063 | 1 | HapMap | HapMap | T | 0.019 | C | 0.981 | T/C |
| CHD | rs10175045 | 2 | 102469664 | 0.133 | 0.768 | HapMap | HapMap | T | 0.641 | C | 0.359 | T/C |
| GIH | rs10175045 | 2 | 102469664 | 0.059 | 0.713 | HapMap | HapMap | T | 0.295 | C | 0.705 | T/C |
| JPT | rs10175045 | 2 | 102469664 | 0.102 | 0.604 | HapMap | HapMap | T | 0.605 | C | 0.395 | T/C |
| CHB | rs10176820 | 2 | 102420852 | 0.64 | 1 | HapMap | HapMap | T | 0.915 | C | 0.085 | T/C |
| CEU | rs10176820 | 2 | 102420852 | 0.193 | 1 | HapMap | HapMap | T | 0.851 | C | 0.149 | T/C |
| ASW | rs10176820 | 2 | 102420852 | 0.166 | 0.738 | HapMap | HapMap | T | 0.644 | C | 0.356 | T/C |
| CHD | rs10176820 | 2 | 102420852 | 0.713 | 1 | HapMap | HapMap | T | 0.918 | C | 0.082 | T/C |
| GIH | rs10176820 | 2 | 102420852 | 0.22 | 0.74 | HapMap | HapMap | T | 0.903 | C | 0.097 | T/C |
| JPT | rs10176820 | 2 | 102420852 | 0.654 | 1 | HapMap | HapMap | T | 0.882 | C | 0.118 | T/C |
| LWK | rs10176820 | 2 | 102420852 | 0.115 | 0.825 | HapMap | HapMap | T | 0.646 | C | 0.354 | T/C |
| ASW | rs10177815 | 2 | 102400747 | 0.055 | 1 | HapMap | HapMap | C | 0.906 | T | 0.094 | C/T |
| LWK | rs10177815 | 2 | 102400747 | 0.06 | 1 | HapMap | HapMap | C | 0.839 | T | 0.161 | C/T |
| MKK | rs10177815 | 2 | 102400747 | 0.051 | 1 | HapMap | HapMap | C | 0.934 | T | 0.066 | C/T |
| YRI | rs10177815 | 2 | 102400747 | 0.038 | 0.729 | HapMap | HapMap | C | 0.819 | T | 0.181 | C/T |
| ASW | rs10178191 | 2 | 102279524 | 0.03 | 1 | HapMap | HapMap | G | 0.953 | T | 0.047 | G/T |
| LWK | rs10178191 | 2 | 102279524 | 0.005 | 1 | HapMap | HapMap | G | 0.983 | T | 0.017 | G/T |
| MEX | rs10178191 | 2 | 102279524 | 0.031 | 1 | HapMap | HapMap | G | 0.99 | T | 0.01 | G/T |
| MKK | rs10178191 | 2 | 102279524 | 0.04 | 1 | HapMap | HapMap | G | 0.948 | T | 0.052 | G/T |
| YRI | rs10178191 | 2 | 102279524 | 0.015 | 1 | HapMap | HapMap | G | 0.96 | T | 0.04 | G/T |
| CEU | rs10178214 | 2 | 102225353 | 0.21 | 1 | HapMap | HapMap | G | 0.839 | T | 0.161 | G/T |
| CHB | rs10178214 | 2 | 102225353 | 0.599 | 0.867 | HapMap | HapMap | G | 0.873 | T | 0.127 | G/T |
| CHD | rs10178214 | 2 | 102225353 | 0.574 | 0.758 | HapMap | HapMap | G | 0.888 | T | 0.112 | G/T |
| GIH | rs10178214 | 2 | 102225353 | 0.217 | 0.736 | HapMap | HapMap | G | 0.903 | T | 0.097 | G/T |
| JPT | rs10178214 | 2 | 102225353 | 0.457 | 0.707 | HapMap | HapMap | G | 0.872 | T | 0.128 | G/T |
| MEX | rs10178214 | 2 | 102225353 | 0.241 | 0.636 | HapMap | HapMap | G | 0.81 | T | 0.19 | G/T |
| CHB | rs10178436 | 2 | 102292943 | 0.141 | 1 | HapMap | HapMap | T | 0.47 | C | 0.53 | T/C |
| CHD | rs10178436 | 2 | 102292943 | 0.132 | 1 | HapMap | HapMap | T | 0.512 | C | 0.488 | T/C |
| JPT | rs10178436 | 2 | 102292943 | 0.095 | 1 | HapMap | HapMap | T | 0.384 | C | 0.616 | T/C |
| CEU | rs10183812 | 2 | 102518362 | 0.047 | 1 | HapMap | HapMap | T | 0.929 | C | 0.071 | T/C |
| CHB | rs10183812 | 2 | 102518362 | 0.385 | 0.68 | HapMap | HapMap | T | 0.863 | C | 0.137 | T/C |
| CHD | rs10183812 | 2 | 102518362 | 0.431 | 0.677 | HapMap | HapMap | T | 0.894 | C | 0.106 | T/C |
| JPT | rs10183812 | 2 | 102518362 | 0.442 | 0.766 | HapMap | HapMap | T | 0.843 | C | 0.157 | T/C |
| ASW | rs10189629 | 2 | 102245896 | 0.124 | 1 | HapMap | HapMap | C | 0.811 | A | 0.189 | C/A |
| CEU | rs10189629 | 2 | 102245896 | 0.159 | 1 | HapMap | HapMap | C | 0.889 | A | 0.111 | C/A |
| CHB | rs10189629 | 2 | 102245896 | 0.366 | 0.819 | HapMap | HapMap | C | 0.911 | A | 0.089 | C/A |
| CHD | rs10189629 | 2 | 102245896 | 0.604 | 1 | HapMap | HapMap | C | 0.929 | A | 0.071 | C/A |
| GIH | rs10189629 | 2 | 102245896 | 0.283 | 0.901 | HapMap | HapMap | C | 0.915 | A | 0.085 | C/A |
| JPT | rs10189629 | 2 | 102245896 | 0.385 | 1 | HapMap | HapMap | C | 0.936 | A | 0.064 | C/A |
| LWK | rs10189629 | 2 | 102245896 | 0.081 | 0.818 | HapMap | HapMap | C | 0.722 | A | 0.278 | C/A |
| MEX | rs10189629 | 2 | 102245896 | 0.344 | 1 | HapMap | HapMap | C | 0.88 | A | 0.12 | C/A |
| MKK | rs10189629 | 2 | 102245896 | 0.257 | 1 | HapMap | HapMap | C | 0.738 | A | 0.262 | C/A |
| YRI | rs10189629 | 2 | 102245896 | 0.072 | 0.77 | HapMap | HapMap | C | 0.741 | A | 0.259 | C/A |
| ASW | rs10192036 | 2 | 102334643 | 1 | 1 | HapMap | HapMap | C | 0.302 | A | 0.698 | C/A |
| CEU | rs10192036 | 2 | 102334643 | 1 | 1 | HapMap | HapMap | C | 0.593 | A | 0.407 | C/A |
| CHB | rs10192036 | 2 | 102334643 | 1 | 1 | HapMap | HapMap | C | 0.857 | A | 0.143 | C/A |
| CHD | rs10192036 | 2 | 102334643 | 1 | 1 | HapMap | HapMap | C | 0.888 | A | 0.112 | C/A |
| GIH | rs10192036 | 2 | 102334643 | 1 | 1 | HapMap | HapMap | C | 0.787 | A | 0.213 | C/A |
| JPT | rs10192036 | 2 | 102334643 | 1 | 1 | HapMap | HapMap | C | 0.843 | A | 0.157 | C/A |
| LWK | rs10192036 | 2 | 102334643 | 1 | 1 | HapMap | HapMap | C | 0.239 | A | 0.761 | C/A |
| MEX | rs10192036 | 2 | 102334643 | 1 | 1 | HapMap | HapMap | C | 0.72 | A | 0.28 | C/A |
| MKK | rs10192036 | 2 | 102334643 | 1 | 1 | HapMap | HapMap | C | 0.42 | A | 0.58 | C/A |
| YRI | rs10192036 | 2 | 102334643 | 1 | 1 | HapMap | HapMap | C | 0.235 | A | 0.765 | C/A |
| ASW | rs10192157 | 2 | 102334788 | 1 | 1 | HapMap | HapMap | C | 0.302 | T | 0.698 | C/T |
| CEU | rs10192157 | 2 | 102334788 | 1 | 1 | HapMap | HapMap | C | 0.593 | T | 0.407 | C/T |
| CHB | rs10192157 | 2 | 102334788 | 1 | 1 | HapMap | HapMap | C | 0.857 | T | 0.143 | C/T |
| CHD | rs10192157 | 2 | 102334788 | 1 | 1 | HapMap | HapMap | C | 0.888 | T | 0.112 | C/T |
| GIH | rs10192157 | 2 | 102334788 | 1 | 1 | HapMap | HapMap | C | 0.79 | T | 0.21 | C/T |
| JPT | rs10192157 | 2 | 102334788 | 1 | 1 | HapMap | HapMap | C | 0.849 | T | 0.151 | C/T |
| LWK | rs10192157 | 2 | 102334788 | 1 | 1 | HapMap | HapMap | C | 0.239 | T | 0.761 | C/T |
| MEX | rs10192157 | 2 | 102334788 | 1 | 1 | HapMap | HapMap | C | 0.73 | T | 0.27 | C/T |
| MKK | rs10192157 | 2 | 102334788 | 1 | 1 | HapMap | HapMap | C | 0.42 | T | 0.58 | C/T |
| YRI | rs10192157 | 2 | 102334788 | 1 | 1 | HapMap | HapMap | C | 0.235 | T | 0.765 | C/T |
| CHD | rs10194822 | 2 | 102531936 | 0.039 | 0.752 | HapMap | HapMap | T | 0.647 | G | 0.353 | T/G |
| ASW | rs10197310 | 2 | 102386462 | 0.119 | 0.699 | HapMap | HapMap | T | 0.689 | A | 0.311 | T/A |
| CEU | rs10197310 | 2 | 102386462 | 0.156 | 0.863 | HapMap | HapMap | T | 0.832 | A | 0.168 | T/A |
| CHB | rs10197310 | 2 | 102386462 | 0.632 | 1 | HapMap | HapMap | T | 0.905 | A | 0.095 | T/A |
| CHD | rs10197310 | 2 | 102386462 | 0.713 | 1 | HapMap | HapMap | T | 0.917 | A | 0.083 | T/A |
| GIH | rs10197310 | 2 | 102386462 | 0.22 | 0.74 | HapMap | HapMap | T | 0.903 | A | 0.097 | T/A |
| JPT | rs10197310 | 2 | 102386462 | 0.753 | 1 | HapMap | HapMap | T | 0.863 | A | 0.137 | T/A |
| LWK | rs10197310 | 2 | 102386462 | 0.068 | 0.649 | HapMap | HapMap | T | 0.661 | A | 0.339 | T/A |
| MEX | rs10197310 | 2 | 102386462 | 0.364 | 0.813 | HapMap | HapMap | T | 0.82 | A | 0.18 | T/A |
| ASW | rs10197862 | 2 | 102332981 | 0.214 | 1 | HapMap | HapMap | A | 0.726 | G | 0.274 | A/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs10197862 | 2 | 102332981 | 0.176 | 1 | HapMap | HapMap | A | 0.872 | G | 0.128 | A/G |
| CHB | rs10197862 | 2 | 102332981 | 0.632 | 1 | HapMap | HapMap | A | 0.905 | G | 0.095 | A/G |
| CHD | rs10197862 | 2 | 102332981 | 0.713 | 1 | HapMap | HapMap | A | 0.918 | G | 0.082 | A/G |
| GIH | rs10197862 | 2 | 102332981 | 0.375 | 1 | HapMap | HapMap | A | 0.909 | G | 0.091 | A/G |
| JPT | rs10197862 | 2 | 102332981 | 0.753 | 1 | HapMap | HapMap | A | 0.872 | G | 0.128 | A/G |
| LWK | rs10197862 | 2 | 102332981 | 0.093 | 1 | HapMap | HapMap | A | 0.772 | G | 0.228 | A/G |
| MEX | rs10197862 | 2 | 102332981 | 0.464 | 1 | HapMap | HapMap | A | 0.85 | G | 0.15 | A/G |
| MKK | rs10197862 | 2 | 102332981 | 0.296 | 1 | HapMap | HapMap | A | 0.71 | G | 0.29 | A/G |
| YRI | rs10197862 | 2 | 102332981 | 0.216 | 1 | HapMap | HapMap | A | 0.668 | G | 0.332 | A/G |
| CHD | rs10201184 | 2 | 102455510 | 0.079 | 0.706 | HapMap | HapMap | G | 0.559 | C | 0.441 | G/C |
| JPT | rs10201184 | 2 | 102455510 | 0.058 | 0.65 | HapMap | HapMap | G | 0.453 | C | 0.547 | G/C |
| ASW | rs10202813 | 2 | 102386172 | 0.119 | 0.699 | HapMap | HapMap | G | 0.689 | T | 0.311 | G/T |
| CEU | rs10202813 | 2 | 102386172 | 0.193 | 1 | HapMap | HapMap | G | 0.842 | T | 0.158 | G/T |
| CHB | rs10202813 | 2 | 102386172 | 0.632 | 1 | HapMap | HapMap | G | 0.905 | T | 0.095 | G/T |
| CHD | rs10202813 | 2 | 102386172 | 0.713 | 1 | HapMap | HapMap | G | 0.917 | T | 0.083 | G/T |
| GIH | rs10202813 | 2 | 102386172 | 0.22 | 0.74 | HapMap | HapMap | G | 0.903 | T | 0.097 | G/T |
| JPT | rs10202813 | 2 | 102386172 | 0.753 | 1 | HapMap | HapMap | G | 0.872 | T | 0.128 | G/T |
| LWK | rs10202813 | 2 | 102386172 | 0.099 | 0.805 | HapMap | HapMap | G | 0.663 | T | 0.337 | G/T |
| MEX | rs10202813 | 2 | 102386172 | 0.364 | 0.813 | HapMap | HapMap | G | 0.82 | T | 0.18 | G/T |
| ASW | rs10204137 | 2 | 102334644 | 1 | 1 | HapMap | HapMap | A | 0.302 | G | 0.698 | A/G |
| CEU | rs10204137 | 2 | 102334644 | 1 | 1 | HapMap | HapMap | A | 0.593 | G | 0.407 | A/G |
| CHB | rs10204137 | 2 | 102334644 | 1 | 1 | HapMap | HapMap | A | 0.857 | G | 0.143 | A/G |
| CHD | rs10204137 | 2 | 102334644 | 1 | 1 | HapMap | HapMap | A | 0.888 | G | 0.112 | A/G |
| GIH | rs10204137 | 2 | 102334644 | 1 | 1 | HapMap | HapMap | A | 0.79 | G | 0.21 | A/G |
| JPT | rs10204137 | 2 | 102334644 | 1 | 1 | HapMap | HapMap | A | 0.849 | G | 0.151 | A/G |
| LWK | rs10204137 | 2 | 102334644 | 1 | 1 | HapMap | HapMap | A | 0.239 | G | 0.761 | A/G |
| MEX | rs10204137 | 2 | 102334644 | 1 | 1 | HapMap | HapMap | A | 0.73 | G | 0.27 | A/G |
| MKK | rs10204137 | 2 | 102334644 | 1 | 1 | HapMap | HapMap | A | 0.42 | G | 0.58 | A/G |
| YRI | rs10204137 | 2 | 102334644 | 1 | 1 | HapMap | HapMap | A | 0.235 | G | 0.765 | A/G |
| ASW | rs10204837 | 2 | 102344162 | 0.877 | 1 | HapMap | HapMap | C | 0.349 | A | 0.651 | C/A |
| CEU | rs10204837 | 2 | 102344162 | 1 | 1 | HapMap | HapMap | C | 0.593 | A | 0.407 | C/A |
| CHB | rs10204837 | 2 | 102344162 | 1 | 1 | HapMap | HapMap | C | 0.857 | A | 0.143 | C/A |
| CHD | rs10204837 | 2 | 102344162 | 1 | 1 | HapMap | HapMap | C | 0.888 | A | 0.112 | C/A |
| GIH | rs10204837 | 2 | 102344162 | 1 | 1 | HapMap | HapMap | C | 0.79 | A | 0.21 | C/A |
| JPT | rs10204837 | 2 | 102344162 | 1 | 1 | HapMap | HapMap | C | 0.849 | A | 0.151 | C/A |
| LWK | rs10204837 | 2 | 102344162 | 0.555 | 1 | HapMap | HapMap | C | 0.361 | A | 0.639 | C/A |
| MEX | rs10204837 | 2 | 102344162 | 1 | 1 | HapMap | HapMap | C | 0.73 | A | 0.27 | C/A |
| MKK | rs10204837 | 2 | 102344162 | 0.855 | 1 | HapMap | HapMap | C | 0.458 | A | 0.542 | C/A |
| YRI | rs10204837 | 2 | 102344162 | 0.916 | 1 | HapMap | HapMap | C | 0.265 | A | 0.735 | C/A |
| ASW | rs10206753 | 2 | 102334794 | 1 | 1 | HapMap | HapMap | T | 0.302 | C | 0.698 | T/C |
| CEU | rs10206753 | 2 | 102334794 | 1 | 1 | HapMap | HapMap | T | 0.589 | C | 0.411 | T/C |
| CHB | rs10206753 | 2 | 102334794 | 1 | 1 | HapMap | HapMap | T | 0.857 | C | 0.143 | T/C |
| CHD | rs10206753 | 2 | 102334794 | 1 | 1 | HapMap | HapMap | T | 0.888 | C | 0.112 | T/C |
| GIH | rs10206753 | 2 | 102334794 | 1 | 1 | HapMap | HapMap | T | 0.79 | C | 0.21 | T/C |
| JPT | rs10206753 | 2 | 102334794 | 1 | 1 | HapMap | HapMap | T | 0.849 | C | 0.151 | T/C |
| LWK | rs10206753 | 2 | 102334794 | 1 | 1 | HapMap | HapMap | T | 0.239 | C | 0.761 | T/C |
| MEX | rs10206753 | 2 | 102334794 | 1 | 1 | HapMap | HapMap | T | 0.73 | C | 0.27 | T/C |
| MKK | rs10206753 | 2 | 102334794 | 1 | 1 | HapMap | HapMap | T | 0.42 | C | 0.58 | T/C |
| YRI | rs10206753 | 2 | 102334794 | 1 | 1 | HapMap | HapMap | T | 0.235 | C | 0.765 | T/C |
| CHD | rs10207579 | 2 | 102469721 | 0.125 | 0.626 | HapMap | HapMap | C | 0.714 | T | 0.286 | C/T |
| ASW | rs10210176 | 2 | 102445948 | 0.119 | 0.699 | HapMap | HapMap | C | 0.689 | A | 0.311 | C/A |
| CEU | rs10210176 | 2 | 102445948 | 0.193 | 1 | HapMap | HapMap | C | 0.835 | A | 0.165 | C/A |
| CHB | rs10210176 | 2 | 102445948 | 0.632 | 1 | HapMap | HapMap | C | 0.905 | A | 0.095 | C/A |
| CHD | rs10210176 | 2 | 102445948 | 0.713 | 1 | HapMap | HapMap | C | 0.918 | A | 0.082 | C/A |
| GIH | rs10210176 | 2 | 102445948 | 0.22 | 0.74 | HapMap | HapMap | C | 0.903 | A | 0.097 | C/A |
| JPT | rs10210176 | 2 | 102445948 | 0.753 | 1 | HapMap | HapMap | C | 0.872 | A | 0.128 | C/A |
| LWK | rs10210176 | 2 | 102445948 | 0.074 | 0.67 | HapMap | HapMap | C | 0.656 | A | 0.344 | C/A |
| MEX | rs10210176 | 2 | 102445948 | 0.405 | 0.826 | HapMap | HapMap | C | 0.81 | A | 0.19 | C/A |
| ASW | rs1030021 | 2 | 102167910 | 0.119 | 0.699 | HapMap | HapMap | A | 0.651 | C | 0.349 | A/C |
| LWK | rs1030021 | 2 | 102167910 | 0.098 | 1 | HapMap | HapMap | A | 0.758 | C | 0.242 | A/C |
| MKK | rs1030021 | 2 | 102167910 | 0.157 | 0.734 | HapMap | HapMap | A | 0.713 | C | 0.287 | A/C |
| CHB | rs1035127 | 2 | 102386351 | 0.141 | 1 | HapMap | HapMap | A | 0.476 | G | 0.524 | A/G |
| CHD | rs1035127 | 2 | 102386351 | 0.128 | 1 | HapMap | HapMap | A | 0.5 | G | 0.5 | A/G |
| GIH | rs1035127 | 2 | 102386351 | 0.155 | 0.821 | HapMap | HapMap | A | 0.455 | G | 0.545 | A/G |
| ASW | rs1035127 | 2 | 102386351 | 0.022 | 1 | HapMap | HapMap | A | 0.057 | G | 0.943 | A/G |
| CEU | rs1035127 | 2 | 102386351 | 0.209 | 1 | HapMap | HapMap | A | 0.204 | G | 0.796 | A/G |
| JPT | rs1035127 | 2 | 102386351 | 0.105 | 1 | HapMap | HapMap | A | 0.413 | G | 0.587 | A/G |
| LWK | rs1035127 | 2 | 102386351 | 0.032 | 0.764 | HapMap | HapMap | A | 0.15 | G | 0.85 | A/G |
| MEX | rs1035127 | 2 | 102386351 | 0.333 | 1 | HapMap | HapMap | A | 0.46 | G | 0.54 | A/G |
| MKK | rs1035127 | 2 | 102386351 | 0.125 | 0.653 | HapMap | HapMap | A | 0.175 | G | 0.825 | A/G |
| ASW | rs1035130 | 2 | 102367834 | 0.448 | 1 | HapMap | HapMap | C | 0.83 | T | 0.17 | C/T |
| CHB | rs1035130 | 2 | 102367834 | 0.038 | 0.636 | HapMap | HapMap | C | 0.639 | T | 0.361 | C/T |
| CHD | rs1035130 | 2 | 102367834 | 0.043 | 0.766 | HapMap | HapMap | C | 0.637 | T | 0.363 | C/T |
| CEU | rs1035130 | 2 | 102367834 | 0.301 | 1 | HapMap | HapMap | C | 0.723 | T | 0.277 | C/T |
| GIH | rs1035130 | 2 | 102367834 | 0.112 | 1 | HapMap | HapMap | C | 0.699 | T | 0.301 | C/T |
| JPT | rs1035130 | 2 | 102367834 | 0.167 | 1 | HapMap | HapMap | C | 0.583 | T | 0.417 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| LWK | rs1035130 | 2 | 102367834 | 0.248 | 1 | HapMap | HapMap | C | 0.928 | T | 0.072 | C/T |
| MEX | rs1035130 | 2 | 102367834 | 0.059 | 0.78 | HapMap | HapMap | C | 0.78 | T | 0.22 | C/T |
| MKK | rs1035130 | 2 | 102367834 | 0.122 | 0.902 | HapMap | HapMap | C | 0.902 | T | 0.098 | C/T |
| CEU | rs1035131 | 2 | 102229073 | 0.345 | 0.774 | HapMap | HapMap | T | 0.588 | G | 0.412 | T/G |
| CHB | rs1035131 | 2 | 102229073 | 0.211 | 0.836 | HapMap | HapMap | T | 0.315 | G | 0.685 | T/G |
| CHD | rs1035131 | 2 | 102229073 | 0.302 | 0.915 | HapMap | HapMap | T | 0.259 | G | 0.741 | T/G |
| GIH | rs1035131 | 2 | 102229073 | 0.429 | 0.95 | HapMap | HapMap | T | 0.358 | G | 0.642 | T/G |
| JPT | rs1035131 | 2 | 102229073 | 0.144 | 0.665 | HapMap | HapMap | T | 0.36 | G | 0.64 | T/G |
| MEX | rs1035131 | 2 | 102229073 | 0.091 | 0.628 | HapMap | HapMap | T | 0.62 | G | 0.38 | T/G |
| GIH | rs10439410 | 2 | 102357220 | 0.703 | 0.924 | HapMap | HapMap | G | 0.756 | T | 0.244 | G/T |
| JPT | rs10439410 | 2 | 102357220 | 0.85 | 1 | HapMap | HapMap | G | 0.831 | T | 0.169 | G/T |
| ASW | rs10439410 | 2 | 102357220 | 0.408 | 0.796 | HapMap | HapMap | G | 0.236 | T | 0.764 | G/T |
| CEU | rs10439410 | 2 | 102357220 | 0.759 | 1 | HapMap | HapMap | G | 0.482 | T | 0.518 | G/T |
| CHB | rs10439410 | 2 | 102357220 | 0.564 | 0.892 | HapMap | HapMap | G | 0.833 | T | 0.167 | G/T |
| CHD | rs10439410 | 2 | 102357220 | 0.615 | 0.874 | HapMap | HapMap | G | 0.865 | T | 0.135 | G/T |
| MEX | rs10439410 | 2 | 102357220 | 0.709 | 0.939 | HapMap | HapMap | G | 0.68 | T | 0.32 | G/T |
| MKK | rs10439410 | 2 | 102357220 | 0.278 | 0.732 | HapMap | HapMap | G | 0.273 | T | 0.727 | G/T |
| CEU | rs10469856 | 2 | 102255261 | 0.245 | 0.637 | HapMap | HapMap | A | 0.336 | T | 0.664 | A/T |
| JPT | rs10469856 | 2 | 102255261 | 0.01 | 1 | HapMap | HapMap | A | 0.035 | T | 0.965 | A/T |
| ASW | rs10490204 | 2 | 102422966 | 0.254 | 1 | HapMap | HapMap | A | 0.904 | C | 0.096 | A/C |
| LWK | rs10490204 | 2 | 102422966 | 0.056 | 1 | HapMap | HapMap | A | 0.983 | C | 0.017 | A/C |
| MEX | rs10490204 | 2 | 102422966 | 0.071 | 0.804 | HapMap | HapMap | A | 0.76 | C | 0.24 | A/C |
| MKK | rs10490204 | 2 | 102422966 | 0.023 | 0.718 | HapMap | HapMap | A | 0.969 | C | 0.031 | A/C |
| CEU | rs10490204 | 2 | 102422966 | 0.301 | 1 | HapMap | HapMap | A | 0.721 | C | 0.279 | A/C |
| CHD | rs10490204 | 2 | 102422966 | 0.041 | 0.76 | HapMap | HapMap | A | 0.641 | C | 0.359 | A/C |
| GIH | rs10490204 | 2 | 102422966 | 0.115 | 1 | HapMap | HapMap | A | 0.693 | C | 0.307 | A/C |
| JPT | rs10490204 | 2 | 102422966 | 0.173 | 1 | HapMap | HapMap | A | 0.581 | C | 0.419 | A/C |
| YRI | rs10490204 | 2 | 102422966 | 0.143 | 0.711 | HapMap | HapMap | A | 0.92 | C | 0.08 | A/C |
| ASW | rs10515921 | 2 | 102347450 | 0.022 | 1 | HapMap | HapMap | T | 0.953 | G | 0.047 | T/G |
| CEU | rs10515921 | 2 | 102347450 | 0.302 | 1 | HapMap | HapMap | T | 0.845 | G | 0.155 | T/G |
| CHB | rs10515921 | 2 | 102347450 | 0.073 | 1 | HapMap | HapMap | T | 0.994 | G | 0.006 | T/G |
| GIH | rs10515921 | 2 | 102347450 | 0.481 | 1 | HapMap | HapMap | T | 0.886 | G | 0.114 | T/G |
| LWK | rs10515921 | 2 | 102347450 | 0.007 | 1 | HapMap | HapMap | T | 0.978 | G | 0.022 | T/G |
| MEX | rs10515921 | 2 | 102347450 | 0.162 | 1 | HapMap | HapMap | T | 0.94 | G | 0.06 | T/G |
| MKK | rs10515921 | 2 | 102347450 | 0.043 | 1 | HapMap | HapMap | T | 0.944 | G | 0.056 | T/G |
| YRI | rs10515921 | 2 | 102347450 | 0.035 | 1 | HapMap | HapMap | T | 0.938 | G | 0.062 | T/G |
| ASW | rs10515922 | 2 | 102281086 | 0.031 | 1 | HapMap | HapMap | A | 0.991 | G | 0.009 | A/G |
| CHB | rs10515922 | 2 | 102281086 | 0.029 | 1 | HapMap | HapMap | A | 0.881 | G | 0.119 | A/G |
| CHD | rs10515922 | 2 | 102281086 | 0.015 | 1 | HapMap | HapMap | A | 0.894 | G | 0.106 | A/G |
| JPT | rs10515922 | 2 | 102281086 | 0.058 | 1 | HapMap | HapMap | A | 0.762 | G | 0.238 | A/G |
| LWK | rs10515922 | 2 | 102281086 | 0.018 | 1 | HapMap | HapMap | A | 0.994 | G | 0.006 | A/G |
| MEX | rs10515922 | 2 | 102281086 | 0.013 | 1 | HapMap | HapMap | A | 0.96 | G | 0.04 | A/G |
| YRI | rs11123914 | 2 | 102213164 | 0.007 | 1 | HapMap | HapMap | T | 0.032 | C | 0.968 | T/C |
| CEU | rs11123915 | 2 | 102247255 | 0.245 | 0.637 | HapMap | HapMap | G | 0.336 | T | 0.664 | G/T |
| JPT | rs11123915 | 2 | 102247255 | 0.01 | 1 | HapMap | HapMap | G | 0.041 | T | 0.959 | G/T |
| ASW | rs11123923 | 2 | 102334276 | 0.643 | 1 | HapMap | HapMap | C | 0.774 | A | 0.226 | C/A |
| CEU | rs11123923 | 2 | 102334276 | 0.414 | 1 | HapMap | HapMap | C | 0.611 | A | 0.389 | C/A |
| CHB | rs11123923 | 2 | 102334276 | 0.111 | 1 | HapMap | HapMap | C | 0.613 | A | 0.387 | C/A |
| CHD | rs11123923 | 2 | 102334276 | 0.074 | 1 | HapMap | HapMap | C | 0.619 | A | 0.381 | C/A |
| GIH | rs11123923 | 2 | 102334276 | 0.135 | 1 | HapMap | HapMap | C | 0.659 | A | 0.341 | C/A |
| JPT | rs11123923 | 2 | 102334276 | 0.21 | 1 | HapMap | HapMap | C | 0.541 | A | 0.459 | C/A |
| LWK | rs11123923 | 2 | 102334276 | 0.562 | 1 | HapMap | HapMap | C | 0.85 | A | 0.15 | C/A |
| MEX | rs11123923 | 2 | 102334276 | 0.125 | 1 | HapMap | HapMap | C | 0.73 | A | 0.27 | C/A |
| MKK | rs11123923 | 2 | 102334276 | 0.615 | 1 | HapMap | HapMap | C | 0.692 | A | 0.308 | C/A |
| YRI | rs11123923 | 2 | 102334276 | 0.466 | 1 | HapMap | HapMap | C | 0.872 | A | 0.128 | C/A |
| JPT | rs11123936 | 2 | 102534189 | 0.442 | 0.766 | HapMap | HapMap | C | 0.843 | T | 0.157 | C/T |
| CHB | rs11123936 | 2 | 102534189 | 0.385 | 0.68 | HapMap | HapMap | C | 0.863 | T | 0.137 | C/T |
| CHD | rs11123936 | 2 | 102534189 | 0.431 | 0.677 | HapMap | HapMap | C | 0.894 | T | 0.106 | C/T |
| CEU | rs11123936 | 2 | 102534189 | 0.047 | 1 | HapMap | HapMap | C | 0.929 | T | 0.071 | C/T |
| ASW | rs1135354 | 2 | 102380734 | 0.448 | 1 | HapMap | HapMap | T | 0.83 | G | 0.17 | T/G |
| CEU | rs1135354 | 2 | 102380734 | 0.301 | 1 | HapMap | HapMap | T | 0.721 | G | 0.279 | T/G |
| CHB | rs1135354 | 2 | 102380734 | 0.038 | 0.642 | HapMap | HapMap | T | 0.637 | G | 0.363 | T/G |
| CHD | rs1135354 | 2 | 102380734 | 0.041 | 0.76 | HapMap | HapMap | T | 0.641 | G | 0.359 | T/G |
| GIH | rs1135354 | 2 | 102380734 | 0.112 | 1 | HapMap | HapMap | T | 0.699 | G | 0.301 | T/G |
| JPT | rs1135354 | 2 | 102380734 | 0.173 | 1 | HapMap | HapMap | T | 0.581 | G | 0.419 | T/G |
| LWK | rs1135354 | 2 | 102380734 | 0.248 | 1 | HapMap | HapMap | T | 0.928 | G | 0.072 | T/G |
| MEX | rs1135354 | 2 | 102380734 | 0.059 | 0.78 | HapMap | HapMap | T | 0.78 | G | 0.22 | T/G |
| MKK | rs1135354 | 2 | 102380734 | 0.116 | 0.898 | HapMap | HapMap | T | 0.906 | G | 0.094 | T/G |
| MEX | rs11465597 | 2 | 102353645 | 0.021 | 1 | HapMap | HapMap | A | 0.94 | G | 0.06 | A/G |
| MKK | rs11465597 | 2 | 102353645 | 0.391 | 1 | HapMap | HapMap | A | 0.78 | G | 0.22 | A/G |
| LWK | rs11465597 | 2 | 102353645 | 0.376 | 1 | HapMap | HapMap | A | 0.894 | G | 0.106 | A/G |
| ASW | rs11465597 | 2 | 102353645 | 0.24 | 1 | HapMap | HapMap | A | 0.877 | G | 0.123 | A/G |
| CEU | rs11465597 | 2 | 102353645 | 0.056 | 1 | HapMap | HapMap | A | 0.889 | G | 0.111 | A/G |
| CHD | rs11465597 | 2 | 102353645 | 0.002 | 0.614 | HapMap | HapMap | A | 0.965 | G | 0.035 | A/G |
| GIH | rs11465597 | 2 | 102353645 | 0.018 | 1 | HapMap | HapMap | A | 0.938 | G | 0.062 | A/G |
| YRI | rs11465597 | 2 | 102353645 | 0.2 | 1 | HapMap | HapMap | A | 0.934 | G | 0.066 | A/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| ASW | rs11465598 | 2 | 102353696 | 0.055 | 1 | HapMap | HapMap | A | 0.906 | G | 0.094 | A/G |
| LWK | rs11465598 | 2 | 102353696 | 0.022 | 1 | HapMap | HapMap | A | 0.933 | G | 0.067 | A/G |
| MKK | rs11465598 | 2 | 102353696 | 0.084 | 1 | HapMap | HapMap | A | 0.897 | G | 0.103 | A/G |
| YRI | rs11465598 | 2 | 102353696 | 0.035 | 1 | HapMap | HapMap | A | 0.938 | G | 0.062 | A/G |
| MEX | rs11465635 | 2 | 102364515 | 0.004 | 1 | HapMap | HapMap | G | 0.99 | A | 0.01 | G/A |
| MKK | rs11465635 | 2 | 102364515 | 0.005 | 1 | HapMap | HapMap | G | 0.997 | A | 0.003 | G/A |
| YRI | rs11465635 | 2 | 102364515 | 0.023 | 1 | HapMap | HapMap | G | 0.996 | A | 0.004 | G/A |
| CEU | rs11465644 | 2 | 102367777 | 0.013 | 1 | HapMap | HapMap | C | 0.991 | A | 0.009 | C/A |
| CHB | rs11465644 | 2 | 102367777 | 0.002 | 1 | HapMap | HapMap | C | 0.994 | A | 0.006 | C/A |
| CHD | rs11465644 | 2 | 102367777 | 0.001 | 1 | HapMap | HapMap | C | 0.994 | A | 0.006 | C/A |
| GIH | rs11465644 | 2 | 102367777 | 0.021 | 1 | HapMap | HapMap | C | 0.994 | A | 0.006 | C/A |
| LWK | rs11465644 | 2 | 102367777 | 0.002 | 1 | HapMap | HapMap | C | 0.994 | A | 0.006 | C/A |
| MEX | rs11465644 | 2 | 102367777 | 0.004 | 1 | HapMap | HapMap | C | 0.98 | A | 0.02 | C/A |
| YRI | rs11465644 | 2 | 102367777 | 0.023 | 1 | HapMap | HapMap | C | 0.996 | A | 0.004 | C/A |
| ASW | rs11465648 | 2 | 102369872 | 0.031 | 1 | HapMap | HapMap | G | 0.99 | A | 0.01 | G/A |
| CHD | rs11465648 | 2 | 102369872 | 0.002 | 1 | HapMap | HapMap | G | 0.988 | A | 0.012 | G/A |
| GIH | rs11465648 | 2 | 102369872 | 0.023 | 1 | HapMap | HapMap | G | 0.994 | A | 0.006 | G/A |
| MEX | rs11465648 | 2 | 102369872 | 0.009 | 1 | HapMap | HapMap | G | 0.969 | A | 0.031 | G/A |
| MKK | rs11465657 | 2 | 102380153 | 0.005 | 1 | HapMap | HapMap | C | 0.997 | T | 0.003 | C/T |
| LWK | rs11465658 | 2 | 102380449 | 0.018 | 1 | HapMap | HapMap | G | 0.994 | A | 0.006 | G/A |
| YRI | rs11465658 | 2 | 102380449 | 0.023 | 1 | HapMap | HapMap | G | 0.996 | A | 0.004 | G/A |
| CEU | rs11465670 | 2 | 102400872 | 0.264 | 1 | HapMap | HapMap | T | 0.845 | C | 0.155 | T/C |
| CHB | rs11465670 | 2 | 102400872 | 0.223 | 1 | HapMap | HapMap | T | 0.976 | C | 0.024 | T/C |
| LWK | rs11465670 | 2 | 102400872 | 0.057 | 1 | HapMap | HapMap | T | 0.848 | C | 0.152 | T/C |
| MEX | rs11465670 | 2 | 102400872 | 0.128 | 1 | HapMap | HapMap | T | 0.95 | C | 0.05 | T/C |
| MKK | rs11465670 | 2 | 102400872 | 0.132 | 0.882 | HapMap | HapMap | T | 0.81 | C | 0.19 | T/C |
| CHD | rs11465670 | 2 | 102400872 | 0.093 | 0.697 | HapMap | HapMap | T | 0.976 | C | 0.024 | T/C |
| GIH | rs11465670 | 2 | 102400872 | 0.481 | 1 | HapMap | HapMap | T | 0.886 | C | 0.114 | T/C |
| JPT | rs11465670 | 2 | 102400872 | 0.185 | 1 | HapMap | HapMap | T | 0.983 | C | 0.017 | T/C |
| ASW | rs11465676 | 2 | 102402097 | 0.03 | 1 | HapMap | HapMap | T | 0.953 | C | 0.047 | T/C |
| LWK | rs11465676 | 2 | 102402097 | 0.046 | 1 | HapMap | HapMap | T | 0.872 | C | 0.128 | T/C |
| MKK | rs11465676 | 2 | 102402097 | 0.023 | 1 | HapMap | HapMap | T | 0.969 | C | 0.031 | T/C |
| ASW | rs11465684 | 2 | 102404056 | 0.038 | 1 | HapMap | HapMap | C | 0.943 | T | 0.057 | C/T |
| LWK | rs11465684 | 2 | 102404056 | 0.046 | 1 | HapMap | HapMap | C | 0.872 | T | 0.128 | C/T |
| MKK | rs11465684 | 2 | 102404056 | 0.023 | 1 | HapMap | HapMap | C | 0.969 | T | 0.031 | C/T |
| ASW | rs11465687 | 2 | 102406175 | 0.055 | 1 | HapMap | HapMap | C | 0.906 | T | 0.094 | C/T |
| LWK | rs11465687 | 2 | 102406175 | 0.06 | 1 | HapMap | HapMap | C | 0.839 | T | 0.161 | C/T |
| YRI | rs11465687 | 2 | 102406175 | 0.036 | 0.713 | HapMap | HapMap | C | 0.817 | T | 0.183 | C/T |
| CEU | rs11465699 | 2 | 102421199 | 0.047 | 1 | HapMap | HapMap | G | 0.96 | A | 0.04 | G/A |
| GIH | rs11465699 | 2 | 102421199 | 0.002 | 1 | HapMap | HapMap | G | 0.994 | A | 0.006 | G/A |
| ASW | rs11465707 | 2 | 102425454 | 0.066 | 1 | HapMap | HapMap | G | 0.972 | A | 0.028 | G/A |
| CEU | rs11465707 | 2 | 102425454 | 0.014 | 1 | HapMap | HapMap | G | 0.991 | A | 0.009 | G/A |
| MKK | rs11465707 | 2 | 102425454 | 0.013 | 1 | HapMap | HapMap | G | 0.982 | A | 0.018 | G/A |
| MEX | rs11465716 | 2 | 102428208 | 0.008 | 1 | HapMap | HapMap | G | 0.98 | A | 0.02 | G/A |
| ASW | rs11465716 | 2 | 102428208 | 0.007 | 1 | HapMap | HapMap | G | 0.991 | A | 0.009 | G/A |
| CHB | rs11465716 | 2 | 102428208 | 0.002 | 1 | HapMap | HapMap | G | 0.994 | A | 0.006 | G/A |
| GIH | rs11465716 | 2 | 102428208 | 0 | 1 | HapMap | HapMap | G | 0.994 | A | 0.006 | G/A |
| LWK | rs11465716 | 2 | 102428208 | 0.002 | 1 | HapMap | HapMap | G | 0.994 | A | 0.006 | G/A |
| YRI | rs11465716 | 2 | 102428208 | 0.004 | 1 | HapMap | HapMap | G | 0.987 | A | 0.013 | G/A |
| ASW | rs11465722 | 2 | 102429921 | 0.063 | 1 | HapMap | HapMap | C | 0.953 | T | 0.047 | C/T |
| CEU | rs11465722 | 2 | 102429921 | 0.21 | 1 | HapMap | HapMap | C | 0.881 | T | 0.119 | C/T |
| LWK | rs11465722 | 2 | 102429921 | 0.002 | 1 | HapMap | HapMap | C | 0.994 | T | 0.006 | C/T |
| MEX | rs11465722 | 2 | 102429921 | 0.196 | 1 | HapMap | HapMap | C | 0.94 | T | 0.06 | C/T |
| YRI | rs11465722 | 2 | 102429921 | 0.019 | 1 | HapMap | HapMap | C | 0.96 | T | 0.04 | C/T |
| ASW | rs11465724 | 2 | 102430287 | 0.066 | 1 | HapMap | HapMap | C | 0.972 | T | 0.028 | C/T |
| CEU | rs11465724 | 2 | 102430287 | 0.047 | 1 | HapMap | HapMap | C | 0.951 | T | 0.049 | C/T |
| GIH | rs11465724 | 2 | 102430287 | 0.002 | 1 | HapMap | HapMap | C | 0.994 | T | 0.006 | C/T |
| MEX | rs11465724 | 2 | 102430287 | 0.004 | 1 | HapMap | HapMap | C | 0.99 | T | 0.01 | C/T |
| MKK | rs11465724 | 2 | 102430287 | 0.071 | 1 | HapMap | HapMap | C | 0.951 | T | 0.049 | C/T |
| CHD | rs11465730 | 2 | 102433290 | 0.081 | 0.707 | HapMap | HapMap | A | 0.56 | G | 0.44 | A/G |
| JPT | rs11465730 | 2 | 102433290 | 0.058 | 0.65 | HapMap | HapMap | A | 0.453 | G | 0.547 | A/G |
| CEU | rs11465732 | 2 | 102434255 | 0.039 | 1 | HapMap | HapMap | C | 0.938 | T | 0.062 | C/T |
| CHB | rs11465732 | 2 | 102434255 | 0.034 | 1 | HapMap | HapMap | C | 0.857 | T | 0.143 | C/T |
| CHD | rs11465732 | 2 | 102434255 | 0.02 | 1 | HapMap | HapMap | C | 0.865 | T | 0.135 | C/T |
| GIH | rs11465732 | 2 | 102434255 | 0.013 | 1 | HapMap | HapMap | C | 0.955 | T | 0.045 | C/T |
| JPT | rs11465732 | 2 | 102434255 | 0.058 | 1 | HapMap | HapMap | C | 0.779 | T | 0.221 | C/T |
| LWK | rs11465732 | 2 | 102434255 | 0.036 | 1 | HapMap | HapMap | C | 0.989 | T | 0.011 | C/T |
| MEX | rs11465732 | 2 | 102434255 | 0.004 | 1 | HapMap | HapMap | C | 0.98 | T | 0.02 | C/T |
| MKK | rs11465732 | 2 | 102434255 | 0.005 | 1 | HapMap | HapMap | C | 0.997 | T | 0.003 | C/T |
| YRI | rs11465732 | 2 | 102434255 | 0.023 | 1 | HapMap | HapMap | C | 0.982 | T | 0.018 | C/T |
| ASW | rs11465732 | 2 | 102434255 | 0.063 | 1 | HapMap | HapMap | C | 0.981 | T | 0.019 | C/T |
| LWK | rs11465739 | 2 | 102435269 | 0.002 | 1 | HapMap | HapMap | C | 0.994 | T | 0.006 | C/T |
| MKK | rs11465739 | 2 | 102435269 | 0.005 | 1 | HapMap | HapMap | C | 0.997 | T | 0.003 | C/T |
| YRI | rs11465739 | 2 | 102435269 | 0.023 | 1 | HapMap | HapMap | C | 0.996 | T | 0.004 | C/T |
| ASW | rs11674302 | 2 | 102253560 | 0.229 | 1 | HapMap | HapMap | T | 0.726 | C | 0.274 | T/C |
| CEU | rs11674302 | 2 | 102253560 | 0.159 | 1 | HapMap | HapMap | T | 0.889 | C | 0.111 | T/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs11674302 | 2 | 102253560 | 0.366 | 0.819 | HapMap | HapMap | T | 0.911 | C | 0.089 | T/C |
| CHD | rs11674302 | 2 | 102253560 | 0.604 | 1 | HapMap | HapMap | T | 0.929 | C | 0.071 | T/C |
| GIH | rs11674302 | 2 | 102253560 | 0.283 | 0.901 | HapMap | HapMap | T | 0.915 | C | 0.085 | T/C |
| JPT | rs11674302 | 2 | 102253560 | 0.385 | 1 | HapMap | HapMap | T | 0.936 | C | 0.064 | T/C |
| LWK | rs11674302 | 2 | 102253560 | 0.069 | 0.708 | HapMap | HapMap | T | 0.694 | C | 0.306 | T/C |
| MEX | rs11674302 | 2 | 102253560 | 0.344 | 1 | HapMap | HapMap | T | 0.88 | C | 0.12 | T/C |
| MKK | rs11674302 | 2 | 102253560 | 0.33 | 0.936 | HapMap | HapMap | T | 0.656 | C | 0.344 | T/C |
| YRI | rs11674302 | 2 | 102253560 | 0.142 | 0.862 | HapMap | HapMap | T | 0.673 | C | 0.327 | T/C |
| ASW | rs11687768 | 2 | 102392170 | 0.093 | 0.648 | HapMap | HapMap | A | 0.716 | G | 0.284 | A/G |
| CEU | rs11687768 | 2 | 102392170 | 0.193 | 1 | HapMap | HapMap | A | 0.851 | G | 0.149 | A/G |
| CHB | rs11687768 | 2 | 102392170 | 0.632 | 1 | HapMap | HapMap | A | 0.916 | G | 0.084 | A/G |
| CHD | rs11687768 | 2 | 102392170 | 0.713 | 1 | HapMap | HapMap | A | 0.918 | G | 0.082 | A/G |
| GIH | rs11687768 | 2 | 102392170 | 0.22 | 0.74 | HapMap | HapMap | A | 0.903 | G | 0.097 | A/G |
| JPT | rs11687768 | 2 | 102392170 | 0.753 | 1 | HapMap | HapMap | A | 0.872 | G | 0.128 | A/G |
| MEX | rs11687768 | 2 | 102392170 | 0.364 | 0.813 | HapMap | HapMap | A | 0.82 | G | 0.18 | A/G |
| ASW | rs11688802 | 2 | 102492971 | 0.031 | 1 | HapMap | HapMap | A | 0.991 | G | 0.009 | A/G |
| CEU | rs11688802 | 2 | 102492971 | 0.039 | 1 | HapMap | HapMap | A | 0.942 | G | 0.058 | A/G |
| MEX | rs11688802 | 2 | 102492971 | 0.004 | 1 | HapMap | HapMap | A | 0.98 | G | 0.02 | A/G |
| CEU | rs11690532 | 2 | 102442858 | 0.2 | 1 | HapMap | HapMap | C | 0.809 | T | 0.191 | C/T |
| CHD | rs11690532 | 2 | 102442858 | 0.002 | 1 | HapMap | HapMap | C | 0.988 | T | 0.012 | C/T |
| MEX | rs11690532 | 2 | 102442858 | 0.017 | 0.617 | HapMap | HapMap | C | 0.885 | T | 0.115 | C/T |
| MKK | rs11690532 | 2 | 102442858 | 0.02 | 1 | HapMap | HapMap | C | 0.986 | T | 0.014 | C/T |
| ASW | rs11692065 | 2 | 102250407 | 0.124 | 1 | HapMap | HapMap | C | 0.811 | T | 0.189 | C/T |
| CEU | rs11692065 | 2 | 102250407 | 0.159 | 1 | HapMap | HapMap | C | 0.889 | T | 0.111 | C/T |
| CHB | rs11692065 | 2 | 102250407 | 0.366 | 0.819 | HapMap | HapMap | C | 0.911 | T | 0.089 | C/T |
| CHD | rs11692065 | 2 | 102250407 | 0.603 | 1 | HapMap | HapMap | C | 0.929 | T | 0.071 | C/T |
| GIH | rs11692065 | 2 | 102250407 | 0.283 | 0.901 | HapMap | HapMap | C | 0.915 | T | 0.085 | C/T |
| JPT | rs11692065 | 2 | 102250407 | 0.385 | 1 | HapMap | HapMap | C | 0.936 | T | 0.064 | C/T |
| LWK | rs11692065 | 2 | 102250407 | 0.081 | 0.818 | HapMap | HapMap | C | 0.722 | T | 0.278 | C/T |
| MEX | rs11692065 | 2 | 102250407 | 0.322 | 1 | HapMap | HapMap | C | 0.888 | T | 0.112 | C/T |
| MKK | rs11692065 | 2 | 102250407 | 0.257 | 1 | HapMap | HapMap | C | 0.738 | T | 0.262 | C/T |
| YRI | rs11692065 | 2 | 102250407 | 0.068 | 0.752 | HapMap | HapMap | C | 0.748 | T | 0.252 | C/T |
| MKK | rs11692230 | 2 | 102221497 | 0.269 | 0.675 | HapMap | HapMap | A | 0.704 | G | 0.296 | A/G |
| JPT | rs11692304 | 2 | 102461836 | 0.071 | 1 | HapMap | HapMap | G | 0.773 | A | 0.227 | G/A |
| CHD | rs11692304 | 2 | 102461836 | 0.035 | 1 | HapMap | HapMap | G | 0.782 | A | 0.218 | G/A |
| MKK | rs11693697 | 2 | 102282094 | 0.015 | 1 | HapMap | HapMap | T | 0.99 | C | 0.01 | T/C |
| MEX | rs11695455 | 2 | 102407134 | 0 | 1 | HapMap | HapMap | A | 0.99 | G | 0.01 | A/G |
| CEU | rs11886793 | 2 | 102438652 | 0.337 | 0.656 | HapMap | HapMap | T | 0.646 | G | 0.354 | T/G |
| GIH | rs11886793 | 2 | 102438652 | 0.319 | 0.685 | HapMap | HapMap | T | 0.847 | G | 0.153 | T/G |
| MEX | rs11886793 | 2 | 102438652 | 0.209 | 0.671 | HapMap | HapMap | T | 0.86 | G | 0.14 | T/G |
| ASW | rs11888547 | 2 | 102249158 | 0.031 | 1 | HapMap | HapMap | G | 0.981 | T | 0.019 | G/T |
| LWK | rs11888547 | 2 | 102249158 | 0.054 | 1 | HapMap | HapMap | G | 0.983 | T | 0.017 | G/T |
| YRI | rs11888547 | 2 | 102249158 | 0.074 | 0.711 | HapMap | HapMap | G | 0.96 | T | 0.04 | G/T |
| ASW | rs11891965 | 2 | 102386928 | 0.055 | 1 | HapMap | HapMap | C | 0.906 | T | 0.094 | C/T |
| LWK | rs11891965 | 2 | 102386928 | 0.063 | 1 | HapMap | HapMap | C | 0.833 | T | 0.167 | C/T |
| MKK | rs11891965 | 2 | 102386928 | 0.051 | 1 | HapMap | HapMap | C | 0.934 | T | 0.066 | C/T |
| YRI | rs11891965 | 2 | 102386928 | 0.038 | 0.729 | HapMap | HapMap | C | 0.819 | T | 0.181 | C/T |
| ASW | rs11900775 | 2 | 102169654 | 0.046 | 1 | HapMap | HapMap | T | 0.906 | C | 0.094 | T/C |
| CHB | rs11900775 | 2 | 102169654 | 0.073 | 1 | HapMap | HapMap | T | 0.97 | C | 0.03 | T/C |
| MKK | rs11900775 | 2 | 102169654 | 0.039 | 0.806 | HapMap | HapMap | T | 0.923 | C | 0.077 | T/C |
| CEU | rs11903354 | 2 | 102176860 | 0.076 | 0.771 | HapMap | HapMap | T | 0.915 | C | 0.085 | T/C |
| CHB | rs11903354 | 2 | 102176860 | 0.012 | 1 | HapMap | HapMap | T | 0.929 | C | 0.071 | T/C |
| GIH | rs11903354 | 2 | 102176860 | 0.021 | 1 | HapMap | HapMap | T | 0.994 | C | 0.006 | T/C |
| JPT | rs11903354 | 2 | 102176860 | 0.005 | 1 | HapMap | HapMap | T | 0.977 | C | 0.023 | T/C |
| MEX | rs11903354 | 2 | 102176860 | 0.095 | 1 | HapMap | HapMap | T | 0.97 | C | 0.03 | T/C |
| MKK | rs11903354 | 2 | 102176860 | 0.035 | 0.71 | HapMap | HapMap | T | 0.913 | C | 0.087 | T/C |
| JPT | rs12053526 | 2 | 102481372 | 0.6 | 1 | HapMap | HapMap | C | 0.872 | T | 0.128 | C/T |
| LWK | rs12053526 | 2 | 102481372 | 0.013 | 1 | HapMap | HapMap | C | 0.961 | T | 0.039 | C/T |
| MEX | rs12053526 | 2 | 102481372 | 0.031 | 1 | HapMap | HapMap | C | 0.99 | T | 0.01 | C/T |
| MKK | rs12053526 | 2 | 102481372 | 0.013 | 1 | HapMap | HapMap | C | 0.983 | T | 0.017 | C/T |
| CHD | rs12053526 | 2 | 102481372 | 0.604 | 1 | HapMap | HapMap | C | 0.929 | T | 0.071 | C/T |
| ASW | rs12053526 | 2 | 102481372 | 0.008 | 1 | HapMap | HapMap | C | 0.961 | T | 0.039 | C/T |
| CHB | rs12053526 | 2 | 102481372 | 0.546 | 1 | HapMap | HapMap | C | 0.911 | T | 0.089 | C/T |
| GIH | rs12053526 | 2 | 102481372 | 0.021 | 1 | HapMap | HapMap | C | 0.994 | T | 0.006 | C/T |
| CEU | rs12469892 | 2 | 102262216 | 0.172 | 0.882 | HapMap | HapMap | G | 0.821 | A | 0.179 | G/A |
| CHB | rs12469892 | 2 | 102262216 | 0.052 | 1 | HapMap | HapMap | G | 0.774 | A | 0.226 | G/A |
| CHD | rs12469892 | 2 | 102262216 | 0.021 | 0.714 | HapMap | HapMap | G | 0.753 | A | 0.247 | G/A |
| GIH | rs12469892 | 2 | 102262216 | 0.132 | 0.893 | HapMap | HapMap | G | 0.625 | A | 0.375 | G/A |
| MEX | rs12475055 | 2 | 102245323 | 0.123 | 0.68 | HapMap | HapMap | A | 0.58 | C | 0.42 | A/C |
| CEU | rs12475055 | 2 | 102245323 | 0.572 | 0.787 | HapMap | HapMap | A | 0.496 | C | 0.504 | A/C |
| CHB | rs12475055 | 2 | 102245323 | 0.396 | 0.776 | HapMap | HapMap | A | 0.179 | C | 0.821 | A/C |
| CHD | rs12475055 | 2 | 102245323 | 0.582 | 0.872 | HapMap | HapMap | A | 0.141 | C | 0.859 | A/C |
| GIH | rs12475055 | 2 | 102245323 | 0.436 | 0.864 | HapMap | HapMap | A | 0.312 | C | 0.688 | A/C |
| CHD | rs12712133 | 2 | 102232705 | 0.021 | 0.972 | HapMap | HapMap | A | 0.153 | G | 0.847 | A/G |
| JPT | rs12712133 | 2 | 102232705 | 0.058 | 1 | HapMap | HapMap | A | 0.233 | G | 0.767 | A/G |
| CHB | rs12712135 | 2 | 102297380 | 0.144 | 1 | HapMap | HapMap | A | 0.47 | G | 0.53 | A/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHD | rs12712135 | 2 | 102297380 | 0.131 | 1 | HapMap | HapMap | A | 0.506 | G | 0.494 | A/G |
| JPT | rs12712135 | 2 | 102297380 | 0.1 | 1 | HapMap | HapMap | A | 0.39 | G | 0.61 | A/G |
| ASW | rs12712142 | 2 | 102327016 | 0.28 | 0.66 | HapMap | HapMap | C | 0.594 | A | 0.406 | C/A |
| CEU | rs12712142 | 2 | 102327016 | 0.414 | 1 | HapMap | HapMap | C | 0.611 | A | 0.389 | C/A |
| CHB | rs12712142 | 2 | 102327016 | 0.111 | 1 | HapMap | HapMap | C | 0.613 | A | 0.387 | C/A |
| CHD | rs12712142 | 2 | 102327016 | 0.076 | 1 | HapMap | HapMap | C | 0.624 | A | 0.376 | C/A |
| GIH | rs12712142 | 2 | 102327016 | 0.132 | 1 | HapMap | HapMap | C | 0.667 | A | 0.333 | C/A |
| JPT | rs12712142 | 2 | 102327016 | 0.216 | 1 | HapMap | HapMap | C | 0.535 | A | 0.465 | C/A |
| MEX | rs12712142 | 2 | 102327016 | 0.125 | 1 | HapMap | HapMap | C | 0.73 | A | 0.27 | C/A |
| CEU | rs12712157 | 2 | 102531561 | 0.145 | 0.859 | HapMap | HapMap | T | 0.19 | C | 0.81 | T/C |
| CHB | rs12712157 | 2 | 102531561 | 0.155 | 1 | HapMap | HapMap | T | 0.518 | C | 0.482 | T/C |
| CHD | rs12712157 | 2 | 102531561 | 0.129 | 1 | HapMap | HapMap | T | 0.506 | C | 0.494 | T/C |
| JPT | rs12712157 | 2 | 102531561 | 0.111 | 1 | HapMap | HapMap | T | 0.413 | C | 0.587 | T/C |
| CHB | rs12905 | 2 | 102326439 | 0.083 | 1 | HapMap | HapMap | G | 0.649 | A | 0.351 | G/A |
| CHD | rs12905 | 2 | 102326439 | 0.065 | 1 | HapMap | HapMap | G | 0.659 | A | 0.341 | G/A |
| MKK | rs12905 | 2 | 102326439 | 0.093 | 1 | HapMap | HapMap | G | 0.937 | A | 0.063 | G/A |
| ASW | rs12905 | 2 | 102326439 | 0.361 | 1 | HapMap | HapMap | G | 0.887 | A | 0.113 | G/A |
| CEU | rs12905 | 2 | 102326439 | 0.301 | 1 | HapMap | HapMap | G | 0.721 | A | 0.279 | G/A |
| GIH | rs12905 | 2 | 102326439 | 0.097 | 1 | HapMap | HapMap | G | 0.727 | A | 0.273 | G/A |
| JPT | rs12905 | 2 | 102326439 | 0.182 | 1 | HapMap | HapMap | G | 0.57 | A | 0.43 | G/A |
| LWK | rs12905 | 2 | 102326439 | 0.129 | 1 | HapMap | HapMap | G | 0.961 | A | 0.039 | G/A |
| MEX | rs12905 | 2 | 102326439 | 0.085 | 1 | HapMap | HapMap | G | 0.796 | A | 0.204 | G/A |
| YRI | rs12905 | 2 | 102326439 | 0.2 | 1 | HapMap | HapMap | G | 0.942 | A | 0.058 | G/A |
| CEU | rs12987222 | 2 | 102180548 | 0.027 | 1 | HapMap | HapMap | G | 0.942 | T | 0.058 | G/T |
| GIH | rs12987222 | 2 | 102180548 | 0.002 | 1 | HapMap | HapMap | G | 0.994 | T | 0.006 | G/T |
| LWK | rs12987222 | 2 | 102180548 | 0.135 | 0.682 | HapMap | HapMap | G | 0.917 | T | 0.083 | G/T |
| MKK | rs12987222 | 2 | 102180548 | 0.206 | 0.941 | HapMap | HapMap | G | 0.858 | T | 0.142 | G/T |
| ASW | rs12987782 | 2 | 102304398 | 0.24 | 1 | HapMap | HapMap | G | 0.877 | A | 0.123 | G/A |
| CEU | rs12987782 | 2 | 102304398 | 0.015 | 1 | HapMap | HapMap | G | 0.929 | A | 0.071 | G/A |
| GIH | rs12987782 | 2 | 102304398 | 0.018 | 1 | HapMap | HapMap | G | 0.938 | A | 0.062 | G/A |
| LWK | rs12987782 | 2 | 102304398 | 0.398 | 1 | HapMap | HapMap | G | 0.889 | A | 0.111 | G/A |
| MEX | rs12987782 | 2 | 102304398 | 0.021 | 1 | HapMap | HapMap | G | 0.94 | A | 0.06 | G/A |
| MKK | rs12987782 | 2 | 102304398 | 0.448 | 1 | HapMap | HapMap | G | 0.755 | A | 0.245 | G/A |
| YRI | rs12987782 | 2 | 102304398 | 0.227 | 1 | HapMap | HapMap | G | 0.929 | A | 0.071 | G/A |
| CEU | rs12987900 | 2 | 102215780 | 0.04 | 1 | HapMap | HapMap | G | 0.947 | A | 0.053 | G/A |
| GIH | rs12987900 | 2 | 102215780 | 0.002 | 1 | HapMap | HapMap | G | 0.994 | A | 0.006 | G/A |
| LWK | rs12987900 | 2 | 102215780 | 0.172 | 0.72 | HapMap | HapMap | G | 0.906 | A | 0.094 | G/A |
| MKK | rs12987900 | 2 | 102215780 | 0.212 | 0.945 | HapMap | HapMap | G | 0.856 | A | 0.144 | G/A |
| CEU | rs12992518 | 2 | 102204030 | 0.04 | 1 | HapMap | HapMap | C | 0.947 | T | 0.053 | C/T |
| GIH | rs12992518 | 2 | 102204030 | 0.002 | 1 | HapMap | HapMap | C | 0.994 | T | 0.006 | C/T |
| LWK | rs12992518 | 2 | 102204030 | 0.135 | 0.682 | HapMap | HapMap | C | 0.917 | T | 0.083 | C/T |
| MKK | rs12992518 | 2 | 102204030 | 0.226 | 0.949 | HapMap | HapMap | C | 0.846 | T | 0.154 | C/T |
| CEU | rs12995644 | 2 | 102246459 | 0.04 | 1 | HapMap | HapMap | C | 0.956 | A | 0.044 | C/A |
| GIH | rs12995644 | 2 | 102246459 | 0.003 | 1 | HapMap | HapMap | C | 0.989 | A | 0.011 | C/A |
| LWK | rs12995644 | 2 | 102246459 | 0.231 | 0.893 | HapMap | HapMap | C | 0.917 | A | 0.083 | C/A |
| MKK | rs12995644 | 2 | 102246459 | 0.2 | 0.938 | HapMap | HapMap | C | 0.862 | A | 0.138 | C/A |
| YRI | rs12995644 | 2 | 102246459 | 0.152 | 0.819 | HapMap | HapMap | C | 0.925 | A | 0.075 | C/A |
| ASW | rs12998521 | 2 | 102340849 | 0.643 | 1 | HapMap | HapMap | G | 0.774 | T | 0.226 | G/T |
| CEU | rs12998521 | 2 | 102340849 | 0.414 | 1 | HapMap | HapMap | G | 0.611 | T | 0.389 | G/T |
| CHB | rs12998521 | 2 | 102340849 | 0.111 | 1 | HapMap | HapMap | G | 0.613 | T | 0.387 | G/T |
| CHD | rs12998521 | 2 | 102340849 | 0.076 | 1 | HapMap | HapMap | G | 0.624 | T | 0.376 | G/T |
| GIH | rs12998521 | 2 | 102340849 | 0.135 | 1 | HapMap | HapMap | G | 0.659 | T | 0.341 | G/T |
| JPT | rs12998521 | 2 | 102340849 | 0.191 | 1 | HapMap | HapMap | G | 0.564 | T | 0.436 | G/T |
| LWK | rs12998521 | 2 | 102340849 | 0.562 | 1 | HapMap | HapMap | G | 0.85 | T | 0.15 | G/T |
| MEX | rs12998521 | 2 | 102340849 | 0.125 | 1 | HapMap | HapMap | G | 0.73 | T | 0.27 | G/T |
| MKK | rs12998521 | 2 | 102340849 | 0.625 | 1 | HapMap | HapMap | G | 0.689 | T | 0.311 | G/T |
| YRI | rs12998521 | 2 | 102340849 | 0.499 | 1 | HapMap | HapMap | G | 0.867 | T | 0.133 | G/T |
| CEU | rs12999517 | 2 | 102325692 | 0.056 | 1 | HapMap | HapMap | T | 0.894 | C | 0.106 | T/C |
| GIH | rs12999517 | 2 | 102325692 | 0.018 | 1 | HapMap | HapMap | T | 0.938 | C | 0.062 | T/C |
| MEX | rs12999517 | 2 | 102325692 | 0.021 | 1 | HapMap | HapMap | T | 0.94 | C | 0.06 | T/C |
| CEU | rs13002972 | 2 | 102218293 | 0.04 | 1 | HapMap | HapMap | G | 0.947 | A | 0.053 | G/A |
| GIH | rs13002972 | 2 | 102218293 | 0.002 | 1 | HapMap | HapMap | G | 0.994 | A | 0.006 | G/A |
| LWK | rs13002972 | 2 | 102218293 | 0.153 | 0.702 | HapMap | HapMap | G | 0.911 | A | 0.089 | G/A |
| MKK | rs13002972 | 2 | 102218293 | 0.213 | 0.946 | HapMap | HapMap | G | 0.853 | A | 0.147 | G/A |
| GIH | rs13014084 | 2 | 102221197 | 0.002 | 1 | HapMap | HapMap | A | 0.994 | G | 0.006 | A/G |
| MKK | rs13014084 | 2 | 102221197 | 0.187 | 0.852 | HapMap | HapMap | A | 0.843 | G | 0.157 | A/G |
| ASW | rs13015714 | 2 | 102338297 | 0.202 | 1 | HapMap | HapMap | G | 0.075 | T | 0.925 | G/T |
| CEU | rs13015714 | 2 | 102338297 | 0.209 | 1 | HapMap | HapMap | G | 0.204 | T | 0.796 | G/T |
| CHB | rs13015714 | 2 | 102338297 | 0.135 | 1 | HapMap | HapMap | G | 0.47 | T | 0.53 | G/T |
| CHD | rs13015714 | 2 | 102338297 | 0.132 | 1 | HapMap | HapMap | G | 0.512 | T | 0.488 | G/T |
| GIH | rs13015714 | 2 | 102338297 | 0.225 | 1 | HapMap | HapMap | G | 0.449 | T | 0.551 | G/T |
| JPT | rs13015714 | 2 | 102338297 | 0.095 | 1 | HapMap | HapMap | G | 0.39 | T | 0.61 | G/T |
| LWK | rs13015714 | 2 | 102338297 | 0.311 | 1 | HapMap | HapMap | G | 0.089 | T | 0.911 | G/T |
| MEX | rs13015714 | 2 | 102338297 | 0.333 | 1 | HapMap | HapMap | G | 0.46 | T | 0.54 | G/T |
| MKK | rs13015714 | 2 | 102338297 | 0.174 | 1 | HapMap | HapMap | G | 0.112 | T | 0.888 | G/T |
| YRI | rs13015714 | 2 | 102338297 | 0.372 | 1 | HapMap | HapMap | G | 0.106 | T | 0.894 | G/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs13018263 | 2 | 102458702 | 0.213 | 0.63 | HapMap | HapMap | T | 0.753 | C | 0.247 | T/C |
| CHD | rs13018263 | 2 | 102458702 | 0.216 | 0.822 | HapMap | HapMap | T | 0.714 | C | 0.286 | T/C |
| JPT | rs13018263 | 2 | 102458702 | 0.263 | 0.747 | HapMap | HapMap | T | 0.735 | C | 0.265 | T/C |
| ASW | rs13018263 | 2 | 102458702 | 0.101 | 0.686 | HapMap | HapMap | T | 0.708 | C | 0.292 | T/C |
| ASW | rs13019081 | 2 | 102317254 | 0.643 | 1 | HapMap | HapMap | A | 0.774 | C | 0.226 | A/C |
| CEU | rs13019081 | 2 | 102317254 | 0.292 | 0.918 | HapMap | HapMap | A | 0.646 | C | 0.354 | A/C |
| CHB | rs13019081 | 2 | 102317254 | 0.111 | 1 | HapMap | HapMap | A | 0.607 | C | 0.393 | A/C |
| CHD | rs13019081 | 2 | 102317254 | 0.074 | 1 | HapMap | HapMap | A | 0.629 | C | 0.371 | A/C |
| GIH | rs13019081 | 2 | 102317254 | 0.095 | 0.839 | HapMap | HapMap | A | 0.659 | C | 0.341 | A/C |
| JPT | rs13019081 | 2 | 102317254 | 0.21 | 1 | HapMap | HapMap | A | 0.541 | C | 0.459 | A/C |
| LWK | rs13019081 | 2 | 102317254 | 0.538 | 1 | HapMap | HapMap | A | 0.856 | C | 0.144 | A/C |
| MEX | rs13019081 | 2 | 102317254 | 0.125 | 1 | HapMap | HapMap | A | 0.73 | C | 0.27 | A/C |
| MKK | rs13019081 | 2 | 102317254 | 0.587 | 0.957 | HapMap | HapMap | A | 0.684 | C | 0.316 | A/C |
| YRI | rs13019081 | 2 | 102317254 | 0.466 | 1 | HapMap | HapMap | A | 0.872 | C | 0.128 | A/C |
| CHD | rs13019784 | 2 | 102489733 | 0.034 | 0.607 | HapMap | HapMap | A | 0.577 | G | 0.423 | A/G |
| CEU | rs13019784 | 2 | 102489733 | 0.145 | 0.859 | HapMap | HapMap | A | 0.19 | G | 0.81 | A/G |
| ASW | rs13019803 | 2 | 102142634 | 0.054 | 0.603 | HapMap | HapMap | C | 0.774 | T | 0.226 | C/T |
| CHD | rs13019803 | 2 | 102142634 | 0.026 | 1 | HapMap | HapMap | C | 0.829 | T | 0.171 | C/T |
| GIH | rs13019803 | 2 | 102142634 | 0.044 | 1 | HapMap | HapMap | C | 0.862 | T | 0.138 | C/T |
| MEX | rs13019803 | 2 | 102142634 | 0.048 | 1 | HapMap | HapMap | C | 0.878 | T | 0.122 | C/T |
| ASW | rs13383035 | 2 | 102421766 | 0.03 | 1 | HapMap | HapMap | C | 0.943 | A | 0.057 | C/A |
| LWK | rs13383035 | 2 | 102421766 | 0.01 | 0.964 | HapMap | HapMap | C | 0.967 | A | 0.033 | C/A |
| MKK | rs13383035 | 2 | 102421766 | 0.026 | 1 | HapMap | HapMap | C | 0.965 | A | 0.035 | C/A |
| YRI | rs13383035 | 2 | 102421766 | 0.039 | 1 | HapMap | HapMap | C | 0.912 | A | 0.088 | C/A |
| ASW | rs13386900 | 2 | 102247181 | 0.102 | 1 | HapMap | HapMap | G | 0.849 | A | 0.151 | G/A |
| CHB | rs13386900 | 2 | 102247181 | 0.208 | 0.738 | HapMap | HapMap | G | 0.946 | A | 0.054 | G/A |
| CHD | rs13386900 | 2 | 102247181 | 0.444 | 1 | HapMap | HapMap | G | 0.947 | A | 0.053 | G/A |
| JPT | rs13386900 | 2 | 102247181 | 0.385 | 1 | HapMap | HapMap | G | 0.936 | A | 0.064 | G/A |
| LWK | rs13386900 | 2 | 102247181 | 0.081 | 0.818 | HapMap | HapMap | G | 0.722 | A | 0.278 | G/A |
| MEX | rs13386900 | 2 | 102247181 | 0.031 | 1 | HapMap | HapMap | G | 0.99 | A | 0.01 | G/A |
| MKK | rs13386900 | 2 | 102247181 | 0.225 | 1 | HapMap | HapMap | G | 0.762 | A | 0.238 | G/A |
| YRI | rs13386900 | 2 | 102247181 | 0.064 | 0.762 | HapMap | HapMap | G | 0.752 | A | 0.248 | G/A |
| CEU | rs13413002 | 2 | 102216915 | 0.008 | 1 | HapMap | HapMap | C | 0.987 | T | 0.013 | C/T |
| LWK | rs13413002 | 2 | 102216915 | 0.011 | 1 | HapMap | HapMap | C | 0.967 | T | 0.033 | C/T |
| MKK | rs13413002 | 2 | 102216915 | 0.032 | 1 | HapMap | HapMap | C | 0.958 | T | 0.042 | C/T |
| ASW | rs13416708 | 2 | 102265736 | 0.03 | 1 | HapMap | HapMap | G | 0.953 | A | 0.047 | G/A |
| CEU | rs13416708 | 2 | 102265736 | 0.014 | 1 | HapMap | HapMap | G | 0.996 | A | 0.004 | G/A |
| LWK | rs13416708 | 2 | 102265736 | 0.005 | 1 | HapMap | HapMap | G | 0.983 | A | 0.017 | G/A |
| MEX | rs13416708 | 2 | 102265736 | 0.031 | 1 | HapMap | HapMap | G | 0.99 | A | 0.01 | G/A |
| MKK | rs13416708 | 2 | 102265736 | 0.032 | 1 | HapMap | HapMap | G | 0.958 | A | 0.042 | G/A |
| YRI | rs13416708 | 2 | 102265736 | 0.015 | 1 | HapMap | HapMap | G | 0.956 | A | 0.044 | G/A |
| ASW | rs13431828 | 2 | 102321085 | 0.214 | 1 | HapMap | HapMap | C | 0.726 | T | 0.274 | C/T |
| CEU | rs13431828 | 2 | 102321085 | 0.159 | 1 | HapMap | HapMap | C | 0.876 | T | 0.124 | C/T |
| CHB | rs13431828 | 2 | 102321085 | 0.632 | 1 | HapMap | HapMap | C | 0.905 | T | 0.095 | C/T |
| CHD | rs13431828 | 2 | 102321085 | 0.713 | 1 | HapMap | HapMap | C | 0.917 | T | 0.083 | C/T |
| GIH | rs13431828 | 2 | 102321085 | 0.374 | 1 | HapMap | HapMap | C | 0.908 | T | 0.092 | C/T |
| JPT | rs13431828 | 2 | 102321085 | 0.753 | 1 | HapMap | HapMap | C | 0.872 | T | 0.128 | C/T |
| LWK | rs13431828 | 2 | 102321085 | 0.096 | 1 | HapMap | HapMap | C | 0.767 | T | 0.233 | C/T |
| MEX | rs13431828 | 2 | 102321085 | 0.423 | 1 | HapMap | HapMap | C | 0.86 | T | 0.14 | C/T |
| MKK | rs13431828 | 2 | 102321085 | 0.296 | 1 | HapMap | HapMap | C | 0.71 | T | 0.29 | C/T |
| YRI | rs13431828 | 2 | 102321085 | 0.216 | 1 | HapMap | HapMap | C | 0.664 | T | 0.336 | C/T |
| ASW | rs1362348 | 2 | 102351056 | 0.877 | 1 | HapMap | HapMap | C | 0.358 | G | 0.642 | C/G |
| CEU | rs1362348 | 2 | 102351056 | 1 | 1 | HapMap | HapMap | C | 0.593 | G | 0.407 | C/G |
| CHB | rs1362348 | 2 | 102351056 | 1 | 1 | HapMap | HapMap | C | 0.857 | G | 0.143 | C/G |
| CHD | rs1362348 | 2 | 102351056 | 1 | 1 | HapMap | HapMap | C | 0.888 | G | 0.112 | C/G |
| GIH | rs1362348 | 2 | 102351056 | 1 | 1 | HapMap | HapMap | C | 0.79 | G | 0.21 | C/G |
| JPT | rs1362348 | 2 | 102351056 | 1 | 1 | HapMap | HapMap | C | 0.849 | G | 0.151 | C/G |
| LWK | rs1362348 | 2 | 102351056 | 0.554 | 1 | HapMap | HapMap | C | 0.365 | G | 0.635 | C/G |
| MEX | rs1362348 | 2 | 102351056 | 1 | 1 | HapMap | HapMap | C | 0.724 | G | 0.276 | C/G |
| MKK | rs1362348 | 2 | 102351056 | 0.855 | 1 | HapMap | HapMap | C | 0.458 | G | 0.542 | C/G |
| YRI | rs1362348 | 2 | 102351056 | 0.916 | 1 | HapMap | HapMap | C | 0.284 | G | 0.716 | C/G |
| CEU | rs1403548 | 2 | 102476807 | 0.213 | 0.887 | HapMap | HapMap | C | 0.261 | T | 0.739 | C/T |
| CHB | rs1403548 | 2 | 102476807 | 0.11 | 0.657 | HapMap | HapMap | C | 0.622 | T | 0.378 | C/T |
| CHD | rs1403548 | 2 | 102476807 | 0.083 | 0.621 | HapMap | HapMap | C | 0.617 | T | 0.383 | C/T |
| GIH | rs1403548 | 2 | 102476807 | 0.059 | 0.713 | HapMap | HapMap | C | 0.295 | T | 0.705 | C/T |
| YRI | rs1403548 | 2 | 102476807 | 0.015 | 1 | HapMap | HapMap | C | 0.031 | T | 0.969 | C/T |
| ASW | rs1403548 | 2 | 102476807 | 0.063 | 1 | HapMap | HapMap | C | 0.019 | T | 0.981 | C/T |
| ASW | rs1403550 | 2 | 102502741 | 0.031 | 1 | HapMap | HapMap | T | 0.009 | C | 0.991 | T/C |
| CEU | rs1403550 | 2 | 102502741 | 0.145 | 0.859 | HapMap | HapMap | T | 0.19 | C | 0.81 | T/C |
| CHB | rs1403550 | 2 | 102502741 | 0.148 | 1 | HapMap | HapMap | T | 0.5 | C | 0.5 | T/C |
| CHD | rs1403550 | 2 | 102502741 | 0.126 | 1 | HapMap | HapMap | T | 0.5 | C | 0.5 | T/C |
| JPT | rs1403550 | 2 | 102502741 | 0.111 | 1 | HapMap | HapMap | T | 0.407 | C | 0.593 | T/C |
| YRI | rs1403550 | 2 | 102502741 | 0.011 | 1 | HapMap | HapMap | T | 0.027 | C | 0.973 | T/C |
| CEU | rs1403551 | 2 | 102502878 | 0.145 | 0.859 | HapMap | HapMap | T | 0.19 | G | 0.81 | T/G |
| CHB | rs1403551 | 2 | 102502878 | 0.148 | 1 | HapMap | HapMap | T | 0.5 | G | 0.5 | T/G |
| CHD | rs1403551 | 2 | 102502878 | 0.126 | 1 | HapMap | HapMap | T | 0.5 | G | 0.5 | T/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| JPT | rs1403551 | 2 | 102502878 | 0.111 | 1 | HapMap | HapMap | T | 0.407 | G | 0.593 | T/G |
| ASW | rs1403552 | 2 | 102455209 | 0.119 | 0.699 | HapMap | HapMap | C | 0.689 | T | 0.311 | C/T |
| CEU | rs1403552 | 2 | 102455209 | 0.193 | 1 | HapMap | HapMap | C | 0.836 | T | 0.164 | C/T |
| CHB | rs1403552 | 2 | 102455209 | 0.632 | 1 | HapMap | HapMap | C | 0.905 | T | 0.095 | C/T |
| CHD | rs1403552 | 2 | 102455209 | 0.713 | 1 | HapMap | HapMap | C | 0.918 | T | 0.082 | C/T |
| MEX | rs1403552 | 2 | 102455209 | 0.364 | 0.813 | HapMap | HapMap | C | 0.82 | T | 0.18 | C/T |
| LWK | rs1403552 | 2 | 102455209 | 0.074 | 0.67 | HapMap | HapMap | C | 0.656 | T | 0.344 | C/T |
| GIH | rs1403552 | 2 | 102455209 | 0.22 | 0.74 | HapMap | HapMap | C | 0.903 | T | 0.097 | C/T |
| JPT | rs1403552 | 2 | 102455209 | 0.753 | 1 | HapMap | HapMap | C | 0.872 | T | 0.128 | C/T |
| CEU | rs1420089 | 2 | 102304821 | 0.193 | 1 | HapMap | HapMap | T | 0.876 | C | 0.124 | T/C |
| GIH | rs1420089 | 2 | 102304821 | 0.021 | 1 | HapMap | HapMap | T | 0.994 | C | 0.006 | T/C |
| LWK | rs1420089 | 2 | 102304821 | 0.051 | 0.82 | HapMap | HapMap | T | 0.806 | C | 0.194 | T/C |
| MEX | rs1420089 | 2 | 102304821 | 0.196 | 1 | HapMap | HapMap | T | 0.94 | C | 0.06 | T/C |
| MKK | rs1420089 | 2 | 102304821 | 0.091 | 1 | HapMap | HapMap | T | 0.888 | C | 0.112 | T/C |
| YRI | rs1420089 | 2 | 102304821 | 0.023 | 0.61 | HapMap | HapMap | T | 0.796 | C | 0.204 | T/C |
| ASW | rs1420092 | 2 | 102240817 | 0.031 | 1 | HapMap | HapMap | A | 0.009 | C | 0.991 | A/C |
| CEU | rs1420092 | 2 | 102240817 | 0.047 | 1 | HapMap | HapMap | A | 0.102 | C | 0.898 | A/C |
| CHB | rs1420092 | 2 | 102240817 | 0.006 | 0.749 | HapMap | HapMap | A | 0.036 | C | 0.964 | A/C |
| GIH | rs1420092 | 2 | 102240817 | 0.019 | 0.79 | HapMap | HapMap | A | 0.102 | C | 0.898 | A/C |
| JPT | rs1420092 | 2 | 102240817 | 0.01 | 1 | HapMap | HapMap | A | 0.041 | C | 0.959 | A/C |
| MEX | rs1420092 | 2 | 102240817 | 0.021 | 1 | HapMap | HapMap | A | 0.06 | C | 0.94 | A/C |
| MKK | rs1420092 | 2 | 102240817 | 0.124 | 0.86 | HapMap | HapMap | A | 0.108 | C | 0.892 | A/C |
| YRI | rs1420092 | 2 | 102240817 | 0.004 | 1 | HapMap | HapMap | A | 0.018 | C | 0.982 | A/C |
| ASW | rs1420094 | 2 | 102382119 | 0.358 | 0.778 | HapMap | HapMap | C | 0.226 | T | 0.774 | C/T |
| CEU | rs1420094 | 2 | 102382119 | 0.759 | 1 | HapMap | HapMap | C | 0.478 | T | 0.522 | C/T |
| CHB | rs1420094 | 2 | 102382119 | 0.622 | 1 | HapMap | HapMap | C | 0.837 | T | 0.163 | C/T |
| CHD | rs1420094 | 2 | 102382119 | 0.583 | 0.873 | HapMap | HapMap | C | 0.859 | T | 0.141 | C/T |
| GIH | rs1420094 | 2 | 102382119 | 0.703 | 0.924 | HapMap | HapMap | C | 0.756 | T | 0.244 | C/T |
| JPT | rs1420094 | 2 | 102382119 | 0.92 | 1 | HapMap | HapMap | C | 0.835 | T | 0.165 | C/T |
| MEX | rs1420094 | 2 | 102382119 | 0.709 | 0.939 | HapMap | HapMap | C | 0.68 | T | 0.32 | C/T |
| MKK | rs1420094 | 2 | 102382119 | 0.278 | 0.732 | HapMap | HapMap | C | 0.273 | T | 0.727 | C/T |
| ASW | rs1420097 | 2 | 102375786 | 0.408 | 0.796 | HapMap | HapMap | C | 0.236 | G | 0.764 | C/G |
| CEU | rs1420097 | 2 | 102375786 | 0.759 | 1 | HapMap | HapMap | C | 0.478 | G | 0.522 | C/G |
| CHB | rs1420097 | 2 | 102375786 | 0.564 | 0.892 | HapMap | HapMap | C | 0.833 | G | 0.167 | C/G |
| CHD | rs1420097 | 2 | 102375786 | 0.615 | 0.874 | HapMap | HapMap | C | 0.865 | G | 0.135 | C/G |
| GIH | rs1420097 | 2 | 102375786 | 0.703 | 0.924 | HapMap | HapMap | C | 0.756 | G | 0.244 | C/G |
| JPT | rs1420097 | 2 | 102375786 | 0.85 | 1 | HapMap | HapMap | C | 0.831 | G | 0.169 | C/G |
| MEX | rs1420097 | 2 | 102375786 | 0.709 | 0.939 | HapMap | HapMap | C | 0.68 | G | 0.32 | C/G |
| MKK | rs1420097 | 2 | 102375786 | 0.278 | 0.732 | HapMap | HapMap | C | 0.273 | G | 0.727 | C/G |
| ASW | rs1420101 | 2 | 102324148 | 0.28 | 0.66 | HapMap | HapMap | C | 0.594 | T | 0.406 | C/T |
| CEU | rs1420101 | 2 | 102324148 | 0.331 | 1 | HapMap | HapMap | C | 0.65 | T | 0.35 | C/T |
| CHB | rs1420101 | 2 | 102324148 | 0.113 | 1 | HapMap | HapMap | C | 0.614 | T | 0.386 | C/T |
| CHD | rs1420101 | 2 | 102324148 | 0.077 | 1 | HapMap | HapMap | C | 0.625 | T | 0.375 | C/T |
| GIH | rs1420101 | 2 | 102324148 | 0.132 | 1 | HapMap | HapMap | C | 0.665 | T | 0.335 | C/T |
| JPT | rs1420101 | 2 | 102324148 | 0.21 | 1 | HapMap | HapMap | C | 0.535 | T | 0.465 | C/T |
| MEX | rs1420101 | 2 | 102324148 | 0.125 | 1 | HapMap | HapMap | C | 0.73 | T | 0.27 | C/T |
| CHD | rs1420105 | 2 | 102401551 | 0.619 | 0.862 | HapMap | HapMap | T | 0.88 | C | 0.12 | T/C |
| GIH | rs1420105 | 2 | 102401551 | 0.68 | 0.923 | HapMap | HapMap | T | 0.75 | C | 0.25 | T/C |
| CHB | rs1420105 | 2 | 102401551 | 0.564 | 0.892 | HapMap | HapMap | T | 0.833 | C | 0.167 | T/C |
| ASW | rs1420105 | 2 | 102401551 | 0.358 | 0.778 | HapMap | HapMap | T | 0.226 | C | 0.774 | T/C |
| CEU | rs1420105 | 2 | 102401551 | 0.754 | 1 | HapMap | HapMap | T | 0.482 | C | 0.518 | T/C |
| JPT | rs1420105 | 2 | 102401551 | 0.85 | 1 | HapMap | HapMap | T | 0.831 | C | 0.169 | T/C |
| MEX | rs1420105 | 2 | 102401551 | 0.692 | 0.934 | HapMap | HapMap | T | 0.688 | C | 0.312 | T/C |
| MKK | rs1420105 | 2 | 102401551 | 0.223 | 0.699 | HapMap | HapMap | T | 0.248 | C | 0.752 | T/C |
| CEU | rs1420106 | 2 | 102401476 | 0.209 | 1 | HapMap | HapMap | A | 0.205 | G | 0.795 | A/G |
| CHB | rs1420106 | 2 | 102401476 | 0.141 | 1 | HapMap | HapMap | A | 0.482 | G | 0.518 | A/G |
| CHD | rs1420106 | 2 | 102401476 | 0.122 | 1 | HapMap | HapMap | A | 0.5 | G | 0.5 | A/G |
| GIH | rs1420106 | 2 | 102401476 | 0.149 | 0.816 | HapMap | HapMap | A | 0.449 | G | 0.551 | A/G |
| JPT | rs1420106 | 2 | 102401476 | 0.105 | 1 | HapMap | HapMap | A | 0.405 | G | 0.595 | A/G |
| LWK | rs1420106 | 2 | 102401476 | 0.034 | 0.806 | HapMap | HapMap | A | 0.149 | G | 0.851 | A/G |
| MEX | rs1420106 | 2 | 102401476 | 0.333 | 1 | HapMap | HapMap | A | 0.458 | G | 0.542 | A/G |
| MKK | rs1420106 | 2 | 102401476 | 0.128 | 0.701 | HapMap | HapMap | A | 0.16 | G | 0.84 | A/G |
| CEU | rs1523196 | 2 | 102530132 | 0.245 | 1 | HapMap | HapMap | T | 0.867 | G | 0.133 | T/G |
| CHB | rs1523196 | 2 | 102530132 | 0.147 | 1 | HapMap | HapMap | T | 0.988 | G | 0.012 | T/G |
| JPT | rs1523196 | 2 | 102530132 | 0.122 | 1 | HapMap | HapMap | T | 0.983 | G | 0.017 | T/G |
| LWK | rs1523196 | 2 | 102530132 | 0.044 | 1 | HapMap | HapMap | T | 0.878 | G | 0.122 | T/G |
| MKK | rs1523196 | 2 | 102530132 | 0.088 | 1 | HapMap | HapMap | T | 0.892 | G | 0.108 | T/G |
| ASW | rs1523198 | 2 | 102464906 | 0.063 | 1 | HapMap | HapMap | C | 0.019 | T | 0.981 | C/T |
| CEU | rs1523198 | 2 | 102464906 | 0.273 | 1 | HapMap | HapMap | C | 0.265 | T | 0.735 | C/T |
| CHB | rs1523198 | 2 | 102464906 | 0.132 | 0.677 | HapMap | HapMap | C | 0.643 | T | 0.357 | C/T |
| CHD | rs1523198 | 2 | 102464906 | 0.133 | 0.768 | HapMap | HapMap | C | 0.641 | T | 0.359 | C/T |
| GIH | rs1523198 | 2 | 102464906 | 0.059 | 0.713 | HapMap | HapMap | C | 0.295 | T | 0.705 | C/T |
| JPT | rs1523198 | 2 | 102464906 | 0.102 | 0.604 | HapMap | HapMap | C | 0.605 | T | 0.395 | C/T |
| LWK | rs1523198 | 2 | 102464906 | 0.129 | 1 | HapMap | HapMap | C | 0.039 | T | 0.961 | C/T |
| MKK | rs1523198 | 2 | 102464906 | 0.063 | 0.761 | HapMap | HapMap | C | 0.073 | T | 0.927 | C/T |
| YRI | rs1523198 | 2 | 102464906 | 0.071 | 1 | HapMap | HapMap | C | 0.027 | T | 0.973 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHD | rs1558625 | 2 | 102228596 | 0.021 | 0.972 | HapMap | HapMap | A | 0.153 | G | 0.847 | A/G |
| JPT | rs1558625 | 2 | 102228596 | 0.058 | 1 | HapMap | HapMap | A | 0.233 | G | 0.767 | A/G |
| YRI | rs1558625 | 2 | 102228596 | 0.033 | 0.705 | HapMap | HapMap | A | 0.181 | G | 0.819 | A/G |
| ASW | rs1558646 | 2 | 102179710 | 0.103 | 0.712 | HapMap | HapMap | G | 0.915 | A | 0.085 | G/A |
| JPT | rs1558653 | 2 | 102507155 | 0.456 | 0.751 | HapMap | HapMap | C | 0.847 | T | 0.153 | C/T |
| CHD | rs1558653 | 2 | 102507155 | 0.431 | 0.677 | HapMap | HapMap | C | 0.894 | T | 0.106 | C/T |
| CHB | rs1558653 | 2 | 102507155 | 0.385 | 0.68 | HapMap | HapMap | C | 0.861 | T | 0.139 | C/T |
| CEU | rs1558653 | 2 | 102507155 | 0.047 | 1 | HapMap | HapMap | C | 0.929 | T | 0.071 | C/T |
| LWK | rs17026782 | 2 | 102183509 | 0.036 | 1 | HapMap | HapMap | A | 0.989 | G | 0.011 | A/G |
| MKK | rs17026782 | 2 | 102183509 | 0.04 | 1 | HapMap | HapMap | A | 0.972 | G | 0.028 | A/G |
| YRI | rs17026782 | 2 | 102183509 | 0.023 | 1 | HapMap | HapMap | A | 0.996 | G | 0.004 | A/G |
| ASW | rs17026974 | 2 | 102318792 | 0.319 | 1 | HapMap | HapMap | G | 0.896 | A | 0.104 | G/A |
| CEU | rs17026974 | 2 | 102318792 | 0.301 | 1 | HapMap | HapMap | G | 0.721 | A | 0.279 | G/A |
| CHB | rs17026974 | 2 | 102318792 | 0.083 | 1 | HapMap | HapMap | G | 0.649 | A | 0.351 | G/A |
| CHD | rs17026974 | 2 | 102318792 | 0.065 | 1 | HapMap | HapMap | G | 0.659 | A | 0.341 | G/A |
| GIH | rs17026974 | 2 | 102318792 | 0.097 | 1 | HapMap | HapMap | G | 0.727 | A | 0.273 | G/A |
| JPT | rs17026974 | 2 | 102318792 | 0.182 | 1 | HapMap | HapMap | G | 0.57 | A | 0.43 | G/A |
| LWK | rs17026974 | 2 | 102318792 | 0.072 | 1 | HapMap | HapMap | G | 0.978 | A | 0.022 | G/A |
| MEX | rs17026974 | 2 | 102318792 | 0.091 | 1 | HapMap | HapMap | G | 0.79 | A | 0.21 | G/A |
| MKK | rs17026974 | 2 | 102318792 | 0.071 | 1 | HapMap | HapMap | G | 0.951 | A | 0.049 | G/A |
| YRI | rs17026974 | 2 | 102318792 | 0.2 | 1 | HapMap | HapMap | G | 0.942 | A | 0.058 | G/A |
| ASW | rs17027006 | 2 | 102331764 | 0.361 | 1 | HapMap | HapMap | G | 0.887 | C | 0.113 | G/C |
| CEU | rs17027006 | 2 | 102331764 | 0.287 | 1 | HapMap | HapMap | G | 0.726 | C | 0.274 | G/C |
| CHB | rs17027006 | 2 | 102331764 | 0.091 | 1 | HapMap | HapMap | G | 0.643 | C | 0.357 | G/C |
| CHD | rs17027006 | 2 | 102331764 | 0.065 | 1 | HapMap | HapMap | G | 0.659 | C | 0.341 | G/C |
| GIH | rs17027006 | 2 | 102331764 | 0.097 | 1 | HapMap | HapMap | G | 0.727 | C | 0.273 | G/C |
| JPT | rs17027006 | 2 | 102331764 | 0.182 | 1 | HapMap | HapMap | G | 0.576 | C | 0.424 | G/C |
| LWK | rs17027006 | 2 | 102331764 | 0.129 | 1 | HapMap | HapMap | G | 0.961 | C | 0.039 | G/C |
| MEX | rs17027006 | 2 | 102331764 | 0.091 | 1 | HapMap | HapMap | G | 0.79 | C | 0.21 | G/C |
| MKK | rs17027006 | 2 | 102331764 | 0.093 | 1 | HapMap | HapMap | G | 0.937 | C | 0.063 | G/C |
| YRI | rs17027006 | 2 | 102331764 | 0.2 | 1 | HapMap | HapMap | G | 0.942 | C | 0.058 | G/C |
| ASW | rs17027056 | 2 | 102373483 | 0.031 | 1 | HapMap | HapMap | C | 0.991 | T | 0.009 | C/T |
| MEX | rs17027056 | 2 | 102373483 | 0.008 | 1 | HapMap | HapMap | C | 0.96 | T | 0.04 | C/T |
| CEU | rs17027056 | 2 | 102373483 | 0.039 | 1 | HapMap | HapMap | C | 0.942 | T | 0.058 | C/T |
| CHB | rs17027056 | 2 | 102373483 | 0.032 | 1 | HapMap | HapMap | C | 0.863 | T | 0.137 | C/T |
| CHD | rs17027056 | 2 | 102373483 | 0.02 | 1 | HapMap | HapMap | C | 0.865 | T | 0.135 | C/T |
| GIH | rs17027056 | 2 | 102373483 | 0.011 | 1 | HapMap | HapMap | C | 0.96 | T | 0.04 | C/T |
| JPT | rs17027056 | 2 | 102373483 | 0.058 | 1 | HapMap | HapMap | C | 0.773 | T | 0.227 | C/T |
| ASW | rs17027087 | 2 | 102382350 | 0.448 | 1 | HapMap | HapMap | C | 0.83 | T | 0.17 | C/T |
| CEU | rs17027087 | 2 | 102382350 | 0.301 | 1 | HapMap | HapMap | C | 0.721 | T | 0.279 | C/T |
| LWK | rs17027087 | 2 | 102382350 | 0.248 | 1 | HapMap | HapMap | C | 0.928 | T | 0.072 | C/T |
| MEX | rs17027087 | 2 | 102382350 | 0.059 | 0.78 | HapMap | HapMap | C | 0.78 | T | 0.22 | C/T |
| MKK | rs17027087 | 2 | 102382350 | 0.102 | 0.809 | HapMap | HapMap | C | 0.899 | T | 0.101 | C/T |
| CHB | rs17027087 | 2 | 102382350 | 0.033 | 0.62 | HapMap | HapMap | C | 0.643 | T | 0.357 | C/T |
| CHD | rs17027087 | 2 | 102382350 | 0.043 | 0.766 | HapMap | HapMap | C | 0.637 | T | 0.363 | C/T |
| GIH | rs17027087 | 2 | 102382350 | 0.112 | 1 | HapMap | HapMap | C | 0.699 | T | 0.301 | C/T |
| JPT | rs17027087 | 2 | 102382350 | 0.173 | 1 | HapMap | HapMap | C | 0.581 | T | 0.419 | C/T |
| CEU | rs17027166 | 2 | 102421852 | 0.301 | 1 | HapMap | HapMap | G | 0.721 | A | 0.279 | G/A |
| CHB | rs17027166 | 2 | 102421852 | 0.033 | 0.62 | HapMap | HapMap | G | 0.643 | A | 0.357 | G/A |
| CHD | rs17027166 | 2 | 102421852 | 0.043 | 0.764 | HapMap | HapMap | G | 0.639 | A | 0.361 | G/A |
| GIH | rs17027166 | 2 | 102421852 | 0.112 | 1 | HapMap | HapMap | G | 0.698 | A | 0.302 | G/A |
| JPT | rs17027166 | 2 | 102421852 | 0.173 | 1 | HapMap | HapMap | G | 0.581 | A | 0.419 | G/A |
| MEX | rs17027166 | 2 | 102421852 | 0.071 | 0.804 | HapMap | HapMap | G | 0.76 | A | 0.24 | G/A |
| CHD | rs17027173 | 2 | 102423475 | 0.093 | 0.697 | HapMap | HapMap | G | 0.976 | A | 0.024 | G/A |
| GIH | rs17027173 | 2 | 102423475 | 0.469 | 0.936 | HapMap | HapMap | G | 0.875 | A | 0.125 | G/A |
| JPT | rs17027173 | 2 | 102423475 | 0.185 | 1 | HapMap | HapMap | G | 0.983 | A | 0.017 | G/A |
| LWK | rs17027173 | 2 | 102423475 | 0.063 | 1 | HapMap | HapMap | G | 0.831 | A | 0.169 | G/A |
| MEX | rs17027173 | 2 | 102423475 | 0.344 | 1 | HapMap | HapMap | G | 0.89 | A | 0.11 | G/A |
| MKK | rs17027173 | 2 | 102423475 | 0.14 | 0.881 | HapMap | HapMap | G | 0.806 | A | 0.194 | G/A |
| YRI | rs17027173 | 2 | 102423475 | 0.042 | 0.617 | HapMap | HapMap | G | 0.792 | A | 0.208 | G/A |
| CEU | rs17027173 | 2 | 102423475 | 0.592 | 1 | HapMap | HapMap | G | 0.728 | A | 0.272 | G/A |
| CHB | rs17027173 | 2 | 102423475 | 0.223 | 1 | HapMap | HapMap | G | 0.976 | A | 0.024 | G/A |
| CHB | rs17027255 | 2 | 102456559 | 0.033 | 0.62 | HapMap | HapMap | C | 0.643 | T | 0.357 | C/T |
| CHD | rs17027255 | 2 | 102456559 | 0.039 | 0.752 | HapMap | HapMap | C | 0.647 | T | 0.353 | C/T |
| GIH | rs17027255 | 2 | 102456559 | 0.115 | 1 | HapMap | HapMap | C | 0.693 | T | 0.307 | C/T |
| JPT | rs17027255 | 2 | 102456559 | 0.173 | 1 | HapMap | HapMap | C | 0.581 | T | 0.419 | C/T |
| MEX | rs17027255 | 2 | 102456559 | 0.071 | 0.804 | HapMap | HapMap | C | 0.76 | T | 0.24 | C/T |
| CEU | rs17027255 | 2 | 102456559 | 0.301 | 1 | HapMap | HapMap | C | 0.712 | T | 0.288 | C/T |
| MKK | rs17027275 | 2 | 102461819 | 0.005 | 1 | HapMap | HapMap | G | 0.993 | A | 0.007 | G/A |
| ASW | rs17027275 | 2 | 102461819 | 0.038 | 1 | HapMap | HapMap | G | 0.934 | A | 0.066 | G/A |
| CHB | rs17027275 | 2 | 102461819 | 0.002 | 1 | HapMap | HapMap | G | 0.994 | A | 0.006 | G/A |
| GIH | rs17027275 | 2 | 102461819 | 0 | 1 | HapMap | HapMap | G | 0.994 | A | 0.006 | G/A |
| LWK | rs17027275 | 2 | 102461819 | 0.007 | 1 | HapMap | HapMap | G | 0.978 | A | 0.022 | G/A |
| YRI | rs17027275 | 2 | 102461819 | 0.015 | 1 | HapMap | HapMap | G | 0.951 | A | 0.049 | G/A |
| CEU | rs17027293 | 2 | 102465272 | 0.047 | 1 | HapMap | HapMap | A | 0.934 | G | 0.066 | A/G |
| MEX | rs17027293 | 2 | 102465272 | 0.017 | 1 | HapMap | HapMap | A | 0.96 | G | 0.04 | A/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHD | rs17027293 | 2 | 102465272 | 0.002 | 0.614 | HapMap | HapMap | A | 0.965 | G | 0.035 | A/G |
| GIH | rs17027293 | 2 | 102465272 | 0.01 | 1 | HapMap | HapMap | A | 0.966 | G | 0.034 | A/G |
| JPT | rs17027293 | 2 | 102465272 | 0.005 | 1 | HapMap | HapMap | A | 0.977 | G | 0.023 | A/G |
| GIH | rs17027295 | 2 | 102465303 | 0.01 | 1 | HapMap | HapMap | G | 0.966 | A | 0.034 | G/A |
| JPT | rs17027295 | 2 | 102465303 | 0.005 | 1 | HapMap | HapMap | G | 0.977 | A | 0.023 | G/A |
| MEX | rs17027295 | 2 | 102465303 | 0.017 | 1 | HapMap | HapMap | G | 0.96 | A | 0.04 | G/A |
| CEU | rs17027295 | 2 | 102465303 | 0.047 | 1 | HapMap | HapMap | G | 0.929 | A | 0.071 | G/A |
| CHD | rs17027295 | 2 | 102465303 | 0.002 | 0.614 | HapMap | HapMap | G | 0.965 | A | 0.035 | G/A |
| LWK | rs17027341 | 2 | 102502991 | 0.053 | 1 | HapMap | HapMap | T | 0.856 | C | 0.144 | T/C |
| MKK | rs17027341 | 2 | 102502991 | 0.096 | 0.905 | HapMap | HapMap | T | 0.86 | C | 0.14 | T/C |
| JPT | rs17027341 | 2 | 102502991 | 0.122 | 1 | HapMap | HapMap | T | 0.983 | C | 0.017 | T/C |
| CEU | rs17027341 | 2 | 102502991 | 0.245 | 1 | HapMap | HapMap | T | 0.863 | C | 0.137 | T/C |
| CHB | rs17027341 | 2 | 102502991 | 0.147 | 1 | HapMap | HapMap | T | 0.988 | C | 0.012 | T/C |
| MKK | rs17027347 | 2 | 102504736 | 0.014 | 0.639 | HapMap | HapMap | G | 0.976 | A | 0.024 | G/A |
| YRI | rs17027347 | 2 | 102504736 | 0.015 | 1 | HapMap | HapMap | G | 0.951 | A | 0.049 | G/A |
| ASW | rs17027347 | 2 | 102504736 | 0.038 | 1 | HapMap | HapMap | G | 0.934 | A | 0.066 | G/A |
| CEU | rs17027413 | 2 | 102520099 | 0.245 | 1 | HapMap | HapMap | C | 0.865 | T | 0.135 | C/T |
| CHB | rs17027413 | 2 | 102520099 | 0.147 | 1 | HapMap | HapMap | C | 0.988 | T | 0.012 | C/T |
| LWK | rs17027413 | 2 | 102520099 | 0.046 | 1 | HapMap | HapMap | C | 0.872 | T | 0.128 | C/T |
| MKK | rs17027413 | 2 | 102520099 | 0.045 | 0.617 | HapMap | HapMap | C | 0.862 | T | 0.138 | C/T |
| CEU | rs17027442 | 2 | 102531380 | 0.245 | 1 | HapMap | HapMap | C | 0.867 | T | 0.133 | C/T |
| CHB | rs17027442 | 2 | 102531380 | 0.147 | 1 | HapMap | HapMap | C | 0.988 | T | 0.012 | C/T |
| JPT | rs17027442 | 2 | 102531380 | 0.122 | 1 | HapMap | HapMap | C | 0.983 | T | 0.017 | C/T |
| MKK | rs17027442 | 2 | 102531380 | 0.089 | 1 | HapMap | HapMap | C | 0.89 | T | 0.11 | C/T |
| MEX | rs17637748 | 2 | 102208147 | 0.226 | 0.629 | HapMap | HapMap | A | 0.39 | G | 0.61 | A/G |
| LWK | rs17651485 | 2 | 102368082 | 0.19 | 0.799 | HapMap | HapMap | C | 0.916 | T | 0.084 | C/T |
| MKK | rs17651485 | 2 | 102368082 | 0.15 | 1 | HapMap | HapMap | C | 0.902 | T | 0.098 | C/T |
| CEU | rs17651485 | 2 | 102368082 | 0.056 | 1 | HapMap | HapMap | C | 0.919 | T | 0.081 | C/T |
| CHD | rs17651485 | 2 | 102368082 | 0.004 | 1 | HapMap | HapMap | C | 0.971 | T | 0.029 | C/T |
| GIH | rs17651485 | 2 | 102368082 | 0.008 | 1 | HapMap | HapMap | C | 0.972 | T | 0.028 | C/T |
| JPT | rs17651485 | 2 | 102368082 | 0.005 | 1 | HapMap | HapMap | C | 0.977 | T | 0.023 | C/T |
| YRI | rs17651485 | 2 | 102368082 | 0.036 | 0.609 | HapMap | HapMap | C | 0.973 | T | 0.027 | C/T |
| CHD | rs17772203 | 2 | 102482292 | 0.002 | 0.637 | HapMap | HapMap | C | 0.964 | G | 0.036 | C/G |
| LWK | rs17772203 | 2 | 102482292 | 0.021 | 0.827 | HapMap | HapMap | C | 0.911 | G | 0.089 | C/G |
| YRI | rs17772203 | 2 | 102482292 | 0.053 | 1 | HapMap | HapMap | C | 0.907 | G | 0.093 | C/G |
| JPT | rs17772203 | 2 | 102482292 | 0.005 | 1 | HapMap | HapMap | C | 0.977 | G | 0.023 | C/G |
| CEU | rs17772203 | 2 | 102482292 | 0.048 | 1 | HapMap | HapMap | C | 0.933 | G | 0.067 | C/G |
| JPT | rs1829849 | 2 | 102516130 | 0.05 | 0.62 | HapMap | HapMap | A | 0.429 | C | 0.571 | A/C |
| CHB | rs1829849 | 2 | 102516130 | 0.17 | 1 | HapMap | HapMap | A | 0.531 | C | 0.469 | A/C |
| CHD | rs1829849 | 2 | 102516130 | 0.086 | 0.776 | HapMap | HapMap | A | 0.554 | C | 0.446 | A/C |
| ASW | rs1921622 | 2 | 102332499 | 0.569 | 0.838 | HapMap | HapMap | G | 0.726 | A | 0.274 | G/A |
| JPT | rs1921622 | 2 | 102332499 | 0.097 | 0.634 | HapMap | HapMap | G | 0.517 | A | 0.483 | G/A |
| LWK | rs1921622 | 2 | 102332499 | 0.376 | 0.728 | HapMap | HapMap | G | 0.818 | A | 0.182 | G/A |
| MKK | rs1921622 | 2 | 102332499 | 0.46 | 0.763 | HapMap | HapMap | G | 0.636 | A | 0.364 | G/A |
| CEU | rs1946131 | 2 | 102328361 | 0.056 | 1 | HapMap | HapMap | C | 0.889 | T | 0.111 | C/T |
| CHD | rs1946131 | 2 | 102328361 | 0.002 | 0.614 | HapMap | HapMap | C | 0.965 | T | 0.035 | C/T |
| GIH | rs1946131 | 2 | 102328361 | 0.018 | 1 | HapMap | HapMap | C | 0.938 | T | 0.062 | C/T |
| MEX | rs1946131 | 2 | 102328361 | 0.021 | 1 | HapMap | HapMap | C | 0.94 | T | 0.06 | C/T |
| MKK | rs1946131 | 2 | 102328361 | 0.267 | 0.682 | HapMap | HapMap | C | 0.706 | T | 0.294 | C/T |
| ASW | rs1997502 | 2 | 102210681 | 0.014 | 0.992 | HapMap | HapMap | A | 0.019 | G | 0.981 | A/G |
| LWK | rs1997502 | 2 | 102210681 | 0.018 | 1 | HapMap | HapMap | A | 0.006 | G | 0.994 | A/G |
| YRI | rs1997502 | 2 | 102210681 | 0.071 | 1 | HapMap | HapMap | A | 0.018 | G | 0.982 | A/G |
| CEU | rs1997503 | 2 | 102175667 | 0.076 | 0.771 | HapMap | HapMap | C | 0.903 | T | 0.097 | C/T |
| CHB | rs1997503 | 2 | 102175667 | 0.012 | 1 | HapMap | HapMap | C | 0.929 | T | 0.071 | C/T |
| GIH | rs1997503 | 2 | 102175667 | 0.021 | 1 | HapMap | HapMap | C | 0.994 | T | 0.006 | C/T |
| JPT | rs1997503 | 2 | 102175667 | 0.005 | 1 | HapMap | HapMap | C | 0.977 | T | 0.023 | C/T |
| LWK | rs1997503 | 2 | 102175667 | 0.03 | 0.652 | HapMap | HapMap | C | 0.817 | T | 0.183 | C/T |
| MKK | rs1997503 | 2 | 102175667 | 0.057 | 1 | HapMap | HapMap | C | 0.926 | T | 0.074 | C/T |
| YRI | rs1997503 | 2 | 102175667 | 0.053 | 1 | HapMap | HapMap | C | 0.853 | T | 0.147 | C/T |
| CHD | rs2008157 | 2 | 102515614 | 0.098 | 0.814 | HapMap | HapMap | A | 0.541 | G | 0.459 | A/G |
| CHB | rs2008157 | 2 | 102515614 | 0.17 | 1 | HapMap | HapMap | A | 0.53 | G | 0.47 | A/G |
| JPT | rs2008157 | 2 | 102515614 | 0.05 | 0.62 | HapMap | HapMap | A | 0.436 | G | 0.564 | A/G |
| CHB | rs2008159 | 2 | 102515594 | 0.17 | 1 | HapMap | HapMap | A | 0.53 | G | 0.47 | A/G |
| JPT | rs2008159 | 2 | 102515594 | 0.05 | 0.62 | HapMap | HapMap | A | 0.436 | G | 0.564 | A/G |
| CHD | rs2008159 | 2 | 102515594 | 0.098 | 0.814 | HapMap | HapMap | A | 0.541 | G | 0.459 | A/G |
| JPT | rs2015478 | 2 | 102507879 | 0.05 | 0.62 | HapMap | HapMap | A | 0.436 | G | 0.564 | A/G |
| CHB | rs2015478 | 2 | 102507879 | 0.17 | 1 | HapMap | HapMap | A | 0.53 | G | 0.47 | A/G |
| CHD | rs2015478 | 2 | 102507879 | 0.098 | 0.814 | HapMap | HapMap | A | 0.541 | G | 0.459 | A/G |
| GIH | rs2041739 | 2 | 102360765 | 0.703 | 0.924 | HapMap | HapMap | C | 0.756 | T | 0.244 | C/T |
| JPT | rs2041739 | 2 | 102360765 | 0.85 | 1 | HapMap | HapMap | C | 0.831 | T | 0.169 | C/T |
| MEX | rs2041739 | 2 | 102360765 | 0.709 | 0.939 | HapMap | HapMap | C | 0.68 | T | 0.32 | C/T |
| MKK | rs2041739 | 2 | 102360765 | 0.278 | 0.732 | HapMap | HapMap | C | 0.273 | T | 0.727 | C/T |
| ASW | rs2041739 | 2 | 102360765 | 0.408 | 0.796 | HapMap | HapMap | C | 0.236 | T | 0.764 | C/T |
| CEU | rs2041739 | 2 | 102360765 | 0.759 | 1 | HapMap | HapMap | C | 0.482 | T | 0.518 | C/T |
| CHB | rs2041739 | 2 | 102360765 | 0.564 | 0.892 | HapMap | HapMap | C | 0.831 | T | 0.169 | C/T |
| CHD | rs2041739 | 2 | 102360765 | 0.615 | 0.874 | HapMap | HapMap | C | 0.865 | T | 0.135 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| ASW | rs2041756 | 2 | 102416342 | 0.022 | 1 | HapMap | HapMap | A | 0.038 | G | 0.962 | A/G |
| CEU | rs2041756 | 2 | 102416342 | 0.209 | 1 | HapMap | HapMap | A | 0.204 | G | 0.796 | A/G |
| CHB | rs2041756 | 2 | 102416342 | 0.141 | 1 | HapMap | HapMap | A | 0.476 | G | 0.524 | A/G |
| CHD | rs2041756 | 2 | 102416342 | 0.129 | 1 | HapMap | HapMap | A | 0.506 | G | 0.494 | A/G |
| GIH | rs2041756 | 2 | 102416342 | 0.141 | 0.803 | HapMap | HapMap | A | 0.443 | G | 0.557 | A/G |
| JPT | rs2041756 | 2 | 102416342 | 0.105 | 1 | HapMap | HapMap | A | 0.413 | G | 0.587 | A/G |
| LWK | rs2041756 | 2 | 102416342 | 0.053 | 1 | HapMap | HapMap | A | 0.144 | G | 0.856 | A/G |
| MEX | rs2041756 | 2 | 102416342 | 0.304 | 1 | HapMap | HapMap | A | 0.44 | G | 0.56 | A/G |
| MKK | rs2041756 | 2 | 102416342 | 0.118 | 0.643 | HapMap | HapMap | A | 0.171 | G | 0.829 | A/G |
| YRI | rs2041756 | 2 | 102416342 | 0.048 | 0.626 | HapMap | HapMap | A | 0.049 | G | 0.951 | A/G |
| CEU | rs2058659 | 2 | 102420988 | 0.759 | 1 | HapMap | HapMap | G | 0.482 | A | 0.518 | G/A |
| CHB | rs2058659 | 2 | 102420988 | 0.564 | 0.892 | HapMap | HapMap | G | 0.837 | A | 0.163 | G/A |
| CHD | rs2058659 | 2 | 102420988 | 0.615 | 0.874 | HapMap | HapMap | G | 0.865 | A | 0.135 | G/A |
| GIH | rs2058659 | 2 | 102420988 | 0.716 | 0.961 | HapMap | HapMap | G | 0.744 | A | 0.256 | G/A |
| JPT | rs2058659 | 2 | 102420988 | 0.85 | 1 | HapMap | HapMap | G | 0.831 | A | 0.169 | G/A |
| CEU | rs2058660 | 2 | 102420881 | 0.209 | 1 | HapMap | HapMap | G | 0.192 | A | 0.808 | G/A |
| CHB | rs2058660 | 2 | 102420881 | 0.135 | 1 | HapMap | HapMap | G | 0.47 | A | 0.53 | G/A |
| CHD | rs2058660 | 2 | 102420881 | 0.126 | 1 | HapMap | HapMap | G | 0.5 | A | 0.5 | G/A |
| GIH | rs2058660 | 2 | 102420881 | 0.141 | 0.803 | HapMap | HapMap | G | 0.443 | A | 0.557 | G/A |
| JPT | rs2058660 | 2 | 102420881 | 0.105 | 1 | HapMap | HapMap | G | 0.413 | A | 0.587 | G/A |
| LWK | rs2058660 | 2 | 102420881 | 0.048 | 1 | HapMap | HapMap | G | 0.133 | A | 0.867 | G/A |
| ASW | rs2058660 | 2 | 102420881 | 0.022 | 1 | HapMap | HapMap | G | 0.038 | A | 0.962 | G/A |
| MEX | rs2058660 | 2 | 102420881 | 0.298 | 1 | HapMap | HapMap | G | 0.418 | A | 0.582 | G/A |
| MKK | rs2058660 | 2 | 102420881 | 0.118 | 0.643 | HapMap | HapMap | G | 0.171 | A | 0.829 | G/A |
| ASW | rs2075186 | 2 | 102423683 | 0.119 | 0.699 | HapMap | HapMap | G | 0.689 | T | 0.311 | G/T |
| CEU | rs2075186 | 2 | 102423683 | 0.193 | 1 | HapMap | HapMap | G | 0.836 | T | 0.164 | G/T |
| CHB | rs2075186 | 2 | 102423683 | 0.632 | 1 | HapMap | HapMap | G | 0.905 | T | 0.095 | G/T |
| CHD | rs2075186 | 2 | 102423683 | 0.713 | 1 | HapMap | HapMap | G | 0.918 | T | 0.082 | G/T |
| GIH | rs2075186 | 2 | 102423683 | 0.22 | 0.74 | HapMap | HapMap | G | 0.903 | T | 0.097 | G/T |
| JPT | rs2075186 | 2 | 102423683 | 0.753 | 1 | HapMap | HapMap | G | 0.872 | T | 0.128 | G/T |
| LWK | rs2075186 | 2 | 102423683 | 0.068 | 0.649 | HapMap | HapMap | G | 0.661 | T | 0.339 | G/T |
| MEX | rs2075186 | 2 | 102423683 | 0.364 | 0.813 | HapMap | HapMap | G | 0.82 | T | 0.18 | G/T |
| GIH | rs2075187 | 2 | 102486743 | 0.059 | 0.713 | HapMap | HapMap | G | 0.295 | A | 0.705 | G/A |
| YRI | rs2075187 | 2 | 102486743 | 0.019 | 1 | HapMap | HapMap | G | 0.04 | A | 0.96 | G/A |
| ASW | rs2075187 | 2 | 102486743 | 0.063 | 1 | HapMap | HapMap | G | 0.038 | A | 0.962 | G/A |
| CEU | rs2075187 | 2 | 102486743 | 0.232 | 0.898 | HapMap | HapMap | G | 0.27 | A | 0.73 | G/A |
| CHB | rs2075187 | 2 | 102486743 | 0.132 | 0.677 | HapMap | HapMap | G | 0.643 | A | 0.357 | G/A |
| CHD | rs2075187 | 2 | 102486743 | 0.126 | 0.759 | HapMap | HapMap | G | 0.631 | A | 0.369 | G/A |
| CEU | rs2075188 | 2 | 102486664 | 0.232 | 0.898 | HapMap | HapMap | G | 0.27 | A | 0.73 | G/A |
| CHD | rs2075188 | 2 | 102486664 | 0.021 | 0.639 | HapMap | HapMap | G | 0.706 | A | 0.294 | G/A |
| JPT | rs2075188 | 2 | 102486664 | 0.09 | 1 | HapMap | HapMap | G | 0.733 | A | 0.267 | G/A |
| CHB | rs2075193 | 2 | 102484459 | 0.132 | 0.677 | HapMap | HapMap | G | 0.643 | A | 0.357 | G/A |
| CHD | rs2075193 | 2 | 102484459 | 0.131 | 0.765 | HapMap | HapMap | G | 0.637 | A | 0.363 | G/A |
| GIH | rs2075193 | 2 | 102484459 | 0.059 | 0.713 | HapMap | HapMap | G | 0.295 | A | 0.705 | G/A |
| MKK | rs2075193 | 2 | 102484459 | 0.063 | 0.761 | HapMap | HapMap | G | 0.073 | A | 0.927 | G/A |
| YRI | rs2075193 | 2 | 102484459 | 0.023 | 1 | HapMap | HapMap | G | 0.018 | A | 0.982 | G/A |
| CEU | rs2075193 | 2 | 102484459 | 0.232 | 0.898 | HapMap | HapMap | G | 0.27 | A | 0.73 | G/A |
| JPT | rs2075193 | 2 | 102484459 | 0.102 | 0.604 | HapMap | HapMap | G | 0.605 | A | 0.395 | G/A |
| LWK | rs2075193 | 2 | 102484459 | 0.129 | 1 | HapMap | HapMap | G | 0.039 | A | 0.961 | G/A |
| ASW | rs2075193 | 2 | 102484459 | 0.063 | 1 | HapMap | HapMap | G | 0.019 | A | 0.981 | G/A |
| GIH | rs2080315 | 2 | 102470720 | 0.01 | 1 | HapMap | HapMap | G | 0.966 | T | 0.034 | G/T |
| MEX | rs2080315 | 2 | 102470720 | 0.017 | 1 | HapMap | HapMap | G | 0.96 | T | 0.04 | G/T |
| CHB | rs2080315 | 2 | 102470720 | 0.016 | 0.859 | HapMap | HapMap | G | 0.893 | T | 0.107 | G/T |
| CHD | rs2080315 | 2 | 102470720 | 0.007 | 0.81 | HapMap | HapMap | G | 0.924 | T | 0.076 | G/T |
| CEU | rs2080315 | 2 | 102470720 | 0.047 | 1 | HapMap | HapMap | G | 0.934 | T | 0.066 | G/T |
| CEU | rs2110661 | 2 | 102229653 | 0.345 | 0.774 | HapMap | HapMap | G | 0.588 | A | 0.412 | G/A |
| CHB | rs2110661 | 2 | 102229653 | 0.211 | 0.836 | HapMap | HapMap | G | 0.315 | A | 0.685 | G/A |
| CHD | rs2110661 | 2 | 102229653 | 0.281 | 0.911 | HapMap | HapMap | G | 0.274 | A | 0.726 | G/A |
| GIH | rs2110661 | 2 | 102229653 | 0.427 | 0.949 | HapMap | HapMap | G | 0.362 | A | 0.638 | G/A |
| JPT | rs2110661 | 2 | 102229653 | 0.144 | 0.665 | HapMap | HapMap | G | 0.36 | A | 0.64 | G/A |
| MEX | rs2110661 | 2 | 102229653 | 0.091 | 0.628 | HapMap | HapMap | G | 0.622 | A | 0.378 | G/A |
| ASW | rs2110726 | 2 | 102160714 | 0.067 | 0.635 | HapMap | HapMap | G | 0.934 | A | 0.066 | G/A |
| LWK | rs2110726 | 2 | 102160714 | 0.076 | 0.77 | HapMap | HapMap | G | 0.961 | A | 0.039 | G/A |
| YRI | rs2110726 | 2 | 102160714 | 0.071 | 1 | HapMap | HapMap | G | 0.982 | A | 0.018 | G/A |
| CEU | rs2141781 | 2 | 102449338 | 0.337 | 0.656 | HapMap | HapMap | G | 0.655 | A | 0.345 | G/A |
| GIH | rs2141781 | 2 | 102449338 | 0.319 | 0.685 | HapMap | HapMap | G | 0.847 | A | 0.153 | G/A |
| MEX | rs2141781 | 2 | 102449338 | 0.319 | 0.671 | HapMap | HapMap | G | 0.86 | A | 0.14 | G/A |
| MKK | rs2160203 | 2 | 102327256 | 0.442 | 0.974 | HapMap | HapMap | A | 0.608 | G | 0.392 | A/G |
| YRI | rs2160203 | 2 | 102327256 | 0.307 | 0.917 | HapMap | HapMap | A | 0.482 | G | 0.518 | A/G |
| ASW | rs2160203 | 2 | 102327256 | 0.401 | 1 | HapMap | HapMap | A | 0.519 | G | 0.481 | A/G |
| CEU | rs2160203 | 2 | 102327256 | 0.406 | 1 | HapMap | HapMap | A | 0.757 | G | 0.243 | A/G |
| CHB | rs2160203 | 2 | 102327256 | 0.632 | 1 | HapMap | HapMap | A | 0.905 | G | 0.095 | A/G |
| CHD | rs2160203 | 2 | 102327256 | 0.713 | 1 | HapMap | HapMap | A | 0.918 | G | 0.082 | A/G |
| GIH | rs2160203 | 2 | 102327256 | 0.401 | 1 | HapMap | HapMap | A | 0.903 | G | 0.097 | A/G |
| JPT | rs2160203 | 2 | 102327256 | 0.737 | 1 | HapMap | HapMap | A | 0.875 | G | 0.125 | A/G |
| LWK | rs2160203 | 2 | 102327256 | 0.219 | 1 | HapMap | HapMap | A | 0.589 | G | 0.411 | A/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MEX | rs2160203 | 2 | 102327256 | 0.687 | 1 | HapMap | HapMap | A | 0.8 | G | 0.2 | A/G |
| CEU | rs2192752 | 2 | 102135805 | 0.112 | 0.732 | HapMap | HapMap | G | 0.23 | T | 0.77 | G/T |
| JPT | rs2192752 | 2 | 102135805 | 0.03 | 1 | HapMap | HapMap | G | 0.105 | T | 0.895 | G/T |
| MKK | rs2192752 | 2 | 102135805 | 0.106 | 0.793 | HapMap | HapMap | G | 0.108 | T | 0.892 | G/T |
| ASW | rs2241116 | 2 | 102369697 | 0.202 | 1 | HapMap | HapMap | C | 0.915 | A | 0.085 | C/A |
| CEU | rs2241116 | 2 | 102369697 | 0.233 | 1 | HapMap | HapMap | C | 0.779 | A | 0.221 | C/A |
| CHD | rs2241116 | 2 | 102369697 | 0.036 | 1 | HapMap | HapMap | C | 0.776 | A | 0.224 | C/A |
| GIH | rs2241116 | 2 | 102369697 | 0.089 | 1 | HapMap | HapMap | C | 0.744 | A | 0.256 | C/A |
| JPT | rs2241116 | 2 | 102369697 | 0.062 | 1 | HapMap | HapMap | C | 0.808 | A | 0.192 | C/A |
| MEX | rs2241116 | 2 | 102369697 | 0.053 | 0.766 | HapMap | HapMap | C | 0.8 | A | 0.2 | C/A |
| MKK | rs2241116 | 2 | 102369697 | 0.02 | 0.704 | HapMap | HapMap | C | 0.972 | A | 0.028 | C/A |
| YRI | rs2241116 | 2 | 102369697 | 0.121 | 0.688 | HapMap | HapMap | C | 0.938 | A | 0.062 | C/A |
| LWK | rs2241116 | 2 | 102369697 | 0.037 | 1 | HapMap | HapMap | C | 0.989 | A | 0.011 | C/A |
| ASW | rs2241130 | 2 | 102202138 | 0.085 | 0.794 | HapMap | HapMap | T | 0.783 | C | 0.217 | T/C |
| LWK | rs2241130 | 2 | 102202138 | 0.075 | 1 | HapMap | HapMap | T | 0.809 | C | 0.191 | T/C |
| MEX | rs2241130 | 2 | 102202138 | 0.118 | 0.845 | HapMap | HapMap | T | 0.684 | C | 0.316 | T/C |
| MKK | rs2241130 | 2 | 102202138 | 0.13 | 0.766 | HapMap | HapMap | T | 0.766 | C | 0.234 | T/C |
| JPT | rs2272128 | 2 | 102406361 | 0.105 | 1 | HapMap | HapMap | G | 0.413 | A | 0.587 | G/A |
| ASW | rs2272128 | 2 | 102406361 | 0.022 | 1 | HapMap | HapMap | G | 0.057 | A | 0.943 | G/A |
| CEU | rs2272128 | 2 | 102406361 | 0.209 | 1 | HapMap | HapMap | G | 0.204 | A | 0.796 | G/A |
| CHB | rs2272128 | 2 | 102406361 | 0.141 | 1 | HapMap | HapMap | G | 0.476 | A | 0.524 | G/A |
| CHD | rs2272128 | 2 | 102406361 | 0.129 | 1 | HapMap | HapMap | G | 0.506 | A | 0.494 | G/A |
| GIH | rs2272128 | 2 | 102406361 | 0.149 | 0.816 | HapMap | HapMap | G | 0.449 | A | 0.551 | G/A |
| MEX | rs2272128 | 2 | 102406361 | 0.333 | 1 | HapMap | HapMap | G | 0.46 | A | 0.54 | G/A |
| MKK | rs2272128 | 2 | 102406361 | 0.113 | 0.652 | HapMap | HapMap | G | 0.171 | A | 0.829 | G/A |
| CEU | rs2287033 | 2 | 102377669 | 0.754 | 1 | HapMap | HapMap | T | 0.487 | C | 0.513 | T/C |
| CHB | rs2287033 | 2 | 102377669 | 0.564 | 0.892 | HapMap | HapMap | T | 0.833 | C | 0.167 | T/C |
| CHD | rs2287033 | 2 | 102377669 | 0.615 | 0.874 | HapMap | HapMap | T | 0.865 | C | 0.135 | T/C |
| GIH | rs2287033 | 2 | 102377669 | 0.703 | 0.924 | HapMap | HapMap | T | 0.756 | C | 0.244 | T/C |
| JPT | rs2287033 | 2 | 102377669 | 0.85 | 1 | HapMap | HapMap | T | 0.831 | C | 0.169 | T/C |
| MEX | rs2287033 | 2 | 102377669 | 0.709 | 0.939 | HapMap | HapMap | T | 0.68 | C | 0.32 | T/C |
| MKK | rs2287033 | 2 | 102377669 | 0.274 | 0.729 | HapMap | HapMap | T | 0.271 | C | 0.729 | T/C |
| ASW | rs2287034 | 2 | 102377020 | 0.279 | 1 | HapMap | HapMap | C | 0.896 | A | 0.104 | C/A |
| CEU | rs2287034 | 2 | 102377020 | 0.301 | 1 | HapMap | HapMap | C | 0.721 | A | 0.279 | C/A |
| YRI | rs2287034 | 2 | 102377020 | 0.171 | 0.74 | HapMap | HapMap | C | 0.916 | A | 0.084 | C/A |
| CHB | rs2287034 | 2 | 102377020 | 0.038 | 0.642 | HapMap | HapMap | C | 0.637 | A | 0.363 | C/A |
| CHD | rs2287034 | 2 | 102377020 | 0.067 | 1 | HapMap | HapMap | C | 0.643 | A | 0.357 | C/A |
| GIH | rs2287034 | 2 | 102377020 | 0.112 | 1 | HapMap | HapMap | C | 0.699 | A | 0.301 | C/A |
| JPT | rs2287034 | 2 | 102377020 | 0.173 | 1 | HapMap | HapMap | C | 0.581 | A | 0.419 | C/A |
| LWK | rs2287034 | 2 | 102377020 | 0.148 | 1 | HapMap | HapMap | C | 0.956 | A | 0.044 | C/A |
| MEX | rs2287034 | 2 | 102377020 | 0.059 | 0.78 | HapMap | HapMap | C | 0.78 | A | 0.22 | C/A |
| MKK | rs2287034 | 2 | 102377020 | 0.111 | 0.895 | HapMap | HapMap | C | 0.909 | A | 0.091 | C/A |
| ASW | rs2287035 | 2 | 102376962 | 0.279 | 1 | HapMap | HapMap | G | 0.896 | A | 0.104 | G/A |
| GIH | rs2287035 | 2 | 102376962 | 0.112 | 1 | HapMap | HapMap | G | 0.699 | A | 0.301 | G/A |
| JPT | rs2287035 | 2 | 102376962 | 0.173 | 1 | HapMap | HapMap | G | 0.581 | A | 0.419 | G/A |
| CEU | rs2287035 | 2 | 102376962 | 0.301 | 1 | HapMap | HapMap | G | 0.721 | A | 0.279 | G/A |
| CHB | rs2287035 | 2 | 102376962 | 0.038 | 0.642 | HapMap | HapMap | G | 0.637 | A | 0.363 | G/A |
| CHD | rs2287035 | 2 | 102376962 | 0.041 | 0.76 | HapMap | HapMap | G | 0.641 | A | 0.359 | G/A |
| LWK | rs2287035 | 2 | 102376962 | 0.129 | 1 | HapMap | HapMap | G | 0.961 | A | 0.039 | G/A |
| MEX | rs2287035 | 2 | 102376962 | 0.059 | 0.78 | HapMap | HapMap | G | 0.776 | A | 0.224 | G/A |
| MKK | rs2287035 | 2 | 102376962 | 0.071 | 0.847 | HapMap | HapMap | G | 0.934 | A | 0.066 | G/A |
| YRI | rs2287035 | 2 | 102376962 | 0.143 | 0.711 | HapMap | HapMap | G | 0.92 | A | 0.08 | G/A |
| ASW | rs2287037 | 2 | 102345460 | 0.87 | 1 | HapMap | HapMap | C | 0.712 | T | 0.288 | C/T |
| CEU | rs2287037 | 2 | 102345460 | 0.414 | 1 | HapMap | HapMap | C | 0.611 | T | 0.389 | C/T |
| CHB | rs2287037 | 2 | 102345460 | 0.117 | 1 | HapMap | HapMap | C | 0.607 | T | 0.393 | C/T |
| CHD | rs2287037 | 2 | 102345460 | 0.076 | 1 | HapMap | HapMap | C | 0.624 | T | 0.376 | C/T |
| GIH | rs2287037 | 2 | 102345460 | 0.135 | 1 | HapMap | HapMap | C | 0.659 | T | 0.341 | C/T |
| JPT | rs2287037 | 2 | 102345460 | 0.191 | 1 | HapMap | HapMap | C | 0.564 | T | 0.436 | C/T |
| LWK | rs2287037 | 2 | 102345460 | 0.85 | 0.966 | HapMap | HapMap | C | 0.778 | T | 0.222 | C/T |
| MKK | rs2287037 | 2 | 102345460 | 0.677 | 1 | HapMap | HapMap | C | 0.671 | T | 0.329 | C/T |
| YRI | rs2287037 | 2 | 102345460 | 0.78 | 0.948 | HapMap | HapMap | C | 0.782 | T | 0.218 | C/T |
| MEX | rs2287041 | 2 | 102219298 | 0.118 | 0.848 | HapMap | HapMap | G | 0.69 | T | 0.31 | G/T |
| CEU | rs2287047 | 2 | 102140486 | 0.133 | 0.624 | HapMap | HapMap | G | 0.77 | A | 0.23 | G/A |
| CHB | rs2287047 | 2 | 102140486 | 0.111 | 1 | HapMap | HapMap | G | 0.59 | A | 0.41 | G/A |
| CHB | rs2287049 | 2 | 102137170 | 0.111 | 1 | HapMap | HapMap | A | 0.583 | G | 0.417 | A/G |
| ASW | rs2293223 | 2 | 102401900 | 0.119 | 0.699 | HapMap | HapMap | C | 0.689 | T | 0.311 | C/T |
| CEU | rs2293223 | 2 | 102401900 | 0.193 | 1 | HapMap | HapMap | C | 0.836 | T | 0.164 | C/T |
| CHB | rs2293223 | 2 | 102401900 | 0.632 | 1 | HapMap | HapMap | C | 0.905 | T | 0.095 | C/T |
| CHD | rs2293223 | 2 | 102401900 | 0.655 | 0.923 | HapMap | HapMap | C | 0.912 | T | 0.088 | C/T |
| JPT | rs2293223 | 2 | 102401900 | 0.753 | 1 | HapMap | HapMap | C | 0.872 | T | 0.128 | C/T |
| LWK | rs2293223 | 2 | 102401900 | 0.068 | 0.649 | HapMap | HapMap | C | 0.661 | T | 0.339 | C/T |
| MEX | rs2293223 | 2 | 102401900 | 0.361 | 0.812 | HapMap | HapMap | C | 0.816 | T | 0.184 | C/T |
| ASW | rs2293225 | 2 | 102402321 | 0.202 | 1 | HapMap | HapMap | C | 0.915 | T | 0.085 | C/T |
| LWK | rs2293225 | 2 | 102402321 | 0.018 | 1 | HapMap | HapMap | C | 0.994 | T | 0.006 | C/T |
| MKK | rs2293225 | 2 | 102402321 | 0.02 | 0.704 | HapMap | HapMap | C | 0.972 | T | 0.028 | C/T |
| YRI | rs2293225 | 2 | 102402321 | 0.121 | 0.688 | HapMap | HapMap | C | 0.938 | T | 0.062 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs2293225 | 2 | 102402321 | 0.233 | 1 | HapMap | HapMap | C | 0.779 | T | 0.221 | C/T |
| CHD | rs2293225 | 2 | 102402321 | 0.036 | 1 | HapMap | HapMap | C | 0.776 | T | 0.224 | C/T |
| GIH | rs2293225 | 2 | 102402321 | 0.089 | 1 | HapMap | HapMap | C | 0.744 | T | 0.256 | C/T |
| JPT | rs2293225 | 2 | 102402321 | 0.062 | 1 | HapMap | HapMap | C | 0.808 | T | 0.192 | C/T |
| MEX | rs2293225 | 2 | 102402321 | 0.053 | 0.766 | HapMap | HapMap | C | 0.8 | T | 0.2 | C/T |
| GIH | rs2302612 | 2 | 102218140 | 0.015 | 0.606 | HapMap | HapMap | T | 0.869 | C | 0.131 | T/C |
| MEX | rs2302612 | 2 | 102218140 | 0.085 | 0.607 | HapMap | HapMap | T | 0.61 | C | 0.39 | T/C |
| ASW | rs2302620 | 2 | 102208899 | 0.085 | 0.794 | HapMap | HapMap | T | 0.783 | C | 0.217 | T/C |
| LWK | rs2302620 | 2 | 102208899 | 0.055 | 1 | HapMap | HapMap | T | 0.85 | C | 0.15 | T/C |
| MEX | rs2302620 | 2 | 102208899 | 0.118 | 0.848 | HapMap | HapMap | T | 0.69 | C | 0.31 | T/C |
| MKK | rs2302620 | 2 | 102208899 | 0.148 | 0.87 | HapMap | HapMap | T | 0.787 | C | 0.213 | T/C |
| ASW | rs2310300 | 2 | 102415506 | 0.358 | 0.778 | HapMap | HapMap | A | 0.208 | G | 0.792 | A/G |
| GIH | rs2310300 | 2 | 102415506 | 0.674 | 0.921 | HapMap | HapMap | A | 0.753 | G | 0.247 | A/G |
| JPT | rs2310300 | 2 | 102415506 | 0.85 | 1 | HapMap | HapMap | A | 0.831 | G | 0.169 | A/G |
| MEX | rs2310300 | 2 | 102415506 | 0.709 | 0.939 | HapMap | HapMap | A | 0.68 | G | 0.32 | A/G |
| MKK | rs2310300 | 2 | 102415506 | 0.223 | 0.699 | HapMap | HapMap | A | 0.248 | G | 0.752 | A/G |
| CEU | rs2310300 | 2 | 102415506 | 0.759 | 1 | HapMap | HapMap | A | 0.482 | G | 0.518 | A/G |
| CHB | rs2310300 | 2 | 102415506 | 0.564 | 0.892 | HapMap | HapMap | A | 0.833 | G | 0.167 | A/G |
| CHD | rs2310300 | 2 | 102415506 | 0.615 | 0.874 | HapMap | HapMap | A | 0.865 | G | 0.135 | A/G |
| CHB | rs2310303 | 2 | 102470311 | 0.142 | 0.667 | HapMap | HapMap | A | 0.655 | G | 0.345 | A/G |
| CHD | rs2310303 | 2 | 102470311 | 0.123 | 0.683 | HapMap | HapMap | A | 0.676 | G | 0.324 | A/G |
| CEU | rs28362304 | 2 | 102157518 | 0.017 | 1 | HapMap | HapMap | C | 0.991 | T | 0.009 | C/T |
| GIH | rs28362304 | 2 | 102157518 | 0.03 | 1 | HapMap | HapMap | C | 0.901 | T | 0.099 | C/T |
| MKK | rs28362304 | 2 | 102157518 | 0.015 | 1 | HapMap | HapMap | C | 0.99 | T | 0.01 | C/T |
| YRI | rs28362304 | 2 | 102157518 | 0.077 | 1 | HapMap | HapMap | C | 0.981 | T | 0.019 | C/T |
| YRI | rs28634469 | 2 | 102382598 | 0.038 | 0.729 | HapMap | HapMap | C | 0.819 | T | 0.181 | C/T |
| MKK | rs28634469 | 2 | 102382598 | 0.041 | 1 | HapMap | HapMap | C | 0.947 | T | 0.053 | C/T |
| ASW | rs28634469 | 2 | 102382598 | 0.055 | 1 | HapMap | HapMap | C | 0.906 | T | 0.094 | C/T |
| LWK | rs28634469 | 2 | 102382598 | 0.063 | 1 | HapMap | HapMap | C | 0.833 | T | 0.167 | C/T |
| GIH | rs3171845 | 2 | 102157813 | 0.021 | 1 | HapMap | HapMap | G | 0.994 | A | 0.006 | G/A |
| LWK | rs3171845 | 2 | 102157813 | 0.099 | 1 | HapMap | HapMap | G | 0.761 | A | 0.239 | G/A |
| MEX | rs3171845 | 2 | 102157813 | 0.128 | 1 | HapMap | HapMap | G | 0.96 | A | 0.04 | G/A |
| MKK | rs3171845 | 2 | 102157813 | 0.061 | 0.665 | HapMap | HapMap | G | 0.839 | A | 0.161 | G/A |
| CHB | rs3213733 | 2 | 102364316 | 0.632 | 1 | HapMap | HapMap | C | 0.905 | A | 0.095 | C/A |
| CHD | rs3213733 | 2 | 102364316 | 0.713 | 1 | HapMap | HapMap | C | 0.918 | A | 0.082 | C/A |
| CEU | rs3213733 | 2 | 102364316 | 0.193 | 1 | HapMap | HapMap | C | 0.841 | A | 0.159 | C/A |
| ASW | rs3213733 | 2 | 102364316 | 0.086 | 0.636 | HapMap | HapMap | C | 0.708 | A | 0.292 | C/A |
| GIH | rs3213733 | 2 | 102364316 | 0.25 | 0.816 | HapMap | HapMap | C | 0.908 | A | 0.092 | C/A |
| JPT | rs3213733 | 2 | 102364316 | 0.753 | 1 | HapMap | HapMap | C | 0.872 | A | 0.128 | C/A |
| LWK | rs3213733 | 2 | 102364316 | 0.074 | 0.666 | HapMap | HapMap | C | 0.657 | A | 0.343 | C/A |
| MEX | rs3213733 | 2 | 102364316 | 0.364 | 0.813 | HapMap | HapMap | C | 0.82 | A | 0.18 | C/A |
| ASW | rs3213734 | 2 | 102175115 | 0.085 | 0.794 | HapMap | HapMap | G | 0.783 | A | 0.217 | G/A |
| LWK | rs3213734 | 2 | 102175115 | 0.052 | 1 | HapMap | HapMap | G | 0.858 | A | 0.142 | G/A |
| MEX | rs3213734 | 2 | 102175115 | 0.132 | 0.851 | HapMap | HapMap | G | 0.67 | A | 0.33 | G/A |
| MKK | rs3213734 | 2 | 102175115 | 0.131 | 0.808 | HapMap | HapMap | G | 0.783 | A | 0.217 | G/A |
| CHB | rs3213736 | 2 | 102151574 | 0.056 | 1 | HapMap | HapMap | G | 0.78 | C | 0.22 | G/C |
| CEU | rs3732123 | 2 | 102384509 | 0.301 | 1 | HapMap | HapMap | C | 0.721 | G | 0.279 | C/G |
| CHD | rs3732123 | 2 | 102384509 | 0.043 | 0.766 | HapMap | HapMap | C | 0.637 | G | 0.363 | C/G |
| MKK | rs3732123 | 2 | 102384509 | 0.087 | 0.87 | HapMap | HapMap | C | 0.923 | G | 0.077 | C/G |
| ASW | rs3732123 | 2 | 102384509 | 0.448 | 1 | HapMap | HapMap | C | 0.83 | G | 0.17 | C/G |
| CHB | rs3732123 | 2 | 102384509 | 0.033 | 0.62 | HapMap | HapMap | C | 0.643 | G | 0.357 | C/G |
| GIH | rs3732123 | 2 | 102384509 | 0.112 | 1 | HapMap | HapMap | C | 0.699 | G | 0.301 | C/G |
| JPT | rs3732123 | 2 | 102384509 | 0.173 | 1 | HapMap | HapMap | C | 0.581 | G | 0.419 | C/G |
| LWK | rs3732123 | 2 | 102384509 | 0.228 | 1 | HapMap | HapMap | C | 0.933 | G | 0.067 | C/G |
| MEX | rs3732123 | 2 | 102384509 | 0.059 | 0.78 | HapMap | HapMap | C | 0.78 | G | 0.22 | C/G |
| ASW | rs3732124 | 2 | 102384484 | 0.358 | 0.778 | HapMap | HapMap | C | 0.226 | T | 0.774 | C/T |
| CEU | rs3732124 | 2 | 102384484 | 0.759 | 1 | HapMap | HapMap | C | 0.482 | T | 0.518 | C/T |
| CHB | rs3732124 | 2 | 102384484 | 0.564 | 0.892 | HapMap | HapMap | C | 0.825 | T | 0.175 | C/T |
| CHD | rs3732124 | 2 | 102384484 | 0.614 | 0.874 | HapMap | HapMap | C | 0.863 | T | 0.137 | C/T |
| GIH | rs3732124 | 2 | 102384484 | 0.703 | 0.924 | HapMap | HapMap | C | 0.756 | T | 0.244 | C/T |
| JPT | rs3732124 | 2 | 102384484 | 0.85 | 1 | HapMap | HapMap | C | 0.831 | T | 0.169 | C/T |
| MEX | rs3732124 | 2 | 102384484 | 0.709 | 0.939 | HapMap | HapMap | C | 0.68 | T | 0.32 | C/T |
| MKK | rs3732124 | 2 | 102384484 | 0.231 | 0.705 | HapMap | HapMap | C | 0.252 | T | 0.748 | C/T |
| ASW | rs3732126 | 2 | 102380394 | 0.279 | 1 | HapMap | HapMap | A | 0.896 | C | 0.104 | A/C |
| CHB | rs3732126 | 2 | 102380394 | 0.038 | 0.642 | HapMap | HapMap | A | 0.637 | C | 0.363 | A/C |
| CHD | rs3732126 | 2 | 102380394 | 0.041 | 0.76 | HapMap | HapMap | A | 0.641 | C | 0.359 | A/C |
| GIH | rs3732126 | 2 | 102380394 | 0.112 | 1 | HapMap | HapMap | A | 0.699 | C | 0.301 | A/C |
| MKK | rs3732126 | 2 | 102380394 | 0.052 | 0.821 | HapMap | HapMap | A | 0.948 | C | 0.052 | A/C |
| YRI | rs3732126 | 2 | 102380394 | 0.143 | 0.711 | HapMap | HapMap | A | 0.92 | C | 0.08 | A/C |
| MEX | rs3732126 | 2 | 102380394 | 0.059 | 0.78 | HapMap | HapMap | A | 0.78 | C | 0.22 | A/C |
| CEU | rs3732126 | 2 | 102380394 | 0.301 | 1 | HapMap | HapMap | A | 0.721 | C | 0.279 | A/C |
| JPT | rs3732126 | 2 | 102380394 | 0.173 | 1 | HapMap | HapMap | A | 0.581 | C | 0.419 | A/C |
| LWK | rs3732126 | 2 | 102380394 | 0.072 | 1 | HapMap | HapMap | A | 0.978 | C | 0.022 | A/C |
| CEU | rs3732131 | 2 | 102161035 | 0.023 | 1 | HapMap | HapMap | A | 0.951 | G | 0.049 | A/G |
| LWK | rs3732131 | 2 | 102161035 | 0.06 | 1 | HapMap | HapMap | A | 0.839 | G | 0.161 | A/G |
| MEX | rs3732131 | 2 | 102161035 | 0.123 | 0.844 | HapMap | HapMap | A | 0.68 | G | 0.32 | A/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MKK | rs3732131 | 2 | 102161035 | 0.101 | 0.767 | HapMap | HapMap | A | 0.808 | G | 0.192 | A/G |
| CHD | rs3732134 | 2 | 102160649 | 0.026 | 1 | HapMap | HapMap | C | 0.833 | G | 0.167 | C/G |
| GIH | rs3732134 | 2 | 102160649 | 0.031 | 1 | HapMap | HapMap | C | 0.898 | G | 0.102 | C/G |
| JPT | rs3732134 | 2 | 102160649 | 0.051 | 1 | HapMap | HapMap | C | 0.797 | G | 0.203 | C/G |
| MEX | rs3732134 | 2 | 102160649 | 0.032 | 1 | HapMap | HapMap | C | 0.918 | G | 0.082 | C/G |
| MKK | rs3732134 | 2 | 102160649 | 0.005 | 1 | HapMap | HapMap | C | 0.993 | G | 0.007 | C/G |
| CHD | rs3755266 | 2 | 102409144 | 0.615 | 0.874 | HapMap | HapMap | G | 0.865 | A | 0.135 | G/A |
| GIH | rs3755266 | 2 | 102409144 | 0.68 | 0.923 | HapMap | HapMap | G | 0.75 | A | 0.25 | G/A |
| MEX | rs3755266 | 2 | 102409144 | 0.709 | 0.939 | HapMap | HapMap | G | 0.68 | A | 0.32 | G/A |
| MKK | rs3755266 | 2 | 102409144 | 0.223 | 0.696 | HapMap | HapMap | G | 0.246 | A | 0.754 | G/A |
| ASW | rs3755266 | 2 | 102409144 | 0.358 | 0.778 | HapMap | HapMap | G | 0.208 | A | 0.792 | G/A |
| CEU | rs3755266 | 2 | 102409144 | 0.759 | 1 | HapMap | HapMap | G | 0.482 | A | 0.518 | G/A |
| CHB | rs3755266 | 2 | 102409144 | 0.564 | 0.892 | HapMap | HapMap | G | 0.833 | A | 0.167 | G/A |
| JPT | rs3755266 | 2 | 102409144 | 0.85 | 1 | HapMap | HapMap | G | 0.831 | A | 0.169 | G/A |
| CHB | rs3755267 | 2 | 102405019 | 0.141 | 1 | HapMap | HapMap | T | 0.476 | G | 0.524 | T/G |
| CHD | rs3755267 | 2 | 102405019 | 0.131 | 1 | HapMap | HapMap | T | 0.518 | G | 0.482 | T/G |
| GIH | rs3755267 | 2 | 102405019 | 0.149 | 0.816 | HapMap | HapMap | T | 0.449 | G | 0.551 | T/G |
| JPT | rs3755267 | 2 | 102405019 | 0.105 | 1 | HapMap | HapMap | T | 0.411 | G | 0.589 | T/G |
| CEU | rs3755267 | 2 | 102405019 | 0.209 | 1 | HapMap | HapMap | T | 0.218 | G | 0.782 | T/G |
| MEX | rs3755267 | 2 | 102405019 | 0.342 | 1 | HapMap | HapMap | T | 0.458 | G | 0.542 | T/G |
| ASW | rs3755267 | 2 | 102405019 | 0.022 | 1 | HapMap | HapMap | T | 0.057 | G | 0.943 | T/G |
| CHB | rs3755276 | 2 | 102344891 | 1 | 1 | HapMap | HapMap | C | 0.857 | T | 0.143 | C/T |
| ASW | rs3755276 | 2 | 102344891 | 0.877 | 1 | HapMap | HapMap | C | 0.349 | T | 0.651 | C/T |
| CEU | rs3755276 | 2 | 102344891 | 1 | 1 | HapMap | HapMap | C | 0.593 | T | 0.407 | C/T |
| CHD | rs3755276 | 2 | 102344891 | 1 | 1 | HapMap | HapMap | C | 0.887 | T | 0.113 | C/T |
| GIH | rs3755276 | 2 | 102344891 | 1 | 1 | HapMap | HapMap | C | 0.79 | T | 0.21 | C/T |
| JPT | rs3755276 | 2 | 102344891 | 1 | 1 | HapMap | HapMap | C | 0.849 | T | 0.151 | C/T |
| LWK | rs3755276 | 2 | 102344891 | 0.555 | 1 | HapMap | HapMap | C | 0.361 | T | 0.639 | C/T |
| MKK | rs3755276 | 2 | 102344891 | 0.855 | 1 | HapMap | HapMap | C | 0.458 | T | 0.542 | C/T |
| YRI | rs3755276 | 2 | 102344891 | 0.916 | 1 | HapMap | HapMap | C | 0.265 | T | 0.735 | C/T |
| ASW | rs3755287 | 2 | 102206288 | 0.085 | 0.794 | HapMap | HapMap | G | 0.783 | A | 0.217 | G/A |
| LWK | rs3755287 | 2 | 102206288 | 0.075 | 1 | HapMap | HapMap | G | 0.812 | A | 0.188 | G/A |
| MEX | rs3755287 | 2 | 102206288 | 0.118 | 0.845 | HapMap | HapMap | G | 0.684 | A | 0.316 | G/A |
| MKK | rs3755287 | 2 | 102206288 | 0.135 | 0.773 | HapMap | HapMap | G | 0.762 | A | 0.238 | G/A |
| CHD | rs3771150 | 2 | 102427283 | 0.041 | 0.76 | HapMap | HapMap | G | 0.641 | A | 0.359 | G/A |
| GIH | rs3771150 | 2 | 102427283 | 0.115 | 1 | HapMap | HapMap | G | 0.693 | A | 0.307 | G/A |
| JPT | rs3771150 | 2 | 102427283 | 0.173 | 1 | HapMap | HapMap | G | 0.581 | A | 0.419 | G/A |
| LWK | rs3771150 | 2 | 102427283 | 0.11 | 1 | HapMap | HapMap | G | 0.966 | A | 0.034 | G/A |
| MEX | rs3771150 | 2 | 102427283 | 0.071 | 0.804 | HapMap | HapMap | G | 0.76 | A | 0.24 | G/A |
| ASW | rs3771150 | 2 | 102427283 | 0.279 | 1 | HapMap | HapMap | G | 0.896 | A | 0.104 | G/A |
| CHB | rs3771150 | 2 | 102427283 | 0.033 | 0.62 | HapMap | HapMap | G | 0.643 | A | 0.357 | G/A |
| MKK | rs3771150 | 2 | 102427283 | 0.039 | 0.769 | HapMap | HapMap | G | 0.955 | A | 0.045 | G/A |
| CEU | rs3771150 | 2 | 102427283 | 0.301 | 1 | HapMap | HapMap | G | 0.721 | A | 0.279 | G/A |
| YRI | rs3771150 | 2 | 102427283 | 0.143 | 0.711 | HapMap | HapMap | G | 0.92 | A | 0.08 | G/A |
| GIH | rs3771157 | 2 | 102379864 | 0.013 | 1 | HapMap | HapMap | C | 0.955 | A | 0.045 | C/A |
| LWK | rs3771157 | 2 | 102379864 | 0.018 | 1 | HapMap | HapMap | C | 0.994 | A | 0.006 | C/A |
| MEX | rs3771157 | 2 | 102379864 | 0.04 | 1 | HapMap | HapMap | C | 0.9 | A | 0.1 | C/A |
| MKK | rs3771157 | 2 | 102379864 | 0.008 | 0.896 | HapMap | HapMap | C | 0.986 | A | 0.014 | C/A |
| ASW | rs3771157 | 2 | 102379864 | 0.066 | 1 | HapMap | HapMap | C | 0.972 | A | 0.028 | C/A |
| CEU | rs3771157 | 2 | 102379864 | 0.031 | 1 | HapMap | HapMap | C | 0.965 | A | 0.035 | C/A |
| CHD | rs3771157 | 2 | 102379864 | 0.031 | 1 | HapMap | HapMap | C | 0.8 | A | 0.2 | C/A |
| JPT | rs3771157 | 2 | 102379864 | 0.04 | 1 | HapMap | HapMap | C | 0.86 | A | 0.14 | C/A |
| ASW | rs3771158 | 2 | 102376326 | 0.119 | 0.699 | HapMap | HapMap | A | 0.689 | G | 0.311 | A/G |
| CEU | rs3771158 | 2 | 102376326 | 0.193 | 1 | HapMap | HapMap | A | 0.841 | G | 0.159 | A/G |
| CHB | rs3771158 | 2 | 102376326 | 0.632 | 1 | HapMap | HapMap | A | 0.905 | G | 0.095 | A/G |
| LWK | rs3771158 | 2 | 102376326 | 0.068 | 0.649 | HapMap | HapMap | A | 0.661 | G | 0.339 | A/G |
| MEX | rs3771158 | 2 | 102376326 | 0.343 | 0.801 | HapMap | HapMap | A | 0.827 | G | 0.173 | A/G |
| CHD | rs3771158 | 2 | 102376326 | 0.713 | 1 | HapMap | HapMap | A | 0.917 | G | 0.083 | A/G |
| GIH | rs3771158 | 2 | 102376326 | 0.234 | 0.805 | HapMap | HapMap | A | 0.914 | G | 0.086 | A/G |
| JPT | rs3771158 | 2 | 102376326 | 0.753 | 1 | HapMap | HapMap | A | 0.872 | G | 0.128 | A/G |
| CHD | rs3771161 | 2 | 102370393 | 0.713 | 1 | HapMap | HapMap | C | 0.918 | A | 0.082 | C/A |
| GIH | rs3771161 | 2 | 102370393 | 0.25 | 0.816 | HapMap | HapMap | C | 0.909 | A | 0.091 | C/A |
| JPT | rs3771161 | 2 | 102370393 | 0.753 | 1 | HapMap | HapMap | C | 0.866 | A | 0.134 | C/A |
| ASW | rs3771161 | 2 | 102370393 | 0.107 | 0.67 | HapMap | HapMap | C | 0.679 | A | 0.321 | C/A |
| CEU | rs3771161 | 2 | 102370393 | 0.198 | 1 | HapMap | HapMap | C | 0.839 | A | 0.161 | C/A |
| CHB | rs3771161 | 2 | 102370393 | 0.632 | 1 | HapMap | HapMap | C | 0.904 | A | 0.096 | C/A |
| LWK | rs3771161 | 2 | 102370393 | 0.067 | 0.644 | HapMap | HapMap | C | 0.663 | A | 0.337 | C/A |
| MEX | rs3771161 | 2 | 102370393 | 0.364 | 0.813 | HapMap | HapMap | C | 0.816 | A | 0.184 | C/A |
| ASW | rs3771166 | 2 | 102352654 | 0.877 | 1 | HapMap | HapMap | G | 0.349 | A | 0.651 | G/A |
| CEU | rs3771166 | 2 | 102352654 | 1 | 1 | HapMap | HapMap | G | 0.593 | A | 0.407 | G/A |
| CHB | rs3771166 | 2 | 102352654 | 1 | 1 | HapMap | HapMap | G | 0.857 | A | 0.143 | G/A |
| CHD | rs3771166 | 2 | 102352654 | 1 | 1 | HapMap | HapMap | G | 0.888 | A | 0.112 | G/A |
| GIH | rs3771166 | 2 | 102352654 | 1 | 1 | HapMap | HapMap | G | 0.79 | A | 0.21 | G/A |
| JPT | rs3771166 | 2 | 102352654 | 1 | 1 | HapMap | HapMap | G | 0.849 | A | 0.151 | G/A |
| LWK | rs3771166 | 2 | 102352654 | 0.55 | 1 | HapMap | HapMap | G | 0.36 | A | 0.64 | G/A |
| MEX | rs3771166 | 2 | 102352654 | 1 | 1 | HapMap | HapMap | G | 0.73 | A | 0.27 | G/A |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MKK | rs3771166 | 2 | 102352654 | 0.855 | 1 | HapMap | HapMap | G | 0.458 | A | 0.542 | G/A |
| YRI | rs3771166 | 2 | 102352654 | 0.916 | 1 | HapMap | HapMap | G | 0.265 | A | 0.735 | G/A |
| LWK | rs3771175 | 2 | 102326642 | 0.093 | 1 | HapMap | HapMap | T | 0.772 | A | 0.228 | T/A |
| MEX | rs3771175 | 2 | 102326642 | 0.423 | 1 | HapMap | HapMap | T | 0.86 | A | 0.14 | T/A |
| MKK | rs3771175 | 2 | 102326642 | 0.296 | 1 | HapMap | HapMap | T | 0.71 | A | 0.29 | T/A |
| YRI | rs3771175 | 2 | 102326642 | 0.216 | 1 | HapMap | HapMap | T | 0.664 | A | 0.336 | T/A |
| ASW | rs3771175 | 2 | 102326642 | 0.214 | 1 | HapMap | HapMap | T | 0.726 | A | 0.274 | T/A |
| CEU | rs3771175 | 2 | 102326642 | 0.159 | 1 | HapMap | HapMap | T | 0.876 | A | 0.124 | T/A |
| CHB | rs3771175 | 2 | 102326642 | 0.462 | 1 | HapMap | HapMap | T | 0.917 | A | 0.083 | T/A |
| CHD | rs3771175 | 2 | 102326642 | 0.658 | 1 | HapMap | HapMap | T | 0.924 | A | 0.076 | T/A |
| GIH | rs3771175 | 2 | 102326642 | 0.375 | 1 | HapMap | HapMap | T | 0.909 | A | 0.091 | T/A |
| JPT | rs3771175 | 2 | 102326642 | 0.753 | 1 | HapMap | HapMap | T | 0.866 | A | 0.134 | T/A |
| ASW | rs3771179 | 2 | 102320324 | 0.24 | 1 | HapMap | HapMap | T | 0.877 | G | 0.123 | T/G |
| CEU | rs3771179 | 2 | 102320324 | 0.015 | 1 | HapMap | HapMap | T | 0.929 | G | 0.071 | T/G |
| CHD | rs3771179 | 2 | 102320324 | 0.002 | 0.614 | HapMap | HapMap | T | 0.965 | G | 0.035 | T/G |
| GIH | rs3771179 | 2 | 102320324 | 0.018 | 1 | HapMap | HapMap | T | 0.938 | G | 0.062 | T/G |
| LWK | rs3771179 | 2 | 102320324 | 0.398 | 1 | HapMap | HapMap | T | 0.889 | G | 0.111 | T/G |
| MEX | rs3771179 | 2 | 102320324 | 0.021 | 1 | HapMap | HapMap | T | 0.94 | G | 0.06 | T/G |
| MKK | rs3771179 | 2 | 102320324 | 0.393 | 1 | HapMap | HapMap | T | 0.782 | G | 0.218 | T/G |
| YRI | rs3771179 | 2 | 102320324 | 0.227 | 1 | HapMap | HapMap | T | 0.933 | G | 0.067 | T/G |
| ASW | rs3771180 | 2 | 102320049 | 0.214 | 1 | HapMap | HapMap | G | 0.726 | T | 0.274 | G/T |
| CEU | rs3771180 | 2 | 102320049 | 0.176 | 1 | HapMap | HapMap | G | 0.872 | T | 0.128 | G/T |
| CHB | rs3771180 | 2 | 102320049 | 0.538 | 0.864 | HapMap | HapMap | G | 0.899 | T | 0.101 | G/T |
| CHD | rs3771180 | 2 | 102320049 | 0.655 | 0.923 | HapMap | HapMap | G | 0.912 | T | 0.088 | G/T |
| GIH | rs3771180 | 2 | 102320049 | 0.401 | 1 | HapMap | HapMap | G | 0.903 | T | 0.097 | G/T |
| JPT | rs3771180 | 2 | 102320049 | 0.753 | 1 | HapMap | HapMap | G | 0.867 | T | 0.133 | G/T |
| LWK | rs3771180 | 2 | 102320049 | 0.093 | 1 | HapMap | HapMap | G | 0.772 | T | 0.228 | G/T |
| MEX | rs3771180 | 2 | 102320049 | 0.369 | 0.892 | HapMap | HapMap | G | 0.84 | T | 0.16 | G/T |
| MKK | rs3771180 | 2 | 102320049 | 0.296 | 1 | HapMap | HapMap | G | 0.71 | T | 0.29 | G/T |
| YRI | rs3771180 | 2 | 102320049 | 0.216 | 1 | HapMap | HapMap | G | 0.664 | T | 0.336 | G/T |
| LWK | rs3771184 | 2 | 102209384 | 0.076 | 1 | HapMap | HapMap | G | 0.806 | A | 0.194 | G/A |
| MKK | rs3771184 | 2 | 102209384 | 0.132 | 0.769 | HapMap | HapMap | G | 0.766 | A | 0.234 | G/A |
| ASW | rs3771188 | 2 | 102206780 | 0.085 | 0.794 | HapMap | HapMap | T | 0.783 | C | 0.217 | T/C |
| LWK | rs3771188 | 2 | 102206780 | 0.073 | 1 | HapMap | HapMap | T | 0.811 | C | 0.189 | T/C |
| MEX | rs3771188 | 2 | 102206780 | 0.118 | 0.848 | HapMap | HapMap | T | 0.69 | C | 0.31 | T/C |
| MKK | rs3771188 | 2 | 102206780 | 0.132 | 0.772 | HapMap | HapMap | T | 0.766 | C | 0.234 | T/C |
| CHB | rs3771200 | 2 | 102155206 | 0.047 | 0.603 | HapMap | HapMap | G | 0.542 | A | 0.458 | G/A |
| CHD | rs3917225 | 2 | 102135734 | 0.045 | 0.861 | HapMap | HapMap | A | 0.676 | G | 0.324 | A/G |
| YRI | rs3917225 | 2 | 102135734 | 0.047 | 1 | HapMap | HapMap | A | 0.969 | G | 0.031 | A/G |
| ASW | rs3917232 | 2 | 102137838 | 0.014 | 1 | HapMap | HapMap | C | 0.981 | T | 0.019 | C/T |
| LWK | rs3917232 | 2 | 102137838 | 0.013 | 1 | HapMap | HapMap | C | 0.961 | T | 0.039 | C/T |
| MKK | rs3917232 | 2 | 102137838 | 0.005 | 1 | HapMap | HapMap | C | 0.993 | T | 0.007 | C/T |
| YRI | rs3917232 | 2 | 102137838 | 0.023 | 1 | HapMap | HapMap | C | 0.973 | T | 0.027 | C/T |
| ASW | rs3917234 | 2 | 102138227 | 0.031 | 1 | HapMap | HapMap | G | 0.981 | A | 0.019 | G/A |
| YRI | rs3917235 | 2 | 102138283 | 0.004 | 1 | HapMap | HapMap | A | 0.996 | G | 0.004 | A/G |
| LWK | rs3917249 | 2 | 102141882 | 0.058 | 1 | HapMap | HapMap | G | 0.844 | A | 0.156 | G/A |
| MEX | rs3917249 | 2 | 102141882 | 0 | 1 | HapMap | HapMap | G | 0.99 | A | 0.01 | G/A |
| GIH | rs3917254 | 2 | 102142950 | 0.031 | 0.618 | HapMap | HapMap | G | 0.773 | A | 0.227 | G/A |
| ASW | rs3917285 | 2 | 102147598 | 0.007 | 1 | HapMap | HapMap | T | 0.991 | A | 0.009 | T/A |
| CEU | rs3917285 | 2 | 102147598 | 0.112 | 1 | HapMap | HapMap | T | 0.92 | A | 0.08 | T/A |
| GIH | rs3917285 | 2 | 102147598 | 0.046 | 1 | HapMap | HapMap | T | 0.989 | A | 0.011 | T/A |
| LWK | rs3917285 | 2 | 102147598 | 0.002 | 1 | HapMap | HapMap | T | 0.994 | A | 0.006 | T/A |
| MEX | rs3917285 | 2 | 102147598 | 0.267 | 1 | HapMap | HapMap | T | 0.908 | A | 0.092 | T/A |
| CEU | rs3917286 | 2 | 102148061 | 0.008 | 1 | HapMap | HapMap | G | 0.991 | A | 0.009 | G/A |
| GIH | rs3917286 | 2 | 102148061 | 0.029 | 1 | HapMap | HapMap | G | 0.902 | A | 0.098 | G/A |
| LWK | rs3917286 | 2 | 102148061 | 0.018 | 1 | HapMap | HapMap | G | 0.994 | A | 0.006 | G/A |
| MEX | rs3917286 | 2 | 102148061 | 0.004 | 1 | HapMap | HapMap | G | 0.99 | A | 0.01 | G/A |
| MKK | rs3917286 | 2 | 102148061 | 0.015 | 1 | HapMap | HapMap | G | 0.989 | A | 0.011 | G/A |
| YRI | rs3917286 | 2 | 102148061 | 0.047 | 1 | HapMap | HapMap | G | 0.987 | A | 0.013 | G/A |
| CHB | rs3917288 | 2 | 102148288 | 0.073 | 1 | HapMap | HapMap | T | 0.97 | G | 0.03 | T/G |
| CHD | rs3917289 | 2 | 102148343 | 0.001 | 1 | HapMap | HapMap | G | 0.994 | T | 0.006 | G/T |
| GIH | rs3917289 | 2 | 102148343 | 0.022 | 1 | HapMap | HapMap | G | 0.994 | T | 0.006 | G/T |
| JPT | rs3917289 | 2 | 102148343 | 0.003 | 1 | HapMap | HapMap | G | 0.994 | T | 0.006 | G/T |
| LWK | rs3917289 | 2 | 102148343 | 0.098 | 1 | HapMap | HapMap | G | 0.756 | T | 0.244 | G/T |
| MEX | rs3917289 | 2 | 102148343 | 0.081 | 0.706 | HapMap | HapMap | G | 0.95 | T | 0.05 | G/T |
| MKK | rs3917289 | 2 | 102148343 | 0.062 | 0.655 | HapMap | HapMap | G | 0.83 | T | 0.17 | G/T |
| ASW | rs3917292 | 2 | 102149484 | 0.031 | 1 | HapMap | HapMap | G | 0.991 | A | 0.009 | G/A |
| GIH | rs3917292 | 2 | 102149484 | 0.008 | 1 | HapMap | HapMap | G | 0.971 | A | 0.029 | G/A |
| MEX | rs3917292 | 2 | 102149484 | 0.013 | 1 | HapMap | HapMap | G | 0.969 | A | 0.031 | G/A |
| MKK | rs3917292 | 2 | 102149484 | 0.05 | 1 | HapMap | HapMap | G | 0.965 | A | 0.035 | G/A |
| CEU | rs3917296 | 2 | 102151265 | 0.123 | 0.8 | HapMap | HapMap | A | 0.898 | G | 0.102 | A/G |
| CHB | rs3917296 | 2 | 102151265 | 0.015 | 0.609 | HapMap | HapMap | A | 0.833 | G | 0.167 | A/G |
| CHD | rs3917296 | 2 | 102151265 | 0.021 | 1 | HapMap | HapMap | A | 0.857 | G | 0.143 | A/G |
| GIH | rs3917296 | 2 | 102151265 | 0.025 | 1 | HapMap | HapMap | A | 0.915 | G | 0.085 | A/G |
| JPT | rs3917296 | 2 | 102151265 | 0.04 | 1 | HapMap | HapMap | A | 0.865 | G | 0.135 | A/G |
| CEU | rs3917301 | 2 | 102153396 | 0.008 | 1 | HapMap | HapMap | C | 0.991 | T | 0.009 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| GIH | rs3917301 | 2 | 102153396 | 0.029 | 1 | HapMap | HapMap | C | 0.903 | T | 0.097 | C/T |
| MEX | rs3917301 | 2 | 102153396 | 0.004 | 1 | HapMap | HapMap | C | 0.99 | T | 0.01 | C/T |
| MKK | rs3917301 | 2 | 102153396 | 0.02 | 1 | HapMap | HapMap | C | 0.986 | T | 0.014 | C/T |
| YRI | rs3917301 | 2 | 102153396 | 0.046 | 1 | HapMap | HapMap | C | 0.982 | T | 0.018 | C/T |
| ASW | rs3917304 | 2 | 102154557 | 0.119 | 0.699 | HapMap | HapMap | G | 0.651 | T | 0.349 | G/T |
| LWK | rs3917304 | 2 | 102154557 | 0.102 | 1 | HapMap | HapMap | G | 0.756 | T | 0.244 | G/T |
| MKK | rs3917304 | 2 | 102154557 | 0.158 | 0.741 | HapMap | HapMap | G | 0.715 | T | 0.285 | G/T |
| ASW | rs3917318 | 2 | 102159192 | 0.119 | 0.699 | HapMap | HapMap | A | 0.651 | G | 0.349 | A/G |
| LWK | rs3917318 | 2 | 102159192 | 0.093 | 1 | HapMap | HapMap | A | 0.772 | G | 0.228 | A/G |
| MKK | rs3917318 | 2 | 102159192 | 0.146 | 0.728 | HapMap | HapMap | A | 0.724 | G | 0.276 | A/G |
| ASW | rs3917323 | 2 | 102159873 | 0.014 | 1 | HapMap | HapMap | G | 0.953 | A | 0.047 | G/A |
| CHB | rs3917323 | 2 | 102159873 | 0.008 | 1 | HapMap | HapMap | G | 0.964 | A | 0.036 | G/A |
| MKK | rs3917323 | 2 | 102159873 | 0.015 | 1 | HapMap | HapMap | G | 0.979 | A | 0.021 | G/A |
| CEU | rs3917325 | 2 | 102160339 | 0.04 | 1 | HapMap | HapMap | T | 0.947 | G | 0.053 | T/G |
| GIH | rs3917325 | 2 | 102160339 | 0.002 | 1 | HapMap | HapMap | T | 0.994 | G | 0.006 | T/G |
| MKK | rs3917325 | 2 | 102160339 | 0.227 | 0.904 | HapMap | HapMap | T | 0.833 | G | 0.167 | T/G |
| CEU | rs3917328 | 2 | 102160973 | 0.04 | 1 | HapMap | HapMap | C | 0.947 | T | 0.053 | C/T |
| GIH | rs3917328 | 2 | 102160973 | 0.002 | 1 | HapMap | HapMap | C | 0.994 | T | 0.006 | C/T |
| MKK | rs3917328 | 2 | 102160973 | 0.209 | 0.899 | HapMap | HapMap | C | 0.843 | T | 0.157 | C/T |
| CEU | rs3917329 | 2 | 102162295 | 0.045 | 0.684 | HapMap | HapMap | G | 0.929 | T | 0.071 | G/T |
| GIH | rs3917329 | 2 | 102162295 | 0.021 | 1 | HapMap | HapMap | G | 0.994 | T | 0.006 | G/T |
| LWK | rs3917329 | 2 | 102162295 | 0.076 | 1 | HapMap | HapMap | G | 0.806 | T | 0.194 | G/T |
| MEX | rs3917329 | 2 | 102162295 | 0.128 | 1 | HapMap | HapMap | G | 0.96 | T | 0.04 | G/T |
| MKK | rs3917329 | 2 | 102162295 | 0.033 | 0.763 | HapMap | HapMap | G | 0.927 | T | 0.073 | G/T |
| YRI | rs3917329 | 2 | 102162295 | 0.016 | 0.645 | HapMap | HapMap | G | 0.934 | T | 0.066 | G/T |
| CHB | rs3917332 | 2 | 102162956 | 0.01 | 1 | HapMap | HapMap | A | 0.043 | T | 0.957 | A/T |
| GIH | rs3917332 | 2 | 102162956 | 0.045 | 1 | HapMap | HapMap | A | 0.142 | T | 0.858 | A/T |
| ASW | rs3917335 | 2 | 102137725 | 0.007 | 1 | HapMap | HapMap | C | 0.991 | T | 0.009 | C/T |
| GIH | rs3917335 | 2 | 102137725 | 0.021 | 1 | HapMap | HapMap | C | 0.994 | T | 0.006 | C/T |
| LWK | rs41319148 | 2 | 102488718 | 0.012 | 0.698 | HapMap | HapMap | C | 0.928 | G | 0.072 | C/G |
| MKK | rs41319148 | 2 | 102488718 | 0.018 | 1 | HapMap | HapMap | C | 0.976 | G | 0.024 | C/G |
| MEX | rs41319148 | 2 | 102488718 | 0.008 | 1 | HapMap | HapMap | C | 0.98 | G | 0.02 | C/G |
| GIH | rs41348650 | 2 | 102470631 | 0.01 | 1 | HapMap | HapMap | G | 0.966 | A | 0.034 | G/A |
| JPT | rs41348650 | 2 | 102470631 | 0.005 | 1 | HapMap | HapMap | G | 0.977 | A | 0.023 | G/A |
| CHD | rs41348650 | 2 | 102470631 | 0.002 | 0.614 | HapMap | HapMap | G | 0.965 | A | 0.035 | G/A |
| MEX | rs41348650 | 2 | 102470631 | 0.021 | 1 | HapMap | HapMap | G | 0.95 | A | 0.05 | G/A |
| CEU | rs41348650 | 2 | 102470631 | 0.056 | 1 | HapMap | HapMap | G | 0.925 | A | 0.075 | G/A |
| ASW | rs41484147 | 2 | 102490927 | 0.038 | 1 | HapMap | HapMap | C | 0.915 | T | 0.085 | C/T |
| LWK | rs41484147 | 2 | 102490927 | 0.004 | 0.919 | HapMap | HapMap | C | 0.983 | T | 0.017 | C/T |
| MKK | rs41484147 | 2 | 102490927 | 0.014 | 0.639 | HapMap | HapMap | C | 0.976 | T | 0.024 | C/T |
| YRI | rs41484147 | 2 | 102490927 | 0.015 | 1 | HapMap | HapMap | C | 0.951 | T | 0.049 | C/T |
| CEU | rs4851003 | 2 | 102275709 | 0.483 | 0.937 | HapMap | HapMap | T | 0.726 | C | 0.274 | T/C |
| CHB | rs4851003 | 2 | 102275709 | 0.073 | 1 | HapMap | HapMap | T | 0.994 | C | 0.006 | T/C |
| CHD | rs4851003 | 2 | 102275709 | 0.047 | 1 | HapMap | HapMap | T | 0.994 | C | 0.006 | T/C |
| GIH | rs4851003 | 2 | 102275709 | 0.405 | 0.87 | HapMap | HapMap | T | 0.875 | C | 0.125 | T/C |
| MEX | rs4851003 | 2 | 102275709 | 0.28 | 0.661 | HapMap | HapMap | T | 0.82 | C | 0.18 | T/C |
| CEU | rs4851004 | 2 | 102375969 | 0.755 | 1 | HapMap | HapMap | C | 0.478 | T | 0.522 | C/T |
| CHB | rs4851004 | 2 | 102375969 | 0.562 | 0.891 | HapMap | HapMap | C | 0.831 | T | 0.169 | C/T |
| ASW | rs4851004 | 2 | 102375969 | 0.408 | 0.796 | HapMap | HapMap | C | 0.236 | T | 0.764 | C/T |
| CHD | rs4851004 | 2 | 102375969 | 0.614 | 0.874 | HapMap | HapMap | C | 0.863 | T | 0.137 | C/T |
| GIH | rs4851004 | 2 | 102375969 | 0.703 | 0.924 | HapMap | HapMap | C | 0.756 | T | 0.244 | C/T |
| JPT | rs4851004 | 2 | 102375969 | 0.85 | 1 | HapMap | HapMap | C | 0.831 | T | 0.169 | C/T |
| MEX | rs4851004 | 2 | 102375969 | 0.709 | 0.939 | HapMap | HapMap | C | 0.68 | T | 0.32 | C/T |
| MKK | rs4851004 | 2 | 102375969 | 0.278 | 0.732 | HapMap | HapMap | C | 0.273 | T | 0.727 | C/T |
| ASW | rs4851005 | 2 | 102377984 | 0.219 | 0.829 | HapMap | HapMap | C | 0.858 | T | 0.142 | C/T |
| CHB | rs4851005 | 2 | 102377984 | 0.038 | 0.642 | HapMap | HapMap | C | 0.637 | T | 0.363 | C/T |
| CHD | rs4851005 | 2 | 102377984 | 0.041 | 0.76 | HapMap | HapMap | C | 0.641 | T | 0.359 | C/T |
| GIH | rs4851005 | 2 | 102377984 | 0.078 | 0.803 | HapMap | HapMap | C | 0.682 | T | 0.318 | C/T |
| JPT | rs4851005 | 2 | 102377984 | 0.173 | 1 | HapMap | HapMap | C | 0.582 | T | 0.418 | C/T |
| LWK | rs4851005 | 2 | 102377984 | 0.04 | 0.667 | HapMap | HapMap | C | 0.972 | T | 0.028 | C/T |
| MKK | rs4851005 | 2 | 102377984 | 0.047 | 0.709 | HapMap | HapMap | C | 0.937 | T | 0.063 | C/T |
| CEU | rs4851010 | 2 | 102422559 | 0.337 | 0.656 | HapMap | HapMap | A | 0.646 | T | 0.354 | A/T |
| GIH | rs4851010 | 2 | 102422559 | 0.319 | 0.685 | HapMap | HapMap | A | 0.847 | T | 0.153 | A/T |
| MEX | rs4851010 | 2 | 102422559 | 0.209 | 0.671 | HapMap | HapMap | A | 0.86 | T | 0.14 | A/T |
| ASW | rs4851011 | 2 | 102456110 | 0.279 | 1 | HapMap | HapMap | C | 0.896 | T | 0.104 | C/T |
| CEU | rs4851011 | 2 | 102456110 | 0.301 | 1 | HapMap | HapMap | C | 0.712 | T | 0.288 | C/T |
| CHB | rs4851011 | 2 | 102456110 | 0.033 | 0.62 | HapMap | HapMap | C | 0.643 | T | 0.357 | C/T |
| CHD | rs4851011 | 2 | 102456110 | 0.041 | 0.76 | HapMap | HapMap | C | 0.641 | T | 0.359 | C/T |
| LWK | rs4851011 | 2 | 102456110 | 0.054 | 1 | HapMap | HapMap | C | 0.983 | T | 0.017 | C/T |
| MKK | rs4851011 | 2 | 102456110 | 0.035 | 1 | HapMap | HapMap | C | 0.976 | T | 0.024 | C/T |
| GIH | rs4851011 | 2 | 102456110 | 0.115 | 1 | HapMap | HapMap | C | 0.693 | T | 0.307 | C/T |
| JPT | rs4851011 | 2 | 102456110 | 0.173 | 1 | HapMap | HapMap | C | 0.581 | T | 0.419 | C/T |
| MEX | rs4851011 | 2 | 102456110 | 0.071 | 0.804 | HapMap | HapMap | C | 0.76 | T | 0.24 | C/T |
| YRI | rs4851011 | 2 | 102456110 | 0.113 | 0.603 | HapMap | HapMap | C | 0.916 | T | 0.084 | C/T |
| CEU | rs4851012 | 2 | 102482347 | 0.237 | 0.898 | HapMap | HapMap | C | 0.272 | T | 0.728 | C/T |
| CHD | rs4851012 | 2 | 102482347 | 0.021 | 0.633 | HapMap | HapMap | C | 0.708 | T | 0.292 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| JPT | rs4851012 | 2 | 102482347 | 0.09 | 1 | HapMap | HapMap | C | 0.733 | T | 0.267 | C/T |
| CEU | rs4851014 | 2 | 102482708 | 0.232 | 0.898 | HapMap | HapMap | C | 0.27 | T | 0.73 | C/T |
| CHD | rs4851014 | 2 | 102482708 | 0.021 | 0.633 | HapMap | HapMap | C | 0.708 | T | 0.292 | C/T |
| JPT | rs4851014 | 2 | 102482708 | 0.09 | 1 | HapMap | HapMap | C | 0.733 | T | 0.267 | C/T |
| JPT | rs4851016 | 2 | 102486832 | 0.09 | 1 | HapMap | HapMap | C | 0.733 | T | 0.267 | C/T |
| CEU | rs4851016 | 2 | 102486832 | 0.232 | 0.898 | HapMap | HapMap | C | 0.27 | T | 0.73 | C/T |
| CHD | rs4851016 | 2 | 102486832 | 0.023 | 0.649 | HapMap | HapMap | C | 0.702 | T | 0.298 | C/T |
| CHD | rs4851017 | 2 | 102487201 | 0.023 | 0.655 | HapMap | HapMap | C | 0.7 | A | 0.3 | C/A |
| JPT | rs4851017 | 2 | 102487201 | 0.09 | 1 | HapMap | HapMap | C | 0.733 | A | 0.267 | C/A |
| CEU | rs4851017 | 2 | 102487201 | 0.232 | 0.898 | HapMap | HapMap | C | 0.268 | A | 0.732 | C/A |
| CEU | rs4851561 | 2 | 102218269 | 0.112 | 1 | HapMap | HapMap | G | 0.925 | A | 0.075 | G/A |
| GIH | rs4851561 | 2 | 102218269 | 0.021 | 1 | HapMap | HapMap | G | 0.994 | A | 0.006 | G/A |
| LWK | rs4851561 | 2 | 102218269 | 0.007 | 1 | HapMap | HapMap | G | 0.978 | A | 0.022 | G/A |
| MEX | rs4851561 | 2 | 102218269 | 0.095 | 1 | HapMap | HapMap | G | 0.97 | A | 0.03 | G/A |
| MKK | rs4851561 | 2 | 102218269 | 0.008 | 0.896 | HapMap | HapMap | G | 0.986 | A | 0.014 | G/A |
| ASW | rs4851563 | 2 | 102251967 | 0.026 | 1 | HapMap | HapMap | A | 0.934 | T | 0.066 | A/T |
| CEU | rs4851563 | 2 | 102251967 | 0.159 | 1 | HapMap | HapMap | A | 0.898 | T | 0.102 | A/T |
| GIH | rs4851563 | 2 | 102251967 | 0.021 | 1 | HapMap | HapMap | A | 0.994 | T | 0.006 | A/T |
| MEX | rs4851563 | 2 | 102251967 | 0.128 | 1 | HapMap | HapMap | A | 0.96 | T | 0.04 | A/T |
| MEX | rs4851574 | 2 | 102391142 | 0.04 | 1 | HapMap | HapMap | A | 0.9 | T | 0.1 | A/T |
| MKK | rs4851574 | 2 | 102391142 | 0.008 | 0.896 | HapMap | HapMap | A | 0.986 | T | 0.014 | A/T |
| GIH | rs4851574 | 2 | 102391142 | 0.013 | 1 | HapMap | HapMap | A | 0.955 | T | 0.045 | A/T |
| JPT | rs4851574 | 2 | 102391142 | 0.04 | 1 | HapMap | HapMap | A | 0.86 | T | 0.14 | A/T |
| LWK | rs4851574 | 2 | 102391142 | 0.018 | 1 | HapMap | HapMap | A | 0.994 | T | 0.006 | A/T |
| ASW | rs4851574 | 2 | 102391142 | 0.066 | 1 | HapMap | HapMap | A | 0.972 | T | 0.028 | A/T |
| CEU | rs4851574 | 2 | 102391142 | 0.031 | 1 | HapMap | HapMap | A | 0.965 | T | 0.035 | A/T |
| CHD | rs4851574 | 2 | 102391142 | 0.031 | 1 | HapMap | HapMap | A | 0.8 | T | 0.2 | A/T |
| CEU | rs4851581 | 2 | 102401181 | 0.216 | 1 | HapMap | HapMap | A | 0.878 | G | 0.122 | A/G |
| MEX | rs4851581 | 2 | 102401181 | 0.195 | 1 | HapMap | HapMap | A | 0.939 | G | 0.061 | A/G |
| GIH | rs4851589 | 2 | 102443577 | 0.319 | 0.685 | HapMap | HapMap | A | 0.847 | G | 0.153 | A/G |
| MEX | rs4851589 | 2 | 102443577 | 0.185 | 0.645 | HapMap | HapMap | A | 0.867 | G | 0.133 | A/G |
| CEU | rs4851589 | 2 | 102443577 | 0.337 | 0.656 | HapMap | HapMap | A | 0.646 | G | 0.354 | A/G |
| CEU | rs4851593 | 2 | 102455659 | 0.337 | 0.656 | HapMap | HapMap | A | 0.655 | G | 0.345 | A/G |
| GIH | rs4851593 | 2 | 102455659 | 0.319 | 0.685 | HapMap | HapMap | A | 0.847 | G | 0.153 | A/G |
| MEX | rs4851593 | 2 | 102455659 | 0.209 | 0.671 | HapMap | HapMap | A | 0.86 | G | 0.14 | A/G |
| CHD | rs4851600 | 2 | 102482655 | 0.021 | 0.633 | HapMap | HapMap | C | 0.708 | G | 0.292 | C/G |
| JPT | rs4851600 | 2 | 102482655 | 0.09 | 1 | HapMap | HapMap | C | 0.733 | G | 0.267 | C/G |
| CEU | rs4851600 | 2 | 102482655 | 0.232 | 0.898 | HapMap | HapMap | C | 0.27 | G | 0.73 | C/G |
| CHD | rs4851601 | 2 | 102482693 | 0.004 | 1 | HapMap | HapMap | G | 0.971 | A | 0.029 | G/A |
| MKK | rs4851601 | 2 | 102482693 | 0.04 | 1 | HapMap | HapMap | G | 0.972 | A | 0.028 | G/A |
| CHB | rs4851601 | 2 | 102482693 | 0.008 | 1 | HapMap | HapMap | G | 0.94 | A | 0.06 | G/A |
| CHD | rs4851602 | 2 | 102482737 | 0.044 | 1 | HapMap | HapMap | G | 0.744 | A | 0.256 | G/A |
| JPT | rs4851602 | 2 | 102482737 | 0.08 | 1 | HapMap | HapMap | G | 0.75 | A | 0.25 | G/A |
| JPT | rs4851604 | 2 | 102485313 | 0.071 | 1 | HapMap | HapMap | G | 0.773 | A | 0.227 | G/A |
| CHD | rs4851604 | 2 | 102485313 | 0.035 | 1 | HapMap | HapMap | G | 0.782 | A | 0.218 | G/A |
| CHD | rs4851615 | 2 | 102513431 | 0.039 | 0.752 | HapMap | HapMap | G | 0.647 | T | 0.353 | G/T |
| CEU | rs4851616 | 2 | 102518294 | 0.145 | 0.859 | HapMap | HapMap | C | 0.19 | T | 0.81 | C/T |
| CHB | rs4851616 | 2 | 102518294 | 0.155 | 1 | HapMap | HapMap | C | 0.518 | T | 0.482 | C/T |
| CHD | rs4851616 | 2 | 102518294 | 0.129 | 1 | HapMap | HapMap | C | 0.506 | T | 0.494 | C/T |
| JPT | rs4851616 | 2 | 102518294 | 0.111 | 1 | HapMap | HapMap | C | 0.413 | T | 0.587 | C/T |
| ASW | rs4988955 | 2 | 102334360 | 1 | 1 | HapMap | HapMap | A | 0.314 | G | 0.686 | A/G |
| CEU | rs4988955 | 2 | 102334360 | 1 | 1 | HapMap | HapMap | A | 0.59 | G | 0.41 | A/G |
| CHB | rs4988955 | 2 | 102334360 | 1 | 1 | HapMap | HapMap | A | 0.857 | G | 0.143 | A/G |
| CHD | rs4988955 | 2 | 102334360 | 1 | 1 | HapMap | HapMap | A | 0.887 | G | 0.113 | A/G |
| GIH | rs4988955 | 2 | 102334360 | 1 | 1 | HapMap | HapMap | A | 0.791 | G | 0.209 | A/G |
| JPT | rs4988955 | 2 | 102334360 | 1 | 1 | HapMap | HapMap | A | 0.845 | G | 0.155 | A/G |
| LWK | rs4988955 | 2 | 102334360 | 1 | 1 | HapMap | HapMap | A | 0.242 | G | 0.758 | A/G |
| MEX | rs4988955 | 2 | 102334360 | 1 | 1 | HapMap | HapMap | A | 0.724 | G | 0.276 | A/G |
| MKK | rs4988955 | 2 | 102334360 | 1 | 1 | HapMap | HapMap | A | 0.421 | G | 0.579 | A/G |
| YRI | rs4988955 | 2 | 102334360 | 1 | 1 | HapMap | HapMap | A | 0.235 | G | 0.765 | A/G |
| CHB | rs4988957 | 2 | 102334507 | 1 | 1 | HapMap | HapMap | T | 0.857 | C | 0.143 | T/C |
| ASW | rs4988957 | 2 | 102334507 | 1 | 1 | HapMap | HapMap | T | 0.302 | C | 0.698 | T/C |
| CEU | rs4988957 | 2 | 102334507 | 1 | 1 | HapMap | HapMap | T | 0.593 | C | 0.407 | T/C |
| CHD | rs4988957 | 2 | 102334507 | 1 | 1 | HapMap | HapMap | T | 0.888 | C | 0.112 | T/C |
| GIH | rs4988957 | 2 | 102334507 | 1 | 1 | HapMap | HapMap | T | 0.79 | C | 0.21 | T/C |
| JPT | rs4988957 | 2 | 102334507 | 1 | 1 | HapMap | HapMap | T | 0.849 | C | 0.151 | T/C |
| LWK | rs4988957 | 2 | 102334507 | 1 | 1 | HapMap | HapMap | T | 0.239 | C | 0.761 | T/C |
| MEX | rs4988957 | 2 | 102334507 | 1 | 1 | HapMap | HapMap | T | 0.73 | C | 0.27 | T/C |
| MKK | rs4988957 | 2 | 102334507 | 1 | 1 | HapMap | HapMap | T | 0.42 | C | 0.58 | T/C |
| YRI | rs4988957 | 2 | 102334507 | 1 | 1 | HapMap | HapMap | T | 0.235 | C | 0.765 | T/C |
| ASW | rs4988958 | 2 | 102334717 | 1 | 1 | HapMap | HapMap | T | 0.302 | C | 0.698 | T/C |
| CEU | rs4988958 | 2 | 102334717 | 1 | 1 | HapMap | HapMap | T | 0.593 | C | 0.407 | T/C |
| CHB | rs4988958 | 2 | 102334717 | 1 | 1 | HapMap | HapMap | T | 0.857 | C | 0.143 | T/C |
| CHD | rs4988958 | 2 | 102334717 | 1 | 1 | HapMap | HapMap | T | 0.888 | C | 0.112 | T/C |
| GIH | rs4988958 | 2 | 102334717 | 1 | 1 | HapMap | HapMap | T | 0.79 | C | 0.21 | T/C |
| JPT | rs4988958 | 2 | 102334717 | 1 | 1 | HapMap | HapMap | T | 0.849 | C | 0.151 | T/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| LWK | rs4988958 | 2 | 102334717 | 0.97 | 1 | HapMap | HapMap | T | 0.244 | C | 0.756 | T/C |
| MEX | rs4988958 | 2 | 102334717 | 1 | 1 | HapMap | HapMap | T | 0.735 | C | 0.265 | T/C |
| MKK | rs4988958 | 2 | 102334717 | 1 | 1 | HapMap | HapMap | T | 0.42 | C | 0.58 | T/C |
| YRI | rs4988958 | 2 | 102334717 | 1 | 1 | HapMap | HapMap | T | 0.237 | C | 0.763 | T/C |
| CEU | rs6543113 | 2 | 102277489 | 0.535 | 0.942 | HapMap | HapMap | C | 0.699 | T | 0.301 | C/T |
| CHB | rs6543113 | 2 | 102277489 | 0.073 | 1 | HapMap | HapMap | C | 0.994 | T | 0.006 | C/T |
| CHD | rs6543113 | 2 | 102277489 | 0.047 | 1 | HapMap | HapMap | C | 0.994 | T | 0.006 | C/T |
| GIH | rs6543113 | 2 | 102277489 | 0.405 | 0.87 | HapMap | HapMap | C | 0.875 | T | 0.125 | C/T |
| MEX | rs6543113 | 2 | 102277489 | 0.307 | 0.628 | HapMap | HapMap | C | 0.796 | T | 0.204 | C/T |
| CHB | rs6543146 | 2 | 102463127 | 0.142 | 0.667 | HapMap | HapMap | T | 0.655 | G | 0.345 | T/G |
| CHD | rs6543146 | 2 | 102463127 | 0.121 | 0.679 | HapMap | HapMap | T | 0.673 | G | 0.327 | T/G |
| CEU | rs6543148 | 2 | 102466651 | 0.047 | 1 | HapMap | HapMap | A | 0.934 | G | 0.066 | A/G |
| CHD | rs6543148 | 2 | 102466651 | 0.002 | 0.614 | HapMap | HapMap | A | 0.965 | G | 0.035 | A/G |
| GIH | rs6543148 | 2 | 102466651 | 0.01 | 1 | HapMap | HapMap | A | 0.966 | G | 0.034 | A/G |
| JPT | rs6543148 | 2 | 102466651 | 0.005 | 1 | HapMap | HapMap | A | 0.977 | G | 0.023 | A/G |
| MEX | rs6543148 | 2 | 102466651 | 0.017 | 1 | HapMap | HapMap | A | 0.96 | G | 0.04 | A/G |
| CEU | rs6543150 | 2 | 102480415 | 0.232 | 0.898 | HapMap | HapMap | C | 0.275 | T | 0.725 | C/T |
| CHB | rs6543150 | 2 | 102480415 | 0.132 | 0.677 | HapMap | HapMap | C | 0.649 | T | 0.351 | C/T |
| CHD | rs6543150 | 2 | 102480415 | 0.147 | 0.776 | HapMap | HapMap | C | 0.648 | T | 0.352 | C/T |
| JPT | rs6543150 | 2 | 102480415 | 0.102 | 0.604 | HapMap | HapMap | C | 0.61 | T | 0.39 | C/T |
| YRI | rs6543150 | 2 | 102480415 | 0.015 | 1 | HapMap | HapMap | C | 0.031 | T | 0.969 | C/T |
| JPT | rs6543156 | 2 | 102482582 | 0.6 | 1 | HapMap | HapMap | C | 0.872 | T | 0.128 | C/T |
| MEX | rs6543156 | 2 | 102482582 | 0.031 | 1 | HapMap | HapMap | C | 0.99 | T | 0.01 | C/T |
| GIH | rs6543156 | 2 | 102482582 | 0.021 | 1 | HapMap | HapMap | C | 0.994 | T | 0.006 | C/T |
| CHB | rs6543156 | 2 | 102482582 | 0.546 | 1 | HapMap | HapMap | C | 0.909 | T | 0.091 | C/T |
| CHD | rs6543156 | 2 | 102482582 | 0.603 | 1 | HapMap | HapMap | C | 0.929 | T | 0.071 | C/T |
| ASW | rs6708413 | 2 | 102429801 | 0.022 | 1 | HapMap | HapMap | G | 0.038 | A | 0.962 | G/A |
| CHB | rs6708413 | 2 | 102429801 | 0.141 | 1 | HapMap | HapMap | G | 0.476 | A | 0.524 | G/A |
| CHD | rs6708413 | 2 | 102429801 | 0.129 | 1 | HapMap | HapMap | G | 0.506 | A | 0.494 | G/A |
| GIH | rs6708413 | 2 | 102429801 | 0.141 | 0.803 | HapMap | HapMap | G | 0.443 | A | 0.557 | G/A |
| JPT | rs6708413 | 2 | 102429801 | 0.105 | 1 | HapMap | HapMap | G | 0.413 | A | 0.587 | G/A |
| CEU | rs6708413 | 2 | 102429801 | 0.209 | 1 | HapMap | HapMap | G | 0.204 | A | 0.796 | G/A |
| MEX | rs6708413 | 2 | 102429801 | 0.304 | 1 | HapMap | HapMap | G | 0.44 | A | 0.56 | G/A |
| MKK | rs6708413 | 2 | 102429801 | 0.118 | 0.643 | HapMap | HapMap | G | 0.171 | A | 0.829 | G/A |
| LWK | rs6708413 | 2 | 102429801 | 0.051 | 1 | HapMap | HapMap | G | 0.139 | A | 0.861 | G/A |
| YRI | rs6708949 | 2 | 102490397 | 0.023 | 1 | HapMap | HapMap | G | 0.018 | C | 0.982 | G/C |
| MKK | rs6708949 | 2 | 102490397 | 0.072 | 0.774 | HapMap | HapMap | G | 0.08 | C | 0.92 | G/C |
| CEU | rs6708949 | 2 | 102490397 | 0.145 | 0.859 | HapMap | HapMap | G | 0.186 | C | 0.814 | G/C |
| GIH | rs6708949 | 2 | 102490397 | 0.045 | 0.658 | HapMap | HapMap | G | 0.273 | C | 0.727 | G/C |
| JPT | rs6708949 | 2 | 102490397 | 0.111 | 1 | HapMap | HapMap | G | 0.407 | C | 0.593 | G/C |
| ASW | rs6708949 | 2 | 102490397 | 0.031 | 1 | HapMap | HapMap | G | 0.009 | C | 0.991 | G/C |
| CHB | rs6708949 | 2 | 102490397 | 0.148 | 1 | HapMap | HapMap | G | 0.5 | C | 0.5 | G/C |
| CHD | rs6708949 | 2 | 102490397 | 0.125 | 1 | HapMap | HapMap | G | 0.494 | C | 0.506 | G/C |
| LWK | rs6708949 | 2 | 102490397 | 0.129 | 1 | HapMap | HapMap | G | 0.039 | C | 0.961 | G/C |
| GIH | rs6710528 | 2 | 102382574 | 0.703 | 0.924 | HapMap | HapMap | C | 0.756 | T | 0.244 | C/T |
| JPT | rs6710528 | 2 | 102382574 | 0.85 | 1 | HapMap | HapMap | C | 0.831 | T | 0.169 | C/T |
| MEX | rs6710528 | 2 | 102382574 | 0.709 | 0.939 | HapMap | HapMap | C | 0.68 | T | 0.32 | C/T |
| MKK | rs6710528 | 2 | 102382574 | 0.278 | 0.732 | HapMap | HapMap | C | 0.273 | T | 0.727 | C/T |
| ASW | rs6710528 | 2 | 102382574 | 0.353 | 0.712 | HapMap | HapMap | C | 0.245 | T | 0.755 | C/T |
| CEU | rs6710528 | 2 | 102382574 | 0.759 | 1 | HapMap | HapMap | C | 0.482 | T | 0.518 | C/T |
| CHB | rs6710528 | 2 | 102382574 | 0.564 | 0.892 | HapMap | HapMap | C | 0.833 | T | 0.167 | C/T |
| CHD | rs6710528 | 2 | 102382574 | 0.614 | 0.874 | HapMap | HapMap | C | 0.863 | T | 0.137 | C/T |
| ASW | rs6710885 | 2 | 102343969 | 0.871 | 1 | HapMap | HapMap | A | 0.717 | G | 0.283 | A/G |
| CEU | rs6710885 | 2 | 102343969 | 0.414 | 1 | HapMap | HapMap | A | 0.622 | G | 0.378 | A/G |
| CHB | rs6710885 | 2 | 102343969 | 0.111 | 1 | HapMap | HapMap | A | 0.613 | G | 0.387 | A/G |
| CHD | rs6710885 | 2 | 102343969 | 0.074 | 1 | HapMap | HapMap | A | 0.629 | G | 0.371 | A/G |
| GIH | rs6710885 | 2 | 102343969 | 0.132 | 1 | HapMap | HapMap | A | 0.665 | G | 0.335 | A/G |
| JPT | rs6710885 | 2 | 102343969 | 0.187 | 1 | HapMap | HapMap | A | 0.577 | G | 0.423 | A/G |
| LWK | rs6710885 | 2 | 102343969 | 0.818 | 0.965 | HapMap | HapMap | A | 0.787 | G | 0.213 | A/G |
| MKK | rs6710885 | 2 | 102343969 | 0.666 | 1 | HapMap | HapMap | A | 0.675 | G | 0.325 | A/G |
| YRI | rs6710885 | 2 | 102343969 | 0.829 | 1 | HapMap | HapMap | A | 0.792 | G | 0.208 | A/G |
| CEU | rs6724109 | 2 | 102491450 | 0.145 | 0.859 | HapMap | HapMap | C | 0.19 | G | 0.81 | C/G |
| CHD | rs6724109 | 2 | 102491450 | 0.039 | 0.627 | HapMap | HapMap | C | 0.565 | G | 0.435 | C/G |
| ASW | rs6731042 | 2 | 102214688 | 0.074 | 0.657 | HapMap | HapMap | C | 0.736 | A | 0.264 | C/A |
| MEX | rs6731042 | 2 | 102214688 | 0.118 | 0.848 | HapMap | HapMap | C | 0.69 | A | 0.31 | C/A |
| MKK | rs6731042 | 2 | 102214688 | 0.096 | 0.635 | HapMap | HapMap | C | 0.752 | A | 0.248 | C/A |
| CEU | rs6737325 | 2 | 102465225 | 0.047 | 1 | HapMap | HapMap | C | 0.929 | T | 0.071 | C/T |
| CHD | rs6737325 | 2 | 102465225 | 0.002 | 0.637 | HapMap | HapMap | C | 0.964 | T | 0.036 | C/T |
| GIH | rs6737325 | 2 | 102465225 | 0.01 | 1 | HapMap | HapMap | C | 0.966 | T | 0.034 | C/T |
| JPT | rs6737325 | 2 | 102465225 | 0.005 | 1 | HapMap | HapMap | C | 0.977 | T | 0.023 | C/T |
| MEX | rs6737325 | 2 | 102465225 | 0.017 | 1 | HapMap | HapMap | C | 0.96 | T | 0.04 | C/T |
| ASW | rs6741230 | 2 | 102436063 | 0.043 | 0.65 | HapMap | HapMap | C | 0.802 | T | 0.198 | C/T |
| CEU | rs6741230 | 2 | 102436063 | 0.264 | 1 | HapMap | HapMap | C | 0.845 | T | 0.155 | C/T |
| CHB | rs6741230 | 2 | 102436063 | 0.223 | 1 | HapMap | HapMap | C | 0.976 | T | 0.024 | C/T |
| CHD | rs6741230 | 2 | 102436063 | 0.093 | 0.697 | HapMap | HapMap | C | 0.976 | T | 0.024 | C/T |
| GIH | rs6741230 | 2 | 102436063 | 0.481 | 1 | HapMap | HapMap | C | 0.886 | T | 0.114 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| JPT | rs6741230 | 2 | 102436063 | 0.185 | 1 | HapMap | HapMap | C | 0.983 | T | 0.017 | C/T |
| LWK | rs6741230 | 2 | 102436063 | 0.058 | 1 | HapMap | HapMap | C | 0.844 | T | 0.156 | C/T |
| MEX | rs6741230 | 2 | 102436063 | 0.128 | 1 | HapMap | HapMap | C | 0.95 | T | 0.05 | C/T |
| MKK | rs6741230 | 2 | 102436063 | 0.111 | 0.863 | HapMap | HapMap | C | 0.829 | T | 0.171 | C/T |
| CEU | rs6741235 | 2 | 102483715 | 0.232 | 0.898 | HapMap | HapMap | G | 0.265 | A | 0.735 | G/A |
| CHD | rs6741235 | 2 | 102483715 | 0.021 | 0.639 | HapMap | HapMap | G | 0.706 | A | 0.294 | G/A |
| JPT | rs6741235 | 2 | 102483715 | 0.09 | 1 | HapMap | HapMap | G | 0.733 | A | 0.267 | G/A |
| ASW | rs6742280 | 2 | 102502769 | 0.038 | 1 | HapMap | HapMap | A | 0.915 | G | 0.085 | A/G |
| LWK | rs6742280 | 2 | 102502769 | 0.01 | 0.964 | HapMap | HapMap | A | 0.967 | G | 0.033 | A/G |
| YRI | rs6742280 | 2 | 102502769 | 0.035 | 1 | HapMap | HapMap | A | 0.912 | G | 0.088 | A/G |
| ASW | rs6743516 | 2 | 102402767 | 0.358 | 0.778 | HapMap | HapMap | A | 0.226 | G | 0.774 | A/G |
| CEU | rs6743516 | 2 | 102402767 | 0.759 | 1 | HapMap | HapMap | A | 0.473 | G | 0.527 | A/G |
| CHB | rs6743516 | 2 | 102402767 | 0.564 | 0.892 | HapMap | HapMap | A | 0.833 | G | 0.167 | A/G |
| CHD | rs6743516 | 2 | 102402767 | 0.615 | 0.874 | HapMap | HapMap | A | 0.865 | G | 0.135 | A/G |
| MEX | rs6743516 | 2 | 102402767 | 0.707 | 0.938 | HapMap | HapMap | A | 0.673 | G | 0.327 | A/G |
| MKK | rs6743516 | 2 | 102402767 | 0.223 | 0.699 | HapMap | HapMap | A | 0.248 | G | 0.752 | A/G |
| GIH | rs6743516 | 2 | 102402767 | 0.678 | 0.923 | HapMap | HapMap | A | 0.744 | G | 0.256 | A/G |
| JPT | rs6743516 | 2 | 102402767 | 0.85 | 1 | HapMap | HapMap | A | 0.829 | G | 0.171 | A/G |
| ASW | rs6744454 | 2 | 102165584 | 0.063 | 1 | HapMap | HapMap | G | 0.019 | A | 0.981 | G/A |
| CHB | rs6744454 | 2 | 102165584 | 0.002 | 1 | HapMap | HapMap | G | 0.006 | A | 0.994 | G/A |
| CHD | rs6744454 | 2 | 102165584 | 0.001 | 1 | HapMap | HapMap | G | 0.006 | A | 0.994 | G/A |
| GIH | rs6744454 | 2 | 102165584 | 0.045 | 1 | HapMap | HapMap | G | 0.142 | A | 0.858 | G/A |
| MKK | rs6744454 | 2 | 102165584 | 0.076 | 0.701 | HapMap | HapMap | G | 0.102 | A | 0.898 | G/A |
| CEU | rs6747153 | 2 | 102270259 | 0.148 | 0.622 | HapMap | HapMap | A | 0.246 | G | 0.754 | A/G |
| YRI | rs6747153 | 2 | 102270259 | 0.035 | 1 | HapMap | HapMap | A | 0.071 | G | 0.929 | A/G |
| CHD | rs6749014 | 2 | 102372880 | 0.649 | 0.876 | HapMap | HapMap | C | 0.869 | T | 0.131 | C/T |
| MKK | rs6749014 | 2 | 102372880 | 0.278 | 0.732 | HapMap | HapMap | C | 0.273 | T | 0.727 | C/T |
| CHB | rs6749014 | 2 | 102372880 | 0.564 | 0.892 | HapMap | HapMap | C | 0.833 | T | 0.167 | C/T |
| ASW | rs6749014 | 2 | 102372880 | 0.408 | 0.796 | HapMap | HapMap | C | 0.236 | T | 0.764 | C/T |
| CEU | rs6749014 | 2 | 102372880 | 0.759 | 1 | HapMap | HapMap | C | 0.482 | T | 0.518 | C/T |
| GIH | rs6749014 | 2 | 102372880 | 0.703 | 0.924 | HapMap | HapMap | C | 0.756 | T | 0.244 | C/T |
| JPT | rs6749014 | 2 | 102372880 | 0.85 | 1 | HapMap | HapMap | C | 0.831 | T | 0.169 | C/T |
| MEX | rs6749014 | 2 | 102372880 | 0.709 | 0.939 | HapMap | HapMap | C | 0.68 | T | 0.32 | C/T |
| CEU | rs6750851 | 2 | 102505193 | 0.145 | 0.859 | HapMap | HapMap | A | 0.192 | G | 0.808 | A/G |
| CHB | rs6750851 | 2 | 102505193 | 0.148 | 1 | HapMap | HapMap | A | 0.5 | G | 0.5 | A/G |
| CHD | rs6750851 | 2 | 102505193 | 0.119 | 1 | HapMap | HapMap | A | 0.494 | G | 0.506 | A/G |
| JPT | rs6750851 | 2 | 102505193 | 0.111 | 1 | HapMap | HapMap | A | 0.407 | G | 0.593 | A/G |
| GIH | rs6750851 | 2 | 102505193 | 0.04 | 0.625 | HapMap | HapMap | A | 0.273 | G | 0.727 | A/G |
| CEU | rs6751666 | 2 | 102465003 | 0.047 | 1 | HapMap | HapMap | A | 0.934 | G | 0.066 | A/G |
| CHD | rs6751666 | 2 | 102465003 | 0.002 | 0.614 | HapMap | HapMap | A | 0.965 | G | 0.035 | A/G |
| GIH | rs6751666 | 2 | 102465003 | 0.01 | 1 | HapMap | HapMap | A | 0.966 | G | 0.034 | A/G |
| JPT | rs6751666 | 2 | 102465003 | 0.005 | 1 | HapMap | HapMap | A | 0.977 | G | 0.023 | A/G |
| MEX | rs6751666 | 2 | 102465003 | 0.017 | 1 | HapMap | HapMap | A | 0.96 | G | 0.04 | A/G |
| CHD | rs6752589 | 2 | 102221730 | 0.02 | 1 | HapMap | HapMap | A | 0.135 | G | 0.865 | A/G |
| JPT | rs6752589 | 2 | 102221730 | 0.062 | 1 | HapMap | HapMap | A | 0.227 | G | 0.773 | A/G |
| LWK | rs6752589 | 2 | 102221730 | 0.018 | 0.676 | HapMap | HapMap | A | 0.111 | G | 0.889 | A/G |
| MEX | rs6752589 | 2 | 102221730 | 0.161 | 0.779 | HapMap | HapMap | A | 0.42 | G | 0.58 | A/G |
| MEX | rs6756407 | 2 | 102402533 | 0.013 | 1 | HapMap | HapMap | G | 0.97 | T | 0.03 | G/T |
| MKK | rs6756407 | 2 | 102402533 | 0.093 | 0.625 | HapMap | HapMap | G | 0.853 | T | 0.147 | G/T |
| CEU | rs6756407 | 2 | 102402533 | 0.056 | 1 | HapMap | HapMap | G | 0.92 | T | 0.08 | G/T |
| CHD | rs6756407 | 2 | 102402533 | 0.004 | 1 | HapMap | HapMap | G | 0.971 | T | 0.029 | G/T |
| GIH | rs6756407 | 2 | 102402533 | 0.008 | 1 | HapMap | HapMap | G | 0.972 | T | 0.028 | G/T |
| JPT | rs6756407 | 2 | 102402533 | 0.005 | 1 | HapMap | HapMap | G | 0.976 | T | 0.024 | G/T |
| LWK | rs6756407 | 2 | 102402533 | 0.177 | 0.731 | HapMap | HapMap | G | 0.906 | T | 0.094 | G/T |
| GIH | rs6758443 | 2 | 102214494 | 0.015 | 0.606 | HapMap | HapMap | G | 0.869 | T | 0.131 | G/T |
| MEX | rs6758443 | 2 | 102214494 | 0.085 | 0.607 | HapMap | HapMap | G | 0.61 | T | 0.39 | G/T |
| CHD | rs6758936 | 2 | 102357801 | 0.615 | 0.874 | HapMap | HapMap | G | 0.865 | A | 0.135 | G/A |
| GIH | rs6758936 | 2 | 102357801 | 0.703 | 0.924 | HapMap | HapMap | G | 0.756 | A | 0.244 | G/A |
| JPT | rs6758936 | 2 | 102357801 | 0.85 | 1 | HapMap | HapMap | G | 0.829 | A | 0.171 | G/A |
| MEX | rs6758936 | 2 | 102357801 | 0.709 | 0.939 | HapMap | HapMap | G | 0.68 | A | 0.32 | G/A |
| MKK | rs6758936 | 2 | 102357801 | 0.274 | 0.729 | HapMap | HapMap | G | 0.271 | A | 0.729 | G/A |
| CHB | rs6758936 | 2 | 102357801 | 0.562 | 0.891 | HapMap | HapMap | G | 0.831 | A | 0.169 | G/A |
| ASW | rs6758936 | 2 | 102357801 | 0.408 | 0.796 | HapMap | HapMap | G | 0.236 | A | 0.764 | G/A |
| CEU | rs6758936 | 2 | 102357801 | 0.759 | 1 | HapMap | HapMap | G | 0.482 | A | 0.518 | G/A |
| CHD | rs6761291 | 2 | 102521501 | 0.039 | 0.752 | HapMap | HapMap | C | 0.647 | T | 0.353 | C/T |
| JPT | rs741285 | 2 | 102514601 | 0.05 | 0.62 | HapMap | HapMap | C | 0.436 | T | 0.564 | C/T |
| CHB | rs741285 | 2 | 102514601 | 0.17 | 1 | HapMap | HapMap | C | 0.53 | T | 0.47 | C/T |
| CHD | rs741285 | 2 | 102514601 | 0.098 | 0.814 | HapMap | HapMap | C | 0.541 | T | 0.459 | C/T |
| LWK | rs7559479 | 2 | 102435219 | 0.032 | 0.764 | HapMap | HapMap | G | 0.15 | A | 0.85 | G/A |
| MEX | rs7559479 | 2 | 102435219 | 0.304 | 1 | HapMap | HapMap | G | 0.429 | A | 0.571 | G/A |
| MKK | rs7559479 | 2 | 102435219 | 0.117 | 0.64 | HapMap | HapMap | G | 0.173 | A | 0.827 | G/A |
| YRI | rs7559479 | 2 | 102435219 | 0.054 | 0.666 | HapMap | HapMap | G | 0.049 | A | 0.951 | G/A |
| ASW | rs7559479 | 2 | 102435219 | 0.022 | 1 | HapMap | HapMap | G | 0.038 | A | 0.962 | G/A |
| CEU | rs7559479 | 2 | 102435219 | 0.209 | 1 | HapMap | HapMap | G | 0.204 | A | 0.796 | G/A |
| CHB | rs7559479 | 2 | 102435219 | 0.141 | 1 | HapMap | HapMap | G | 0.476 | A | 0.524 | G/A |
| CHD | rs7559479 | 2 | 102435219 | 0.129 | 1 | HapMap | HapMap | G | 0.506 | A | 0.494 | G/A |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| GIH | rs7559479 | 2 | 102435219 | 0.141 | 0.803 | HapMap | HapMap | G | 0.443 | A | 0.557 | G/A |
| JPT | rs7559479 | 2 | 102435219 | 0.105 | 1 | HapMap | HapMap | G | 0.412 | A | 0.588 | G/A |
| ASW | rs7560478 | 2 | 102178958 | 0.085 | 0.794 | HapMap | HapMap | T | 0.783 | C | 0.217 | T/C |
| LWK | rs7560478 | 2 | 102178958 | 0.051 | 1 | HapMap | HapMap | T | 0.861 | C | 0.139 | T/C |
| MEX | rs7560478 | 2 | 102178958 | 0.118 | 0.848 | HapMap | HapMap | T | 0.69 | C | 0.31 | T/C |
| MKK | rs7560478 | 2 | 102178958 | 0.131 | 0.808 | HapMap | HapMap | T | 0.783 | C | 0.217 | T/C |
| JPT | rs7566613 | 2 | 102466927 | 0.005 | 1 | HapMap | HapMap | G | 0.977 | A | 0.023 | G/A |
| MEX | rs7566613 | 2 | 102466927 | 0.017 | 1 | HapMap | HapMap | G | 0.96 | A | 0.04 | G/A |
| CEU | rs7566613 | 2 | 102466927 | 0.047 | 1 | HapMap | HapMap | G | 0.934 | A | 0.066 | G/A |
| GIH | rs7566613 | 2 | 102466927 | 0.011 | 1 | HapMap | HapMap | G | 0.96 | A | 0.04 | G/A |
| CEU | rs7567885 | 2 | 102475284 | 0.222 | 0.893 | HapMap | HapMap | T | 0.268 | G | 0.732 | T/G |
| JPT | rs7567885 | 2 | 102475284 | 0.09 | 1 | HapMap | HapMap | T | 0.738 | G | 0.262 | T/G |
| CHB | rs7568913 | 2 | 102286469 | 0.141 | 1 | HapMap | HapMap | T | 0.47 | C | 0.53 | T/C |
| CHD | rs7568913 | 2 | 102286469 | 0.134 | 1 | HapMap | HapMap | T | 0.512 | C | 0.488 | T/C |
| JPT | rs7568913 | 2 | 102286469 | 0.095 | 1 | HapMap | HapMap | T | 0.384 | C | 0.616 | T/C |
| CEU | rs7570468 | 2 | 102206539 | 0.008 | 1 | HapMap | HapMap | C | 0.982 | A | 0.018 | C/A |
| MKK | rs7570468 | 2 | 102206539 | 0.017 | 0.655 | HapMap | HapMap | C | 0.972 | A | 0.028 | C/A |
| ASW | rs7571371 | 2 | 102320159 | 0.046 | 1 | HapMap | HapMap | C | 0.925 | T | 0.075 | C/T |
| JPT | rs7571371 | 2 | 102320159 | 0.002 | 1 | HapMap | HapMap | C | 0.994 | T | 0.006 | C/T |
| LWK | rs7571371 | 2 | 102320159 | 0.02 | 1 | HapMap | HapMap | C | 0.939 | T | 0.061 | C/T |
| MKK | rs7571371 | 2 | 102320159 | 0.037 | 1 | HapMap | HapMap | C | 0.951 | T | 0.049 | C/T |
| YRI | rs7571371 | 2 | 102320159 | 0.024 | 1 | HapMap | HapMap | C | 0.96 | T | 0.04 | C/T |
| CEU | rs7575867 | 2 | 102486611 | 0.245 | 1 | HapMap | HapMap | C | 0.863 | T | 0.137 | C/T |
| MKK | rs7575867 | 2 | 102486611 | 0.1 | 0.909 | HapMap | HapMap | C | 0.857 | T | 0.143 | C/T |
| LWK | rs7575867 | 2 | 102486611 | 0.055 | 1 | HapMap | HapMap | C | 0.85 | T | 0.15 | C/T |
| JPT | rs7575867 | 2 | 102486611 | 0.122 | 1 | HapMap | HapMap | C | 0.983 | T | 0.017 | C/T |
| CHB | rs7575867 | 2 | 102486611 | 0.147 | 1 | HapMap | HapMap | C | 0.988 | T | 0.012 | C/T |
| CEU | rs7579737 | 2 | 102353793 | 0.26 | 0.614 | HapMap | HapMap | A | 0.646 | G | 0.354 | A/G |
| GIH | rs7579737 | 2 | 102353793 | 0.291 | 0.669 | HapMap | HapMap | A | 0.852 | G | 0.148 | A/G |
| YRI | rs7582710 | 2 | 102353917 | 0.027 | 1 | HapMap | HapMap | T | 0.92 | G | 0.08 | T/G |
| ASW | rs7582710 | 2 | 102353917 | 0.046 | 1 | HapMap | HapMap | T | 0.925 | G | 0.075 | T/G |
| LWK | rs7582710 | 2 | 102353917 | 0.013 | 1 | HapMap | HapMap | T | 0.961 | G | 0.039 | T/G |
| MKK | rs7582710 | 2 | 102353917 | 0.032 | 1 | HapMap | HapMap | T | 0.958 | G | 0.042 | T/G |
| MEX | rs7583215 | 2 | 102220486 | 0.132 | 0.851 | HapMap | HapMap | C | 0.67 | T | 0.33 | C/T |
| MKK | rs7583215 | 2 | 102220486 | 0.112 | 0.619 | HapMap | HapMap | C | 0.708 | T | 0.292 | C/T |
| CEU | rs7583683 | 2 | 102480195 | 0.245 | 1 | HapMap | HapMap | A | 0.863 | G | 0.137 | A/G |
| CHB | rs7583683 | 2 | 102480195 | 0.073 | 1 | HapMap | HapMap | A | 0.994 | G | 0.006 | A/G |
| LWK | rs7583683 | 2 | 102480195 | 0.053 | 1 | HapMap | HapMap | A | 0.856 | G | 0.144 | A/G |
| MKK | rs7583683 | 2 | 102480195 | 0.101 | 1 | HapMap | HapMap | A | 0.878 | G | 0.122 | A/G |
| CHD | rs7591872 | 2 | 102479073 | 0.133 | 0.768 | HapMap | HapMap | G | 0.641 | C | 0.359 | G/C |
| GIH | rs7591872 | 2 | 102479073 | 0.059 | 0.713 | HapMap | HapMap | G | 0.295 | C | 0.705 | G/C |
| JPT | rs7591872 | 2 | 102479073 | 0.102 | 0.604 | HapMap | HapMap | G | 0.605 | C | 0.395 | G/C |
| YRI | rs7591872 | 2 | 102479073 | 0.015 | 1 | HapMap | HapMap | G | 0.031 | C | 0.969 | G/C |
| ASW | rs7591872 | 2 | 102479073 | 0.063 | 1 | HapMap | HapMap | G | 0.038 | C | 0.962 | G/C |
| CEU | rs7591872 | 2 | 102479073 | 0.232 | 0.898 | HapMap | HapMap | G | 0.27 | C | 0.73 | G/C |
| CHB | rs7591872 | 2 | 102479073 | 0.132 | 0.677 | HapMap | HapMap | G | 0.643 | C | 0.357 | G/C |
| CEU | rs759382 | 2 | 102460645 | 0.209 | 1 | HapMap | HapMap | G | 0.221 | T | 0.779 | G/T |
| CHB | rs759382 | 2 | 102460645 | 0.148 | 1 | HapMap | HapMap | G | 0.5 | T | 0.5 | G/T |
| CHD | rs759382 | 2 | 102460645 | 0.138 | 1 | HapMap | HapMap | G | 0.524 | T | 0.476 | G/T |
| JPT | rs759382 | 2 | 102460645 | 0.111 | 1 | HapMap | HapMap | G | 0.424 | T | 0.576 | G/T |
| MKK | rs759382 | 2 | 102460645 | 0.109 | 0.625 | HapMap | HapMap | G | 0.168 | T | 0.832 | G/T |
| GIH | rs759382 | 2 | 102460645 | 0.108 | 0.71 | HapMap | HapMap | G | 0.438 | T | 0.562 | G/T |
| MEX | rs759382 | 2 | 102460645 | 0.304 | 1 | HapMap | HapMap | G | 0.44 | T | 0.56 | G/T |
| LWK | rs7600961 | 2 | 102401887 | 0.055 | 1 | HapMap | HapMap | G | 0.85 | A | 0.15 | G/A |
| MEX | rs7600961 | 2 | 102401887 | 0.128 | 1 | HapMap | HapMap | G | 0.95 | A | 0.05 | G/A |
| MKK | rs7600961 | 2 | 102401887 | 0.134 | 0.882 | HapMap | HapMap | G | 0.808 | A | 0.192 | G/A |
| CEU | rs7600961 | 2 | 102401887 | 0.264 | 1 | HapMap | HapMap | G | 0.845 | A | 0.155 | G/A |
| CHB | rs7600961 | 2 | 102401887 | 0.223 | 1 | HapMap | HapMap | G | 0.976 | A | 0.024 | G/A |
| CHD | rs7600961 | 2 | 102401887 | 0.093 | 0.697 | HapMap | HapMap | G | 0.976 | A | 0.024 | G/A |
| GIH | rs7600961 | 2 | 102401887 | 0.481 | 1 | HapMap | HapMap | G | 0.886 | A | 0.114 | G/A |
| JPT | rs7600961 | 2 | 102401887 | 0.185 | 1 | HapMap | HapMap | G | 0.983 | A | 0.017 | G/A |
| CEU | rs7601773 | 2 | 102486915 | 0.245 | 1 | HapMap | HapMap | G | 0.863 | T | 0.137 | G/T |
| CHB | rs7601773 | 2 | 102486915 | 0.147 | 1 | HapMap | HapMap | G | 0.988 | T | 0.012 | G/T |
| JPT | rs7601773 | 2 | 102486915 | 0.122 | 1 | HapMap | HapMap | G | 0.983 | T | 0.017 | G/T |
| MKK | rs7601773 | 2 | 102486915 | 0.1 | 0.909 | HapMap | HapMap | G | 0.857 | T | 0.143 | G/T |
| LWK | rs7601773 | 2 | 102486915 | 0.055 | 1 | HapMap | HapMap | G | 0.85 | T | 0.15 | G/T |
| ASW | rs7603730 | 2 | 102340803 | 0.877 | 1 | HapMap | HapMap | A | 0.33 | C | 0.67 | A/C |
| CEU | rs7603730 | 2 | 102340803 | 1 | 1 | HapMap | HapMap | A | 0.593 | C | 0.407 | A/C |
| CHB | rs7603730 | 2 | 102340803 | 1 | 1 | HapMap | HapMap | A | 0.857 | C | 0.143 | A/C |
| CHD | rs7603730 | 2 | 102340803 | 1 | 1 | HapMap | HapMap | A | 0.888 | C | 0.112 | A/C |
| GIH | rs7603730 | 2 | 102340803 | 1 | 1 | HapMap | HapMap | A | 0.79 | C | 0.21 | A/C |
| JPT | rs7603730 | 2 | 102340803 | 1 | 1 | HapMap | HapMap | A | 0.849 | C | 0.151 | A/C |
| LWK | rs7603730 | 2 | 102340803 | 0.569 | 1 | HapMap | HapMap | A | 0.356 | C | 0.644 | A/C |
| MEX | rs7603730 | 2 | 102340803 | 1 | 1 | HapMap | HapMap | A | 0.73 | C | 0.27 | A/C |
| MKK | rs7603730 | 2 | 102340803 | 0.855 | 1 | HapMap | HapMap | A | 0.458 | C | 0.542 | A/C |
| YRI | rs7603730 | 2 | 102340803 | 0.956 | 1 | HapMap | HapMap | A | 0.257 | C | 0.743 | A/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs871657 | 2 | 102137773 | 0.189 | 0.878 | HapMap | HapMap | C | 0.836 | T | 0.164 | C/T |
| CHB | rs871657 | 2 | 102137773 | 0.063 | 1 | HapMap | HapMap | C | 0.732 | T | 0.268 | C/T |
| MEX | rs871657 | 2 | 102137773 | 0.369 | 0.892 | HapMap | HapMap | C | 0.85 | T | 0.15 | C/T |
| CEU | rs871659 | 2 | 102138287 | 0.112 | 0.732 | HapMap | HapMap | G | 0.23 | A | 0.77 | G/A |
| JPT | rs871659 | 2 | 102138287 | 0.03 | 1 | HapMap | HapMap | G | 0.105 | A | 0.895 | G/A |
| YRI | rs871659 | 2 | 102138287 | 0.054 | 0.666 | HapMap | HapMap | G | 0.062 | A | 0.938 | G/A |
| CHB | rs885088 | 2 | 102405476 | 0.564 | 0.892 | HapMap | HapMap | A | 0.833 | G | 0.167 | A/G |
| CHD | rs885088 | 2 | 102405476 | 0.615 | 0.874 | HapMap | HapMap | A | 0.865 | G | 0.135 | A/G |
| GIH | rs885088 | 2 | 102405476 | 0.68 | 0.923 | HapMap | HapMap | A | 0.75 | G | 0.25 | A/G |
| JPT | rs885088 | 2 | 102405476 | 0.85 | 1 | HapMap | HapMap | A | 0.831 | G | 0.169 | A/G |
| MEX | rs885088 | 2 | 102405476 | 0.672 | 0.937 | HapMap | HapMap | A | 0.67 | G | 0.33 | A/G |
| MKK | rs885088 | 2 | 102405476 | 0.214 | 0.692 | HapMap | HapMap | A | 0.245 | G | 0.755 | A/G |
| ASW | rs885088 | 2 | 102405476 | 0.358 | 0.778 | HapMap | HapMap | A | 0.226 | G | 0.774 | A/G |
| CEU | rs885088 | 2 | 102405476 | 0.759 | 1 | HapMap | HapMap | A | 0.482 | G | 0.518 | A/G |
| JPT | rs917997 | 2 | 102437000 | 0.105 | 1 | HapMap | HapMap | T | 0.413 | C | 0.587 | T/C |
| LWK | rs917997 | 2 | 102437000 | 0.032 | 0.764 | HapMap | HapMap | T | 0.15 | C | 0.85 | T/C |
| MEX | rs917997 | 2 | 102437000 | 0.304 | 1 | HapMap | HapMap | T | 0.44 | C | 0.56 | T/C |
| CHB | rs917997 | 2 | 102437000 | 0.141 | 1 | HapMap | HapMap | T | 0.476 | C | 0.524 | T/C |
| CHD | rs917997 | 2 | 102437000 | 0.129 | 1 | HapMap | HapMap | T | 0.506 | C | 0.494 | T/C |
| GIH | rs917997 | 2 | 102437000 | 0.141 | 0.803 | HapMap | HapMap | T | 0.443 | C | 0.557 | T/C |
| ASW | rs917997 | 2 | 102437000 | 0.022 | 1 | HapMap | HapMap | T | 0.038 | C | 0.962 | T/C |
| CEU | rs917997 | 2 | 102437000 | 0.209 | 1 | HapMap | HapMap | T | 0.204 | C | 0.796 | T/C |
| MKK | rs917997 | 2 | 102437000 | 0.118 | 0.643 | HapMap | HapMap | T | 0.171 | C | 0.829 | T/C |
| YRI | rs917997 | 2 | 102437000 | 0.054 | 0.666 | HapMap | HapMap | T | 0.049 | C | 0.951 | T/C |
| ASW | rs917998 | 2 | 102434588 | 0.031 | 1 | HapMap | HapMap | C | 0.962 | T | 0.038 | C/T |
| CEU | rs917998 | 2 | 102434588 | 0.21 | 1 | HapMap | HapMap | C | 0.881 | T | 0.119 | C/T |
| LWK | rs917998 | 2 | 102434588 | 0.002 | 1 | HapMap | HapMap | C | 0.994 | T | 0.006 | C/T |
| MEX | rs917998 | 2 | 102434588 | 0.196 | 1 | HapMap | HapMap | C | 0.94 | T | 0.06 | C/T |
| YRI | rs917998 | 2 | 102434588 | 0.019 | 1 | HapMap | HapMap | C | 0.96 | T | 0.04 | C/T |
| ASW | rs9308856 | 2 | 102261874 | 0.038 | 1 | HapMap | HapMap | A | 0.943 | G | 0.057 | A/G |
| LWK | rs9308856 | 2 | 102261874 | 0.017 | 1 | HapMap | HapMap | A | 0.95 | G | 0.05 | A/G |
| MEX | rs9308856 | 2 | 102261874 | 0.031 | 1 | HapMap | HapMap | A | 0.99 | G | 0.01 | A/G |
| MKK | rs9308856 | 2 | 102261874 | 0.078 | 1 | HapMap | HapMap | A | 0.902 | G | 0.098 | A/G |
| YRI | rs9308856 | 2 | 102261874 | 0.023 | 1 | HapMap | HapMap | A | 0.947 | G | 0.053 | A/G |
| CEU | rs949963 | 2 | 102136218 | 0.189 | 0.878 | HapMap | HapMap | C | 0.836 | T | 0.164 | C/T |
| CHB | rs949963 | 2 | 102136218 | 0.063 | 1 | HapMap | HapMap | C | 0.732 | T | 0.268 | C/T |
| MEX | rs949963 | 2 | 102136218 | 0.369 | 0.892 | HapMap | HapMap | C | 0.85 | T | 0.15 | C/T |
| GIH | rs951193 | 2 | 102152231 | 0.003 | 1 | HapMap | HapMap | C | 0.989 | T | 0.011 | C/T |
| ASW | rs951774 | 2 | 102279096 | 0.063 | 1 | HapMap | HapMap | C | 0.953 | A | 0.047 | C/A |
| CEU | rs951774 | 2 | 102279096 | 0.209 | 1 | HapMap | HapMap | C | 0.823 | A | 0.177 | C/A |
| CHB | rs951774 | 2 | 102279096 | 0.049 | 1 | HapMap | HapMap | C | 0.78 | A | 0.22 | C/A |
| CHD | rs951774 | 2 | 102279096 | 0.018 | 0.681 | HapMap | HapMap | C | 0.759 | A | 0.241 | C/A |
| GIH | rs951774 | 2 | 102279096 | 0.149 | 0.9 | HapMap | HapMap | C | 0.603 | A | 0.397 | C/A |
| LWK | rs951774 | 2 | 102279096 | 0.112 | 0.646 | HapMap | HapMap | C | 0.921 | A | 0.079 | C/A |
| MEX | rs951774 | 2 | 102279096 | 0.242 | 1 | HapMap | HapMap | C | 0.61 | A | 0.39 | C/A |
| MKK | rs951774 | 2 | 102279096 | 0.115 | 1 | HapMap | HapMap | C | 0.923 | A | 0.077 | C/A |
| YRI | rs951774 | 2 | 102279096 | 0.131 | 0.81 | HapMap | HapMap | C | 0.947 | A | 0.053 | C/A |
| GIH | rs955754 | 2 | 102215513 | 0.015 | 0.606 | HapMap | HapMap | T | 0.869 | C | 0.131 | T/C |
| MEX | rs955754 | 2 | 102215513 | 0.085 | 0.607 | HapMap | HapMap | T | 0.61 | C | 0.39 | T/C |
| ASW | rs995515 | 2 | 102205814 | 0.103 | 0.712 | HapMap | HapMap | T | 0.915 | C | 0.085 | T/C |
| LWK | rs995515 | 2 | 102205814 | 0.077 | 0.771 | HapMap | HapMap | T | 0.961 | C | 0.039 | T/C |
| YRI | rs995515 | 2 | 102205814 | 0.047 | 1 | HapMap | HapMap | T | 0.987 | C | 0.013 | T/C |
| LWK | rs17026901 | 2 | 102256818 | 0.018 | 1 | HapMap | HapMap | T | 0.994 | C | 0.006 | T/C |
| CHB | rs17026901 | 2 | 102256818 | 0.028 | 1 | HapMap | HapMap | T | 0.869 | C | 0.131 | T/C |
| CHB | rs11904409 | 2 | 102169616 | 0.073 | 1 | HapMap | HapMap | G | 0.97 | A | 0.03 | G/A |
| LWK | rs2310239 | 2 | 102190633 | 0.072 | 0.657 | HapMap | HapMap | G | 0.95 | A | 0.05 | G/A |
| ASW | rs2310239 | 2 | 102190633 | 0.072 | 0.64 | HapMap | HapMap | G | 0.923 | A | 0.077 | G/A |
| MKK | rs887972 | 2 | 102407377 | 0.023 | 0.714 | HapMap | HapMap | G | 0.968 | A | 0.032 | G/A |
| GIH | rs887972 | 2 | 102407377 | 0.119 | 0.86 | HapMap | HapMap | G | 0.625 | A | 0.375 | G/A |
| MEX | rs1041973 | 2 | 102321900 | 0.284 | 0.666 | HapMap | HapMap | C | 0.796 | A | 0.204 | C/A |
| CHD | rs1041973 | 2 | 102321900 | 0.537 | 0.783 | HapMap | HapMap | C | 0.89 | A | 0.11 | C/A |
| JPT | rs1041973 | 2 | 102321900 | 0.531 | 0.729 | HapMap | HapMap | C | 0.823 | A | 0.177 | C/A |
| CEU | rs1041973 | 2 | 102321900 | 0.148 | 0.852 | HapMap | HapMap | C | 0.802 | A | 0.198 | C/A |
| MKK | rs1362347 | 2 | 102286017 | 0.412 | 1 | HapMap | HapMap | C | 0.77 | T | 0.23 | C/T |
| YRI | rs1362347 | 2 | 102286017 | 0.227 | 1 | HapMap | HapMap | C | 0.928 | T | 0.072 | C/T |
| CHB | rs1861245 | 2 | 102966906 | 1 | 1 | HapMap | 1000GP | A | NA | G | NA | A/G |
| JPT | rs1861245 | 2 | 102966906 | 1 | 1 | HapMap | 1000GP | A | NA | G | NA | A/G |
| JPT | rs7559566 | 2 | 103028041 | 0.831 | 1 | HapMap | 1000GP | G | NA | T | NA | G/T |
| CHB | rs7559566 | 2 | 103028041 | 0.562 | 0.891 | HapMap | 1000GP | G | NA | T | NA | G/T |
| JPT | rs6705385 | 2 | 103076569 | 0.058 | 0.65 | HapMap | 1000GP | A | 0.53 | C | 0.47 | A/C |
| JPT | rs6705498 | 2 | 103076670 | 0.058 | 0.65 | HapMap | 1000GP | A | 0.53 | G | 0.47 | A/G |
| JPT | rs6719196 | 2 | 103076888 | 0.058 | 0.65 | HapMap | 1000GP | G | 0.53 | T | 0.47 | G/T |
| JPT | rs12463588 | 2 | 103085257 | 0.058 | 0.65 | HapMap | 1000GP | C | 0.53 | G | 0.47 | C/G |
| JPT | rs2310302 | 2 | 103086049 | 0.058 | 0.65 | HapMap | 1000GP | G | 0.53 | C | 0.47 | G/C |
| JPT | rs12469887 | 2 | 103086758 | 0.058 | 0.65 | HapMap | 1000GP | T | 0.53 | C | 0.47 | T/C |
| JPT | rs4140786 | 2 | 103088176 | 0.058 | 0.65 | HapMap | 1000GP | G | 0.53 | T | 0.47 | G/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| JPT | rs4851614 | 2 | 103140398 | 0.05 | 0.62 | HapMap | 1000GP | C | 0.53 | T | 0.47 | C/T |
| CHB | rs4851614 | 2 | 103140398 | 0.175 | 1 | HapMap | 1000GP | C | 0.53 | T | 0.47 | C/T |
| JPT | rs1357471 | 2 | 103140472 | 0.05 | 0.62 | HapMap | 1000GP | C | 0.53 | T | 0.47 | C/T |
| CHB | rs1357471 | 2 | 103140472 | 0.17 | 1 | HapMap | 1000GP | C | 0.53 | T | 0.47 | C/T |
| JPT | rs4241211 | 2 | 103143159 | 0.05 | 0.62 | HapMap | 1000GP | T | 0.53 | G | 0.47 | T/G |
| CHB | rs4241211 | 2 | 103143159 | 0.17 | 1 | HapMap | 1000GP | T | 0.53 | G | 0.47 | T/G |
| JPT | rs12712156 | 2 | 103144020 | 0.05 | 0.62 | HapMap | 1000GP | A | 0.53 | C | 0.47 | A/C |
| CHB | rs12712156 | 2 | 103144020 | 0.163 | 1 | HapMap | 1000GP | A | 0.53 | C | 0.47 | A/C |
| CHB | rs3849364 | 2 | 103144242 | 0.17 | 1 | HapMap | 1000GP | T | 0.53 | C | 0.47 | T/C |
| JPT | rs3849364 | 2 | 103144242 | 0.05 | 0.62 | HapMap | 1000GP | T | 0.53 | C | 0.47 | T/C |
| JPT | rs3849365 | 2 | 103144391 | 0.05 | 0.615 | HapMap | 1000GP | G | 0.53 | A | 0.47 | G/A |
| CHB | rs3849365 | 2 | 103144391 | 0.17 | 1 | HapMap | 1000GP | G | 0.53 | A | 0.47 | G/A |
| CHB | rs1005042 | 2 | 103145359 | 0.186 | 1 | HapMap | 1000GP | A | 0.53 | G | 0.47 | A/G |
| JPT | rs1005042 | 2 | 103145359 | 0.05 | 0.615 | HapMap | 1000GP | A | 0.53 | G | 0.47 | A/G |
| JPT | rs4851018 | 2 | 103146615 | 0.05 | 0.62 | HapMap | 1000GP | C | 0.53 | T | 0.47 | C/T |
| CHB | rs4851018 | 2 | 103146615 | 0.17 | 1 | HapMap | 1000GP | C | 0.53 | T | 0.47 | C/T |
| CHB | rs6737119 | 2 | 103151109 | 0.158 | 1 | HapMap | 1000GP | G | 0.53 | A | 0.47 | G/A |
| JPT | rs6737119 | 2 | 103151109 | 0.05 | 0.62 | HapMap | 1000GP | G | 0.53 | A | 0.47 | G/A |
| CHB | rs6709284 | 2 | 103151164 | 0.17 | 1 | HapMap | 1000GP | C | 0.53 | G | 0.47 | C/G |
| JPT | rs6709284 | 2 | 103151164 | 0.05 | 0.62 | HapMap | 1000GP | C | 0.53 | G | 0.47 | C/G |
| JPT | rs2177317 | 2 | 103151319 | 0.05 | 0.62 | HapMap | 1000GP | A | 0.53 | G | 0.47 | A/G |
| CHB | rs2177317 | 2 | 103151319 | 0.17 | 1 | HapMap | 1000GP | A | 0.53 | G | 0.47 | A/G |
| JPT | rs4851617 | 2 | 103152060 | 0.05 | 0.62 | HapMap | 1000GP | C | 0.53 | T | 0.47 | C/T |
| CHB | rs4851617 | 2 | 103152060 | 0.17 | 1 | HapMap | 1000GP | C | 0.53 | T | 0.47 | C/T |
| JPT | rs4292112 | 2 | 103153780 | 0.05 | 0.62 | HapMap | 1000GP | G | 0.53 | A | 0.47 | G/A |
| CHB | rs4292112 | 2 | 103153780 | 0.17 | 1 | HapMap | 1000GP | G | 0.53 | A | 0.47 | G/A |
| JPT | rs10490202 | 2 | 103160832 | 0.05 | 0.62 | HapMap | 1000GP | C | 0.53 | G | 0.47 | C/G |
| CHB | rs10490202 | 2 | 103160832 | 0.17 | 1 | HapMap | 1000GP | C | 0.53 | G | 0.47 | C/G |
| CHB | rs7581853 | 2 | 103167724 | 0.17 | 1 | HapMap | 1000GP | C | 0.53 | T | 0.47 | C/T |
| CHB | rs950880 | 2 | 102932562 | 0.111 | 1 | HapMap | 1000GP | C | 0.56 | A | 0.44 | C/A |
| JPT | rs950880 | 2 | 102932562 | 0.21 | 1 | HapMap | 1000GP | C | 0.56 | A | 0.44 | C/A |
| CHB | rs13001325 | 2 | 102939036 | 0.111 | 1 | HapMap | 1000GP | C | 0.56 | T | 0.44 | C/T |
| JPT | rs13001325 | 2 | 102939036 | 0.21 | 1 | HapMap | 1000GP | C | 0.56 | T | 0.44 | C/T |
| CHB | rs12479210 | 2 | 102949161 | 0.111 | 1 | HapMap | 1000GP | C | 0.56 | T | 0.44 | C/T |
| JPT | rs12479210 | 2 | 102949161 | 0.21 | 1 | HapMap | 1000GP | C | 0.56 | T | 0.44 | C/T |
| CHB | rs13017455 | 2 | 102964742 | 0.111 | 1 | HapMap | 1000GP | C | 0.56 | T | 0.44 | C/T |
| JPT | rs13017455 | 2 | 102964742 | 0.21 | 1 | HapMap | 1000GP | C | 0.56 | T | 0.44 | C/T |
| CHB | rs1024798 | 2 | 103141651 | 0.155 | 1 | HapMap | 1000GP | G | 0.56 | C | 0.44 | G/C |
| JPT | rs1024798 | 2 | 103141651 | 0.111 | 1 | HapMap | 1000GP | G | 0.56 | C | 0.44 | G/C |
| JPT | rs2871474 | 2 | 103151441 | 0.111 | 1 | HapMap | 1000GP | G | 0.56 | A | 0.44 | G/A |
| CHB | rs2871474 | 2 | 103151441 | 0.155 | 1 | HapMap | 1000GP | G | 0.56 | A | 0.44 | G/A |
| CHB | rs11685483 | 2 | 103159093 | 0.155 | 1 | HapMap | 1000GP | A | 0.56 | C | 0.44 | A/C |
| JPT | rs11685483 | 2 | 103159093 | 0.111 | 1 | HapMap | 1000GP | A | 0.56 | C | 0.44 | A/C |
| JPT | rs6739426 | 2 | 103160443 | 0.111 | 1 | HapMap | 1000GP | A | 0.56 | G | 0.44 | A/G |
| CHB | rs6739426 | 2 | 103160443 | 0.155 | 1 | HapMap | 1000GP | A | 0.56 | G | 0.44 | A/G |
| JPT | rs11899041 | 2 | 103161053 | 0.111 | 1 | HapMap | 1000GP | T | 0.56 | A | 0.44 | T/A |
| CHB | rs11899041 | 2 | 103161053 | 0.155 | 1 | HapMap | 1000GP | T | 0.56 | A | 0.44 | T/A |
| CHB | rs1303960 | 2 | 103165832 | 0.155 | 1 | HapMap | 1000GP | G | 0.56 | A | 0.44 | G/A |
| JPT | rs1303960 | 2 | 103165832 | 0.111 | 1 | HapMap | 1000GP | G | 0.56 | A | 0.44 | G/A |
| JPT | rs6543119 | 2 | 102963072 | 0.21 | 1 | HapMap | 1000GP | A | 0.57 | T | 0.43 | A/T |
| CHB | rs6543119 | 2 | 102963072 | 0.111 | 1 | HapMap | 1000GP | A | 0.57 | T | 0.43 | A/T |
| JPT | rs6718157 | 2 | 103079814 | 0.105 | 1 | HapMap | 1000GP | A | 0.57 | T | 0.43 | A/T |
| CHB | rs6718157 | 2 | 103079814 | 0.141 | 1 | HapMap | 1000GP | A | 0.57 | T | 0.43 | A/T |
| CHB | rs6737668 | 2 | 103093081 | 0.148 | 1 | HapMap | 1000GP | C | 0.57 | T | 0.43 | C/T |
| JPT | rs6737668 | 2 | 103093081 | 0.105 | 1 | HapMap | 1000GP | C | 0.57 | T | 0.43 | C/T |
| CHB | rs759381 | 2 | 103094323 | 0.141 | 1 | HapMap | 1000GP | A | 0.57 | T | 0.43 | A/T |
| JPT | rs759381 | 2 | 103094323 | 0.117 | 1 | HapMap | 1000GP | A | 0.57 | T | 0.43 | A/T |
| CHB | rs6724322 | 2 | 103125182 | 0.148 | 1 | HapMap | 1000GP | C | 0.57 | T | 0.43 | C/T |
| JPT | rs6724322 | 2 | 103125182 | 0.111 | 1 | HapMap | 1000GP | C | 0.57 | T | 0.43 | C/T |
| CHB | rs4851609 | 2 | 103128866 | 0.148 | 1 | HapMap | 1000GP | T | 0.57 | C | 0.43 | T/C |
| JPT | rs4851609 | 2 | 103128866 | 0.111 | 1 | HapMap | 1000GP | T | 0.57 | C | 0.43 | T/C |
| JPT | rs2192758 | 2 | 103132269 | 0.111 | 1 | HapMap | 1000GP | C | 0.57 | G | 0.43 | C/G |
| CHB | rs2192758 | 2 | 103132269 | 0.148 | 1 | HapMap | 1000GP | C | 0.57 | G | 0.43 | C/G |
| CHB | rs2192757 | 2 | 103132378 | 0.148 | 1 | HapMap | 1000GP | C | 0.57 | T | 0.43 | C/T |
| JPT | rs2192757 | 2 | 103132378 | 0.111 | 1 | HapMap | 1000GP | C | 0.57 | T | 0.43 | C/T |
| CHB | rs6714379 | 2 | 103133310 | 0.144 | 1 | HapMap | 1000GP | A | 0.57 | G | 0.43 | A/G |
| JPT | rs6714379 | 2 | 103133310 | 0.109 | 1 | HapMap | 1000GP | A | 0.57 | G | 0.43 | A/G |
| CHB | rs4851610 | 2 | 103134652 | 0.148 | 1 | HapMap | 1000GP | C | 0.57 | G | 0.43 | C/G |
| JPT | rs4851610 | 2 | 103134652 | 0.111 | 1 | HapMap | 1000GP | C | 0.57 | G | 0.43 | C/G |
| CHB | rs1523203 | 2 | 103135759 | 0.148 | 1 | HapMap | 1000GP | A | 0.57 | G | 0.43 | A/G |
| JPT | rs1523203 | 2 | 103135759 | 0.111 | 1 | HapMap | 1000GP | A | 0.57 | G | 0.43 | A/G |
| JPT | rs4851611 | 2 | 103135938 | 0.111 | 1 | HapMap | 1000GP | A | 0.57 | T | 0.43 | A/T |
| CHB | rs4851611 | 2 | 103135938 | 0.148 | 1 | HapMap | 1000GP | A | 0.57 | T | 0.43 | A/T |
| CHB | rs4851613 | 2 | 103137990 | 0.148 | 1 | HapMap | 1000GP | T | 0.57 | C | 0.43 | T/C |
| JPT | rs4851613 | 2 | 103137990 | 0.111 | 1 | HapMap | 1000GP | T | 0.57 | C | 0.43 | T/C |
| CHB | rs6750971 | 2 | 103138825 | 0.148 | 1 | HapMap | 1000GP | A | 0.57 | G | 0.43 | A/G |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| JPT | rs6750971 | 2 | 103138825 | 0.111 | 1 | HapMap | 1000GP | A | 0.57 | G | 0.43 | A/G |
| JPT | rs11123935 | 2 | 103139751 | 0.111 | 1 | HapMap | 1000GP | A | 0.57 | G | 0.43 | A/G |
| CHB | rs11123935 | 2 | 103139751 | 0.148 | 1 | HapMap | 1000GP | A | 0.57 | G | 0.43 | A/G |
| CHB | rs997049 | 2 | 102782433 | 0.047 | 0.603 | HapMap | 1000GP | T | 0.58 | A | 0.42 | T/A |
| JPT | rs2310220 | 2 | 102951851 | 0.095 | 1 | HapMap | 1000GP | G | 0.58 | A | 0.42 | G/A |
| CHB | rs2310220 | 2 | 102951851 | 0.135 | 1 | HapMap | 1000GP | G | 0.58 | A | 0.42 | G/A |
| JPT | rs2058622 | 2 | 102985424 | 0.107 | 1 | HapMap | 1000GP | A | 0.58 | G | 0.42 | A/G |
| CHB | rs2058622 | 2 | 102985424 | 0.127 | 1 | HapMap | 1000GP | A | 0.58 | G | 0.42 | A/G |
| JPT | rs3771170 | 2 | 102985980 | 0.105 | 1 | HapMap | 1000GP | T | 0.58 | A | 0.42 | T/A |
| CHB | rs3771170 | 2 | 102985980 | 0.124 | 1 | HapMap | 1000GP | T | 0.58 | A | 0.42 | T/A |
| JPT | rs2058623 | 2 | 102986170 | 0.107 | 1 | HapMap | 1000GP | C | 0.58 | T | 0.42 | C/T |
| CHB | rs2058623 | 2 | 102986170 | 0.124 | 1 | HapMap | 1000GP | C | 0.58 | T | 0.42 | C/T |
| CHB | rs1465321 | 2 | 102986618 | 0.127 | 1 | HapMap | 1000GP | T | 0.58 | C | 0.42 | T/C |
| JPT | rs1465321 | 2 | 102986618 | 0.108 | 1 | HapMap | 1000GP | T | 0.58 | C | 0.42 | T/C |
| JPT | rs2270297 | 2 | 102992675 | 0.105 | 1 | HapMap | 1000GP | T | 0.58 | C | 0.42 | T/C |
| CHB | rs2270297 | 2 | 102992675 | 0.135 | 1 | HapMap | 1000GP | T | 0.58 | C | 0.42 | T/C |
| CHB | rs6753717 | 2 | 102993161 | 0.135 | 1 | HapMap | 1000GP | A | 0.58 | C | 0.42 | A/C |
| JPT | rs6753717 | 2 | 102993161 | 0.105 | 1 | HapMap | 1000GP | A | 0.58 | C | 0.42 | A/C |
| JPT | rs6750020 | 2 | 102994714 | 0.109 | 1 | HapMap | 1000GP | G | 0.58 | A | 0.42 | G/A |
| CHB | rs6750020 | 2 | 102994714 | 0.144 | 1 | HapMap | 1000GP | G | 0.58 | A | 0.42 | G/A |
| CHB | rs17027037 | 2 | 102994884 | 0.038 | 0.642 | HapMap | 1000GP | A | 0.58 | G | 0.42 | A/G |
| JPT | rs17027037 | 2 | 102994884 | 0.173 | 1 | HapMap | 1000GP | A | 0.58 | G | 0.42 | A/G |
| JPT | rs2080289 | 2 | 102995020 | 0.173 | 1 | HapMap | 1000GP | G | 0.58 | A | 0.42 | G/A |
| CHB | rs2080289 | 2 | 102995020 | 0.038 | 0.642 | HapMap | 1000GP | G | 0.58 | A | 0.42 | G/A |
| JPT | rs11683700 | 2 | 102996805 | 0.191 | 1 | HapMap | 1000GP | C | 0.58 | T | 0.42 | C/T |
| CHB | rs4851570 | 2 | 103006387 | 0.038 | 0.642 | HapMap | 1000GP | A | 0.58 | G | 0.42 | A/G |
| JPT | rs4851570 | 2 | 103006387 | 0.173 | 1 | HapMap | 1000GP | A | 0.58 | G | 0.42 | A/G |
| JPT | rs4851007 | 2 | 103024813 | 0.105 | 1 | HapMap | 1000GP | T | 0.58 | G | 0.42 | T/G |
| CHB | rs4851007 | 2 | 103024813 | 0.141 | 1 | HapMap | 1000GP | T | 0.58 | G | 0.42 | T/G |
| CHB | rs4851575 | 2 | 103025203 | 0.141 | 1 | HapMap | 1000GP | G | 0.58 | A | 0.42 | G/A |
| JPT | rs4851575 | 2 | 103025203 | 0.105 | 1 | HapMap | 1000GP | G | 0.58 | A | 0.42 | G/A |
| JPT | rs4851008 | 2 | 103026611 | 0.105 | 1 | HapMap | 1000GP | G | 0.58 | C | 0.42 | G/C |
| CHB | rs4851008 | 2 | 103026611 | 0.141 | 1 | HapMap | 1000GP | G | 0.58 | C | 0.42 | G/C |
| CHB | rs1807782 | 2 | 103033147 | 0.141 | 1 | HapMap | 1000GP | C | 0.58 | T | 0.42 | C/T |
| JPT | rs1807782 | 2 | 103033147 | 0.105 | 1 | HapMap | 1000GP | C | 0.58 | T | 0.42 | C/T |
| CHB | rs3771156 | 2 | 103036677 | 0.033 | 0.62 | HapMap | 1000GP | C | 0.58 | T | 0.42 | C/T |
| JPT | rs3771156 | 2 | 103036677 | 0.173 | 1 | HapMap | 1000GP | C | 0.58 | T | 0.42 | C/T |
| JPT | rs3755268 | 2 | 103038527 | 0.105 | 1 | HapMap | 1000GP | C | 0.58 | G | 0.42 | C/G |
| CHB | rs3755268 | 2 | 103038527 | 0.141 | 1 | HapMap | 1000GP | C | 0.58 | G | 0.42 | C/G |
| CHB | rs3817465 | 2 | 103039584 | 0.141 | 1 | HapMap | 1000GP | A | 0.58 | T | 0.42 | A/T |
| JPT | rs3817465 | 2 | 103039584 | 0.105 | 1 | HapMap | 1000GP | A | 0.58 | T | 0.42 | A/T |
| JPT | rs887971 | 2 | 103041167 | 0.173 | 1 | HapMap | 1000GP | T | 0.58 | C | 0.42 | T/C |
| CHB | rs887971 | 2 | 103041167 | 0.033 | 0.62 | HapMap | 1000GP | T | 0.58 | C | 0.42 | T/C |
| JPT | rs2160232 | 2 | 103046880 | 0.105 | 1 | HapMap | 1000GP | G | 0.58 | A | 0.42 | G/A |
| CHB | rs2160232 | 2 | 103046880 | 0.148 | 1 | HapMap | 1000GP | G | 0.58 | A | 0.42 | G/A |
| CHB | rs6716784 | 2 | 103048467 | 0.138 | 1 | HapMap | 1000GP | T | 0.58 | G | 0.42 | T/G |
| JPT | rs6716784 | 2 | 103048467 | 0.103 | 1 | HapMap | 1000GP | T | 0.58 | G | 0.42 | T/G |
| CHB | rs6543134 | 2 | 103050458 | 0.141 | 1 | HapMap | 1000GP | T | 0.58 | G | 0.42 | T/G |
| JPT | rs6543134 | 2 | 103050458 | 0.117 | 1 | HapMap | 1000GP | T | 0.58 | G | 0.42 | T/G |
| JPT | rs2110735 | 2 | 103050925 | 0.105 | 1 | HapMap | 1000GP | A | 0.58 | G | 0.42 | A/G |
| CHB | rs2110735 | 2 | 103050925 | 0.141 | 1 | HapMap | 1000GP | A | 0.58 | G | 0.42 | A/G |
| JPT | rs11681718 | 2 | 103051144 | 0.173 | 1 | HapMap | 1000GP | A | 0.58 | G | 0.42 | A/G |
| CHB | rs11681718 | 2 | 103051144 | 0.033 | 0.613 | HapMap | 1000GP | A | 0.58 | G | 0.42 | A/G |
| CHB | rs4851582 | 2 | 103051558 | 0.033 | 0.62 | HapMap | 1000GP | T | 0.58 | C | 0.42 | T/C |
| JPT | rs4851582 | 2 | 103051558 | 0.178 | 1 | HapMap | 1000GP | T | 0.58 | C | 0.42 | T/C |
| JPT | rs2110734 | 2 | 103052206 | 0.113 | 1 | HapMap | 1000GP | C | 0.58 | T | 0.42 | C/T |
| CHB | rs2110734 | 2 | 103052206 | 0.141 | 1 | HapMap | 1000GP | C | 0.58 | T | 0.42 | C/T |
| CHB | rs6746271 | 2 | 103052995 | 0.141 | 1 | HapMap | 1000GP | G | 0.58 | C | 0.42 | G/C |
| JPT | rs6746271 | 2 | 103052995 | 0.105 | 1 | HapMap | 1000GP | G | 0.58 | C | 0.42 | G/C |
| CHB | rs2058658 | 2 | 103054803 | 0.141 | 1 | HapMap | 1000GP | T | 0.58 | C | 0.42 | T/C |
| JPT | rs2058658 | 2 | 103054803 | 0.105 | 1 | HapMap | 1000GP | T | 0.58 | C | 0.42 | T/C |
| CHB | rs4851009 | 2 | 103055644 | 0.141 | 1 | HapMap | 1000GP | G | 0.58 | A | 0.42 | G/A |
| JPT | rs4851009 | 2 | 103055644 | 0.105 | 1 | HapMap | 1000GP | G | 0.58 | A | 0.42 | G/A |
| CHB | rs17027179 | 2 | 103057159 | 0.033 | 0.62 | HapMap | 1000GP | C | 0.58 | T | 0.42 | C/T |
| JPT | rs17027179 | 2 | 103057159 | 0.173 | 1 | HapMap | 1000GP | C | 0.58 | T | 0.42 | C/T |
| CHB | rs10490203 | 2 | 103059237 | 0.033 | 0.62 | HapMap | 1000GP | T | 0.58 | G | 0.42 | T/G |
| JPT | rs10490203 | 2 | 103059237 | 0.173 | 1 | HapMap | 1000GP | T | 0.58 | G | 0.42 | T/G |
| JPT | rs1558650 | 2 | 103060024 | 0.113 | 1 | HapMap | 1000GP | T | 0.58 | A | 0.42 | T/A |
| CHB | rs1558650 | 2 | 103060024 | 0.141 | 1 | HapMap | 1000GP | T | 0.58 | A | 0.42 | T/A |
| JPT | rs4851583 | 2 | 103060300 | 0.173 | 1 | HapMap | 1000GP | T | 0.58 | C | 0.42 | T/C |
| CHB | rs4851584 | 2 | 103060313 | 0.084 | 0.752 | HapMap | 1000GP | A | 0.58 | G | 0.42 | A/G |
| JPT | rs4851584 | 2 | 103060313 | 0.105 | 1 | HapMap | 1000GP | A | 0.58 | G | 0.42 | A/G |
| JPT | rs11694360 | 2 | 103061147 | 0.173 | 1 | HapMap | 1000GP | G | 0.58 | A | 0.42 | G/A |
| JPT | rs11123928 | 2 | 103061286 | 0.173 | 1 | HapMap | 1000GP | G | 0.58 | A | 0.42 | G/A |
| JPT | rs7597017 | 2 | 103062116 | 0.173 | 1 | HapMap | 1000GP | A | 0.58 | G | 0.42 | A/G |
| JPT | rs6734736 | 2 | 103062880 | 0.103 | 1 | HapMap | 1000GP | C | 0.58 | T | 0.42 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs6734736 | 2 | 103062880 | 0.12 | 1 | HapMap | 1000GP | C | 0.58 | T | 0.42 | C/T |
| CHB | rs6543137 | 2 | 103065908 | 0.084 | 0.752 | HapMap | 1000GP | T | 0.58 | G | 0.42 | T/G |
| JPT | rs6543137 | 2 | 103065908 | 0.105 | 1 | HapMap | 1000GP | T | 0.58 | G | 0.42 | T/G |
| CHB | rs7603250 | 2 | 103068834 | 0.084 | 0.752 | HapMap | 1000GP | T | 0.58 | A | 0.42 | T/A |
| JPT | rs7603250 | 2 | 103068834 | 0.105 | 1 | HapMap | 1000GP | T | 0.58 | A | 0.42 | T/A |
| JPT | rs2075185 | 2 | 103070988 | 0.105 | 1 | HapMap | 1000GP | A | 0.58 | G | 0.42 | A/G |
| CHB | rs2075185 | 2 | 103070988 | 0.141 | 1 | HapMap | 1000GP | A | 0.58 | G | 0.42 | A/G |
| JPT | rs4070554 | 2 | 103074493 | 0.105 | 1 | HapMap | 1000GP | A | 0.58 | G | 0.42 | A/G |
| CHB | rs4070554 | 2 | 103074493 | 0.141 | 1 | HapMap | 1000GP | A | 0.58 | G | 0.42 | A/G |
| JPT | rs6761825 | 2 | 103075561 | 0.105 | 1 | HapMap | 1000GP | T | 0.58 | C | 0.42 | T/C |
| CHB | rs6761825 | 2 | 103075561 | 0.141 | 1 | HapMap | 1000GP | T | 0.58 | C | 0.42 | T/C |
| CHB | rs6705001 | 2 | 103076210 | 0.141 | 1 | HapMap | 1000GP | A | 0.58 | G | 0.42 | A/G |
| JPT | rs6705001 | 2 | 103076210 | 0.105 | 1 | HapMap | 1000GP | A | 0.58 | G | 0.42 | A/G |
| CHB | rs6543141 | 2 | 103076351 | 0.141 | 1 | HapMap | 1000GP | G | 0.58 | A | 0.42 | G/A |
| JPT | rs6543141 | 2 | 103076351 | 0.105 | 1 | HapMap | 1000GP | G | 0.58 | A | 0.42 | G/A |
| CHB | rs4241210 | 2 | 103078740 | 0.141 | 1 | HapMap | 1000GP | G | 0.58 | A | 0.42 | G/A |
| JPT | rs4241210 | 2 | 103078740 | 0.105 | 1 | HapMap | 1000GP | G | 0.58 | A | 0.42 | G/A |
| CHB | rs6720564 | 2 | 103079297 | 0.141 | 1 | HapMap | 1000GP | T | 0.58 | C | 0.42 | T/C |
| JPT | rs6720564 | 2 | 103079297 | 0.105 | 1 | HapMap | 1000GP | T | 0.58 | C | 0.42 | T/C |
| CHB | rs17027230 | 2 | 103079330 | 0.038 | 0.636 | HapMap | 1000GP | C | 0.58 | T | 0.42 | C/T |
| JPT | rs17027230 | 2 | 103079330 | 0.171 | 1 | HapMap | 1000GP | C | 0.58 | T | 0.42 | C/T |
| JPT | rs6717915 | 2 | 103079619 | 0.099 | 1 | HapMap | 1000GP | A | 0.58 | C | 0.42 | A/C |
| CHB | rs6717915 | 2 | 103079619 | 0.137 | 1 | HapMap | 1000GP | A | 0.58 | C | 0.42 | A/C |
| CHB | rs917996 | 2 | 103082273 | 0.141 | 1 | HapMap | 1000GP | C | 0.58 | A | 0.42 | C/A |
| JPT | rs917996 | 2 | 103082273 | 0.105 | 1 | HapMap | 1000GP | C | 0.58 | A | 0.42 | C/A |
| CHB | rs990171 | 2 | 103086770 | 0.141 | 1 | HapMap | 1000GP | A | 0.58 | C | 0.42 | A/C |
| JPT | rs990171 | 2 | 103086770 | 0.105 | 1 | HapMap | 1000GP | A | 0.58 | C | 0.42 | A/C |
| JPT | rs1474309 | 2 | 103091001 | 0.173 | 1 | HapMap | 1000GP | C | 0.58 | T | 0.42 | C/T |
| CHB | rs1474309 | 2 | 103091001 | 0.033 | 0.62 | HapMap | 1000GP | C | 0.58 | T | 0.42 | C/T |
| JPT | rs17027258 | 2 | 103091540 | 0.178 | 1 | HapMap | 1000GP | A | 0.58 | G | 0.42 | A/G |
| JPT | rs1468791 | 2 | 103092021 | 0.105 | 1 | HapMap | 1000GP | A | 0.58 | G | 0.42 | A/G |
| CHB | rs1468791 | 2 | 103092021 | 0.141 | 1 | HapMap | 1000GP | A | 0.58 | G | 0.42 | A/G |
| JPT | rs7597819 | 2 | 103092906 | 0.105 | 1 | HapMap | 1000GP | A | 0.58 | G | 0.42 | A/G |
| CHB | rs7597819 | 2 | 103092906 | 0.141 | 1 | HapMap | 1000GP | A | 0.58 | G | 0.42 | A/G |
| JPT | rs10469840 | 2 | 103093243 | 0.105 | 1 | HapMap | 1000GP | T | 0.58 | C | 0.42 | T/C |
| CHB | rs10469840 | 2 | 103093243 | 0.144 | 1 | HapMap | 1000GP | T | 0.58 | C | 0.42 | T/C |
| CHB | rs10193407 | 2 | 103139298 | 0.148 | 1 | HapMap | 1000GP | C | 0.58 | T | 0.42 | C/T |
| JPT | rs10193407 | 2 | 103139298 | 0.111 | 1 | HapMap | 1000GP | C | 0.58 | T | 0.42 | C/T |
| JPT | rs4577297 | 2 | 102918018 | 0.092 | 1 | HapMap | 1000GP | G | 0.59 | A | 0.41 | G/A |
| CHB | rs4577297 | 2 | 102918018 | 0.13 | 1 | HapMap | 1000GP | G | 0.59 | A | 0.41 | G/A |
| CHB | rs953934 | 2 | 102932293 | 0.141 | 1 | HapMap | 1000GP | C | 0.59 | T | 0.41 | C/T |
| JPT | rs953934 | 2 | 102932293 | 0.095 | 1 | HapMap | 1000GP | C | 0.59 | T | 0.41 | C/T |
| CHB | rs1420103 | 2 | 102948632 | 0.135 | 1 | HapMap | 1000GP | A | 0.59 | C | 0.41 | A/C |
| JPT | rs1420103 | 2 | 102948632 | 0.095 | 1 | HapMap | 1000GP | A | 0.59 | C | 0.41 | A/C |
| CHB | rs3821204 | 2 | 102960281 | 0.091 | 1 | HapMap | 1000GP | C | 0.59 | G | 0.41 | C/G |
| JPT | rs3821204 | 2 | 102960281 | 0.182 | 1 | HapMap | 1000GP | C | 0.59 | G | 0.41 | C/G |
| JPT | rs12469506 | 2 | 102965871 | 0.182 | 1 | HapMap | 1000GP | C | 0.59 | T | 0.41 | C/T |
| CHB | rs12469506 | 2 | 102965871 | 0.091 | 1 | HapMap | 1000GP | C | 0.59 | T | 0.41 | C/T |
| CHB | rs11693955 | 2 | 103029165 | 0.033 | 0.62 | HapMap | 1000GP | A | 0.59 | T | 0.41 | A/T |
| JPT | rs11693955 | 2 | 103029165 | 0.173 | 1 | HapMap | 1000GP | A | 0.59 | T | 0.41 | A/T |
| CHB | rs887972 | 2 | 103040945 | 0.033 | 0.62 | HapMap | 1000GP | G | 0.59 | A | 0.41 | G/A |
| JPT | rs887972 | 2 | 103040945 | 0.173 | 1 | HapMap | 1000GP | G | 0.59 | A | 0.41 | G/A |
| CHB | rs873022 | 2 | 102955683 | 0.083 | 1 | HapMap | 1000GP | G | 0.6 | T | 0.4 | G/T |
| JPT | rs873022 | 2 | 102955683 | 0.182 | 1 | HapMap | 1000GP | G | 0.6 | T | 0.4 | G/T |
| JPT | rs3771177 | 2 | 102955860 | 0.182 | 1 | HapMap | 1000GP | G | 0.6 | T | 0.4 | G/T |
| CHB | rs3771177 | 2 | 102955860 | 0.083 | 1 | HapMap | 1000GP | G | 0.6 | T | 0.4 | G/T |
| CHB | rs3732129 | 2 | 102957532 | 0.083 | 1 | HapMap | 1000GP | T | 0.6 | C | 0.4 | T/C |
| JPT | rs3732129 | 2 | 102957532 | 0.182 | 1 | HapMap | 1000GP | T | 0.6 | C | 0.4 | T/C |
| CHB | rs3771172 | 2 | 102985812 | 0.091 | 1 | HapMap | 1000GP | C | 0.6 | T | 0.4 | C/T |
| JPT | rs3771172 | 2 | 102985812 | 0.165 | 1 | HapMap | 1000GP | C | 0.6 | T | 0.4 | C/T |
| CHB | rs3771171 | 2 | 102985950 | 0.084 | 1 | HapMap | 1000GP | T | 0.6 | C | 0.4 | T/C |
| JPT | rs3771171 | 2 | 102985950 | 0.165 | 1 | HapMap | 1000GP | T | 0.6 | C | 0.4 | T/C |
| CHB | rs2160202 | 2 | 102986154 | 0.084 | 1 | HapMap | 1000GP | G | 0.6 | A | 0.4 | G/A |
| JPT | rs2160202 | 2 | 102986154 | 0.169 | 1 | HapMap | 1000GP | G | 0.6 | A | 0.4 | G/A |
| CHB | rs7566063 | 2 | 103112565 | 0.132 | 0.677 | HapMap | 1000GP | C | 0.6 | A | 0.4 | C/A |
| JPT | rs7566063 | 2 | 103112565 | 0.102 | 0.604 | HapMap | 1000GP | C | 0.6 | A | 0.4 | C/A |
| JPT | rs7591878 | 2 | 103112658 | 0.151 | 0.764 | HapMap | 1000GP | G | 0.6 | A | 0.4 | G/A |
| CHB | rs7591878 | 2 | 103112658 | 0.12 | 0.654 | HapMap | 1000GP | G | 0.6 | A | 0.4 | G/A |
| JPT | rs6543154 | 2 | 103114334 | 0.102 | 0.604 | HapMap | 1000GP | T | 0.6 | C | 0.4 | T/C |
| CHB | rs6543154 | 2 | 103114334 | 0.132 | 0.677 | HapMap | 1000GP | T | 0.6 | C | 0.4 | T/C |
| JPT | rs6543155 | 2 | 103114895 | 0.123 | 0.737 | HapMap | 1000GP | G | 0.6 | A | 0.4 | G/A |
| CHB | rs6543155 | 2 | 103114895 | 0.139 | 0.68 | HapMap | 1000GP | G | 0.6 | A | 0.4 | G/A |
| JPT | rs11123934 | 2 | 103115568 | 0.102 | 0.604 | HapMap | 1000GP | G | 0.6 | A | 0.4 | G/A |
| CHB | rs11123934 | 2 | 103115568 | 0.132 | 0.677 | HapMap | 1000GP | G | 0.6 | A | 0.4 | G/A |
| CHB | rs1030026 | 2 | 103098178 | 0.142 | 0.667 | HapMap | 1000GP | A | 0.62 | C | 0.38 | A/C |
| CHB | rs2140316 | 2 | 103098676 | 0.142 | 0.667 | HapMap | 1000GP | T | 0.62 | A | 0.38 | T/A |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs12468355 | 2 | 102861250 | 0.222 | 0.835 | HapMap | 1000GP | T | 0.66 | G | 0.34 | T/G |
| JPT | rs12468355 | 2 | 102861250 | 0.144 | 0.665 | HapMap | 1000GP | T | 0.66 | G | 0.34 | T/G |
| JPT | rs1558626 | 2 | 102862070 | 0.144 | 0.665 | HapMap | 1000GP | T | 0.66 | A | 0.34 | T/A |
| CHB | rs1558626 | 2 | 102862070 | 0.211 | 0.836 | HapMap | 1000GP | T | 0.66 | A | 0.34 | T/A |
| CHB | rs1558624 | 2 | 102862233 | 0.211 | 0.836 | HapMap | 1000GP | A | 0.66 | G | 0.34 | A/G |
| JPT | rs1558624 | 2 | 102862233 | 0.144 | 0.665 | HapMap | 1000GP | A | 0.66 | G | 0.34 | A/G |
| CHB | rs1558623 | 2 | 102862402 | 0.211 | 0.836 | HapMap | 1000GP | T | 0.66 | A | 0.34 | T/A |
| JPT | rs1558623 | 2 | 102862402 | 0.144 | 0.665 | HapMap | 1000GP | T | 0.66 | A | 0.34 | T/A |
| JPT | rs17689452 | 2 | 102864681 | 0.144 | 0.665 | HapMap | 1000GP | A | 0.66 | G | 0.34 | A/G |
| CHB | rs17689452 | 2 | 102864681 | 0.211 | 0.836 | HapMap | 1000GP | A | 0.66 | G | 0.34 | A/G |
| CHB | rs10186746 | 2 | 102866377 | 0.211 | 0.836 | HapMap | 1000GP | G | 0.66 | A | 0.34 | G/A |
| JPT | rs10186746 | 2 | 102866377 | 0.144 | 0.665 | HapMap | 1000GP | G | 0.66 | A | 0.34 | G/A |
| JPT | rs7572871 | 2 | 102853838 | 0.049 | 1 | HapMap | 1000GP | G | 0.7 | A | 0.3 | G/A |
| JPT | rs12712153 | 2 | 103111761 | 0.09 | 1 | HapMap | 1000GP | C | 0.71 | T | 0.29 | C/T |
| JPT | rs11687071 | 2 | 103111920 | 0.09 | 1 | HapMap | 1000GP | G | 0.71 | A | 0.29 | G/A |
| JPT | rs6543153 | 2 | 103114203 | 0.032 | 0.607 | HapMap | 1000GP | T | 0.71 | C | 0.29 | T/C |
| JPT | rs7573566 | 2 | 103115205 | 0.09 | 1 | HapMap | 1000GP | T | 0.71 | C | 0.29 | T/C |
| JPT | rs12987295 | 2 | 103115838 | 0.09 | 1 | HapMap | 1000GP | G | 0.71 | A | 0.29 | G/A |
| JPT | rs12995030 | 2 | 103116466 | 0.09 | 1 | HapMap | 1000GP | C | 0.71 | G | 0.29 | C/G |
| JPT | rs6728288 | 2 | 103117268 | 0.09 | 1 | HapMap | 1000GP | A | 0.71 | T | 0.29 | A/T |
| JPT | rs2075192 | 2 | 103118228 | 0.09 | 1 | HapMap | 1000GP | A | 0.71 | G | 0.29 | A/G |
| JPT | rs2075191 | 2 | 103118299 | 0.09 | 1 | HapMap | 1000GP | G | 0.71 | T | 0.29 | G/T |
| JPT | rs2075190 | 2 | 103118559 | 0.09 | 1 | HapMap | 1000GP | A | 0.71 | T | 0.29 | A/T |
| JPT | rs2075189 | 2 | 103118689 | 0.09 | 1 | HapMap | 1000GP | C | 0.71 | G | 0.29 | C/G |
| JPT | rs11690932 | 2 | 103119029 | 0.09 | 1 | HapMap | 1000GP | G | 0.71 | A | 0.29 | G/A |
| JPT | rs4851605 | 2 | 103120868 | 0.09 | 1 | HapMap | 1000GP | A | 0.71 | G | 0.29 | A/G |
| JPT | rs4851606 | 2 | 103120889 | 0.09 | 1 | HapMap | 1000GP | G | 0.71 | A | 0.29 | G/A |
| JPT | rs7600901 | 2 | 102915571 | 0.053 | 1 | HapMap | 1000GP | A | 0.73 | G | 0.27 | A/G |
| JPT | rs7605606 | 2 | 103121536 | 0.08 | 1 | HapMap | 1000GP | G | 0.73 | A | 0.27 | G/A |
| CHB | rs3755292 | 2 | 102769137 | 0.057 | 1 | HapMap | 1000GP | T | 0.74 | G | 0.26 | T/G |
| CHB | rs871656 | 2 | 102771282 | 0.057 | 1 | HapMap | 1000GP | T | 0.75 | A | 0.25 | T/A |
| CHB | rs2287048 | 2 | 102773999 | 0.066 | 1 | HapMap | 1000GP | C | 0.75 | T | 0.25 | C/T |
| CHB | rs1468789 | 2 | 103092503 | 0.045 | 1 | HapMap | 1000GP | C | 0.76 | T | 0.24 | C/T |
| CHB | rs1882510 | 2 | 102883618 | 0.052 | 1 | HapMap | 1000GP | C | 0.77 | T | 0.23 | C/T |
| JPT | rs3755294 | 2 | 102768376 | 0.058 | 1 | HapMap | 1000GP | G | 0.82 | A | 0.18 | G/A |
| CHB | rs12465829 | 2 | 103072320 | 0.034 | 1 | HapMap | 1000GP | T | 0.82 | C | 0.18 | T/C |
| JPT | rs12465829 | 2 | 103072320 | 0.058 | 1 | HapMap | 1000GP | T | 0.82 | C | 0.18 | T/C |
| CHB | rs10200410 | 2 | 102870871 | 0.396 | 0.776 | HapMap | 1000GP | G | 0.83 | A | 0.17 | G/A |
| CHB | rs1345301 | 2 | 102875587 | 0.396 | 0.776 | HapMap | 1000GP | A | 0.83 | G | 0.17 | A/G |
| CHB | rs2310243 | 2 | 102877560 | 0.396 | 0.776 | HapMap | 1000GP | A | 0.83 | G | 0.17 | A/G |
| CHB | rs13405355 | 2 | 102878206 | 0.396 | 0.776 | HapMap | 1000GP | C | 0.83 | T | 0.17 | C/T |
| JPT | rs17026901 | 2 | 102890386 | 0.03 | 0.826 | HapMap | 1000GP | T | 0.83 | C | 0.17 | T/C |
| JPT | rs10206291 | 2 | 103038863 | 0.85 | 1 | HapMap | 1000GP | T | 0.83 | C | 0.17 | T/C |
| CHB | rs10206291 | 2 | 103038863 | 0.564 | 0.892 | HapMap | 1000GP | T | 0.83 | C | 0.17 | T/C |
| CHB | rs10208196 | 2 | 102996345 | 0.564 | 0.892 | HapMap | 1000GP | G | 0.84 | A | 0.16 | G/A |
| JPT | rs10208196 | 2 | 102996345 | 0.849 | 1 | HapMap | 1000GP | G | 0.84 | A | 0.16 | G/A |
| CHB | rs3213732 | 2 | 102998279 | 0.564 | 0.892 | HapMap | 1000GP | A | 0.84 | G | 0.16 | A/G |
| JPT | rs3213732 | 2 | 102998279 | 0.85 | 1 | HapMap | 1000GP | A | 0.84 | G | 0.16 | A/G |
| JPT | rs6760621 | 2 | 102999952 | 0.84 | 1 | HapMap | 1000GP | T | 0.84 | C | 0.16 | T/C |
| CHB | rs6760621 | 2 | 102999952 | 0.558 | 0.889 | HapMap | 1000GP | T | 0.84 | C | 0.16 | T/C |
| JPT | rs6706002 | 2 | 103006104 | 0.85 | 1 | HapMap | 1000GP | A | 0.84 | G | 0.16 | A/G |
| CHB | rs6706002 | 2 | 103006104 | 0.564 | 0.892 | HapMap | 1000GP | A | 0.84 | G | 0.16 | A/G |
| CHB | rs4851571 | 2 | 103019000 | 0.564 | 0.892 | HapMap | 1000GP | C | 0.84 | T | 0.16 | C/T |
| JPT | rs4851571 | 2 | 103019000 | 0.85 | 1 | HapMap | 1000GP | C | 0.84 | T | 0.16 | C/T |
| CHB | rs4851572 | 2 | 103019031 | 0.564 | 0.892 | HapMap | 1000GP | G | 0.84 | A | 0.16 | G/A |
| JPT | rs4851572 | 2 | 103019031 | 0.85 | 1 | HapMap | 1000GP | G | 0.84 | A | 0.16 | G/A |
| CHB | rs2110662 | 2 | 103020139 | 0.564 | 0.892 | HapMap | 1000GP | A | 0.84 | T | 0.16 | A/T |
| JPT | rs2110662 | 2 | 103020139 | 0.85 | 1 | HapMap | 1000GP | A | 0.84 | T | 0.16 | A/T |
| CHB | rs7594402 | 2 | 103021267 | 0.564 | 0.892 | HapMap | 1000GP | A | 0.84 | T | 0.16 | A/T |
| JPT | rs7594402 | 2 | 103021267 | 0.85 | 1 | HapMap | 1000GP | A | 0.84 | T | 0.16 | A/T |
| JPT | rs6710034 | 2 | 103023678 | 0.85 | 1 | HapMap | 1000GP | G | 0.84 | A | 0.16 | G/A |
| CHB | rs6710034 | 2 | 103023678 | 0.564 | 0.892 | HapMap | 1000GP | G | 0.84 | A | 0.16 | G/A |
| CHB | rs7589142 | 2 | 103024660 | 0.736 | 0.899 | HapMap | 1000GP | T | 0.84 | C | 0.16 | T/C |
| JPT | rs7589142 | 2 | 103024660 | 1 | 1 | HapMap | 1000GP | T | 0.84 | C | 0.16 | T/C |
| CHB | rs10203558 | 2 | 103027640 | 0.562 | 0.891 | HapMap | 1000GP | T | 0.84 | C | 0.16 | T/C |
| JPT | rs10203558 | 2 | 103027640 | 0.841 | 1 | HapMap | 1000GP | T | 0.84 | C | 0.16 | T/C |
| JPT | rs4851576 | 2 | 103028895 | 0.85 | 1 | HapMap | 1000GP | C | 0.84 | T | 0.16 | C/T |
| CHB | rs4851576 | 2 | 103028895 | 0.564 | 0.892 | HapMap | 1000GP | C | 0.84 | T | 0.16 | C/T |
| JPT | rs4851577 | 2 | 103028921 | 0.85 | 1 | HapMap | 1000GP | T | 0.84 | C | 0.16 | T/C |
| CHB | rs4851577 | 2 | 103028921 | 0.564 | 0.892 | HapMap | 1000GP | T | 0.84 | C | 0.16 | T/C |
| CHB | rs4851579 | 2 | 103028984 | 0.564 | 0.892 | HapMap | 1000GP | G | 0.84 | A | 0.16 | G/A |
| JPT | rs4851579 | 2 | 103028984 | 0.85 | 1 | HapMap | 1000GP | G | 0.84 | A | 0.16 | G/A |
| JPT | rs1592458 | 2 | 103031749 | 0.85 | 1 | HapMap | 1000GP | A | 0.84 | T | 0.16 | A/T |
| CHB | rs1592458 | 2 | 103031749 | 0.564 | 0.892 | HapMap | 1000GP | A | 0.84 | T | 0.16 | A/T |
| JPT | rs2160201 | 2 | 103033961 | 0.822 | 1 | HapMap | 1000GP | T | 0.84 | C | 0.16 | T/C |
| CHB | rs2160201 | 2 | 103033961 | 0.778 | 1 | HapMap | 1000GP | T | 0.84 | C | 0.16 | T/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| JPT | rs2293224 | 2 | 103035779 | 0.85 | 1 | HapMap | 1000GP | T | 0.84 | C | 0.16 | T/C |
| CHB | rs2293224 | 2 | 103035779 | 0.564 | 0.892 | HapMap | 1000GP | T | 0.84 | C | 0.16 | T/C |
| CHB | rs1420100 | 2 | 103037002 | 0.564 | 0.892 | HapMap | 1000GP | C | 0.84 | A | 0.16 | C/A |
| JPT | rs1420100 | 2 | 103037002 | 0.85 | 1 | HapMap | 1000GP | C | 0.84 | A | 0.16 | C/A |
| JPT | rs3771155 | 2 | 103037826 | 0.85 | 1 | HapMap | 1000GP | A | 0.84 | G | 0.16 | A/G |
| CHB | rs3771155 | 2 | 103037826 | 0.564 | 0.892 | HapMap | 1000GP | A | 0.84 | G | 0.16 | A/G |
| CHB | rs3771154 | 2 | 103039360 | 0.564 | 0.892 | HapMap | 1000GP | C | 0.84 | T | 0.16 | C/T |
| JPT | rs3771154 | 2 | 103039360 | 0.85 | 1 | HapMap | 1000GP | C | 0.84 | T | 0.16 | C/T |
| JPT | rs6759479 | 2 | 103040047 | 0.85 | 1 | HapMap | 1000GP | A | 0.84 | C | 0.16 | A/C |
| CHB | rs6759479 | 2 | 103040047 | 0.564 | 0.892 | HapMap | 1000GP | A | 0.84 | C | 0.16 | A/C |
| JPT | rs6543133 | 2 | 103040177 | 0.179 | 0.628 | HapMap | 1000GP | A | 0.84 | T | 0.16 | A/T |
| CHB | rs7559845 | 2 | 103046214 | 0.564 | 0.892 | HapMap | 1000GP | T | 0.84 | G | 0.16 | T/G |
| JPT | rs7559845 | 2 | 103046214 | 0.85 | 1 | HapMap | 1000GP | T | 0.84 | G | 0.16 | T/G |
| CHB | rs3755265 | 2 | 103052816 | 0.564 | 0.892 | HapMap | 1000GP | C | 0.84 | A | 0.16 | C/A |
| JPT | rs3755265 | 2 | 103052816 | 0.85 | 1 | HapMap | 1000GP | C | 0.84 | A | 0.16 | C/A |
| JPT | rs4479442 | 2 | 103054074 | 0.833 | 1 | HapMap | 1000GP | A | 0.84 | T | 0.16 | A/T |
| CHB | rs4479442 | 2 | 103054074 | 0.541 | 0.883 | HapMap | 1000GP | A | 0.84 | T | 0.16 | A/T |
| CHB | rs13021177 | 2 | 103056493 | 0.564 | 0.892 | HapMap | 1000GP | A | 0.84 | G | 0.16 | A/G |
| JPT | rs13021177 | 2 | 103056493 | 0.85 | 1 | HapMap | 1000GP | A | 0.84 | G | 0.16 | A/G |
| JPT | rs3771202 | 2 | 102772669 | 0.034 | 1 | HapMap | 1000GP | C | 0.85 | G | 0.15 | C/G |
| JPT | rs2080312 | 2 | 102774810 | 0.03 | 1 | HapMap | 1000GP | A | 0.85 | G | 0.15 | A/G |
| JPT | rs3917245 | 2 | 102775155 | 0.027 | 1 | HapMap | 1000GP | G | 0.85 | A | 0.15 | G/A |
| JPT | rs3917246 | 2 | 102775164 | 0.027 | 1 | HapMap | 1000GP | T | 0.85 | C | 0.15 | T/C |
| CHB | rs1041973 | 2 | 102955468 | 0.52 | 0.79 | HapMap | 1000GP | C | 0.85 | A | 0.15 | C/A |
| CHB | rs10208293 | 2 | 102966310 | 1 | 1 | HapMap | 1000GP | G | 0.85 | A | 0.15 | G/A |
| JPT | rs10208293 | 2 | 102966310 | 1 | 1 | HapMap | 1000GP | G | 0.85 | A | 0.15 | G/A |
| JPT | rs13424006 | 2 | 102967236 | 1 | 1 | HapMap | 1000GP | T | 0.85 | C | 0.15 | T/C |
| CHB | rs13424006 | 2 | 102967236 | 1 | 1 | HapMap | 1000GP | T | 0.85 | C | 0.15 | T/C |
| JPT | rs6751967 | 2 | 102967413 | 1 | 1 | HapMap | 1000GP | T | 0.85 | C | 0.15 | T/C |
| CHB | rs6751967 | 2 | 102967413 | 1 | 1 | HapMap | 1000GP | T | 0.85 | C | 0.15 | T/C |
| CHB | rs6749114 | 2 | 102967587 | 1 | 1 | HapMap | 1000GP | A | 0.85 | C | 0.15 | A/C |
| JPT | rs6749114 | 2 | 102967587 | 1 | 1 | HapMap | 1000GP | A | 0.85 | C | 0.15 | A/C |
| CHB | rs10170583 | 2 | 102974764 | 1 | 1 | HapMap | 1000GP | G | 0.85 | A | 0.15 | G/A |
| JPT | rs10170583 | 2 | 102974764 | 1 | 1 | HapMap | 1000GP | G | 0.85 | A | 0.15 | G/A |
| CHB | rs10176664 | 2 | 102976172 | 1 | 1 | HapMap | 1000GP | G | 0.85 | A | 0.15 | G/A |
| JPT | rs10176664 | 2 | 102976172 | 1 | 1 | HapMap | 1000GP | G | 0.85 | A | 0.15 | G/A |
| JPT | rs1974675 | 2 | 102986375 | 1 | 1 | HapMap | 1000GP | G | 0.85 | A | 0.15 | G/A |
| CHB | rs1974675 | 2 | 102986375 | 1 | 1 | HapMap | 1000GP | G | 0.85 | A | 0.15 | G/A |
| JPT | rs17027352 | 2 | 103138836 | 0.442 | 0.766 | HapMap | 1000GP | C | 0.85 | T | 0.15 | C/T |
| CHB | rs17027352 | 2 | 103138836 | 0.385 | 0.68 | HapMap | 1000GP | C | 0.85 | T | 0.15 | C/T |
| CHB | rs7576682 | 2 | 103143312 | 0.375 | 0.66 | HapMap | 1000GP | G | 0.86 | A | 0.14 | G/A |
| JPT | rs7576682 | 2 | 103143312 | 0.299 | 0.757 | HapMap | 1000GP | G | 0.86 | A | 0.14 | G/A |
| CHB | rs3849363 | 2 | 103143548 | 0.385 | 0.68 | HapMap | 1000GP | T | 0.86 | G | 0.14 | T/G |
| JPT | rs3849363 | 2 | 103143548 | 0.442 | 0.766 | HapMap | 1000GP | T | 0.86 | G | 0.14 | T/G |
| CHB | rs13388541 | 2 | 103147818 | 0.388 | 0.655 | HapMap | 1000GP | T | 0.86 | C | 0.14 | T/C |
| JPT | rs13388541 | 2 | 103147818 | 0.437 | 0.763 | HapMap | 1000GP | T | 0.86 | C | 0.14 | T/C |
| CHB | rs10183491 | 2 | 103151587 | 0.385 | 0.68 | HapMap | 1000GP | T | 0.86 | G | 0.14 | T/G |
| JPT | rs10183491 | 2 | 103151587 | 0.442 | 0.766 | HapMap | 1000GP | T | 0.86 | G | 0.14 | T/G |
| JPT | rs17027415 | 2 | 103154594 | 0.442 | 0.766 | HapMap | 1000GP | C | 0.86 | A | 0.14 | C/A |
| CHB | rs17027415 | 2 | 103154594 | 0.385 | 0.68 | HapMap | 1000GP | C | 0.86 | A | 0.14 | C/A |
| JPT | rs13027294 | 2 | 102860074 | 0.595 | 1 | HapMap | 1000GP | G | 0.87 | C | 0.13 | G/C |
| CHB | rs13027294 | 2 | 102860074 | 0.547 | 1 | HapMap | 1000GP | G | 0.87 | C | 0.13 | G/C |
| CHB | rs11677452 | 2 | 102865236 | 0.627 | 0.879 | HapMap | 1000GP | A | 0.87 | T | 0.13 | A/T |
| JPT | rs11677452 | 2 | 102865236 | 0.457 | 0.707 | HapMap | 1000GP | A | 0.87 | T | 0.13 | A/T |
| CHB | rs9646944 | 2 | 102865875 | 0.627 | 0.879 | HapMap | 1000GP | G | 0.87 | C | 0.13 | G/C |
| JPT | rs9646944 | 2 | 102865875 | 0.457 | 0.707 | HapMap | 1000GP | G | 0.87 | C | 0.13 | G/C |
| CHB | rs13418548 | 2 | 102917239 | 0.223 | 1 | HapMap | 1000GP | C | 0.88 | T | 0.12 | C/T |
| JPT | rs13418548 | 2 | 102917239 | 0.329 | 1 | HapMap | 1000GP | C | 0.88 | T | 0.12 | C/T |
| CHB | rs950881 | 2 | 102932512 | 0.369 | 1 | HapMap | 1000GP | G | 0.88 | T | 0.12 | G/T |
| JPT | rs950881 | 2 | 102932512 | 0.574 | 1 | HapMap | 1000GP | G | 0.88 | T | 0.12 | G/T |
| CHB | rs13408569 | 2 | 102955056 | 0.632 | 1 | HapMap | 1000GP | G | 0.88 | C | 0.12 | G/C |
| JPT | rs13408569 | 2 | 102955056 | 0.753 | 1 | HapMap | 1000GP | G | 0.88 | C | 0.12 | G/C |
| CHB | rs13408661 | 2 | 102955082 | 0.632 | 1 | HapMap | 1000GP | G | 0.88 | A | 0.12 | G/A |
| JPT | rs13408661 | 2 | 102955082 | 0.753 | 1 | HapMap | 1000GP | G | 0.88 | A | 0.12 | G/A |
| JPT | rs10173081 | 2 | 102957348 | 0.753 | 1 | HapMap | 1000GP | C | 0.88 | T | 0.12 | C/T |
| CHB | rs10173081 | 2 | 102957348 | 0.632 | 1 | HapMap | 1000GP | C | 0.88 | T | 0.12 | C/T |
| CHB | rs17027029 | 2 | 102990648 | 0.632 | 1 | HapMap | 1000GP | G | 0.88 | C | 0.12 | G/C |
| JPT | rs17027029 | 2 | 102990648 | 0.753 | 1 | HapMap | 1000GP | G | 0.88 | C | 0.12 | G/C |
| JPT | rs3771164 | 2 | 102991786 | 0.753 | 1 | HapMap | 1000GP | A | 0.88 | T | 0.12 | A/T |
| CHB | rs3771164 | 2 | 102991786 | 0.632 | 1 | HapMap | 1000GP | A | 0.88 | T | 0.12 | A/T |
| JPT | rs3732127 | 2 | 103013750 | 0.753 | 1 | HapMap | 1000GP | G | 0.88 | C | 0.12 | G/C |
| CHB | rs3732127 | 2 | 103013750 | 0.632 | 1 | HapMap | 1000GP | G | 0.88 | C | 0.12 | G/C |
| JPT | rs12991737 | 2 | 103018128 | 0.752 | 1 | HapMap | 1000GP | T | 0.88 | A | 0.12 | T/A |
| CHB | rs12991737 | 2 | 103018128 | 0.754 | 1 | HapMap | 1000GP | T | 0.88 | A | 0.12 | T/A |
| CHB | rs10181785 | 2 | 103025274 | 0.632 | 1 | HapMap | 1000GP | C | 0.88 | T | 0.12 | C/T |
| JPT | rs10181785 | 2 | 103025274 | 0.753 | 1 | HapMap | 1000GP | C | 0.88 | T | 0.12 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs12712148 | 2 | 103025547 | 0.632 | 1 | HapMap | 1000GP | G | 0.88 | A | 0.12 | G/A |
| JPT | rs12712148 | 2 | 103025547 | 0.676 | 1 | HapMap | 1000GP | G | 0.88 | A | 0.12 | G/A |
| CHB | rs7586983 | 2 | 103028066 | 0.632 | 1 | HapMap | 1000GP | C | 0.88 | T | 0.12 | C/T |
| JPT | rs7586983 | 2 | 103028066 | 0.753 | 1 | HapMap | 1000GP | C | 0.88 | T | 0.12 | C/T |
| CHB | rs2272127 | 2 | 103039873 | 0.632 | 1 | HapMap | 1000GP | C | 0.88 | G | 0.12 | C/G |
| JPT | rs2272127 | 2 | 103039873 | 0.718 | 1 | HapMap | 1000GP | C | 0.88 | G | 0.12 | C/G |
| CHB | rs10166330 | 2 | 103050390 | 0.632 | 1 | HapMap | 1000GP | C | 0.89 | T | 0.11 | C/T |
| JPT | rs10166330 | 2 | 103050390 | 0.753 | 1 | HapMap | 1000GP | C | 0.89 | T | 0.11 | C/T |
| CHB | rs11465736 | 2 | 103067930 | 0.462 | 1 | HapMap | 1000GP | C | 0.89 | T | 0.11 | C/T |
| JPT | rs11465736 | 2 | 103067930 | 0.752 | 1 | HapMap | 1000GP | C | 0.89 | T | 0.11 | C/T |
| JPT | rs10169676 | 2 | 103074919 | 0.753 | 1 | HapMap | 1000GP | G | 0.89 | A | 0.11 | G/A |
| CHB | rs10169676 | 2 | 103074919 | 0.632 | 1 | HapMap | 1000GP | G | 0.89 | A | 0.11 | G/A |
| JPT | rs17027246 | 2 | 103080055 | 0.753 | 1 | HapMap | 1000GP | C | 0.89 | G | 0.11 | C/G |
| CHB | rs17027246 | 2 | 103080055 | 0.603 | 1 | HapMap | 1000GP | C | 0.89 | G | 0.11 | C/G |
| CHB | rs741284 | 2 | 103083324 | 0.632 | 1 | HapMap | 1000GP | G | 0.89 | C | 0.11 | G/C |
| JPT | rs741284 | 2 | 103083324 | 0.753 | 1 | HapMap | 1000GP | G | 0.89 | C | 0.11 | G/C |
| JPT | rs10172116 | 2 | 103087573 | 0.753 | 1 | HapMap | 1000GP | C | 0.89 | T | 0.11 | C/T |
| CHB | rs10172116 | 2 | 103087573 | 0.632 | 1 | HapMap | 1000GP | C | 0.89 | T | 0.11 | C/T |
| CHB | rs13030642 | 2 | 103091585 | 0.632 | 1 | HapMap | 1000GP | C | 0.89 | A | 0.11 | C/A |
| JPT | rs13030642 | 2 | 103091585 | 0.753 | 1 | HapMap | 1000GP | C | 0.89 | A | 0.11 | C/A |
| JPT | rs11892768 | 2 | 103096936 | 0.6 | 1 | HapMap | 1000GP | C | 0.89 | T | 0.11 | C/T |
| CHB | rs11892768 | 2 | 103096936 | 0.546 | 1 | HapMap | 1000GP | C | 0.89 | T | 0.11 | C/T |
| CHB | rs7579846 | 2 | 103112585 | 0.546 | 1 | HapMap | 1000GP | A | 0.89 | C | 0.11 | A/C |
| JPT | rs7579846 | 2 | 103112585 | 0.6 | 1 | HapMap | 1000GP | A | 0.89 | C | 0.11 | A/C |
| JPT | rs10208027 | 2 | 103121372 | 0.455 | 1 | HapMap | 1000GP | G | 0.89 | T | 0.11 | G/T |
| CHB | rs10208027 | 2 | 103121372 | 0.546 | 1 | HapMap | 1000GP | G | 0.89 | T | 0.11 | G/T |
| JPT | rs10185897 | 2 | 102966790 | 0.455 | 1 | HapMap | 1000GP | C | 0.9 | A | 0.1 | C/A |
| CHB | rs10185897 | 2 | 102966790 | 0.223 | 1 | HapMap | 1000GP | C | 0.9 | A | 0.1 | C/A |
| JPT | rs10196556 | 2 | 103075079 | 0.753 | 1 | HapMap | 1000GP | C | 0.9 | T | 0.1 | C/T |
| CHB | rs10196556 | 2 | 103075079 | 0.462 | 1 | HapMap | 1000GP | C | 0.9 | T | 0.1 | C/T |
| JPT | rs2302622 | 2 | 102836521 | 0.005 | 0.684 | HapMap | 1000GP | G | 0.91 | C | 0.09 | G/C |
| CHB | rs2302622 | 2 | 102836521 | 0.009 | 0.658 | HapMap | 1000GP | G | 0.91 | C | 0.09 | G/C |
| JPT | rs17820338 | 2 | 102809182 | 0.005 | 1 | HapMap | 1000GP | G | 0.95 | C | 0.05 | G/C |
| CHB | rs17820338 | 2 | 102809182 | 0.012 | 1 | HapMap | 1000GP | G | 0.95 | C | 0.05 | G/C |
| CHB | rs1558648 | 2 | 102810168 | 0.014 | 1 | HapMap | 1000GP | T | 0.95 | G | 0.05 | T/G |
| JPT | rs1558648 | 2 | 102810168 | 0.005 | 1 | HapMap | 1000GP | T | 0.95 | G | 0.05 | T/G |
| JPT | rs17769234 | 2 | 102811716 | 0.005 | 1 | HapMap | 1000GP | T | 0.95 | C | 0.05 | T/C |
| CHB | rs17769234 | 2 | 102811716 | 0.011 | 1 | HapMap | 1000GP | T | 0.95 | C | 0.05 | T/C |
| JPT | rs17026757 | 2 | 102813912 | 0.002 | 1 | HapMap | 1000GP | A | 0.95 | C | 0.05 | A/C |
| CHB | rs17026757 | 2 | 102813912 | 0.011 | 1 | HapMap | 1000GP | A | 0.95 | C | 0.05 | A/C |
| CHB | rs12996377 | 2 | 102830478 | 0.014 | 1 | HapMap | 1000GP | T | 0.95 | A | 0.05 | T/A |
| JPT | rs12996377 | 2 | 102830478 | 0.005 | 1 | HapMap | 1000GP | T | 0.95 | A | 0.05 | T/A |
| CHB | rs7582378 | 2 | 103162263 | 0.147 | 1 | HapMap | 1000GP | C | 0.95 | A | 0.05 | C/A |
| CHB | rs3917306 | 2 | 102788839 | 0.006 | 0.749 | HapMap | 1000GP | A | 0.96 | G | 0.04 | A/G |
| JPT | rs6728945 | 2 | 102986471 | 0.07 | 1 | HapMap | 1000GP | T | 0.96 | C | 0.04 | T/C |
| CHB | rs6728945 | 2 | 102986471 | 0.202 | 1 | HapMap | 1000GP | T | 0.96 | C | 0.04 | T/C |
| CHB | rs3917322 | 2 | 102793246 | 0.008 | 1 | HapMap | 1000GP | A | 0.97 | G | 0.03 | A/G |
| CHB | rs3917326 | 2 | 102794326 | 0.008 | 1 | HapMap | 1000GP | C | 0.97 | T | 0.03 | C/T |
| JPT | rs1882511 | 2 | 102883721 | 0.01 | 1 | HapMap | 1000GP | G | 0.97 | A | 0.03 | G/A |
| JPT | rs10200945 | 2 | 102884757 | 0.01 | 1 | HapMap | 1000GP | A | 0.97 | T | 0.03 | A/T |
| JPT | rs1922288 | 2 | 102888565 | 0.01 | 1 | HapMap | 1000GP | T | 0.97 | C | 0.03 | T/C |
| JPT | rs9308855 | 2 | 102890795 | 0.01 | 1 | HapMap | 1000GP | A | 0.97 | G | 0.03 | A/G |
| JPT | rs1115281 | 2 | 102891107 | 0.01 | 1 | HapMap | 1000GP | C | 0.97 | G | 0.03 | C/G |
| JPT | rs10179570 | 2 | 102891632 | 0.01 | 1 | HapMap | 1000GP | T | 0.97 | C | 0.03 | T/C |
| CHB | rs17026916 | 2 | 102900381 | 0.006 | 1 | HapMap | 1000GP | A | 0.97 | T | 0.03 | A/T |
| CHB | rs985523 | 2 | 102954376 | 0.301 | 1 | HapMap | 1000GP | G | 0.97 | A | 0.03 | G/A |
| JPT | rs985523 | 2 | 102954376 | 0.185 | 1 | HapMap | 1000GP | G | 0.97 | A | 0.03 | G/A |
| CHB | rs6719130 | 2 | 102958236 | 0.301 | 1 | HapMap | 1000GP | C | 0.97 | T | 0.03 | C/T |
| JPT | rs6719130 | 2 | 102958236 | 0.185 | 1 | HapMap | 1000GP | C | 0.97 | T | 0.03 | C/T |
| CHB | rs3771167 | 2 | 102986188 | 0.274 | 1 | HapMap | 1000GP | A | 0.97 | G | 0.03 | A/G |
| JPT | rs3771167 | 2 | 102986188 | 0.133 | 1 | HapMap | 1000GP | A | 0.97 | G | 0.03 | A/G |
| JPT | rs11465623 | 2 | 102993039 | 0.005 | 1 | HapMap | 1000GP | G | 0.97 | T | 0.03 | G/T |
| JPT | rs11465673 | 2 | 103035375 | 0.005 | 1 | HapMap | 1000GP | T | 0.97 | C | 0.03 | T/C |
| JPT | rs11465689 | 2 | 103040167 | 0.005 | 1 | HapMap | 1000GP | C | 0.97 | A | 0.03 | C/A |
| JPT | rs11465711 | 2 | 103060092 | 0.005 | 1 | HapMap | 1000GP | T | 0.97 | C | 0.03 | T/C |
| JPT | rs17821875 | 2 | 103071030 | 0.005 | 1 | HapMap | 1000GP | A | 0.97 | G | 0.03 | A/G |
| JPT | rs6753066 | 2 | 103095946 | 0.005 | 1 | HapMap | 1000GP | G | 0.97 | C | 0.03 | G/C |
| JPT | rs6756536 | 2 | 103096400 | 0.005 | 1 | HapMap | 1000GP | G | 0.97 | T | 0.03 | G/T |
| JPT | rs6543145 | 2 | 103096436 | 0.005 | 1 | HapMap | 1000GP | C | 0.97 | A | 0.03 | C/A |
| JPT | rs7582118 | 2 | 103096999 | 0.005 | 1 | HapMap | 1000GP | C | 0.97 | T | 0.03 | C/T |
| JPT | rs7607856 | 2 | 103097036 | 0.005 | 1 | HapMap | 1000GP | G | 0.97 | A | 0.03 | G/A |
| JPT | rs6747752 | 2 | 103097679 | 0.005 | 1 | HapMap | 1000GP | A | 0.97 | C | 0.03 | A/C |
| JPT | rs6751282 | 2 | 103098207 | 0.005 | 1 | HapMap | 1000GP | A | 0.97 | G | 0.03 | A/G |
| JPT | rs6736822 | 2 | 103098403 | 0.005 | 1 | HapMap | 1000GP | C | 0.97 | T | 0.03 | C/T |
| JPT | rs6741464 | 2 | 103099887 | 0.005 | 1 | HapMap | 1000GP | C | 0.97 | T | 0.03 | C/T |
| CHB | rs6543147 | 2 | 103099945 | 0.009 | 1 | HapMap | 1000GP | G | 0.97 | A | 0.03 | G/A |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| JPT | rs6543147 | 2 | 103099945 | 0.005 | 1 | HapMap | 1000GP | G | 0.97 | A | 0.03 | G/A |
| JPT | rs2080316 | 2 | 103104229 | 0.005 | 1 | HapMap | 1000GP | A | 0.97 | G | 0.03 | A/G |
| JPT | rs7558013 | 2 | 102992806 | 0.221 | 1 | HapMap | 1000GP | G | 0.98 | T | 0.02 | G/T |
| CHB | rs7558013 | 2 | 102992806 | 0.222 | 1 | HapMap | 1000GP | G | 0.98 | T | 0.02 | G/T |
| JPT | rs11465698 | 2 | 103054577 | 0.185 | 1 | HapMap | 1000GP | T | 0.98 | C | 0.02 | T/C |
| CHB | rs11465698 | 2 | 103054577 | 0.223 | 1 | HapMap | 1000GP | T | 0.98 | C | 0.02 | T/C |
| JPT | rs6543135 | 2 | 103062406 | 0.185 | 1 | HapMap | 1000GP | C | 0.98 | T | 0.02 | C/T |
| CHB | rs6543135 | 2 | 103062406 | 0.223 | 1 | HapMap | 1000GP | C | 0.98 | T | 0.02 | C/T |
| CHB | rs1880000 | 2 | 103099953 | 0.147 | 1 | HapMap | 1000GP | T | 0.98 | C | 0.02 | T/C |
| JPT | rs1880000 | 2 | 103099953 | 0.122 | 1 | HapMap | 1000GP | T | 0.98 | C | 0.02 | T/C |
| CHB | rs6749440 | 2 | 103101846 | 0.147 | 1 | HapMap | 1000GP | C | 0.98 | T | 0.02 | C/T |
| JPT | rs6749440 | 2 | 103101846 | 0.122 | 1 | HapMap | 1000GP | C | 0.98 | T | 0.02 | C/T |
| JPT | rs1403549 | 2 | 103110745 | 0.122 | 1 | HapMap | 1000GP | G | 0.98 | C | 0.02 | G/C |
| CHB | rs1403549 | 2 | 103110745 | 0.147 | 1 | HapMap | 1000GP | G | 0.98 | C | 0.02 | G/C |
| JPT | rs17027327 | 2 | 103122513 | 0.122 | 1 | HapMap | 1000GP | C | 0.98 | A | 0.02 | C/A |
| CHB | rs17027327 | 2 | 103122513 | 0.147 | 1 | HapMap | 1000GP | C | 0.98 | A | 0.02 | C/A |
| CHB | rs7587856 | 2 | 103144305 | 0.147 | 1 | HapMap | 1000GP | C | 0.98 | A | 0.02 | C/A |
| CHB | rs9677607 | 2 | 103149520 | 0.147 | 1 | HapMap | 1000GP | A | 0.98 | T | 0.02 | A/T |
| CHB | rs7593444 | 2 | 103158561 | 0.147 | 1 | HapMap | 1000GP | G | 0.98 | A | 0.02 | G/A |
| CHB | rs17027421 | 2 | 103159882 | 0.146 | 1 | HapMap | 1000GP | A | 0.98 | G | 0.02 | A/G |
| CHB | rs17027428 | 2 | 103163175 | 0.147 | 1 | HapMap | 1000GP | G | 0.98 | A | 0.02 | G/A |
| JPT | rs17027428 | 2 | 103163175 | 0.122 | 1 | HapMap | 1000GP | G | 0.98 | A | 0.02 | G/A |
| CHB | rs17027430 | 2 | 103163237 | 0.147 | 1 | HapMap | 1000GP | T | 0.98 | C | 0.02 | T/C |
| JPT | rs17027430 | 2 | 103163237 | 0.122 | 1 | HapMap | 1000GP | T | 0.98 | C | 0.02 | T/C |
| JPT | rs1523197 | 2 | 103163732 | 0.122 | 1 | HapMap | 1000GP | A | 0.98 | G | 0.02 | A/G |
| CHB | rs1523197 | 2 | 103163732 | 0.147 | 1 | HapMap | 1000GP | A | 0.98 | G | 0.02 | A/G |
| CHB | rs2310294 | 2 | 103165706 | 0.147 | 1 | HapMap | 1000GP | A | 0.98 | G | 0.02 | A/G |
| JPT | rs2310294 | 2 | 103165706 | 0.122 | 1 | HapMap | 1000GP | A | 0.98 | G | 0.02 | A/G |
| CHB | rs1989399 | 2 | 103166742 | 0.147 | 1 | HapMap | 1000GP | G | 0.98 | A | 0.02 | G/A |
| JPT | rs1989399 | 2 | 103166742 | 0.122 | 1 | HapMap | 1000GP | G | 0.98 | A | 0.02 | G/A |
| CHB | rs723292 | 2 | 103166804 | 0.147 | 1 | HapMap | 1000GP | A | 0.98 | G | 0.02 | A/G |
| CHB | rs3917256 | 2 | 102776855 | 0.002 | 1 | HapMap | 1000GP | C | 0.99 | T | 0.01 | C/T |
| CHB | rs3917281 | 2 | 102780653 | 0.002 | 1 | HapMap | 1000GP | G | 0.99 | T | 0.01 | G/T |
| CHB | rs11895033 | 2 | 102799751 | 0.072 | 1 | HapMap | 1000GP | T | 0.99 | C | 0.01 | T/C |
| CHB | rs4851550 | 2 | 102800046 | 0.002 | 1 | HapMap | 1000GP | A | 0.99 | G | 0.01 | A/G |
| JPT | rs11904409 | 2 | 102803184 | 0.003 | 1 | HapMap | 1000GP | G | 0.99 | A | 0.01 | G/A |
| JPT | rs12619169 | 2 | 103011084 | 0.002 | 1 | HapMap | 1000GP | G | 0.99 | A | 0.01 | G/A |
| CHB | rs12619169 | 2 | 103011084 | 0.002 | 1 | HapMap | 1000GP | G | 0.99 | A | 0.01 | G/A |
| CHB | rs952437 | 2 | 102897159 | 0.073 | 1 | HapMap | 1000GP | C | 0.9965 | T | 0.0035 | C/T |
| CHB | rs17639215 | 2 | 102953444 | 0.073 | 1 | HapMap | 1000GP | G | 0.9983 | A | 0.0017 | G/A |
| CHB | rs11465596 | 2 | 102987093 | 0.072 | 1 | HapMap | 1000GP | C | 0.9983 | A | 0.0017 | C/A |
| JPT | rs7606834 | 2 | 102811400 | 0.066 | 1 | HapMap | 1000GP | A | 1 | T | 0 | A/T |
| JPT | rs952438 | 2 | 102897385 | 0.06 | 1 | HapMap | 1000GP | G | 1 | A | 0 | G/A |
| CEU | rs17026762 | 2 | 102814372 | 0.017 | 1 | HapMap | 1000GP | A | NA | G | — | A/G |
| CEU | rs1861245 | 2 | 102966906 | 1 | 1 | HapMap | 1000GP | A | NA | G | — | A/G |
| CEU | rs7559566 | 2 | 103028041 | 0.761 | 1 | HapMap | 1000GP | G | NA | T | — | G/T |
| CEU | rs10208196 | 2 | 102996345 | 0.754 | 1 | HapMap | 1000GP | G | 0.54 | A | 0.46 | G/A |
| CEU | rs3213732 | 2 | 102998279 | 0.759 | 1 | HapMap | 1000GP | A | 0.54 | G | 0.46 | A/G |
| CEU | rs6760621 | 2 | 102999952 | 0.74 | 1 | HapMap | 1000GP | T | 0.54 | C | 0.46 | T/C |
| CEU | rs6706002 | 2 | 103006104 | 0.759 | 1 | HapMap | 1000GP | A | 0.54 | G | 0.46 | A/G |
| CEU | rs4851571 | 2 | 103019000 | 0.759 | 1 | HapMap | 1000GP | C | 0.54 | T | 0.46 | C/T |
| CEU | rs4851572 | 2 | 103019031 | 0.759 | 1 | HapMap | 1000GP | G | 0.54 | A | 0.46 | G/A |
| CEU | rs2110662 | 2 | 103020139 | 0.759 | 1 | HapMap | 1000GP | A | 0.54 | T | 0.46 | A/T |
| CEU | rs7594402 | 2 | 103021267 | 0.759 | 1 | HapMap | 1000GP | A | 0.54 | T | 0.46 | A/T |
| CEU | rs6710034 | 2 | 103023678 | 0.759 | 1 | HapMap | 1000GP | G | 0.54 | A | 0.46 | G/A |
| CEU | rs10203558 | 2 | 103027640 | 0.754 | 1 | HapMap | 1000GP | T | 0.54 | C | 0.46 | T/C |
| CEU | rs10200952 | 2 | 103027651 | 0.722 | 1 | HapMap | 1000GP | A | 0.54 | C | 0.46 | A/C |
| CEU | rs4851576 | 2 | 103028895 | 0.759 | 1 | HapMap | 1000GP | C | 0.54 | T | 0.46 | C/T |
| CEU | rs4851577 | 2 | 103028921 | 0.759 | 1 | HapMap | 1000GP | T | 0.54 | C | 0.46 | T/C |
| CEU | rs4851579 | 2 | 103028984 | 0.759 | 1 | HapMap | 1000GP | G | 0.54 | A | 0.46 | G/A |
| CEU | rs1592458 | 2 | 103031749 | 0.759 | 1 | HapMap | 1000GP | A | 0.54 | T | 0.46 | A/T |
| CEU | rs2293224 | 2 | 103035779 | 0.759 | 1 | HapMap | 1000GP | T | 0.54 | C | 0.46 | T/C |
| CEU | rs1420100 | 2 | 103037002 | 0.759 | 1 | HapMap | 1000GP | C | 0.54 | A | 0.46 | C/A |
| CEU | rs3771155 | 2 | 103037826 | 0.754 | 1 | HapMap | 1000GP | A | 0.54 | G | 0.46 | A/G |
| CEU | rs10206291 | 2 | 103038863 | 0.759 | 1 | HapMap | 1000GP | T | 0.54 | C | 0.46 | T/C |
| CEU | rs3771154 | 2 | 103039360 | 0.759 | 1 | HapMap | 1000GP | C | 0.54 | T | 0.46 | C/T |
| CEU | rs6759479 | 2 | 103040047 | 0.759 | 1 | HapMap | 1000GP | A | 0.54 | C | 0.46 | A/C |
| CEU | rs7559845 | 2 | 103046214 | 0.759 | 1 | HapMap | 1000GP | T | 0.54 | G | 0.46 | T/G |
| CEU | rs3755265 | 2 | 103052816 | 0.754 | 1 | HapMap | 1000GP | C | 0.54 | A | 0.46 | C/A |
| CEU | rs4479442 | 2 | 103054074 | 0.759 | 1 | HapMap | 1000GP | A | 0.54 | T | 0.46 | A/T |
| CEU | rs13021177 | 2 | 103056493 | 0.759 | 1 | HapMap | 1000GP | A | 0.54 | G | 0.46 | A/G |
| CEU | rs10200410 | 2 | 102870871 | 0.573 | 0.788 | HapMap | 1000GP | G | 0.55 | A | 0.45 | G/A |
| CEU | rs1345301 | 2 | 102875587 | 0.573 | 0.788 | HapMap | 1000GP | A | 0.55 | G | 0.45 | A/G |
| CEU | rs2310243 | 2 | 102877560 | 0.573 | 0.788 | HapMap | 1000GP | A | 0.55 | G | 0.45 | A/G |
| CEU | rs13405355 | 2 | 102878206 | 0.573 | 0.788 | HapMap | 1000GP | C | 0.55 | T | 0.45 | C/T |
| CEU | rs13424006 | 2 | 102967236 | 1 | 1 | HapMap | 1000GP | T | 0.59 | C | 0.41 | T/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs6751967 | 2 | 102967413 | 1 | 1 | HapMap | 1000GP | T | 0.59 | C | 0.41 | T/C |
| CEU | rs6749114 | 2 | 102967587 | 1 | 1 | HapMap | 1000GP | A | 0.59 | C | 0.41 | A/C |
| CEU | rs10170583 | 2 | 102974764 | 1 | 1 | HapMap | 1000GP | G | 0.59 | A | 0.41 | G/A |
| CEU | rs10176664 | 2 | 102976172 | 1 | 1 | HapMap | 1000GP | G | 0.59 | A | 0.41 | G/A |
| CEU | rs1974675 | 2 | 102986375 | 0.954 | 1 | HapMap | 1000GP | G | 0.59 | A | 0.41 | G/A |
| CEU | rs6543119 | 2 | 102963072 | 0.414 | 1 | HapMap | 1000GP | A | 0.62 | T | 0.38 | A/T |
| CEU | rs13017455 | 2 | 102964742 | 0.414 | 1 | HapMap | 1000GP | C | 0.62 | T | 0.38 | C/T |
| CEU | rs12468355 | 2 | 102861250 | 0.238 | 0.611 | HapMap | 1000GP | T | 0.63 | G | 0.37 | T/G |
| CEU | rs1558626 | 2 | 102862070 | 0.345 | 0.774 | HapMap | 1000GP | T | 0.63 | A | 0.37 | T/A |
| CEU | rs1558623 | 2 | 102862402 | 0.345 | 0.774 | HapMap | 1000GP | T | 0.63 | A | 0.37 | T/A |
| CEU | rs17689452 | 2 | 102864681 | 0.345 | 0.774 | HapMap | 1000GP | A | 0.63 | G | 0.37 | A/G |
| CEU | rs1035126 | 2 | 103019981 | 0.337 | 0.656 | HapMap | 1000GP | C | 0.63 | T | 0.37 | C/T |
| CEU | rs2080288 | 2 | 103022166 | 0.337 | 0.656 | HapMap | 1000GP | G | 0.63 | A | 0.37 | G/A |
| CEU | rs4851578 | 2 | 103028951 | 0.341 | 0.649 | HapMap | 1000GP | T | 0.63 | G | 0.37 | T/G |
| CEU | rs7602207 | 2 | 103032366 | 0.359 | 0.653 | HapMap | 1000GP | C | 0.63 | G | 0.37 | C/G |
| CEU | rs6543144 | 2 | 103092575 | 0.337 | 0.656 | HapMap | 1000GP | A | 0.63 | G | 0.37 | A/G |
| CEU | rs10186746 | 2 | 102866377 | 0.437 | 0.882 | HapMap | 1000GP | G | 0.64 | A | 0.36 | G/A |
| CEU | rs11465700 | 2 | 103057668 | 0.337 | 0.656 | HapMap | 1000GP | G | 0.64 | A | 0.36 | G/A |
| CEU | rs10169192 | 2 | 103072211 | 0.337 | 0.656 | HapMap | 1000GP | A | 0.64 | G | 0.36 | A/G |
| CEU | rs2310301 | 2 | 103072935 | 0.337 | 0.656 | HapMap | 1000GP | C | 0.64 | T | 0.36 | C/T |
| CEU | rs6543140 | 2 | 103074274 | 0.337 | 0.656 | HapMap | 1000GP | G | 0.64 | T | 0.36 | G/T |
| CEU | rs13390895 | 2 | 103075499 | 0.337 | 0.656 | HapMap | 1000GP | G | 0.64 | A | 0.36 | G/A |
| CEU | rs4851591 | 2 | 103077423 | 0.337 | 0.656 | HapMap | 1000GP | T | 0.64 | C | 0.36 | T/C |
| CEU | rs7561351 | 2 | 103077780 | 0.337 | 0.656 | HapMap | 1000GP | A | 0.64 | G | 0.36 | A/G |
| CEU | rs13393175 | 2 | 103078849 | 0.337 | 0.656 | HapMap | 1000GP | T | 0.64 | G | 0.36 | T/G |
| CEU | rs6734203 | 2 | 103080066 | 0.301 | 0.626 | HapMap | 1000GP | G | 0.64 | C | 0.36 | G/C |
| CEU | rs6543142 | 2 | 103082006 | 0.36 | 0.705 | HapMap | 1000GP | T | 0.64 | C | 0.36 | T/C |
| CEU | rs10200945 | 2 | 102884757 | 0.245 | 0.637 | HapMap | 1000GP | A | 0.65 | T | 0.35 | A/T |
| CEU | rs1115281 | 2 | 102891107 | 0.245 | 0.637 | HapMap | 1000GP | C | 0.65 | G | 0.35 | C/G |
| CEU | rs950880 | 2 | 102932562 | 0.293 | 0.92 | HapMap | 1000GP | C | 0.65 | A | 0.35 | C/A |
| CEU | rs13001325 | 2 | 102939036 | 0.268 | 0.909 | HapMap | 1000GP | C | 0.65 | T | 0.35 | C/T |
| CEU | rs12479210 | 2 | 102949161 | 0.293 | 0.92 | HapMap | 1000GP | C | 0.65 | T | 0.35 | C/T |
| CEU | rs10208293 | 2 | 102966310 | 0.576 | 1 | HapMap | 1000GP | G | 0.72 | A | 0.28 | G/A |
| CEU | rs7600901 | 2 | 102915571 | 0.097 | 0.635 | HapMap | 1000GP | A | 0.73 | G | 0.27 | A/G |
| CEU | rs887972 | 2 | 103040945 | 0.313 | 1 | HapMap | 1000GP | G | 0.73 | A | 0.27 | G/A |
| CEU | rs887971 | 2 | 103041167 | 0.316 | 1 | HapMap | 1000GP | T | 0.73 | C | 0.27 | T/C |
| CEU | rs2310220 | 2 | 102951851 | 0.273 | 1 | HapMap | 1000GP | G | 0.74 | A | 0.26 | G/A |
| CEU | rs17027258 | 2 | 103091540 | 0.301 | 1 | HapMap | 1000GP | A | 0.74 | G | 0.26 | A/G |
| CEU | rs1420103 | 2 | 102948632 | 0.273 | 1 | HapMap | 1000GP | A | 0.75 | C | 0.25 | A/C |
| CEU | rs873022 | 2 | 102955683 | 0.301 | 1 | HapMap | 1000GP | G | 0.75 | T | 0.25 | G/T |
| CEU | rs3771177 | 2 | 102955860 | 0.301 | 1 | HapMap | 1000GP | G | 0.75 | T | 0.25 | G/T |
| CEU | rs3732129 | 2 | 102957532 | 0.301 | 1 | HapMap | 1000GP | T | 0.75 | C | 0.25 | T/C |
| CEU | rs3821204 | 2 | 102960281 | 0.301 | 1 | HapMap | 1000GP | C | 0.75 | G | 0.25 | C/G |
| CEU | rs12469506 | 2 | 102965871 | 0.301 | 1 | HapMap | 1000GP | C | 0.75 | T | 0.25 | C/T |
| CEU | rs3771172 | 2 | 102985812 | 0.301 | 1 | HapMap | 1000GP | C | 0.75 | T | 0.25 | C/T |
| CEU | rs3771171 | 2 | 102985950 | 0.285 | 1 | HapMap | 1000GP | T | 0.75 | C | 0.25 | T/C |
| CEU | rs2160202 | 2 | 102986154 | 0.296 | 1 | HapMap | 1000GP | G | 0.75 | A | 0.25 | G/A |
| CEU | rs7558013 | 2 | 102992806 | 0.604 | 1 | HapMap | 1000GP | G | 0.75 | T | 0.25 | G/T |
| CEU | rs17027037 | 2 | 102994884 | 0.301 | 1 | HapMap | 1000GP | A | 0.75 | G | 0.25 | A/G |
| CEU | rs2080289 | 2 | 102995020 | 0.301 | 1 | HapMap | 1000GP | G | 0.75 | A | 0.25 | G/A |
| CEU | rs11683700 | 2 | 102996805 | 0.308 | 1 | HapMap | 1000GP | C | 0.75 | T | 0.25 | C/T |
| CEU | rs4851570 | 2 | 103006387 | 0.301 | 1 | HapMap | 1000GP | A | 0.75 | G | 0.25 | A/G |
| CEU | rs11693955 | 2 | 103029165 | 0.301 | 1 | HapMap | 1000GP | A | 0.75 | T | 0.25 | A/T |
| CEU | rs3771156 | 2 | 103036677 | 0.301 | 1 | HapMap | 1000GP | C | 0.75 | T | 0.25 | C/T |
| CEU | rs11681718 | 2 | 103051144 | 0.301 | 1 | HapMap | 1000GP | A | 0.75 | G | 0.25 | A/G |
| CEU | rs4851582 | 2 | 103051558 | 0.301 | 1 | HapMap | 1000GP | T | 0.75 | C | 0.25 | T/C |
| CEU | rs17027179 | 2 | 103057159 | 0.301 | 1 | HapMap | 1000GP | C | 0.75 | T | 0.25 | C/T |
| CEU | rs10490203 | 2 | 103059237 | 0.301 | 1 | HapMap | 1000GP | T | 0.75 | G | 0.25 | T/G |
| CEU | rs11694360 | 2 | 103061147 | 0.177 | 0.732 | HapMap | 1000GP | G | 0.75 | A | 0.25 | G/A |
| CEU | rs11123928 | 2 | 103061286 | 0.177 | 0.732 | HapMap | 1000GP | G | 0.75 | A | 0.25 | G/A |
| CEU | rs7597017 | 2 | 103062116 | 0.185 | 0.73 | HapMap | 1000GP | A | 0.75 | G | 0.25 | A/G |
| CEU | rs6543135 | 2 | 103062406 | 0.708 | 1 | HapMap | 1000GP | C | 0.75 | T | 0.25 | C/T |
| CEU | rs17027230 | 2 | 103079330 | 0.301 | 1 | HapMap | 1000GP | C | 0.75 | T | 0.25 | C/T |
| CEU | rs3771202 | 2 | 102772669 | 0.104 | 0.712 | HapMap | 1000GP | C | 0.77 | G | 0.23 | C/G |
| CEU | rs3917245 | 2 | 102775155 | 0.112 | 0.732 | HapMap | 1000GP | G | 0.77 | A | 0.23 | G/A |
| CEU | rs3917246 | 2 | 102775164 | 0.112 | 0.732 | HapMap | 1000GP | T | 0.77 | C | 0.23 | T/C |
| CEU | rs759381 | 2 | 103094323 | 0.26 | 1 | HapMap | 1000GP | A | 0.77 | T | 0.23 | A/T |
| CEU | rs4851008 | 2 | 103026611 | 0.209 | 1 | HapMap | 1000GP | G | 0.78 | C | 0.22 | G/C |
| CEU | rs12712153 | 2 | 103111761 | 0.227 | 0.893 | HapMap | 1000GP | C | 0.78 | T | 0.22 | C/T |
| CEU | rs11687071 | 2 | 103111920 | 0.232 | 0.898 | HapMap | 1000GP | G | 0.78 | A | 0.22 | G/A |
| CEU | rs7566063 | 2 | 103112565 | 0.237 | 0.898 | HapMap | 1000GP | C | 0.78 | A | 0.22 | C/A |
| CEU | rs7591878 | 2 | 103112658 | 0.227 | 0.893 | HapMap | 1000GP | G | 0.78 | A | 0.22 | G/A |
| CEU | rs6543153 | 2 | 103114203 | 0.232 | 0.898 | HapMap | 1000GP | T | 0.78 | C | 0.22 | T/C |
| CEU | rs6543154 | 2 | 103114334 | 0.222 | 0.893 | HapMap | 1000GP | T | 0.78 | C | 0.22 | T/C |
| CEU | rs6543155 | 2 | 103114895 | 0.222 | 0.893 | HapMap | 1000GP | G | 0.78 | A | 0.22 | G/A |
| CEU | rs7573566 | 2 | 103115205 | 0.232 | 0.898 | HapMap | 1000GP | T | 0.78 | C | 0.22 | T/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs11123934 | 2 | 103115568 | 0.232 | 0.898 | HapMap | 1000GP | G | 0.78 | A | 0.22 | G/A |
| CEU | rs12987295 | 2 | 103115838 | 0.232 | 0.898 | HapMap | 1000GP | G | 0.78 | A | 0.22 | G/A |
| CEU | rs12995030 | 2 | 103116466 | 0.248 | 0.898 | HapMap | 1000GP | C | 0.78 | G | 0.22 | C/G |
| CEU | rs6728288 | 2 | 103117268 | 0.232 | 0.898 | HapMap | 1000GP | A | 0.78 | T | 0.22 | A/T |
| CEU | rs2075192 | 2 | 103118228 | 0.232 | 0.898 | HapMap | 1000GP | A | 0.78 | G | 0.22 | A/G |
| CEU | rs2075191 | 2 | 103118299 | 0.184 | 0.872 | HapMap | 1000GP | G | 0.78 | T | 0.22 | G/T |
| CEU | rs2075190 | 2 | 103118559 | 0.232 | 0.898 | HapMap | 1000GP | A | 0.78 | T | 0.22 | A/T |
| CEU | rs2075189 | 2 | 103118689 | 0.237 | 0.898 | HapMap | 1000GP | C | 0.78 | G | 0.22 | C/G |
| CEU | rs11690932 | 2 | 103119029 | 0.232 | 0.898 | HapMap | 1000GP | G | 0.78 | A | 0.22 | G/A |
| CEU | rs4851605 | 2 | 103120868 | 0.258 | 0.894 | HapMap | 1000GP | A | 0.78 | G | 0.22 | A/G |
| CEU | rs4851606 | 2 | 103120889 | 0.237 | 0.898 | HapMap | 1000GP | G | 0.78 | A | 0.22 | G/A |
| CEU | rs3917256 | 2 | 102776855 | 0.094 | 0.712 | HapMap | 1000GP | C | 0.79 | T | 0.21 | C/T |
| CEU | rs2058622 | 2 | 102985424 | 0.167 | 1 | HapMap | 1000GP | A | 0.79 | G | 0.21 | A/G |
| CEU | rs3771170 | 2 | 102985980 | 0.137 | 0.855 | HapMap | 1000GP | T | 0.79 | A | 0.21 | T/A |
| CEU | rs2058623 | 2 | 102986170 | 0.175 | 1 | HapMap | 1000GP | C | 0.79 | T | 0.21 | C/T |
| CEU | rs1465321 | 2 | 102986618 | 0.167 | 1 | HapMap | 1000GP | T | 0.79 | C | 0.21 | T/C |
| CEU | rs2270297 | 2 | 102992675 | 0.209 | 1 | HapMap | 1000GP | T | 0.79 | C | 0.21 | T/C |
| CEU | rs6753717 | 2 | 102993161 | 0.209 | 1 | HapMap | 1000GP | A | 0.79 | C | 0.21 | A/C |
| CEU | rs6750020 | 2 | 102994714 | 0.209 | 1 | HapMap | 1000GP | G | 0.79 | A | 0.21 | G/A |
| CEU | rs4851007 | 2 | 103024813 | 0.209 | 1 | HapMap | 1000GP | T | 0.79 | G | 0.21 | T/G |
| CEU | rs4851575 | 2 | 103025203 | 0.209 | 1 | HapMap | 1000GP | G | 0.79 | A | 0.21 | G/A |
| CEU | rs1807782 | 2 | 103033147 | 0.209 | 1 | HapMap | 1000GP | C | 0.79 | T | 0.21 | C/T |
| CEU | rs3755268 | 2 | 103038527 | 0.209 | 1 | HapMap | 1000GP | C | 0.79 | G | 0.21 | C/G |
| CEU | rs3817465 | 2 | 103039584 | 0.209 | 1 | HapMap | 1000GP | A | 0.79 | T | 0.21 | A/T |
| CEU | rs11694658 | 2 | 103045020 | 0.195 | 1 | HapMap | 1000GP | A | 0.79 | G | 0.21 | A/G |
| CEU | rs2160232 | 2 | 103046880 | 0.237 | 1 | HapMap | 1000GP | G | 0.79 | A | 0.21 | G/A |
| CEU | rs6716784 | 2 | 103048467 | 0.196 | 1 | HapMap | 1000GP | T | 0.79 | G | 0.21 | T/G |
| CEU | rs6543134 | 2 | 103050458 | 0.187 | 1 | HapMap | 1000GP | T | 0.79 | G | 0.21 | T/G |
| CEU | rs2110735 | 2 | 103050925 | 0.209 | 1 | HapMap | 1000GP | A | 0.79 | G | 0.21 | A/G |
| CEU | rs2110734 | 2 | 103052206 | 0.201 | 1 | HapMap | 1000GP | C | 0.79 | T | 0.21 | C/T |
| CEU | rs6746271 | 2 | 103052995 | 0.213 | 1 | HapMap | 1000GP | G | 0.79 | C | 0.21 | G/C |
| CEU | rs2058658 | 2 | 103054803 | 0.209 | 1 | HapMap | 1000GP | T | 0.79 | C | 0.21 | T/C |
| CEU | rs4851009 | 2 | 103055644 | 0.209 | 1 | HapMap | 1000GP | G | 0.79 | A | 0.21 | G/A |
| CEU | rs1558650 | 2 | 103060024 | 0.209 | 1 | HapMap | 1000GP | T | 0.79 | A | 0.21 | T/A |
| CEU | rs6734736 | 2 | 103062880 | 0.122 | 1 | HapMap | 1000GP | C | 0.79 | T | 0.21 | C/T |
| CEU | rs4070554 | 2 | 103074493 | 0.209 | 1 | HapMap | 1000GP | A | 0.79 | G | 0.21 | A/G |
| CEU | rs6761825 | 2 | 103075561 | 0.209 | 1 | HapMap | 1000GP | T | 0.79 | C | 0.21 | T/C |
| CEU | rs6705001 | 2 | 103076210 | 0.209 | 1 | HapMap | 1000GP | A | 0.79 | G | 0.21 | A/G |
| CEU | rs6543141 | 2 | 103076351 | 0.209 | 1 | HapMap | 1000GP | G | 0.79 | A | 0.21 | G/A |
| CEU | rs4241210 | 2 | 103078740 | 0.209 | 1 | HapMap | 1000GP | G | 0.79 | A | 0.21 | G/A |
| CEU | rs6720564 | 2 | 103079297 | 0.209 | 1 | HapMap | 1000GP | T | 0.79 | C | 0.21 | T/C |
| CEU | rs6717915 | 2 | 103079619 | 0.209 | 1 | HapMap | 1000GP | A | 0.79 | C | 0.21 | A/C |
| CEU | rs6718157 | 2 | 103079814 | 0.201 | 1 | HapMap | 1000GP | A | 0.79 | T | 0.21 | A/T |
| CEU | rs917996 | 2 | 103082273 | 0.209 | 1 | HapMap | 1000GP | C | 0.79 | A | 0.21 | C/A |
| CEU | rs990171 | 2 | 103086770 | 0.201 | 1 | HapMap | 1000GP | A | 0.79 | C | 0.21 | A/C |
| CEU | rs1468791 | 2 | 103092021 | 0.209 | 1 | HapMap | 1000GP | A | 0.79 | G | 0.21 | A/G |
| CEU | rs7597819 | 2 | 103092906 | 0.209 | 1 | HapMap | 1000GP | A | 0.79 | G | 0.21 | A/G |
| CEU | rs6737668 | 2 | 103093081 | 0.209 | 1 | HapMap | 1000GP | C | 0.79 | T | 0.21 | C/T |
| CEU | rs10469840 | 2 | 103093243 | 0.221 | 1 | HapMap | 1000GP | T | 0.79 | C | 0.21 | T/C |
| CEU | rs13027294 | 2 | 102860074 | 0.159 | 1 | HapMap | 1000GP | G | 0.8 | C | 0.2 | G/C |
| CEU | rs11677452 | 2 | 102865236 | 0.21 | 1 | HapMap | 1000GP | A | 0.8 | T | 0.2 | A/T |
| CEU | rs9646944 | 2 | 102865875 | 0.21 | 1 | HapMap | 1000GP | G | 0.8 | C | 0.2 | G/C |
| CEU | rs11685483 | 2 | 103159093 | 0.145 | 0.859 | HapMap | 1000GP | A | 0.8 | C | 0.2 | A/C |
| CEU | rs6739426 | 2 | 103160443 | 0.145 | 0.859 | HapMap | 1000GP | A | 0.8 | G | 0.2 | A/G |
| CEU | rs11899041 | 2 | 103161053 | 0.145 | 0.859 | HapMap | 1000GP | T | 0.8 | A | 0.2 | T/A |
| CEU | rs1303960 | 2 | 103165832 | 0.145 | 0.859 | HapMap | 1000GP | G | 0.8 | A | 0.2 | G/A |
| CEU | rs9989842 | 2 | 103123633 | 0.145 | 0.859 | HapMap | 1000GP | C | 0.81 | G | 0.19 | C/G |
| CEU | rs9989749 | 2 | 103123642 | 0.145 | 0.859 | HapMap | 1000GP | G | 0.81 | A | 0.19 | G/A |
| CEU | rs6751949 | 2 | 103125138 | 0.145 | 0.859 | HapMap | 1000GP | G | 0.81 | A | 0.19 | G/A |
| CEU | rs6724322 | 2 | 103125182 | 0.145 | 0.859 | HapMap | 1000GP | C | 0.81 | T | 0.19 | C/T |
| CEU | rs4851607 | 2 | 103125632 | 0.157 | 0.827 | HapMap | 1000GP | C | 0.81 | T | 0.19 | C/T |
| CEU | rs10195948 | 2 | 103125736 | 0.134 | 0.843 | HapMap | 1000GP | T | 0.81 | C | 0.19 | T/C |
| CEU | rs12712155 | 2 | 103127963 | 0.145 | 0.859 | HapMap | 1000GP | A | 0.81 | T | 0.19 | A/T |
| CEU | rs4851609 | 2 | 103128866 | 0.145 | 0.859 | HapMap | 1000GP | T | 0.81 | C | 0.19 | T/C |
| CEU | rs11676371 | 2 | 103129692 | 0.123 | 0.828 | HapMap | 1000GP | G | 0.81 | C | 0.19 | G/C |
| CEU | rs2192758 | 2 | 103132269 | 0.145 | 0.859 | HapMap | 1000GP | C | 0.81 | G | 0.19 | C/G |
| CEU | rs2192757 | 2 | 103132378 | 0.156 | 0.864 | HapMap | 1000GP | C | 0.81 | T | 0.19 | C/T |
| CEU | rs6714379 | 2 | 103133310 | 0.147 | 0.857 | HapMap | 1000GP | A | 0.81 | G | 0.19 | A/G |
| CEU | rs1523203 | 2 | 103135759 | 0.156 | 0.864 | HapMap | 1000GP | A | 0.81 | G | 0.19 | A/G |
| CEU | rs4851611 | 2 | 103135938 | 0.156 | 0.864 | HapMap | 1000GP | A | 0.81 | T | 0.19 | A/T |
| CEU | rs4851613 | 2 | 103137990 | 0.157 | 0.868 | HapMap | 1000GP | T | 0.81 | C | 0.19 | T/C |
| CEU | rs6750971 | 2 | 103138825 | 0.156 | 0.864 | HapMap | 1000GP | A | 0.81 | G | 0.19 | A/G |
| CEU | rs10193407 | 2 | 103139298 | 0.156 | 0.864 | HapMap | 1000GP | C | 0.81 | T | 0.19 | C/T |
| CEU | rs11123935 | 2 | 103139751 | 0.156 | 0.864 | HapMap | 1000GP | A | 0.81 | G | 0.19 | A/G |
| CEU | rs1024798 | 2 | 103141651 | 0.145 | 0.859 | HapMap | 1000GP | G | 0.81 | C | 0.19 | G/C |
| CEU | rs6724213 | 2 | 103151219 | 0.13 | 0.822 | HapMap | 1000GP | A | 0.81 | C | 0.19 | A/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs2871474 | 2 | 103151441 | 0.145 | 0.859 | HapMap | 1000GP | G | 0.81 | A | 0.19 | G/A |
| CEU | rs2287048 | 2 | 102773999 | 0.227 | 1 | HapMap | 1000GP | C | 0.82 | T | 0.18 | C/T |
| CEU | rs17027029 | 2 | 102990648 | 0.181 | 1 | HapMap | 1000GP | G | 0.82 | C | 0.18 | G/C |
| CEU | rs3771164 | 2 | 102991786 | 0.178 | 1 | HapMap | 1000GP | A | 0.82 | T | 0.18 | A/T |
| CEU | rs12991737 | 2 | 103018128 | 0.198 | 1 | HapMap | 1000GP | T | 0.82 | A | 0.18 | T/A |
| CEU | rs10181785 | 2 | 103025274 | 0.193 | 1 | HapMap | 1000GP | C | 0.82 | T | 0.18 | C/T |
| CEU | rs12712148 | 2 | 103025547 | 0.193 | 1 | HapMap | 1000GP | G | 0.82 | A | 0.18 | G/A |
| CEU | rs7586983 | 2 | 103028066 | 0.193 | 1 | HapMap | 1000GP | C | 0.82 | T | 0.18 | C/T |
| CEU | rs2272127 | 2 | 103039873 | 0.21 | 1 | HapMap | 1000GP | C | 0.82 | G | 0.18 | C/G |
| CEU | rs10166330 | 2 | 103050390 | 0.193 | 1 | HapMap | 1000GP | C | 0.82 | T | 0.18 | C/T |
| CEU | rs11465736 | 2 | 103067930 | 0 | 1 | HapMap | 1000GP | C | 0.82 | T | 0.18 | C/T |
| CEU | rs10169676 | 2 | 103074919 | 0.193 | 1 | HapMap | 1000GP | G | 0.82 | A | 0.18 | G/A |
| CEU | rs741284 | 2 | 103083324 | 0.193 | 1 | HapMap | 1000GP | G | 0.82 | C | 0.18 | G/C |
| CEU | rs10172116 | 2 | 103087573 | 0.164 | 1 | HapMap | 1000GP | C | 0.82 | T | 0.18 | C/T |
| CEU | rs13030642 | 2 | 103091585 | 0.193 | 1 | HapMap | 1000GP | C | 0.82 | A | 0.18 | C/A |
| CEU | rs3732127 | 2 | 103013750 | 0.193 | 1 | HapMap | 1000GP | G | 0.83 | C | 0.17 | G/C |
| CEU | rs2241132 | 2 | 102804035 | 0.086 | 1 | HapMap | 1000GP | C | 0.84 | A | 0.16 | C/A |
| CEU | rs1882510 | 2 | 102883618 | 0.209 | 1 | HapMap | 1000GP | C | 0.84 | T | 0.16 | C/T |
| CEU | rs4851610 | 2 | 103134652 | 0.077 | 0.81 | HapMap | 1000GP | C | 0.84 | G | 0.16 | C/G |
| CEU | rs950881 | 2 | 102932512 | 0.046 | 1 | HapMap | 1000GP | G | 0.85 | T | 0.15 | G/T |
| CEU | rs1558648 | 2 | 102810168 | 0.1 | 0.792 | HapMap | 1000GP | T | 0.86 | G | 0.14 | T/G |
| CEU | rs12996377 | 2 | 102830478 | 0.12 | 0.827 | HapMap | 1000GP | T | 0.86 | A | 0.14 | T/A |
| CEU | rs7572871 | 2 | 102853838 | 0.053 | 0.719 | HapMap | 1000GP | G | 0.86 | A | 0.14 | G/A |
| CEU | rs11690644 | 2 | 102914214 | 0.181 | 1 | HapMap | 1000GP | A | 0.86 | G | 0.14 | A/G |
| CEU | rs985523 | 2 | 102954376 | 0.322 | 1 | HapMap | 1000GP | G | 0.86 | A | 0.14 | G/A |
| CEU | rs13408569 | 2 | 102955056 | 0.159 | 1 | HapMap | 1000GP | G | 0.86 | C | 0.14 | G/C |
| CEU | rs13408661 | 2 | 102955082 | 0.159 | 1 | HapMap | 1000GP | G | 0.86 | A | 0.14 | G/A |
| CEU | rs10173081 | 2 | 102957348 | 0.159 | 1 | HapMap | 1000GP | C | 0.86 | T | 0.14 | C/T |
| CEU | rs6719130 | 2 | 102958236 | 0.322 | 1 | HapMap | 1000GP | C | 0.86 | T | 0.14 | C/T |
| CEU | rs3771167 | 2 | 102986188 | 0.277 | 1 | HapMap | 1000GP | A | 0.86 | G | 0.14 | A/G |
| CEU | rs6728945 | 2 | 102986471 | 0.31 | 1 | HapMap | 1000GP | T | 0.86 | C | 0.14 | T/C |
| CEU | rs17639215 | 2 | 102953444 | 0.322 | 1 | HapMap | 1000GP | G | 0.87 | A | 0.13 | G/A |
| CEU | rs12989197 | 2 | 102962739 | 0.056 | 1 | HapMap | 1000GP | G | 0.87 | A | 0.13 | G/A |
| CEU | rs12996097 | 2 | 102963628 | 0.056 | 1 | HapMap | 1000GP | G | 0.87 | A | 0.13 | G/A |
| CEU | rs13028993 | 2 | 102963949 | 0.056 | 1 | HapMap | 1000GP | T | 0.87 | C | 0.13 | T/C |
| CEU | rs17696376 | 2 | 102965153 | 0.193 | 1 | HapMap | 1000GP | C | 0.87 | T | 0.13 | C/T |
| CEU | rs12999542 | 2 | 102965392 | 0.056 | 1 | HapMap | 1000GP | A | 0.87 | C | 0.13 | A/C |
| CEU | rs4851567 | 2 | 102972807 | 0.193 | 1 | HapMap | 1000GP | G | 0.87 | A | 0.13 | G/A |
| CEU | rs12105808 | 2 | 102974222 | 0.198 | 1 | HapMap | 1000GP | A | 0.87 | T | 0.13 | A/T |
| CEU | rs11465596 | 2 | 102987093 | 0.301 | 1 | HapMap | 1000GP | C | 0.87 | A | 0.13 | C/A |
| CEU | rs6759588 | 2 | 103040159 | 0.241 | 1 | HapMap | 1000GP | A | 0.87 | G | 0.13 | A/G |
| CEU | rs11465698 | 2 | 103054577 | 0.264 | 1 | HapMap | 1000GP | T | 0.87 | C | 0.13 | T/C |
| CEU | rs1880000 | 2 | 103099953 | 0.245 | 1 | HapMap | 1000GP | T | 0.87 | C | 0.13 | T/C |
| CEU | rs6749440 | 2 | 103101846 | 0.245 | 1 | HapMap | 1000GP | C | 0.87 | T | 0.13 | C/T |
| CEU | rs1403549 | 2 | 103110745 | 0.245 | 1 | HapMap | 1000GP | G | 0.87 | C | 0.13 | G/C |
| CEU | rs17027327 | 2 | 103122513 | 0.245 | 1 | HapMap | 1000GP | C | 0.87 | A | 0.13 | C/A |
| CEU | rs7587856 | 2 | 103144305 | 0.242 | 1 | HapMap | 1000GP | C | 0.87 | A | 0.13 | C/A |
| CEU | rs9677607 | 2 | 103149520 | 0.245 | 1 | HapMap | 1000GP | A | 0.87 | T | 0.13 | A/T |
| CEU | rs7593444 | 2 | 103158561 | 0.245 | 1 | HapMap | 1000GP | G | 0.87 | A | 0.13 | G/A |
| CEU | rs17027421 | 2 | 103159882 | 0.252 | 1 | HapMap | 1000GP | A | 0.87 | G | 0.13 | A/G |
| CEU | rs7582378 | 2 | 103162263 | 0.245 | 1 | HapMap | 1000GP | C | 0.87 | A | 0.13 | C/A |
| CEU | rs17027428 | 2 | 103163175 | 0.245 | 1 | HapMap | 1000GP | G | 0.87 | A | 0.13 | G/A |
| CEU | rs17027430 | 2 | 103163237 | 0.245 | 1 | HapMap | 1000GP | T | 0.87 | C | 0.13 | T/C |
| CEU | rs1523197 | 2 | 103163732 | 0.245 | 1 | HapMap | 1000GP | A | 0.87 | G | 0.13 | A/G |
| CEU | rs2310294 | 2 | 103165706 | 0.245 | 1 | HapMap | 1000GP | A | 0.87 | G | 0.13 | A/G |
| CEU | rs1989399 | 2 | 103166742 | 0.245 | 1 | HapMap | 1000GP | G | 0.87 | A | 0.13 | G/A |
| CEU | rs723292 | 2 | 103166804 | 0.245 | 1 | HapMap | 1000GP | A | 0.87 | G | 0.13 | A/G |
| CEU | rs1476984 | 2 | 102912269 | 0.176 | 1 | HapMap | 1000GP | C | 0.88 | T | 0.12 | C/T |
| CEU | rs13425475 | 2 | 103025181 | 0.188 | 1 | HapMap | 1000GP | G | 0.88 | A | 0.12 | G/A |
| CEU | rs6724273 | 2 | 103080103 | 0.21 | 1 | HapMap | 1000GP | T | 0.88 | A | 0.12 | T/A |
| CEU | rs13008334 | 2 | 103167031 | 0.05 | 0.721 | HapMap | 1000GP | A | 0.88 | G | 0.12 | A/G |
| CEU | rs11465623 | 2 | 102993039 | 0.05 | 1 | HapMap | 1000GP | G | 0.89 | T | 0.11 | G/T |
| CEU | rs11465673 | 2 | 103035375 | 0.034 | 1 | HapMap | 1000GP | T | 0.89 | C | 0.11 | T/C |
| CEU | rs17821875 | 2 | 103071030 | 0.056 | 1 | HapMap | 1000GP | A | 0.89 | G | 0.11 | A/G |
| CEU | rs6753066 | 2 | 103095946 | 0.047 | 1 | HapMap | 1000GP | G | 0.9 | C | 0.1 | G/C |
| CEU | rs6756536 | 2 | 103096400 | 0.047 | 1 | HapMap | 1000GP | G | 0.9 | T | 0.1 | G/T |
| CEU | rs6543145 | 2 | 103096436 | 0.047 | 1 | HapMap | 1000GP | C | 0.9 | A | 0.1 | C/A |
| CEU | rs7582118 | 2 | 103096999 | 0.047 | 1 | HapMap | 1000GP | C | 0.9 | T | 0.1 | C/T |
| CEU | rs7607856 | 2 | 103097036 | 0.047 | 1 | HapMap | 1000GP | G | 0.9 | A | 0.1 | G/A |
| CEU | rs6747752 | 2 | 103097679 | 0.047 | 1 | HapMap | 1000GP | A | 0.9 | C | 0.1 | A/C |
| CEU | rs6751282 | 2 | 103098207 | 0.047 | 1 | HapMap | 1000GP | A | 0.9 | G | 0.1 | A/G |
| CEU | rs6736822 | 2 | 103098403 | 0.047 | 1 | HapMap | 1000GP | C | 0.9 | T | 0.1 | C/T |
| CEU | rs6741464 | 2 | 103099887 | 0.047 | 1 | HapMap | 1000GP | C | 0.9 | T | 0.1 | C/T |
| CEU | rs6543147 | 2 | 103099945 | 0.047 | 1 | HapMap | 1000GP | G | 0.9 | A | 0.1 | G/A |
| CEU | rs2080316 | 2 | 103104229 | 0.047 | 1 | HapMap | 1000GP | A | 0.9 | G | 0.1 | A/G |
| CEU | rs17027352 | 2 | 103138836 | 0.042 | 1 | HapMap | 1000GP | C | 0.9 | T | 0.1 | C/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs7576682 | 2 | 103143312 | 0.026 | 1 | HapMap | 1000GP | G | 0.9 | A | 0.1 | G/A |
| CEU | rs3849363 | 2 | 103143548 | 0.047 | 1 | HapMap | 1000GP | T | 0.9 | G | 0.1 | T/G |
| CEU | rs13388541 | 2 | 103147818 | 0.042 | 1 | HapMap | 1000GP | T | 0.9 | C | 0.1 | T/C |
| CEU | rs10183491 | 2 | 103151587 | 0.047 | 1 | HapMap | 1000GP | T | 0.9 | G | 0.1 | T/G |
| CEU | rs17027415 | 2 | 103154594 | 0.047 | 1 | HapMap | 1000GP | C | 0.9 | A | 0.1 | C/A |
| CEU | rs4851553 | 2 | 102811808 | 0.073 | 0.766 | HapMap | 1000GP | A | 0.91 | G | 0.09 | A/G |
| CEU | rs1362347 | 2 | 102919585 | 0.015 | 1 | HapMap | 1000GP | C | 0.91 | T | 0.09 | C/T |
| CEU | rs13001301 | 2 | 102938998 | 0.015 | 1 | HapMap | 1000GP | C | 0.91 | T | 0.09 | C/T |
| CEU | rs17695648 | 2 | 102948181 | 0.015 | 1 | HapMap | 1000GP | A | 0.91 | G | 0.09 | A/G |
| CEU | rs3755278 | 2 | 102952217 | 0.015 | 1 | HapMap | 1000GP | T | 0.91 | C | 0.09 | T/C |
| CEU | rs13016771 | 2 | 102959080 | 0.015 | 1 | HapMap | 1000GP | G | 0.91 | A | 0.09 | G/A |
| CEU | rs2228139 | 2 | 102781649 | 0.045 | 0.684 | HapMap | 1000GP | C | 0.92 | G | 0.08 | C/G |
| CEU | rs3917299 | 2 | 102786086 | 0.045 | 0.684 | HapMap | 1000GP | A | 0.92 | G | 0.08 | A/G |
| CEU | rs3917268 | 2 | 102778862 | 0.015 | 1 | HapMap | 1000GP | A | 0.95 | T | 0.05 | A/T |
| CEU | rs3917291 | 2 | 102782166 | 0.04 | 1 | HapMap | 1000GP | G | 0.95 | A | 0.05 | G/A |
| CEU | rs3917314 | 2 | 102790863 | 0.04 | 1 | HapMap | 1000GP | A | 0.95 | C | 0.05 | A/C |
| CEU | rs3917320 | 2 | 102792875 | 0.04 | 1 | HapMap | 1000GP | A | 0.95 | C | 0.05 | A/C |
| CEU | rs12995229 | 2 | 102846907 | 0.039 | 1 | HapMap | 1000GP | A | 0.95 | G | 0.05 | A/G |
| CEU | rs2041747 | 2 | 102788409 | 0.023 | 1 | HapMap | 1000GP | G | 0.96 | A | 0.04 | G/A |
| CEU | rs9808381 | 2 | 102816909 | 0.023 | 1 | HapMap | 1000GP | C | 0.96 | T | 0.04 | C/T |
| CEU | rs1922300 | 2 | 102819594 | 0.023 | 1 | HapMap | 1000GP | C | 0.96 | T | 0.04 | C/T |
| CEU | rs13021607 | 2 | 102824726 | 0.042 | 1 | HapMap | 1000GP | G | 0.96 | A | 0.04 | G/A |
| CEU | rs10490570 | 2 | 102827739 | 0.04 | 1 | HapMap | 1000GP | C | 0.96 | T | 0.04 | C/T |
| CEU | rs12989930 | 2 | 102829822 | 0.04 | 1 | HapMap | 1000GP | T | 0.96 | C | 0.04 | T/C |
| CEU | rs13002813 | 2 | 102831280 | 0.04 | 1 | HapMap | 1000GP | T | 0.96 | C | 0.04 | T/C |
| CEU | rs13028635 | 2 | 102832284 | 0.04 | 1 | HapMap | 1000GP | C | 0.96 | T | 0.04 | C/T |
| CEU | rs13033782 | 2 | 102843833 | 0.039 | 1 | HapMap | 1000GP | G | 0.96 | A | 0.04 | G/A |
| CEU | rs13017475 | 2 | 102853208 | 0.04 | 1 | HapMap | 1000GP | C | 0.96 | T | 0.04 | C/T |
| CEU | rs12993937 | 2 | 102855831 | 0.054 | 1 | HapMap | 1000GP | G | 0.96 | T | 0.04 | G/T |
| CEU | rs13018912 | 2 | 102864310 | 0.04 | 1 | HapMap | 1000GP | G | 0.96 | T | 0.04 | G/T |
| CEU | rs12997225 | 2 | 102864748 | 0.04 | 1 | HapMap | 1000GP | A | 0.96 | C | 0.04 | A/C |
| CEU | rs13015695 | 2 | 102888441 | 0.04 | 1 | HapMap | 1000GP | C | 0.96 | A | 0.04 | C/A |
| CEU | rs12989419 | 2 | 102900754 | 0.013 | 1 | HapMap | 1000GP | A | 0.96 | C | 0.04 | A/C |
| CEU | rs13024772 | 2 | 102902173 | 0.013 | 1 | HapMap | 1000GP | G | 0.96 | A | 0.04 | G/A |
| CEU | rs13407644 | 2 | 102905351 | 0.013 | 1 | HapMap | 1000GP | A | 0.96 | G | 0.04 | A/G |
| CEU | rs13017541 | 2 | 102906176 | 0.015 | 1 | HapMap | 1000GP | C | 0.96 | T | 0.04 | C/T |
| CEU | rs13024003 | 2 | 102907761 | 0.015 | 1 | HapMap | 1000GP | G | 0.96 | C | 0.04 | G/C |
| CEU | rs12465829 | 2 | 103072320 | 0.039 | 1 | HapMap | 1000GP | T | 0.96 | C | 0.04 | T/C |
| CEU | rs17824661 | 2 | 103162027 | 0.031 | 1 | HapMap | 1000GP | A | 0.96 | C | 0.04 | A/C |
| CEU | rs17696274 | 2 | 102963227 | 0.039 | 1 | HapMap | 1000GP | C | 0.97 | G | 0.03 | C/G |
| CEU | rs11465677 | 2 | 103035764 | 0.008 | 1 | HapMap | 1000GP | G | 0.97 | A | 0.03 | G/A |
| CEU | rs12987260 | 2 | 103055634 | 0 | 1 | HapMap | 1000GP | G | 0.97 | T | 0.03 | G/T |
| CEU | rs10196556 | 2 | 103075079 | 0 | 1 | HapMap | 1000GP | C | 0.97 | T | 0.03 | C/T |
| CEU | rs3917236 | 2 | 102772268 | 0.008 | 1 | HapMap | 1000GP | C | 0.98 | T | 0.02 | C/T |
| CEU | rs2080312 | 2 | 102774810 | 0.008 | 1 | HapMap | 1000GP | A | 0.98 | G | 0.02 | A/G |
| CEU | rs17026899 | 2 | 102890137 | 0.008 | 1 | HapMap | 1000GP | A | 0.98 | C | 0.02 | A/C |
| CEU | rs1200327 | 2 | 102900355 | 0.031 | 1 | HapMap | 1000GP | A | 0.98 | G | 0.02 | A/G |
| CEU | rs13029918 | 2 | 102957291 | 0.013 | 1 | HapMap | 1000GP | A | 0.98 | G | 0.02 | A/G |
| CEU | rs12997015 | 2 | 103042401 | 0 | 1 | HapMap | 1000GP | A | 0.98 | G | 0.02 | A/G |
| CEU | rs3917226 | 2 | 102769457 | 0.008 | 1 | HapMap | 1000GP | A | 0.99 | T | 0.01 | A/T |
| CEU | rs3917270 | 2 | 102779392 | 0.008 | 1 | HapMap | 1000GP | A | 0.99 | G | 0.01 | A/G |
| CEU | rs3917271 | 2 | 102779509 | 0.008 | 1 | HapMap | 1000GP | G | 0.99 | A | 0.01 | G/A |
| CEU | rs3917298 | 2 | 102785255 | 0.008 | 1 | HapMap | 1000GP | G | 0.99 | A | 0.01 | G/A |
| CEU | rs3917312 | 2 | 102790182 | 0.008 | 1 | HapMap | 1000GP | G | 0.99 | C | 0.01 | G/C |
| CEU | rs3917313 | 2 | 102790240 | 0.008 | 1 | HapMap | 1000GP | T | 0.99 | C | 0.01 | T/C |
| CEU | rs3917327 | 2 | 102794379 | 0.008 | 1 | HapMap | 1000GP | C | 0.99 | G | 0.01 | C/G |
| CEU | rs3917333 | 2 | 102796783 | 0.008 | 1 | HapMap | 1000GP | T | 0.99 | A | 0.01 | T/A |
| CEU | rs3917334 | 2 | 102796880 | 0.008 | 1 | HapMap | 1000GP | G | 0.99 | T | 0.01 | G/T |
| CEU | rs7562706 | 2 | 102810899 | 0.008 | 1 | HapMap | 1000GP | G | 0.99 | T | 0.01 | G/T |
| CEU | rs7606834 | 2 | 102811400 | 0.008 | 1 | HapMap | 1000GP | A | 0.99 | T | 0.01 | A/T |
| CEU | rs7596051 | 2 | 102817675 | 0.008 | 1 | HapMap | 1000GP | C | 0.99 | T | 0.01 | C/T |
| CEU | rs6713939 | 2 | 102823188 | 0.008 | 1 | HapMap | 1000GP | C | 0.99 | T | 0.01 | C/T |
| CEU | rs6730496 | 2 | 102839010 | 0.008 | 1 | HapMap | 1000GP | A | 0.99 | G | 0.01 | A/G |
| CEU | rs6752537 | 2 | 102841912 | 0.026 | 1 | HapMap | 1000GP | G | 0.99 | A | 0.01 | G/A |
| CEU | rs13428595 | 2 | 102850317 | 0.008 | 1 | HapMap | 1000GP | T | 0.99 | G | 0.01 | T/G |
| CEU | rs11465674 | 2 | 103035434 | 0.008 | 1 | HapMap | 1000GP | T | 0.99 | G | 0.01 | T/G |
| CEU | rs11465731 | 2 | 103066939 | 0.008 | 1 | HapMap | 1000GP | G | 0.99 | A | 0.01 | G/A |
| YRI | rs3917321 | 2 | 102793221 | 0.023 | 1 | HapMap | 1000GP | A | NA | G | NA | A/G |
| YRI | rs3917302 | 2 | 102787096 | 0.024 | 1 | HapMap | 1000GP | C | NA | T | NA | C/T |
| YRI | rs1861245 | 2 | 102966906 | 1 | 1 | HapMap | 1000GP | A | NA | G | NA | A/G |
| YRI | rs11465679 | 2 | 103036409 | 0.023 | 1 | HapMap | 1000GP | A | NA | G | NA | A/G |
| YRI | rs10208293 | 2 | 102966310 | 0.489 | 1 | HapMap | 1000GP | G | 0.55 | A | 0.45 | G/A |
| YRI | rs6734742 | 2 | 102967857 | 0.852 | 1 | HapMap | 1000GP | C | 0.66 | T | 0.34 | C/T |
| YRI | rs6752482 | 2 | 102967858 | 0.827 | 1 | HapMap | 1000GP | T | 0.66 | C | 0.34 | T/C |
| YRI | rs10176664 | 2 | 102976172 | 0.916 | 1 | HapMap | 1000GP | G | 0.67 | A | 0.33 | G/A |
| YRI | rs1974675 | 2 | 102986375 | 0.951 | 1 | HapMap | 1000GP | G | 0.67 | A | 0.33 | G/A |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| YRI | rs10170583 | 2 | 102974764 | 0.956 | 1 | HapMap | 1000GP | G | 0.68 | A | 0.32 | G/A |
| YRI | rs10181869 | 2 | 102801852 | 0.072 | 0.686 | HapMap | 1000GP | C | 0.7 | A | 0.3 | C/A |
| YRI | rs6543117 | 2 | 102929445 | 0.072 | 1 | HapMap | 1000GP | A | 0.7 | G | 0.3 | A/G |
| YRI | rs6751977 | 2 | 102967430 | 0.806 | 1 | HapMap | 1000GP | T | 0.7 | C | 0.3 | T/C |
| YRI | rs13408569 | 2 | 102955056 | 0.216 | 1 | HapMap | 1000GP | G | 0.73 | C | 0.27 | G/C |
| YRI | rs13408661 | 2 | 102955082 | 0.216 | 1 | HapMap | 1000GP | G | 0.73 | A | 0.27 | G/A |
| YRI | rs10173081 | 2 | 102957348 | 0.216 | 1 | HapMap | 1000GP | C | 0.73 | T | 0.27 | C/T |
| YRI | rs1882511 | 2 | 102883721 | 0.043 | 0.749 | HapMap | 1000GP | G | 0.74 | A | 0.26 | G/A |
| YRI | rs1922288 | 2 | 102888565 | 0.043 | 0.749 | HapMap | 1000GP | T | 0.75 | C | 0.25 | T/C |
| YRI | rs9308855 | 2 | 102890795 | 0.043 | 0.749 | HapMap | 1000GP | A | 0.75 | G | 0.25 | A/G |
| YRI | rs13424006 | 2 | 102967236 | 1 | 1 | HapMap | 1000GP | T | 0.76 | C | 0.24 | T/C |
| YRI | rs6751967 | 2 | 102967413 | 1 | 1 | HapMap | 1000GP | T | 0.76 | C | 0.24 | T/C |
| YRI | rs6749114 | 2 | 102967587 | 1 | 1 | HapMap | 1000GP | A | 0.76 | C | 0.24 | A/C |
| YRI | rs7572871 | 2 | 102853838 | 0.056 | 0.674 | HapMap | 1000GP | G | 0.77 | A | 0.23 | G/A |
| YRI | rs10185897 | 2 | 102966790 | 0.145 | 0.881 | HapMap | 1000GP | C | 0.77 | A | 0.23 | C/A |
| YRI | rs17026825 | 2 | 102836665 | 0.046 | 0.616 | HapMap | 1000GP | A | 0.78 | T | 0.22 | A/T |
| YRI | rs1024791 | 2 | 102837910 | 0.046 | 0.616 | HapMap | 1000GP | T | 0.78 | C | 0.22 | T/C |
| YRI | rs3771186 | 2 | 102840411 | 0.047 | 0.623 | HapMap | 1000GP | G | 0.78 | A | 0.22 | G/A |
| YRI | rs10198860 | 2 | 102842633 | 0.051 | 0.634 | HapMap | 1000GP | T | 0.78 | A | 0.22 | T/A |
| YRI | rs13416449 | 2 | 102842665 | 0.045 | 0.607 | HapMap | 1000GP | A | 0.78 | G | 0.22 | A/G |
| YRI | rs12105808 | 2 | 102974222 | 0.07 | 1 | HapMap | 1000GP | A | 0.79 | T | 0.21 | A/T |
| YRI | rs10166535 | 2 | 102809860 | 0.042 | 0.601 | HapMap | 1000GP | G | 0.8 | T | 0.2 | G/T |
| YRI | rs3821206 | 2 | 102817648 | 0.042 | 0.601 | HapMap | 1000GP | C | 0.8 | T | 0.2 | C/T |
| YRI | rs4851567 | 2 | 102972807 | 0.077 | 1 | HapMap | 1000GP | G | 0.8 | A | 0.2 | G/A |
| YRI | rs13425475 | 2 | 103025181 | 0.064 | 0.806 | HapMap | 1000GP | G | 0.81 | A | 0.19 | G/A |
| YRI | rs13415651 | 2 | 103052038 | 0.043 | 0.749 | HapMap | 1000GP | G | 0.82 | C | 0.18 | G/C |
| YRI | rs10202399 | 2 | 103019317 | 0.038 | 0.729 | HapMap | 1000GP | G | 0.83 | T | 0.17 | G/T |
| YRI | rs13001325 | 2 | 102939036 | 0.376 | 0.901 | HapMap | 1000GP | C | 0.84 | T | 0.16 | C/T |
| YRI | rs12479210 | 2 | 102949161 | 0.466 | 1 | HapMap | 1000GP | C | 0.84 | T | 0.16 | C/T |
| YRI | rs6736287 | 2 | 103017996 | 0.036 | 0.713 | HapMap | 1000GP | T | 0.84 | C | 0.16 | T/C |
| YRI | rs2310239 | 2 | 102824201 | 0.051 | 1 | HapMap | 1000GP | G | 0.85 | A | 0.15 | G/A |
| YRI | rs950880 | 2 | 102932562 | 0.466 | 1 | HapMap | 1000GP | C | 0.85 | A | 0.15 | C/A |
| YRI | rs2075185 | 2 | 103070988 | 0.054 | 0.666 | HapMap | 1000GP | A | 0.85 | G | 0.15 | A/G |
| YRI | rs10179570 | 2 | 102891632 | 0.031 | 1 | HapMap | 1000GP | T | 0.87 | C | 0.13 | T/C |
| YRI | rs3917299 | 2 | 102786086 | 0.016 | 0.645 | HapMap | 1000GP | A | 0.88 | G | 0.12 | A/G |
| YRI | rs4070554 | 2 | 103074493 | 0.054 | 0.666 | HapMap | 1000GP | A | 0.88 | G | 0.12 | A/G |
| YRI | rs6761825 | 2 | 103075561 | 0.054 | 0.666 | HapMap | 1000GP | T | 0.88 | C | 0.12 | T/C |
| YRI | rs6720564 | 2 | 103079297 | 0.054 | 0.666 | HapMap | 1000GP | T | 0.88 | C | 0.12 | T/C |
| YRI | rs2058622 | 2 | 102985424 | 0.053 | 0.662 | HapMap | 1000GP | A | 0.89 | G | 0.11 | A/G |
| YRI | rs1465321 | 2 | 102986618 | 0.053 | 0.662 | HapMap | 1000GP | T | 0.89 | C | 0.11 | T/C |
| YRI | rs2160232 | 2 | 103046880 | 0.058 | 1 | HapMap | 1000GP | G | 0.89 | A | 0.11 | G/A |
| YRI | rs6705001 | 2 | 103076210 | 0.054 | 0.666 | HapMap | 1000GP | A | 0.89 | G | 0.11 | A/G |
| YRI | rs6543141 | 2 | 103076351 | 0.054 | 0.666 | HapMap | 1000GP | G | 0.89 | A | 0.11 | G/A |
| YRI | rs4241210 | 2 | 103078740 | 0.054 | 0.666 | HapMap | 1000GP | G | 0.89 | A | 0.11 | G/A |
| YRI | rs6717915 | 2 | 103079619 | 0.054 | 0.666 | HapMap | 1000GP | A | 0.89 | C | 0.11 | A/C |
| YRI | rs6718157 | 2 | 103079814 | 0.054 | 0.666 | HapMap | 1000GP | A | 0.89 | T | 0.11 | A/T |
| YRI | rs917996 | 2 | 103082273 | 0.054 | 0.666 | HapMap | 1000GP | C | 0.89 | A | 0.11 | C/A |
| YRI | rs1468791 | 2 | 103092021 | 0.054 | 0.666 | HapMap | 1000GP | A | 0.89 | G | 0.11 | A/G |
| YRI | rs13001301 | 2 | 102938998 | 0.173 | 1 | HapMap | 1000GP | C | 0.9 | T | 0.1 | C/T |
| YRI | rs17695648 | 2 | 102948181 | 0.227 | 1 | HapMap | 1000GP | A | 0.9 | G | 0.1 | A/G |
| YRI | rs3755278 | 2 | 102952217 | 0.227 | 1 | HapMap | 1000GP | T | 0.9 | C | 0.1 | T/C |
| YRI | rs6716784 | 2 | 103048467 | 0.07 | 1 | HapMap | 1000GP | T | 0.9 | G | 0.1 | T/G |
| YRI | rs2110735 | 2 | 103050925 | 0.054 | 0.666 | HapMap | 1000GP | A | 0.9 | G | 0.1 | A/G |
| YRI | rs2110734 | 2 | 103052206 | 0.066 | 0.672 | HapMap | 1000GP | C | 0.9 | T | 0.1 | C/T |
| YRI | rs4851009 | 2 | 103055644 | 0.054 | 0.666 | HapMap | 1000GP | G | 0.9 | A | 0.1 | G/A |
| YRI | rs3917245 | 2 | 102775155 | 0.028 | 1 | HapMap | 1000GP | G | 0.91 | A | 0.09 | G/A |
| YRI | rs13018912 | 2 | 102864310 | 0.155 | 0.826 | HapMap | 1000GP | G | 0.91 | T | 0.09 | G/T |
| YRI | rs12997225 | 2 | 102864748 | 0.155 | 0.826 | HapMap | 1000GP | A | 0.91 | C | 0.09 | A/C |
| YRI | rs13015695 | 2 | 102888441 | 0.137 | 0.811 | HapMap | 1000GP | C | 0.91 | A | 0.09 | C/A |
| YRI | rs2310220 | 2 | 102951851 | 0.342 | 1 | HapMap | 1000GP | G | 0.92 | A | 0.08 | G/A |
| YRI | rs17696376 | 2 | 102965153 | 0.023 | 1 | HapMap | 1000GP | C | 0.92 | T | 0.08 | C/T |
| YRI | rs11465623 | 2 | 102993039 | 0.036 | 0.609 | HapMap | 1000GP | G | 0.93 | T | 0.07 | G/T |
| YRI | rs3771156 | 2 | 103036677 | 0.143 | 0.711 | HapMap | 1000GP | C | 0.93 | T | 0.07 | C/T |
| YRI | rs11465689 | 2 | 103040167 | 0.036 | 0.609 | HapMap | 1000GP | C | 0.93 | A | 0.07 | C/A |
| YRI | rs10208920 | 2 | 103054132 | 0.039 | 1 | HapMap | 1000GP | C | 0.93 | T | 0.07 | C/T |
| YRI | rs9308858 | 2 | 103056004 | 0.039 | 1 | HapMap | 1000GP | C | 0.93 | T | 0.07 | C/T |
| YRI | rs17027177 | 2 | 103057056 | 0.039 | 1 | HapMap | 1000GP | T | 0.93 | C | 0.07 | T/C |
| YRI | rs13401597 | 2 | 103060818 | 0.041 | 1 | HapMap | 1000GP | C | 0.93 | G | 0.07 | C/G |
| YRI | rs13406732 | 2 | 103137911 | 0.035 | 1 | HapMap | 1000GP | C | 0.93 | A | 0.07 | C/A |
| YRI | rs3917242 | 2 | 102774268 | 0.015 | 1 | HapMap | 1000GP | T | 0.94 | C | 0.06 | T/C |
| YRI | rs3917268 | 2 | 102778862 | 0.065 | 0.695 | HapMap | 1000GP | A | 0.94 | T | 0.06 | A/T |
| YRI | rs3917275 | 2 | 102779944 | 0.011 | 1 | HapMap | 1000GP | A | 0.94 | G | 0.06 | A/G |
| YRI | rs3755282 | 2 | 102854882 | 0.007 | 1 | HapMap | 1000GP | C | 0.94 | T | 0.06 | C/T |
| YRI | rs12993937 | 2 | 102855831 | 0.071 | 1 | HapMap | 1000GP | G | 0.94 | T | 0.06 | G/T |
| YRI | rs952437 | 2 | 102897159 | 0.007 | 1 | HapMap | 1000GP | C | 0.94 | T | 0.06 | C/T |
| YRI | rs12989419 | 2 | 102900754 | 0.071 | 1 | HapMap | 1000GP | A | 0.94 | C | 0.06 | A/C |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| YRI | rs13024772 | 2 | 102902173 | 0.071 | 1 | HapMap | 1000GP | G | 0.94 | A | 0.06 | G/A |
| YRI | rs13017541 | 2 | 102906176 | 0.071 | 1 | HapMap | 1000GP | C | 0.94 | T | 0.06 | C/T |
| YRI | rs884517 | 2 | 102906457 | 0.019 | 1 | HapMap | 1000GP | T | 0.94 | C | 0.06 | T/C |
| YRI | rs13024003 | 2 | 102907761 | 0.048 | 1 | HapMap | 1000GP | G | 0.94 | C | 0.06 | G/C |
| YRI | rs873022 | 2 | 102955683 | 0.2 | 1 | HapMap | 1000GP | G | 0.94 | T | 0.06 | G/T |
| YRI | rs3771177 | 2 | 102955860 | 0.2 | 1 | HapMap | 1000GP | G | 0.94 | T | 0.06 | G/T |
| YRI | rs3732129 | 2 | 102957532 | 0.2 | 1 | HapMap | 1000GP | T | 0.94 | C | 0.06 | T/C |
| YRI | rs3821204 | 2 | 102960281 | 0.2 | 1 | HapMap | 1000GP | C | 0.94 | G | 0.06 | C/G |
| YRI | rs12469506 | 2 | 102965871 | 0.2 | 1 | HapMap | 1000GP | C | 0.94 | T | 0.06 | C/T |
| YRI | rs3771171 | 2 | 102985950 | 0.2 | 1 | HapMap | 1000GP | T | 0.94 | C | 0.06 | T/C |
| YRI | rs2160202 | 2 | 102986154 | 0.2 | 1 | HapMap | 1000GP | G | 0.94 | A | 0.06 | G/A |
| YRI | rs11683700 | 2 | 102996805 | 0.085 | 0.717 | HapMap | 1000GP | C | 0.94 | T | 0.06 | C/T |
| YRI | rs887972 | 2 | 103040945 | 0.15 | 0.714 | HapMap | 1000GP | G | 0.94 | A | 0.06 | G/A |
| YRI | rs11681718 | 2 | 103051144 | 0.143 | 0.711 | HapMap | 1000GP | A | 0.94 | G | 0.06 | A/G |
| YRI | rs11465711 | 2 | 103060092 | 0.071 | 1 | HapMap | 1000GP | T | 0.94 | C | 0.06 | T/C |
| YRI | rs17821875 | 2 | 103071030 | 0.071 | 1 | HapMap | 1000GP | A | 0.94 | G | 0.06 | A/G |
| YRI | rs3917239 | 2 | 102773548 | 0.023 | 1 | HapMap | 1000GP | C | 0.95 | T | 0.05 | C/T |
| YRI | rs17026775 | 2 | 102815794 | 0.011 | 1 | HapMap | 1000GP | C | 0.95 | T | 0.05 | C/T |
| YRI | rs11678722 | 2 | 102829807 | 0.047 | 1 | HapMap | 1000GP | C | 0.95 | T | 0.05 | C/T |
| YRI | rs985523 | 2 | 102954376 | 0.035 | 1 | HapMap | 1000GP | G | 0.95 | A | 0.05 | G/A |
| YRI | rs6719130 | 2 | 102958236 | 0.035 | 1 | HapMap | 1000GP | C | 0.95 | T | 0.05 | C/T |
| YRI | rs3771172 | 2 | 102985812 | 0.2 | 1 | HapMap | 1000GP | C | 0.95 | T | 0.05 | C/T |
| YRI | rs3771167 | 2 | 102986188 | 0.027 | 1 | HapMap | 1000GP | A | 0.95 | G | 0.05 | A/G |
| YRI | rs7566063 | 2 | 103112565 | 0.012 | 1 | HapMap | 1000GP | C | 0.95 | A | 0.05 | C/A |
| YRI | rs7591878 | 2 | 103112658 | 0.013 | 1 | HapMap | 1000GP | G | 0.95 | A | 0.05 | G/A |
| YRI | rs2228139 | 2 | 102781649 | 0.028 | 1 | HapMap | 1000GP | C | 0.96 | G | 0.04 | C/G |
| YRI | rs3771196 | 2 | 102815727 | 0.023 | 1 | HapMap | 1000GP | T | 0.96 | A | 0.04 | T/A |
| YRI | rs6733727 | 2 | 102839219 | 0.024 | 1 | HapMap | 1000GP | T | 0.96 | C | 0.04 | T/C |
| YRI | rs17026874 | 2 | 102861682 | 0.007 | 1 | HapMap | 1000GP | T | 0.96 | C | 0.04 | T/C |
| YRI | rs17026878 | 2 | 102862835 | 0.007 | 1 | HapMap | 1000GP | C | 0.96 | T | 0.04 | C/T |
| YRI | rs17026889 | 2 | 102882916 | 0.007 | 1 | HapMap | 1000GP | G | 0.96 | C | 0.04 | G/C |
| YRI | rs7340445 | 2 | 102901879 | 0.007 | 1 | HapMap | 1000GP | G | 0.96 | A | 0.04 | G/A |
| YRI | rs12987260 | 2 | 103055634 | 0.138 | 1 | HapMap | 1000GP | G | 0.96 | T | 0.04 | G/T |
| YRI | rs6708944 | 2 | 103123951 | 0.015 | 1 | HapMap | 1000GP | G | 0.96 | C | 0.04 | G/C |
| YRI | rs6737329 | 2 | 103128892 | 0.015 | 1 | HapMap | 1000GP | C | 0.96 | T | 0.04 | C/T |
| YRI | rs6752045 | 2 | 103128931 | 0.015 | 1 | HapMap | 1000GP | A | 0.96 | T | 0.04 | A/T |
| YRI | rs7597566 | 2 | 103159938 | 0.011 | 1 | HapMap | 1000GP | G | 0.96 | A | 0.04 | G/A |
| YRI | rs10195375 | 2 | 102806641 | 0.01 | 1 | HapMap | 1000GP | T | 0.97 | C | 0.03 | T/C |
| YRI | rs10201203 | 2 | 102814004 | 0.011 | 1 | HapMap | 1000GP | A | 0.97 | G | 0.03 | A/G |
| YRI | rs10201417 | 2 | 102814233 | 0.011 | 1 | HapMap | 1000GP | A | 0.97 | G | 0.03 | A/G |
| YRI | rs7596051 | 2 | 102817675 | 0.054 | 0.666 | HapMap | 1000GP | C | 0.97 | T | 0.03 | C/T |
| YRI | rs10184622 | 2 | 102825818 | 0.011 | 1 | HapMap | 1000GP | G | 0.97 | A | 0.03 | G/A |
| YRI | rs10179283 | 2 | 102826350 | 0.011 | 1 | HapMap | 1000GP | T | 0.97 | C | 0.03 | T/C |
| YRI | rs10168021 | 2 | 102827446 | 0.011 | 1 | HapMap | 1000GP | C | 0.97 | A | 0.03 | C/A |
| YRI | rs10207764 | 2 | 102835474 | 0.011 | 1 | HapMap | 1000GP | C | 0.97 | T | 0.03 | C/T |
| YRI | rs6730496 | 2 | 102839010 | 0.057 | 0.67 | HapMap | 1000GP | A | 0.97 | G | 0.03 | A/G |
| YRI | rs11903870 | 2 | 102886180 | 0.074 | 0.711 | HapMap | 1000GP | T | 0.97 | C | 0.03 | T/C |
| YRI | rs7594361 | 2 | 102932332 | 0.007 | 1 | HapMap | 1000GP | T | 0.97 | C | 0.03 | T/C |
| YRI | rs13397711 | 2 | 102934427 | 0.011 | 1 | HapMap | 1000GP | C | 0.97 | G | 0.03 | C/G |
| YRI | rs10174243 | 2 | 102940014 | 0.015 | 1 | HapMap | 1000GP | G | 0.97 | A | 0.03 | G/A |
| YRI | rs1420103 | 2 | 102948632 | 0.096 | 1 | HapMap | 1000GP | A | 0.97 | C | 0.03 | A/C |
| YRI | rs17639215 | 2 | 102953444 | 0.027 | 1 | HapMap | 1000GP | G | 0.97 | A | 0.03 | G/A |
| YRI | rs11465695 | 2 | 103041764 | 0.096 | 1 | HapMap | 1000GP | T | 0.97 | C | 0.03 | T/C |
| YRI | rs10177895 | 2 | 103049529 | 0.019 | 1 | HapMap | 1000GP | T | 0.97 | C | 0.03 | T/C |
| YRI | rs11889853 | 2 | 103080313 | 0.096 | 1 | HapMap | 1000GP | A | 0.97 | C | 0.03 | A/C |
| YRI | rs6729198 | 2 | 103096712 | 0.074 | 1 | HapMap | 1000GP | C | 0.97 | T | 0.03 | C/T |
| YRI | rs6543154 | 2 | 103114334 | 0.026 | 1 | HapMap | 1000GP | T | 0.97 | C | 0.03 | T/C |
| YRI | rs11123934 | 2 | 103115568 | 0.026 | 1 | HapMap | 1000GP | G | 0.97 | A | 0.03 | G/A |
| YRI | rs6714379 | 2 | 103133310 | 0.023 | 1 | HapMap | 1000GP | A | 0.97 | G | 0.03 | A/G |
| YRI | rs3917248 | 2 | 102775377 | 0.007 | 1 | HapMap | 1000GP | G | 0.98 | A | 0.02 | G/A |
| YRI | rs3917255 | 2 | 102776730 | 0.012 | 1 | HapMap | 1000GP | T | 0.98 | A | 0.02 | T/A |
| YRI | rs3917305 | 2 | 102788760 | 0.011 | 1 | HapMap | 1000GP | C | 0.98 | T | 0.02 | C/T |
| YRI | rs10181153 | 2 | 102801109 | 0.007 | 1 | HapMap | 1000GP | C | 0.98 | T | 0.02 | C/T |
| YRI | rs6722601 | 2 | 102813173 | 0.011 | 1 | HapMap | 1000GP | G | 0.98 | T | 0.02 | G/T |
| YRI | rs13405631 | 2 | 102828620 | 0.019 | 1 | HapMap | 1000GP | T | 0.98 | C | 0.02 | T/C |
| YRI | rs7567539 | 2 | 102839839 | 0.011 | 1 | HapMap | 1000GP | C | 0.98 | T | 0.02 | C/T |
| YRI | rs10209002 | 2 | 102860848 | 0.011 | 1 | HapMap | 1000GP | C | 0.98 | T | 0.02 | C/T |
| YRI | rs13423746 | 2 | 102883673 | 0.011 | 1 | HapMap | 1000GP | C | 0.98 | T | 0.02 | C/T |
| YRI | rs10175804 | 2 | 102890163 | 0.011 | 1 | HapMap | 1000GP | T | 0.98 | C | 0.02 | T/C |
| YRI | rs10180574 | 2 | 102892822 | 0.013 | 1 | HapMap | 1000GP | A | 0.98 | G | 0.02 | A/G |
| YRI | rs10211352 | 2 | 102896894 | 0.011 | 1 | HapMap | 1000GP | C | 0.98 | T | 0.02 | C/T |
| YRI | rs10200993 | 2 | 102908695 | 0.012 | 1 | HapMap | 1000GP | T | 0.98 | G | 0.02 | T/G |
| YRI | rs4577297 | 2 | 102918018 | 0.023 | 1 | HapMap | 1000GP | G | 0.98 | A | 0.02 | G/A |
| YRI | rs13429528 | 2 | 102948868 | 0.019 | 1 | HapMap | 1000GP | C | 0.98 | T | 0.02 | C/T |
| YRI | rs10181632 | 2 | 102956150 | 0.019 | 1 | HapMap | 1000GP | A | 0.98 | G | 0.02 | A/G |
| YRI | rs10168510 | 2 | 102963125 | 0.019 | 1 | HapMap | 1000GP | G | 0.98 | T | 0.02 | G/T |

TABLE 3-continued

SNPs in high LD with rs4988956

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| YRI | rs10193102 | 2 | 102963340 | 0.019 | 1 | HapMap | 1000GP | C | 0.98 | T | 0.02 | C/T |
| YRI | rs10178584 | 2 | 102994251 | 0.019 | 1 | HapMap | 1000GP | C | 0.98 | G | 0.02 | C/G |
| YRI | rs13388673 | 2 | 103032668 | 0.019 | 1 | HapMap | 1000GP | A | 0.98 | G | 0.02 | A/G |
| YRI | rs11465669 | 2 | 103034292 | 0.004 | 1 | HapMap | 1000GP | T | 0.98 | C | 0.02 | T/C |
| YRI | rs10199166 | 2 | 103066430 | 0.024 | 1 | HapMap | 1000GP | T | 0.98 | C | 0.02 | T/C |
| YRI | rs9631044 | 2 | 103070622 | 0.019 | 1 | HapMap | 1000GP | G | 0.98 | A | 0.02 | G/A |
| YRI | rs13386538 | 2 | 103077527 | 0.02 | 1 | HapMap | 1000GP | A | 0.98 | T | 0.02 | A/T |
| YRI | rs10169647 | 2 | 103081470 | 0.019 | 1 | HapMap | 1000GP | C | 0.98 | T | 0.02 | C/T |
| YRI | rs10190130 | 2 | 103094638 | 0.019 | 1 | HapMap | 1000GP | A | 0.98 | G | 0.02 | A/G |
| YRI | rs6724322 | 2 | 103125182 | 0.023 | 1 | HapMap | 1000GP | C | 0.98 | T | 0.02 | C/T |
| YRI | rs13423747 | 2 | 103128429 | 0.015 | 1 | HapMap | 1000GP | A | 0.98 | G | 0.02 | A/G |
| YRI | rs4851609 | 2 | 103128866 | 0.023 | 1 | HapMap | 1000GP | T | 0.98 | C | 0.02 | T/C |
| YRI | rs13417556 | 2 | 103130158 | 0.019 | 1 | HapMap | 1000GP | C | 0.98 | T | 0.02 | C/T |
| YRI | rs10180466 | 2 | 103132946 | 0.019 | 1 | HapMap | 1000GP | G | 0.98 | A | 0.02 | G/A |
| YRI | rs3917240 | 2 | 102773553 | 0.023 | 1 | HapMap | 1000GP | A | 0.99 | G | 0.01 | A/G |
| YRI | rs3917241 | 2 | 102774015 | 0 | 1 | HapMap | 1000GP | G | 0.99 | A | 0.01 | G/A |
| YRI | rs3917270 | 2 | 102779392 | 0.047 | 1 | HapMap | 1000GP | A | 0.99 | G | 0.01 | A/G |
| YRI | rs3732133 | 2 | 102794278 | 0.05 | 1 | HapMap | 1000GP | C | 0.99 | T | 0.01 | C/T |
| YRI | rs11465628 | 2 | 102993700 | 0.004 | 1 | HapMap | 1000GP | G | 0.99 | C | 0.01 | G/C |
| YRI | rs11465671 | 2 | 103034582 | 0 | 1 | HapMap | 1000GP | A | 0.99 | G | 0.01 | A/G |
| YRI | rs11895701 | 2 | 103055977 | 0.011 | 1 | HapMap | 1000GP | G | 0.99 | T | 0.01 | G/T |
| YRI | rs11465717 | 2 | 103061890 | 0.007 | 1 | HapMap | 1000GP | C | 0.99 | T | 0.01 | C/T |
| YRI | rs11465738 | 2 | 103068545 | 0.004 | 1 | HapMap | 1000GP | G | 0.99 | A | 0.01 | G/A |
| YRI | rs3917313 | 2 | 102790240 | 0.047 | 1 | HapMap | 1000GP | T | 0.9959 | C | 0.0041 | T/C |
| YRI | rs3917341 | 2 | 102783439 | 0.004 | 1 | HapMap | 1000GP | A | 1 | G | 0 | A/G |
| YRI | rs1922300 | 2 | 102819594 | 0 | 1 | HapMap | 1000GP | C | 1 | T | 0 | C/T |

TABLE 4

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs10117792 | 9 | 6148778 | 0.211 | 0.659 | HapMap | HapMap | T | 0.837 | C | 0.163 | T/C |
| JPT | rs10117792 | 9 | 6148778 | 0.417 | 0.726 | HapMap | HapMap | T | 0.918 | C | 0.082 | T/C |
| MKK | rs10117792 | 9 | 6148778 | 0.551 | 0.791 | HapMap | HapMap | T | 0.867 | C | 0.133 | T/C |
| CHD | rs10117792 | 9 | 6148778 | 0.404 | 0.674 | HapMap | HapMap | T | 0.882 | C | 0.118 | T/C |
| MEX | rs10117792 | 9 | 6148778 | 0.741 | 1 | HapMap | HapMap | T | 0.949 | C | 0.051 | T/C |
| GIH | rs10117792 | 9 | 6148778 | 0.884 | 1 | HapMap | HapMap | T | 0.949 | C | 0.051 | T/C |
| CEU | rs10117792 | 9 | 6148778 | 0.8 | 1 | HapMap | HapMap | T | 0.912 | C | 0.088 | T/C |
| CEU | rs10118795 | 9 | 6230658 | 0.217 | 1 | HapMap | HapMap | T | 0.345 | C | 0.655 | T/C |
| GIH | rs10118795 | 9 | 6230658 | 0.085 | 1 | HapMap | HapMap | T | 0.358 | C | 0.642 | T/C |
| JPT | rs10118795 | 9 | 6230658 | 0.05 | 1 | HapMap | HapMap | T | 0.535 | C | 0.465 | T/C |
| CEU | rs10119713 | 9 | 6153823 | 0.109 | 1 | HapMap | HapMap | G | 0.545 | A | 0.455 | G/A |
| CHD | rs10119713 | 9 | 6153823 | 0.152 | 0.784 | HapMap | HapMap | G | 0.676 | A | 0.324 | G/A |
| GIH | rs10119713 | 9 | 6153823 | 0.073 | 1 | HapMap | HapMap | G | 0.608 | A | 0.392 | G/A |
| JPT | rs10119713 | 9 | 6153823 | 0.131 | 0.698 | HapMap | HapMap | G | 0.808 | A | 0.192 | G/A |
| MKK | rs10119713 | 9 | 6153823 | 0.066 | 0.802 | HapMap | HapMap | G | 0.434 | A | 0.566 | G/A |
| MEX | rs10119713 | 9 | 6153823 | 0.052 | 0.693 | HapMap | HapMap | G | 0.66 | A | 0.34 | G/A |
| GIH | rs10120134 | 9 | 6078457 | 0.004 | 1 | HapMap | HapMap | G | 0.926 | A | 0.074 | G/A |
| JPT | rs10120134 | 9 | 6078457 | 0.041 | 0.632 | HapMap | HapMap | G | 0.698 | A | 0.302 | G/A |
| MEX | rs10120935 | 9 | 6355852 | 0.001 | 1 | HapMap | HapMap | G | 0.98 | C | 0.02 | G/C |
| MEX | rs10121888 | 9 | 6304179 | 0.001 | 1 | HapMap | HapMap | T | 0.02 | C | 0.98 | T/C |
| LWK | rs10121888 | 9 | 6304179 | 0.102 | 0.793 | HapMap | HapMap | T | 0.039 | C | 0.961 | T/C |
| MKK | rs10121888 | 9 | 6304179 | 0.007 | 1 | HapMap | HapMap | T | 0.047 | C | 0.953 | T/C |
| ASW | rs10121888 | 9 | 6304179 | 0.04 | 1 | HapMap | HapMap | T | 0.104 | C | 0.896 | T/C |
| GIH | rs10121888 | 9 | 6304179 | 0.001 | 1 | HapMap | HapMap | T | 0.017 | C | 0.983 | T/C |
| CEU | rs10124250 | 9 | 6151686 | 0.109 | 1 | HapMap | HapMap | C | 0.549 | T | 0.451 | C/T |
| MEX | rs10124250 | 9 | 6151686 | 0.059 | 0.703 | HapMap | HapMap | C | 0.68 | T | 0.32 | C/T |
| CHB | rs10124250 | 9 | 6151686 | 0.13 | 0.619 | HapMap | HapMap | C | 0.726 | T | 0.274 | C/T |
| CHD | rs10124250 | 9 | 6151686 | 0.183 | 0.804 | HapMap | HapMap | C | 0.706 | T | 0.294 | C/T |
| GIH | rs10124250 | 9 | 6151686 | 0.075 | 1 | HapMap | HapMap | C | 0.614 | T | 0.386 | C/T |
| JPT | rs10124250 | 9 | 6151686 | 0.163 | 0.718 | HapMap | HapMap | C | 0.837 | T | 0.163 | C/T |
| MKK | rs10124250 | 9 | 6151686 | 0.066 | 0.802 | HapMap | HapMap | C | 0.434 | T | 0.566 | C/T |
| ASW | rs1037885 | 9 | 6320915 | 0.04 | 0.626 | HapMap | HapMap | G | 0.245 | A | 0.755 | G/A |
| GIH | rs1037885 | 9 | 6320915 | 0.001 | 1 | HapMap | HapMap | G | 0.017 | A | 0.983 | G/A |
| MEX | rs1037885 | 9 | 6320915 | 0.001 | 1 | HapMap | HapMap | G | 0.03 | A | 0.97 | G/A |
| GIH | rs1048274 | 9 | 6246292 | 0.039 | 1 | HapMap | HapMap | G | 0.545 | A | 0.455 | G/A |
| MKK | rs1048274 | 9 | 6246292 | 0.057 | 0.698 | HapMap | HapMap | G | 0.535 | A | 0.465 | G/A |
| CEU | rs10491836 | 9 | 6321421 | 0.052 | 1 | HapMap | HapMap | C | 0.717 | A | 0.283 | C/A |
| ASW | rs10491836 | 9 | 6321421 | 0.041 | 0.663 | HapMap | HapMap | C | 0.736 | A | 0.264 | C/A |
| GIH | rs10491836 | 9 | 6321421 | 0.008 | 1 | HapMap | HapMap | C | 0.864 | A | 0.136 | C/A |
| MEX | rs10491836 | 9 | 6321421 | 0.013 | 1 | HapMap | HapMap | C | 0.82 | A | 0.18 | C/A |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MKK | rs10491836 | 9 | 6321421 | 0.025 | 0.718 | HapMap | HapMap | C | 0.739 | A | 0.261 | C/A |
| MEX | rs10491837 | 9 | 6357615 | 0.001 | 1 | HapMap | HapMap | A | 0.98 | G | 0.02 | A/G |
| YRI | rs1052335 | 9 | 6320380 | 0.105 | 0.645 | HapMap | HapMap | A | 0.907 | C | 0.093 | A/C |
| LWK | rs1052335 | 9 | 6320380 | 0.019 | 1 | HapMap | HapMap | A | 0.928 | C | 0.072 | A/C |
| MEX | rs1052335 | 9 | 6320380 | 0.04 | 0.671 | HapMap | HapMap | A | 0.6 | C | 0.4 | A/C |
| JPT | rs1052335 | 9 | 6320380 | 0.004 | 0.615 | HapMap | HapMap | A | 0.843 | C | 0.157 | A/C |
| ASW | rs1052335 | 9 | 6320380 | 0.303 | 1 | HapMap | HapMap | A | 0.925 | C | 0.075 | A/C |
| MKK | rs106033 | 9 | 6002734 | 0.069 | 0.638 | HapMap | HapMap | A | 0.556 | C | 0.444 | A/C |
| CEU | rs10733522 | 9 | 5982192 | 0.001 | 1 | HapMap | HapMap | C | 0.009 | T | 0.991 | C/T |
| MEX | rs10733522 | 9 | 5982192 | 0.003 | 1 | HapMap | HapMap | C | 0.06 | T | 0.94 | C/T |
| GIH | rs10733522 | 9 | 5982192 | 0.006 | 1 | HapMap | HapMap | C | 0.108 | T | 0.892 | C/T |
| CHB | rs10733522 | 9 | 5982192 | 0.116 | 0.758 | HapMap | HapMap | C | 0.307 | T | 0.693 | C/T |
| CHB | rs10739082 | 9 | 5971901 | 0.116 | 0.758 | HapMap | HapMap | A | 0.321 | G | 0.679 | A/G |
| GIH | rs10739082 | 9 | 5971901 | 0.006 | 1 | HapMap | HapMap | A | 0.103 | G | 0.897 | A/G |
| CEU | rs10739082 | 9 | 5971901 | 0.001 | 1 | HapMap | HapMap | A | 0.009 | G | 0.991 | A/G |
| MEX | rs10739082 | 9 | 5971901 | 0.003 | 1 | HapMap | HapMap | A | 0.06 | G | 0.94 | A/G |
| ASW | rs10739083 | 9 | 6057122 | 0.024 | 1 | HapMap | HapMap | T | 0.896 | C | 0.104 | T/C |
| CHD | rs10739083 | 9 | 6057122 | 0.027 | 1 | HapMap | HapMap | T | 0.812 | C | 0.188 | T/C |
| JPT | rs10739083 | 9 | 6057122 | 0.007 | 1 | HapMap | HapMap | T | 0.86 | C | 0.14 | T/C |
| MKK | rs10739090 | 9 | 6277142 | 0.001 | 1 | HapMap | HapMap | C | 0.01 | A | 0.99 | C/A |
| MEX | rs10739090 | 9 | 6277142 | 0.001 | 1 | HapMap | HapMap | C | 0.02 | A | 0.98 | C/A |
| LWK | rs10739090 | 9 | 6277142 | 0.138 | 1 | HapMap | HapMap | C | 0.033 | A | 0.967 | C/A |
| YRI | rs10739090 | 9 | 6277142 | 0.03 | 1 | HapMap | HapMap | C | 0.013 | A | 0.987 | C/A |
| ASW | rs10739090 | 9 | 6277142 | 0.019 | 1 | HapMap | HapMap | C | 0.047 | A | 0.953 | C/A |
| GIH | rs10739090 | 9 | 6277142 | 0.001 | 1 | HapMap | HapMap | C | 0.017 | A | 0.983 | C/A |
| MEX | rs10758732 | 9 | 5981772 | 0.005 | 1 | HapMap | HapMap | C | 0.08 | T | 0.92 | C/T |
| CEU | rs10758732 | 9 | 5981772 | 0.001 | 1 | HapMap | HapMap | C | 0.04 | T | 0.96 | C/T |
| CHB | rs10758732 | 9 | 5981772 | 0.076 | 0.683 | HapMap | HapMap | C | 0.331 | T | 0.669 | C/T |
| GIH | rs10758732 | 9 | 5981772 | 0.014 | 1 | HapMap | HapMap | C | 0.222 | T | 0.778 | C/T |
| CEU | rs10758734 | 9 | 5990551 | 0.001 | 1 | HapMap | HapMap | T | 0.009 | C | 0.991 | T/C |
| GIH | rs10758734 | 9 | 5990551 | 0.013 | 1 | HapMap | HapMap | T | 0.216 | C | 0.784 | T/C |
| MEX | rs10758734 | 9 | 5990551 | 0.005 | 1 | HapMap | HapMap | T | 0.08 | C | 0.92 | T/C |
| CHB | rs10758736 | 9 | 6001757 | 0.023 | 1 | HapMap | HapMap | G | 0.798 | A | 0.202 | G/A |
| CHD | rs10758736 | 9 | 6001757 | 0.031 | 1 | HapMap | HapMap | G | 0.794 | A | 0.206 | G/A |
| MEX | rs10758739 | 9 | 6013927 | 0.051 | 0.639 | HapMap | HapMap | T | 0.7 | C | 0.3 | T/C |
| CHB | rs10758739 | 9 | 6013927 | 0.017 | 0.889 | HapMap | HapMap | T | 0.815 | C | 0.185 | T/C |
| MEX | rs10815335 | 9 | 5988919 | 0.005 | 1 | HapMap | HapMap | T | 0.08 | C | 0.92 | T/C |
| CHB | rs10815335 | 9 | 5988919 | 0.092 | 0.729 | HapMap | HapMap | T | 0.339 | C | 0.661 | T/C |
| GIH | rs10815335 | 9 | 5988919 | 0.014 | 1 | HapMap | HapMap | T | 0.222 | C | 0.778 | T/C |
| CEU | rs10815335 | 9 | 5988919 | 0.001 | 1 | HapMap | HapMap | T | 0.009 | C | 0.991 | T/C |
| CHD | rs10815337 | 9 | 5991599 | 0.018 | 1 | HapMap | HapMap | T | 0.871 | C | 0.129 | T/C |
| JPT | rs10815347 | 9 | 6054103 | 0.006 | 1 | HapMap | HapMap | G | 0.884 | A | 0.116 | G/A |
| LWK | rs10815347 | 9 | 6054103 | 0.003 | 1 | HapMap | HapMap | G | 0.989 | A | 0.011 | G/A |
| MEX | rs10815347 | 9 | 6054103 | 0.087 | 0.729 | HapMap | HapMap | G | 0.75 | A | 0.25 | G/A |
| ASW | rs10815347 | 9 | 6054103 | 0.004 | 1 | HapMap | HapMap | G | 0.953 | A | 0.047 | G/A |
| CHD | rs10815347 | 9 | 6054103 | 0.024 | 1 | HapMap | HapMap | G | 0.833 | A | 0.167 | G/A |
| CHB | rs10815357 | 9 | 6134025 | 0.265 | 0.678 | HapMap | HapMap | A | 0.839 | G | 0.161 | A/G |
| GIH | rs10815357 | 9 | 6134025 | 0.159 | 0.692 | HapMap | HapMap | A | 0.875 | G | 0.125 | A/G |
| CHB | rs10815358 | 9 | 6134065 | 0.265 | 0.678 | HapMap | HapMap | G | 0.851 | A | 0.149 | G/A |
| GIH | rs10815358 | 9 | 6134065 | 0.162 | 0.697 | HapMap | HapMap | G | 0.874 | A | 0.126 | G/A |
| JPT | rs10815388 | 9 | 6222242 | 0.05 | 1 | HapMap | HapMap | C | 0.535 | T | 0.465 | C/T |
| CEU | rs10815388 | 9 | 6222242 | 0.217 | 1 | HapMap | HapMap | C | 0.341 | T | 0.659 | C/T |
| GIH | rs10815388 | 9 | 6222242 | 0.085 | 1 | HapMap | HapMap | C | 0.358 | T | 0.642 | C/T |
| MKK | rs10815393 | 9 | 6230324 | 0.005 | 0.601 | HapMap | HapMap | T | 0.906 | C | 0.094 | T/C |
| ASW | rs10815393 | 9 | 6230324 | 0.046 | 1 | HapMap | HapMap | T | 0.827 | C | 0.173 | T/C |
| CEU | rs10815393 | 9 | 6230324 | 0.041 | 1 | HapMap | HapMap | T | 0.768 | C | 0.232 | T/C |
| GIH | rs10815393 | 9 | 6230324 | 0.006 | 1 | HapMap | HapMap | T | 0.885 | C | 0.115 | T/C |
| MEX | rs10815393 | 9 | 6230324 | 0.007 | 0.819 | HapMap | HapMap | T | 0.867 | C | 0.133 | T/C |
| CEU | rs10815398 | 9 | 6262766 | 0.025 | 0.626 | HapMap | HapMap | C | 0.354 | A | 0.646 | C/A |
| GIH | rs10815398 | 9 | 6262766 | 0.039 | 1 | HapMap | HapMap | C | 0.455 | A | 0.545 | C/A |
| GIH | rs10815402 | 9 | 6283715 | 0.036 | 1 | HapMap | HapMap | G | 0.568 | A | 0.432 | G/A |
| ASW | rs10815402 | 9 | 6283715 | 0.23 | 0.671 | HapMap | HapMap | G | 0.877 | A | 0.123 | G/A |
| CEU | rs10975412 | 9 | 6039547 | 0.016 | 1 | HapMap | HapMap | A | 0.858 | G | 0.142 | A/G |
| CHB | rs10975412 | 9 | 6039547 | 0.004 | 1 | HapMap | HapMap | A | 0.958 | G | 0.042 | A/G |
| GIH | rs10975412 | 9 | 6039547 | 0.016 | 1 | HapMap | HapMap | A | 0.756 | G | 0.244 | A/G |
| MEX | rs10975412 | 9 | 6039547 | 0.011 | 1 | HapMap | HapMap | A | 0.851 | G | 0.149 | A/G |
| MEX | rs10975413 | 9 | 6039843 | 0.01 | 1 | HapMap | HapMap | A | 0.857 | G | 0.143 | A/G |
| CEU | rs10975413 | 9 | 6039843 | 0.016 | 1 | HapMap | HapMap | A | 0.858 | G | 0.142 | A/G |
| CHB | rs10975413 | 9 | 6039843 | 0.004 | 1 | HapMap | HapMap | A | 0.958 | G | 0.042 | A/G |
| GIH | rs10975413 | 9 | 6039843 | 0.015 | 1 | HapMap | HapMap | A | 0.756 | G | 0.244 | A/G |
| GIH | rs10975416 | 9 | 6041924 | 0.015 | 1 | HapMap | HapMap | T | 0.756 | G | 0.244 | T/G |
| MEX | rs10975416 | 9 | 6041924 | 0.009 | 1 | HapMap | HapMap | T | 0.87 | G | 0.13 | T/G |
| CEU | rs10975416 | 9 | 6041924 | 0.016 | 1 | HapMap | HapMap | T | 0.858 | G | 0.142 | T/G |
| CHB | rs10975416 | 9 | 6041924 | 0.004 | 1 | HapMap | HapMap | T | 0.958 | G | 0.042 | T/G |
| JPT | rs10975422 | 9 | 6063817 | 0.001 | 1 | HapMap | HapMap | G | 0.988 | C | 0.012 | G/C |
| CHD | rs10975422 | 9 | 6063817 | 0.001 | 1 | HapMap | HapMap | G | 0.994 | C | 0.006 | G/C |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| ASW | rs10975422 | 9 | 6063817 | 0.019 | 1 | HapMap | HapMap | G | 0.952 | C | 0.048 | G/C |
| CHB | rs10975422 | 9 | 6063817 | 0.001 | 1 | HapMap | HapMap | G | 0.988 | C | 0.012 | G/C |
| YRI | rs10975438 | 9 | 6103103 | 0.103 | 0.743 | HapMap | HapMap | C | 0.965 | T | 0.035 | C/T |
| MKK | rs10975438 | 9 | 6103103 | 0.127 | 0.825 | HapMap | HapMap | C | 0.976 | T | 0.024 | C/T |
| GIH | rs10975444 | 9 | 6109329 | 0.139 | 0.822 | HapMap | HapMap | A | 0.812 | G | 0.188 | A/G |
| ASW | rs10975444 | 9 | 6109329 | 0.019 | 1 | HapMap | HapMap | A | 0.934 | G | 0.066 | A/G |
| CHB | rs10975444 | 9 | 6109329 | 0.201 | 0.796 | HapMap | HapMap | A | 0.774 | G | 0.226 | A/G |
| ASW | rs10975450 | 9 | 6123672 | 0.018 | 1 | HapMap | HapMap | A | 0.933 | T | 0.067 | A/T |
| CHB | rs10975450 | 9 | 6123672 | 0.232 | 0.804 | HapMap | HapMap | A | 0.775 | T | 0.225 | A/T |
| GIH | rs10975450 | 9 | 6123672 | 0.182 | 0.835 | HapMap | HapMap | A | 0.843 | T | 0.157 | A/T |
| YRI | rs10975454 | 9 | 6125411 | 0.025 | 1 | HapMap | HapMap | C | 0.924 | A | 0.076 | C/A |
| LWK | rs10975454 | 9 | 6125411 | 0.006 | 1 | HapMap | HapMap | C | 0.978 | A | 0.022 | C/A |
| MKK | rs10975454 | 9 | 6125411 | 0.007 | 1 | HapMap | HapMap | C | 0.948 | A | 0.052 | C/A |
| JPT | rs10975454 | 9 | 6125411 | 0.007 | 1 | HapMap | HapMap | C | 0.878 | A | 0.122 | C/A |
| GIH | rs10975454 | 9 | 6125411 | 0.008 | 1 | HapMap | HapMap | C | 0.858 | A | 0.142 | C/A |
| CHD | rs10975454 | 9 | 6125411 | 0.025 | 1 | HapMap | HapMap | C | 0.827 | A | 0.173 | C/A |
| CHB | rs10975454 | 9 | 6125411 | 0.017 | 1 | HapMap | HapMap | C | 0.863 | A | 0.137 | C/A |
| CEU | rs10975463 | 9 | 6139006 | 0.014 | 1 | HapMap | HapMap | A | 0.903 | G | 0.097 | A/G |
| LWK | rs10975463 | 9 | 6139006 | 0.023 | 1 | HapMap | HapMap | A | 0.917 | G | 0.083 | A/G |
| MEX | rs10975463 | 9 | 6139006 | 0.003 | 1 | HapMap | HapMap | A | 0.96 | G | 0.04 | A/G |
| MKK | rs10975463 | 9 | 6139006 | 0.02 | 1 | HapMap | HapMap | A | 0.871 | G | 0.129 | A/G |
| YRI | rs10975463 | 9 | 6139006 | 0.028 | 1 | HapMap | HapMap | A | 0.925 | G | 0.075 | A/G |
| MEX | rs10975501 | 9 | 6223221 | 0.002 | 1 | HapMap | HapMap | A | 0.041 | C | 0.959 | A/C |
| CEU | rs10975501 | 9 | 6223221 | 0.005 | 0.757 | HapMap | HapMap | A | 0.05 | C | 0.95 | A/C |
| GIH | rs10975501 | 9 | 6223221 | 0 | 1 | HapMap | HapMap | A | 0.006 | C | 0.994 | A/C |
| MKK | rs10975501 | 9 | 6223221 | 0.037 | 1 | HapMap | HapMap | A | 0.213 | C | 0.787 | A/C |
| JPT | rs10975514 | 9 | 6236144 | 0.053 | 1 | HapMap | HapMap | G | 0.561 | A | 0.439 | G/A |
| GIH | rs10975514 | 9 | 6236144 | 0.039 | 1 | HapMap | HapMap | G | 0.545 | A | 0.455 | G/A |
| CEU | rs10975514 | 9 | 6236144 | 0.043 | 1 | HapMap | HapMap | G | 0.694 | A | 0.306 | G/A |
| JPT | rs10975516 | 9 | 6237693 | 0.02 | 0.666 | HapMap | HapMap | G | 0.57 | A | 0.43 | G/A |
| GIH | rs10975516 | 9 | 6237693 | 0.039 | 1 | HapMap | HapMap | G | 0.545 | A | 0.455 | G/A |
| GIH | rs10975519 | 9 | 6243571 | 0.043 | 1 | HapMap | HapMap | C | 0.529 | T | 0.471 | C/T |
| JPT | rs10975519 | 9 | 6243571 | 0.069 | 1 | HapMap | HapMap | C | 0.589 | T | 0.411 | C/T |
| MKK | rs10975519 | 9 | 6243571 | 0.058 | 0.684 | HapMap | HapMap | C | 0.525 | T | 0.475 | C/T |
| GIH | rs10975520 | 9 | 6243710 | 0.039 | 1 | HapMap | HapMap | G | 0.545 | C | 0.455 | G/C |
| JPT | rs10975527 | 9 | 6278738 | 0.418 | 0.727 | HapMap | HapMap | G | 0.93 | T | 0.07 | G/T |
| MEX | rs10975527 | 9 | 6278738 | 0 | 1 | HapMap | HapMap | G | 0.99 | T | 0.01 | G/T |
| GIH | rs10975539 | 9 | 6298729 | 0.007 | 1 | HapMap | HapMap | C | 0.875 | T | 0.125 | C/T |
| LWK | rs10975539 | 9 | 6298729 | 0.001 | 1 | HapMap | HapMap | C | 0.994 | T | 0.006 | C/T |
| MKK | rs10975539 | 9 | 6298729 | 0.002 | 1 | HapMap | HapMap | C | 0.986 | T | 0.014 | C/T |
| CEU | rs10975539 | 9 | 6298729 | 0.027 | 1 | HapMap | HapMap | C | 0.792 | T | 0.208 | C/T |
| ASW | rs10975539 | 9 | 6298729 | 0.014 | 1 | HapMap | HapMap | C | 0.894 | T | 0.106 | C/T |
| CHD | rs10975543 | 9 | 6307385 | 0.05 | 1 | HapMap | HapMap | C | 0.006 | T | 0.994 | C/T |
| MEX | rs10975543 | 9 | 6307385 | 0.001 | 1 | HapMap | HapMap | C | 0.01 | T | 0.99 | C/T |
| MKK | rs10975543 | 9 | 6307385 | 0.002 | 1 | HapMap | HapMap | C | 0.014 | T | 0.986 | C/T |
| ASW | rs10975543 | 9 | 6307385 | 0.022 | 1 | HapMap | HapMap | C | 0.049 | T | 0.951 | C/T |
| GIH | rs10975543 | 9 | 6307385 | 0.001 | 1 | HapMap | HapMap | C | 0.017 | T | 0.983 | C/T |
| LWK | rs10975543 | 9 | 6307385 | 0.078 | 1 | HapMap | HapMap | C | 0.017 | T | 0.983 | C/T |
| CHD | rs10975552 | 9 | 6341834 | 0.047 | 1 | HapMap | HapMap | T | 0.718 | C | 0.282 | T/C |
| GIH | rs10975552 | 9 | 6341834 | 0.029 | 1 | HapMap | HapMap | T | 0.625 | C | 0.375 | T/C |
| LWK | rs10975552 | 9 | 6341834 | 0.03 | 0.614 | HapMap | HapMap | T | 0.761 | C | 0.239 | T/C |
| MEX | rs10975552 | 9 | 6341834 | 0.023 | 1 | HapMap | HapMap | T | 0.73 | C | 0.27 | T/C |
| MKK | rs10975552 | 9 | 6341834 | 0.022 | 0.684 | HapMap | HapMap | T | 0.745 | C | 0.255 | T/C |
| CEU | rs10975552 | 9 | 6341834 | 0.073 | 1 | HapMap | HapMap | T | 0.628 | C | 0.372 | T/C |
| CHB | rs10975552 | 9 | 6341834 | 0.033 | 1 | HapMap | HapMap | T | 0.738 | C | 0.262 | T/C |
| MEX | rs10975556 | 9 | 6353043 | 0.191 | 1 | HapMap | HapMap | C | 0.99 | G | 0.01 | C/G |
| CEU | rs10975556 | 9 | 6353043 | 0.579 | 0.86 | HapMap | HapMap | C | 0.938 | G | 0.062 | C/G |
| MKK | rs10975556 | 9 | 6353043 | 0.001 | 1 | HapMap | HapMap | C | 0.99 | G | 0.01 | C/G |
| YRI | rs10975558 | 9 | 6354449 | 0.049 | 1 | HapMap | HapMap | C | 0.854 | T | 0.146 | C/T |
| ASW | rs10975558 | 9 | 6354449 | 0.052 | 1 | HapMap | HapMap | C | 0.811 | T | 0.189 | C/T |
| MKK | rs10975558 | 9 | 6354449 | 0.012 | 0.72 | HapMap | HapMap | C | 0.848 | T | 0.152 | C/T |
| MEX | rs10975558 | 9 | 6354449 | 0.009 | 1 | HapMap | HapMap | C | 0.86 | T | 0.14 | C/T |
| CEU | rs10975558 | 9 | 6354449 | 0.052 | 1 | HapMap | HapMap | C | 0.721 | T | 0.279 | C/T |
| GIH | rs10975558 | 9 | 6354449 | 0.008 | 1 | HapMap | HapMap | C | 0.858 | T | 0.142 | C/T |
| CHB | rs11506678 | 9 | 6030282 | 0.004 | 1 | HapMap | HapMap | C | 0.958 | A | 0.042 | C/A |
| GIH | rs11506678 | 9 | 6030282 | 0.013 | 1 | HapMap | HapMap | C | 0.784 | A | 0.216 | C/A |
| MEX | rs11506678 | 9 | 6030282 | 0.002 | 1 | HapMap | HapMap | C | 0.97 | A | 0.03 | C/A |
| LWK | rs11787939 | 9 | 6212553 | 0.098 | 0.776 | HapMap | HapMap | G | 0.606 | A | 0.394 | G/A |
| MKK | rs11787939 | 9 | 6212553 | 0.033 | 0.781 | HapMap | HapMap | G | 0.713 | A | 0.287 | G/A |
| YRI | rs11787939 | 9 | 6212553 | 0.056 | 0.612 | HapMap | HapMap | G | 0.664 | A | 0.336 | G/A |
| CEU | rs11787939 | 9 | 6212553 | 0.007 | 1 | HapMap | HapMap | G | 0.956 | A | 0.044 | G/A |
| CHD | rs11793017 | 9 | 6068204 | 0.02 | 1 | HapMap | HapMap | C | 0.853 | T | 0.147 | C/T |
| GIH | rs11793017 | 9 | 6068204 | 0.015 | 1 | HapMap | HapMap | C | 0.767 | T | 0.233 | C/T |
| JPT | rs11793017 | 9 | 6068204 | 0.007 | 1 | HapMap | HapMap | C | 0.876 | T | 0.124 | C/T |
| LWK | rs11793017 | 9 | 6068204 | 0.007 | 0.831 | HapMap | HapMap | C | 0.961 | T | 0.039 | C/T |
| CHB | rs11793017 | 9 | 6068204 | 0.013 | 1 | HapMap | HapMap | C | 0.881 | T | 0.119 | C/T |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MKK | rs11793017 | 9 | 6068204 | 0.01 | 1 | HapMap | HapMap | C | 0.934 | T | 0.066 | C/T |
| YRI | rs11793017 | 9 | 6068204 | 0.038 | 1 | HapMap | HapMap | C | 0.889 | T | 0.111 | C/T |
| MKK | rs12000491 | 9 | 6247367 | 0.026 | 1 | HapMap | HapMap | T | 0.839 | C | 0.161 | T/C |
| YRI | rs12000491 | 9 | 6247367 | 0.059 | 0.767 | HapMap | HapMap | T | 0.732 | C | 0.268 | T/C |
| ASW | rs12000491 | 9 | 6247367 | 0.086 | 1 | HapMap | HapMap | T | 0.811 | C | 0.189 | T/C |
| GIH | rs12000491 | 9 | 6247367 | 0.001 | 1 | HapMap | HapMap | T | 0.989 | C | 0.011 | T/C |
| MEX | rs12000491 | 9 | 6247367 | 0.001 | 1 | HapMap | HapMap | T | 0.97 | C | 0.03 | T/C |
| CEU | rs12000491 | 9 | 6247367 | 0.004 | 1 | HapMap | HapMap | T | 0.965 | C | 0.035 | T/C |
| ASW | rs12003769 | 9 | 6158335 | 0.427 | 0.759 | HapMap | HapMap | T | 0.821 | C | 0.179 | T/C |
| CEU | rs12003769 | 9 | 6158335 | 0.815 | 1 | HapMap | HapMap | T | 0.907 | C | 0.093 | T/C |
| CHB | rs12003769 | 9 | 6158335 | 0.307 | 0.827 | HapMap | HapMap | T | 0.827 | C | 0.173 | T/C |
| CHD | rs12003769 | 9 | 6158335 | 0.433 | 0.678 | HapMap | HapMap | T | 0.888 | C | 0.112 | T/C |
| GIH | rs12003769 | 9 | 6158335 | 0.884 | 1 | HapMap | HapMap | T | 0.949 | C | 0.051 | T/C |
| JPT | rs12003769 | 9 | 6158335 | 0.499 | 0.779 | HapMap | HapMap | T | 0.913 | C | 0.087 | T/C |
| MEX | rs12003769 | 9 | 6158335 | 0.791 | 1 | HapMap | HapMap | T | 0.94 | C | 0.06 | T/C |
| MKK | rs12003769 | 9 | 6158335 | 0.384 | 0.842 | HapMap | HapMap | T | 0.801 | C | 0.199 | T/C |
| YRI | rs12237914 | 9 | 6296896 | 0.025 | 0.687 | HapMap | HapMap | A | 0.821 | G | 0.179 | A/G |
| CEU | rs12237914 | 9 | 6296896 | 0.128 | 0.817 | HapMap | HapMap | A | 0.593 | G | 0.407 | A/G |
| GIH | rs12237914 | 9 | 6296896 | 0.076 | 1 | HapMap | HapMap | A | 0.615 | G | 0.385 | A/G |
| CHD | rs12337790 | 9 | 6015559 | 0.101 | 1 | HapMap | HapMap | T | 0.988 | C | 0.012 | T/C |
| GIH | rs12337790 | 9 | 6015559 | 0.012 | 1 | HapMap | HapMap | T | 0.807 | C | 0.193 | T/C |
| LWK | rs12337790 | 9 | 6015559 | 0.048 | 1 | HapMap | HapMap | T | 0.839 | C | 0.161 | T/C |
| MEX | rs12337790 | 9 | 6015559 | 0.001 | 1 | HapMap | HapMap | T | 0.98 | C | 0.02 | T/C |
| CHB | rs12337790 | 9 | 6015559 | 0.004 | 1 | HapMap | HapMap | T | 0.97 | C | 0.03 | T/C |
| LWK | rs12339889 | 9 | 5998989 | 0.015 | 1 | HapMap | HapMap | C | 0.944 | G | 0.056 | C/G |
| GIH | rs12339889 | 9 | 5998989 | 0.006 | 1 | HapMap | HapMap | C | 0.886 | G | 0.114 | C/G |
| MEX | rs12339889 | 9 | 5998989 | 0.001 | 1 | HapMap | HapMap | C | 0.98 | G | 0.02 | C/G |
| CHB | rs12339889 | 9 | 5998989 | 0.004 | 1 | HapMap | HapMap | C | 0.97 | G | 0.03 | C/G |
| YRI | rs12339889 | 9 | 5998989 | 0.134 | 0.612 | HapMap | HapMap | C | 0.929 | G | 0.071 | C/G |
| CEU | rs12349559 | 9 | 6135491 | 0.815 | 1 | HapMap | HapMap | T | 0.898 | C | 0.102 | T/C |
| CHB | rs12349559 | 9 | 6135491 | 0.505 | 0.85 | HapMap | HapMap | T | 0.869 | C | 0.131 | T/C |
| ASW | rs12349559 | 9 | 6135491 | 0.427 | 0.759 | HapMap | HapMap | T | 0.84 | C | 0.16 | T/C |
| CHD | rs12349559 | 9 | 6135491 | 0.54 | 0.785 | HapMap | HapMap | T | 0.905 | C | 0.095 | T/C |
| MEX | rs12349559 | 9 | 6135491 | 0.791 | 1 | HapMap | HapMap | T | 0.94 | C | 0.06 | T/C |
| MKK | rs12349559 | 9 | 6135491 | 0.56 | 0.761 | HapMap | HapMap | T | 0.878 | C | 0.122 | T/C |
| YRI | rs12349559 | 9 | 6135491 | 0.338 | 0.814 | HapMap | HapMap | T | 0.881 | C | 0.119 | T/C |
| JPT | rs12349559 | 9 | 6135491 | 0.79 | 1 | HapMap | HapMap | T | 0.942 | C | 0.058 | T/C |
| GIH | rs12349559 | 9 | 6135491 | 0.884 | 1 | HapMap | HapMap | T | 0.949 | C | 0.051 | T/C |
| GIH | rs12378118 | 9 | 6023278 | 0.004 | 1 | HapMap | HapMap | G | 0.932 | A | 0.068 | G/A |
| MEX | rs12378118 | 9 | 6023278 | 0.016 | 1 | HapMap | HapMap | G | 0.78 | A | 0.22 | G/A |
| ASW | rs12378311 | 9 | 6078903 | 0.019 | 1 | HapMap | HapMap | G | 0.934 | C | 0.066 | G/C |
| GIH | rs12378311 | 9 | 6078903 | 0.119 | 0.673 | HapMap | HapMap | G | 0.847 | C | 0.153 | G/C |
| JPT | rs12378311 | 9 | 6078903 | 0.002 | 1 | HapMap | HapMap | G | 0.942 | C | 0.058 | G/C |
| GIH | rs12551256 | 9 | 6221239 | 0.05 | 1 | HapMap | HapMap | A | 0.483 | G | 0.517 | A/G |
| CEU | rs12551256 | 9 | 6221239 | 0.076 | 1 | HapMap | HapMap | A | 0.566 | G | 0.434 | A/G |
| JPT | rs12551256 | 9 | 6221239 | 0.047 | 1 | HapMap | HapMap | A | 0.541 | G | 0.459 | A/G |
| ASW | rs1317230 | 9 | 6241012 | 0.224 | 0.779 | HapMap | HapMap | C | 0.896 | A | 0.104 | C/A |
| JPT | rs1317230 | 9 | 6241012 | 0.02 | 0.666 | HapMap | HapMap | C | 0.57 | A | 0.43 | C/A |
| GIH | rs1317230 | 9 | 6241012 | 0.037 | 1 | HapMap | HapMap | C | 0.557 | A | 0.443 | C/A |
| CEU | rs1322166 | 9 | 6299862 | 0.07 | 1 | HapMap | HapMap | C | 0.332 | T | 0.668 | C/T |
| GIH | rs1322166 | 9 | 6299862 | 0.009 | 1 | HapMap | HapMap | C | 0.153 | T | 0.847 | C/T |
| MKK | rs1322166 | 9 | 6299862 | 0.049 | 0.781 | HapMap | HapMap | C | 0.374 | T | 0.626 | C/T |
| MEX | rs1322166 | 9 | 6299862 | 0.018 | 1 | HapMap | HapMap | C | 0.24 | T | 0.76 | C/T |
| GIH | rs13291323 | 9 | 6175360 | 0 | 1 | HapMap | HapMap | T | 0.994 | C | 0.006 | T/C |
| ASW | rs13291323 | 9 | 6175360 | 0.009 | 1 | HapMap | HapMap | T | 0.972 | C | 0.028 | T/C |
| CEU | rs13291323 | 9 | 6175360 | 0.008 | 0.921 | HapMap | HapMap | T | 0.951 | C | 0.049 | T/C |
| LWK | rs13291323 | 9 | 6175360 | 0.012 | 1 | HapMap | HapMap | T | 0.956 | C | 0.044 | T/C |
| MEX | rs13291323 | 9 | 6175360 | 0.001 | 1 | HapMap | HapMap | T | 0.98 | C | 0.02 | T/C |
| MKK | rs13291323 | 9 | 6175360 | 0.002 | 0.727 | HapMap | HapMap | T | 0.979 | C | 0.021 | T/C |
| ASW | rs13293142 | 9 | 6160924 | 0.008 | 0.741 | HapMap | HapMap | A | 0.962 | C | 0.038 | A/C |
| CEU | rs13293142 | 9 | 6160924 | 0.008 | 0.921 | HapMap | HapMap | A | 0.947 | C | 0.053 | A/C |
| MEX | rs13293142 | 9 | 6160924 | 0.001 | 1 | HapMap | HapMap | A | 0.98 | C | 0.02 | A/C |
| GIH | rs13293142 | 9 | 6160924 | 0 | 1 | HapMap | HapMap | A | 0.994 | C | 0.006 | A/C |
| CEU | rs13296741 | 9 | 6177395 | 0.01 | 0.996 | HapMap | HapMap | G | 0.941 | T | 0.059 | G/T |
| CHB | rs13296741 | 9 | 6177395 | 0.115 | 1 | HapMap | HapMap | G | 0.982 | T | 0.018 | G/T |
| MKK | rs13296741 | 9 | 6177395 | 0.004 | 0.999 | HapMap | HapMap | G | 0.975 | T | 0.025 | G/T |
| MEX | rs13296741 | 9 | 6177395 | 0.003 | 1 | HapMap | HapMap | G | 0.958 | T | 0.042 | G/T |
| ASW | rs13296741 | 9 | 6177395 | 0.009 | 1 | HapMap | HapMap | G | 0.962 | T | 0.038 | G/T |
| JPT | rs13296741 | 9 | 6177395 | 0.002 | 1 | HapMap | HapMap | G | 0.976 | T | 0.024 | G/T |
| CHD | rs13296741 | 9 | 6177395 | 0.001 | 1 | HapMap | HapMap | G | 0.988 | T | 0.012 | G/T |
| GIH | rs13296741 | 9 | 6177395 | 0 | 1 | HapMap | HapMap | G | 0.989 | T | 0.011 | G/T |
| GIH | rs13298872 | 9 | 6348385 | 0 | 1 | HapMap | HapMap | G | 0.994 | A | 0.006 | G/A |
| ASW | rs13298872 | 9 | 6348385 | 0.019 | 1 | HapMap | HapMap | G | 0.953 | A | 0.047 | G/A |
| MEX | rs13298872 | 9 | 6348385 | 0.001 | 1 | HapMap | HapMap | G | 0.98 | A | 0.02 | G/A |
| MKK | rs13298872 | 9 | 6348385 | 0.001 | 1 | HapMap | HapMap | G | 0.99 | A | 0.01 | G/A |
| YRI | rs13298872 | 9 | 6348385 | 0.006 | 1 | HapMap | HapMap | G | 0.982 | A | 0.018 | G/A |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs1330124 | 9 | 6043098 | 0.016 | 1 | HapMap | HapMap | A | 0.858 | C | 0.142 | A/C |
| CHB | rs1330124 | 9 | 6043098 | 0.004 | 1 | HapMap | HapMap | A | 0.958 | C | 0.042 | A/C |
| GIH | rs1330124 | 9 | 6043098 | 0.015 | 1 | HapMap | HapMap | A | 0.761 | C | 0.239 | A/C |
| MKK | rs1330124 | 9 | 6043098 | 0.029 | 1 | HapMap | HapMap | A | 0.822 | C | 0.178 | A/C |
| ASW | rs1330380 | 9 | 6300829 | 0.019 | 1 | HapMap | HapMap | C | 0.047 | A | 0.953 | C/A |
| GIH | rs1330380 | 9 | 6300829 | 0.001 | 1 | HapMap | HapMap | C | 0.017 | A | 0.983 | C/A |
| MKK | rs1330380 | 9 | 6300829 | 0.001 | 1 | HapMap | HapMap | C | 0.007 | A | 0.993 | C/A |
| YRI | rs1330380 | 9 | 6300829 | 0.03 | 1 | HapMap | HapMap | C | 0.013 | A | 0.987 | C/A |
| MEX | rs1330380 | 9 | 6300829 | 0.001 | 1 | HapMap | HapMap | C | 0.02 | A | 0.98 | C/A |
| LWK | rs1330380 | 9 | 6300829 | 0.138 | 1 | HapMap | HapMap | C | 0.033 | A | 0.967 | C/A |
| MKK | rs1330383 | 9 | 6241507 | 0.05 | 0.666 | HapMap | HapMap | G | 0.545 | T | 0.455 | G/T |
| JPT | rs1330383 | 9 | 6241507 | 0.047 | 1 | HapMap | HapMap | G | 0.564 | T | 0.436 | G/T |
| GIH | rs1330383 | 9 | 6241507 | 0.039 | 1 | HapMap | HapMap | G | 0.545 | T | 0.455 | G/T |
| CEU | rs1332290 | 9 | 6245881 | 0.025 | 0.626 | HapMap | HapMap | T | 0.353 | G | 0.647 | T/G |
| GIH | rs1332290 | 9 | 6245881 | 0.04 | 1 | HapMap | HapMap | T | 0.46 | G | 0.54 | T/G |
| MKK | rs1332290 | 9 | 6245881 | 0.115 | 0.601 | HapMap | HapMap | T | 0.703 | G | 0.297 | T/G |
| ASW | rs1342326 | 9 | 6180076 | 0.062 | 0.726 | HapMap | HapMap | A | 0.679 | C | 0.321 | A/C |
| CEU | rs1342326 | 9 | 6180076 | 0.03 | 1 | HapMap | HapMap | A | 0.832 | C | 0.168 | A/C |
| GIH | rs1342326 | 9 | 6180076 | 0.008 | 1 | HapMap | HapMap | A | 0.858 | C | 0.142 | A/C |
| YRI | rs1342326 | 9 | 6180076 | 0.144 | 1 | HapMap | HapMap | A | 0.668 | C | 0.332 | A/C |
| LWK | rs1342326 | 9 | 6180076 | 0.12 | 0.774 | HapMap | HapMap | A | 0.556 | C | 0.444 | A/C |
| MEX | rs1342326 | 9 | 6180076 | 0.012 | 1 | HapMap | HapMap | A | 0.84 | C | 0.16 | A/C |
| ASW | rs1342328 | 9 | 6200785 | 0.034 | 1 | HapMap | HapMap | A | 0.906 | G | 0.094 | A/G |
| GIH | rs1342328 | 9 | 6200785 | 0.001 | 1 | HapMap | HapMap | A | 0.983 | G | 0.017 | A/G |
| LWK | rs1342328 | 9 | 6200785 | 0.028 | 1 | HapMap | HapMap | A | 0.9 | G | 0.1 | A/G |
| MKK | rs1342328 | 9 | 6200785 | 0.012 | 1 | HapMap | HapMap | A | 0.916 | G | 0.084 | A/G |
| GIH | rs1381038 | 9 | 6323156 | 0.001 | 1 | HapMap | HapMap | C | 0.017 | A | 0.983 | C/A |
| ASW | rs1381038 | 9 | 6323156 | 0.04 | 0.626 | HapMap | HapMap | C | 0.255 | A | 0.745 | C/A |
| MEX | rs1381038 | 9 | 6323156 | 0.001 | 1 | HapMap | HapMap | C | 0.03 | A | 0.97 | C/A |
| MKK | rs1381038 | 9 | 6323156 | 0.015 | 1 | HapMap | HapMap | C | 0.101 | A | 0.899 | C/A |
| GIH | rs1381039 | 9 | 6332682 | 0.001 | 1 | HapMap | HapMap | A | 0.017 | G | 0.983 | A/G |
| MEX | rs1381039 | 9 | 6332682 | 0.001 | 1 | HapMap | HapMap | A | 0.031 | G | 0.969 | A/G |
| CEU | rs1381039 | 9 | 6332682 | 0.006 | 1 | HapMap | HapMap | A | 0.031 | G | 0.969 | A/G |
| JPT | rs1411341 | 9 | 6108982 | 0.007 | 1 | HapMap | HapMap | T | 0.878 | C | 0.122 | T/C |
| CHB | rs1411341 | 9 | 6108982 | 0.017 | 1 | HapMap | HapMap | T | 0.863 | C | 0.137 | T/C |
| CHD | rs1411341 | 9 | 6108982 | 0.024 | 1 | HapMap | HapMap | T | 0.833 | C | 0.167 | T/C |
| GIH | rs1411341 | 9 | 6108982 | 0.009 | 1 | HapMap | HapMap | T | 0.841 | C | 0.159 | T/C |
| LWK | rs1411341 | 9 | 6108982 | 0.048 | 1 | HapMap | HapMap | T | 0.839 | C | 0.161 | T/C |
| CEU | rs1411948 | 9 | 5972797 | 0.008 | 0.921 | HapMap | HapMap | G | 0.925 | A | 0.075 | G/A |
| GIH | rs1411948 | 9 | 5972797 | 0.001 | 1 | HapMap | HapMap | G | 0.972 | A | 0.028 | G/A |
| LWK | rs1411948 | 9 | 5972797 | 0.003 | 1 | HapMap | HapMap | G | 0.989 | A | 0.011 | G/A |
| MKK | rs1411948 | 9 | 5972797 | 0.002 | 1 | HapMap | HapMap | G | 0.982 | A | 0.018 | G/A |
| YRI | rs1411948 | 9 | 5972797 | 0.015 | 1 | HapMap | HapMap | G | 0.965 | A | 0.035 | G/A |
| ASW | rs1412420 | 9 | 6245152 | 0.029 | 1 | HapMap | HapMap | A | 0.075 | G | 0.925 | A/G |
| MEX | rs1412420 | 9 | 6245152 | 0.001 | 1 | HapMap | HapMap | A | 0.02 | G | 0.98 | A/G |
| GIH | rs1412420 | 9 | 6245152 | 0 | 1 | HapMap | HapMap | A | 0.006 | G | 0.994 | A/G |
| CEU | rs1412420 | 9 | 6245152 | 0.004 | 0.676 | HapMap | HapMap | A | 0.044 | G | 0.956 | A/G |
| LWK | rs1412424 | 9 | 6079129 | 0.021 | 0.904 | HapMap | HapMap | G | 0.906 | C | 0.094 | G/C |
| MEX | rs1412424 | 9 | 6079129 | 0.001 | 1 | HapMap | HapMap | G | 0.99 | C | 0.01 | G/C |
| CHD | rs1412426 | 9 | 6178652 | 0.638 | 0.918 | HapMap | HapMap | A | 0.085 | C | 0.915 | A/C |
| GIH | rs1412426 | 9 | 6178652 | 0.12 | 1 | HapMap | HapMap | A | 0.284 | C | 0.716 | A/C |
| JPT | rs1412426 | 9 | 6178652 | 0.499 | 0.779 | HapMap | HapMap | A | 0.052 | C | 0.948 | A/C |
| ASW | rs1412426 | 9 | 6178652 | 0.063 | 0.705 | HapMap | HapMap | A | 0.642 | C | 0.358 | A/C |
| LWK | rs1412426 | 9 | 6178652 | 0.04 | 0.7 | HapMap | HapMap | A | 0.756 | C | 0.244 | A/C |
| CHB | rs1412426 | 9 | 6178652 | 0.273 | 0.611 | HapMap | HapMap | A | 0.077 | C | 0.923 | A/C |
| CEU | rs1412426 | 9 | 6178652 | 0.149 | 1 | HapMap | HapMap | A | 0.336 | C | 0.664 | A/C |
| MKK | rs1412426 | 9 | 6178652 | 0.092 | 0.897 | HapMap | HapMap | A | 0.546 | C | 0.454 | A/C |
| MKK | rs1478940 | 9 | 6058048 | 0.024 | 1 | HapMap | HapMap | C | 0.85 | A | 0.15 | C/A |
| LWK | rs1478940 | 9 | 6058048 | 0.024 | 1 | HapMap | HapMap | C | 0.911 | A | 0.089 | C/A |
| MEX | rs1478940 | 9 | 6058048 | 0 | 1 | HapMap | HapMap | C | 0.99 | A | 0.01 | C/A |
| ASW | rs1478940 | 9 | 6058048 | 0.019 | 1 | HapMap | HapMap | C | 0.925 | A | 0.075 | C/A |
| CEU | rs1478940 | 9 | 6058048 | 0.001 | 1 | HapMap | HapMap | C | 0.991 | A | 0.009 | C/A |
| ASW | rs1551761 | 9 | 6303518 | 0.046 | 1 | HapMap | HapMap | C | 0.17 | G | 0.83 | C/G |
| GIH | rs1551761 | 9 | 6303518 | 0.001 | 1 | HapMap | HapMap | C | 0.017 | G | 0.983 | C/G |
| MKK | rs1551761 | 9 | 6303518 | 0.015 | 1 | HapMap | HapMap | C | 0.101 | G | 0.899 | C/G |
| MEX | rs1551761 | 9 | 6303518 | 0.001 | 1 | HapMap | HapMap | C | 0.031 | G | 0.969 | C/G |
| ASW | rs16924068 | 9 | 6154596 | 0.015 | 1 | HapMap | HapMap | C | 0.971 | T | 0.029 | C/T |
| YRI | rs16924068 | 9 | 6154596 | 0.019 | 1 | HapMap | HapMap | C | 0.932 | T | 0.068 | C/T |
| YRI | rs16924081 | 9 | 6159135 | 0.038 | 1 | HapMap | HapMap | G | 0.889 | A | 0.111 | G/A |
| MKK | rs16924081 | 9 | 6159135 | 0.018 | 1 | HapMap | HapMap | G | 0.88 | A | 0.12 | G/A |
| LWK | rs16924081 | 9 | 6159135 | 0.039 | 0.967 | HapMap | HapMap | G | 0.856 | A | 0.144 | G/A |
| MEX | rs16924081 | 9 | 6159135 | 0.001 | 1 | HapMap | HapMap | G | 0.97 | A | 0.03 | G/A |
| GIH | rs16924081 | 9 | 6159135 | 0.002 | 1 | HapMap | HapMap | G | 0.96 | A | 0.04 | G/A |
| ASW | rs16924081 | 9 | 6159135 | 0.024 | 1 | HapMap | HapMap | G | 0.925 | A | 0.075 | G/A |
| CHD | rs16924081 | 9 | 6159135 | 0.101 | 1 | HapMap | HapMap | G | 0.988 | A | 0.012 | G/A |
| CHB | rs16924081 | 9 | 6159135 | 0.232 | 1 | HapMap | HapMap | G | 0.976 | A | 0.024 | G/A |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MKK | rs16924144 | 9 | 6211246 | 0.032 | 0.774 | HapMap | HapMap | T | 0.717 | C | 0.283 | T/C |
| JPT | rs16924144 | 9 | 6211246 | 0.015 | 1 | HapMap | HapMap | T | 0.75 | C | 0.25 | T/C |
| LWK | rs16924144 | 9 | 6211246 | 0.035 | 1 | HapMap | HapMap | T | 0.878 | C | 0.122 | T/C |
| CEU | rs16924144 | 9 | 6211246 | 0.05 | 1 | HapMap | HapMap | T | 0.69 | C | 0.31 | T/C |
| GIH | rs16924144 | 9 | 6211246 | 0.023 | 1 | HapMap | HapMap | T | 0.676 | C | 0.324 | T/C |
| YRI | rs16924161 | 9 | 6220912 | 0.012 | 1 | HapMap | HapMap | T | 0.969 | C | 0.031 | T/C |
| ASW | rs16924161 | 9 | 6220912 | 0.014 | 1 | HapMap | HapMap | T | 0.953 | C | 0.047 | T/C |
| MEX | rs16924161 | 9 | 6220912 | 0.008 | 1 | HapMap | HapMap | T | 0.89 | C | 0.11 | T/C |
| JPT | rs16924161 | 9 | 6220912 | 0.073 | 1 | HapMap | HapMap | T | 0.506 | C | 0.494 | T/C |
| LWK | rs16924161 | 9 | 6220912 | 0.022 | 1 | HapMap | HapMap | T | 0.994 | C | 0.006 | T/C |
| CHD | rs16924161 | 9 | 6220912 | 0.061 | 1 | HapMap | HapMap | T | 0.659 | C | 0.341 | T/C |
| ASW | rs16924241 | 9 | 6246144 | 0.008 | 0.741 | HapMap | HapMap | C | 0.962 | G | 0.038 | C/G |
| LWK | rs16924241 | 9 | 6246144 | 0.007 | 0.831 | HapMap | HapMap | C | 0.961 | G | 0.039 | C/G |
| ASW | rs16924243 | 9 | 6247054 | 0.086 | 1 | HapMap | HapMap | T | 0.811 | C | 0.189 | T/C |
| CEU | rs16924243 | 9 | 6247054 | 0.004 | 1 | HapMap | HapMap | T | 0.965 | C | 0.035 | T/C |
| GIH | rs16924243 | 9 | 6247054 | 0.001 | 1 | HapMap | HapMap | T | 0.989 | C | 0.011 | T/C |
| MEX | rs16924243 | 9 | 6247054 | 0.001 | 1 | HapMap | HapMap | T | 0.97 | C | 0.03 | T/C |
| MKK | rs16924243 | 9 | 6247054 | 0.026 | 1 | HapMap | HapMap | T | 0.839 | C | 0.161 | T/C |
| YRI | rs16924243 | 9 | 6247054 | 0.059 | 0.767 | HapMap | HapMap | T | 0.73 | C | 0.27 | T/C |
| YRI | rs16924277 | 9 | 6269324 | 0.015 | 1 | HapMap | HapMap | C | 0.965 | T | 0.035 | C/T |
| MKK | rs16924277 | 9 | 6269324 | 0 | 1 | HapMap | HapMap | C | 0.997 | T | 0.003 | C/T |
| ASW | rs16924277 | 9 | 6269324 | 0.034 | 1 | HapMap | HapMap | C | 0.925 | T | 0.075 | C/T |
| LWK | rs16924301 | 9 | 6296093 | 0.004 | 1 | HapMap | HapMap | A | 0.983 | G | 0.017 | A/G |
| JPT | rs16924301 | 9 | 6296093 | 0.004 | 0.615 | HapMap | HapMap | A | 0.831 | G | 0.169 | A/G |
| ASW | rs16924301 | 9 | 6296093 | 0.176 | 1 | HapMap | HapMap | A | 0.943 | G | 0.057 | A/G |
| GIH | rs16924301 | 9 | 6296093 | 0.016 | 1 | HapMap | HapMap | A | 0.744 | G | 0.256 | A/G |
| YRI | rs16924301 | 9 | 6296093 | 0.06 | 1 | HapMap | HapMap | A | 0.96 | G | 0.04 | A/G |
| MKK | rs16924301 | 9 | 6296093 | 0.004 | 1 | HapMap | HapMap | A | 0.972 | G | 0.028 | A/G |
| MKK | rs16924356 | 9 | 6321610 | 0.017 | 0.656 | HapMap | HapMap | G | 0.776 | A | 0.224 | G/A |
| MEX | rs16924356 | 9 | 6321610 | 0.013 | 1 | HapMap | HapMap | G | 0.82 | A | 0.18 | G/A |
| ASW | rs16924356 | 9 | 6321610 | 0.041 | 0.663 | HapMap | HapMap | G | 0.736 | A | 0.264 | G/A |
| GIH | rs16924356 | 9 | 6321610 | 0.008 | 1 | HapMap | HapMap | G | 0.864 | A | 0.136 | G/A |
| CEU | rs16924356 | 9 | 6321610 | 0.052 | 1 | HapMap | HapMap | G | 0.717 | A | 0.283 | G/A |
| MKK | rs16924360 | 9 | 6321840 | 0.014 | 1 | HapMap | HapMap | T | 0.906 | G | 0.094 | T/G |
| MEX | rs16924360 | 9 | 6321840 | 0.001 | 1 | HapMap | HapMap | T | 0.98 | G | 0.02 | T/G |
| LWK | rs16924360 | 9 | 6321840 | 0.02 | 0.668 | HapMap | HapMap | T | 0.85 | G | 0.15 | T/G |
| GIH | rs16924360 | 9 | 6321840 | 0 | 1 | HapMap | HapMap | T | 0.994 | G | 0.006 | T/G |
| MKK | rs16924434 | 9 | 6348334 | 0.005 | 1 | HapMap | HapMap | A | 0.965 | G | 0.035 | A/G |
| MEX | rs16924434 | 9 | 6348334 | 0.009 | 1 | HapMap | HapMap | A | 0.87 | G | 0.13 | A/G |
| CHD | rs16924434 | 9 | 6348334 | 0.047 | 1 | HapMap | HapMap | A | 0.718 | G | 0.282 | A/G |
| CHB | rs16924434 | 9 | 6348334 | 0.033 | 1 | HapMap | HapMap | A | 0.738 | G | 0.262 | A/G |
| CEU | rs16924434 | 9 | 6348334 | 0.011 | 1 | HapMap | HapMap | A | 0.898 | G | 0.102 | A/G |
| ASW | rs16924434 | 9 | 6348334 | 0 | 1 | HapMap | HapMap | A | 0.991 | G | 0.009 | A/G |
| CEU | rs17498168 | 9 | 6227186 | 0.378 | 0.811 | HapMap | HapMap | T | 0.965 | C | 0.035 | T/C |
| MEX | rs17498196 | 9 | 6227547 | 0.006 | 0.77 | HapMap | HapMap | A | 0.87 | C | 0.13 | A/C |
| GIH | rs17498196 | 9 | 6227547 | 0.007 | 1 | HapMap | HapMap | A | 0.875 | C | 0.125 | A/C |
| MKK | rs17498196 | 9 | 6227547 | 0.002 | 1 | HapMap | HapMap | A | 0.983 | C | 0.017 | A/C |
| ASW | rs17498196 | 9 | 6227547 | 0.014 | 1 | HapMap | HapMap | A | 0.906 | C | 0.094 | A/C |
| CEU | rs17498196 | 9 | 6227547 | 0.041 | 1 | HapMap | HapMap | A | 0.765 | C | 0.235 | A/C |
| CEU | rs1755531 | 9 | 6114250 | 0.013 | 1 | HapMap | HapMap | T | 0.129 | G | 0.871 | T/G |
| CHB | rs1755531 | 9 | 6114250 | 0.002 | 1 | HapMap | HapMap | T | 0.03 | G | 0.97 | T/G |
| GIH | rs1755531 | 9 | 6114250 | 0.016 | 1 | HapMap | HapMap | T | 0.25 | G | 0.75 | T/G |
| MEX | rs1755531 | 9 | 6114250 | 0.009 | 1 | HapMap | HapMap | T | 0.13 | G | 0.87 | T/G |
| MKK | rs1755531 | 9 | 6114250 | 0.032 | 1 | HapMap | HapMap | T | 0.186 | G | 0.814 | T/G |
| ASW | rs17580721 | 9 | 6007252 | 0.004 | 1 | HapMap | HapMap | A | 0.962 | G | 0.038 | A/G |
| MEX | rs17580721 | 9 | 6007252 | 0.003 | 1 | HapMap | HapMap | A | 0.96 | G | 0.04 | A/G |
| CEU | rs17580721 | 9 | 6007252 | 0.016 | 1 | HapMap | HapMap | A | 0.832 | G | 0.168 | A/G |
| CHD | rs17580721 | 9 | 6007252 | 0.001 | 1 | HapMap | HapMap | A | 0.994 | G | 0.006 | A/G |
| GIH | rs17580721 | 9 | 6007252 | 0.003 | 1 | HapMap | HapMap | A | 0.943 | G | 0.057 | A/G |
| CHD | rs17705436 | 9 | 6300908 | 0.001 | 1 | HapMap | HapMap | C | 0.994 | G | 0.006 | C/G |
| GIH | rs17705436 | 9 | 6300908 | 0.007 | 1 | HapMap | HapMap | C | 0.869 | G | 0.131 | C/G |
| ASW | rs17705436 | 9 | 6300908 | 0.014 | 1 | HapMap | HapMap | C | 0.896 | G | 0.104 | C/G |
| CEU | rs17705436 | 9 | 6300908 | 0.043 | 1 | HapMap | HapMap | C | 0.743 | G | 0.257 | C/G |
| MKK | rs17705436 | 9 | 6300908 | 0.002 | 1 | HapMap | HapMap | C | 0.986 | G | 0.014 | C/G |
| GIH | rs17756142 | 9 | 6291578 | 0.007 | 1 | HapMap | HapMap | A | 0.875 | C | 0.125 | A/C |
| MEX | rs17756142 | 9 | 6291578 | 0.009 | 0.925 | HapMap | HapMap | A | 0.86 | C | 0.14 | A/C |
| ASW | rs17756142 | 9 | 6291578 | 0.014 | 1 | HapMap | HapMap | A | 0.896 | C | 0.104 | A/C |
| MKK | rs17756142 | 9 | 6291578 | 0.002 | 1 | HapMap | HapMap | A | 0.986 | C | 0.014 | A/C |
| CHD | rs17756142 | 9 | 6291578 | 0.004 | 1 | HapMap | HapMap | A | 0.97 | C | 0.03 | A/C |
| CEU | rs17756142 | 9 | 6291578 | 0.043 | 1 | HapMap | HapMap | A | 0.735 | C | 0.265 | A/C |
| GIH | rs1888703 | 9 | 5973508 | 0.008 | 1 | HapMap | HapMap | T | 0.132 | G | 0.868 | T/G |
| CHB | rs1888703 | 9 | 5973508 | 0.116 | 0.758 | HapMap | HapMap | T | 0.315 | G | 0.685 | T/G |
| CEU | rs1888909 | 9 | 6187392 | 0.208 | 1 | HapMap | HapMap | T | 0.288 | C | 0.712 | T/C |
| ASW | rs1888909 | 9 | 6187392 | 0.11 | 0.646 | HapMap | HapMap | T | 0.462 | C | 0.538 | T/C |
| CHB | rs1888909 | 9 | 6187392 | 0.232 | 1 | HapMap | HapMap | T | 0.036 | C | 0.964 | T/C |
| CHD | rs1888909 | 9 | 6187392 | 0.417 | 1 | HapMap | HapMap | T | 0.047 | C | 0.953 | T/C |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| YRI | rs1888909 | 9 | 6187392 | 0.212 | 0.89 | HapMap | HapMap | T | 0.535 | C | 0.465 | T/C |
| GIH | rs1888909 | 9 | 6187392 | 0.151 | 1 | HapMap | HapMap | T | 0.239 | C | 0.761 | T/C |
| JPT | rs1888909 | 9 | 6187392 | 0.585 | 1 | HapMap | HapMap | T | 0.035 | C | 0.965 | T/C |
| MKK | rs1888909 | 9 | 6187392 | 0.148 | 0.699 | HapMap | HapMap | T | 0.308 | C | 0.692 | T/C |
| ASW | rs1891385 | 9 | 6209845 | 0 | 1 | HapMap | HapMap | A | 0.991 | C | 0.009 | A/C |
| CEU | rs1891385 | 9 | 6209845 | 0.012 | 1 | HapMap | HapMap | A | 0.894 | C | 0.106 | A/C |
| CHD | rs1891385 | 9 | 6209845 | 0.035 | 1 | HapMap | HapMap | A | 0.771 | C | 0.229 | A/C |
| LWK | rs1891385 | 9 | 6209845 | 0.045 | 1 | HapMap | HapMap | A | 0.989 | C | 0.011 | A/C |
| MEX | rs1891385 | 9 | 6209845 | 0.005 | 1 | HapMap | HapMap | A | 0.93 | C | 0.07 | A/C |
| MKK | rs1891385 | 9 | 6209845 | 0.006 | 1 | HapMap | HapMap | A | 0.955 | C | 0.045 | A/C |
| JPT | rs189309 | 9 | 6101393 | 0.014 | 1 | HapMap | HapMap | T | 0.215 | C | 0.785 | T/C |
| CHB | rs189309 | 9 | 6101393 | 0.063 | 0.65 | HapMap | HapMap | T | 0.393 | C | 0.607 | T/C |
| GIH | rs189309 | 9 | 6101393 | 0.038 | 1 | HapMap | HapMap | T | 0.557 | C | 0.443 | T/C |
| MEX | rs189309 | 9 | 6101393 | 0.022 | 0.609 | HapMap | HapMap | T | 0.48 | C | 0.52 | T/C |
| CEU | rs1929994 | 9 | 6214308 | 0.007 | 1 | HapMap | HapMap | T | 0.956 | C | 0.044 | T/C |
| LWK | rs1929994 | 9 | 6214308 | 0.048 | 1 | HapMap | HapMap | T | 0.839 | C | 0.161 | T/C |
| MKK | rs1929994 | 9 | 6214308 | 0.024 | 0.938 | HapMap | HapMap | T | 0.831 | C | 0.169 | T/C |
| CHB | rs1970089 | 9 | 6114359 | 0.002 | 1 | HapMap | HapMap | T | 0.03 | C | 0.97 | T/C |
| GIH | rs1970089 | 9 | 6114359 | 0.016 | 1 | HapMap | HapMap | T | 0.241 | C | 0.759 | T/C |
| MEX | rs1970089 | 9 | 6114359 | 0.009 | 1 | HapMap | HapMap | T | 0.14 | C | 0.86 | T/C |
| CEU | rs1970089 | 9 | 6114359 | 0.013 | 1 | HapMap | HapMap | T | 0.125 | C | 0.875 | T/C |
| MKK | rs1970089 | 9 | 6114359 | 0.033 | 1 | HapMap | HapMap | T | 0.191 | C | 0.809 | T/C |
| MEX | rs1993912 | 9 | 5977781 | 0.001 | 1 | HapMap | HapMap | A | 0.98 | C | 0.02 | A/C |
| CHB | rs1993912 | 9 | 5977781 | 0.004 | 1 | HapMap | HapMap | A | 0.97 | C | 0.03 | A/C |
| GIH | rs1993912 | 9 | 5977781 | 0.004 | 1 | HapMap | HapMap | A | 0.92 | C | 0.08 | A/C |
| LWK | rs1993912 | 9 | 5977781 | 0.03 | 1 | HapMap | HapMap | A | 0.894 | C | 0.106 | A/C |
| ASW | rs2000199 | 9 | 6258893 | 0.158 | 0.705 | HapMap | HapMap | G | 0.509 | A | 0.491 | G/A |
| CEU | rs2000199 | 9 | 6258893 | 0.013 | 1 | HapMap | HapMap | G | 0.075 | A | 0.925 | G/A |
| GIH | rs2000199 | 9 | 6258893 | 0.001 | 1 | HapMap | HapMap | G | 0.017 | A | 0.983 | G/A |
| MEX | rs2000199 | 9 | 6258893 | 0.005 | 1 | HapMap | HapMap | G | 0.09 | A | 0.91 | G/A |
| MKK | rs2000199 | 9 | 6258893 | 0.043 | 0.752 | HapMap | HapMap | G | 0.36 | A | 0.64 | G/A |
| ASW | rs2026991 | 9 | 6256440 | 0.158 | 0.705 | HapMap | HapMap | A | 0.509 | G | 0.491 | A/G |
| CEU | rs2026991 | 9 | 6256440 | 0.013 | 1 | HapMap | HapMap | A | 0.075 | G | 0.925 | A/G |
| GIH | rs2026991 | 9 | 6256440 | 0.001 | 1 | HapMap | HapMap | A | 0.017 | G | 0.983 | A/G |
| MEX | rs2026991 | 9 | 6256440 | 0.005 | 1 | HapMap | HapMap | A | 0.09 | G | 0.91 | A/G |
| MKK | rs2026991 | 9 | 6256440 | 0.045 | 0.76 | HapMap | HapMap | A | 0.367 | G | 0.633 | A/G |
| ASW | rs2039386 | 9 | 6258204 | 0.146 | 0.794 | HapMap | HapMap | G | 0.396 | C | 0.604 | G/C |
| CEU | rs2039386 | 9 | 6258204 | 0.013 | 1 | HapMap | HapMap | G | 0.075 | C | 0.925 | G/C |
| GIH | rs2039386 | 9 | 6258204 | 0.001 | 1 | HapMap | HapMap | G | 0.017 | C | 0.983 | G/C |
| MEX | rs2039386 | 9 | 6258204 | 0.004 | 1 | HapMap | HapMap | G | 0.08 | C | 0.92 | G/C |
| JPT | rs2054314 | 9 | 6281125 | 0.001 | 1 | HapMap | HapMap | T | 0.006 | C | 0.994 | T/C |
| MEX | rs2054314 | 9 | 6281125 | 0.003 | 1 | HapMap | HapMap | T | 0.07 | C | 0.93 | T/C |
| MKK | rs2054314 | 9 | 6281125 | 0.016 | 0.608 | HapMap | HapMap | T | 0.236 | C | 0.764 | T/C |
| CHB | rs2054314 | 9 | 6281125 | 0.001 | 1 | HapMap | HapMap | T | 0.012 | C | 0.988 | T/C |
| CEU | rs2054314 | 9 | 6281125 | 0.014 | 1 | HapMap | HapMap | T | 0.078 | C | 0.922 | T/C |
| GIH | rs2054314 | 9 | 6281125 | 0.001 | 1 | HapMap | HapMap | T | 0.028 | C | 0.972 | T/C |
| CEU | rs2066362 | 9 | 6209176 | 0.026 | 1 | HapMap | HapMap | G | 0.835 | T | 0.165 | G/T |
| GIH | rs2066362 | 9 | 6209176 | 0.013 | 1 | HapMap | HapMap | G | 0.784 | T | 0.216 | G/T |
| MEX | rs2066362 | 9 | 6209176 | 0.014 | 1 | HapMap | HapMap | G | 0.82 | T | 0.18 | G/T |
| JPT | rs2069264 | 9 | 6124787 | 0.007 | 1 | HapMap | HapMap | T | 0.878 | C | 0.122 | T/C |
| LWK | rs2069264 | 9 | 6124787 | 0.033 | 1 | HapMap | HapMap | T | 0.883 | C | 0.117 | T/C |
| YRI | rs2069264 | 9 | 6124787 | 0.028 | 0.679 | HapMap | HapMap | T | 0.839 | C | 0.161 | T/C |
| ASW | rs2069264 | 9 | 6124787 | 0.041 | 0.663 | HapMap | HapMap | T | 0.764 | C | 0.236 | T/C |
| CHB | rs2069264 | 9 | 6124787 | 0.018 | 1 | HapMap | HapMap | T | 0.857 | C | 0.143 | T/C |
| GIH | rs2069264 | 9 | 6124787 | 0.008 | 1 | HapMap | HapMap | T | 0.852 | C | 0.148 | T/C |
| CHD | rs2069264 | 9 | 6124787 | 0.025 | 1 | HapMap | HapMap | T | 0.824 | C | 0.176 | T/C |
| CEU | rs2169282 | 9 | 6340235 | 0.089 | 1 | HapMap | HapMap | A | 0.389 | G | 0.611 | A/G |
| CHD | rs2169282 | 9 | 6340235 | 0.047 | 1 | HapMap | HapMap | A | 0.282 | G | 0.718 | A/G |
| GIH | rs2169282 | 9 | 6340235 | 0.03 | 1 | HapMap | HapMap | A | 0.386 | G | 0.614 | A/G |
| MEX | rs2169282 | 9 | 6340235 | 0.02 | 1 | HapMap | HapMap | A | 0.26 | G | 0.74 | A/G |
| MKK | rs2169282 | 9 | 6340235 | 0.067 | 0.761 | HapMap | HapMap | A | 0.462 | G | 0.538 | A/G |
| CHB | rs2169282 | 9 | 6340235 | 0.033 | 1 | HapMap | HapMap | A | 0.262 | G | 0.738 | A/G |
| CEU | rs2210463 | 9 | 6217752 | 0.287 | 1 | HapMap | HapMap | A | 0.699 | G | 0.301 | A/G |
| GIH | rs2210463 | 9 | 6217752 | 0.094 | 1 | HapMap | HapMap | A | 0.665 | G | 0.335 | A/G |
| JPT | rs2210463 | 9 | 6217752 | 0.056 | 1 | HapMap | HapMap | A | 0.482 | G | 0.518 | A/G |
| MKK | rs2210463 | 9 | 6217752 | 0.099 | 0.729 | HapMap | HapMap | A | 0.58 | G | 0.42 | A/G |
| CEU | rs2210464 | 9 | 6213903 | 0.446 | 1 | HapMap | HapMap | A | 0.757 | T | 0.243 | A/T |
| MKK | rs2210464 | 9 | 6213903 | 0.187 | 0.626 | HapMap | HapMap | A | 0.78 | T | 0.22 | A/T |
| JPT | rs2210464 | 9 | 6213903 | 0.052 | 1 | HapMap | HapMap | A | 0.477 | T | 0.523 | A/T |
| MKK | rs2290913 | 9 | 6320321 | 0 | 1 | HapMap | HapMap | T | 0.996 | A | 0.004 | T/A |
| JPT | rs2290913 | 9 | 6320321 | 0.006 | 1 | HapMap | HapMap | T | 0.936 | A | 0.064 | T/A |
| CHD | rs2290913 | 9 | 6320321 | 0.014 | 1 | HapMap | HapMap | T | 0.894 | A | 0.106 | T/A |
| ASW | rs2295843 | 9 | 6318871 | 0.004 | 1 | HapMap | HapMap | G | 0.991 | A | 0.009 | G/A |
| CHB | rs2295843 | 9 | 6318871 | 0.115 | 1 | HapMap | HapMap | G | 0.994 | A | 0.006 | G/A |
| JPT | rs2295843 | 9 | 6318871 | 0.19 | 1 | HapMap | HapMap | G | 0.994 | A | 0.006 | G/A |
| MEX | rs2295843 | 9 | 6318871 | 0 | 1 | HapMap | HapMap | G | 0.99 | A | 0.01 | G/A |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHD | rs2295843 | 9 | 6318871 | 0.256 | 1 | HapMap | HapMap | G | 0.971 | A | 0.029 | G/A |
| CHD | rs2381413 | 9 | 6157017 | 0.177 | 0.8 | HapMap | HapMap | C | 0.7 | G | 0.3 | C/G |
| GIH | rs2381413 | 9 | 6157017 | 0.075 | 1 | HapMap | HapMap | C | 0.614 | G | 0.386 | C/G |
| JPT | rs2381413 | 9 | 6157017 | 0.163 | 0.718 | HapMap | HapMap | C | 0.831 | G | 0.169 | C/G |
| MEX | rs2381413 | 9 | 6157017 | 0.052 | 0.693 | HapMap | HapMap | C | 0.66 | G | 0.34 | C/G |
| MKK | rs2381413 | 9 | 6157017 | 0.064 | 0.796 | HapMap | HapMap | C | 0.427 | G | 0.573 | C/G |
| CEU | rs2381413 | 9 | 6157017 | 0.1 | 1 | HapMap | HapMap | C | 0.54 | G | 0.46 | C/G |
| CHB | rs2381413 | 9 | 6157017 | 0.151 | 0.776 | HapMap | HapMap | C | 0.69 | G | 0.31 | C/G |
| ASW | rs2381422 | 9 | 6271211 | 0.058 | 1 | HapMap | HapMap | C | 0.123 | T | 0.877 | C/T |
| LWK | rs2381422 | 9 | 6271211 | 0.096 | 0.675 | HapMap | HapMap | C | 0.05 | T | 0.95 | C/T |
| GIH | rs2381422 | 9 | 6271211 | 0.001 | 1 | HapMap | HapMap | C | 0.017 | T | 0.983 | C/T |
| MKK | rs2381422 | 9 | 6271211 | 0.002 | 1 | HapMap | HapMap | C | 0.014 | T | 0.986 | C/T |
| MEX | rs2381422 | 9 | 6271211 | 0.001 | 1 | HapMap | HapMap | C | 0.02 | T | 0.98 | C/T |
| CEU | rs2381438 | 9 | 6332855 | 0.006 | 1 | HapMap | HapMap | G | 0.031 | A | 0.969 | G/A |
| GIH | rs2381438 | 9 | 6332855 | 0.001 | 1 | HapMap | HapMap | G | 0.017 | A | 0.983 | G/A |
| MEX | rs2381438 | 9 | 6332855 | 0.001 | 1 | HapMap | HapMap | G | 0.031 | A | 0.969 | G/A |
| ASW | rs2381438 | 9 | 6332855 | 0.046 | 0.621 | HapMap | HapMap | G | 0.274 | A | 0.726 | G/A |
| CHD | rs2890704 | 9 | 6174165 | 0.417 | 1 | HapMap | HapMap | T | 0.047 | C | 0.953 | T/C |
| GIH | rs2890704 | 9 | 6174165 | 0.445 | 1 | HapMap | HapMap | T | 0.097 | C | 0.903 | T/C |
| MEX | rs2890704 | 9 | 6174165 | 0.587 | 1 | HapMap | HapMap | T | 0.03 | C | 0.97 | T/C |
| MKK | rs2890704 | 9 | 6174165 | 0.484 | 0.851 | HapMap | HapMap | T | 0.168 | C | 0.832 | T/C |
| YRI | rs2890704 | 9 | 6174165 | 0.567 | 0.886 | HapMap | HapMap | T | 0.292 | C | 0.708 | T/C |
| JPT | rs2890704 | 9 | 6174165 | 0.585 | 1 | HapMap | HapMap | T | 0.035 | C | 0.965 | T/C |
| LWK | rs2890704 | 9 | 6174165 | 0.499 | 0.767 | HapMap | HapMap | T | 0.228 | C | 0.772 | T/C |
| CEU | rs2890704 | 9 | 6174165 | 0.683 | 1 | HapMap | HapMap | T | 0.119 | C | 0.881 | T/C |
| CHB | rs2890704 | 9 | 6174165 | 0.232 | 1 | HapMap | HapMap | T | 0.036 | C | 0.964 | T/C |
| ASW | rs2890704 | 9 | 6174165 | 0.541 | 0.802 | HapMap | HapMap | T | 0.198 | C | 0.802 | T/C |
| ASW | rs2890707 | 9 | 6321324 | 0.04 | 0.626 | HapMap | HapMap | A | 0.255 | G | 0.745 | A/G |
| GIH | rs2890707 | 9 | 6321324 | 0.001 | 1 | HapMap | HapMap | A | 0.017 | G | 0.983 | A/G |
| MEX | rs2890707 | 9 | 6321324 | 0.001 | 1 | HapMap | HapMap | A | 0.03 | G | 0.97 | A/G |
| MKK | rs2890707 | 9 | 6321324 | 0.015 | 1 | HapMap | HapMap | A | 0.101 | G | 0.899 | A/G |
| MEX | rs340890 | 9 | 6090169 | 0.016 | 1 | HapMap | HapMap | C | 0.735 | T | 0.265 | C/T |
| MKK | rs340890 | 9 | 6090169 | 0.019 | 0.615 | HapMap | HapMap | C | 0.724 | T | 0.276 | C/T |
| CHD | rs340890 | 9 | 6090169 | 0.014 | 0.612 | HapMap | HapMap | C | 0.759 | T | 0.241 | C/T |
| YRI | rs340890 | 9 | 6090169 | 0.018 | 1 | HapMap | HapMap | C | 0.942 | T | 0.058 | C/T |
| MEX | rs340892 | 9 | 6088662 | 0.022 | 0.609 | HapMap | HapMap | T | 0.48 | G | 0.52 | T/G |
| GIH | rs340892 | 9 | 6088662 | 0.027 | 1 | HapMap | HapMap | T | 0.636 | G | 0.364 | T/G |
| CHB | rs340892 | 9 | 6088662 | 0.063 | 0.65 | HapMap | HapMap | T | 0.392 | G | 0.608 | T/G |
| MEX | rs340899 | 9 | 6099080 | 0.024 | 0.617 | HapMap | HapMap | C | 0.47 | T | 0.53 | C/T |
| CHB | rs340899 | 9 | 6099080 | 0.063 | 0.65 | HapMap | HapMap | C | 0.399 | T | 0.601 | C/T |
| GIH | rs340899 | 9 | 6099080 | 0.034 | 1 | HapMap | HapMap | C | 0.585 | T | 0.415 | C/T |
| MEX | rs340900 | 9 | 6098921 | 0.022 | 0.609 | HapMap | HapMap | T | 0.48 | C | 0.52 | T/C |
| CHB | rs340900 | 9 | 6098921 | 0.063 | 0.65 | HapMap | HapMap | T | 0.393 | C | 0.607 | T/C |
| GIH | rs340900 | 9 | 6098921 | 0.034 | 1 | HapMap | HapMap | T | 0.585 | C | 0.415 | T/C |
| MKK | rs340904 | 9 | 6096779 | 0.029 | 1 | HapMap | HapMap | C | 0.175 | A | 0.825 | C/A |
| CHB | rs340904 | 9 | 6096779 | 0.002 | 1 | HapMap | HapMap | C | 0.03 | A | 0.97 | C/A |
| GIH | rs340904 | 9 | 6096779 | 0.015 | 1 | HapMap | HapMap | C | 0.244 | A | 0.756 | C/A |
| CEU | rs340904 | 9 | 6096779 | 0.013 | 1 | HapMap | HapMap | C | 0.124 | A | 0.876 | C/A |
| MEX | rs340904 | 9 | 6096779 | 0.009 | 1 | HapMap | HapMap | C | 0.13 | A | 0.87 | C/A |
| CEU | rs340908 | 9 | 6118897 | 0.013 | 1 | HapMap | HapMap | T | 0.124 | C | 0.876 | T/C |
| CHB | rs340908 | 9 | 6118897 | 0.002 | 1 | HapMap | HapMap | T | 0.03 | C | 0.97 | T/C |
| GIH | rs340908 | 9 | 6118897 | 0.015 | 1 | HapMap | HapMap | T | 0.244 | C | 0.756 | T/C |
| MKK | rs340908 | 9 | 6118897 | 0.029 | 1 | HapMap | HapMap | T | 0.175 | C | 0.825 | T/C |
| MEX | rs340908 | 9 | 6118897 | 0.009 | 1 | HapMap | HapMap | T | 0.13 | C | 0.87 | T/C |
| MEX | rs340921 | 9 | 6080160 | 0.009 | 1 | HapMap | HapMap | G | 0.133 | T | 0.867 | G/T |
| MKK | rs340921 | 9 | 6080160 | 0.027 | 1 | HapMap | HapMap | G | 0.164 | T | 0.836 | G/T |
| GIH | rs340921 | 9 | 6080160 | 0.015 | 1 | HapMap | HapMap | G | 0.244 | T | 0.756 | G/T |
| CHB | rs340921 | 9 | 6080160 | 0.004 | 1 | HapMap | HapMap | G | 0.036 | T | 0.964 | G/T |
| CEU | rs340921 | 9 | 6080160 | 0.013 | 1 | HapMap | HapMap | G | 0.125 | T | 0.875 | G/T |
| CHB | rs340923 | 9 | 6078628 | 0.003 | 1 | HapMap | HapMap | G | 0.03 | A | 0.97 | G/A |
| GIH | rs340923 | 9 | 6078628 | 0.015 | 1 | HapMap | HapMap | G | 0.239 | A | 0.761 | G/A |
| MEX | rs340923 | 9 | 6078628 | 0.009 | 1 | HapMap | HapMap | G | 0.14 | A | 0.86 | G/A |
| MKK | rs340923 | 9 | 6078628 | 0.018 | 0.692 | HapMap | HapMap | G | 0.22 | A | 0.78 | G/A |
| CEU | rs340923 | 9 | 6078628 | 0.013 | 1 | HapMap | HapMap | G | 0.124 | A | 0.876 | G/A |
| YRI | rs340930 | 9 | 6076676 | 0.05 | 0.642 | HapMap | HapMap | T | 0.054 | G | 0.946 | T/G |
| LWK | rs340930 | 9 | 6076676 | 0.161 | 1 | HapMap | HapMap | T | 0.039 | G | 0.961 | T/G |
| ASW | rs340930 | 9 | 6076676 | 0.062 | 1 | HapMap | HapMap | T | 0.01 | G | 0.99 | T/G |
| CHB | rs340933 | 9 | 6075078 | 0.004 | 1 | HapMap | HapMap | T | 0.037 | G | 0.963 | T/G |
| GIH | rs340933 | 9 | 6075078 | 0.015 | 1 | HapMap | HapMap | T | 0.241 | G | 0.759 | T/G |
| MEX | rs340933 | 9 | 6075078 | 0.01 | 1 | HapMap | HapMap | T | 0.135 | G | 0.865 | T/G |
| CEU | rs340933 | 9 | 6075078 | 0.014 | 1 | HapMap | HapMap | T | 0.125 | G | 0.875 | T/G |
| CEU | rs340934 | 9 | 6071804 | 0.014 | 1 | HapMap | HapMap | G | 0.119 | T | 0.881 | G/T |
| JPT | rs340934 | 9 | 6071804 | 0.001 | 1 | HapMap | HapMap | G | 0.017 | T | 0.983 | G/T |
| GIH | rs340934 | 9 | 6071804 | 0.013 | 1 | HapMap | HapMap | G | 0.216 | T | 0.784 | G/T |
| MEX | rs340934 | 9 | 6071804 | 0.008 | 1 | HapMap | HapMap | G | 0.13 | T | 0.87 | G/T |
| MKK | rs340934 | 9 | 6071804 | 0.027 | 1 | HapMap | HapMap | G | 0.163 | T | 0.837 | G/T |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHD | rs343470 | 9 | 6034937 | 0.035 | 0.787 | HapMap | HapMap | T | 0.324 | C | 0.676 | T/C |
| LWK | rs343470 | 9 | 6034937 | 0.015 | 1 | HapMap | HapMap | T | 0.056 | C | 0.944 | T/C |
| CHB | rs343471 | 9 | 6033593 | 0.122 | 0.6 | HapMap | HapMap | T | 0.78 | C | 0.22 | T/C |
| ASW | rs343471 | 9 | 6033593 | 0.026 | 1 | HapMap | HapMap | T | 0.923 | C | 0.077 | T/C |
| CEU | rs343471 | 9 | 6033593 | 0.001 | 1 | HapMap | HapMap | T | 0.991 | C | 0.009 | T/C |
| CHB | rs343473 | 9 | 6064936 | 0.005 | 1 | HapMap | HapMap | A | 0.054 | G | 0.946 | A/G |
| JPT | rs343473 | 9 | 6064936 | 0.001 | 1 | HapMap | HapMap | A | 0.023 | G | 0.977 | A/G |
| MEX | rs343474 | 9 | 6063843 | 0.027 | 0.632 | HapMap | HapMap | A | 0.44 | G | 0.56 | A/G |
| CHD | rs343474 | 9 | 6063843 | 0.024 | 1 | HapMap | HapMap | A | 0.163 | G | 0.837 | A/G |
| JPT | rs343474 | 9 | 6063843 | 0.008 | 1 | HapMap | HapMap | A | 0.145 | G | 0.855 | A/G |
| CHB | rs343474 | 9 | 6063843 | 0.017 | 0.889 | HapMap | HapMap | A | 0.179 | G | 0.821 | A/G |
| CEU | rs343477 | 9 | 5999761 | 0.097 | 0.67 | HapMap | HapMap | G | 0.712 | A | 0.288 | G/A |
| MEX | rs343477 | 9 | 5999761 | 0.053 | 0.671 | HapMap | HapMap | G | 0.68 | A | 0.32 | G/A |
| CEU | rs343484 | 9 | 6015606 | 0.058 | 0.609 | HapMap | HapMap | G | 0.659 | A | 0.341 | G/A |
| MEX | rs343484 | 9 | 6015606 | 0.088 | 1 | HapMap | HapMap | G | 0.612 | A | 0.388 | G/A |
| CEU | rs343485 | 9 | 6016180 | 0.058 | 0.609 | HapMap | HapMap | T | 0.659 | G | 0.341 | T/G |
| MEX | rs343485 | 9 | 6016180 | 0.097 | 1 | HapMap | HapMap | T | 0.633 | G | 0.367 | T/G |
| GIH | rs343485 | 9 | 6016180 | 0.035 | 1 | HapMap | HapMap | T | 0.426 | G | 0.574 | T/G |
| CEU | rs343489 | 9 | 6054299 | 0.016 | 1 | HapMap | HapMap | C | 0.858 | G | 0.142 | C/G |
| CHB | rs343489 | 9 | 6054299 | 0.004 | 1 | HapMap | HapMap | C | 0.958 | G | 0.042 | C/G |
| GIH | rs343489 | 9 | 6054299 | 0.015 | 1 | HapMap | HapMap | C | 0.761 | G | 0.239 | C/G |
| MEX | rs343489 | 9 | 6054299 | 0.009 | 1 | HapMap | HapMap | C | 0.87 | G | 0.13 | C/G |
| MKK | rs343489 | 9 | 6054299 | 0.023 | 1 | HapMap | HapMap | C | 0.857 | G | 0.143 | C/G |
| CEU | rs343491 | 9 | 6054640 | 0.016 | 1 | HapMap | HapMap | G | 0.858 | C | 0.142 | G/C |
| CHB | rs343491 | 9 | 6054640 | 0.004 | 1 | HapMap | HapMap | G | 0.958 | C | 0.042 | G/C |
| GIH | rs343491 | 9 | 6054640 | 0.015 | 1 | HapMap | HapMap | G | 0.761 | C | 0.239 | G/C |
| MEX | rs343491 | 9 | 6054640 | 0.009 | 1 | HapMap | HapMap | G | 0.87 | C | 0.13 | G/C |
| MKK | rs343491 | 9 | 6054640 | 0.023 | 1 | HapMap | HapMap | G | 0.857 | C | 0.143 | G/C |
| GIH | rs343494 | 9 | 6060342 | 0.029 | 1 | HapMap | HapMap | C | 0.381 | T | 0.619 | C/T |
| MEX | rs343494 | 9 | 6060342 | 0.026 | 0.624 | HapMap | HapMap | C | 0.54 | T | 0.46 | C/T |
| CHD | rs343497 | 9 | 6057744 | 0.024 | 1 | HapMap | HapMap | C | 0.829 | T | 0.171 | C/T |
| JPT | rs343497 | 9 | 6057744 | 0.007 | 1 | HapMap | HapMap | C | 0.866 | T | 0.134 | C/T |
| MEX | rs343497 | 9 | 6057744 | 0.027 | 0.632 | HapMap | HapMap | C | 0.56 | T | 0.44 | C/T |
| CHB | rs343497 | 9 | 6057744 | 0.01 | 0.699 | HapMap | HapMap | C | 0.833 | T | 0.167 | C/T |
| GIH | rs343500 | 9 | 6005011 | 0.006 | 1 | HapMap | HapMap | T | 0.898 | C | 0.102 | T/C |
| MEX | rs343500 | 9 | 6005011 | 0.001 | 1 | HapMap | HapMap | T | 0.97 | C | 0.03 | T/C |
| CHB | rs343500 | 9 | 6005011 | 0.136 | 0.613 | HapMap | HapMap | T | 0.78 | C | 0.22 | T/C |
| CEU | rs343500 | 9 | 6005011 | 0.001 | 1 | HapMap | HapMap | T | 0.991 | C | 0.009 | T/C |
| CHB | rs371454 | 9 | 6068614 | 0.004 | 1 | HapMap | HapMap | C | 0.042 | T | 0.958 | C/T |
| GIH | rs371454 | 9 | 6068614 | 0.015 | 1 | HapMap | HapMap | C | 0.244 | T | 0.756 | C/T |
| MEX | rs371454 | 9 | 6068614 | 0.009 | 1 | HapMap | HapMap | C | 0.13 | T | 0.87 | C/T |
| MKK | rs371454 | 9 | 6068614 | 0.023 | 1 | HapMap | HapMap | C | 0.147 | T | 0.853 | C/T |
| YRI | rs371454 | 9 | 6068614 | 0.157 | 0.63 | HapMap | HapMap | C | 0.133 | T | 0.867 | C/T |
| CEU | rs371454 | 9 | 6068614 | 0.014 | 1 | HapMap | HapMap | C | 0.133 | T | 0.867 | C/T |
| CHB | rs376382 | 9 | 6124999 | 0.02 | 1 | HapMap | HapMap | C | 0.167 | T | 0.833 | C/T |
| CHD | rs376382 | 9 | 6124999 | 0.026 | 1 | HapMap | HapMap | C | 0.182 | T | 0.818 | C/T |
| GIH | rs376382 | 9 | 6124999 | 0.031 | 1 | HapMap | HapMap | C | 0.392 | T | 0.608 | C/T |
| JPT | rs376382 | 9 | 6124999 | 0.007 | 1 | HapMap | HapMap | C | 0.122 | T | 0.878 | C/T |
| CEU | rs380568 | 9 | 6045531 | 0.016 | 1 | HapMap | HapMap | T | 0.863 | C | 0.137 | T/C |
| CHB | rs380568 | 9 | 6045531 | 0.004 | 1 | HapMap | HapMap | T | 0.958 | C | 0.042 | T/C |
| GIH | rs380568 | 9 | 6045531 | 0.016 | 1 | HapMap | HapMap | T | 0.75 | C | 0.25 | T/C |
| MEX | rs380568 | 9 | 6045531 | 0.009 | 1 | HapMap | HapMap | T | 0.87 | C | 0.13 | T/C |
| MKK | rs380568 | 9 | 6045531 | 0.012 | 1 | HapMap | HapMap | T | 0.918 | C | 0.082 | T/C |
| ASW | rs3847261 | 9 | 6299188 | 0.101 | 1 | HapMap | HapMap | T | 0.25 | A | 0.75 | T/A |
| GIH | rs3847261 | 9 | 6299188 | 0.001 | 1 | HapMap | HapMap | T | 0.017 | A | 0.983 | T/A |
| MEX | rs3847261 | 9 | 6299188 | 0.001 | 1 | HapMap | HapMap | T | 0.031 | A | 0.969 | T/A |
| MKK | rs3847261 | 9 | 6299188 | 0.018 | 1 | HapMap | HapMap | T | 0.115 | A | 0.885 | T/A |
| ASW | rs3847262 | 9 | 6318947 | 0.093 | 1 | HapMap | HapMap | T | 0.264 | C | 0.736 | T/C |
| GIH | rs3847262 | 9 | 6318947 | 0.001 | 1 | HapMap | HapMap | T | 0.017 | C | 0.983 | T/C |
| MEX | rs3847262 | 9 | 6318947 | 0.001 | 1 | HapMap | HapMap | T | 0.03 | C | 0.97 | T/C |
| MKK | rs3847262 | 9 | 6318947 | 0.016 | 1 | HapMap | HapMap | T | 0.108 | C | 0.892 | T/C |
| MEX | rs386775 | 9 | 6134486 | 0.002 | 1 | HapMap | HapMap | T | 0.03 | C | 0.97 | T/C |
| CHB | rs386775 | 9 | 6134486 | 0.001 | 1 | HapMap | HapMap | T | 0.012 | C | 0.988 | T/C |
| GIH | rs386775 | 9 | 6134486 | 0.011 | 1 | HapMap | HapMap | T | 0.188 | C | 0.812 | T/C |
| MKK | rs386775 | 9 | 6134486 | 0.023 | 0.886 | HapMap | HapMap | T | 0.178 | C | 0.822 | T/C |
| CHD | rs386880 | 9 | 6134333 | 0.052 | 1 | HapMap | HapMap | C | 0.304 | T | 0.696 | C/T |
| GIH | rs386880 | 9 | 6134333 | 0.026 | 1 | HapMap | HapMap | C | 0.352 | T | 0.648 | C/T |
| JPT | rs386880 | 9 | 6134333 | 0.011 | 1 | HapMap | HapMap | C | 0.188 | T | 0.812 | C/T |
| MKK | rs386880 | 9 | 6134333 | 0.05 | 0.666 | HapMap | HapMap | C | 0.455 | T | 0.545 | C/T |
| MEX | rs387149 | 9 | 6135022 | 0.016 | 1 | HapMap | HapMap | C | 0.22 | T | 0.78 | C/T |
| LWK | rs387149 | 9 | 6135022 | 0.237 | 0.804 | HapMap | HapMap | C | 0.386 | T | 0.614 | C/T |
| CHB | rs387149 | 9 | 6135022 | 0.036 | 0.604 | HapMap | HapMap | C | 0.494 | T | 0.506 | C/T |
| CEU | rs387149 | 9 | 6135022 | 0.031 | 1 | HapMap | HapMap | C | 0.308 | T | 0.692 | C/T |
| CHB | rs3939286 | 9 | 6200099 | 0.232 | 1 | HapMap | HapMap | T | 0.036 | C | 0.964 | T/C |
| CHD | rs3939286 | 9 | 6200099 | 0.417 | 1 | HapMap | HapMap | T | 0.047 | C | 0.953 | T/C |
| YRI | rs3939286 | 9 | 6200099 | 0.206 | 0.895 | HapMap | HapMap | T | 0.54 | C | 0.46 | T/C |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MKK | rs3939286 | 9 | 6200099 | 0.141 | 0.817 | HapMap | HapMap | T | 0.391 | C | 0.609 | T/C |
| GIH | rs3939286 | 9 | 6200099 | 0.151 | 1 | HapMap | HapMap | T | 0.239 | C | 0.761 | T/C |
| JPT | rs3939286 | 9 | 6200099 | 0.585 | 1 | HapMap | HapMap | T | 0.029 | C | 0.971 | T/C |
| ASW | rs3939286 | 9 | 6200099 | 0.136 | 0.676 | HapMap | HapMap | T | 0.462 | C | 0.538 | T/C |
| CEU | rs3939286 | 9 | 6200099 | 0.208 | 1 | HapMap | HapMap | T | 0.283 | C | 0.717 | T/C |
| ASW | rs3955036 | 9 | 6271660 | 0.019 | 1 | HapMap | HapMap | G | 0.953 | A | 0.047 | G/A |
| GIH | rs3955036 | 9 | 6271660 | 0 | 1 | HapMap | HapMap | G | 0.994 | A | 0.006 | G/A |
| MEX | rs3955036 | 9 | 6271660 | 0.001 | 1 | HapMap | HapMap | G | 0.98 | A | 0.02 | G/A |
| MKK | rs3955036 | 9 | 6271660 | 0.001 | 1 | HapMap | HapMap | G | 0.989 | A | 0.011 | G/A |
| CHB | rs406322 | 9 | 6136121 | 0.02 | 1 | HapMap | HapMap | C | 0.839 | T | 0.161 | C/T |
| CHD | rs406322 | 9 | 6136121 | 0.03 | 1 | HapMap | HapMap | C | 0.8 | T | 0.2 | C/T |
| GIH | rs406322 | 9 | 6136121 | 0.013 | 1 | HapMap | HapMap | C | 0.784 | T | 0.216 | C/T |
| JPT | rs406322 | 9 | 6136121 | 0.008 | 1 | HapMap | HapMap | C | 0.888 | T | 0.112 | C/T |
| CEU | rs406322 | 9 | 6136121 | 0.035 | 1 | HapMap | HapMap | C | 0.748 | T | 0.252 | C/T |
| ASW | rs406322 | 9 | 6136121 | 0.04 | 1 | HapMap | HapMap | C | 0.858 | T | 0.142 | C/T |
| MKK | rs409038 | 9 | 6124750 | 0.05 | 0.611 | HapMap | HapMap | A | 0.497 | G | 0.503 | A/G |
| JPT | rs409038 | 9 | 6124750 | 0.007 | 1 | HapMap | HapMap | A | 0.134 | G | 0.866 | A/G |
| GIH | rs409038 | 9 | 6124750 | 0.031 | 1 | HapMap | HapMap | A | 0.392 | G | 0.608 | A/G |
| CHD | rs409038 | 9 | 6124750 | 0.027 | 1 | HapMap | HapMap | A | 0.188 | G | 0.812 | A/G |
| CHB | rs409038 | 9 | 6124750 | 0.022 | 1 | HapMap | HapMap | A | 0.173 | G | 0.827 | A/G |
| CHB | rs413382 | 9 | 6132948 | 0.001 | 1 | HapMap | HapMap | C | 0.018 | A | 0.982 | C/A |
| MEX | rs413382 | 9 | 6132948 | 0.009 | 1 | HapMap | HapMap | C | 0.13 | A | 0.87 | C/A |
| GIH | rs413382 | 9 | 6132948 | 0.016 | 1 | HapMap | HapMap | C | 0.25 | A | 0.75 | C/A |
| MKK | rs413382 | 9 | 6132948 | 0.016 | 0.618 | HapMap | HapMap | C | 0.232 | A | 0.768 | C/A |
| CEU | rs413382 | 9 | 6132948 | 0.019 | 1 | HapMap | HapMap | C | 0.142 | A | 0.858 | C/A |
| GIH | rs418014 | 9 | 6110336 | 0.032 | 1 | HapMap | HapMap | C | 0.403 | T | 0.597 | C/T |
| JPT | rs418014 | 9 | 6110336 | 0.007 | 1 | HapMap | HapMap | C | 0.134 | T | 0.866 | C/T |
| CHB | rs418014 | 9 | 6110336 | 0.02 | 1 | HapMap | HapMap | C | 0.167 | T | 0.833 | C/T |
| CHD | rs418014 | 9 | 6110336 | 0.027 | 1 | HapMap | HapMap | C | 0.188 | T | 0.812 | C/T |
| ASW | rs4361812 | 9 | 6355737 | 0.014 | 1 | HapMap | HapMap | C | 0.934 | A | 0.066 | C/A |
| CEU | rs4361812 | 9 | 6355737 | 0.027 | 1 | HapMap | HapMap | C | 0.841 | A | 0.159 | C/A |
| GIH | rs4361812 | 9 | 6355737 | 0.007 | 1 | HapMap | HapMap | C | 0.875 | A | 0.125 | C/A |
| MEX | rs4361812 | 9 | 6355737 | 0.005 | 1 | HapMap | HapMap | C | 0.93 | A | 0.07 | C/A |
| GIH | rs4367609 | 9 | 6155405 | 1 | 1 | HapMap | HapMap | C | 0.955 | T | 0.045 | C/T |
| MKK | rs4367609 | 9 | 6155405 | 0.384 | 0.842 | HapMap | HapMap | C | 0.801 | T | 0.199 | C/T |
| CHD | rs4367609 | 9 | 6155405 | 0.473 | 0.822 | HapMap | HapMap | C | 0.923 | T | 0.077 | C/T |
| CEU | rs4367609 | 9 | 6155405 | 0.815 | 1 | HapMap | HapMap | C | 0.906 | T | 0.094 | C/T |
| JPT | rs4367609 | 9 | 6155405 | 0.585 | 1 | HapMap | HapMap | C | 0.948 | T | 0.052 | C/T |
| MEX | rs4367609 | 9 | 6155405 | 0.791 | 1 | HapMap | HapMap | C | 0.95 | T | 0.05 | C/T |
| ASW | rs4367609 | 9 | 6155405 | 0.358 | 0.736 | HapMap | HapMap | C | 0.821 | T | 0.179 | C/T |
| CHB | rs4395943 | 9 | 5981006 | 0.116 | 0.758 | HapMap | HapMap | T | 0.31 | C | 0.69 | T/C |
| GIH | rs4395943 | 9 | 5981006 | 0.006 | 1 | HapMap | HapMap | T | 0.108 | C | 0.892 | T/C |
| CEU | rs4395943 | 9 | 5981006 | 0.001 | 1 | HapMap | HapMap | T | 0.009 | C | 0.991 | T/C |
| MEX | rs4395943 | 9 | 5981006 | 0.003 | 1 | HapMap | HapMap | T | 0.06 | C | 0.94 | T/C |
| GIH | rs448115 | 9 | 6124642 | 0.031 | 1 | HapMap | HapMap | G | 0.392 | A | 0.608 | G/A |
| CHD | rs448115 | 9 | 6124642 | 0.029 | 1 | HapMap | HapMap | G | 0.194 | A | 0.806 | G/A |
| JPT | rs448115 | 9 | 6124642 | 0.007 | 1 | HapMap | HapMap | G | 0.134 | A | 0.866 | G/A |
| CHB | rs448115 | 9 | 6124642 | 0.022 | 1 | HapMap | HapMap | G | 0.173 | A | 0.827 | G/A |
| MKK | rs451361 | 9 | 6039892 | 0.003 | 1 | HapMap | HapMap | G | 0.976 | A | 0.024 | G/A |
| ASW | rs451361 | 9 | 6039892 | 0.014 | 1 | HapMap | HapMap | G | 0.972 | A | 0.028 | G/A |
| CEU | rs451361 | 9 | 6039892 | 0.001 | 1 | HapMap | HapMap | G | 0.991 | A | 0.009 | G/A |
| MEX | rs451361 | 9 | 6039892 | 0 | 1 | HapMap | HapMap | G | 0.99 | A | 0.01 | G/A |
| YRI | rs451361 | 9 | 6039892 | 0.028 | 1 | HapMap | HapMap | G | 0.929 | A | 0.071 | G/A |
| GIH | rs459525 | 9 | 6022924 | 0.035 | 1 | HapMap | HapMap | C | 0.426 | T | 0.574 | C/T |
| MKK | rs459525 | 9 | 6022924 | 0.053 | 0.709 | HapMap | HapMap | C | 0.441 | T | 0.559 | C/T |
| MKK | rs4740840 | 9 | 6219110 | 0.092 | 0.724 | HapMap | HapMap | A | 0.566 | G | 0.434 | A/G |
| JPT | rs4740840 | 9 | 6219110 | 0.052 | 1 | HapMap | HapMap | A | 0.477 | G | 0.523 | A/G |
| GIH | rs4740840 | 9 | 6219110 | 0.094 | 1 | HapMap | HapMap | A | 0.665 | G | 0.335 | A/G |
| CEU | rs4740840 | 9 | 6219110 | 0.287 | 1 | HapMap | HapMap | A | 0.699 | G | 0.301 | A/G |
| GIH | rs4742170 | 9 | 6232950 | 0.085 | 1 | HapMap | HapMap | C | 0.358 | T | 0.642 | C/T |
| JPT | rs4742170 | 9 | 6232950 | 0.047 | 1 | HapMap | HapMap | C | 0.541 | T | 0.459 | C/T |
| CEU | rs4742170 | 9 | 6232950 | 0.208 | 1 | HapMap | HapMap | C | 0.354 | T | 0.646 | C/T |
| GIH | rs544253 | 9 | 6132157 | 0.024 | 1 | HapMap | HapMap | A | 0.665 | C | 0.335 | A/C |
| CHD | rs544253 | 9 | 6132157 | 0.022 | 0.605 | HapMap | HapMap | A | 0.659 | C | 0.341 | A/C |
| LWK | rs544253 | 9 | 6132157 | 0.022 | 1 | HapMap | HapMap | A | 0.994 | C | 0.006 | A/C |
| MKK | rs544253 | 9 | 6132157 | 0.004 | 1 | HapMap | HapMap | A | 0.969 | C | 0.031 | A/C |
| YRI | rs544253 | 9 | 6132157 | 0.006 | 1 | HapMap | HapMap | A | 0.978 | C | 0.022 | A/C |
| CHD | rs6477029 | 9 | 6017931 | 0.024 | 1 | HapMap | HapMap | T | 0.833 | C | 0.167 | T/C |
| CHB | rs6477029 | 9 | 6017931 | 0.01 | 0.699 | HapMap | HapMap | T | 0.821 | C | 0.179 | T/C |
| MEX | rs6477029 | 9 | 6017931 | 0.103 | 1 | HapMap | HapMap | T | 0.66 | C | 0.34 | T/C |
| CHB | rs6477037 | 9 | 6108174 | 0.017 | 1 | HapMap | HapMap | T | 0.863 | C | 0.137 | T/C |
| LWK | rs6477037 | 9 | 6108174 | 0.048 | 1 | HapMap | HapMap | T | 0.839 | C | 0.161 | T/C |
| CHD | rs6477037 | 9 | 6108174 | 0.025 | 1 | HapMap | HapMap | T | 0.827 | C | 0.173 | T/C |
| GIH | rs6477037 | 9 | 6108174 | 0.009 | 1 | HapMap | HapMap | T | 0.841 | C | 0.159 | T/C |
| JPT | rs6477037 | 9 | 6108174 | 0.007 | 1 | HapMap | HapMap | T | 0.876 | C | 0.124 | T/C |
| CHB | rs6477040 | 9 | 6123074 | 0.017 | 1 | HapMap | HapMap | C | 0.863 | T | 0.137 | C/T |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| ASW | rs6477040 | 9 | 6123074 | 0.048 | 0.687 | HapMap | HapMap | C | 0.736 | T | 0.264 | C/T |
| YRI | rs6477040 | 9 | 6123074 | 0.039 | 0.625 | HapMap | HapMap | C | 0.765 | T | 0.235 | C/T |
| JPT | rs6477040 | 9 | 6123074 | 0.007 | 1 | HapMap | HapMap | C | 0.878 | T | 0.122 | C/T |
| GIH | rs6477040 | 9 | 6123074 | 0.008 | 1 | HapMap | HapMap | C | 0.852 | T | 0.148 | C/T |
| LWK | rs6477040 | 9 | 6123074 | 0.054 | 1 | HapMap | HapMap | C | 0.822 | T | 0.178 | C/T |
| CHD | rs6477040 | 9 | 6123074 | 0.024 | 1 | HapMap | HapMap | C | 0.829 | T | 0.171 | C/T |
| MKK | rs6477040 | 9 | 6123074 | 0.05 | 1 | HapMap | HapMap | C | 0.732 | T | 0.268 | C/T |
| CHB | rs694796 | 9 | 6122621 | 0.002 | 1 | HapMap | HapMap | A | 0.03 | G | 0.97 | A/G |
| GIH | rs7021445 | 9 | 6346657 | 0.001 | 1 | HapMap | HapMap | C | 0.017 | T | 0.983 | C/T |
| MEX | rs7021445 | 9 | 6346657 | 0.001 | 1 | HapMap | HapMap | C | 0.02 | T | 0.98 | C/T |
| CHD | rs7024677 | 9 | 6076073 | 0.025 | 1 | HapMap | HapMap | C | 0.824 | T | 0.176 | C/T |
| JPT | rs7024677 | 9 | 6076073 | 0.007 | 1 | HapMap | HapMap | C | 0.878 | T | 0.122 | C/T |
| LWK | rs7024677 | 9 | 6076073 | 0.007 | 1 | HapMap | HapMap | C | 0.972 | T | 0.028 | C/T |
| MKK | rs7024677 | 9 | 6076073 | 0.007 | 1 | HapMap | HapMap | C | 0.948 | T | 0.052 | C/T |
| YRI | rs7024677 | 9 | 6076073 | 0.028 | 1 | HapMap | HapMap | C | 0.929 | T | 0.071 | C/T |
| GIH | rs7024677 | 9 | 6076073 | 0.015 | 1 | HapMap | HapMap | C | 0.761 | T | 0.239 | C/T |
| JPT | rs7025417 | 9 | 6230084 | 0.05 | 1 | HapMap | HapMap | T | 0.465 | C | 0.535 | T/C |
| CEU | rs7025417 | 9 | 6230084 | 0.395 | 1 | HapMap | HapMap | T | 0.739 | C | 0.261 | T/C |
| LWK | rs7032572 | 9 | 6162380 | 0.056 | 1 | HapMap | HapMap | A | 0.817 | G | 0.183 | A/G |
| MEX | rs7032572 | 9 | 6162380 | 0.01 | 0.973 | HapMap | HapMap | A | 0.857 | G | 0.143 | A/G |
| YRI | rs7032572 | 9 | 6162380 | 0.041 | 1 | HapMap | HapMap | A | 0.907 | G | 0.093 | A/G |
| ASW | rs7032572 | 9 | 6162380 | 0.046 | 1 | HapMap | HapMap | A | 0.846 | G | 0.154 | A/G |
| MKK | rs7032572 | 9 | 6162380 | 0.015 | 1 | HapMap | HapMap | A | 0.901 | G | 0.099 | A/G |
| CEU | rs7032572 | 9 | 6162380 | 0.024 | 1 | HapMap | HapMap | A | 0.857 | G | 0.143 | A/G |
| GIH | rs7032572 | 9 | 6162380 | 0.011 | 1 | HapMap | HapMap | A | 0.812 | G | 0.188 | A/G |
| CEU | rs7033258 | 9 | 6224131 | 0.217 | 1 | HapMap | HapMap | G | 0.341 | A | 0.659 | G/A |
| GIH | rs7033258 | 9 | 6224131 | 0.085 | 1 | HapMap | HapMap | G | 0.358 | A | 0.642 | G/A |
| JPT | rs7033258 | 9 | 6224131 | 0.052 | 1 | HapMap | HapMap | G | 0.529 | A | 0.471 | G/A |
| ASW | rs7034801 | 9 | 6312415 | 0.093 | 1 | HapMap | HapMap | C | 0.255 | A | 0.745 | C/A |
| MKK | rs7034801 | 9 | 6312415 | 0.016 | 1 | HapMap | HapMap | C | 0.105 | A | 0.895 | C/A |
| GIH | rs7034801 | 9 | 6312415 | 0.001 | 1 | HapMap | HapMap | C | 0.017 | A | 0.983 | C/A |
| MEX | rs7034801 | 9 | 6312415 | 0.001 | 1 | HapMap | HapMap | C | 0.03 | A | 0.97 | C/A |
| GIH | rs7034861 | 9 | 6284824 | 0.001 | 1 | HapMap | HapMap | C | 0.017 | T | 0.983 | C/T |
| MEX | rs7034861 | 9 | 6284824 | 0.001 | 1 | HapMap | HapMap | C | 0.03 | T | 0.97 | C/T |
| MKK | rs7034861 | 9 | 6284824 | 0.015 | 1 | HapMap | HapMap | C | 0.101 | T | 0.899 | C/T |
| ASW | rs7034861 | 9 | 6284824 | 0.046 | 1 | HapMap | HapMap | C | 0.17 | T | 0.83 | C/T |
| CHD | rs7035152 | 9 | 6036694 | 0.021 | 1 | HapMap | HapMap | G | 0.847 | T | 0.153 | G/T |
| MEX | rs7035152 | 9 | 6036694 | 0.057 | 0.678 | HapMap | HapMap | G | 0.7 | T | 0.3 | G/T |
| CEU | rs7035594 | 9 | 6115353 | 0.013 | 1 | HapMap | HapMap | A | 0.124 | T | 0.876 | A/T |
| MEX | rs7035594 | 9 | 6115353 | 0.009 | 1 | HapMap | HapMap | A | 0.14 | T | 0.86 | A/T |
| CHB | rs7035594 | 9 | 6115353 | 0.002 | 1 | HapMap | HapMap | A | 0.03 | T | 0.97 | A/T |
| GIH | rs7035594 | 9 | 6115353 | 0.015 | 1 | HapMap | HapMap | A | 0.244 | T | 0.756 | A/T |
| ASW | rs7035741 | 9 | 6279504 | 0.058 | 1 | HapMap | HapMap | C | 0.123 | T | 0.877 | C/T |
| GIH | rs7035741 | 9 | 6279504 | 0.001 | 1 | HapMap | HapMap | C | 0.017 | T | 0.983 | C/T |
| LWK | rs7035741 | 9 | 6279504 | 0.096 | 0.675 | HapMap | HapMap | C | 0.05 | T | 0.95 | C/T |
| MEX | rs7035741 | 9 | 6279504 | 0.001 | 1 | HapMap | HapMap | C | 0.02 | T | 0.98 | C/T |
| MKK | rs7035741 | 9 | 6279504 | 0.002 | 1 | HapMap | HapMap | C | 0.014 | T | 0.986 | C/T |
| CEU | rs7037276 | 9 | 6237430 | 0.013 | 1 | HapMap | HapMap | C | 0.071 | T | 0.929 | C/T |
| GIH | rs7037276 | 9 | 6237430 | 0 | 1 | HapMap | HapMap | C | 0.006 | T | 0.994 | C/T |
| MEX | rs7037276 | 9 | 6237430 | 0.001 | 1 | HapMap | HapMap | C | 0.03 | T | 0.97 | C/T |
| LWK | rs7037276 | 9 | 6237430 | 0.076 | 0.637 | HapMap | HapMap | C | 0.044 | T | 0.956 | C/T |
| YRI | rs7037276 | 9 | 6237430 | 0.122 | 1 | HapMap | HapMap | C | 0.044 | T | 0.956 | C/T |
| MKK | rs7037276 | 9 | 6237430 | 0.001 | 1 | HapMap | HapMap | C | 0.011 | T | 0.989 | C/T |
| LWK | rs7037534 | 9 | 6245511 | 0.016 | 1 | HapMap | HapMap | T | 0.939 | A | 0.061 | T/A |
| ASW | rs7037534 | 9 | 6245511 | 0.04 | 1 | HapMap | HapMap | T | 0.906 | A | 0.094 | T/A |
| LWK | rs7040888 | 9 | 6103735 | 0.037 | 1 | HapMap | HapMap | T | 0.872 | C | 0.128 | T/C |
| JPT | rs7040888 | 9 | 6103735 | 0.007 | 1 | HapMap | HapMap | T | 0.878 | C | 0.122 | T/C |
| GIH | rs7040888 | 9 | 6103735 | 0.01 | 1 | HapMap | HapMap | T | 0.835 | C | 0.165 | T/C |
| CHB | rs7040888 | 9 | 6103735 | 0.017 | 1 | HapMap | HapMap | T | 0.863 | C | 0.137 | T/C |
| CHD | rs7040888 | 9 | 6103735 | 0.024 | 1 | HapMap | HapMap | T | 0.829 | C | 0.171 | T/C |
| GIH | rs7041863 | 9 | 6317690 | 0.001 | 1 | HapMap | HapMap | A | 0.017 | C | 0.983 | A/C |
| MKK | rs7041863 | 9 | 6317690 | 0.015 | 1 | HapMap | HapMap | A | 0.101 | C | 0.899 | A/C |
| CHD | rs7041863 | 9 | 6317690 | 0.001 | 1 | HapMap | HapMap | A | 0.006 | C | 0.994 | A/C |
| MEX | rs7041863 | 9 | 6317690 | 0.001 | 1 | HapMap | HapMap | A | 0.03 | C | 0.97 | A/C |
| ASW | rs7041863 | 9 | 6317690 | 0.093 | 1 | HapMap | HapMap | A | 0.245 | C | 0.755 | A/C |
| MEX | rs7042561 | 9 | 6101473 | 0.001 | 1 | HapMap | HapMap | G | 0.99 | A | 0.01 | G/A |
| LWK | rs7042561 | 9 | 6101473 | 0.021 | 0.904 | HapMap | HapMap | G | 0.906 | A | 0.094 | G/A |
| MKK | rs7043459 | 9 | 6256718 | 0.032 | 1 | HapMap | HapMap | C | 0.804 | T | 0.196 | C/T |
| MEX | rs7043459 | 9 | 6256718 | 0.003 | 1 | HapMap | HapMap | C | 0.96 | T | 0.04 | C/T |
| MEX | rs7045164 | 9 | 6317778 | 0.001 | 1 | HapMap | HapMap | T | 0.02 | C | 0.98 | T/C |
| YRI | rs7045164 | 9 | 6317778 | 0.03 | 1 | HapMap | HapMap | T | 0.013 | C | 0.987 | T/C |
| LWK | rs7045164 | 9 | 6317778 | 0.138 | 1 | HapMap | HapMap | T | 0.033 | C | 0.967 | T/C |
| GIH | rs7045164 | 9 | 6317778 | 0.001 | 1 | HapMap | HapMap | T | 0.017 | C | 0.983 | T/C |
| ASW | rs7045164 | 9 | 6317778 | 0.019 | 1 | HapMap | HapMap | T | 0.047 | C | 0.953 | T/C |
| MKK | rs7045164 | 9 | 6317778 | 0.001 | 1 | HapMap | HapMap | T | 0.01 | C | 0.99 | T/C |
| ASW | rs7046661 | 9 | 6199199 | 0.063 | 0.705 | HapMap | HapMap | C | 0.642 | G | 0.358 | C/G |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs7046661 | 9 | 6199199 | 0.143 | 1 | HapMap | HapMap | C | 0.35 | G | 0.65 | C/G |
| MKK | rs7046661 | 9 | 6199199 | 0.091 | 0.898 | HapMap | HapMap | C | 0.545 | G | 0.455 | C/G |
| GIH | rs7046661 | 9 | 6199199 | 0.116 | 1 | HapMap | HapMap | C | 0.29 | G | 0.71 | C/G |
| CHD | rs7046661 | 9 | 6199199 | 0.699 | 1 | HapMap | HapMap | C | 0.077 | G | 0.923 | C/G |
| LWK | rs7046661 | 9 | 6199199 | 0.036 | 0.678 | HapMap | HapMap | C | 0.761 | G | 0.239 | C/G |
| CHB | rs7046661 | 9 | 6199199 | 0.236 | 0.705 | HapMap | HapMap | C | 0.06 | G | 0.94 | C/G |
| JPT | rs7046661 | 9 | 6199199 | 0.499 | 0.779 | HapMap | HapMap | C | 0.047 | G | 0.953 | C/G |
| GIH | rs7047921 | 9 | 6245319 | 0.039 | 1 | HapMap | HapMap | G | 0.545 | A | 0.455 | G/A |
| MKK | rs7047921 | 9 | 6245319 | 0.057 | 0.698 | HapMap | HapMap | G | 0.535 | A | 0.465 | G/A |
| GIH | rs719724 | 9 | 6355614 | 0.033 | 1 | HapMap | HapMap | T | 0.401 | A | 0.599 | T/A |
| MEX | rs719724 | 9 | 6355614 | 0.031 | 1 | HapMap | HapMap | T | 0.337 | A | 0.663 | T/A |
| CHD | rs719724 | 9 | 6355614 | 0.044 | 1 | HapMap | HapMap | T | 0.271 | A | 0.729 | T/A |
| CHB | rs719724 | 9 | 6355614 | 0.031 | 1 | HapMap | HapMap | T | 0.265 | A | 0.735 | T/A |
| CEU | rs719724 | 9 | 6355614 | 0.097 | 1 | HapMap | HapMap | T | 0.41 | A | 0.59 | T/A |
| MEX | rs721352 | 9 | 6322901 | 0.018 | 1 | HapMap | HapMap | A | 0.24 | C | 0.76 | A/C |
| MKK | rs721352 | 9 | 6322901 | 0.049 | 0.689 | HapMap | HapMap | A | 0.434 | C | 0.566 | A/C |
| GIH | rs721352 | 9 | 6322901 | 0.009 | 1 | HapMap | HapMap | A | 0.153 | C | 0.847 | A/C |
| CEU | rs721352 | 9 | 6322901 | 0.067 | 1 | HapMap | HapMap | A | 0.314 | C | 0.686 | A/C |
| CHB | rs7425 | 9 | 6001335 | 0.017 | 0.889 | HapMap | HapMap | T | 0.81 | C | 0.19 | T/C |
| CHD | rs7425 | 9 | 6001335 | 0.024 | 1 | HapMap | HapMap | T | 0.829 | C | 0.171 | T/C |
| GIH | rs7850988 | 9 | 6325760 | 0.008 | 1 | HapMap | HapMap | A | 0.864 | T | 0.136 | A/T |
| LWK | rs7850988 | 9 | 6325760 | 0.033 | 0.654 | HapMap | HapMap | A | 0.767 | T | 0.233 | A/T |
| MEX | rs7850988 | 9 | 6325760 | 0.013 | 1 | HapMap | HapMap | A | 0.82 | T | 0.18 | A/T |
| MKK | rs7850988 | 9 | 6325760 | 0.016 | 0.662 | HapMap | HapMap | A | 0.79 | T | 0.21 | A/T |
| CEU | rs7850988 | 9 | 6325760 | 0.052 | 1 | HapMap | HapMap | A | 0.728 | T | 0.272 | A/T |
| ASW | rs7850988 | 9 | 6325760 | 0.035 | 0.635 | HapMap | HapMap | A | 0.745 | T | 0.255 | A/T |
| GIH | rs7851246 | 9 | 6352365 | 0.009 | 1 | HapMap | HapMap | G | 0.847 | A | 0.153 | G/A |
| MKK | rs7851246 | 9 | 6352365 | 0.014 | 0.61 | HapMap | HapMap | G | 0.78 | A | 0.22 | G/A |
| LWK | rs7851246 | 9 | 6352365 | 0.03 | 0.614 | HapMap | HapMap | G | 0.761 | A | 0.239 | G/A |
| MEX | rs7851246 | 9 | 6352365 | 0.009 | 1 | HapMap | HapMap | G | 0.86 | A | 0.14 | G/A |
| CEU | rs7851246 | 9 | 6352365 | 0.052 | 1 | HapMap | HapMap | G | 0.721 | A | 0.279 | G/A |
| CHD | rs7852365 | 9 | 6058910 | 0.001 | 1 | HapMap | HapMap | C | 0.994 | T | 0.006 | C/T |
| CHB | rs7852365 | 9 | 6058910 | 0.002 | 1 | HapMap | HapMap | C | 0.982 | T | 0.018 | C/T |
| JPT | rs7852365 | 9 | 6058910 | 0.001 | 1 | HapMap | HapMap | C | 0.988 | T | 0.012 | C/T |
| YRI | rs7855264 | 9 | 6291923 | 0.03 | 1 | HapMap | HapMap | A | 0.009 | G | 0.991 | A/G |
| LWK | rs7855264 | 9 | 6291923 | 0.138 | 1 | HapMap | HapMap | A | 0.033 | G | 0.967 | A/G |
| GIH | rs7859139 | 9 | 6296294 | 0.001 | 1 | HapMap | HapMap | G | 0.017 | A | 0.983 | G/A |
| MEX | rs7859139 | 9 | 6296294 | 0.001 | 1 | HapMap | HapMap | G | 0.03 | A | 0.97 | G/A |
| CHD | rs7859139 | 9 | 6296294 | 0.001 | 1 | HapMap | HapMap | G | 0.006 | A | 0.994 | G/A |
| ASW | rs7859139 | 9 | 6296294 | 0.046 | 1 | HapMap | HapMap | G | 0.17 | A | 0.83 | G/A |
| MKK | rs7859139 | 9 | 6296294 | 0.018 | 1 | HapMap | HapMap | G | 0.115 | A | 0.885 | G/A |
| MKK | rs7861831 | 9 | 6254463 | 0.033 | 1 | HapMap | HapMap | C | 0.804 | T | 0.196 | C/T |
| MEX | rs7861831 | 9 | 6254463 | 0.003 | 1 | HapMap | HapMap | C | 0.96 | T | 0.04 | C/T |
| CHB | rs7865727 | 9 | 6080276 | 0.127 | 0.601 | HapMap | HapMap | T | 0.976 | C | 0.024 | T/C |
| ASW | rs7865727 | 9 | 6080276 | 0.004 | 1 | HapMap | HapMap | T | 0.972 | C | 0.028 | T/C |
| MKK | rs7865727 | 9 | 6080276 | 0.008 | 1 | HapMap | HapMap | T | 0.944 | C | 0.056 | T/C |
| MEX | rs7865727 | 9 | 6080276 | 0.001 | 1 | HapMap | HapMap | T | 0.98 | C | 0.02 | T/C |
| JPT | rs7865727 | 9 | 6080276 | 0.001 | 1 | HapMap | HapMap | T | 0.994 | C | 0.006 | T/C |
| CEU | rs8172 | 9 | 6247898 | 0.013 | 1 | HapMap | HapMap | A | 0.08 | G | 0.92 | A/G |
| GIH | rs8172 | 9 | 6247898 | 0.001 | 1 | HapMap | HapMap | A | 0.017 | G | 0.983 | A/G |
| MEX | rs8172 | 9 | 6247898 | 0.005 | 1 | HapMap | HapMap | A | 0.09 | G | 0.91 | A/G |
| MKK | rs8172 | 9 | 6247898 | 0.051 | 0.753 | HapMap | HapMap | A | 0.399 | G | 0.601 | A/G |
| JPT | rs8172 | 9 | 6247898 | 0.001 | 1 | HapMap | HapMap | A | 0.006 | G | 0.994 | A/G |
| ASW | rs8172 | 9 | 6247898 | 0.158 | 0.705 | HapMap | HapMap | A | 0.509 | G | 0.491 | A/G |
| CEU | rs821164 | 9 | 6080989 | 0.012 | 1 | HapMap | HapMap | C | 0.121 | G | 0.879 | C/G |
| GIH | rs821164 | 9 | 6080989 | 0.015 | 1 | HapMap | HapMap | C | 0.241 | G | 0.759 | C/G |
| MEX | rs821164 | 9 | 6080989 | 0.009 | 1 | HapMap | HapMap | C | 0.14 | G | 0.86 | C/G |
| CHB | rs821164 | 9 | 6080989 | 0.002 | 1 | HapMap | HapMap | C | 0.03 | G | 0.97 | C/G |
| CEU | rs899381 | 9 | 6024076 | 0.001 | 1 | HapMap | HapMap | T | 0.991 | C | 0.009 | T/C |
| GIH | rs899381 | 9 | 6024076 | 0.013 | 0.898 | HapMap | HapMap | T | 0.75 | C | 0.25 | T/C |
| MEX | rs899381 | 9 | 6024076 | 0.003 | 1 | HapMap | HapMap | T | 0.95 | C | 0.05 | T/C |
| MKK | rs928413 | 9 | 6203387 | 0.126 | 0.808 | HapMap | HapMap | G | 0.413 | A | 0.587 | G/A |
| YRI | rs928413 | 9 | 6203387 | 0.206 | 1 | HapMap | HapMap | G | 0.588 | A | 0.412 | G/A |
| JPT | rs928413 | 9 | 6203387 | 0.79 | 1 | HapMap | HapMap | G | 0.047 | A | 0.953 | G/A |
| ASW | rs928413 | 9 | 6203387 | 0.139 | 0.799 | HapMap | HapMap | G | 0.538 | A | 0.462 | G/A |
| CEU | rs928413 | 9 | 6203387 | 0.208 | 1 | HapMap | HapMap | G | 0.288 | A | 0.712 | G/A |
| CHB | rs928413 | 9 | 6203387 | 0.236 | 0.705 | HapMap | HapMap | G | 0.048 | A | 0.952 | G/A |
| CHD | rs928413 | 9 | 6203387 | 0.587 | 0.847 | HapMap | HapMap | G | 0.088 | A | 0.912 | G/A |
| GIH | rs928413 | 9 | 6203387 | 0.098 | 0.79 | HapMap | HapMap | G | 0.233 | A | 0.767 | G/A |
| JPT | rs928414 | 9 | 6226350 | 0.052 | 1 | HapMap | HapMap | G | 0.529 | A | 0.471 | G/A |
| CEU | rs928414 | 9 | 6226350 | 0.208 | 1 | HapMap | HapMap | G | 0.35 | A | 0.65 | G/A |
| GIH | rs928414 | 9 | 6226350 | 0.085 | 1 | HapMap | HapMap | G | 0.358 | A | 0.642 | G/A |
| GIH | rs9408638 | 9 | 6086931 | 0.016 | 1 | HapMap | HapMap | A | 0.25 | G | 0.75 | A/G |
| CEU | rs9408638 | 9 | 6086931 | 0.013 | 1 | HapMap | HapMap | A | 0.124 | G | 0.876 | A/G |
| CHB | rs9408638 | 9 | 6086931 | 0.002 | 1 | HapMap | HapMap | A | 0.03 | G | 0.97 | A/G |
| MEX | rs9408638 | 9 | 6086931 | 0.009 | 1 | HapMap | HapMap | A | 0.13 | G | 0.87 | A/G |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| MKK | rs9408638 | 9 | 6086931 | 0.03 | 1 | HapMap | HapMap | A | 0.18 | G | 0.82 | A/G |
| CEU | rs992969 | 9 | 6199697 | 0.208 | 1 | HapMap | HapMap | A | 0.283 | G | 0.717 | A/G |
| JPT | rs992969 | 9 | 6199697 | 0.585 | 1 | HapMap | HapMap | A | 0.029 | G | 0.971 | A/G |
| LWK | rs992969 | 9 | 6199697 | 0.395 | 1 | HapMap | HapMap | A | 0.278 | G | 0.722 | A/G |
| MKK | rs992969 | 9 | 6199697 | 0.321 | 0.761 | HapMap | HapMap | A | 0.196 | G | 0.804 | A/G |
| GIH | rs992969 | 9 | 6199697 | 0.167 | 1 | HapMap | HapMap | A | 0.222 | G | 0.778 | A/G |
| ASW | rs992969 | 9 | 6199697 | 0.259 | 0.745 | HapMap | HapMap | A | 0.33 | G | 0.67 | A/G |
| CHB | rs992969 | 9 | 6199697 | 0.232 | 1 | HapMap | HapMap | A | 0.036 | G | 0.964 | A/G |
| CHD | rs992969 | 9 | 6199697 | 0.417 | 1 | HapMap | HapMap | A | 0.047 | G | 0.953 | A/G |
| YRI | rs992969 | 9 | 6199697 | 0.315 | 0.792 | HapMap | HapMap | A | 0.363 | G | 0.637 | A/G |
| CEU | rs993951 | 9 | 6294401 | 0.128 | 0.817 | HapMap | HapMap | A | 0.589 | G | 0.411 | A/G |
| GIH | rs993951 | 9 | 6294401 | 0.07 | 1 | HapMap | HapMap | A | 0.597 | G | 0.403 | A/G |
| CHB | rs996029 | 9 | 6212302 | 0.115 | 1 | HapMap | HapMap | T | 0.006 | G | 0.994 | T/G |
| CHD | rs996029 | 9 | 6212302 | 0.001 | 1 | HapMap | HapMap | T | 0.006 | G | 0.994 | T/G |
| MKK | rs996029 | 9 | 6212302 | 0.007 | 1 | HapMap | HapMap | T | 0.049 | G | 0.951 | T/G |
| MKK | rs16924159 | 9 | 6219417 | 0.033 | 0.77 | HapMap | HapMap | G | 0.712 | A | 0.288 | G/A |
| JPT | rs16924159 | 9 | 6219417 | 0.015 | 1 | HapMap | HapMap | G | 0.783 | A | 0.217 | G/A |
| GIH | rs17496153 | 9 | 6060037 | 0.002 | 1 | HapMap | HapMap | G | 0.96 | C | 0.04 | G/C |
| CHD | rs17496153 | 9 | 6060037 | 0.001 | 1 | HapMap | HapMap | G | 0.994 | C | 0.006 | G/C |
| ASW | rs17496153 | 9 | 6060037 | 0.004 | 1 | HapMap | HapMap | G | 0.971 | C | 0.029 | G/C |
| CEU | rs17496153 | 9 | 6060037 | 0.01 | 0.996 | HapMap | HapMap | G | 0.867 | C | 0.133 | G/C |
| JPT | rs2079 | 9 | 6156653 | 0.008 | 1 | HapMap | HapMap | G | 0.901 | A | 0.099 | G/A |
| CHB | rs2079 | 9 | 6156653 | 0.02 | 1 | HapMap | HapMap | G | 0.821 | A | 0.179 | G/A |
| CEU | rs2079 | 9 | 6156653 | 0.073 | 1 | HapMap | HapMap | G | 0.633 | A | 0.367 | G/A |
| GIH | rs2079 | 9 | 6156653 | 0.021 | 1 | HapMap | HapMap | G | 0.699 | A | 0.301 | G/A |
| CHD | rs2079 | 9 | 6156653 | 0.032 | 1 | HapMap | HapMap | G | 0.788 | A | 0.212 | G/A |
| ASW | rs2079 | 9 | 6156653 | 0.11 | 1 | HapMap | HapMap | G | 0.731 | A | 0.269 | G/A |
| MKK | rs2079 | 9 | 6156653 | 0.04 | 1 | HapMap | HapMap | G | 0.773 | A | 0.227 | G/A |
| MEX | rs2079 | 9 | 6156653 | 0.021 | 1 | HapMap | HapMap | G | 0.75 | A | 0.25 | G/A |
| GIH | rs12339713 | 9 | 5968437 | 0.004 | 1 | HapMap | HapMap | C | 0.92 | T | 0.08 | C/T |
| LWK | rs12339713 | 9 | 5968437 | 0.046 | 1 | HapMap | HapMap | C | 0.844 | T | 0.156 | C/T |
| LWK | rs4742172 | 9 | 6266733 | 0.124 | 0.816 | HapMap | HapMap | C | 0.045 | T | 0.955 | C/T |
| GIH | rs4742172 | 9 | 6266733 | 0.001 | 1 | HapMap | HapMap | C | 0.017 | T | 0.983 | C/T |
| ASW | rs4742172 | 9 | 6266733 | 0.058 | 1 | HapMap | HapMap | C | 0.132 | T | 0.868 | C/T |
| MKK | rs4742172 | 9 | 6266733 | 0.003 | 1 | HapMap | HapMap | C | 0.025 | T | 0.975 | C/T |
| MEX | rs4742172 | 9 | 6266733 | 0.001 | 1 | HapMap | HapMap | C | 0.02 | T | 0.98 | C/T |
| MKK | rs7863536 | 9 | 6154771 | 0.529 | 0.752 | HapMap | HapMap | C | 0.877 | A | 0.123 | C/A |
| JPT | rs7863536 | 9 | 6154771 | 0.585 | 1 | HapMap | HapMap | C | 0.948 | A | 0.052 | C/A |
| GIH | rs7863536 | 9 | 6154771 | 1 | 1 | HapMap | HapMap | C | 0.955 | A | 0.045 | C/A |
| YRI | rs7863536 | 9 | 6154771 | 0.378 | 0.899 | HapMap | HapMap | C | 0.891 | A | 0.109 | C/A |
| CHD | rs7863536 | 9 | 6154771 | 0.43 | 0.753 | HapMap | HapMap | C | 0.918 | A | 0.082 | C/A |
| ASW | rs7863536 | 9 | 6154771 | 0.508 | 1 | HapMap | HapMap | C | 0.865 | A | 0.135 | C/A |
| ASW | rs2169285 | 9 | 6270786 | 0.125 | 0.732 | HapMap | HapMap | A | 0.42 | G | 0.58 | A/G |
| GIH | rs2169285 | 9 | 6270786 | 0.001 | 1 | HapMap | HapMap | A | 0.03 | G | 0.97 | A/G |
| JPT | rs7044468 | 9 | 6120398 | 0.005 | 1 | HapMap | 1000GP | A | NA | G | NA | A/G |
| CHB | rs7044468 | 9 | 6120398 | 0.007 | 0.794 | HapMap | 1000GP | A | NA | G | NA | A/G |
| JPT | rs10758750 | 9 | 6230513 | 0.048 | 1 | HapMap | 1000GP | C | 0.5 | G | 0.5 | C/G |
| JPT | rs10815383 | 9 | 6230670 | 0.048 | 1 | HapMap | 1000GP | C | 0.5 | G | 0.5 | C/G |
| JPT | rs16924171 | 9 | 6233279 | 0.05 | 1 | HapMap | 1000GP | A | 0.5 | T | 0.5 | A/T |
| JPT | rs7019575 | 9 | 6243935 | 0.047 | 1 | HapMap | 1000GP | G | 0.5 | C | 0.5 | G/C |
| JPT | rs7034720 | 9 | 6234546 | 0.051 | 1 | HapMap | 1000GP | C | 0.51 | A | 0.49 | C/A |
| JPT | rs1375 | 9 | 6235753 | 0.052 | 1 | HapMap | 1000GP | G | 0.51 | T | 0.49 | G/T |
| JPT | rs4237164 | 9 | 6236501 | 0.052 | 1 | HapMap | 1000GP | T | 0.51 | G | 0.49 | T/G |
| JPT | rs10975509 | 9 | 6237263 | 0.053 | 1 | HapMap | 1000GP | G | 0.51 | A | 0.49 | G/A |
| JPT | rs1929992 | 9 | 6251588 | 0.047 | 1 | HapMap | 1000GP | T | 0.51 | C | 0.49 | T/C |
| JPT | rs10435816 | 9 | 6225535 | 0.055 | 1 | HapMap | 1000GP | A | 0.52 | G | 0.48 | A/G |
| JPT | rs10975497 | 9 | 6226592 | 0.062 | 1 | HapMap | 1000GP | C | 0.52 | T | 0.48 | C/T |
| JPT | rs10975498 | 9 | 6226688 | 0.052 | 1 | HapMap | 1000GP | T | 0.52 | C | 0.48 | T/C |
| JPT | rs10815397 | 9 | 6265256 | 0.051 | 1 | HapMap | 1000GP | C | 0.52 | G | 0.48 | C/G |
| JPT | rs1113573 | 9 | 6253301 | 0.02 | 0.666 | HapMap | 1000GP | T | 0.54 | C | 0.46 | T/C |
| JPT | rs7044343 | 9 | 6254208 | 0.038 | 1 | HapMap | 1000GP | C | 0.54 | T | 0.46 | C/T |
| JPT | rs7871381 | 9 | 6254900 | 0.047 | 1 | HapMap | 1000GP | G | 0.54 | A | 0.46 | G/A |
| CHB | rs10758733 | 9 | 5992100 | 0.051 | 0.69 | HapMap | 1000GP | C | 0.55 | T | 0.45 | C/T |
| CHB | rs1475614 | 9 | 5992594 | 0.051 | 0.69 | HapMap | 1000GP | G | 0.55 | C | 0.45 | G/C |
| CHB | rs4742145 | 9 | 5995278 | 0.068 | 0.689 | HapMap | 1000GP | G | 0.55 | A | 0.45 | G/A |
| JPT | rs1412421 | 9 | 6255010 | 0.058 | 1 | HapMap | 1000GP | A | 0.55 | C | 0.45 | A/C |
| CHB | rs10975386 | 9 | 5982246 | 0.05 | 0.659 | HapMap | 1000GP | T | 0.56 | C | 0.44 | T/C |
| JPT | rs10975555 | 9 | 6360299 | 0.049 | 1 | HapMap | 1000GP | C | 0.6 | G | 0.4 | C/G |
| CHB | rs10975555 | 9 | 6360299 | 0.055 | 1 | HapMap | 1000GP | C | 0.6 | G | 0.4 | C/G |
| CHB | rs340910 | 9 | 6128620 | 0.063 | 0.65 | HapMap | 1000GP | A | 0.68 | G | 0.32 | A/G |
| CHB | rs407153 | 9 | 6133014 | 0.059 | 0.634 | HapMap | 1000GP | C | 0.68 | T | 0.32 | C/T |
| CHB | rs4389996 | 9 | 5991399 | 0.092 | 0.729 | HapMap | 1000GP | C | 0.69 | T | 0.31 | C/T |
| CHB | rs182908 | 9 | 6098381 | 0.063 | 0.65 | HapMap | 1000GP | A | 0.69 | C | 0.31 | A/C |
| CHB | rs436300 | 9 | 6112044 | 0.063 | 0.65 | HapMap | 1000GP | G | 0.69 | C | 0.31 | G/C |
| CHB | rs444826 | 9 | 6114483 | 0.063 | 0.65 | HapMap | 1000GP | G | 0.69 | C | 0.31 | G/C |
| CHB | rs340916 | 9 | 6126372 | 0.07 | 0.668 | HapMap | 1000GP | T | 0.69 | C | 0.31 | T/C |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs16924328 | 9 | 6324744 | 0.037 | 1 | HapMap | 1000GP | T | 0.69 | C | 0.31 | T/C |
| CHB | rs10975553 | 9 | 6352819 | 0.033 | 1 | HapMap | 1000GP | T | 0.69 | C | 0.31 | T/C |
| CHB | rs7022186 | 9 | 6359144 | 0.033 | 1 | HapMap | 1000GP | T | 0.69 | C | 0.31 | T/C |
| CHB | rs4742181 | 9 | 6363694 | 0.031 | 1 | HapMap | 1000GP | A | 0.7 | G | 0.3 | A/G |
| CHB | rs719725 | 9 | 6365683 | 0.031 | 1 | HapMap | 1000GP | A | 0.7 | C | 0.3 | A/C |
| CHB | rs2291055 | 9 | 5988333 | 0.116 | 0.758 | HapMap | 1000GP | C | 0.71 | T | 0.29 | C/T |
| CHB | rs6477024 | 9 | 5990450 | 0.122 | 0.761 | HapMap | 1000GP | C | 0.71 | T | 0.29 | C/T |
| CHB | rs7851749 | 9 | 5993652 | 0.116 | 0.758 | HapMap | 1000GP | T | 0.71 | A | 0.29 | T/A |
| CHB | rs7875450 | 9 | 5996739 | 0.116 | 0.758 | HapMap | 1000GP | C | 0.71 | T | 0.29 | C/T |
| CHB | rs4740834 | 9 | 5979717 | 0.116 | 0.758 | HapMap | 1000GP | C | 0.72 | T | 0.28 | C/T |
| CHB | rs4742142 | 9 | 5981316 | 0.116 | 0.758 | HapMap | 1000GP | C | 0.72 | T | 0.28 | C/T |
| CHB | rs4742143 | 9 | 5981647 | 0.116 | 0.758 | HapMap | 1000GP | T | 0.72 | A | 0.28 | T/A |
| CHB | rs10815330 | 9 | 5983481 | 0.147 | 0.776 | HapMap | 1000GP | G | 0.72 | C | 0.28 | G/C |
| JPT | rs7044750 | 9 | 5983655 | 0.008 | 1 | HapMap | 1000GP | G | 0.72 | A | 0.28 | G/A |
| CHB | rs2381360 | 9 | 5990250 | 0.116 | 0.758 | HapMap | 1000GP | T | 0.72 | G | 0.28 | T/G |
| CHB | rs10733523 | 9 | 5992256 | 0.116 | 0.758 | HapMap | 1000GP | C | 0.72 | T | 0.28 | C/T |
| CHB | rs1331379 | 9 | 6003377 | 0.116 | 0.758 | HapMap | 1000GP | C | 0.72 | T | 0.28 | C/T |
| CHB | rs186913 | 9 | 6008826 | 0.125 | 0.766 | HapMap | 1000GP | T | 0.72 | C | 0.28 | T/C |
| CHB | rs7875812 | 9 | 6364533 | 0.033 | 1 | HapMap | 1000GP | A | 0.72 | T | 0.28 | A/T |
| JPT | rs343493 | 9 | 6071061 | 0.011 | 0.971 | HapMap | 1000GP | A | 0.73 | G | 0.27 | A/G |
| JPT | rs340920 | 9 | 6090484 | 0.01 | 1 | HapMap | 1000GP | T | 0.75 | G | 0.25 | T/G |
| JPT | rs1116795 | 9 | 6155226 | 0.183 | 0.728 | HapMap | 1000GP | G | 0.77 | T | 0.23 | G/T |
| CHB | rs1116795 | 9 | 6155226 | 0.163 | 0.783 | HapMap | 1000GP | G | 0.77 | T | 0.23 | G/T |
| JPT | rs2225537 | 9 | 6160578 | 0.163 | 0.718 | HapMap | 1000GP | C | 0.77 | T | 0.23 | C/T |
| JPT | rs10491835 | 9 | 6325345 | 0.004 | 0.615 | HapMap | 1000GP | G | 0.8 | A | 0.2 | G/A |
| JPT | rs7872052 | 9 | 6026757 | 0.007 | 0.753 | HapMap | 1000GP | T | 0.82 | C | 0.18 | T/C |
| CHB | rs7872052 | 9 | 6026757 | 0.01 | 0.699 | HapMap | 1000GP | T | 0.82 | C | 0.18 | T/C |
| CHB | rs343469 | 9 | 6046486 | 0.136 | 0.613 | HapMap | 1000GP | A | 0.84 | G | 0.16 | A/G |
| CHB | rs340889 | 9 | 6100476 | 0.025 | 1 | HapMap | 1000GP | G | 0.84 | C | 0.16 | G/C |
| JPT | rs340889 | 9 | 6100476 | 0.008 | 1 | HapMap | 1000GP | G | 0.84 | C | 0.16 | G/C |
| CHB | rs13299104 | 9 | 6101432 | 0.201 | 0.796 | HapMap | 1000GP | C | 0.84 | T | 0.16 | C/T |
| CHB | rs439190 | 9 | 6114076 | 0.02 | 1 | HapMap | 1000GP | C | 0.84 | T | 0.16 | C/T |
| JPT | rs439190 | 9 | 6114076 | 0.007 | 1 | HapMap | 1000GP | C | 0.84 | T | 0.16 | C/T |
| CHB | rs391813 | 9 | 6114094 | 0.004 | 1 | HapMap | 1000GP | C | 0.84 | T | 0.16 | C/T |
| JPT | rs372482 | 9 | 6119872 | 0.007 | 1 | HapMap | 1000GP | G | 0.84 | A | 0.16 | G/A |
| CHB | rs372482 | 9 | 6119872 | 0.02 | 1 | HapMap | 1000GP | G | 0.84 | A | 0.16 | G/A |
| CHB | rs442246 | 9 | 6121504 | 0.022 | 1 | HapMap | 1000GP | G | 0.84 | T | 0.16 | G/T |
| JPT | rs442246 | 9 | 6121504 | 0.007 | 1 | HapMap | 1000GP | G | 0.84 | T | 0.16 | G/T |
| CHB | rs13289987 | 9 | 6121900 | 0.218 | 0.803 | HapMap | 1000GP | T | 0.84 | A | 0.16 | T/A |
| CHB | rs381702 | 9 | 6122331 | 0.024 | 1 | HapMap | 1000GP | C | 0.84 | T | 0.16 | C/T |
| JPT | rs381702 | 9 | 6122331 | 0.007 | 1 | HapMap | 1000GP | C | 0.84 | T | 0.16 | C/T |
| CHB | rs693838 | 9 | 6122556 | 0.022 | 1 | HapMap | 1000GP | C | 0.84 | T | 0.16 | C/T |
| JPT | rs693838 | 9 | 6122556 | 0.007 | 1 | HapMap | 1000GP | C | 0.84 | T | 0.16 | C/T |
| CHB | rs13293742 | 9 | 6129017 | 0.201 | 0.796 | HapMap | 1000GP | T | 0.84 | C | 0.16 | T/C |
| CHB | rs10739086 | 9 | 6130822 | 0.022 | 1 | HapMap | 1000GP | C | 0.84 | T | 0.16 | C/T |
| JPT | rs10739086 | 9 | 6130822 | 0.006 | 1 | HapMap | 1000GP | C | 0.84 | T | 0.16 | C/T |
| JPT | rs10758743 | 9 | 6066175 | 0.007 | 1 | HapMap | 1000GP | T | 0.85 | C | 0.15 | T/C |
| CHB | rs694965 | 9 | 6117329 | 0.02 | 1 | HapMap | 1000GP | C | 0.85 | T | 0.15 | C/T |
| JPT | rs694965 | 9 | 6117329 | 0.007 | 1 | HapMap | 1000GP | C | 0.85 | T | 0.15 | C/T |
| CHB | rs381486 | 9 | 6118911 | 0.02 | 1 | HapMap | 1000GP | G | 0.85 | A | 0.15 | G/A |
| JPT | rs381486 | 9 | 6118911 | 0.007 | 1 | HapMap | 1000GP | G | 0.85 | A | 0.15 | G/A |
| CHB | rs340909 | 9 | 6128646 | 0.02 | 1 | HapMap | 1000GP | G | 0.85 | A | 0.15 | G/A |
| JPT | rs340909 | 9 | 6128646 | 0.007 | 1 | HapMap | 1000GP | G | 0.85 | A | 0.15 | G/A |
| CHB | rs16924009 | 9 | 6129374 | 0.218 | 0.803 | HapMap | 1000GP | A | 0.85 | T | 0.15 | A/T |
| JPT | rs489464 | 9 | 6132664 | 0.007 | 1 | HapMap | 1000GP | A | 0.85 | T | 0.15 | A/T |
| CHB | rs489464 | 9 | 6132664 | 0.019 | 1 | HapMap | 1000GP | A | 0.85 | T | 0.15 | A/T |
| CHB | rs386412 | 9 | 6132904 | 0.02 | 1 | HapMap | 1000GP | T | 0.85 | A | 0.15 | T/A |
| JPT | rs386412 | 9 | 6132904 | 0.007 | 1 | HapMap | 1000GP | T | 0.85 | A | 0.15 | T/A |
| CHB | rs369756 | 9 | 6146441 | 0.019 | 1 | HapMap | 1000GP | G | 0.85 | T | 0.15 | G/T |
| JPT | rs369756 | 9 | 6146441 | 0.004 | 1 | HapMap | 1000GP | G | 0.85 | T | 0.15 | G/T |
| JPT | rs4579584 | 9 | 6166919 | 0.004 | 1 | HapMap | 1000GP | T | 0.85 | C | 0.15 | T/C |
| CHB | rs4579584 | 9 | 6166919 | 0.016 | 1 | HapMap | 1000GP | T | 0.85 | C | 0.15 | T/C |
| CHB | rs10758742 | 9 | 6064670 | 0.008 | 0.636 | HapMap | 1000GP | C | 0.86 | G | 0.14 | C/G |
| JPT | rs10758742 | 9 | 6064670 | 0.006 | 1 | HapMap | 1000GP | C | 0.86 | G | 0.14 | C/G |
| CHB | rs4740837 | 9 | 6089527 | 0.017 | 1 | HapMap | 1000GP | C | 0.87 | T | 0.13 | C/T |
| JPT | rs4740837 | 9 | 6089527 | 0.007 | 1 | HapMap | 1000GP | C | 0.87 | T | 0.13 | C/T |
| CHB | rs10975436 | 9 | 6108729 | 0.017 | 1 | HapMap | 1000GP | T | 0.87 | C | 0.13 | T/C |
| JPT | rs10975436 | 9 | 6108729 | 0.007 | 1 | HapMap | 1000GP | T | 0.87 | C | 0.13 | T/C |
| CHB | rs7024136 | 9 | 6110470 | 0.017 | 1 | HapMap | 1000GP | A | 0.87 | C | 0.13 | A/C |
| JPT | rs7024136 | 9 | 6110470 | 0.006 | 1 | HapMap | 1000GP | A | 0.87 | C | 0.13 | A/C |
| JPT | rs7869888 | 9 | 6111007 | 0.007 | 1 | HapMap | 1000GP | C | 0.87 | T | 0.13 | C/T |
| CHB | rs7869888 | 9 | 6111007 | 0.017 | 1 | HapMap | 1000GP | C | 0.87 | T | 0.13 | C/T |
| CHB | rs7869064 | 9 | 6111078 | 0.002 | 1 | HapMap | 1000GP | G | 0.87 | T | 0.13 | G/T |
| CHB | rs7043663 | 9 | 6111603 | 0.017 | 1 | HapMap | 1000GP | C | 0.87 | T | 0.13 | C/T |
| JPT | rs7043663 | 9 | 6111603 | 0.008 | 1 | HapMap | 1000GP | C | 0.87 | T | 0.13 | C/T |
| JPT | rs7048296 | 9 | 6120702 | 0.007 | 1 | HapMap | 1000GP | T | 0.87 | C | 0.13 | T/C |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs7048296 | 9 | 6120702 | 0.018 | 1 | HapMap | 1000GP | T | 0.87 | C | 0.13 | T/C |
| JPT | rs10975446 | 9 | 6123309 | 0.005 | 1 | HapMap | 1000GP | T | 0.87 | C | 0.13 | T/C |
| CHB | rs10975446 | 9 | 6123309 | 0.018 | 1 | HapMap | 1000GP | T | 0.87 | C | 0.13 | T/C |
| JPT | rs6477038 | 9 | 6127921 | 0.007 | 1 | HapMap | 1000GP | A | 0.87 | C | 0.13 | A/C |
| CHB | rs6477038 | 9 | 6127921 | 0.017 | 1 | HapMap | 1000GP | A | 0.87 | C | 0.13 | A/C |
| CHB | rs4742158 | 9 | 6128137 | 0.017 | 1 | HapMap | 1000GP | A | 0.87 | C | 0.13 | A/C |
| JPT | rs4742158 | 9 | 6128137 | 0.007 | 1 | HapMap | 1000GP | A | 0.87 | C | 0.13 | A/C |
| CHB | rs13296527 | 9 | 6127082 | 0.297 | 0.685 | HapMap | 1000GP | G | 0.89 | T | 0.11 | G/T |
| CHB | rs13290080 | 9 | 6117291 | 0.265 | 0.678 | HapMap | 1000GP | G | 0.9 | A | 0.1 | G/A |
| JPT | rs10975465 | 9 | 6155014 | 0.79 | 1 | HapMap | 1000GP | G | 0.92 | A | 0.08 | G/A |
| CHB | rs10975465 | 9 | 6155014 | 0.463 | 0.83 | HapMap | 1000GP | G | 0.92 | A | 0.08 | G/A |
| JPT | rs10815363 | 9 | 6174316 | 0.822 | 1 | HapMap | 1000GP | T | 0.92 | C | 0.08 | T/C |
| CHB | rs10815363 | 9 | 6174316 | 0.648 | 1 | HapMap | 1000GP | T | 0.92 | C | 0.08 | T/C |
| JPT | rs1012715 | 9 | 6151320 | 0.585 | 1 | HapMap | 1000GP | C | 0.93 | A | 0.07 | C/A |
| JPT | rs12352464 | 9 | 6157329 | 0.487 | 1 | HapMap | 1000GP | C | 0.93 | T | 0.07 | C/T |
| JPT | rs6477048 | 9 | 6161253 | 0.585 | 1 | HapMap | 1000GP | C | 0.93 | T | 0.07 | C/T |
| CHB | rs4742166 | 9 | 6188124 | 0.273 | 0.611 | HapMap | 1000GP | G | 0.93 | C | 0.07 | G/C |
| JPT | rs4742166 | 9 | 6188124 | 0.499 | 0.779 | HapMap | 1000GP | G | 0.93 | C | 0.07 | G/C |
| CHB | rs1412425 | 9 | 6188740 | 0.346 | 0.761 | HapMap | 1000GP | A | 0.93 | C | 0.07 | A/C |
| JPT | rs1412425 | 9 | 6188740 | 0.61 | 0.781 | HapMap | 1000GP | A | 0.93 | C | 0.07 | A/C |
| JPT | rs2095044 | 9 | 6192796 | 0.499 | 0.779 | HapMap | 1000GP | T | 0.93 | C | 0.07 | T/C |
| CHB | rs2095044 | 9 | 6192796 | 0.273 | 0.611 | HapMap | 1000GP | T | 0.93 | C | 0.07 | T/C |
| CHB | rs10815370 | 9 | 6194831 | 0.273 | 0.611 | HapMap | 1000GP | C | 0.93 | A | 0.07 | C/A |
| JPT | rs10815370 | 9 | 6194831 | 0.499 | 0.779 | HapMap | 1000GP | C | 0.93 | A | 0.07 | C/A |
| JPT | rs4742167 | 9 | 6195285 | 0.499 | 0.779 | HapMap | 1000GP | C | 0.93 | T | 0.07 | C/T |
| CHB | rs4742167 | 9 | 6195285 | 0.273 | 0.611 | HapMap | 1000GP | C | 0.93 | T | 0.07 | C/T |
| JPT | rs1929996 | 9 | 6187636 | 0.499 | 0.779 | HapMap | 1000GP | C | 0.94 | G | 0.06 | C/G |
| CHB | rs1929996 | 9 | 6187636 | 0.354 | 0.767 | HapMap | 1000GP | C | 0.94 | G | 0.06 | C/G |
| CHB | rs7848215 | 9 | 6213468 | 0.236 | 0.705 | HapMap | 1000GP | C | 0.94 | T | 0.06 | C/T |
| JPT | rs7848215 | 9 | 6213468 | 0.616 | 0.785 | HapMap | 1000GP | C | 0.94 | T | 0.06 | C/T |
| JPT | rs10815362 | 9 | 6173798 | 0.79 | 1 | HapMap | 1000GP | T | 0.95 | C | 0.05 | T/C |
| CHB | rs10815362 | 9 | 6173798 | 0.475 | 1 | HapMap | 1000GP | T | 0.95 | C | 0.05 | T/C |
| CHB | rs2150970 | 9 | 6201364 | 0.354 | 0.767 | HapMap | 1000GP | G | 0.95 | A | 0.05 | G/A |
| JPT | rs2150970 | 9 | 6201364 | 0.79 | 1 | HapMap | 1000GP | G | 0.95 | A | 0.05 | G/A |
| JPT | rs12683048 | 9 | 6160944 | 0.004 | 1 | HapMap | 1000GP | T | 0.96 | C | 0.04 | T/C |
| CHB | rs12683048 | 9 | 6160944 | 0.005 | 1 | HapMap | 1000GP | T | 0.96 | C | 0.04 | T/C |
| JPT | rs2381416 | 9 | 6193455 | 0.585 | 1 | HapMap | 1000GP | C | 0.96 | A | 0.04 | C/A |
| CHB | rs2381416 | 9 | 6193455 | 0.127 | 0.601 | HapMap | 1000GP | C | 0.96 | A | 0.04 | C/A |
| CHB | rs12352918 | 9 | 5992351 | 0.004 | 1 | HapMap | 1000GP | G | 0.97 | C | 0.03 | G/C |
| CHB | rs12341021 | 9 | 6009656 | 0.004 | 1 | HapMap | 1000GP | C | 0.97 | G | 0.03 | C/G |
| CHB | rs10124484 | 9 | 6046505 | 0.004 | 1 | HapMap | 1000GP | T | 0.97 | G | 0.03 | T/G |
| CHB | rs12351447 | 9 | 6046950 | 0.002 | 1 | HapMap | 1000GP | T | 0.97 | G | 0.03 | T/G |
| CHB | rs343490 | 9 | 6064575 | 0.004 | 1 | HapMap | 1000GP | A | 0.97 | G | 0.03 | A/G |
| CHB | rs343496 | 9 | 6068077 | 0.004 | 1 | HapMap | 1000GP | A | 0.97 | T | 0.03 | A/T |
| CHB | rs343476 | 9 | 6072597 | 0.004 | 1 | HapMap | 1000GP | T | 0.97 | C | 0.03 | T/C |
| CHB | rs343475 | 9 | 6073013 | 0.004 | 1 | HapMap | 1000GP | C | 0.97 | G | 0.03 | C/G |
| CHB | rs189348 | 9 | 6073194 | 0.004 | 1 | HapMap | 1000GP | T | 0.97 | C | 0.03 | T/C |
| CHB | rs378952 | 9 | 6078146 | 0.004 | 1 | HapMap | 1000GP | C | 0.97 | T | 0.03 | C/T |
| CHB | rs454664 | 9 | 6078763 | 0.004 | 1 | HapMap | 1000GP | A | 0.97 | G | 0.03 | A/G |
| CHB | rs401834 | 9 | 6078991 | 0.004 | 1 | HapMap | 1000GP | T | 0.97 | C | 0.03 | T/C |
| CHB | rs340925 | 9 | 6088398 | 0.004 | 1 | HapMap | 1000GP | T | 0.97 | G | 0.03 | T/G |
| CHB | rs340922 | 9 | 6088815 | 0.004 | 1 | HapMap | 1000GP | A | 0.97 | C | 0.03 | A/C |
| JPT | rs10758748 | 9 | 6187862 | 0.585 | 1 | HapMap | 1000GP | T | 0.97 | C | 0.03 | T/C |
| CHB | rs10758748 | 9 | 6187862 | 0.232 | 1 | HapMap | 1000GP | T | 0.97 | C | 0.03 | T/C |
| CHB | rs12339713 | 9 | 5978437 | 0.002 | 1 | HapMap | 1000GP | C | 0.98 | T | 0.02 | C/T |
| CHB | rs11793956 | 9 | 5987402 | 0.001 | 1 | HapMap | 1000GP | T | 0.98 | A | 0.02 | T/A |
| CHB | rs7859471 | 9 | 6023626 | 0.004 | 1 | HapMap | 1000GP | T | 0.98 | C | 0.02 | T/C |
| CHB | rs340919 | 9 | 6090704 | 0.002 | 1 | HapMap | 1000GP | A | 0.98 | G | 0.02 | A/G |
| CHB | rs340918 | 9 | 6091048 | 0.002 | 1 | HapMap | 1000GP | A | 0.98 | C | 0.02 | A/C |
| CHB | rs695013 | 9 | 6091565 | 0.002 | 1 | HapMap | 1000GP | C | 0.98 | T | 0.02 | C/T |
| CHB | rs531759 | 9 | 6091996 | 0.001 | 1 | HapMap | 1000GP | C | 0.98 | T | 0.02 | C/T |
| CHB | rs639247 | 9 | 6092089 | 0.002 | 1 | HapMap | 1000GP | T | 0.98 | G | 0.02 | T/G |
| CHB | rs420445 | 9 | 6092154 | 0.001 | 1 | HapMap | 1000GP | G | 0.98 | A | 0.02 | G/A |
| CHB | rs503384 | 9 | 6092804 | 0.004 | 1 | HapMap | 1000GP | T | 0.98 | A | 0.02 | T/A |
| JPT | rs503384 | 9 | 6092804 | 0.001 | 1 | HapMap | 1000GP | T | 0.98 | A | 0.02 | T/A |
| CHB | rs398561 | 9 | 6093132 | 0.002 | 1 | HapMap | 1000GP | G | 0.98 | A | 0.02 | G/A |
| CHB | rs2150969 | 9 | 6093963 | 0.002 | 1 | HapMap | 1000GP | C | 0.98 | G | 0.02 | C/G |
| CHB | rs437389 | 9 | 6099531 | 0.002 | 1 | HapMap | 1000GP | T | 0.98 | C | 0.02 | T/C |
| CHB | rs340906 | 9 | 6106086 | 0.002 | 1 | HapMap | 1000GP | T | 0.98 | C | 0.02 | T/C |
| CHB | rs340905 | 9 | 6106169 | 0.003 | 1 | HapMap | 1000GP | A | 0.98 | C | 0.02 | A/C |
| CHB | rs340903 | 9 | 6107113 | 0.002 | 1 | HapMap | 1000GP | C | 0.98 | G | 0.02 | C/G |
| CHB | rs340901 | 9 | 6108398 | 0.002 | 1 | HapMap | 1000GP | G | 0.98 | C | 0.02 | G/C |
| CHB | rs974936 | 9 | 6111703 | 0.002 | 1 | HapMap | 1000GP | A | 0.98 | C | 0.02 | A/C |
| CHB | rs441616 | 9 | 6113940 | 0.002 | 1 | HapMap | 1000GP | T | 0.98 | C | 0.02 | T/C |
| CHB | rs375560 | 9 | 6114744 | 0.002 | 1 | HapMap | 1000GP | T | 0.98 | C | 0.02 | T/C |
| CHB | rs1556470 | 9 | 6115538 | 0.003 | 1 | HapMap | 1000GP | C | 0.98 | T | 0.02 | C/T |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CHB | rs374672 | 9 | 6119038 | 0.002 | 1 | HapMap | 1000GP | C | 0.98 | T | 0.02 | C/T |
| CHB | rs443175 | 9 | 6123556 | 0.003 | 1 | HapMap | 1000GP | T | 0.98 | C | 0.02 | T/C |
| CHB | rs1332291 | 9 | 6124101 | 0.002 | 1 | HapMap | 1000GP | T | 0.98 | C | 0.02 | T/C |
| CHB | rs1537285 | 9 | 6124584 | 0.002 | 1 | HapMap | 1000GP | T | 0.98 | G | 0.02 | T/G |
| CHB | rs1332292 | 9 | 6124862 | 0.002 | 1 | HapMap | 1000GP | T | 0.98 | C | 0.02 | T/C |
| CHB | rs7039066 | 9 | 6125539 | 0.002 | 1 | HapMap | 1000GP | T | 0.98 | C | 0.02 | T/C |
| CHB | rs340915 | 9 | 6126588 | 0.002 | 1 | HapMap | 1000GP | A | 0.98 | G | 0.02 | A/G |
| CHB | rs340914 | 9 | 6126799 | 0.004 | 1 | HapMap | 1000GP | A | 0.98 | G | 0.02 | A/G |
| CHB | rs340913 | 9 | 6127330 | 0.002 | 1 | HapMap | 1000GP | T | 0.98 | C | 0.02 | T/C |
| CHB | rs340912 | 9 | 6127851 | 0.002 | 1 | HapMap | 1000GP | A | 0.98 | G | 0.02 | A/G |
| CHB | rs340907 | 9 | 6129637 | 0.002 | 1 | HapMap | 1000GP | A | 0.98 | C | 0.02 | A/C |
| CHB | rs1888906 | 9 | 6131460 | 0.002 | 1 | HapMap | 1000GP | G | 0.98 | A | 0.02 | G/A |
| CHB | rs4742159 | 9 | 6131612 | 0.002 | 1 | HapMap | 1000GP | A | 0.98 | T | 0.02 | A/T |
| CHB | rs376690 | 9 | 6134926 | 0.002 | 1 | HapMap | 1000GP | C | 0.98 | T | 0.02 | C/T |
| JPT | rs16924291 | 9 | 6293305 | 0.001 | 1 | HapMap | 1000GP | C | 0.98 | A | 0.02 | C/A |
| CHB | rs986295 | 9 | 6069435 | 0.002 | 1 | HapMap | 1000GP | G | 0.99 | A | 0.01 | G/A |
| JPT | rs986295 | 9 | 6069435 | 0.001 | 1 | HapMap | 1000GP | G | 0.99 | A | 0.01 | G/A |
| CHB | rs10975453 | 9 | 6135000 | 0.003 | 1 | HapMap | 1000GP | G | 0.99 | A | 0.01 | G/A |
| CHB | rs12684265 | 9 | 6327828 | 0.002 | 1 | HapMap | 1000GP | G | 0.99 | A | 0.01 | G/A |
| CHB | rs12683480 | 9 | 6349964 | 0.002 | 1 | HapMap | 1000GP | G | 0.99 | A | 0.01 | G/A |
| JPT | rs17496153 | 9 | 6070037 | 0.19 | 1 | HapMap | 1000GP | G | 0.9965 | C | 0.0035 | G/C |
| JPT | rs10975442 | 9 | 6116768 | 0.001 | 1 | HapMap | 1000GP | G | 0.9983 | A | 0.0017 | G/A |
| CHB | rs10975442 | 9 | 6116768 | 0.001 | 1 | HapMap | 1000GP | G | 0.9983 | A | 0.0017 | G/A |
| CHB | rs12380605 | 9 | 6118873 | 0.001 | 1 | HapMap | 1000GP | A | 0.9983 | T | 0.0017 | A/T |
| CHB | rs2094756 | 9 | 6135696 | 0.018 | 1 | HapMap | 1000GP | A | 1 | C | 0 | A/C |
| JPT | rs2094756 | 9 | 6135696 | 0.007 | 1 | HapMap | 1000GP | A | 1 | C | 0 | A/C |
| CHB | rs13302749 | 9 | 6171731 | 0.155 | 1 | HapMap | 1000GP | T | 1 | C | 0 | T/C |
| JPT | rs7048482 | 9 | 6225659 | 0.001 | 1 | HapMap | 1000GP | G | 1 | A | 0 | G/A |
| JPT | rs4742172 | 9 | 6276733 | 0 | 1 | HapMap | 1000GP | C | 1 | T | 0 | C/T |
| CEU | rs7019575 | 9 | 6243935 | 0.113 | 1 | HapMap | 1000GP | G | 0.54 | C | 0.46 | G/C |
| CEU | rs450108 | 9 | 6153485 | 0.089 | 1 | HapMap | 1000GP | T | 0.59 | C | 0.41 | T/C |
| CEU | rs1116795 | 9 | 6155226 | 0.109 | 1 | HapMap | 1000GP | G | 0.59 | T | 0.41 | G/T |
| CEU | rs2225537 | 9 | 6160578 | 0.105 | 1 | HapMap | 1000GP | C | 0.59 | T | 0.41 | C/T |
| CEU | rs10975553 | 9 | 6352819 | 0.07 | 1 | HapMap | 1000GP | T | 0.6 | C | 0.4 | T/C |
| CEU | rs7022186 | 9 | 6359144 | 0.076 | 1 | HapMap | 1000GP | T | 0.6 | C | 0.4 | T/C |
| CEU | rs719725 | 9 | 6365683 | 0.076 | 1 | HapMap | 1000GP | A | 0.6 | C | 0.4 | A/C |
| CEU | rs7875812 | 9 | 6364533 | 0.076 | 1 | HapMap | 1000GP | A | 0.63 | T | 0.37 | A/T |
| CEU | rs731585 | 9 | 6342328 | 0.065 | 1 | HapMap | 1000GP | G | 0.65 | A | 0.35 | G/A |
| CEU | rs343481 | 9 | 6024285 | 0.055 | 0.601 | HapMap | 1000GP | C | 0.66 | G | 0.34 | C/G |
| CEU | rs1113573 | 9 | 6253301 | 0.019 | 0.612 | HapMap | 1000GP | T | 0.67 | C | 0.33 | T/C |
| CEU | rs10758733 | 9 | 5992100 | 0.104 | 0.676 | HapMap | 1000GP | C | 0.68 | T | 0.32 | C/T |
| CEU | rs16924159 | 9 | 6229417 | 0.038 | 1 | HapMap | 1000GP | G | 0.68 | A | 0.32 | G/A |
| CEU | rs1375 | 9 | 6235753 | 0.208 | 1 | HapMap | 1000GP | G | 0.69 | T | 0.31 | G/T |
| CEU | rs10975386 | 9 | 5982246 | 0.115 | 0.792 | HapMap | 1000GP | T | 0.7 | C | 0.3 | T/C |
| CEU | rs1475614 | 9 | 5992594 | 0.104 | 0.676 | HapMap | 1000GP | G | 0.7 | C | 0.3 | G/C |
| CEU | rs340911 | 9 | 6128446 | 0.025 | 1 | HapMap | 1000GP | C | 0.7 | G | 0.3 | C/G |
| CEU | rs16924171 | 9 | 6233279 | 0.217 | 1 | HapMap | 1000GP | A | 0.7 | T | 0.3 | A/T |
| CEU | rs7034720 | 9 | 6234546 | 0.194 | 1 | HapMap | 1000GP | C | 0.7 | A | 0.3 | C/A |
| CEU | rs10758764 | 9 | 6326825 | 0.068 | 1 | HapMap | 1000GP | T | 0.7 | A | 0.3 | T/A |
| CEU | rs10758741 | 9 | 6054645 | 0.08 | 0.649 | HapMap | 1000GP | G | 0.71 | A | 0.29 | G/A |
| CEU | rs10758743 | 9 | 6066175 | 0.131 | 0.827 | HapMap | 1000GP | T | 0.71 | C | 0.29 | T/C |
| CEU | rs4742179 | 9 | 6324376 | 0.067 | 1 | HapMap | 1000GP | A | 0.71 | C | 0.29 | A/C |
| CEU | rs10758742 | 9 | 6064670 | 0.134 | 0.821 | HapMap | 1000GP | C | 0.72 | G | 0.28 | C/G |
| CEU | rs1929996 | 9 | 6187636 | 0.149 | 1 | HapMap | 1000GP | C | 0.72 | G | 0.28 | C/G |
| CEU | rs4742166 | 9 | 6188124 | 0.147 | 1 | HapMap | 1000GP | G | 0.72 | C | 0.28 | G/C |
| CEU | rs1412425 | 9 | 6188740 | 0.153 | 1 | HapMap | 1000GP | A | 0.72 | C | 0.28 | A/C |
| CEU | rs10815370 | 9 | 6194831 | 0.143 | 1 | HapMap | 1000GP | C | 0.72 | A | 0.28 | C/A |
| CEU | rs4742167 | 9 | 6195285 | 0.143 | 1 | HapMap | 1000GP | C | 0.72 | T | 0.28 | C/T |
| CEU | rs10975509 | 9 | 6237263 | 0.249 | 1 | HapMap | 1000GP | G | 0.72 | A | 0.28 | G/A |
| CEU | rs10975498 | 9 | 6226688 | 0.306 | 1 | HapMap | 1000GP | T | 0.73 | C | 0.27 | T/C |
| CEU | rs2006682 | 9 | 6227045 | 0.03 | 1 | HapMap | 1000GP | G | 0.73 | C | 0.27 | G/C |
| CEU | rs10435816 | 9 | 6225535 | 0.287 | 1 | HapMap | 1000GP | A | 0.74 | G | 0.26 | A/G |
| CEU | rs10975497 | 9 | 6226592 | 0.304 | 1 | HapMap | 1000GP | C | 0.74 | T | 0.26 | C/T |
| CEU | rs10758750 | 9 | 6230513 | 0.289 | 1 | HapMap | 1000GP | C | 0.74 | G | 0.26 | C/G |
| CEU | rs10815383 | 9 | 6230670 | 0.29 | 1 | HapMap | 1000GP | C | 0.74 | G | 0.26 | C/G |
| CEU | rs16924428 | 9 | 6351111 | 0.05 | 1 | HapMap | 1000GP | A | 0.74 | G | 0.26 | A/G |
| CEU | rs369756 | 9 | 6146441 | 0.033 | 1 | HapMap | 1000GP | G | 0.75 | T | 0.25 | G/T |
| CEU | rs7848215 | 9 | 6213468 | 0.191 | 1 | HapMap | 1000GP | C | 0.75 | T | 0.25 | C/T |
| CEU | rs2095044 | 9 | 6192796 | 0.208 | 1 | HapMap | 1000GP | T | 0.76 | C | 0.24 | T/C |
| CEU | rs2381416 | 9 | 6193455 | 0.199 | 1 | HapMap | 1000GP | C | 0.76 | A | 0.24 | C/A |
| CEU | rs10815397 | 9 | 6265256 | 0.206 | 0.7 | HapMap | 1000GP | C | 0.76 | G | 0.24 | C/G |
| CEU | rs744567 | 9 | 6292602 | 0.041 | 1 | HapMap | 1000GP | C | 0.77 | G | 0.23 | C/G |
| CEU | rs12339348 | 9 | 6233082 | 0.041 | 1 | HapMap | 1000GP | A | 0.78 | T | 0.22 | A/T |
| CEU | rs17582919 | 9 | 6233376 | 0.041 | 1 | HapMap | 1000GP | T | 0.78 | C | 0.22 | T/C |
| CEU | rs10975507 | 9 | 6236977 | 0.041 | 1 | HapMap | 1000GP | A | 0.78 | T | 0.22 | A/T |
| CEU | rs343490 | 9 | 6064575 | 0.016 | 1 | HapMap | 1000GP | A | 0.81 | G | 0.19 | A/G |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs343496 | 9 | 6068077 | 0.014 | 1 | HapMap | 1000GP | A | 0.81 | T | 0.19 | A/T |
| CEU | rs343476 | 9 | 6072597 | 0.014 | 1 | HapMap | 1000GP | T | 0.81 | C | 0.19 | T/C |
| CEU | rs343475 | 9 | 6073013 | 0.014 | 1 | HapMap | 1000GP | C | 0.81 | G | 0.19 | C/G |
| CEU | rs189348 | 9 | 6073194 | 0.014 | 1 | HapMap | 1000GP | T | 0.81 | C | 0.19 | T/C |
| CEU | rs378952 | 9 | 6078146 | 0.014 | 1 | HapMap | 1000GP | C | 0.81 | T | 0.19 | C/T |
| CEU | rs1332291 | 9 | 6124101 | 0.014 | 1 | HapMap | 1000GP | T | 0.81 | C | 0.19 | T/C |
| CEU | rs340918 | 9 | 6091048 | 0.013 | 1 | HapMap | 1000GP | A | 0.82 | C | 0.18 | A/C |
| CEU | rs695013 | 9 | 6091565 | 0.013 | 1 | HapMap | 1000GP | C | 0.82 | T | 0.18 | C/T |
| CEU | rs531759 | 9 | 6091996 | 0.012 | 1 | HapMap | 1000GP | C | 0.82 | T | 0.18 | C/T |
| CEU | rs639247 | 9 | 6092089 | 0.013 | 1 | HapMap | 1000GP | T | 0.82 | G | 0.18 | T/G |
| CEU | rs420445 | 9 | 6092154 | 0.013 | 1 | HapMap | 1000GP | G | 0.82 | A | 0.18 | G/A |
| CEU | rs503507 | 9 | 6092757 | 0.013 | 1 | HapMap | 1000GP | G | 0.82 | A | 0.18 | G/A |
| CEU | rs503384 | 9 | 6092804 | 0.014 | 1 | HapMap | 1000GP | T | 0.82 | A | 0.18 | T/A |
| CEU | rs425489 | 9 | 6093790 | 0.014 | 1 | HapMap | 1000GP | T | 0.82 | C | 0.18 | T/C |
| CEU | rs2150969 | 9 | 6093990 | 0.014 | 1 | HapMap | 1000GP | C | 0.82 | G | 0.18 | C/G |
| CEU | rs437389 | 9 | 6099531 | 0.013 | 1 | HapMap | 1000GP | T | 0.82 | C | 0.18 | T/C |
| CEU | rs340896 | 9 | 6102891 | 0.013 | 1 | HapMap | 1000GP | T | 0.82 | C | 0.18 | T/C |
| CEU | rs340906 | 9 | 6106086 | 0.012 | 1 | HapMap | 1000GP | T | 0.82 | C | 0.18 | T/C |
| CEU | rs340905 | 9 | 6106169 | 0.013 | 1 | HapMap | 1000GP | A | 0.82 | C | 0.18 | A/C |
| CEU | rs340903 | 9 | 6107113 | 0.013 | 1 | HapMap | 1000GP | C | 0.82 | G | 0.18 | C/G |
| CEU | rs340901 | 9 | 6108398 | 0.013 | 1 | HapMap | 1000GP | G | 0.82 | C | 0.18 | G/C |
| CEU | rs974936 | 9 | 6111703 | 0.013 | 1 | HapMap | 1000GP | A | 0.82 | C | 0.18 | A/C |
| CEU | rs441616 | 9 | 6113940 | 0.012 | 1 | HapMap | 1000GP | T | 0.82 | C | 0.18 | T/C |
| CEU | rs1556470 | 9 | 6115538 | 0.012 | 1 | HapMap | 1000GP | C | 0.82 | T | 0.18 | C/T |
| CEU | rs374672 | 9 | 6119038 | 0.013 | 1 | HapMap | 1000GP | C | 0.82 | T | 0.18 | C/T |
| CEU | rs443175 | 9 | 6123556 | 0.012 | 1 | HapMap | 1000GP | T | 0.82 | C | 0.18 | T/C |
| CEU | rs1537285 | 9 | 6124584 | 0.013 | 1 | HapMap | 1000GP | T | 0.82 | G | 0.18 | T/G |
| CEU | rs1332292 | 9 | 6124862 | 0.013 | 1 | HapMap | 1000GP | T | 0.82 | C | 0.18 | T/C |
| CEU | rs7039066 | 9 | 6125539 | 0.011 | 1 | HapMap | 1000GP | T | 0.82 | C | 0.18 | T/C |
| CEU | rs340915 | 9 | 6126588 | 0.013 | 1 | HapMap | 1000GP | A | 0.82 | G | 0.18 | A/G |
| CEU | rs340914 | 9 | 6126799 | 0.011 | 1 | HapMap | 1000GP | A | 0.82 | G | 0.18 | A/G |
| CEU | rs340913 | 9 | 6127330 | 0.013 | 1 | HapMap | 1000GP | T | 0.82 | C | 0.18 | T/C |
| CEU | rs340912 | 9 | 6127851 | 0.012 | 1 | HapMap | 1000GP | A | 0.82 | G | 0.18 | A/G |
| CEU | rs340907 | 9 | 6129637 | 0.013 | 1 | HapMap | 1000GP | A | 0.82 | C | 0.18 | A/C |
| CEU | rs10114457 | 9 | 6130940 | 0.014 | 1 | HapMap | 1000GP | A | 0.82 | G | 0.18 | A/G |
| CEU | rs1888906 | 9 | 6131460 | 0.013 | 1 | HapMap | 1000GP | G | 0.82 | A | 0.18 | G/A |
| CEU | rs4742159 | 9 | 6131612 | 0.013 | 1 | HapMap | 1000GP | A | 0.82 | T | 0.18 | A/T |
| CEU | rs376690 | 9 | 6134926 | 0.013 | 1 | HapMap | 1000GP | C | 0.82 | T | 0.18 | C/T |
| CEU | rs16924291 | 9 | 6293305 | 0.017 | 1 | HapMap | 1000GP | C | 0.84 | A | 0.16 | C/A |
| CEU | rs16924328 | 9 | 6324744 | 0.011 | 1 | HapMap | 1000GP | T | 0.87 | C | 0.13 | T/C |
| CEU | rs4579584 | 9 | 6166919 | 0.005 | 1 | HapMap | 1000GP | T | 0.88 | C | 0.12 | T/C |
| CEU | rs10815362 | 9 | 6173798 | 0.659 | 1 | HapMap | 1000GP | T | 0.91 | C | 0.09 | T/C |
| CEU | rs10758748 | 9 | 6187862 | 0.744 | 1 | HapMap | 1000GP | T | 0.91 | C | 0.09 | T/C |
| CEU | rs2150970 | 9 | 6201364 | 0.683 | 1 | HapMap | 1000GP | G | 0.91 | A | 0.09 | G/A |
| CEU | rs7859471 | 9 | 6023626 | 0.008 | 0.921 | HapMap | 1000GP | T | 0.93 | C | 0.07 | T/C |
| CEU | rs13300552 | 9 | 6095799 | 0.011 | 1 | HapMap | 1000GP | T | 0.93 | C | 0.07 | T/C |
| CEU | rs13298861 | 9 | 6150279 | 0.015 | 1 | HapMap | 1000GP | A | 0.93 | T | 0.07 | A/T |
| CEU | rs10975464 | 9 | 6151609 | 0.014 | 1 | HapMap | 1000GP | G | 0.93 | C | 0.07 | G/C |
| CEU | rs4742143 | 9 | 5981647 | 0.001 | 1 | HapMap | 1000GP | T | 0.94 | A | 0.06 | T/A |
| CEU | rs1012715 | 9 | 6151320 | 0.815 | 1 | HapMap | 1000GP | C | 0.94 | A | 0.06 | C/A |
| CEU | rs10975465 | 9 | 6155014 | 0.815 | 1 | HapMap | 1000GP | G | 0.94 | A | 0.06 | G/A |
| CEU | rs12352464 | 9 | 6157329 | 0.8 | 1 | HapMap | 1000GP | C | 0.94 | T | 0.06 | C/T |
| CEU | rs12352510 | 9 | 6157433 | 0.815 | 1 | HapMap | 1000GP | C | 0.94 | T | 0.06 | C/T |
| CEU | rs6477048 | 9 | 6161253 | 0.815 | 1 | HapMap | 1000GP | C | 0.94 | T | 0.06 | C/T |
| CEU | rs13302008 | 9 | 6162881 | 0.014 | 1 | HapMap | 1000GP | T | 0.94 | C | 0.06 | T/C |
| CEU | rs7863536 | 9 | 6164771 | 0.815 | 1 | HapMap | 1000GP | C | 0.94 | A | 0.06 | C/A |
| CEU | rs10118918 | 9 | 6170162 | 0.815 | 1 | HapMap | 1000GP | T | 0.94 | G | 0.06 | T/G |
| CEU | rs1041538 | 9 | 6270359 | 0.013 | 1 | HapMap | 1000GP | A | 0.94 | G | 0.06 | A/G |
| CEU | rs1041537 | 9 | 6271238 | 0.013 | 1 | HapMap | 1000GP | A | 0.94 | G | 0.06 | A/G |
| CEU | rs10123059 | 9 | 6275456 | 0.013 | 1 | HapMap | 1000GP | T | 0.94 | C | 0.06 | T/C |
| CEU | rs10758754 | 9 | 6277740 | 0.013 | 1 | HapMap | 1000GP | G | 0.94 | A | 0.06 | G/A |
| CEU | rs2169284 | 9 | 6278071 | 0.012 | 1 | HapMap | 1000GP | A | 0.94 | G | 0.06 | A/G |
| CEU | rs2169285 | 9 | 6280786 | 0.013 | 1 | HapMap | 1000GP | A | 0.94 | G | 0.06 | A/G |
| CEU | rs10739091 | 9 | 6292919 | 0.008 | 0.884 | HapMap | 1000GP | A | 0.94 | T | 0.06 | A/T |
| CEU | rs4389996 | 9 | 5991399 | 0.001 | 1 | HapMap | 1000GP | C | 0.95 | T | 0.05 | C/T |
| CEU | rs10118537 | 9 | 6135155 | 0.003 | 1 | HapMap | 1000GP | A | 0.95 | T | 0.05 | A/T |
| CEU | rs7048482 | 9 | 6225659 | 0.005 | 1 | HapMap | 1000GP | G | 0.95 | A | 0.05 | G/A |
| CEU | rs13298301 | 9 | 6187242 | 0.008 | 0.921 | HapMap | 1000GP | A | 0.96 | G | 0.04 | A/G |
| CEU | rs13284060 | 9 | 6202701 | 0.004 | 0.676 | HapMap | 1000GP | A | 0.96 | C | 0.04 | A/C |
| CEU | rs11794419 | 9 | 6222110 | 0.006 | 1 | HapMap | 1000GP | T | 0.97 | C | 0.03 | T/C |
| CEU | rs1854709 | 9 | 6251455 | 0.004 | 0.676 | HapMap | 1000GP | T | 0.97 | C | 0.03 | T/C |
| CEU | rs7047769 | 9 | 6267718 | 0.004 | 1 | HapMap | 1000GP | C | 0.97 | T | 0.03 | C/T |
| CEU | rs980850 | 9 | 6269458 | 0.004 | 0.676 | HapMap | 1000GP | G | 0.97 | C | 0.03 | G/C |
| CEU | rs2381440 | 9 | 6373548 | 0.001 | 1 | HapMap | 1000GP | G | 0.97 | A | 0.03 | G/A |
| CEU | rs4740834 | 9 | 5979717 | 0.001 | 1 | HapMap | 1000GP | C | 0.98 | T | 0.02 | C/T |
| CEU | rs4742142 | 9 | 5981316 | 0.001 | 1 | HapMap | 1000GP | C | 0.98 | T | 0.02 | C/T |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| CEU | rs10815330 | 9 | 5983481 | 0.001 | 1 | HapMap | 1000GP | G | 0.98 | C | 0.02 | G/C |
| CEU | rs7044750 | 9 | 5983655 | 0.001 | 1 | HapMap | 1000GP | G | 0.98 | A | 0.02 | G/A |
| CEU | rs2291055 | 9 | 5988333 | 0.001 | 1 | HapMap | 1000GP | C | 0.98 | T | 0.02 | C/T |
| CEU | rs2381360 | 9 | 5990250 | 0.001 | 1 | HapMap | 1000GP | T | 0.98 | G | 0.02 | T/G |
| CEU | rs6477024 | 9 | 5990450 | 0.001 | 1 | HapMap | 1000GP | C | 0.98 | T | 0.02 | C/T |
| CEU | rs10733523 | 9 | 5992256 | 0.001 | 1 | HapMap | 1000GP | C | 0.98 | T | 0.02 | C/T |
| CEU | rs12352918 | 9 | 5992351 | 0.001 | 1 | HapMap | 1000GP | G | 0.98 | C | 0.02 | G/C |
| CEU | rs7851749 | 9 | 5993652 | 0.001 | 1 | HapMap | 1000GP | T | 0.98 | A | 0.02 | T/A |
| CEU | rs7875450 | 9 | 5996739 | 0.001 | 1 | HapMap | 1000GP | C | 0.98 | T | 0.02 | C/T |
| CEU | rs1331379 | 9 | 6003377 | 0.001 | 1 | HapMap | 1000GP | C | 0.98 | T | 0.02 | C/T |
| CEU | rs186913 | 9 | 6008826 | 0.001 | 1 | HapMap | 1000GP | T | 0.98 | C | 0.02 | T/C |
| CEU | rs7852538 | 9 | 6026472 | 0.002 | 1 | HapMap | 1000GP | G | 0.98 | A | 0.02 | G/A |
| CEU | rs343480 | 9 | 6023030 | 0.001 | 1 | HapMap | 1000GP | A | 0.99 | G | 0.01 | A/G |
| CEU | rs343482 | 9 | 6024347 | 0.001 | 1 | HapMap | 1000GP | T | 0.99 | G | 0.01 | T/G |
| CEU | rs343469 | 9 | 6046486 | 0.001 | 1 | HapMap | 1000GP | A | 0.99 | G | 0.01 | A/G |
| CEU | rs13290235 | 9 | 6052352 | 0.004 | 1 | HapMap | 1000GP | G | 0.99 | A | 0.01 | G/A |
| CEU | rs7866793 | 9 | 6055039 | 0.001 | 1 | HapMap | 1000GP | T | 0.99 | C | 0.01 | T/C |
| CEU | rs7857802 | 9 | 6075321 | 0.001 | 1 | HapMap | 1000GP | G | 0.99 | A | 0.01 | G/A |
| CEU | rs10975442 | 9 | 6116768 | 0.002 | 1 | HapMap | 1000GP | G | 0.996 | A | 0.004 | G/A |
| CEU | rs12336478 | 9 | 6247287 | 0.001 | 1 | HapMap | 1000GP | G | 1 | A | 0 | G/A |
| YRI | rs1969732 | 9 | 6278604 | 0.015 | 1 | HapMap | 1000GP | A | NA | G | NA | A/G |
| YRI | rs2381416 | 9 | 6193455 | 0.138 | 0.865 | HapMap | 1000GP | C | 0.61 | A | 0.39 | C/A |
| YRI | rs343481 | 9 | 6024285 | 0.042 | 0.663 | HapMap | 1000GP | C | 0.64 | G | 0.36 | C/G |
| YRI | rs2095044 | 9 | 6192796 | 0.052 | 0.625 | HapMap | 1000GP | T | 0.66 | C | 0.34 | T/C |
| YRI | rs1412425 | 9 | 6188740 | 0.037 | 0.633 | HapMap | 1000GP | A | 0.72 | C | 0.28 | A/C |
| YRI | rs2150970 | 9 | 6201364 | 0.542 | 1 | HapMap | 1000GP | G | 0.72 | A | 0.28 | G/A |
| YRI | rs10815370 | 9 | 6194831 | 0.082 | 1 | HapMap | 1000GP | C | 0.73 | A | 0.27 | C/A |
| YRI | rs10758748 | 9 | 6187862 | 0.567 | 0.886 | HapMap | 1000GP | T | 0.75 | C | 0.25 | T/C |
| YRI | rs7047769 | 9 | 6267718 | 0.038 | 1 | HapMap | 1000GP | C | 0.76 | T | 0.24 | C/T |
| YRI | rs2079 | 9 | 6166653 | 0.049 | 0.714 | HapMap | 1000GP | G | 0.78 | A | 0.22 | G/A |
| YRI | rs10975424 | 9 | 6077716 | 0.056 | 0.787 | HapMap | 1000GP | T | 0.83 | C | 0.17 | T/C |
| YRI | rs401834 | 9 | 6078991 | 0.137 | 0.604 | HapMap | 1000GP | T | 0.83 | C | 0.17 | T/C |
| YRI | rs343476 | 9 | 6072597 | 0.157 | 0.63 | HapMap | 1000GP | T | 0.84 | C | 0.16 | T/C |
| YRI | rs343475 | 9 | 6073013 | 0.137 | 0.604 | HapMap | 1000GP | C | 0.84 | G | 0.16 | C/G |
| YRI | rs189348 | 9 | 6073194 | 0.137 | 0.604 | HapMap | 1000GP | T | 0.84 | C | 0.16 | T/C |
| YRI | rs378952 | 9 | 6078146 | 0.157 | 0.63 | HapMap | 1000GP | C | 0.84 | T | 0.16 | C/T |
| YRI | rs10815340 | 9 | 6005037 | 0.031 | 0.935 | HapMap | 1000GP | T | 0.85 | G | 0.15 | T/G |
| YRI | rs343496 | 9 | 6068077 | 0.157 | 0.63 | HapMap | 1000GP | A | 0.85 | T | 0.15 | A/T |
| YRI | rs6477038 | 9 | 6127921 | 0.02 | 0.62 | HapMap | 1000GP | A | 0.87 | C | 0.13 | A/C |
| YRI | rs10118918 | 9 | 6170162 | 0.55 | 1 | HapMap | 1000GP | T | 0.87 | G | 0.13 | T/G |
| YRI | rs2094756 | 9 | 6135696 | 0.012 | 1 | HapMap | 1000GP | A | 0.88 | C | 0.12 | A/C |
| YRI | rs12352464 | 9 | 6157329 | 0.382 | 0.9 | HapMap | 1000GP | C | 0.88 | T | 0.12 | C/T |
| YRI | rs1012715 | 9 | 6151320 | 0.402 | 0.902 | HapMap | 1000GP | C | 0.89 | A | 0.11 | C/A |
| YRI | rs10975465 | 9 | 6155014 | 0.397 | 1 | HapMap | 1000GP | G | 0.89 | A | 0.11 | G/A |
| YRI | rs12352510 | 9 | 6157433 | 0.396 | 1 | HapMap | 1000GP | C | 0.89 | T | 0.11 | C/T |
| YRI | rs13302008 | 9 | 6162881 | 0.045 | 1 | HapMap | 1000GP | T | 0.9 | C | 0.1 | T/C |
| YRI | rs1888910 | 9 | 6190650 | 0.024 | 1 | HapMap | 1000GP | C | 0.9 | T | 0.1 | C/T |
| YRI | rs13298861 | 9 | 6150279 | 0.026 | 1 | HapMap | 1000GP | A | 0.92 | T | 0.08 | A/T |
| YRI | rs10975464 | 9 | 6151609 | 0.028 | 1 | HapMap | 1000GP | G | 0.93 | C | 0.07 | G/C |
| YRI | rs7854452 | 9 | 6132673 | 0.018 | 1 | HapMap | 1000GP | G | 0.94 | A | 0.06 | G/A |
| YRI | rs7850282 | 9 | 6217232 | 0.03 | 1 | HapMap | 1000GP | A | 0.94 | G | 0.06 | A/G |
| YRI | rs7042708 | 9 | 6023059 | 0.044 | 0.601 | HapMap | 1000GP | C | 0.95 | G | 0.05 | C/G |
| YRI | rs1556471 | 9 | 6170677 | 0.007 | 1 | HapMap | 1000GP | A | 0.95 | G | 0.05 | A/G |
| YRI | rs1332293 | 9 | 6172604 | 0.018 | 1 | HapMap | 1000GP | G | 0.95 | A | 0.05 | G/A |
| YRI | rs1854709 | 9 | 6251455 | 0.029 | 1 | HapMap | 1000GP | T | 0.95 | C | 0.05 | T/C |
| YRI | rs2000198 | 9 | 6268569 | 0.031 | 1 | HapMap | 1000GP | T | 0.95 | C | 0.05 | T/C |
| YRI | rs980850 | 9 | 6269458 | 0.029 | 1 | HapMap | 1000GP | G | 0.95 | C | 0.05 | G/C |
| YRI | rs980849 | 9 | 6269689 | 0.03 | 1 | HapMap | 1000GP | T | 0.95 | C | 0.05 | T/C |
| YRI | rs10123132 | 9 | 6275720 | 0.03 | 1 | HapMap | 1000GP | T | 0.95 | C | 0.05 | T/C |
| YRI | rs10758763 | 9 | 6326371 | 0.03 | 1 | HapMap | 1000GP | T | 0.95 | C | 0.05 | T/C |
| YRI | rs7865566 | 9 | 5990717 | 0.009 | 1 | HapMap | 1000GP | A | 0.96 | G | 0.04 | A/G |
| YRI | rs480246 | 9 | 6095728 | 0.05 | 0.642 | HapMap | 1000GP | C | 0.96 | T | 0.04 | C/T |
| YRI | rs1888907 | 9 | 6131376 | 0.05 | 0.642 | HapMap | 1000GP | A | 0.96 | G | 0.04 | A/G |
| YRI | rs4567097 | 9 | 6159523 | 0.018 | 1 | HapMap | 1000GP | G | 0.96 | T | 0.04 | G/T |
| YRI | rs1322167 | 9 | 6282089 | 0.03 | 1 | HapMap | 1000GP | A | 0.96 | T | 0.04 | A/T |
| YRI | rs7858373 | 9 | 6301948 | 0.03 | 1 | HapMap | 1000GP | T | 0.96 | G | 0.04 | T/G |
| YRI | rs1407357 | 9 | 6302126 | 0.031 | 1 | HapMap | 1000GP | C | 0.96 | G | 0.04 | C/G |
| YRI | rs1407358 | 9 | 6302297 | 0.03 | 1 | HapMap | 1000GP | T | 0.96 | G | 0.04 | T/G |
| YRI | rs1923359 | 9 | 6310773 | 0.03 | 1 | HapMap | 1000GP | C | 0.96 | T | 0.04 | C/T |
| YRI | rs1330379 | 9 | 6310933 | 0.03 | 1 | HapMap | 1000GP | T | 0.96 | C | 0.04 | T/C |
| YRI | rs10491835 | 9 | 6325345 | 0.06 | 1 | HapMap | 1000GP | G | 0.96 | A | 0.04 | G/A |
| YRI | rs7040374 | 9 | 6348594 | 0.03 | 1 | HapMap | 1000GP | C | 0.96 | T | 0.04 | C/T |
| YRI | rs4742180 | 9 | 6352776 | 0.031 | 1 | HapMap | 1000GP | C | 0.96 | T | 0.04 | C/T |
| YRI | rs10758768 | 9 | 6354290 | 0.03 | 1 | HapMap | 1000GP | A | 0.96 | T | 0.04 | A/T |
| YRI | rs7350177 | 9 | 6357262 | 0.03 | 1 | HapMap | 1000GP | C | 0.96 | T | 0.04 | C/T |
| YRI | rs6477071 | 9 | 6358849 | 0.03 | 1 | HapMap | 1000GP | T | 0.96 | C | 0.04 | T/C |

TABLE 4-continued

SNPs in high LD with rs4742165

| ANC | LD_SNP | CHR | BP | RSQ | DPRIME | LD SOURCE | FREQ SOURCE | A1 | A1 FREQ | A2 | A2 FREQ | ALLELES |
|---|---|---|---|---|---|---|---|---|---|---|---|---|
| YRI | rs13302749 | 9 | 6171731 | 0.01 | 1 | HapMap | 1000GP | T | 0.97 | C | 0.03 | T/C |
| YRI | rs12000756 | 9 | 6188025 | 0.012 | 1 | HapMap | 1000GP | A | 0.97 | C | 0.03 | A/C |
| YRI | rs1969733 | 9 | 6278591 | 0.015 | 1 | HapMap | 1000GP | T | 0.97 | C | 0.03 | T/C |
| YRI | rs1535425 | 9 | 6278774 | 0.015 | 1 | HapMap | 1000GP | C | 0.97 | T | 0.03 | C/T |
| YRI | rs7859105 | 9 | 6288641 | 0.015 | 1 | HapMap | 1000GP | C | 0.97 | A | 0.03 | C/A |
| YRI | rs7042279 | 9 | 6324234 | 0.003 | 1 | HapMap | 1000GP | G | 0.97 | A | 0.03 | G/A |
| YRI | rs1599369 | 9 | 6349335 | 0.015 | 1 | HapMap | 1000GP | A | 0.97 | T | 0.03 | A/T |
| YRI | rs4740837 | 9 | 6089527 | 0.012 | 1 | HapMap | 1000GP | C | 0.98 | T | 0.02 | C/T |
| YRI | rs13300552 | 9 | 6095799 | 0.036 | 1 | HapMap | 1000GP | T | 0.98 | C | 0.02 | T/C |
| YRI | rs7048296 | 9 | 6120702 | 0.012 | 1 | HapMap | 1000GP | T | 0.98 | C | 0.02 | T/C |
| YRI | rs7041151 | 9 | 6326934 | 0.015 | 1 | HapMap | 1000GP | T | 0.98 | A | 0.02 | T/A |
| YRI | rs12339585 | 9 | 6272584 | 0.012 | 1 | HapMap | 1000GP | C | 0.99 | T | 0.01 | C/T |

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating a patient suffering from an IL-33-mediated disorder whose genotype has been determined to comprise a G allele at polymorphism rs4988956 (SEQ ID NO: 1), an A allele at polymorphism rs10204137 (SEQ ID NO: 2), a C allele at polymorphism rs10192036 (SEQ ID NO: 3), a C allele at polymorphism rs10192157 (SEQ ID NO: 4), or a T allele at polymorphism rs10206753 (SEQ ID NO: 5), the method comprising administering to the patient a therapy comprising an IL-33 axis binding antagonist, wherein the IL-33 axis binding antagonist is an IL-33 binding antagonist, an ST2 binding antagonist, or an IL-1RAcP binding antagonist, wherein:
   (i) the IL-33 binding antagonist is an anti-IL-33 antibody or antigen-binding fragment thereof;
   (ii) the ST2 binding antagonist is an ST2-Fc protein or an anti-ST2 antibody or antigen-binding fragment thereof; or
   (iii) the IL-1RAcP binding antagonist is an anti-IL-1RAcP antibody; and
   wherein the IL-33-mediated disorder is an inflammatory disorder or an ophthalmologic disorder.

2. A method of treating a patient suffering from an IL-33-mediated disorder, the method comprising:
   (a) determining the genotype at polymorphism rs4988956 (SEQ ID NO: 1), polymorphism rs10204137 (SEQ ID NO: 2), polymorphism rs10192036 (SEQ ID NO: 3), polymorphism rs10192157 (SEQ ID NO: 4), or polymorphism rs10206753 (SEQ ID NO: 5) in a sample derived from the patient; and
   (b) administering a therapy comprising an IL-33 axis binding antagonist to the patient who has been determined to comprise a G allele at polymorphism rs4988956 (SEQ ID NO: 1), an A allele at polymorphism rs10204137 (SEQ ID NO: 2), a C allele at polymorphism rs10192036 (SEQ ID NO: 3), a C allele at polymorphism rs10192157 (SEQ ID NO: 4), or a T allele at polymorphism rs10206753 (SEQ ID NO: 5),
   wherein the IL-33 axis binding antagonist is an IL-33 binding antagonist, an ST2 binding antagonist, or an IL-1RAcP binding antagonist, wherein:
   (i) the IL-33 binding antagonist is an anti-IL-33 antibody or antigen-binding fragment thereof;
   (ii) the ST2 binding antagonist is an ST2-Fc protein or an anti-ST2 antibody or antigen-binding fragment thereof; or
   (iii) the IL-1RAcP binding antagonist is an anti-IL-1RAcP antibody; and
   wherein the IL-33-mediated disorder is an inflammatory disorder or an ophthalmologic disorder.

3. The method of claim 1, further comprising determining the level of periostin in a sample derived from the patient.

4. The method of claim 1, wherein the IL-33 axis binding antagonist is administered in combination with a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist.

5. The method of claim 1, wherein the inflammatory disorder is asthma, chronic obstructive pulmonary disease (COPD), pneumonia, acute respiratory distress syndrome (ARDS), or atopic dermatitis.

6. The method of claim 5, wherein the inflammatory disorder is asthma.

7. The method of claim 6, wherein the IL-33 axis binding antagonist is an anti-ST2 antibody or antigen-binding fragment thereof.

8. The method of claim 5, wherein the inflammatory disorder is COPD.

9. The method of claim 8, wherein the IL-33 axis binding antagonist is an anti-ST2 antibody or antigen-binding fragment thereof.

10. The method of claim 5, wherein the pneumonia is viral pneumonia.

11. The method of claim 1, wherein the ophthalmologic disorder is age-related macular degeneration (AMD).

12. The method of claim 11, wherein the AMD is geographic atrophy (GA).

* * * * *

```
                        SEQUENCE LISTING

<160> NUMBER OF SEQ ID NOS: 8

<210> SEQ ID NO 1
<211> LENGTH: 51
<212> TYPE: DNA
<213> ORGANISM: Homo sapiens

<400> SEQUENCE: 1
tcttgtatga ctagatgtag tcactrcagt ggaaaccaac atacgaaaga g          51

<210> SEQ ID NO 2
<211> LENGTH: 51
<212> TYPE: DNA
<213> ORGANISM: Homo sapiens

<400> SEQUENCE: 2
gctgaggcgc ttcaggactc cctccrgcat cttatgaaag tacagggggac c          51

<210> SEQ ID NO 3
<211> LENGTH: 51
<212> TYPE: DNA
<213> ORGANISM: Homo sapiens

<400> SEQUENCE: 3
ggctgaggcg cttcaggact ccctcmagca tcttatgaaa gtacagggga c          51

<210> SEQ ID NO 4
<211> LENGTH: 51
<212> TYPE: DNA
<213> ORGANISM: Homo sapiens

<400> SEQUENCE: 4
attcccagaa aggcctctag tttgaytccc ttggctgccc agaagcaata g          51

<210> SEQ ID NO 5
<211> LENGTH: 51
<212> TYPE: DNA
<213> ORGANISM: Homo sapiens

<400> SEQUENCE: 5
agaaaggcct ctagtttgac tccctyggct gcccagaagc aatagtgcct g          51
```

```
<210> SEQ ID NO 6
<211> LENGTH: 51
<212> TYPE: DNA
<213> ORGANISM: Homo sapiens

<400> SEQUENCE: 6
gattttgcag gtgtgattaa attagkaatt tttttagat gaagagatta t            51

<210> SEQ ID NO 7
<211> LENGTH: 51
<212> TYPE: DNA
<213> ORGANISM: Homo sapiens

<400> SEQUENCE: 7
ccaatctttt ctcatgaaga caccakcatg acctcttatt cttatttata t            51

<210> SEQ ID NO 8
<211> LENGTH: 51
<212> TYPE: DNA
<213> ORGANISM: Homo sapiens

<400> SEQUENCE: 8
aaaaattaaa gaattactgt tctaayggga aattttcagg tgtaaagtct g            51
```